(12) United States Patent
Zhang et al.

(10) Patent No.: US 12,168,789 B2
(45) Date of Patent: Dec. 17, 2024

(54) ENGINEERING AND OPTIMIZATION OF SYSTEMS, METHODS, ENZYMES AND GUIDE SCAFFOLDS OF CAS9 ORTHOLOGS AND VARIANTS FOR SEQUENCE MANIPULATION

(71) Applicants: The Broad Institute, Inc., Cambridge, MA (US); Massachusetts Institute of Technology, Cambridge, MA (US); President and Fellows of Harvard College, Cambridge, MA (US); University of Tokyo, Tokyo (JP)

(72) Inventors: Feng Zhang, Cambridge, MA (US); Winston Yan, Cambridge, MA (US); Osamu Nureki, Tokyo (JP); Kaijie Zheng, Cambridge, MA (US); Le Cong, Cambridge, MA (US); Hiroshi Nishimasu, Tokyo (JP); Fei Ran, Cambridge, MA (US); Yinqing Li, Cambridge, MA (US)

(73) Assignees: THE BROAD INSTITUTE, INC., Cambridge, MA (US); MASSACHUSETTS INSTITUTE OF TECHNOLOGY, Cambridge, MA (US); PRESIDENT AND FELLOWS OF HARVARD COLLEGE, Cambridge, MA (US); UNIVERSITY OF TOKYO, Tokyo (JP)

( * ) Notice: Subject to any disclaimer, the term of this patent is extended or adjusted under 35 U.S.C. 154(b) by 84 days.

(21) Appl. No.: 18/101,867

(22) Filed: Jan. 26, 2023

(65) Prior Publication Data

US 2023/0287373 A1    Sep. 14, 2023

Related U.S. Application Data

(63) Continuation of application No. 15/838,720, filed on Dec. 12, 2017, now Pat. No. 11,578,312, which is a continuation-in-part of application No. PCT/US2016/038252, filed on Jun. 17, 2016.

(60) Provisional application No. 62/207,318, filed on Aug. 19, 2015, provisional application No. 62/181,659, filed on Jun. 18, 2015.

(51) Int. Cl.
| | |
|---|---|
| *C12N 9/22* | (2006.01) |
| *C12N 15/10* | (2006.01) |
| *C12N 15/11* | (2006.01) |
| *G16B 15/00* | (2019.01) |
| *G16B 15/20* | (2019.01) |
| *G16B 15/30* | (2019.01) |

(52) U.S. Cl.
CPC ............ *C12N 9/22* (2013.01); *C12N 15/102* (2013.01); *C12N 15/11* (2013.01); *G16B 15/00* (2019.02); *G16B 15/20* (2019.02); *G16B 15/30* (2019.02); *C07K 2299/00* (2013.01); *C07K 2319/09* (2013.01); *C07K 2319/095* (2013.01); *C07K 2319/20* (2013.01); *C07K 2319/70* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| | | | |
|---|---|---|---|
| 5,622,856 | A  | 4/1997  | Natsoulis |
| 6,251,677 | B1 | 6/2001  | Wilson et al. |
| 7,601,492 | B2 | 10/2009 | Fu et al. |
| 7,691,995 | B2 | 4/2010  | Zamore et al. |
| 8,697,359 | B1 | 4/2014  | Zhang |
| 8,771,945 | B1 | 7/2014  | Zhang |
| 8,865,406 | B2 | 10/2014 | Zhang et al. |

(Continued)

FOREIGN PATENT DOCUMENTS

| | | |
|---|---|---|
| BR | 112015013784 | 7/2017 |
| CA | 2619833 A1 | 3/2007 |

(Continued)

OTHER PUBLICATIONS

Bachman et al., "Dnmt3a and Dnmt3b Are Transcriptional Repressors That Exhibit Unique Localization Properties to Heterochromatin," the Journal of Biological Chemistry, Aug. 24, 2001, vol. 276, No. 34,(pp. 32282-32287).

(Continued)

*Primary Examiner* — Neil P Hammell
*Assistant Examiner* — Khaleda B Hasan
(74) *Attorney, Agent, or Firm* — FOLEY & LARDNER LLP

(57) ABSTRACT

The invention provides for systems, methods, and compositions for altering expression of target gene sequences and related gene products. Provided are structural information on the Cas protein of the CRISPR-Cas system, use of this information in generating modified components of the CRISPR complex, vectors and vector systems which encode one or more components or modified components of a CRISPR complex, as well as methods for the design and use of such vectors and components. Also provided are methods of directing CRISPR complex formation in eukaryotic cells and methods for utilizing the CRISPR-Cas system. In particular the present invention comprehends optimized functional CRISPR-Cas enzyme systems. In particular the present invention comprehends engineered new guide architectures and enzymes to be used in optimized *Staphylococcus aureus* CRISPR-Cas enzyme systems.

25 Claims, 35 Drawing Sheets

Specification includes a Sequence Listing.

(56) References Cited

U.S. PATENT DOCUMENTS

| | | |
|---|---|---|
| 8,871,445 B2 | 10/2014 | Cong et al. |
| 8,889,418 B2 | 11/2014 | Zhang et al. |
| 8,895,308 B1 | 11/2014 | Zhang et al. |
| 8,932,814 B2 | 1/2015 | Cong et al. |
| 8,945,839 B2 | 2/2015 | Zhang |
| 8,993,233 B2 | 3/2015 | Zhang et al. |
| 9,512,446 B1 | 12/2016 | Joung et al. |
| 9,549,901 B2 | 1/2017 | Shi et al. |
| 9,597,357 B2 | 3/2017 | Gregory et al. |
| 9,623,071 B2 | 4/2017 | Guo et al. |
| 9,637,739 B2 | 5/2017 | Siksnys et al. |
| 9,701,964 B2 | 7/2017 | Clube et al. |
| 9,738,908 B2 | 8/2017 | Wu |
| 9,834,791 B2 | 12/2017 | Zhang et al. |
| 9,873,894 B2 | 1/2018 | Conway et al. |
| 9,926,546 B2 * | 3/2018 | Joung .................. C12N 9/22 |
| 10,190,137 B2 | 1/2019 | Zhang et al. |
| 10,301,651 B2 | 5/2019 | Doudna et al. |
| 10,351,878 B2 | 7/2019 | Doudna et al. |
| 10,494,621 B2 | 12/2019 | Zhang et al. |
| 10,577,630 B2 | 3/2020 | Zhang et al. |
| 10,583,203 B2 | 3/2020 | De Fougerolles et al. |
| 10,640,788 B2 | 5/2020 | Zhang et al. |
| 10,660,943 B2 | 5/2020 | Bikard et al. |
| 10,669,557 B2 | 6/2020 | Guschin et al. |
| 10,767,194 B2 | 9/2020 | Church et al. |
| 10,781,444 B2 | 9/2020 | Zhang et al. |
| 10,851,357 B2 | 12/2020 | Davidson et al. |
| 10,930,367 B2 | 2/2021 | Zhang et al. |
| 10,941,395 B2 | 3/2021 | Yin et al. |
| 11,041,173 B2 | 6/2021 | Zhang |
| 11,116,729 B2 | 9/2021 | Dahlman et al. |
| 11,124,796 B2 | 9/2021 | Sharp |
| 11,390,887 B2 | 7/2022 | Zhang et al. |
| 11,559,588 B2 | 1/2023 | Lundberg et al. |
| 11,578,312 B2 | 2/2023 | Zhang et al. |
| 11,597,949 B2 | 3/2023 | Zhang et al. |
| 2003/0186238 A1 | 10/2003 | Allawi et al. |
| 2004/0111221 A1 | 6/2004 | Beattie et al. |
| 2005/0196851 A1 | 9/2005 | Uckun |
| 2005/0220796 A1 | 10/2005 | Dynan et al. |
| 2006/0178297 A1 | 8/2006 | Troy et al. |
| 2006/0234247 A1 | 10/2006 | Puttaraju et al. |
| 2007/0016012 A1 | 1/2007 | Hartlep et al. |
| 2007/0244031 A1 | 10/2007 | Lu et al. |
| 2008/0293655 A1 | 11/2008 | Aygun et al. |
| 2009/0215169 A1 | 8/2009 | Wandless et al. |
| 2010/0055798 A1 | 3/2010 | Battersby |
| 2010/0076057 A1 | 3/2010 | Sontheimer et al. |
| 2010/0081707 A1 | 4/2010 | Ali et al. |
| 2010/0093617 A1 | 4/2010 | Barrangou et al. |
| 2010/0233084 A1 | 9/2010 | Narasimhaswamy et al. |
| 2011/0016540 A1 | 1/2011 | Weinstein et al. |
| 2011/0059502 A1 | 3/2011 | Chalasani |
| 2011/0189776 A1 | 8/2011 | Terns et al. |
| 2011/0223638 A1 | 9/2011 | Wiedenheft et al. |
| 2011/0239315 A1 | 9/2011 | Bonas et al. |
| 2012/0029891 A1 | 2/2012 | Behlke et al. |
| 2013/0096182 A1 | 4/2013 | Chatterjee et al. |
| 2013/0130248 A1 | 5/2013 | Haurwitz et al. |
| 2013/0315831 A1 | 11/2013 | Shi et al. |
| 2014/0068797 A1 | 3/2014 | Doudna et al. |
| 2014/0186919 A1 | 7/2014 | Zhang et al. |
| 2014/0294771 A1 | 10/2014 | Schaffer et al. |
| 2014/0295557 A1 | 10/2014 | Joung et al. |
| 2014/0315985 A1 | 10/2014 | May et al. |
| 2014/0342456 A1 | 11/2014 | Mali et al. |
| 2014/0356956 A1 | 12/2014 | Church et al. |
| 2014/0357530 A1 | 12/2014 | Zhang et al. |
| 2015/0045546 A1 | 2/2015 | Siksnys et al. |
| 2015/0071899 A1 | 3/2015 | Liu et al. |
| 2015/0071903 A1 | 3/2015 | Liu et al. |
| 2015/0071906 A1 | 3/2015 | Liu et al. |
| 2015/0232881 A1 | 8/2015 | Glucksmann et al. |
| 2015/0247150 A1 | 9/2015 | Zhang et al. |
| 2015/0291965 A1 | 10/2015 | Zhang et al. |
| 2015/0322457 A1 | 11/2015 | Kim et al. |
| 2015/0353905 A1 | 12/2015 | Weiss et al. |
| 2016/0017366 A1 | 1/2016 | Chen et al. |
| 2016/0024510 A1 | 1/2016 | Bikard et al. |
| 2016/0024524 A1 | 1/2016 | Joung et al. |
| 2016/0130609 A1 | 5/2016 | Doudna et al. |
| 2016/0237456 A1 | 8/2016 | Church et al. |
| 2016/0251648 A1 | 9/2016 | Wang et al. |
| 2016/0281072 A1 | 9/2016 | Zhang |
| 2016/0298135 A1 | 10/2016 | Chen et al. |
| 2016/0298137 A1 | 10/2016 | Chen et al. |
| 2016/0312199 A1 * | 10/2016 | Joung .................. C12Y 301/00 |
| 2016/0324938 A1 | 11/2016 | Bikard et al. |
| 2016/0340662 A1 | 11/2016 | Zhang et al. |
| 2017/0175144 A1 | 6/2017 | Zhang et al. |
| 2017/0191082 A1 | 7/2017 | Chen et al. |
| 2017/0327806 A1 | 11/2017 | Joung et al. |
| 2018/0127783 A1 | 5/2018 | Zhang et al. |
| 2018/0230495 A1 | 8/2018 | Doudna et al. |
| 2019/0010471 A1 | 1/2019 | Zhang et al. |
| 2020/0282026 A1 | 9/2020 | Bikard et al. |
| 2020/0282027 A1 | 9/2020 | Bikard et al. |
| 2020/0354742 A1 | 11/2020 | Zhang |
| 2021/0060140 A1 | 3/2021 | Bikard et al. |
| 2021/0060141 A1 | 3/2021 | Bikard et al. |
| 2021/0324370 A1 | 10/2021 | Yin et al. |
| 2022/0054423 A1 | 2/2022 | Dahlman et al. |
| 2022/0273566 A1 | 9/2022 | Dahlman et al. |

FOREIGN PATENT DOCUMENTS

| | | |
|---|---|---|
| CN | 101228176 | 7/2008 |
| CN | 103343120 | 10/2013 |
| CN | 103388006 | 11/2013 |
| CN | 103668472 | 3/2014 |
| CN | 104520429 A | 4/2015 |
| CN | 104854241 A | 8/2015 |
| CN | 107532161 A | 1/2018 |
| EP | 2 591 770 A2 | 5/2013 |
| EP | 2 784 162 | 1/2014 |
| EP | 2 764 103 | 8/2014 |
| EP | 2 771 468 | 9/2014 |
| EP | 2 828 386 A1 | 1/2015 |
| FR | 2872170 A1 | 12/2005 |
| IN | 49/2015 | 12/2015 |
| JP | 2004-519245 A | 7/2004 |
| JP | 2004-537285 A | 12/2004 |
| JP | 2005-509409 A | 4/2005 |
| JP | 2006-513694 A | 4/2006 |
| JP | 2006-518996 A | 8/2006 |
| JP | 2007-501626 A | 2/2007 |
| JP | 2009-502170 A | 1/2009 |
| JP | 2009-536827 A | 10/2009 |
| JP | 2010-507680 A | 3/2010 |
| JP | 2010-522547 A | 7/2010 |
| JP | 2012-506254 A | 3/2012 |
| JP | 2012-508235 | 4/2012 |
| JP | 2012-510812 A | 5/2012 |
| JP | 2012-511332 A | 5/2012 |
| JP | 2012-523234 A | 10/2012 |
| JP | 2012-529287 A | 11/2012 |
| JP | 2013-500045 A | 1/2013 |
| JP | 2013-513389 A | 4/2013 |
| JP | 2013-518602 A | 5/2013 |
| JP | 2013-544077 A | 12/2013 |
| JP | 2014-526279 A | 10/2014 |
| JP | 2015-523856 A | 8/2015 |
| JP | 2016-500003 A | 1/2016 |
| JP | 2016-500262 A | 1/2016 |
| JP | 2016-501531 | 1/2016 |
| JP | 2016-501532 A | 1/2016 |
| JP | 2016-025710 A | 2/2016 |
| JP | 2016-502840 A | 2/2016 |
| JP | 2016-504026 A | 2/2016 |
| JP | 2016-505256 A | 2/2016 |
| JP | 2016-093196 | 5/2016 |
| JP | 2016-516169 A | 6/2016 |
| JP | 2016-517954 A | 6/2016 |

(56) References Cited

FOREIGN PATENT DOCUMENTS

| | | |
|---|---|---|
| JP | 2016-131404 A | 7/2016 |
| JP | 2016-520317 A | 7/2016 |
| JP | 2016-521554 A | 7/2016 |
| JP | 2016-521975 A | 7/2016 |
| JP | 2016-521995 | 7/2016 |
| JP | 2016-523082 A | 8/2016 |
| JP | 2016-524472 | 8/2016 |
| JP | 2016-182140 A | 10/2016 |
| JP | 2017-501151 A | 1/2017 |
| JP | 2017-501699 | 1/2017 |
| JP | 6395765 | 9/2018 |
| RU | 2009136452 A | 4/2011 |
| WO | WO-02/074968 A1 | 9/2002 |
| WO | WO-02/080851 A2 | 10/2002 |
| WO | WO-03/014318 A2 | 2/2003 |
| WO | WO-03/104414 A2 | 12/2003 |
| WO | WO-2004/029219 A2 | 4/2004 |
| WO | WO-2004/046321 A2 | 6/2004 |
| WO | WO-2004/062618 A2 | 7/2004 |
| WO | WO-2005/014791 A2 | 2/2005 |
| WO | WO-2005/049642 A2 | 6/2005 |
| WO | WO-2007/014275 A2 | 2/2007 |
| WO | WO-2007/134161 A2 | 11/2007 |
| WO | WO-2008/093152 A1 | 8/2008 |
| WO | WO-2008/108989 A2 | 9/2008 |
| WO | WO-2008/116860 A2 | 10/2008 |
| WO | WO-2008/147438 | 12/2008 |
| WO | WO-2010/011961 A2 | 1/2010 |
| WO | WO-2010/048228 | 4/2010 |
| WO | WO-2010/054108 A2 | 5/2010 |
| WO | WO-2010/065123 A1 | 6/2010 |
| WO | WO-2010/068816 A1 | 6/2010 |
| WO | WO-2010/075424 A2 | 7/2010 |
| WO | WO-2010/079430 A1 | 7/2010 |
| WO | WO-2010/118077 A1 | 10/2010 |
| WO | WO-2010/143917 A2 | 12/2010 |
| WO | WO-2011/011767 A1 | 1/2011 |
| WO | WO-2011/016840 A2 | 2/2011 |
| WO | WO-2011/036510 A1 | 3/2011 |
| WO | WO-2011/064736 A1 | 6/2011 |
| WO | WO-2011/072246 A1 | 6/2011 |
| WO | WO-2011/076873 A1 | 6/2011 |
| WO | WO-2011/100058 A1 | 8/2011 |
| WO | WO-2011/146121 A1 | 11/2011 |
| WO | WO-2012/012738 A1 | 1/2012 |
| WO | WO-2012/031205 A2 | 3/2012 |
| WO | WO-2012/051343 A1 | 4/2012 |
| WO | WO-2012/149470 A1 | 11/2012 |
| WO | WO-2012/164565 A1 | 12/2012 |
| WO | WO-2013/044008 A2 | 3/2013 |
| WO | WO-2013/052681 A1 | 4/2013 |
| WO | WO-2013/5052681 A1 | 4/2013 |
| WO | WO-2013/071440 A1 | 5/2013 |
| WO | WO-2013/078400 A1 | 5/2013 |
| WO | WO-2013/082519 A2 | 6/2013 |
| WO | WO-2013/098244 A1 | 7/2013 |
| WO | WO-2013/130824 A1 | 9/2013 |
| WO | WO-2013/141680 A1 | 9/2013 |
| WO | WO-2013/142578 A1 | 9/2013 |
| WO | WO-2013/155572 A1 | 10/2013 |
| WO | WO-2013/176772 A1 | 11/2013 |
| WO | WO-2014/165349 A1 | 3/2014 |
| WO | WO-2014/065596 A1 | 5/2014 |
| WO | WO-2014/089290 A1 | 6/2014 |
| WO | WO-2014/093479 A1 | 6/2014 |
| WO | WO-2014/093595 A1 | 6/2014 |
| WO | WO-2014/093622 A2 | 6/2014 |
| WO | WO-2014/093635 A1 | 6/2014 |
| WO | WO-2014/093655 A2 | 6/2014 |
| WO | WO-2014/093661 A2 | 6/2014 |
| WO | WO-2014/093694 A1 | 6/2014 |
| WO | WO-2014/093701 A1 | 6/2014 |
| WO | WO-2014/093709 A1 | 6/2014 |
| WO | WO-2014/093712 A1 | 6/2014 |
| WO | WO-2014/093718 A1 | 6/2014 |
| WO | WO-2014/099744 A1 | 6/2014 |
| WO | WO-2014/099750 A2 | 6/2014 |
| WO | WO-2015/031775 A1 | 8/2014 |
| WO | WO-2014/144761 A2 | 9/2014 |
| WO | WO-2014/165825 A2 | 10/2014 |
| WO | WO-2014/186585 A2 | 11/2014 |
| WO | WO-2014/191518 A1 | 12/2014 |
| WO | WO-2014/197568 A2 | 12/2014 |
| WO | WO-2014/197748 A2 | 12/2014 |
| WO | WO-2014/204724 A1 | 12/2014 |
| WO | WO-2014/204725 A1 | 12/2014 |
| WO | WO-2014/204726 A1 | 12/2014 |
| WO | WO-2014/204727 A1 | 12/2014 |
| WO | WO-2014/204728 A1 | 12/2014 |
| WO | WO-2014/204729 A1 | 12/2014 |
| WO | WO-2015/006747 A2 | 1/2015 |
| WO | WO-2015/035136 A2 | 3/2015 |
| WO | WO-2015/048577 A2 | 4/2015 |
| WO | WO-2015/048690 A1 | 4/2015 |
| WO | WO-2015/065964 A1 | 5/2015 |
| WO | WO-2015/070083 A1 | 5/2015 |
| WO | WO-2015/071474 A2 | 5/2015 |
| WO | WO-2015/089351 A1 | 6/2015 |
| WO | WO-2015/089364 A1 | 6/2015 |
| WO | WO-2015/089419 A2 | 6/2015 |
| WO | WO-2015/089427 A1 | 6/2015 |
| WO | WO-2015/113063 A1 | 7/2015 |
| WO | WO-2016/022866 A1 | 2/2016 |
| WO | WO-2016/073955 A2 | 5/2016 |
| WO | WO-2016/141224 A1 | 9/2016 |

OTHER PUBLICATIONS

Brief of Amici Curiae Scientists in Support of Appellants and Reversal; Case: 22-1594; Document: 18; Nos. 22-1594, 22-1653; Filed: Oct. 7, 2022 (24 pages).

Corrected Opening Brief for Cross-Appellants; Appeal Nos. 2022-1594, 2022-1653; Document: 31; Filed: Feb. 15, 2023 (111 pages).

Cutrona et al., "Effects in live cells of a c-myc anti-gene PNA linked to a nuclear localization signal," Nature Biotechnology, Mar. 2000, vol. 18 (pp. 300-303).

David et al., "Non-viral nanosystems for systemic siRNA delivery," Pharmacological Research, 2010, vol. 62 (pp. 100-114).

GenTarget Inc., "CRISPR gRNA lentivector cloning kits," GenTarget Inc., Jan. 1, 2013 (pp. 1-2).

Gjetting et al., "In vitro and in vivo effects of polyethylene glycol (PEG)-modified lipid in DOTAP/cholesterol-mediated gene transfection," International Journal of Nanomedicine, 2010, vol. 5 (pp. 371-383).

Hwang et al., "Efficient genome editing in zebrafish using a CRISPR-Cas system," Nature Biotechnology, Jan. 1, 2013, vol. 31, No. 3, Supplementary Materials (pp. 1-21).

Johnson et al., "Achromatopsia caused by novel mutations in both CNGA3 and CNGB3," Journal of Medical Genetics, Online mutation report, Feb. 2004, vol. 41, No. 2 (5 pages).

Kocak D. D., "Synthetic Transcription Factors and their Effects on Endogenous DNA Methylation in Human Cells," Thesis Degree of Master of Science, Jan. 1, 2013, Department of Biomedical Engineering Duke University (35 pages).

Mao et al., "Long-Term Rescue of Retinal Structure and Function by Rhodopsin RNA Replacement with a Single Adeno-Associated Viral Vector in P23H RHO Transgenic Mice," Human Gene Therapy, Apr. 2012, vol. 23 (pp. 356-366).

Motion of Regeneron Pharmaceuticals, Inc. For Leave to File a Brief as Amicus Curiae in Support of Appellants and Reversal; Case: 22-1594; Document: 22-1; Nos. 22-1594 and 22-1653; Filed: Oct. 7, 2022 (29 pages).

Opening Brief for Appellants The Regents of the University of California, University of Vienna, Emmanuelle Charpentier; Nos. 2022-1594 & 2022-1653; Case: 22-1594 Document: 17-1 Filed, Sep. 30, 2022 (81 pages).

Patent Interference No. 106,115; Decision on Motions 37 C.F.R. Section 41.125(a); Filed: Sep. 10, 2020 (113 pages).

(56) References Cited

OTHER PUBLICATIONS

Patent Interference No. 106, 115; Decision on Priority 37 C.F.R. Section 41.125(a), Filed: Feb. 28, 2022 (84 pages).
Patent Interference No. 106,126; Decision on Motions 37 C.F.R. Section 125(a); Filed: Sep. 28, 2022 (54 pages).
Patent Interference No. 106,133; Decision on Motions 37 C.F.R. Section 41.125(a) Filed: Dec. 14, 2022 (40 pages).
Kugler et al., "Human synapsin 1 gene promoter confers highly neuron-specific long-term transgene expression from an adenoviral vector in the adult rat brain depending on the transduced area," Gene Therapy, 2003, vol. 10 (pp. 337-347).
Riley et al., "Improving the Performance of Cascade Correlation Neural Networks on Multimodal Functions," Proceedings of the World Congress on Engineering 2010 vol. III WCE 2010, Jun. 30-Jul. 2, 2010, London, U.K. (7 pages).
Satterwhite et al., "The BCL11 gene family: involvement of "BCL11A" in lymphoid malignancies," Blood, Neoplasia, vol. 98, No. 12, Dec. 1, 2001 (pp. 3413-3420).
"Crispr Genome Engineering Resources" XP055167591, Oct. 5, 2013, https://web.archive.org/web/2013100500 [retrieved on Feb. 5, 2015].
"Fixes, extra genomes, and improvements to the Crispr Design Tool" Google Groups, XP055167583, Oct. 21, 2013, URL:https://groups.google.com/forum/#!topic/crispr/g9Q8U1tNSis [retrieved on Feb. 5, 2015].
"The CRISPR Revolution," Catalyst Magazine, College of Chemistry, University of California, Berkeley, http://catalyst.berkeley.edu/slideshow/the-crispr-revolution/[Dec. 19, 2014 12:40:53] (Jul. 9, 2014).
A. Amsterdam et al., "Identification of 315 genes essential for early zebrafish development," proc Natl Acad Sci., vol. 101, Aug. 31, 2004, pp. 12792-12797, 6 pages.
A. Fire et al., "Potent and specific genetic interference by double-stranded RNA in Caenorhabditis elegans," Nature, vol. 391, Feb. 19, 1998, pp. 806-811, 6 pages.
A. Subramanian et al., "Gene set enrichment analysis: a knowledge-based approach for interpreting genome-wide expression profiles," Proc Natl Acad Sci., vol. 102, Oct. 25, 2005, pp. 15545-15550, 6 pages.
A.C. Spradling et al., "The Berkeley *Drosophila* Genome Project Gene Disruption Project: Single P-Element Insertions Mutating 25% of Vital *Drosophila* Genes," Genetics, vol. 153, Sep. 1999, pp. 135-177, 43 pages.
A.H. Tong et al., "Global mapping of the yeast genetic interaction network," Science, vol. 303, Feb. 6, 2004, pp. 808-813, 6 pages.
A.L. Lin and D.H Gutmann, "Advances in the treatment of neurofibromatosis-associated tumours," Nature, vol. 10, Nov. 2013, pp. 616-624, 9 pages.
A.P. Blanchard and L. Hood, "Sequence to array: probing the genome's secrets," Nat Biotechnol, vol. 14, Dec. 14, 1996, p. 1649.
Abudayyeh, et al., "C2c2 is a single-component programmable RNA-guided RNA-targeting Crispr effector," Science, vol. 10, Jun. 2, 2016, pp. 1-16, 18 pages.
Addgene Materials, "CRISPR/cas Plasmids and Resources", downloaded from https://www.addgene.org/crispr/, May 6, 2015, 3 pages.
Addgene Materials, "Engineering with Addgene's Help", Addgene Newsletter, Mar. 2013, downloaded from https://archive.constantcontact.com/fs126/1103481513180/archive/1112756362265.html, Oct. 14, 2014, 4 pages.
Addgene Reagent distribution list for Zhang Lab with Plasmid Name, date unknown (prior to May 10, 2015), 2 pages.
Addgene, "gRNA_Cloning Vector", retrieved on Jan. 30, 2019, <https://www/addgenen.org/41824/> 2 pages.
Adhin et al., "Complete nucleotide sequence of the group I RNA bacteriophage fr," Biochimica et Biophysica Acta, Elsevier, vol. 1050, 1990 pp. 104-109.
Al-Attar, et al., "Clustered regularly interspaced short palindromic repeats (CRISPRs): the hallmark of an ingenious antiviral defense mechanism in prokaryotes" Biol Chem., vol. 392, No. 4, Apr. 2011, pp. 277-289, 13 pages.

Alberts, et al., "Intracellular Compartments and Protein Sorting," Garland Science, 4 ed., 2002, pp. 671-676, 8 pages.
Allen, et al., "Liposomal drug delivery systems: From concept to clinical applications" Advanced Drug Delivery Reviews, vol. 65, 2013, pp. 36-48, 13 pages.
Anders et al., "Structural basis of PAM-dependent target DNA recognition by the Cas9 endonuclease," Nature, vol. 513, Sep. 25, 2014 pp. 569-573.
Andreas, et al., "Enhanced efficiency through nuclear localization signal fusion on phage C31-integrase: activity comparison with Cre and FLPe recombinase in mammalian cells", Nucleic Acids Research, Apr. 15, 2002, vol. 30, No. 11, pp. 2299-2306, 8 pages.
Anguela et al., "Robust ZFN-mediated geno1ne editing in adult hemophilic mice", Blood, vol. 122, No. 19, Nov. 7, 2013, (pp. 3283-3287).
*Arbitron, Inc.* v. *Kiefl*, No. 09-CV-04013 PAC, 2010 WL 3239414, at *1 (S.D.N.Y. Aug. 13, 2010), 7 pages.
Asuri, P., et al., "Directed Evolution of Adeno-Associated Virus for Enhanced Gene Delivery and Gene Targeting in Human Pluripotent Stem Cells," Molecular Therapy, vol. 30, 2012, No. pp. 329-338, 10 pages.
Au, et al., "Characterization of a baculovirus nuclear localization signal domain in the late express factor 3 protein", Virology, vol. 385, 2009, pp. 209-217.
Ausubel, et al. "Compendium of Methods from Current Protocols in Molecular Biology", Short Protocols in Molecular Biology, 4 ed., 1999, 9-0, 9-4, 5 pages.
Autofluorescence MIT Flow Cytometry Core Facility (2018), 6 pages.
B. Langmead et al., "Ultrafast and memory-efficient alignment of short DNA sequences to the human genome," Genome biology, vol. 10, Mar. 4, 2009, 10 pages.
B.Langmead and S.L. Salzberg, "Fast gapped-read alignment with Bowtie 2," Nat Meth, vol. 9, 2012, pp. 357-359, 3 pages.
B.Scappini et al., "Changes associated with the development of resistance to imatinib (STI571) in two leukemia cell lines expressing p210 Bcr/Abl protein," Cancer, vol. 100, Apr. 1, 2004, pp. 1459-1471, 13 pages.
B.Sonnichsen et al., "Full-genome RNAi profiling of early embryogenesis in Caenorhabditis elegans," Nature, vol. 434, Mar. 24, 2005, pp. 462-469, 8 pages.
Bae, T. and Schneewind, O. "Allelic replacement in *Staphylococcus aureus* with inducible counter-selection," Plasmid, vol. 55, 2006, pp. 58-63, 6 pages.
Baena-Lopez, L., et al., "Accelerated homologous recombination and subsequent genome modification in *Drosophila*," Development, vol. 140, 2013, pp. 4818-4835, including Supplementary Material, 8 pages.
Baiker, et al. "The Immediate-Early 63 Protein of Varicella-Zoster Virus: Analysis of Functional Domains Required for Replication In Vitro and for T-Cell and Skin Tropism in the SCIDhu Model In Vivo", Journal of Virology, 2004, vol. 78 pp. 1181-1194, 14 pages.
Baker, M., "Gene editing at CRISPR Speed," Nature Biotechnology, vol. 32, 2014, pp. 309-312, 4 pages.
Balboa, et al., "Conditionally Stabilized dCas9 Activator for Controlling Gene Expression in Human Cell Reprogramming and Differentiation. (plus Supplemental Information)", Stem Cell Reports, vol. 5, Sep. 8, 2015, pp. 448-459, 12 pages.
Banaszewska, A., et al., "Proprotein Convertase Subtilisin/Kexin Type 9: A New Target Molecule For Gene Therapy," Cellular & Molecular Biology Letters, vol. 17, 2012, pp. 228-239, 12 pages.
Barrangou and Van Der Oost (Eds.), "CRISPR-Cas Systems," Springer Heidelberg, 2013, pp. i-299.
Barrangou, R. et al., "CRISPR provides acquired resistance against viruses in prokaryotes," Science, vol. 315, Mar. 23, 2007, pp. 1709-1712, 6 pages.
Barrangou, R., "RNA-mediated programmable DNA cleavage," Nature Biotechnology, vol. 30, No. 9, Sep. 2012 (pp. 836-388, 13 pages).
Bassett, et al. "Highly Efficient Targeted Mutagenesis of *Drosophila* with the CRISPR/Cas9 System" Cell Reports, vol. 4, Jul. 11, 2013, p. 220.

(56) References Cited

OTHER PUBLICATIONS

Bassett, et al., "A Genome-Wide CRISPR Library for High-Throughput Genetic Screening in *Drosophila* Cells," Journal of Genetics and Genomics, vol. 42, Apr. 18, 2015, pp. 301-309, 9 pages.
Bauer et al., "An Erythroid Enhancer of BCL11A Subject to Genetic Variation Determines Fetal Hemoglobin Level," Science, vol. 342, Oct. 11, 2013 (pp. 253-257).
Beerli et al., "Engineering polydactyl zinc-finger transcription factors", Nature Biotechnology, Feb. 2002, vol. 20, (pp. 135-141).
Beerli, et al. "Positive and negative regulation of endogenous genes by designed transcription factors" PNAS, vol. 97, Feb. 15, 2000, pp. 1495-1500.
Beerli, et al., "Toward controlling gene expression at will: Specific regulation of the erbB-2/HER-2 promoter by using polydactyl zinc finger proteins constructed from modular building blocks", Proc. Natl. Acad. Sci., vol. 95, Oct. 7, 1998, pp. 14628-14633.
Bennett, et al., "Stable transgene expression in rod photoreceptors after recombinant adeno-associated virus-mediated gene transfer to monkey retina", Proc. Natl. Acad. Sci., vol. 96, Aug. 1999, pp. 9920-9925.
Bergemann, et al., Excision of specific DNA-sequences from integrated retroviral vectors via site-specific recombination:, Nucleic Acids Res., vol. 23, Oct. 2, 1995, pp. 4451-4456.
Berns, K., et al., "A Large-Scale RNAi Screen in Human Cells Identifies New Components of the p53 Pathway," Nature, vol. 428, Mar. 25, 2004, pp. 431-437.
Bhattacharya et al., "A simple genotyping method to detect small CRISPR-Cas9 induced indels by agarose gel electrophoresis," Scientific Reports, Mar. 14, 2019, vol. 9, No. 4437 (7 pages).
Bhaya, D., et al., "CRISPR-Cas Systems in Bacteria and Archaea: Versatile Small RNAs for Adaptive Defense and Regulation," Annual Review of Genetics, vol. 45, 2011, pp. 273-297, (27 pages).
Bikard et al., "Exploiting Crispr-Cas nucleases to produce sequence-specific antimicrobials", Nature Biotechnology, vol. 32, No. 11, Nov. 2014 (pp. 1146-1151).
Bikard, et al. "CRISPR Interference Can Prevent Natural Transformation And Virulence Acquisition During In Vivo Bacterial Infection," Cell Host & Microbe, vol. 12, 2012, pp. 177-186.
Bikard, et al., Supplementary Information for: "CRISPR Interference Can Prevent Natural Transformation And Virulence Acquisition During In Vivo Bacterial Infection," Cell Host & Microbe, vol. 12, 2012, pp. 177-186.
Birch, et al., "Plant Transformation: Problems and Strategies for Practical Application", Annu. Rev. Plant Physiol. Plant Mol. Biol., vol. 48, 1997, pp. 297-326.
Bloom, et al., "Inactivation of hepatitis B virus replication in cultured cells and in vivo with engineered transcription activator-like effector nucleases", Molecular Therapy, vol. 21, Oct. 2013, pp. 1889-1897.
Bobis-Wozowicz, S., et al., "Targeted genome editing in pluripotent stem cells using zinc-finger nucleases," Methods, vol. 53, 2012, pp. 339-346.
Boch, et al., "Breaking the Code of DNA Binding Specificity of TAL-Type III Effectors," Science, vol. 326, Dec. 11, 2009, pp. 1509-1512.
Boch, et al., "Xanthomonas AvrBs3 Family-Type III Effectors: Discovery And Function", Annu. Rev. Phytopathol, vol. 48, 2010, pp. 419-436 (21 pages).
Boden, et al., "Efficient Gene Transfer of HIV-1-Specific Short Hairpin RNA into Human Lymphocytic Cells Using Recombinant Adeno-associated Virus Vectors", Molecular Therapy, vol. 9, 2004, pp. 396-402.
Bogdanove, et al., "TAL Effectors: Customizable Proteins for DNA Targeting", Science, vol. 333, 2011, pp. 1843-1846.
Bohm et al., "The computer program LUDI: A new method for the de novo design of enzyme inhibitors", Journal of Computer-Aided Molecular Design, vol. 6, 1992, pp. 61-78.
Botta, S. et al, "Transcriptional Repression with Zinc-Finger and Tale Protein Scaffold", Molecular Therapy, 2013, Supplement 1, p. S208, Abstract No. 539.
Bouard, et al., "Themed Section: Vector Design and Drug Delivery Review, Viral vectors: from virology to transgene expression", British Journal of Pharmacology, vol. 157, 2009, pp. 153-165.
Boutros, et al., "Genome-wide RNAi analysis of growth and viability in *Drosophila* cells," Science, American Association for the Advancement of Science, vol. 303, Feb. 6, 2004, pp. 832-835.
Branden, C., and Tooze, J., "Prediction, Engineering, and Design of Protein Structures: Introduction to Protein Structure," Garland Publishing, Inc., Chapter 16, 1991, p. 247.
Briner, et al., "Guide RNA Functional Modules Direct Cas9 Activity and Orthogonality", Molecular Cell, vol. 56, 2014, pp. 333-339.
Brouns, S., "A Swiss Army Knife of Immunity," Science, vol. 337, 2012, pp. 808-809.
Brouns, S., et al., "Small CRISPR RNAs Guide Antiviral Defense in Prokaryotes," Science, vol. 321, Aug. 15, 2008, pp. 960-964.
Brummelkamp TR et al., "A system for stable expression of short interfering RNAs in mammalian cells," Science, vol. 296, Apr. 19, 2002, pp. 550-553.
C. Cayrol et al., "The THAP-zinc finger protein THAP1 regulates endothelial cell proliferation through modulation of pRB/E2F cell-cycle target genes," Blood, vol. 109, 2007, pp. 584-594.
C. Trapnell et al., "Differential gene and transcript expression analysis of RNA-seq experiments with TopHat and Cufflinks," Nature protocols, vol. 7, 2012, p. 562.
C. Trapnell et al., "TopHat: discovering splice junctions with RNA-Seq.," Bioinformatics, vol. 25, 2009, pp. 1105-1111.
C.J, Echeverri et al., "Minimizing the risk of reporting false positives in large-scale RNAi screens," Nature methods, vol. 3, Oct. 2006, p. 777.
C.M Johannessen et al., "COT drives resistance to RAF inhibition through MAP kinase pathway reactivation," Nature, vol. 468, Dec. 16, 2010, p. 968.
C.M. Johnston et al., "Large-scale population study of human cell lines indicate that dosage compensation is virtually complete," PLoS Genet., vol. 4, Jan. 2008, pp. 88-98, 11 pages.
Cameron et al., "Mapping the genomic landscape of CRISPR-Cas9 cleavage," Nature Methods, Jun. 2017, vol. 14, No. 6 (pp. 600-606).
Campeau, et al., "A Versatile Viral System for Expression and Depletion of Proteins in Mammalian Cells", PLoS One, vol. 4, 2009, pp. 1-17.
Canver et al., "BCL11A enhancer dissection by Cas9-mediated in situ saturating mutagenesis," Nature, vol. 527, 2015, pp. 192-197, including Supplementary Material.
Carr, et al., "Genome Engineering", Nature Biotechnology, vol. 27, No. 12, Dec. 2009, pp. 1151-1162.
Carroll, "Progress and prospects: Zinc-finger nucleases as gene therapy agents," Gene Therapy, vol. 15, 2008 9pages 1463-1468).
Carroll, D., "A CRISPR Approach to Gene Targeting," Molecular Therapy, 2012, vol. 20 (pp. 1658-1660).
Carroll., "Genome Engineering With Zing-Finger Nucleases", Genetics, vol. 188, 2011, pp. 773-782.
Carte, J., et al., "Cas6 is an endoribonuclease that generates guide RNAs for invader defense in prokaryotes," Genes Dev., vol. 22, 2008, pp. 3489-3496.
Cermak et al., "Efficient design and assembly of custom TALEN and other TAL effector-based constructs for DNA targeting," Nucleic Acids Research, 2011, (pp. 1-11).
Chadderton, N., et al., "Improved Retinal Function in a Mouse Model of Dominant Retinitis Pigmentosa Following AAV-delivered Gene Therapy", Molecular Therapy, vol. 17, Apr. 2009, pp. 593-599.
Chan, et al. "Characterization of the Kinetochore Binding Domain of CENP-E Reveals Interactions with the Kinetochore Proteins CENP-F and hBuBR1", The Journal of Cell Biology, vol. 143, 1998, pp. 49-63.
Chan, Wai-Ting, et al., "Toxin-Antitoxin Genes of the Gram-Positive Pathogen *Streptococcus pneumoniae*: So Few and Yet So Many", Microbiology and Molecular Biology Reviews, vol. 76, 2012, pp. 773-791.

(56) References Cited

OTHER PUBLICATIONS

Chang, N., et al. "Genome editing with RNA-guided Cas9 nuclease in Zebrafish embryos", Cell Research, vol. 23, 2013, pp. 465-472.
Chapdelaine et al., "Meganucleases can restore the reading frame of a mutated dystrophin", Gene Therapy, vol. 17, 2010 (pp. 846-858).
Chen, B., et al., "Dynamic Imaging of Genomic Loci in Living Human Cells by an Optimized CRISPR/Cas System," Cell, vol. 155, 2013, pp. 1479-1491.
Chen, Fuqiang, et al., "High-frequency genome editing using ssDNA oligonucleotides with zinc-finger nucleases". Nature Methods, 2011, vol. 8, pp. 753-755, including Supplemental Online Methods.
Chen, Jieliang, et al., "An Efficient Antiviral Strategy for Targeting Hepatitis B Virus Genome Using Transcription Activator-Like Effector Nucleases", Molecular Therapy, vol. 22, 2014, pp. 303-311.
Chen, S., et al., "Genome-wide CRISPR Screen in a Mouse Model of Tumor Growth and Metastasis", Cell, vol. 160, 2015, pp. 1-15, http://dx.doi.org/10.1016/j.cell.2015.02.038.
Chevalier et al., "Homing endonuclease: structural and functional insight into the catalysts of intron/intein mobility," Oxford University Press., vol. 29, 2001, pp. 3757-3774.
Chinnasamy, D., et al., "Multicistronic lentiviral vectors containing the FMCV 2A Cleavage factor demonstrate robust expression of encoded genes at limiting MOI," Virology Journal, vol. 3, 2006, pp. 1-16.
Chiu, et al., "Engineered GFP as a vital reporter in plants", Current Biology, vol. 6, 1996, pp. 325-330.
Cho, A., et al., "Generation of Transgenic Mice," Current Protocols in Cell Biology, Chapter Unit 19.11, 2009, pp. 1-29.
Cho, Minseon, et al., "Quantitative selection and parallel characterization of aptamers," PNAS, vol. 110, Nov. 12, 2013, pp. 18460-18465.
Cho, Seung Woo, et al. "Analysis off-target effects of CRISPR/Cas-derived RNA-guided endonucleases and nickases" Genome Research, vol. 24, 2014, pp. 132-141.
Cho, Seung Woo, et al., "Targeted genome engineering in human cells with the Cas9 RNA-guided endonuclease," Nature Biotechnology, vol. 31 pp. 230-232, including Supplementary Information, 14 pages, 2014.
Chou, JY, and Mansfield, BC., "Recombinant AAV-directed gene therapy for type I glycogen storage diseases," Expert Opinion on Biological Therapy, vol. 11, Aug. 2011, pp. 1011-1024.
Choulika, et al., "Transfer of Single Gene-Containing Long Terminal Repeats into the Genome of Mammalian Cells by a Retroviral Vector Carrying the cre Gene and the IoxP site", Journal of Virology, vol. 70, 1996, pp. 1792-1798.
Christian, et al., "Supporting Information-Targeting DNA Double-Strand Breaks With TAL Effector Nucleases", Genetics, 2010, pp. 1-8, DOI: 10.1534/110.120717:1SI-8SI.
Christian, et al., "Targeting DNA Double-Strand Breaks With TAL Effector Nucleases", Genetics, vol. 186, Oct. 2010, pp. 757-761.
Chylinski, et al., "Classification and evolution of type II CRISPR-Cas systems", Nucleic Acids Research, vol. 42, 2014, pp. 6091-6105, doi:10.1093lnarlgku241.
Chylinski, K., et al., "The tracrRNA and Cas9 Families of Type II CRISPR-Cas Immunity Systems," RNA Biology, vol. 10, 2013, pp. 726-737.
Clark, K. et al, "A Tale of Two Nucleases: Gene Targeting for the Masses?" Zebrafish, vol. 8, No. 3, 2011 (pp. 147-149).
Cockrell, "Berkeley's Wikipedian-in-residence is a first," NewsCenter, Feb. 25, 2014, downloaded from https://newscenter.berkeley.edu/2014/02/25/berkeleys-wikipedian-in-residence-is-a-first/, May 8, 2015, 3 pages.
Community Corner, "CRISPR technology for gene therapy," Nature Medicine, vol. 20, May 2014, pp. 476-477.
Cong et al., "Multiplex Genome Engineering Using CRISPR-Cas Systems," Science, 2013 vol. 339 (pp. 819-823).
Cong et al., Supplementary Material for: "Multiplex Genome Engineering Using CRISPR-Cas Systems," Science Express, Jul. 5, 2012 (pp. 1-26).
Cong, et al., Oct. 5, 2012 Manuscript including Supplementary Materials, "CRISPR-Assisted Mammalian Genome Engineering," published as "Multiplex Genome Engineering Using CRISPR-Cas Systems," Science, vol. 339, 2013, pp. 819-823.
Cong, L., et al., "Comprehensive interrogation of natural TALE DNA-binding modules and transcriptional repressor domains," Nature Communications, vol. 3, Jul. 24, 2012, pp. 968-973.
Cong, L., et al., "In Vivo Genome Engineering With AAV Vector Carrying CRISPR-Cas9 System," Molecular Therapy, vol. 22, May 2014, Supplement 1, p. S214.
Connor, S., "Scientific split—the human genome breakthrough dividing former colleagues," The Independent, http://www.independent.co.uk/news/science/scientific-split--the-human-genome-breakthrough-dividing-former-colleagues-9300456.html, dated Apr. 25, 2014, 5 pages.
Costantino, et al., "Enhanced levels of alpha Red-mediated recombinants in mismatch repair mutants", PNAS, vol. 100, 2003, pp. 15748-15753.
Cotropia, et al., "Copying in Patent Law," N.C.L. Rev., Stanford Public Law Working Paper No. 1270160, 2009, pp. 1-46.
Cummings et al., "Fourteen and counting: unraveling trinucleotide repeat diseases", Human Molecular Genetics, vol. 9, 2000, pp. 909-916.
D.J.Burgess et al., "Topoisomerase levels determine chemotherapy response in vitro and in vivo," Proceedings of the National Academy of Sciences, vol. 105, Jul. 1, 2008, pp. 9053-9058.
Daboussi, F., et al., "Chromosomal context and epigenetic mechanisms control the efficacy of genome editing by rare-cutting designer endonucleases," Nucleic Acids Research, vol. 40, 2012, pp. 6367-6379.
Dahlman, J., et al., "In vivo endothelial siRNA delivery using polymeric nanoparticles with low molecular weight," Nature Nanotechnology, vol. 9, 2014, pp. 648-655.
Dai, et al. "Genes:Structures and Regulation: The Transcription Factors GATA4 and dHAND Physically Interact to Synergistically Activate Cardiac Gene Expression through a p300-dependent Mechanism", J. Biol. Chem., vol. 277, 2002 pp. 24390-24398.
Daley, J., and Wilson, T., "Rejoining of DNA Double-Strand Breaks as a Function of Overhang Length," Molecular and Cellular Biology, vol. 25, 2005, pp. 896-906.
Damian, M., and Porteus, M., "A Crisper Look at Genome Editing: RNA-guided Genome Modification," Molecular Therapy, vol. 21, Apr. 2013, pp. 720-722.
Database GenBank, "*Staphylococcus aureus* subsp.aureus ORFX gene and pseudo SCCmec-SCC-SCCCRISPR element, strain M06/0171," Accession No. HE980450, http://www.ncbi.nlm.nih.gov/nuccore/HE980450, dated Aug. 18, 2016, 22 pages.
Database GenBank: "CRISPR-associated protein, Csn1 family, *Staphylococcus pseudintermedius* ED99," Accession No. ADX75954, http://www.uniprot.org/uniprot/G1UFN3.txt?version=3, dated Nov. 21, 2011, 1 page.
Database UniPro Accession No. J7RUA5, 2012, [online] downloaded from https:/lwww.uniprot.org/uniprol/J7RUA5 on Mar. 23, 2021 (10 pages).
Database UniProt: "CRISPR-associated endonuclease Cas9: *Staphylococcus aureus*," UniProtKB, J7RUA5 (CAS9_STAAU), XP002738511M, https://www.uniprot.org/uniprot/J7RUA5#, dated Oct. 31, 2012, 7 pages.
Database UniProtKB/TrEMBL [online], Accession No. Q0P897, "The genome sequence of the food-borne pathogen *Campylobacter jejuni* reveals hypervariable sequences," Subname: Full=Putative CRISPR-associated protein, Oct. 3, 2012 uploaded, [retrieved on Nov. 22, 2017], URL, http://www.uniprot.org/uniprot/Q0P897.txt?version=28.
Database UniProtKB/TrEMBL, Accession No. D0W2Z9, http://www.uniprot.org/uniprot/D0W2Z9.txt?version=4, dated Oct. 3, 2012, 1 page.
Database UniProtKB/TrEMBL, Accession No. G1UFN3, http://www.uniprot.org/uniprot/G1UFN3.txt?version=3, dated Oct. 3, 2012, 1 page.
Database UniProtKB/TrEMBL, Accession No. J3TRJ9, http://www.uniprot.org/uniprot/J3TRJ9.txt?version=2, dated Oct. 31, 2012, 1 page.

(56) References Cited

OTHER PUBLICATIONS

Database UniProtKB/TrEMBL, Accession No. Q6NK13, http://www.uniprot.org/uniprot/Q6NKI3.txt?version=43, dated Jun. 13, 2012, 1 page.
Database UniProtKB/TrEMBL, Accession No. Q73QW6, http://www.uniprot.org/uniprot/Q73QW6.txt?version=4, dated Nov. 28, 2012, 2 pages.
Database WPI, Week 201437 Thomson Scientific, London, GB; an 2014-J79552, XP-002737563, 2 pages, 2014.
Datsenko, et al. "Molecular memory of prior infections activates the CRISPR/Cas adaptive bacterial immunity system", Nature Communications, vol. 3, 2012, pp. 1-7.
Dean., "Recent Advances in Drug Design Methods: Where Will They Lead?", BioEssays, vol. 16, Sep. 1994, pp. 683-687.
Decision on Motions—PTAB, *The Regents of the University of California v. The Broad Institute, Inc.*, filed Sep. 10, 2020, in Patent Interference No. 106,115 (DK), 113 pages.
Declaration of Feng Zhang for U.S. Appl. No. 14/054,414 dated Jan. 30, 2014 (10 pages).
Declaration of Interference—PTAB, *The Broad Institute, Inc., Massachusetts Institute of Technology, and President and Fellows of Harvard College v. Toolgen, Inc.*, filed Dec. 14, 2020, in Patent Interference No. 106,126 (DK), 19 pages.
Declaration of Technical Expert Paul Simons dated Dec. 22, 2015, 76 pages.
Deltcheva, E., et al., "CRISPR RNA Maturation by Trans-Encoded Small RNA and Host Factor RNase III," Nature, vol. 471, Mar. 31, 2011, pp. 602-609.
Deltcheva, et al., "Supplementary Information: CRISPR RNA Maturation By Trans-Encoded Small RNA and Host Factor RNase III" Nature, pp. 1-35, Mar. 31, 2011.
Deveau, H. et. al., "Phage Response to CRISPR-Encoded Resistance in *Streptococcus thermophilus*," Journal of Bacteriology, vol. 190, No. 4, Feb. 2008, pp. 1390-1400.
Deveau, H., et al., "CRISPR/Cas System and Its Role in Phage-Bacteria Interactions," The Annual Review of Microbiology, vol. 64, 2010, pp. 475-493.
Dicarlo, et al., "Genome engineering in *Saccharomyces cerevisiae* using CRISPTR-Cas systems", Nucleic Acids Research, vol. 41, 2013 pp. 4336-4343.
Dingwall et al., "The Nucleoplasmin Nuclear Location Sequence Is Larger and More Complex than That of SV-40 Large T Antigen", The Journal of Cell Biology, 1988, vol. 107 (pp. 841-849).
Dingwall, et al. "A Polypeptide Domain That Specifies Migration Of Nucleoplasmin into The Nucleus", Cell, vol. 30, 1982, pp. 449-458, (Abstract only).
Do, et al., "Identification of multiple nuclear localization signals in murine Elf3, an ETS transcription factor" FEBS Letters, vol. 580, 2006, pp. 1865-1871.
Doench, et al., "Rational design of highly active sgRNAs for CRISPR-Cas9-mediated gene inactivation," Nature Biotechnology, vol. 32, 2014, pp. 1262-1267, including Supplementary Material, 17 pages.
Dominguez, et al., "Beyond editing: repurposing CRISPR-Cas 9 for precision genome regulation and interrogation" Nat Rev Mol Cell Biol., vol. 17, 2016, 17 pp. 5-15.
Dong, et al., "The crystal structure of Cpf1 in complex with CRISPR RNA," Nature, vol. 532, 2016, pp. 523-525.
Drittanti, et al. "High throughput production, screening and analysis of adeno-associated viral vectors", Gene Therapy, vol. 7, 2000, pp. 924-929.
Dworetzky, S., et al., "The Effects of Variations in the Number and Sequence of Targeting Signals on Nuclear Uptake," The Journal of Cell Biology, vol. 107, 1988, pp. 1279-1287.
E.S. Lander, "Initial impact of the sequencing of the human genome," Nature, vol. 470, Feb. 10, 2011, p. 187-197.
Ebina, H., et al., "Harnessing the CRISPR/Cas9 system to disrupt latent HIV-1 provirus," Scientific Reports, vol. 3, 2013, pp. 1-7, art. 2510.

Edgar, R. and Qimron, U., "The *Escherichia coli* CRISPR system protects from ? lysogenization, lysogens, and prophage induction," Journal of Bacteriology, vol. 192, Dec. 2010, pp. 6291-6294.
Ellis, B., et al., "Zinc-finger nuclease-mediated gene correction using single AAV vector transduction and enhanced by Food and Drug Administration—Approved Drugs," Gene Therapy, vol. 20, 2013, pp. 35-42.
Ellis, et al., "Macromolecular Crowding: Obvious But Underappreciated", Trends in Biochemical Sciences, vol. 26, 2001, pp. 597-604.
Ellis, Hilary, et al., "High efficiency mutagenesis, repair, and engineering of chromosomal DNA using single-stranded oligonucleotids" PNAS, vol. 98, 2001, pp. 6742-6746.
Enyeart, et al., "Biotechnological applications of mobile group II introns and their reverse transcriptases: gene targeting, RNA-seq, and non-coding RNA analysis", Mobile DNA, vol. 5, 2014, pp. 1-19 http://www.mobilednajournal.com/contents5/1/2.
Espinoza, et al., "Characterization of the structure, function, and mechanism of B2 RNA, an ncRNA repressor of RNA polymerase II transcription", RNA, vol. 13, 2007, pp. 583-596.
Esvelt et. al., "Orthogonal Cas9 proteins for RNA-guided gene regulation and editing", Nature Methods, vol. 10, No. 11, Nov. 2013 (available online Sep. 29, 2013), pp. 1116-1123.
Excerpt from Dr. Feng Zhang's Jan. 30, 2014 Declaration (Exhibit C1), 11 pages.
Federal Circuit decision in *Dow Chemical Co. v. Nova Chemicals Corp.*, Appeal Nos. 2014-1431, 2014-1462 (Fed. Cir. Aug. 28, 2015) (*Dow v. Nova*), 25 pages.
Feldgarden et al., "*Staphylococcus aureus* M0408 acrHk-supercont1.1, whole genome shotgun sequence", NCBI Reference Sequence: NK_KB821326.1, Direct Submission, Dec. 10, 2012, pp. 1-4.
Fieck, et al., "Modifications of the *E.coli* Lac repressor for expression in eukaryotic cells: effects of nuclear signal sequences on protein activity and nuclear accumulation", Nucleic Acids Research, vol. 20, 1992, pp. 1785-1791.
Finn et al., "A Single Administration of CRISPR/Cas9 Lipid Nanoparticles Achieves Robust and Persistent In Vivo Genome Editing," Cell Reports, Cell Press, 2018, vol. 22 (pp. 2227-2235).
Fischer, S. et al., "An archaeal immune system can detect multiple Protospacer Adjacent Motifs (PAMs) to target invader DNA," J. Biol. Chem., vol. 287, Sep. 28, 2012, pp. 33351-33363.
Fischer-Fantuzzi, L., and Vesco, C., "Cell-dependent efficiency of reiterated nuclear signals in a mutant simian virus 40 oncoprotein targeted to the nucleus," Molecular and Cellular Biology, vol. 8, 1988, pp. 5495-5503.
Flannery, J. G., "Ribozyme-Mediated Gene Therapy for Autosomal Dominant Retinal Degeneration", Retinal Degenerative Diseases and Experimental Therapy, 1999, pp. 277-291.
Fleming, J., et al., "Adeno-Associated Virus and Lentivirus Vectors Mediate Efficient and Sustained Transduction of Cultured Mouse and Human Dorsal Root Ganglia Sensory Neurons," Human Gene Therapy, vol. 12, Jan. 1, 2001, pp. 77-86.
Foecking, et al. "Powerful and versatile enhance-promoter unit for mammalian expression vectors", Gene, vol. 45, 1986, pp. 101-105.
Fonfara et al., "Phylogeny of Cas9 determines functional exchangeability of dual-RNA and Cas9 among orthologous type II CRISPR-Cas systems", Nucleic Acids Research, 2014, vol. 42, No. 4, pp. 2577-2590.
Freitas, et al., "Mechanisms and Signals for the Nuclear Import of Proteins", Current Genomics, vol. 10, 2009, pp. 550-557.
Fu, et al., "High-frequency off-target mutagenesis induced by CRISPR-Cas nucleases in human cells", Nature Biotechnology, vol. 31, 2013, pp. 822-826.
Fu, et al., "Targeted genome editing in human cells using CRISPR/Cas nucleases and truncated guide RNAs", The Use of CRISPR/Cas9 ZFNs and Talens in Generating Site-Specific Genome Alterations; Elsevier Inc., 2014, pp. 21-45.
G. Giaever et al., "Functional profiling of the *Saccharomyces cerevisiae* genome," Nature, vol. 418, Jul. 25, 2002, pp. 387-391.
G. Guo et al., "Mismatch repair genes identified using genetic screens in Blm-deficient embryonic stem cells," Nature, vol. 429, Jun. 24, 2004, p. 891.

(56) References Cited

OTHER PUBLICATIONS

Gabriel, R., et al., "An unbiased genome-wide analysis of zinc-finger nuclease specificity," Nature Biotechnology, vol. 29, 2011, pp. 816-823.
Gaj et al., "ZFN, TALEN, and CRISPR/Cas-Based Methods for Genome Engineering," Trends in Biotechnology, vol. 31, 2013 (pp. 397-405).
Gaj, T., et al., "Targeted Gene knockout by direct delivery of zinc-finger nuclease proteins," Nature Methods, vol. 9, 2012, pp. 805-807, including supplemental pages.
Gama Sosa, M., et al., "Animal transgenesis: an overview," Brain Structure and Function, vol. 214,0 2010, pp. 91-109.
Gao, et al. "Engineered Cpf1 variants with altered PAM specificities", Nature Biotechnology, vol. 35, Jun. 8, 2017, pp. 1-4 (789-792), doi: 10.1038/nbt.3900, advanced online publication including Supplementary Information.
Gao, et al., "A Sustained, Cytoplasmic Transgene Expression System delivered by Cationic Liposomes", Biochemical and Biophysical Research Communications, vol. 200, May 16, 1994, pp. 1201-1206.
Garcia-Bustos, et al., "Nuclear protein localization", Biochimica et Biophysica Acta, vol. 1071, 1991, pp. 83-101.
Gardlik, R., et al., "Vectors and delivery systems in gene therapy," Medical Science Monitor, vol. 11, No. 4, pp. RA110-RA121, dated Apr. 1, 2005, 12 pages.
Garg, et al. "Engineering synthetic TAL effectors with orthogonal target sites", Nucleic Acids Research, 2012, vol. 40, pp. 7584-7595, doi:10.1093/nar/gks404.
Garneau, et al., "The CRISPR/Cas Cleaves Bacteriophage and Plasmid DNA," Nature, vol. 468, Nov. 4, 2010, pp. 67-71.
Garriga-Canut, M., et al., "Synthetic zinc finger repressors reduce mutant huntingtin expression in the brain of R6/2 mice," Proceedings of the National Academy of Sciences, vol. 109, Oct. 10, 2012, pp. E3136-E3145.
Gasiunas, G, et. al., "Cas9-crRNA Ribonucleoprotein Complex Mediates Specific DNA Cleavage for Adaptive Immunity in Bacteria," Proceedings of the National Academy of Sciences, vol. 109, Sep. 4, 2012, pp. E2579-E2586.
Geibler et al., "Transcriptional Activators of Human Genes with Programmable DNA-Specificity," May 19, 2011, PLoS one, vol. 6, No. 5 (pp. 1-7).
Geisinger, et al., "In vivo blunt-end cloning through CRISPR /CAS9-facilitated non-homologous end-joining", Nucleic Acid Research Advance Access, vol. 44, 2016, pp. 1-15.
GenBank: "CRISPR-associated protein Cas9/Csn1 [*Staphylococcus aureus* subsp. *aureus*]", GenBank: CCK74173.1, Year: 2012, http://www.ncbi.nlm.nih.gov/protein/403411236?sat=16&satkey=13804560, dated Dec. 14, 2016, 2 pages.
Gibson, D.G. et al., "Enzymatic assembly of DNA molecules up to several hundred kilobases," Nat methods, vol. 6, 2009, pp. 343-345.
Gilbert, L., et al., "CRISPR-Mediated Modular RNA-Guided Regulation of Transcription in Eukaryotes," Cell, vol. 154, 2013, pp. 442-451.
Goldfarb, et al. "Synthetic peptides as nuclear localization signals", Nature, vol. 322, 1986, pp. 641-644.
Gomaa, et al. "Programmable removal of bacterial strains by use of genome-targeting CRISPR-Cas systems", MBio., vol. 5, 2014, pp. 1-9.
Goncalves, M., et al., "Concerted nicking of donor and chromosomal acceptor DNA promotes homology-directed gene targeting in Human Cells," Nucleic Acids Research, vol. 40, 2012, pp. 3443-3455.
Gratz, et al. "Genome Engineering of *Drosophila* with the CRISPR RNA-Guided Cas9 Nuclease", Genetics, vol. 194, 2013, pp. 1029-1035.
Greenspan, et al., "Two Nuclear Location Signals in the Influenza Virus NS1 Nonstructural Protein", Journal of Virology, vol. 62, 1988, pp. 3020-3026.

Greenwald, D L, et al., "Engineered Zinc Finger Nuclease-Mediated Homologous Recombination of the Human Rhodopsin Gene", Investigative Ophthalmology & Visual Science, vol. 51, Dec. 2010, pp. 6374-6380.
Grens, "Enzyme Improves CRISPR A smaller Cas9 protein enables in vivo genome engineering via viral vectors", The Scientist, Apr. 1, 2015.
Grieger, J., and Samulski, R., "Packaging Capacity of Adeno-Associated Virus Serotypes: Impact of Larger Genomes on Infectivity and Postentry Steps," Journal of Virology, vol. 79, 2005, pp. 9933-9944.
Grissa, I., et al., "CRISPRFinder: a web tool to identify clustered regularly interspaced short palindromic repeats," Nucleic Acids Research, vol. 35, 2007, pp. W52-W57.
Grosse, et al. "Meganuclease-medicated Inhibition of HSV1 Infection in Cultured Cells", Molecular Therapy, vol. 19, No. 4, Apr. 1, 2011, pp. 694-702.
Guan, et al., "Heritable endogenous gene regulation in plants with designed polydactyl zinc finger transcription factors", PNAS, vol. 99, 2002, pp. 13296-13301.
Gudbergsdottir, S. et al., "Dynamic properties of the Sulfolobus CRISPR/Cas and CRISPR/Cmr systems when challenged with vector-borne viral and plasmid genes and protospacers," Mol. Microbiology, vol. 79, 2011, pp. 35-49.
Guilinger et al., "Fusion of catalytically inactive Cas9 to FokI nuclease improves the specificity of genome modification," Nature Biotechnology, vol. 32, No. 6, Jun. 2014 (pp. 577-582).
Gustafsson, et al. "Codon Bias and heterologous protein expression", Trends in Biotechnology, Jul. 2004, vol. 22, pp. 346-353.
H. Davies et al., "Mutations of the BRAF gene in human cancer," Nature, vol. 417, Jun. 27, 2002, p. 949-954.
H.W Cheung et al., "Systematic investigation of genetic vulnerabilities across cancer cell lines reveals lineage-specific dependencies in ovarian cancer," Proceedings of the National Academy of Sciences, vol. 108, Jul. 26, 2011, p. 12372-12377.
Habib, N., Assignment to Broad Institute, dated Jun. 9, 2014, 4 pages.
Haft, D., et al., "A Guild of 45 CRISPR-Associated (Cas) Protein Families and Multiple CRISPR/Cas Subtypes Exist in Prokaryotic Genomes," PLoS Computational Biology, vol. 1, 2005, pp. 0474-0483.
Haft, D.H., "HMM Summary Page: TIGR04330", 2012, XP-002757584, http://jcvi.org/cgi-bin/tigrfams/HmmReportPage.cgi?acc=TIGR04330, 1 page.
Hale et al., "Prokaryotic silencing (psi) RNAs in Pyrococcus furiosus," RNA, 2008, vol. 14 (pp. 2572-2579).
Hale, et al. "Essential Features and Rational Design Of CRISPR RNAs that Function With The Cas RAMP Module Complex To Cleave RNAs", Molecular Cell, vol. 45, 2012, pp. 292-302.
Hale, et al. "RNA-Guided RNA Cleavage by a CRISPR RNA-Cas Protein Complex", Cell, vol. 139, 2009, pp. 945-956.
Hall, B., et al., "Overview: Generation of Gene Knockout Mice," Current Protocols in Cell Biology, unit 19.12, suppl. 44, Sep. 2009, pp. 1-17.
Handel, E., et al., "Versatile and Efficient Genome Editing in Human Cells by Combining Zinc-Finger Nucleases With Adeno-Associated Viral-Vectors," Human Gene Therapy, vol. 23, 2012, pp. 321-329.
Harrison, et al., "A CRISPR view of development", Genes & Development, vol. 28, 2014, pp. 1859-1872.
Hatoum-Aslan, A., et al., "Mature clustered, regularly interspaced, short palindromic repeats RNA (crRNA) length is measured by a ruler mechanism anchored at the precursor processing site," Proc. Natl. Acad. Sci., vol. 108, Dec. 27, 2011, pp. 21218-21222.
Haurwitz, R.E., et al., "Sequence- and structure-specific RNA processing by a CRISPR endonuclease," Science, vol. 329, 2010, pp. 1355-1358.
Havarstein, L.S., et al., "An unmodified heptadecapeptide pheromone induces competence for genetic transformation in *Streptococcus pneumoniae*," Proc. Natl. Acad. Sci., vol. 92, Nov. 1995, pp. 11140-11144.

(56) References Cited

OTHER PUBLICATIONS

He et al., "Pollen fertility restoration by nuclear gene Fr in CMS common bean: an Fr linkage map and the mode of Fr action," Theor. Appl. Genet. vol. 90, 1995, pp. 1056-1062.
Heintze, et al. "A CRISPR CASe for high-throughput silencing", Frontiers in Genetics, vol. 4, 2013, pp. 1-6 DOI:10.3389/gfene.2013.00193.
Hemann et al., "An epi-allelic series of p53 hypomorphs created by stable RNAi produces distinct tumor phenotypes in vivo," Nat Genetics, vol. 33, Mar. 2003, pp. 396-400.
Hemphill et al., "Optical Control of CRISPR/Cas9 Gene Editing," Journal of the American Chemical Society, vol. 137, May 6, 2015 (9 pages).
Hibbitt, O., et al., "RNAi-mediated knockdown of HMG CoA reductase enhances gene expression from physiologically regulated low-density lipoprotein receptor therapeutic vectors in vivo," Gene Therapy, vol. 19, 2012, pp. 463-467.
Hicks, et al. "Protein Import Into the Nucleus: An Integrated View", Annu. Rev. Cell Dev. Biology, vol. 11, 1995, pp. 155-188.
Hirano et al., "Structure and Engineering of Francisella novicida Cas9," Cell, vol. 164, Feb. 25, 2016, pp. 950-961.
Ho, et al., "Targeting non-coding RNAs with the CRISPR/Cas9 system in human cell lines," Nucleic Acids Research, vol. 43, 2015, pp. 1-11.
Hockemeyer et al., "Highly efficient gene targeting of expressed and silent genes in human ESCs and iPSCs using zinc finger nucleases," Nature Biotechnology, 2009, vol. 27 (pp. 851-857).
Holkers, M., et al., "Adenoviral vector DNA for accurate genome editing with engineered nucleases," Nature Methods, vol. 11, 2014, pp. 1051-1057, (Only Abstract Available).
Holmes, "CRISPR Genome Engineering Resources" XP055167586, Oct. 2, 2013, https://groups.google/forum/#!top1c/crispr/5BpJj_Y3yIG [retrieved on Feb. 5, 2015].
Holmes, "Understanding Scores" XP055167918, Oct. 23, 2013, https://groups.google.com/forum/#!profo_nt50txrP9Yb6e_LXccolb9hNf7gKeMLt6rgaVQ4fOsQ/crispr/fkhX7Fu3r-I/rziHxKT76pYJ [retrieved on Feb. 6, 2015].
Horinouchi, S. and Weisblum, B., "Nucleotide sequence and functional map of pC194, a plasmid that specifies inducible chloramphenicol resistance," J. Bacteriology, vol. 150, May 1982, pp. 815-825.
Horton, R.M., "In Vitro recombination and Mutagenesis of DNA: SOEing Together Tailor-Made Genes," Methods Mol. Biology, vol. 15, 1993, pp. 251-261.
Horvath, P. and Barrangou, R. "CRISPR/Cas, the immune system of bacteria and archaea," Science, vol. 327, Jan. 8, 2010, pp. 167-170.
Horvath, P., and Barrangou, R., "RNA-guided genome editing a la carte," Cell Research, vol. 23, 2013, pp. 733-734.
Hosaka, T. et al., "The novel mutation K87E in ribosomal protein S12 enhances protein synthesis activity during the late growth phase in *Escherichia coli*." Mol. Gen. Genomics, vol. 271, 2004, pp. 317-324.
Hoskins, J. et al., "Genome of the bacterium *Streptococcus pneumoniae* strain R6," Journal of Bacteriology, vol. 183, Oct. 2001, pp. 5709-5717.
Hou, Z., et al., "Efficient genome engineering in human pluripotent stem cells using Cas9 from Neisseria meningitides," Proceedings of the National Academy of Sciences, vol. 110, 2013, pp. 15644-15649.
Houdebine, L., "The methods to generate transgenic animals and to control transgene expression," Journal of Biotechnology, vol. 98, 2002, pp. 145-160.
Hsu et al., "Supplementary Information—DNA targeting specificity of RNA-guided Cas9 nucleases," Nature Biotechnology, 2013, doi: 10.1038/nbt.2647.
Hsu, et al., "DNA targeting specificity of RNA-guided Cas9 nucleases," Nature Biotechnology, vol. 31, 2013, pp. 827-834.
Hsu, P., et al., "Development and Applications of CRISPR-Cas9 for Genome Engineering," Cell, vol. 157, 2014, pp. 1262-1278.
Huang and Honkanen, "Molecular Cloning, Expression, and Characterization of a Novel Human Serine/Threonine Protein Phosphatase, PP7, That Is Homologous to '*Drosophila*' Retinal Degeneration C Gene Product (rdgC)*," The Journal of Biological Chemistry, vol. 273, No. 3, Iss. 16, 1998, pp. 1462-1468.
*Huang v. California Institute of Technology*, 2004 WL 2296330 (C.D. Cal. Feb. 18, 2004), 20 pages.
Hung, S., et al., "AAV-Mediated CRISPR/Cas Gene Editing of Retinal Cells in Vivo," Investigative Ophthalmology & Visual Science, vol. 57, 2016, pp. 3470-3476.
Husmann, L.K.,et al., "Expression of the Arp protein, a member of the M protein family, is not sufficient to inhibit phagocytosis of *Streptococcus pyogenes*," Infection and immunity, vol. 63, Jan. 1995, pp. 345-348.
Hwang W., et al., "Efficient In Vivo Genome Editing Using RNA-Guided Nucleases," Nature Biotechnology, vol. 31, No. 3, Mar. 2013, pp. 227-229 (12 pages).
Hwang, W.Y., et al., "Efficient Genome Editing in Zebrafish Using a CRISPR-Cas System", Nature Biotechnology, vol. 31, No. 3, Jan. 29, 2013, pp. 227-229.
Imagawa, et al., "Two nuclear localization signals are required for nuclear translocation of nuclear factor 1-A", FEBS Letters, vol. 484, 2000, pp. 118-124.
Incontro, S., et al., "Efficient, Complete Deletion of Synaptic Proteins using CRISPR," Neuron, vol. 83, 2014, pp. 1051-1057, 13 pages.
International Search Report and Written Opinion for Appl. Ser. No. PCT/US2013/074691 dated Jun. 19, 2014, 14 pages.
International Search Report and Written Opinion for Appl. Ser. No. PCT/US2013/074611 dated Jun. 19, 2015, 11 pages.
International Search Report and Written Opinion for Appl. Ser. No. PCT/US2013/074667 dated Sep. 23, 2014, 12 pages.
International Search Report and Written Opinion for Appl. Ser. No. PCT/US2013/074736 dated Oct. 20, 2014, 11 pages.
International Search Report and Written Opinion for Appl. Ser. No. PCT/US2013/074743 dated Aug. 20, 2014, 11 pages.
International Search Report and Written Opinion for Appl. Ser. No. PCT/US2013/074790 dated Sep. 17, 2014, 10 pages.
International Search Report and Written Opinion for Appl. Ser. No. PCT/US2013/074800 dated Sep. 22, 2014, 10 pages.
International Search Report and Written Opinion for Appl. Ser. No. PCT/US2013/074812 dated Jun. 19, 2014, 10 pages.
International Search Report and Written Opinion for Appl. Ser. No. PCT/US2013/074819 dated Jul. 28, 2014, 11 pages.
International Search Report and Written Opinion for Appl. Ser. No. PCT/US2013/074825 dated Jun. 19, 2014, 12 pages.
International Search Report and Written Opinion for Appl. Ser. No. PCT/US2014/041800 dated Oct. 7, 2014, 10 pages.
International Search Report and Written Opinion for Appl. Ser. No. PCT/US2014/041803 dated Dec. 24, 2014, 12 pages.
International Search Report and Written Opinion for Appl. Ser. No. PCT/US2014/041804 dated Dec. 24, 2014, 15 pages.
International Search Report and Written Opinion for Appl. Ser. No. PCT/US2014/041806 dated Jan. 27, 2015, 14 pages.
International Search Report and Written Opinion for Appl. Ser. No. PCT/US2014/041808 dated Dec. 24, 2014, 15 pages.
International Search Report and Written Opinion for Appl. Ser. No. PCT/US2014/041809 dated Nov. 11, 2014, 13 pages.
International Search Report and Written Opinion for Appl. Ser. No. PCT/US2014/069897 (14 pages), 2014.
International Search Report and Written Opinion for Appl. Ser. No. PCT/US2014/069902 (11 pages), 2014.
International Search Report and Written Opinion for Appl. Ser. No. PCT/US2015/045504, 2015.
International Search Report and Written Opinion for Appl. Ser. No. PCT/US2015/065393 dated Apr. 15, 2016.
International Search Report and Written Opinion for Appl. Ser. No. PCT/US2015/067177 dated Apr. 29, 2016.
International Search Report and Written Opinion for Appl. Ser. No. PCT/US2016/038252, (2016).
International Search Report and Written Opinion for PCT Appl. Ser. No. PCT/US2015/065385 dated Apr. 15, 2016, 16 pages.
International Search Report and Written Opinion for PCT Appl. Ser. No. PCT/US2016/038034 dated Nov. 18, 2016, 15 pages.

(56) References Cited

OTHER PUBLICATIONS

International Search Report and Written Opinion for PCT/US2014/069925 dated May 4, 2015. 14 pages.
International Search Report and Written Opinion for PCT/US2014/070057 dated Jul. 14, 2015, 21 pages.
International Search Report and Written Opinion for PCT/US2014/070127 dated Apr. 15, 2015, 17 pages.
International Search Report and Written Opinion for PCT/US2014/070152 dated May 4, 2015. 15 pages.
International Search Report and Written Opinion for PCT/US2014/070175 dated Jul. 7, 2015. 16 pages.
Ishino Y. et al., "Nucleotide sequence of the iap gene, responsible for alkaline phosphatase isozyme conversion in *Escherichia coli*, and identification of the gene product," J. Bacteriology, vol. 169, Dec. 1987, pp. 5429-5433, 5 pages.
Iwamoto et al., "A General Chemical Method to Regulate Protein Stability in the Mammalian Central Nervous System", Chemistry and Biology, Current Biology, vol. 17, Sep. 24, 2010, pp. 981-988, 8 pages.
J. Merkin et al., "Evolutionary dynamics of gene and isoform regulation in Mammalian tissues," Science, vol. 338, Dec. 21, 2012, p. 1593-1599, 7 pages. Includes Supplementary Information, 34 pages.
J.E. Carette et al., "Haploid genetic screens in human cells identify host factors used by pathogens," Science, vol. 326, Nov. 27, 2009, p. 1231-1235, 5 pages.
J.F. Rual et al., "Toward Improving Caenorhabditis elegans Phenome Mapping with an ORFeome-Based RNAi Library," Genome Research, vol. 14, 2004, pp. 2162-2168, 7 pages.
J.M. Engreitz et al., "The Xist lncRNA exploits three-dimensional genome architecture to spread across the X chromosome," Science, vol. 341, Aug. 16, 2013, pp. 1-8, 8 pages.
Jackson, A., et al., "Widespread siRNA "off-target" transcript silencing mediated by seed region sequence complementarity," RNA vol. 12, 2006, pp. 1179-1187, 10 pages.
Jansen R. et al., "Identification of genes that are associated with DNA repeats in prokaryotes," Molecular Microbiology, vol. 43, 2002, pp. 1565-1575, 11 pages.
Janssen, et al., "Mouse Models of K-ras-Initiated Carcinogenesis", Biochimica et Biophysica Acta, vol. 1756 2005, pp. 145-154, 10 pages.
Jao, et al., "Efficient multiplex biallelic zebrafish genome editing using a CRISPR nuclease system", Proceeding of the National Academy of Sciences, PNAS 2013, pp. 1-6, includes supplementary information, pp. 1-10. www.pnas.org/cgi/doi/10.1073/pnas.1308335110.
Jiang, W., et al., "RNA-guided editing of bacterial genomes using CRISPR-Cas systems," Nature Biotechnology, vol. 31, Mar. 2013, pp. 233-239, 30 pages, including supplementary information.
Jinek et al., "RNA-programmed genome editing in human cells," eLife Research Article, Genetics and Genomics, Jan. 29, 2013, vol. 2, Reviewing editor: Detlef Weigel, Max Planck Institute for Developmental Biology, Germany (pp. 1-9).
Jinek, M., et al., "A Programmable Dual-RNA-Guided DNA Endonuclease In Adaptive Bacterial Immunity," Science, vol. 337, Aug. 17, 2012 pp. 816-821, including supplementary information, 45 pages.
Jinek, M., et al., Figures and figure supplements for: "RNA-programmed genome editing in human cells," eLIFE, vol. 2, Jan. 29, 2013, 5 pages.
JL. Mummery-Widmer et al., "Genome-wide analysis of Notch signalling in *Drosophila* by transgenic RNAi," Nature, vol. 458, Apr. 23, 2009, pp. 987-992, 6 pages. Includes Supplementary information, 2 pages.
Joseph, T., and Osman, R., "Thermodynamic basis of selectivity in guide-target-mismatched RNA interference," Proteins, vol. 80, 2012, pp. 1283-1298, 26 pages.

Joshi, et al., "Evolution of I-ScoI homing endonucleases with increased DNA recognition site specificity", Journal of Molecular Biology, 2011, vol. 405, pp. 185-200, 16 pages. Includes supplementary information, 14 pages.
Joung, et al., "TALENs: a widely applicable technology for targeted genome editing", Nat Ref. Mol. Cell Biology, vol. 14, 2013, pp. 49-55, 7 pages. doi:10.1038/nrm3586.
K. Yoshimoto et al., "Complex DNA repair pathways as possible therapeutic targets to overcome temozolomide resistance in glioblastoma," Front Oncology, vol. 2, Dec. 2012, pp. 1-8, 8 pages.
K.T Flaherty et al., "Inhibition of mutated, activated BRAF in metastatic melanoma," The New England Journal of Medicine, vol. 363, Aug. 26, 2010, pp. 1-22, 22 pages.
Kalderon, et al., "A Short Amino Acid Sequence Able to Specify Nuclear Location", Cell, vol. 39, 1984, pp. 499-509, 11 pages.
Kanasty, R., et al., "Delivery materials for siRNA therapeutics," Nature Materials, vol. 12, 2013, pp. 967-977, 11 pages.
Karvelis, et al., "crRNA and tracrRNA guide Cas9-mediated DNA interference in *Streptococcus thermophiles*" RNA Biology, vol. 10, 2013, pp. 841-851, 11 pages.
Karvelis, et al., "Supplemental Material to: crRNA and tracrRNA guide Cas9-mediated DNA interference in *Streptococcus thermophiles*", Landes Bioscience, vol. 10, 2013, pp. 1-8, 9 pages. http://dx.doi.org/10.4161/rna.24203.
Kiani, et al., "CAS9 gRNA engineering for genome editing, activation and repression", Nature Methods, Advanced Online Publication, 2015, pp. 1-6. DOI:10.1038/NMETH.3580.
Kim et al., "High Cleavage Efficiency of a 2A Peptide Derived from Porcine Teschovirus-1 in Human Cell Lines, Zebrafish and Mice," PLoS One, vol. 6, Apr. 2011, pp. 1-8, 8 pages.
Kim, E., et al., "Precision genome engineering with programmable DNA-nicking enzymes," Genome Research, vol. 22, 2012, pp. 1327-1333, 8 pages.
Kim, et al., "Crystal structure of Cas1 from Archaeoglobus fulgidus and characterization of its nucleolytic activity", Biochemical and Biophysical Research Communications, 2013, vol. 441, 2013, pp. 720-725, 6 pages.
Kim, S., et al., "CRISPER RNAs trigger innate immune responses in human cells," Genome Research, 2018, pp. 1-7, 8 pages.
Kinnevey, P., et al., "Emergence of Sequence Type 779 Methicillin-Resistant *Staphylococcus aureus* Harboring a Novel Pseudo Staphylococcal Cassette Chromosome mec (SCCmec)-SCC-SCC CRISPR Composite Element in Irish Hospitals," Antimicrobial Agents and Chemotherapy, vol. 57, 2013, pp. 524-531, 8 pages. Includes Supplementary information, 9 pages.
Kleinstiver et al., "High-fidelity CRISP-Cas9 nucleases with no detectable genome-wide off-target effects", Nature, vol. 529, Jan. 28, 2016, pp. 490-495, 6 pages. Includes Supplementary information, 12 pages.
Kleinstiver, et al. "Engineered CRISPR-Cas9 nucleases with altered PAM specificities," Nature, vol. 523, vol. 523, 2015, pp. 1-27, 27 pages.
Koike-Yusa, H., et al., "Genome-wide recessive genetic screening in mammalian cells with a lentiviral CRISPR-guide RNA library," Nat Biotechnology, vol. 32, Mar. 2014, pp. 267-273, 7 pages. Including Supplemental information, 3 pages. doi:10.1038/nbt.2800.
Kondo, et al., "Highly Improved Gene Targeting by Germline-Specific Cas9 Expression in *Drosphila*", Genetics, vol. 195, 2013, pp. 715-721, 7 pages. Including Supplemental information 14 pages.
Konermann, et al., "Genome-scale transcriptional activation by an engineered CRISPR-Cas9 complex", Nature, vol. 517, 2015, pp. 583-588, 6 pages. Including Supplemental information, 12 pages.
Koo et al., "Measuring and Reducing Off-Target Activities of Programmable Nucleases Including CRISPR-Cas9", Molecules and Cells, vol. 38, 2015, pp. 475-481, 7 pages.
Koonin et al., "Diversity, classification and evolution of CRISPR-Cas systems", Current Opinion in Microbiology vol. 37, 2017 (pp. 67-78).
Koornneef, A., et al., "Apoliprotein B Knockdown By AAV-Delivered shRNA Lowers Plasma Cholesterol In Mice," Molecular Therapy, vol. 19, 2011, pp. 731-740, 10 pages.

(56) References Cited

OTHER PUBLICATIONS

Kosugi, et al. "Six Classes of Nuclear Localization Signals Specific to Different Binding Grooves of Importin a" The Journal of Biological Chemistry, 2009, vol. 284 pp. 478-485, 8 pages. Including Supplemental information, 21 pages.
Kowalski, Thomas J., PowerPoint Presentation, Presented and Discussed during Sep. 9, 2015 Interview (Exhibit B), 51 pages.
Krauer, et al. "Identification of the nuclear localization signals within the Epstein-Barr virus EBNA-6 protein", Journal of General Virology, vol. 85, 2005, pp. 165-172, 8 pages.
Kuhlman, et al. "A place for everything—Chromosomal integration of large constructs", Bioengineered Bugs, vol. 1, 2010, pp. 296-299, 4 pages.
Kuhlman, et al., "Site-specific chromosomal integration of large synthetic constructs", Nucleic Acids Research, 2010, vol. 38, pp. 1-10, 10 pages. doi:10.1093/nar/gkp1193.
Kumar, M., et al., "Systematic Determination of the Packaging Limit of Lentiviral Vectors," Human Gene Therapy, vol. 12, Oct. 10, 2001, pp. 1893-1905, 21 pages.
Kuwayama, H., "Enhancement of Homologous Recombination Efficiency by Homologous Oligonucleotides," Cell, 2012, pp. 233-244, 12 pages. IntechOpen, DOI: 10.5772/47779.
Laganiere et. al., "An Engineered Zinc Finger Protein Activator of the Endogenous Glial Cell Line-Derived Neurotrophic Factor Gene Provides Functional Neuroprotection in a Rat Model of Parkinson's Disease", The Journal of Neuroscience, vol. 30, Dec. 8, 2010, pp. 16469-16474, 6 pages.
Lambowitz, et al., "Group II Introns: Mobile Ribozymes that Invade DNA", Cold Spring Harb Perspect Biology, 2011, pp. 1-20, 20 pages. 3:a003616.
Lanford, et al., "Induction of Nuclear Transport with a Synthetic Peptide Homologous to the SV40 T Antigen Transport Signal", Cell, vol. 46, Aug. 15, 1986, pp. 575-582, 8 pages.
Lange, et al. "Classical Nuclear Localization Signals: Definition, Function, and Interaction with Importin a'" J. Biology, vol. 282, 2007, pp. 5101-5105, including Supplemental information, 5 pages.
Larson, et al., "CRISPR interference (CRISPRi) for sequence-specific control of gene expression", Nature Protocols, vol. 8, 2013, pp. 2180-2196, 17 pages.
Lebherz, C., et al., "Gene therapy with novel adeno-associated virus vectors substantially diminished atherosclerosis in a murine model of familial hypercholesterolemia," The Journal of Gene Medicine, vol. 6, 2004, pp. 663-672, 10 pages.
Lee, C., et al., "Correction of the F508 Mutation in the Cystic Fibrosis Transmembrane Conductance Regulator Gene by Zinc-Finger Nuclease Homology-Directed Repair," Bioresearch Open Access, vol. 1, No. 3, pp. 99-108, dated 2012, 12 pages.
Leenay, et al., "Identifying and Visualizing Functional PAM Diversity across CRISPR-Cas Systems", Molecular Cell, vol. 62, 2016, pp. 137-147, 11 pages.
Lemay, et al., "Folding of the Adenine Riboswitch", Chemistry & Biology, vol. 13, 2006, pp. 857-868, 12 pages.
Levitt, J., et al., "Intrinsic fluorescence and redox changes associated with apoptosis of primary human epithelial cells," Journal of Biomedical Optics, vol. 11, No. 6, pp. 064012-1 to 064012-10, dated Nov./Dec. 2006, 10 pages.
Lewin, et al., "Nuclear localization sequences target proteins to the nucleus" Cells, vol. 5, 2006, 224.
Lewis, et al., "The c-myc and PyMT oncogenes induce different tumor types in a somatic mouse model for pancreatic cancer" Genes & Development, 2003, vol. 17 pp. 3127-3138, 14 pages.
Li et al., "Coevolution of CRISPR-Cas system with bacteria and phages", Hereditas, vol. 33, 2011, pp. 213-218, 6 pages.
Li, et al., "In vivo genome editing restores hemostasis in a mouse model of hemophilia" Nature, 2011, vol. 475, pp. 217-221, 5 pages. doi: 10.1038/nature10177.
Li, et al., "Multiplex and homologous recombination-mediated genome editing in *Arabidopsis* and Nicotaina benthamiana using guide RNA and Cas9" Nature Biotechnology, 2013, vol. 31 pp. 688-691, 4 pages.

Li, P., et al., "Biallelic knockout of alpha-1,3 galactosyltransferase gene in porcine liver-derived cells using zing finger nucleases," Journal of Surgical Research, vol. 181, 2013, pp. E39-E45, 7 pages.
Li, Ting, et al. "Modularly assembled designer TAL effector nucleases for targeted gene knockout and gene replacement in eukaryotes" Nucleic Acids Research, vol. 39, 2011, pp. 6315-6325, 11 pages.
Liu, et al. "Epstein-Barr Virus DNase Contains Two Nuclear Localization Signals Which Are Different in Sensitivity to the Hydrophobic Regions" Virology, vol. 247, pp. 62-73, 10 pages.
Lombardo, A., et al., "Gene editing in human stem cells using zinc finger nucleases and integrase-defective lentiviral vector delivery," Nature Biotechnology, vol. 25, 2007, pp. 1298-1306, 9 pages.
Los, et al., "Halotag Technology: Cell Imaging and Protein Analysis" Cell Notes, vol. 14, 2006, pp. 10-14, 5 pages.
Love et al., "Lipid-like materials for low-dose, in vivo gene silencing," Proceedings of the National Academy of Sciences, Feb. 2, 2010, vol. 107, No. 5 (pp. 1864-1869).
Luo, B., et al., "Highly parallel identification of essential genes in cancer cells," Proceeding of the National Academy of Sciences, vol. 105, 2006, pp. 20380-20385, 6 pages.
Luo, Ming, et al., "Multiple Nuclear Localization Sequences Allow Modulation of 5-Lipoxygenase Nuclear Import" Traffic, 2004, vol. 5, pp. 847-854, 8 pages.
Lyssenko, et al., "Cognate putative nuclear localization signal effects strong nuclear localization of a GFP reporter and facilitates gene expression studies in Caenorhabditis elegans" BioTechniques, 2007, vol. 43 pp. 596-600, 5 pages.
M. Booker et al., "False negative rates in *Drosophila* cell-based RNAi screens: a case study," BMC Genomics, vol. 12, 2011, pp. 1-11, 11 pages.
M. Costanzo et al., "The genetic landscape of a cell," Science, vol. 327, Jan. 22, 2010, pp. 425-431, 8 pages.
Ma, M., et al., "A Guide RNA Sequence Design Platform for the CRISPR/Cas9 System for Model Organism Genomes," Hindawi, vol. 2013, 2013, art. 270805, pp. 1-5, 5 pages.
Maczuga, P., et al., "Embedding siRNA sequences targeting Apolipoprotein B100 in shRNA and miRNA scaffolds results in differential processing and in vivo efficacy," Molecular Therapy, vol. 21, 2013, pp. 217-227, 11 pages.
Madisen et al., "A robust and high-throughput Cre reporting and characterization system for the whole mouse brain," Nat. Neuroscience, vol. 13, Jan. 2010, pp. 133-140, 8 pages.
Maeder, et al., "CRISPR RNA-guided activation of endogenous human genes" Nature Methods, vol. 10, 2013, pp. 977-979, 3 pages. doi.10.1038/nmeth.2556.
Maeder, M., and Gersbach, C., "Genome-editing Technologies for Gene and Cell Therapy," Molecular Therapy, vol. 24, 2016, pp. 430-446, 17 pages.
Maeder, M., et al., "Robust, synergistic regulation of human gene expression using TALE activators," Nature Methods, vol. 10, 2013, pp. 243-245, 3 pages. Including Supplemental information, 6 pages.
Mahfouz, et al., "Targeted transcriptional repression using a chimeric TALE-SRDX repressor protein" Plant Mol Biology, vol. 78, 2012, pp. 311-321, 11 pages.
Mahfouz, M., et al., "De novo-engineered transcription activator-like effector (TALE) hybrid nuclease with novel DNA binding specificity creates double-strand breaks," Proceedings of the National Academy of Science, 2011, vol. 108 (pp. 2623-2628).
Makarova et al., "Unification of Cas protein families and a simple scenario for the origin and evolution of CRISPR-Cas systems," Biology Direct, 2011, vol. 6, No. 38 (pp. 1-27).
Makarova, et al., "An updated evolutionary classification of CRISPR-Cas systems" Nature Reviews—Microbiology, vol. 13 2015, pp. 722-736, 15 pages.
Makarova, K., et al., "Evolution and Classification of the CRISPR-CAS Systems," Nature Reviews Microbiology, vol. 9, Jun. 2011, pp. 467-477, Including Supplemental information, (23 pages).
Mali et al., "RNA-Guided Human Genome Engineering Via Cas9" Science, vol. 339, pp. 823-826, dated Feb. 15, 2013 (41 pages—Includes Supplemental Information).

(56) References Cited

OTHER PUBLICATIONS

Mali, et al., Supplementary Information for "Use of adjacent sgRNA: Cas9 complexes for transcriptional activation and genome engineering," Nature Biotechnology, pp. 1-36, 36 pages. doi:10.1037/nbt.2675.

Mali, P., et al., "CAS9 transcriptional activators for target specificity screening and paired nickases for cooperative genome engineering," Nature Biotechnology, vol. 31, No. 9, pp. 833-838, dated Aug. 1, 2013, 44 pages (Includes Supplemental Information).

Mali, P., et al., Supplementary Information for: "RNA-Guided Human Genome Engineering via Cas9," Science, vol. 339, pp. 823-826, 2013, 8 pages.

Malina, A., et al., "Repurposing CRISPR/Cas9 for in situ functional assays," Genes & Development, vol. 27, 2013, pp. 2602-2614, 13 pages.

Manjunath, N., et al., "Newer Gene Editing Technologies toward HIV Gene Therapy," Viruses, vol. 5, pp. 2748-2766, 2013, 19 pages.

*Manning* v. *Paradis*, 296 F.3d 1098 (Fed. Cir. 2012), 9 pages.

Marraffini, L., "CRISPR-Cas Immunity against Phages: Its Effects on the Evolution and Survival of Bacterial Pathogens," PLOS, Dec. 12, 2013, pp. 1-6, 6 pages.

Marraffini, L., Assignment to Rockefeller University, dated Dec. 12, 2013, 3 pages.

Marraffini, L., et al., "Self vs. non-self discrimination during CRISPR RNA-directed immunity," Nature, vol. 463, 2010, pp. 568-571, 13 pages.

Marraffini, L.A., et al., "Sortases and the art of anchoring proteins to the envelopes of gram-positive bacteria," Microbiol. Mol. Biology Review vol. 70, Mar. 2006, pp. 192-221, 3 pages.

Martin, M., "Cutadapt removes adapter sequences from high-throughput sequencing reads," EMBnet.journal, vol. 17, 2011, pp. 10-12, 3 pages.

Mastroianni, et al., "Group II Intron-Based Gene Targeting Reactions in Eukaryotes" Plos One, vol. 3, 2008, pp. 1-15, 15 pages. Doi:10.1371/journal.pone.0003121.

*Maxwell* v. *The Stanley Works*, 2006 WL 1967012, *5 (M.D. Tenn. Jul. 11, 2006), 7 pages.

Meshorer, et al., "Chromatin in pluripotent embryonic stem cells and differentiation" Nature Reviews Molecular Cell Biology, vol. 7, 2006, pp. 540-546, 7 pages.

Miller, et al., "A Tale Nuclease Architecture for Efficient Genome Editing," Nature Biotechnology, vol. 29, No. 2, Feb. 2011, pp. 143-150.

Mincer, J., and Simon, S., "Simulations of nuclear pore transport yield mechanistic insights and quantitative predictions," Proceedings of the National Academy of Science, vol. 108, p. E351-E358, 8 pages, 2011.

Minton, "How can biochemical reactions within cells differ from those in test tubes?" Journal Of Cell Science, 2006, vol. 119, pp. 2863-2869, 7 pages.

Moffat J et al., "A lentiviral RNAi library for human and mouse genes applied to an arrayed viral high-content screen," Cell, vol. 124, Mar. 24, 2006, pp. 1283-1298, 16 pages.

Mojica F. J. M et al., "Biological significance of a family of regularly spaced repeats in the genomes of Archaea, Bacteria and mitochondria," Molecular Microbiology, vol. 36, 2000, pp. 244-246, 3 pages.

Mojica, F. J., et al., "Short Motif Sequences Determine the Targets of the Prokaryotic CRISPR Defence System," Microbiology, vol. 155, 2009, pp. 733-740.

Mojica, F. J., et al., Supplementary Material for: "Short Motif Sequences Determine the Targets of the Prokaryotic CRISPR Defence System," Microbiology, vol. 155, 2009, 37 pages.

Morbitzer, et al., "Assembly of custom TALE-type DNA binding domains by modular cloning," Nucleic Acids Research, vol. 39, pp. 5790-5799, 10 pages.

Morbitzer, et al., "Regulation of selected genome loci using de novo-engineered transcription activator-like effector (TALE)-type transcription factors," Proceedings of the National Academy of Sciences, 2010, vol. 108, (pp. 21617-21622), 2011.

Morgan, et al., "Inducible Expression and Cytogenetic Effects of the EcoRI Restriction Endonuclease in Chinese Hamster Ovary Cells" Molecular and Cellular Biology, vol. 8, 1988, pp. 4204-4211, 8 pages.

Morin, et al., "Nuclear Localization of the Adenovirus DNA-Binding Protein: Requirement for Two Signals and Complementation during Viral Infection" Molecular and Cellular Biology, vol. 9, 1989, pp. 4372-4380, 9 pages.

Morris et al., "Distributed automated docking of flexible ligands to proteins: Parallel applications of AutoDock 2.4*", Journal of Computer-Aided Molecular Design, 1996, vol. 10, pp. 293-304.

Moscou, et al., "A Simple Cipher Governs DNA Recognition by TAL Effectors," Science, vol. 326, Dec. 11, 2009, p. 1501.

Motamedi, M.R., et al., "Double-strand-break repair recombination in *Escherichia coli*: physical evidence for a DNA replication mechanism in vivo," Genes Dev., vol. 13, 1999, pp. 2889-2903.

Mukhopadyay, R., "On the Same Wavelength," ASBMB Today, http://www.asbmb.org/asbmbtoday/201408/Features/Doudna/, dated Aug. 2014, 6 pages.

Mussolino, et al., "TALE nucleases: tailored genome engineering made easy" Current Opinion in Biotechnology, vol. 23, 2012, pp. 644-650, 7 pages.

Musunuru, "Abstract 18593: Use of a CRISPR/Cas System for Cardiovascular Disease Modeling and Therapeutic Applications", Circulation, vol. 128, 2013, 4 pages (Meeting info: American Heart Association, 2013 Scientific Sessions and Resuscitation Science Symposium, Dallas, TX, US, Nov. 16-20, 2013).

Muther, N., et al., "Viral Hybrid Vectors for Somatic Integration—Are They the Better Solution?" Viruses, vol. 1, 2009, pp. 1295-1324, 30 pages.

Nagarajan, et al., "A Hierarchy of Nuclear Localization Signals Governs the Import of the Regulatory Factor X Complex Subunits and MHC Class II Expression" The Journal of Immunology, vol. 173, 2004, pp. 410-419, 11 pages.

Nakai, et al., "PSORT: a program for detecting sorting signals in proteins and predicting their subcellular localization" Trends in Biochem Sciences, vol. 24, 1999, pp. 34-35, 2 pages.

Nakamura, et al., "Codon usage tabulated from international DNA sequence databases: status for the year 2000" Nucleic Acids Research, vol. 28, 2000, p. 292.

Nishimasu, et al., "Crystal Structure of Cas9 in Complex with Guide RNA and Target DNA", Cell, Feb. 27, 2014, vol. 156, pp. 935-949.

Nishimasu, H., et al., "Crystal Structure of *Staphylococcus aureus* Cas9," Cell, vol. 162, Aug. 27, 2015, pp. 1113-1126, 15 pages.

Noguchi, et al., "PDX-1 Protein Containing Its Own Antennapedia-Like Protein Transduction Domain Can Transduce Pancreatic Duct and Islet Cells" Diabetes, 2003, vol. 52 pp. 1732-1737, 6 pages.

Nomura, S., et al., "Low-density lipoprotein receptor gene therapy using helper-dependent adenovirus produces long-term protection against atherosclerosis in a mouse model of familial hypercholesterolemia," Gene Therapy, vol. 11, 2004, pp. 1540-1548, 10 pages.

Notice of Opposition filed Aug. 11, 2017 by Schlich against EP Patent No. 2840140, 58 pages.

Notice of Opposition filed Aug. 14, 2017 by Grund against EP Patent No. 2840140, 64 pages.

Notice of Opposition filed Aug. 16, 2017 by Mathys & Squire LLP against EP Patent No. 2840140, 36 pages.

Notice of Opposition filed Aug. 16, 2017 by Vossius against EP Patent No. 2840140, 67 pages.

O'Hare, et al., "Transformation of mouse fibroblasts to methotrexate resistance by a recombinant plasmid expressing a prokaryotic dihydrofolate reductase" Proc. Natl. Acad. Sci., vol. 78 2011, 1527-1531, 5 pages.

Opposition Against Appl. Ser. No. EP13818570.7 submitted by Schlich dated Oct. 26, 2015, 8 pages.

Opposition Against EP Appl. Ser. No. 2771468-B1 dated Oct. 26, 2015, 40 pages.

Ozawa, K., "Gene therapy using AAV," Virus, vol. 57, pp. 47-55, dated, 2007, 13 pages. (with English Abstract; No English Translation).

Paddison et al., "A resource for large-scale RNA-interference-based screens in mammals," Nature, vol. 428, Mar. 25, 2004, pp. 427-431, 5 pages.

(56) References Cited

OTHER PUBLICATIONS

Pandika, et al., www.ozy.com/rising-stars-and-provocateurs/jennifer-doudna-crispr-code-killer/4690; Jan. 7, 2014.
Panyam, J. et al., "Biodegradable nanoparticles for drug and gene delivery to cells and tissue", Advanced Drug Delivery Reviews, vol. No. 55, Issue No. 3, Feb. 2003, pp. 329-347.
Park, et al., "Regulation of Ribosomal S6 Kinase 2 by Mammalian Target of Rapamycin", The Journal of Biological Chemistry, vol. 277, 2002, pp. 31423-31429, 7 pages.
Pattanayak, et al., "High-throughput profiling of off-target DNA cleavage reveals RNA-programmed Cas9 nuclease specificity," Nature Biotechnology, vol. 31, 2013, pp. 839-843, 5 pages. Including Supplementary Materials, 2 pages.
Patterson, et al., "Codon optimization of bacterial luciferase (lux) for expression in mammalian cells" J. Ind. Microbio. Biotechnology, vol. 32, 2005, 115-123, 9 pages.
Perez-Pinera, et al., "Advances in Targeted Genome Editing" Curr Opin Chem Biology, vol. 16, 2012, pp. 268-277, 10 pages. doi:10.1016/j.cbpa.2012.06.007, 17 pages.
Perez-Pinera, et al., "RNA-guided gene activation by CRISPR-Cas9-based transcription factors" Nature Methods, 2013, vol. 10, pp. 1-12.
Phillips, A., "The challenge of gene therapy and DNA delivery," The Journal of Pharmacy and Pharmacology, vol. 53, 2011, pp. 1169-1174, 6 pages.
Planey, et al. "Mechanisms of Signal Transduction: Inhibition of Glucocorticoid-induced Apoptosis in 697 Pre-B Lymphocytes by the Mineralocorticoid Receptor N-terminal Domain", Journal of Biological Chemistry, vol. 277, 2002, pp. 42188-42196, 9 pages.
Platt et al., "CRISPR-Cas9 Knockin Mice for Genome Editing and Cancer Modeling," Cell, vol. 159, 2014, pp. 440-455, 16 pages.
Podbielski, A., et al., "R. Novel series of plasmid vectors for gene inactivation and expression analysis in group A streptococci (GAS)," Gene, vol. 177, 1996, pp. 137-147, 11 pages.
Porteus et al., "Gene targeting using zinc finger nucleases" Nature Biotechnology, Aug. 2005, vol. 23 (pp. 967-973).
Porteus, M., and Balitmore, D., "Chimeric Nucleases Stimulate Gene Targeting in Human Cells," Science, vol. 300, May 2, 2003, p. 763, (2 pages).
Posfai, et al., "Markerless gene replacement in *Escherichia coli* stimulated by a double-strand break in the chromosome" Nucleic Acids Research, vol. 27, 1999, pp. 4409-4415, 7 pages.
Pougach, et al., "Transcription, Processing and Function of CRISPR Cassettes in *Escherichia coli*" Mol. Microbiology, vol. 77, 2010, pp. 1367-1379, 14 pages.
Pougach, K.S., et al., "CRISPR Adaptive Immunity Systems of Prokaryotes," Molecular Biology, 2012, vol. 46 (pp. 175-182).
Pride, D., et al., "Analysis of Streptococcal CRISPRs from Human Saliva Reveals Substantial Sequence Diversity Within and Between Subjects Over Time," Genome Research, vol. 21, 2011, pp. 126-136, 11 pages.
Primo, et al., "Lentiviral vectors for cutaneous RNA managing" Experimental Dermatology, vol. 21, 2012. 162-170, 9 pages.
Qi et al., "Repurposing CRISPR as an RNA-Guided Platform for Sequence-Specific Control of Gene Expression," Cell, 2013, vol. 152 (pp. 1173-1183).
Qi, J., et al., "microRNAs regulate human embryonic stem cell division," Cell Cycle, vol. 8, 2009, pp. 3729-3741, 13 pages.
R. Rad et al., "PiggyBac transposon mutagenesis: a tool for cancer gene discovery in mice," Science, vol. 330, Nov. 19, 2010, p. 1104-1107, 4 pages.
R.D Kolodner and G.T. Marsischky, "Eukaryotic DNA mismatch repair," Current Opinion in Genetics and Development, vol. 9, 1999, p. 89-96, 8 pages.
R.Renella et al., "Codanin-1 mutations in congenital dyserythropoietic anemia type 1 affect HP1a localization in erythroblasts," Blood, vol. 117, Jun. 2011, pp. 6928-6938, 11 pages.

Radecke, S., et al., "Zinc-finger Nuclease-induced Gene Repair With Oligodeoxynucleotides: Wanted and Unwanted Target Locus Modifications," Molecular Therapy, vol. 18, Apr. 2010, pp. 743-753, 11 pages.
Radulovich, et al., "Modified gateway system for double shRNA expression and Cre/lox based gene expression" BMC Biotechnology, 2011, vol. 11, pp. 1-9, 10 pages.
Ran et al., "Double Nicking by RNA-guided CRISPR Cas9 for enhanced genome editing specificity", Cell, Sep. 12, 2013, vol. 154, pp. 1380-1389.
Ran, F., et al., "In vivo genome editing using *Staphylococcus aureus* Cas9," Nature, vol. 520, 2015, pp. 186-191, 6 pages. Includes Supplemental information, 12 pages.
Ran, F., et al., "Genome engineering using the CRISPR-Cas9 system," Nature Protocols, vol. 8, 2013, pp. 2281-2308, 28 pages.
Ran, F.A., "CRISPR-Cas: Development and Applications for Mammalian Genome Editing", Ph.D. Dissertation, Harvard University, Apr. 2014 (190 pages).
Rand, et al. "Argonaute2 Cleaves the Anti-Guide Strand of siRNA during RISC Activation" Cell, vol. 123, 2005, pp. 621-629, 9 pages.
Raveux et al., "Optimization of the production of knock-in alleles by CRISPR/Cas9 microinjection into the mouse zygote," Scientific Reports, Feb. 17, 2017, vol. 7, No. 42661 (11 pages).
Raymond, et al. "High-Efficiency FLP and fC31 Site-Specific Recombination in Mammalian Cells" PLoS One, vol. 2, Jan. 2007, pp. 1-4. Doi. 10.1371/journal.pone.0000162.
Rebar, et al., "Induction of angiogenesis in a mouse model using engineered transcription factors" Nature Medicine, vol. 8, 2002, pp. 1427-1432, 6 pages.
Redeclaration—37 C.F.R. 41.203(c); filed Mar. 17, 2016 in Patent Interference No. 106,048 (DK), 14 pages.
Redeclaration—PTAB, *The Regents of the University of California v. The Broad Institute, Inc.*, filed Aug. 26, 2019, in Patent Interference No. 106,115 (DK), 20 pages.
Redeclaration—PTAB, *The Regents of the University of California v. The Broad Institute, Inc.*, filed Sep. 10, 2020, in Patent Interference No. 106,115 (DK), 3 pages.
Reiss, et al., "RecA protein stimulates homologous recombination in plants" Proc. Natl. Acad. Sci. vol. 93, 1996, pp. 3094-3098, 5 pages.
Response to Third Party Observations in EP No. 13824232.6 filed Oct. 2, 2014, with Redlined and Clean Amended Claims, 14 pages.
Rho, M., et al., "Diverse CRISPRs Evolving in Human Microbiomes," PLOS Genetics, vol. 8, Jun. 2012 e1002441, 12 pages.
Rhun, A., and Charpentier, E., "Small RNAs in streptococci," RNA Biology, vol. 9, 2012, pp. 414-426, 13 pages.
Roberts, et al. "Nuclear location signal-mediated protein transport" Biochimica et Biophysica Act, vol. 1008, 1989, pp. 263-280, 18 pages.
Roberts, et al., "The Effect of Protein Content on Nuclear Location Signal Function" Cell, vol. 50, 1989, pp. 465-475, 11 pages.
Rockefeller University and Broad Institute of MIT and Harvard announce update to CRISPR-Cas9 portfolio filed by Broad, Press Release dated Jan. 15, 2018, retrieved from: https://www.broadinstitute.org/news/rockefeller-university-and-broad-institute-mit-and-harvard-announce-update-crispr-cas9, 3 pages.
Rodrigues, et al., "Red Fluorescent Protein (DsRed) as a Reporter in *Saccharomyces cerevisiae*" Journal of Bacteriology, vol. 183, 2001, pp. 3791-3794, 4 pages.
Rodriguez et al., "AAV-CRISPR: A New Therapeutic Approach To Nucleotide Repeat Diseases", Molecular Therapy, vol. 22, 2014, Supplement 1, Abstract 247, p. S94.
Rolling, "Recombinant AAV-mediated gene transfer to the retina: gene therapy perspectives", Gene Therapy, vol. 11, 2004, pp. S26-S32, 5 pages.
*Rubin v. The General Hospital Corp.*, 2011-1439 (Fed. Cir. Mar. 28, 2013), 8 pages.
S. Huang et al., "MED12 Controls the Response to Multiple Cancer Drugs through Regulation of TGF-ß; Receptor Signaling," Cell, vol. 151, 2012, pp. 937-950, 14 pages.
S. Konermann et al., "Optical control of mammalian endogenous transcription and epigenetic states," Nature, vol. 500, Aug. 22, 2013, pp. 472-476, 5 pages. Includes Supplemental Information, 13 pages.

(56) References Cited

OTHER PUBLICATIONS

S.H. Chen et al., "A Knockout Mouse Approach Reveals that TCTP Functions as an Essential Factor for Cell Proliferation and Survival in a Tissue- or Cell Type-specific Manner," Molecular Biology of the Cell, vol. 18, Jul. 2007, pp. 2525-2532, 8 pages.
S.R. Whittaker et al., "A Genome-Scale RNA Interference Screen Implicates NF1 Loss in Resistance to RAF Inhibition," Cancer Discovery, vol. 3, 2013, pp. 350-362, 14 pages.
S.S. Liu et al., "Identification and characterization of a novel gene, clorf109, encoding a CK2 substrate that is involved in cancer cell proliferation," Journal of Biomedical Science, vol. 19, 2012, 12 pages.
S.Xue and M. Barna, "Specialized ribosomes: a new frontier in gene regulation and organismal biology," Nat Rev Mol Cell Biology, vol. 13, Jun. 2012. pp. 355-369, 15 pages.
Sadowski, M., and Jones, D., "The sequence-structure relationship and protein function prediction," Current Opinion in Structural Biology, vol. 19, 2009, pp. 357-362, 6 pages.
Sambrook, et al., "Molecular Cloning, A Laboratory Manual on the Web", Cold Spring Harbor Laboratory Press, Chapter 16, 2001, downloaded from http://www.molecularcloning.com/members/chapter.jsp?chapter=127 on Feb. 19, 2002, 13 pages.
Sander, et al., "CRISPR-Cas systems for editing, regulating and targeting genomes," Nature Biotechnology, vol. 32, 2014, pp. 347-355, 9 pages.
Sanders, "Cheap and easy technique to snip DNA could revolutionize gene therapy", UC Berkeley Press Release, Jan. 7, 2013, available at http://newscenter.berkeley.edu/2013/01/07/cheap-and-easy-technique-to-snip-dna-could-revolutionize-gene-therapy/.
Sanders, et al., "Use of a macromolecular crowding agent to dissect interactions and define functions in transcriptional activation by a DNA-tracking protein: Bacteriophage T4 gene 45 protein and late transcription" PNAS, vol. 9 2014, pp. 7703-7707, 5 pages.
Sanjana, et al., "Improved vectors and genome-wide libraries for CRISPR screening," HHS Public Access Author Manuscript, vol. 11, 2014, pp. 2145-2148, 4 pages.
Sanjana, N., et al., "A Transcription Activator-Like Effector (TALE) Toolbox for Genome Engineering," Nature Protocols, vol. 7, 2012, pp. 171-192, 39 pages.
Sapranauskas, R., et al., "The *Streptococcus thermophilus* CRISPR/Cas System Provides Immunity in *Escherichia coli*," Nucleic Acids Research, vol. 39, No. 21, Aug. 3, 2011, pp. 9275-9282.
Sarra, G., et al., "Gene replacement therapy in the retinal degeneration slow (rds) mouse: the effect on retinal degeneration following partial transduction of the retina", Human Molecular Genetics, vol. 10, 2001, pp. 2353-2361, 9 pages.
Sato, et al. "Generation of Adeno-Associated Virus Vector Enabling Functional Expression of Oxytocin Receptor and Fluorescence Marker Genes Using the Human elF4G Internal Ribosome Entry Site Elemet" Biosci. Biotechno. Biochem, vol. 73, 2009, pp. 2145-2148, 4 pages.
Sauer, "Functional Expression of the cre-lox Site-Specific Recombination System in the Yeast *Saccharomyces cerevisiae*" Mol. Cell. Biology, vol. 7, 1987, pp. 2087-2096, 10 pages.
Sauer, et al. "Site-specific DNA recombination in mammalian cells by the Cre recombinase of bacteriophage P1" Proc. Natl. Acad. Sci. vol. 85, 1988, pp. 5166-5170, 5 pages.
Schiffer, et al. "Targeted DNA Mutagenesis for the Cure of Chronic Viral Infections" Journal of Virology, vol. 86, No. 17, Jun. 20, 2012, pp. 8920-8936.
Schiffer, et al., "Predictors of Hepatitis B Cure Using Gene Therapy to Deliver DNA Cleavage Enzymes: A Mathematical Modeling Approach" PLOS Computational Biology, vol. 9, 2013, pp. 1-16. www.ploscompbiol.org.
Scholze, et al., "TAL effector-DNA specificity", Virulence, vol. 1, No. 5, Sep. 1, 2010, pp. 428-432, 5 pages. DOI:10.4161/viru.1.5.12863.
Schramm et al., "Recruitment of RNA polymerase III to its target promoters" Genes & Development, vol. 16, 2002, 2593-2620, pp. 28 pages.

Schunder et al., "First indication for a functional CRISPR/Cas system in Francisella tularensis", International Journal of Medical Microbiology, vol. 303, 2013, pp. 51-60, 10 pages.
Sebastiani, et al., "BCL11A enhancer haplotypes and fetal hemoglobin in sickle cell anemia," Blood Cells, vol. 54, 2015, pp. 2240230, 7 pages.
Sebo, et al., "A simplified and efficient germline-specific CRISPR/Cas9 system for *Drosophila* genomic engineering" Fly, 2014, vol. 8, pp. 52-57, 8 pages.
Seffernick, J., et al., "Melamine Deaminase and Atrazine Chlorohydrolase: 98 Percent Identical but Functionally Different," Journal of Bacteriology, vol. 183, No. 8, Apr. 2001, pp. 2405-2410, 6 pages.
Semenova, E. et al., "Interference by clustered regularly interspaced short palindromic repeat (CRISPR) RNA is governed by a seed sequence," Proc. Natl. Acad. Sci., vol. 108, Jun. 21, 2011, pp. 10089-10103, 7 pages.
Semple et al., "Rational design of cationic lipids for siRNA delivery," Nature Biotechnology, Feb. 2010, vol. 28, No. 2 (pp. 172-178).
Senis, E., et al., "CRISPR/Cas9-mediated genome engineering: An adeno-associated viral (AAV) vector toolbox," Biotechnology Journal, vol. 9, 2014, pp. 1402-1412, 12 pages.
Senturk et al., "A rapid and tunable method to temporally control cas9 expression enables the identification of essential genes and the interrogation of functional gene interactions in vitro and in vivo," vol. 9, 2015, pp. 1-27, XP002756303, doi:10.1101/023366, Retrieved from the Internet: URL:http://biorxiv.org/content/early/2015/07/28/023366 [retrieved on Apr. 11, 2016).
Shalem, et al., "High-throughput functional genomics using CRISP-Cas9," Nature Reviews Genetics, vol. 16, No. 5, pp. 299-311, May 2015.
Shalem, O., et al., "Genome-Scale CRISPR-Cas9 Knockout Screening in Human Cells," Science, vol. 343, 2014, pp. 84-87, 5 pages.
Shapiro et al., "Increasing CRISPR Efficiency and Measuring Its Specificity in HSPCs Using a Clinically Relevant System," Molecular Therapy: Methods & Clinical Development, Jun. 12, 2020, vol. 17 (pp. 1097-1107).
Sharan, et al., "Recombineering: A Homologous Recombination-Based Method of Genetic Engineering" Nat. Protoc., 2009, vol. 4 pp. 206-223, 18 pages. doi:10.1038/nprot.2008.227.
Shen, B., et al., "Generation of gene-modified mice via Cas9/RNA-mediated gene targeting," Cell Research, vol. 23, 2013, pp. 720-723.
Shen, et al., "Efficient genome modification by CRISPR-Cas9 nickase with minimal off-target effects" 2014, Nature Methods, vol. 11, pp. 399-404, 6 pages.
Shengdar Tsai et al., "Dimeric CRISPR RNS-guided FokI nucleases for highly specific genome editing", Nature Biotechnology, vol. 32, Jun. 2014, pp. 569-576, 18 pages.
Shieh, et al., "Nuclear Targeting of the Maize R. Protein Requires Two Nuclear Localization Sequences" Plant Physiol, 1993, vol. 101 pp. 353-361, 9 pages.
Siegl, et al., "I-Scel endonuclease: a new tool for DNA repair studies and genetic manipulations in streptomycetes" Appl Microbiol Bitotechnol, vol. 87, 2010, pp. 1525-1532, 8 pages.
Sims, D., et al., "High-throughput RNA interference screening using pooled shRNA libraries and next generation sequencing," Genome Biology, vol. 12, 2011, pp. 1-13.
Singer, et al., "Applications of Lentiviral Vectors for shRNA Delivery and Transgenesis" Curr Gene Ther., vol. 8, 2008 pp. 483-488, 6 pages.
Slaymaker et al., "Rationally engineered Cas9 nucleases with improved specificity", Science, American Association for the Advancement of Science, US, vol. 351, Jan. 1, 2016, pp. 84-88.
Sontheimer, "Project 7: Establishing RNA-Directed DNA Targeting in Eukaryotic Cells" Physical Sciences-Onc., Nov. 16, 2011-Dec. 31, 2012, 2 pages. htt://groups.molbiosci.northwestern.edu/sontheimer/Sontheimer_cv.php) Molecular Biosciences, 2 pages.
Sorek et al., "CRISPR-Mediated Adaptive Immune Systems in Bacteria and Archea", Annual Review of Biochemistry, vol. 82, 2013, (pp. 237-266).

(56) References Cited

OTHER PUBLICATIONS

Spencer, J.M., et al., "Development of a Nuclease Screen to Improve Cas9 Targeting Specificity", Molecular Therapy, May 2015, vol. 23, Suppl. 1, S136(340).
Stewart Sa et al., "Lentivirus-delivered stable gene silencing by RNAi in primary cells," RNA, vol. 9, 2003, pp. 493-501, 9 pages.
Stoddard, "Homing endonuclease structure and function," Quarterly Reviews of Biophysics, Cambridge University Press, 2005 (pp. 1-47).
Stolfi, et al., "Tissue-specific genome editing in Ciona embryos by CRISPR/Cas9," Development, vol. 141, 2014, pp. 4115-4120, 6 pages. doi: 10.1242/dev.114488.
Stoller, J. and Aboussouan, L., "Alpha1-antitrypsin deficiency," The Lancet, Seminar, vol. 365, 2005, pp. 2225-2236, 12 pages.
Stratikopoulos, E., et al., "The hormonal action of IGF1 in postnatal mouse growth," Proceedings of the National Academy of Sciences, vol. 105, Dec. 9, 2008, pp. 19378-19383, 6 pages.
Straub, C., et al., "CRISPR/Cas9-Mediated Gene Knock-Down in Post-Mitotic Neurons," PLOS One, vol. 9, art. E105584, Aug. 20, 2014, pp. 1-5, 6 pages.
Sung, et al., "An rpsL Cassette, Janus, for Gene Replacement through Negative Selectionin *Streptococcus pneumoniae*" Applied and Environmental Microbiology, vol. 67, 2001, pp. 5190-5196, 7 pages.
Sung, M., et al., "The importance of valency in enhancing the import and cell routing potential of protein transduction domain-containing molecules," Biochimica et Biophysica Aeta, vol. 1758, pp. 355-363, dated 2006, 9 pages.
Sung, Young Hoon, et al., "Mouse genetics: Catalogue and scissors" BMB Reports, 2012, vol. 45 pp. 686-692, 7 pages.
Suzuki, K., et al., "In vivo genome editing via CRISPR/Cas9 mediated homology-independent targeted integration," Nature, vol. 540, art. 7631, 2015, pp. 1-44.
Swarthout, J., et al., "Zinc Finger Nucleases: A new era for transgenic animals," Annals of Neurosciences, vol. 18, 2011, pp. 25-28, 4 pages.
Swiech et al., "CRISPR-Mediated Genome Editing in the Mammalian Brain", Molecular Therapy, 747, vol. 22, 2014, p. S289.
Swiech, L., et al., "In vivo interrogation of gene function in the mammalian brain using CRISPR-Cas9," Nature Biotechnology, vol. 33, 2014, pp. 102-106, 5 pages. Including Supplemental information, 4 pages.
Symington et al., "Double-Strand Break End Resection and Repair Pathway Choice", Annual Review of Genetics, vol. 45, 2011, pp. 247-271, 25 pages.
T. Horii et al., "Generation of an ICF Syndrome Model by Efficient Genome Editing of Human Induced Pluripotent Stem Cells Using the CRISPR System," International Journal of Molecular Sciences, vol. 14, 2013, p. 19774-19781, 9 pages.
T.J. Cradick et al., "CRISPR/Cas9 systems targeting ß-globin and CCR5 genes have substantial off-target activity," Nucleic Acids Research, vol. 41, 2013, 9584-9592, 9 pages.
T.Yan et al., "DNA mismatch repair (MMR) mediates 6-thioguanine genetoxicity by introducing single-strand breaks to signal a G2-M arrest in MMR-proficient RKO cells," Clinical Cancer Research, vol. 9, Jun. 2003, p. 2327-2334, 9 pages.
Takara Bio USA, Inc., "Lenti-X™ Tet-On © 3G CRISPR/Cas9 System User Manual", 2016, pp. 1-35.
Tang, T., et al., "A mouse knockout library for secreted and transmembrane proteins," Nature Biotechnology, vol. 28, No. 7, Jul. 2010, pp. 749-755, pages. 7 pages. Including Supplemental information, 2 pages.
Taylor, G., "Introduction to phasing," Acta Crystallographica Section D Biological Crystallography, 2010, D66 (pp. 325-338).
Terns, M., and Terns, R., "CRISPR-based adaptive immune systems," Current Opinion in Microbiology, vol. 14, 2011, pp. 321-327, 8 pages.
*The Broad Inst. v. The Regents of University of UCA*—Decision on Motions for Patent Interference No. 106,048 filed Feb. 15, 2017, 51 pages.
Third Party Observation for Application No. EP20130824232 dated Sep. 22, 2014, 19 pages.
Third Party Observation in Application No. PCT/US2013/074819 dated Apr. 10, 2015, 10 pages.
Third Party Observation Under Article 115 EPC in Application No. 13818570.7 dated Oct. 1, 2014.
Third Party Observations Concerning App. No. GB1420270.9, dated Jun. 30, 2015, 71 pages.
Third Party Observations Concerning Appl. No. EP2800811, dated Jul. 24, 2015, 108 pages.
Third Party Observations Concerning Appl. No. EP2800811, dated Sep. 4, 2015.
Third Party Observations Concerning Appl. No. GB1420270.9 dated Jun. 30, 2015.
Third Party Observations Concerning Appl. No. GB1420270.9, dated Jul. 13, 2015.
Third Party Observations in Accordance with Article 115 EPC, Appl. No. EP13824232.6, Pub. No. EP2764103A, Mar. 25, 2015.
Third Party Observations submitted by Broad Institute Inc. Concerning Appl. Ser. No. EP13793997.1 dated Jul. 24, 2015, 108 pages.
Third Party Observations submitted by Broad Institute Inc. Concerning Appl. Ser. No. EP13793997.1 dated Sep. 4, 2015, 25 pages.
Third Party Observations submitted by Regents of the University of California et al. Concerning App. No. GB1420270.9 dated Jul. 13, 2015, 18 pages.
Third Party-Observations, Appl. No. 1382432.6, Pub. No. EP2764103, dated Feb. 16, 2015, 12 pages.
Third-Party Observation for Application No. EP20130824232 dated Sep. 8, 2014, 47 pages.
Tinland, et al., "The T-DNA-linked VirD2 protein contains two distinct functional nuclear localization signals" Proc. Natl. Acad. Sci, vol. 89, 1992, pp. 7442-7446, 5 pages.
Tiscornia, et al. "Development of Lentiviral Vectors Expressing siRNA" Gene Transfer—Delivery and Expression of DNA and RNA—A Laboratory Manual, 2007, Chapter 3 pp. 23-34, 12 pages.
Tolia, et al., "Slicer and the Argonautes" Nature Chemical Biology, vol. 3, 2007, pp. 36-43, 8 pages.
Trafton, A., "CRISPR-carrying nanoparticles edit the genome," MIT News, dated Nov. 13, 2017, 3 pages.
Trevino, et al., "Genome Editing Using Cas9 Nickases" Methods in Enzymology, vol. 546 pp. 161-174, 14 pages, 2014.
Tulpan, D., et al., "Free energy estimation of short DNA duplex hybridizations," BMC Bioinformatics, vol. 11, 2012, pp. 105-127, 23 pages.
Type V CRISPR-associated protein Cpfi [*Acidaminococcus* sp. Bv3L6], 2017, NCBI Reference Sequence: WP_02173622.1, Non-redundant Protein Sequence, 2 pages.
*Ultra-Precision Mfg. Ltd. v. Ford Motor Co.*, 2004 WL 3507671, *7, *11-12 (E.D. Mich. Mar. 30, 2004).
Urnov et al., "Highly efficient endogenous human gene correction using designed zinc-finger nucleases," Nature, 2005, vol. 435, (pp. 646-651).
Urrutia, et al., "KRAB-containing zing finger repressor proteins" Genome Biology, vol. 4, Sep. 23, 2003, pp. 231-231.8, 8 pages.
US Examiner-Initiated Interview Summary and Response to AF 2.0 Request for U.S. Appl. No. 14/972,927 dated Nov. 9, 2018, 12 pages.
V.N. Ngo et al., "A loss-of-function RNA interference screen for molecular targets in cancer," Nature, vol. 441, May 4, 2006, pp. 106-110, 5 pages.
Van Den Ackerveken, et al., "Recognition of the Bacterial Avirulence Protein AvrBs3 Occurs inside the Host Plant Cell" Cell, vol. 87, Dec. 27, 1996, pp. 1307-1316, 10 pages.
Van Der Oost, "New tool for genome surgery", Science, vol. 339, Feb. 15, 2013, pp. 768-770, 3 pages.
Van Der Oost, J., et al., "CRISPR-based adaptive and heritable immunity in prokaryotes," Trends. Biochem. Sci., vol. 34, 2009, pp. 401-407, 7 pages.
Van Nierop, G., et al., "Stimulation of homology-directed gene targeting at an endogenous human locus by a nicking endonuclease," Nucleic Acids Research, vol. 37, 2009, pp. 5725-5736, 12 pages.

(56) References Cited

OTHER PUBLICATIONS

Venken et al., "P[acman]: A BAC Transgenic Platform for Targeted Insertion of Large DNA Fragments in D. melanogaster", Science, vol. 314, Dec. 15, 2006, pp. 1747-1751, 5 pages.
Vestergaard et al., "CRISPR adaptive immune systems of Archaea", RNA Biology, vol. 11,2014, pp. 156-167, 12 pages.
Villion, et al., "The double-edged sword of CRISPR-Cas systems" Cell Research, 2013, vol. 23 pp. 15-17, 3 pages.
Voytas, Daniel F., "Plant genome engineering with sequence-specific nucleases," Annual Review of Plant Biology May 1, 2013, vol. 64 (pp. 327-350).
W.G. Kaelin., "Use and Abuse of RNAi to Study Mammalian Gene Function," Science, vol. 337, Jul. 27, 2012, p. 421-422, 2 pages.
Wang, et al. "Genetic Screens in Human Cells Using the CRISPR-Cas9 System", Science, 2014, 343:80-84.
Wang, H., et al., "One-Step Generation Of Mice Carrying Mutations In Multiple Genes By CRISPR/Cas-Mediated Genome Engineering," Cell, vol. 153, 2013, pp. 910-918, 9 pages.
Wang, H.H. et al., "Genome-scale promoter engineering by coselection MAGE," Nat methods, vol. 9, Jun. 2012, pp. 591-593, 3 pages.
Wayengera, M., "Identity of zinc finger nucleases with specificity to herpes simplex virus type II genomic DNA; novel HSV-2 vaccine/therapy precursors", Theoretical Biology and Medical Modelling, vol. 8, No. 1, Jun. 24, 2011, p. 23.
Wayengera, M., "Zinc finger arrays binding human papillomavirus types 16 and 18 genomic DNA: precursors of gene-therapeutics for in-situ reversal of associated cervical neoplasia", Theoretical Biology and Medical Modeling, vol. 9, No. 1, Jul. 28, 2012, p. 30.
Weber et al., "TALENs Targeting HBV: Designer Endonuclease Therapies for Viral Infections", Molecular Therapy, vol. 21, Oct. 2013, pp. 1819-1821, 3 pages.
Welch, et al., "Designing Genes For Successful Protein Expression" Methods in Enzymology, 2011, vol. 498, pp. 43-66, 24 pages. DOI: 10.1016/B978-0-12-385120-8.00003-6.
Wiedenheft, B. et al., "RNA-guided complex from a bacterial immune system enhances target recognition through seed sequence interactions," Proc. Natl. Acad. Sci., vol. 108, Jun. 21, 2011, 10092-10097, 7 pages.
Wiedenheft, B. et al., "RNA-guided genetic silencing systems in bacteria and archaea", Nature, vol. 482, Feb. 16, 2012, pp. 331-338.
Wienert, B., et al., "In vitro transcribed guide RNAs trigger an innate immune response via the RIG-I pathway," BioRxiv Preprint, 2018, 1-28, 28 pages.
Wiles et al., "CRISPR-Cas9-medicated genome editing and guide RNA Design," Mammalian Genome, May 20, 2015, vol. 26, No. 9 (10 pages).
Witkowski, A., et al., "Conversion of a Beta-Ketoacyl Synthase to a Malonyl Decarboxylase by Replacement of the Active-Site Cysteine with Glutamine," Biochemistry, vol. 38, 1999, pp. 11643-11650, 8 pages.
Wittmann et al., "Engineered riboswitches: Expanding researchers' toolbox with synthetic RNA regulators", FEBS Letters, vol. 586, 2012, pp. 2076-2083, 8 pages.
Wolff, et al., "Nuclear security breached" Nature Biotechnology, Dec. 2001, vol. 19, 1118-1120, 3 pages.
Workman et al., "A natural single-guide RNA repurposes Cas9 to autoregulate CRISPR-Cas expression," Cell Press, vol. 184, Feb. 4, 2021 (pp. 675-688).
Wu, X., et al., "Genome-wide binding of the CRISPR endonuclease Cas9 in mammalian cells," Nature Biotechnology, 2014, 1-7, 7 pages. Including Supplemental information, 2 pages.
Wu, Y., et al., "Correction of a Genetic Disease in Mouse via Use of CRISPR-Cas9," Cell Stem Cell, vol. 13, 2013, pp. 659-662, 4 pages.
Wu, Z., et al., "Effect of Genome Size on AAV Vector Packaging," The American Society of Gene & Cell Therapy, vol. 18, 2010, pp. 80-86, 7 pages.
X.Liu et al., "STAGA recruits Mediator to the MYC oncoprotein to stimulate transcription and cell proliferation," Molecular and cellular biology, vol. 28, Jan. 2008, p. 108-121, 14 pages.

Xiao et al. "Production of High-Titer Recombinant Adeno-Associated Virus Vectors in the Absence of Helper Adenovirus," Journal of Virology, Mar. 1998, vol. 72 No. 3 (pp. 2224-2232).
Xiao, et al., "Chromosomal deletions and inversions mediated by TALENs and CRIPPR/Cas in zebrafish" Nucleic Acids Research, vol. 41, 2013, pp. 1-11, Including Supplemental information, 31 pages. doi:10.1093/nar/gkt464.
Xiao, W., et al., "Gene Therapy Vectors Based on Adeno-Associated Virus Type 1", Journal of Virology, May 1999, vol. 73, No. 5, p. 3994-4003.
Xie, et al. "RNA-Guided Genome Editing in Plants Using a CRISPR-Cas System" Molecular Plant, vol. 6, Nov. 2013, 1975-1983, 9 pages.
Xu, Zhi-Li et al., "Regulated gene expression from adenovirus vectors: a systematic comparison of various inducible systems," Gene, vol. 309, 2003, pp. 145-151, 7 pages.
Yaghmai, et al., "Optimized Regulation of Gene Expression Using Artificial Transcription Factors", Molecular Therapy, Jun. 2002, vol. 5, No. 6, pp. 685-694.
Yamada et al., "Crystal Structure of the Minimal Cas9 from Campylobacter jejuni Reveals the Molecular Diversity in the CRISPR-Cas9 Systems," Molecular Cell, vol. 65, Mar. 16, 2017, pp. 1109-1121.
Yamano, et al., "Crystal Structure of Cpf1 in Complex with Guide RNA and Target DNA" Cell, vol. 165, May 5, 2016, pp. 949-962, 14 pages.
Yanfang Fu et al., "Improving CRISPR-Cas nuclease specificity using truncated guide RNAs" (with Supplement Table), Nature Biotechnology, vol. 32, Mar. 2014, pp. 1-18.
Yang et al., "HIV-1 TAT-mediated protein transduction and subcellular localization using novel expression vectors," FEBS Letters, vol. 532, 2012, pp. 36-44, 9 pages.
Yang, H., et al., "One-Step Generation of Mice Carrying Reporter and Conditional Alleles by CRISPR/Cas-Mediated Genome Engineering," Cell, vol. 154, 2013, pp. 1370-1379, 10 pages. Including Supplemental information, 4 pages.
Yi, et al., "Current Advances in Retroviral Gene Therapy" Current Gene Therapy, vol. 11, 2011, pp. 218-228, 11 pages.
Yin, H., et al., "Structure-guided chemical modification of guide RNA enables potent non-viral in vivo genome editing," Nature Biotechnology, vol. 35, Dec. 2017, pp. 1-22.
Yu, et al., "An efficient recombination system for chromosome engineering in *Escherichia coli*" PNAS, 2000, vol. 97, pp. 5978-5983, 6 pages.
Yu, W., et al., "Nrl knockdown by AAV-delivered CRISPR/Cas9 prevents retinal degeneration in mice," Nature Communications, vol. 8, 2017, art. 14716, 15 pages.
Yu, Zhongshen, et al., "Highly Efficient Genome Modifications Mediated by CRISPR/Cas9 in *Drosophila*" Genetics, 2013, vol. 195 pp. 289-291, 3 pages.
Yusuke Miyazaki et al., Destabilizing Domains Derived from the Human Estrogen Receptor:, Journal of the American Chemical Society, vol. 134, Mar. 7, 2012, pp. 3942-3945, 4 pages.
Zahner, D. and Hakenbeck, R. "The *Streptococcus pneumoniae* beta-galactosidase is a surface protein," J. Bacteriology, vol. 182, Oct. 2000, pp. 5919-5921, 3 pages.
Zeng Y et al., "Both natural and designed micro RNAs can inhibit the expression of cognate mRNAs when expressed in human cells," Mol Cell., vol. 9, Jun. 2002, pp. 1327-1333, 7 pages.
Zetsche et al., "Cpf1 is a single RNA-guided endonuclease of a class 2 CRISPR-Cas system," Cell, Oct. 22, 2015, vol. 163 (pp. 759-771).
Zetsche et al., "A split-Cas9 architecture for inducible genome editing and transcription modulation" Nature Biotechnology, 2015, vol. 33 (pp. 139-142).
Zhang, "Processing-Independent CRISPR RNAs Limit Natural Transformation in Neisseria meningitidis", Molecular Cell, vol. 50, May 23, 2013 pp. 488-503.
Zhang, et al. "Optogenetic interrogation of neural circuits: technology for probing mammalian brain structures" Nat Protoc., 2010, 5(3):439-456, doi:10.1038/nprot.2009.226.
Zhang, et al., "Optimized CRISPR Design", MIT, XP055167487, Oct. 23, 2013, URL:http//crispr.mit.edu/about[retrieved on Feb. 5, 2015].

(56) References Cited

OTHER PUBLICATIONS

Zhang, et al., "Efficient Construction of Sequence-Specific TAL Effectors for Modulating Mammalian Transcription," Nature Biotechnology, vol. 29, No. 2, Feb. 2011, 149-154.
Zhang, F., PowerPoint Presentation: "Development and Applications of CRISPR-Cas9 for Genome Editing," Broad Institute/MIT, dated Sep. 9, 2015, 50 pages.
Zhang, L., et al., "Efficient Expression of CFTR Function with Adeno-Associated Virus Vectors that Carry Shortened CFTR Genes," Proceedings of the National Academy of Science USA, vol. 95, 1998, pp. 10158-10163, 6 pages.
Zhang, X. D., et al., "cSSMD: assessing collective activity for addressing off-target effects in genome-scale RNA interference screens," Bioinformatics, vol. 27, pp. 2775-2781, 2011, 7 pages.
Zhou, et al., "High-throughput screening of a CRISPR/Cas9 library for functional genomics in human cells," Nature, vol. 509, pp. 487-491, 5 pages, 2014.
Zhu, et al., "Crystal structure of Cmr2 suggests a nucleotide cyclase-related enzyme in type III CRISPR-Cas systems" FEBS Letters, 2012, 939-945, 6 pages. Doi:10.1016/j.febslet2012.02.036.
Zolkiewska, et al., "ADAM Proteases:Ligand Processing and Modulation of the Notch Pathway" Cell Mol Life Sci, 2008, vol. 65 pp. 2056-2068, 13 pages.
Zuris, et al., "Cationic lipid-mediated delivery proteins enables efficient protein-based genome editing in vitro and in vivo", Nature Biotechnology, vol. 33, No. 1, Jan. 2015, pp. 73-80.
Zuris, et al., "Efficient Delivery of Genome-Editing Proteins In Vitro and In Vivo" Nature Biotechnology, vol. 33, No. 1, Jan. 2015, pp. 1-26.
Zuris, et al., Supplementary Information—"Cationic lipid-mediated delivery proteins enables efficient protein-based genome editing in vitro and in vivo" Nature Biotechnology, vol. 33, No. 1, Jan. 2015, pp. 1-49. doi:10.1038/nbt.3081.
Bauer et al., "Fine-Mapping and Genome Editing Reveal an Essential Erythroid Enhancer at the HbF-Associated BCL11A Locus," Blood, Nov. 15, 2013, vol. 122, No. 21 (3 pages).
Bethea et al., "Beta2-Microglobulin: Its Significance and Clinical Usefulness," Annals of Clinical and Laboratory Science, vol. 20, No. 3 (pages), 1990.
Bryant et al., "Gene Therapy for Retinal Disease," Review of Ophthalmology, Apr. 5, 2012 (5 pages).
Chen et al., "Cut Site Selection by the Two Nuclease Domains of the Cas9 RNA-guided Endonuclease," The Journal of Biological Chemistry, May 9, 2014, vol. 289, No. 19 (p. 13284-13294).
Declaration of Feng Zhang dated Jan. 30, 2014 (40 pages).
Heidenreich et al., Applications of CRISPR-Cas systems in neuroscience, Nature, Jan. 2016, vol. 17, No. 1 (pp. 35-44).
Koller et al., "Inactivating the beta2-microglobulin locus in mouse embryonic stem cells by homologous recombination," Proceedings of the National Academy of Sciences, USA, Nov. 1989, vol. 86 (pp. 8932-8935).
Li et al., "Genetic correction using engineered nucleases for gene therapy applications," The Japanese Society of Developmental Biologists; Development, Growth & Differentiation, 2014, vol. 56 (pp. 63-77).
Louwen et al., "The Role of CRISPR-Cas Systems in Virulence of Pathogenic Bacteria," Microbiology and Molecular Biology Reviews, Mar. 2014, vol. 78, No. 1 (pp. 74-88).
Magana et al., "Perspectives on gene Therapy in Myotonic Dystrophy Type 1," Journal of Neuroscience research, 2011, vol. 89 (pp. 275-285).
Reik et al., "Targeted Gene Modification in Hematopoietic Stem Cells: A Potential Treatment for Thalassemia and Sickle Cell Anemia," Blood, American Society of Hematology, Nov. 1, 2013, vol. 122, No. 21 (p. 434).
Singleton, "Exome sequencing: a transformative technology," The Lancet/neurology, Oct. 2011, vol. 10 (pp. 942-946).
Xu et al., "Identification of BCL 11 A Structure Function Domains for Fetal Hemoglobin Silencing," Blood, Nov. 15, 2013, vol. 122, No. 21 (4 pages).
Zoghbi et al., "Spinocerebellar ataxia type 1," Seminars in Cell Biology, Feb. 1995, vol. 6, No. 1 (pp. 29-35).

\* cited by examiner

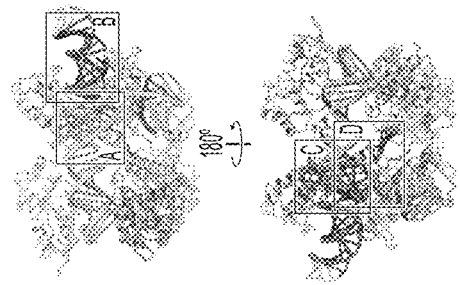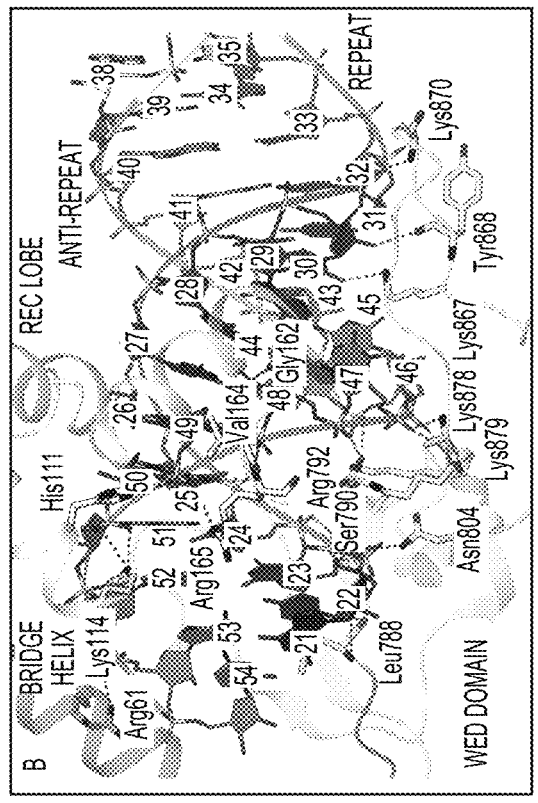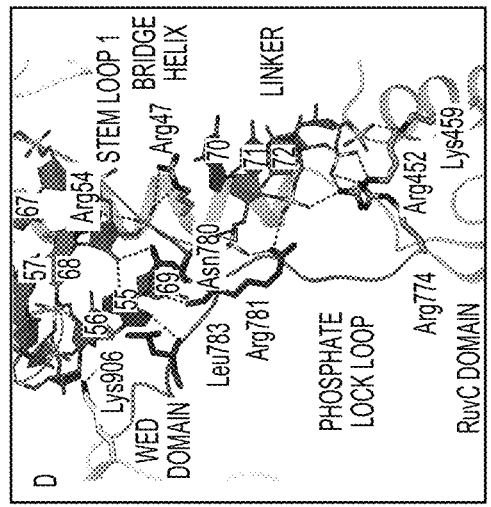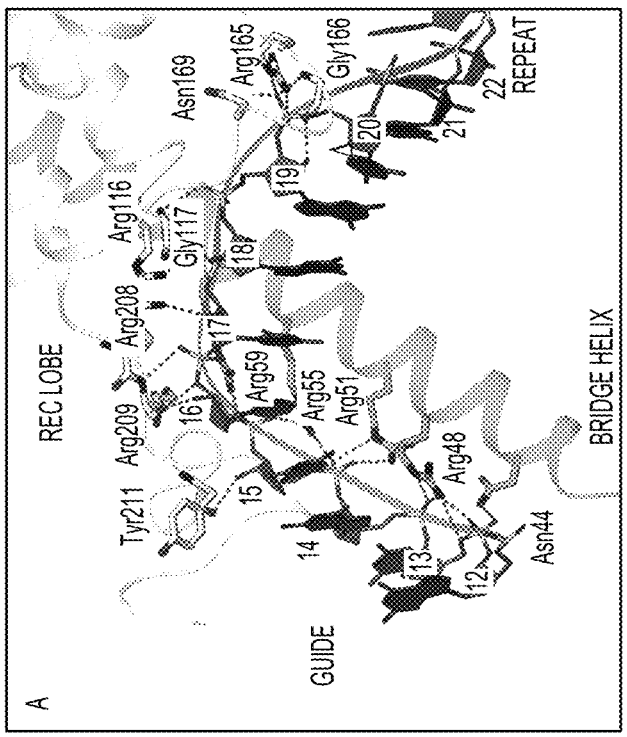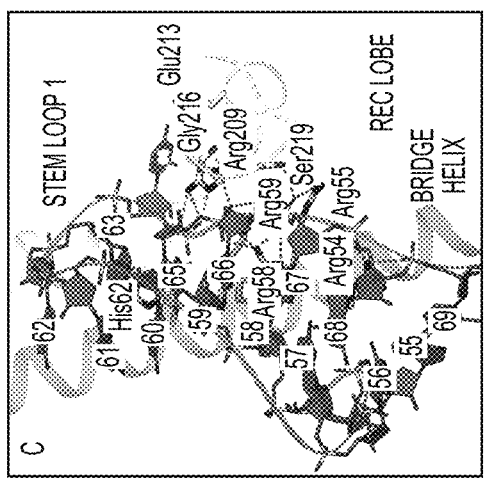
FIG. 4A-4D

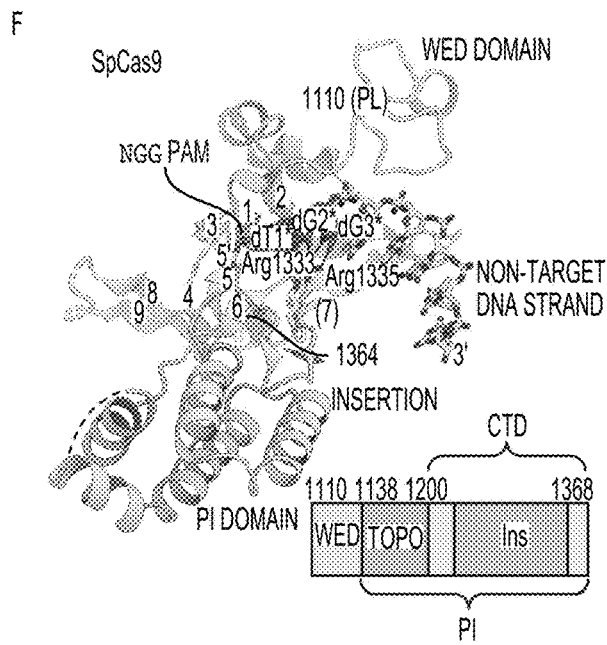
FIG. 7F
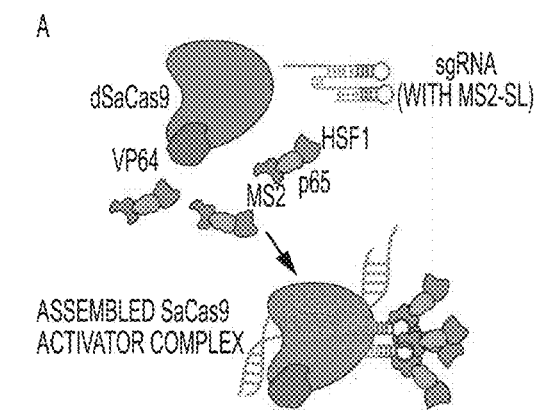
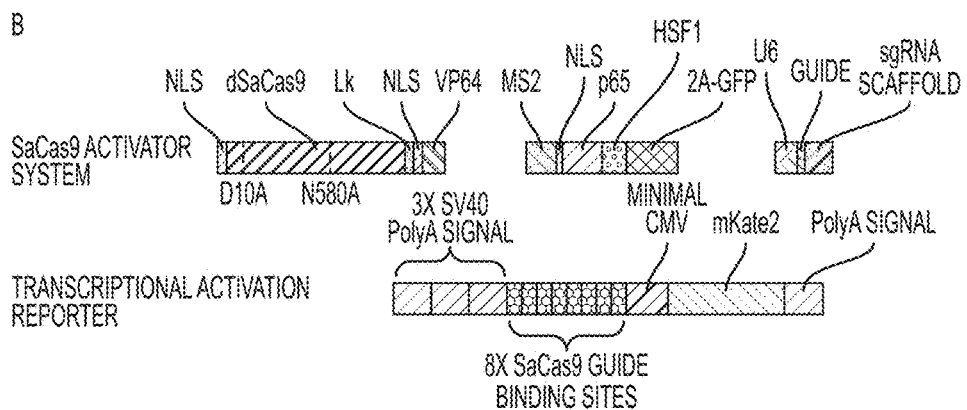
FIG. 8A-8B

A

B

ENGINEERING AND OPTIMIZATION OF SYSTEMS, METHODS, ENZYMES AND GUIDE SCAFFOLDS OF CAS9 ORTHOLOGS AND VARIANTS FOR SEQUENCE MANIPULATION

RELATED APPLICATIONS AND INCORPORATION BY REFERENCE

This application is a continuation of U.S. application Ser. No. 15/838,720, filed on Dec. 12, 2017, which is a continuation-in-part of international patent application Serial No. PCT/US2016/038252 filed Jun. 17, 2016, which published as PCT Publication No. WO2016/205759 on Dec. 22, 2016 and which claims the benefit of U.S. Provisional Patent Application Nos. 62/181,659, filed Jun. 18, 2015 and 62/207,318, filed Aug. 19, 2015.

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

STATEMENT AS TO FEDERALLY SPONSORED RESEARCH

This invention was made with government support under Grant No. MH100706 awarded by the National Institutes of Health. The government has certain rights in the invention. This invention was also supported by JST, PRESTO, JSPS KAKENHI Grant Numbers 26291010 and 15H01463.

SEQUENCE LISTING

The instant application contains a Sequence Listing which has been submitted electronically in XML format and is hereby incorporated by reference in its entirety. Said XML copy, created on Jun. 6, 2023, is named 114203-6055_SL.xml and is 173,287 bytes in size.

FIELD OF THE INVENTION

The present invention generally relates to systems, methods and compositions used for the control of gene expression involving sequence targeting, such as genome perturbation or gene-editing, that may use vector systems related to Clustered Regularly Interspaced Short Palindromic Repeats (CRISPR) and components thereof. In particular the present invention comprehends engineered new guide and enzyme architectures to be used in optimized CRISPR-Cas enzyme systems with particular reference to *Staphylococcus aureus* Cas9 enzyme (SaCas9) systems and corresponding guide scaffolds as well as one or more orthologous CRISPR-Cas enzyme systems.

BACKGROUND OF THE INVENTION

Recent advances in genome sequencing techniques and analysis methods have significantly accelerated the ability to catalog and map genetic factors associated with a diverse range of biological functions and diseases. Precise genome targeting technologies are needed to enable systematic reverse engineering of causal genetic variations by allowing selective perturbation of individual genetic elements, as well as to advance synthetic biology, biotechnological, and medical applications. Although genome-editing techniques such as designer zinc fingers, transcription activator-like effectors (TALEs), or homing meganucleases are available for producing targeted genome perturbations, there remains a need for new genome engineering technologies that are affordable, easy to set up, scalable, and amenable to targeting multiple positions within the eukaryotic genome.

SUMMARY OF THE INVENTION

There exists a pressing need for alternative and robust systems and techniques for sequence targeting with a wide array of applications. This invention addresses this need and provides related advantages. The CRISPR/Cas or the CRISPR-Cas system (both terms are used interchangeably throughout this application) does not require the generation of customized proteins to target specific sequences but rather a single Cas enzyme can be programmed by a short RNA molecule to recognize a specific DNA target, in other words the Cas enzyme can be recruited to a specific DNA target using said short RNA molecule. Adding the CRISPR-Cas system to the repertoire of genome sequencing techniques and analysis methods may significantly simplify the methodology and accelerate the ability to catalog and map genetic factors associated with a diverse range of biological functions and diseases. To utilize the CRISPR-Cas system effectively for genome editing without deleterious effects, it is critical to understand aspects of engineering and optimization of these genome engineering tools, which are aspects of the claimed invention.

In a first aspect, the invention provides a non-naturally occurring or engineered CRISPR-Cas system guide RNA or chimeric single guide RNA molecule (sgRNA), wherein when the sgRNA is in complex with a CRISPR enzyme within a prokaryotic or eukaryotic cell the CRISPR enzyme is capable of effecting the manipulation of a target nucleic acid within the cell, or a non-naturally occurring or engineered composition comprising a CRISPR-Cas system comprising said guide RNA or optionally sgRNA, the guide RNA or optionally sgRNA comprising a guide sequence capable of hybridizing to a target sequence in a genomic locus of interest in a prokaryotic or eukaryotic cell wherein architecture of the guide RNA or optionally sgRNA is modified. The invention particularly provides for a non-naturally occurring or engineered CRISPR-Cas system comprising a *Staphylococcus aureus* Cas9 enzyme (SaCas9) and the corresponding *Staphylococcus aureus* guide RNA (Sa sgRNA), wherein the SaCas9 or the Sa sgRNA are further optimized.

The invention also comprehends one or more orthologous CRISPR-Cas systems which are engineered and optimized in accordance with structural and functional comparative data presented herein. CRISPR-Cas systems have been classified, based on elements of gene organization, into three major types: Type I, represented e.g., by cas3, Type II, represented, e.g., by cas9 (csn1), and Type III, represented, e.g., by cas10. Type II enzymes, including cas9, are large multidomain proteins sufficient for targeting and cleaving DNA. A recently proposed evolutionary scheme encompasses "Class 2" CRISPR-Cas systems are comprised by SaCas9 and orthologous systems characterized by single-subunit effector complexes.

The herein provided structural information for SaCas9 relates to a crystal structure of a complex comprising SaCas9, a SaCas9 sgRNA, a target DNA and a non-target DNA strand. In an aspect of the invention, the crystal structure provides for a structural comparison among Cas9 orthologs (for example, between SaCas9 and SpCas9) as well as with evolutionarily conserved Cas9 proteins and CRISPR-SaCas9 complex components. The structural information further identifies aspects of SaCas9 associated with distinctive differences, including for example, the previously uncharacterized wedge (WED) domain. Furthermore, the structural information detailed herein reveals aspects of small Cas9 variants that possess activity in mammalian cells.

All aspects of the invention also encompass favorable thermodynamic states that allow for the herein described CRISPR-Cas systems to function in a physiologically relevant environment. In a preferred embodiment, the physiologically relevant environment includes but is not limited to an in vivo environment, e.g. in a eukaryotic cell or in an mammalian cell.

In an aspect, there is provided an engineered SaCas9 protein, wherein the protein complexes with a nucleic acid molecule comprising RNA to form a CRISPR complex, wherein when in the CRISPR complex, the nucleic acid molecule targets one or more target polynucleotide loci, the protein comprises at least one modification compared to unmodified SaCas9, and wherein the CRISPR complex comprising the modified protein has altered activity as compared to the complex comprising the unmodified SaCas9 protein.

In an aspect, the altered activity of the engineered SaCas9 protein comprises an altered binding property as to the nucleic acid molecule comprising RNA or the target polynucleotide loci, altered binding kinetics as to the nucleic acid molecule comprising RNA or the target polynucleotide loci, or altered binding specificity as to the nucleic acid molecule comprising RNA or the target polynucleotide loci compared to off-target polynucleotide loci.

In certain embodiments, the altered activity of the engineered SaCas9 protein comprises increased targeting efficiency or decreased off-target binding. In certain embodiments, the altered activity of the engineered SaCas9 protein comprises modified cleavage activity.

In certain embodiments, the altered activity comprises increased cleavage activity as to the target polynucleotide loci. In certain embodiments, the altered activity comprises decreased cleavage activity as to the target polynucleotide loci. In certain embodiments, the altered activity comprises decreased cleavage activity as to off-target polynucleotide loci. In certain embodiments, the altered activity comprises increased cleavage activity as to off-target polynucleotide loci. Accordingly, in certain embodiments, there is increased specificity for target polynucleotide loci as compared to off-target polynucleotide loci. In other embodiments, there is reduced specificity for target polynucleotide loci as compared to off-target polynucleotide loci.

In an aspect of the invention, the altered activity of the engineered SaCas9 protein comprises altered helicase kinetics.

In an aspect of the invention, the engineered SaCas9 protein comprises a modification that alters association of the protein with the nucleic acid molecule comprising RNA, or a strand of the target polynucleotide loci, or a strand of off-target polynucleotide loci. In an aspect of the invention, the engineered SaCas9 protein comprises a modification that alters formation of the CRISPR complex.

In an aspect, SaCas9 quaternary complex structural information described herein provides guidance for altering CRISPR-SaCas9 structural components. Further, the SaCas9 structural information provides guidance for altering SaCas9 orthologs, as well as for incorporating aspects of such orthologs into modified SaCas9 proteins.

In an aspect, the invention provides a non-naturally occurring or engineered composition comprising a Sa guide RNA (e.g. sgRNA) comprising a guide sequence capable of hybridizing to a target sequence in a genomic locus of interest in a cell wherein architecture of the Sa sgRNA is modified.

In some embodiments, at least one loop region, is/are further modified by the insertion of distinct RNA sequence(s) that bind to one or more adaptor proteins, and wherein the adaptor protein is associated with one or more functional domains. In some embodiments, the insertion of distinct RNA sequence(s) that bind to one or more adaptor proteins is an aptamer sequence or two or more aptamer sequences specific to the same or different adaptor protein(s).

In some embodiments, the adaptor protein comprises MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s, PRR1.

In some embodiments, the functional domain is a transcriptional activation domain, a transcriptional repressor domain or comprises a nuclease domain.

In an aspect of the invention, the SaCas9 sgRNA is modified (e.g. by the introduction of one or more nucleotide mutations, by truncation/deletion and/or insertion of specific nucleotides or nucleotide sequences) by affecting the binding of the non-target DNA strand to the RuvC domain.

In an aspect of the invention, the SaCas9 sgRNA is modified to alter the open conformation of the CRISPR-SaCas9 quaternary complex wherein the central channel which accommodates the guide-target heteroduplex either attracts the heteroduplex with high affinity or prevents the heteroduplex from being accommodated.

In an aspect of the invention, the SaCas9 sgRNA is modified (e.g. by the introduction of one or more nucleotide mutations, by truncation/deletion and/or insertion of specific nucleotides or nucleotide sequences) to alter its association with the REC lobe which recognizes the guide:target heteroduplex. Modifications may be made in either the seed sequence of the sgRNA or in the arginine cluster on the bridge helix in SaCas9.

In an aspect of the invention, the SaCas9 sgRNA is modified (e.g. by the introduction of one or more nucleotide mutations, by truncation/deletion and/or insertion of specific nucleotides or nucleotide sequences) to alter recognition of the repeat:anti-repeat duplex by the REC and WED domains.

In an aspect, the invention provides a non-naturally occurring or engineered composition comprising a CRISPR-Cas system comprising a SaCas9 enzyme wherein architecture of the SaCas9 enzyme is modified. In a preferred embodiment the SaCas9 enzyme is modified based on structural and mutational analysis. In a more preferred embodiment the structural analysis is based on the crystal structure of the SaCas9 in complex with the Sa sgRNA and its target DNA or sequence.

In an aspect, the invention provides a non-naturally occurring or engineered composition comprising a SaCas9 enzyme, wherein the SaCas9 enzyme is modified at regions that do not overlap with corresponding conserved regions of the ortholog *Streptococcus pyogenes* Cas9 enzyme (SpCas9). Structural features of SpCas9 which may be amenable to modification (for example, to modify or abolish nuclease activity or to truncate the enzyme while retaining nuclease activity) have been further described in PCT/US14/69925, titled "CRISPR-CAS SYSTEMS, CRYSTAL STRUCTURE AND USES THEREOF" filed on Dec. 12, 2014 and its priority documents, all the contents of which are herein incorporated by reference in their entirety. By structurally aligning SaCas9 and SpCas9 enzymes, the structural features of SaCas9 which correspond to the structural features of SpCas9 may be determined and specific regions may be modified to arrive at SaCas9 modified enzymes with varied functions.

In some embodiments, the functional domain associated with the SaCas9 enzyme is a transcriptional activation domain, a transcriptional repressor domain or comprises a nuclease domain.

In an aspect of the invention, the PI domain of the SaCas9 is modified (e.g. by the introduction of one or more amino acid mutations, by truncation/deletion and/or insertion of specific amino acids or amino acid sequences) to alter PAM specificity.

In some embodiments, the cell is a eukaryotic cell. In some embodiments, the eukaryotic cell is a mammalian cell. In some embodiments, the mammalian cell is a human cell or a mouse cell.

In an aspect, the invention provides a polynucleotide encoding the present guide (e.g. a Sa sgRNA or a modified Sa sgRNA).

In an aspect, the invention provides a vector comprising the polynucleotide operably linked to a suitable promoter. In some embodiments, the vector also comprises a further polynucleotide encoding a Sa Cas9 enzyme.

In an aspect, the invention provides a vector system, comprising one of the present vectors and a second vector comprising a polynucleotide encoding a Sa Cas9 enzyme.

In an aspect, the invention provides a transformant organism or model transformed with any one of the vectors to thereby express the Sa sgRNA or a modified Sa sgRNA and, optionally, the CRISPR enzyme, preferably a SaCas9 enzyme.

In an aspect, the invention provides a method of modifying a genomic locus of interest to alter gene expression in a cell by introducing into the cell the composition, polynucleotide or vectors described herein.

The invention, in its various aspects as described herein, is based on a number of surprising discoveries in relation to RNA and enzyme components of CRISPR-Cas systems comprising a SaCas9 enzyme.

In an aspect the invention also provides a composition as herein discussed which is a non-naturally occurring or engineered Sa sgRNA capable of effecting the manipulation of a target nucleic acid within a prokaryotic or eukaryotic cell when in complex within the cell with a SaCas9 enzyme; the Sa sgRNA comprising, in a tandem arrangement:
 I. a guide sequence or a truncated guide sequence, which is capable of hybridizing to a sequence of the target nucleic acid to be manipulated;
 II. a tracr mate sequence, comprising a region of sense sequence;
 III. a linker sequence; and
 IV. a tracr sequence, comprising a region of antisense sequence which is positioned adjacent the linker sequence and which is capable of hybridizing with the region of sense sequence thereby forming a stem loop; wherein the guide sequence comprises a length of 20-24 nucleotides.

When said sgRNA molecule is present within the cell, the region of antisense sequence is hybridized to the region of sense sequence thereby forming the stem loop; and wherein when said sgRNA molecule binds within the cell to the CRISPR enzyme so forming a CRISPR-Cas complex, the guide sequence hybridizes to a sequence of the target nucleic acid thereby directing sequence-specific binding of the CRISPR/Cas complex to the target nucleic acid, whereupon said sequence of said target nucleic acid is manipulated by the CRISPR enzyme of the complex.

In any of the sgRNAs described herein, the tracr sequence further comprises at least two regions of secondary structure, preferably at least one tetraloop and one stem loop. The tracr sequence may further comprises one or more regions of secondary structure, preferably stem loops. The tracr sequence may further comprise 1 stem loops or more than 1 stem loops, 2 stem loops or more than 2 stem loops, 3 stem loops or more than 3 stem loops. In preferred embodiments of the invention the optimized Sa sgRNA has a tetraloop and two stem loops, as Applicants have identified stem loop 2 to play a role in functionality in vivo.

In any of the sgRNAs described herein, the guide sequence comprises a length of 21 or more nucleotides, 22 or more nucleotides, 23 or more nucleotides, or 24 or more nucleotides; preferably the guide sequence comprises a length of 21, 22, 23 or 24 nucleotides. In all of the sgRNAs described herein, the guide sequence may consist of a length of 21, 22, 23 or 24 nucleotides. In any of the sgRNAs described herein, if the guide sequence is truncated, the truncated guide sequence may consist of a length of 20, 19, 18 or 17 nucleotides.

In any of the sgRNAs described herein, particularly if the sgRNA adopts a +73 nt architecture, the tracr sequence may be 49 or more nucleotides in length, 50 or more nucleotides in length, 51 or more nucleotides in length, 52 or more nucleotides in length, or 53 or more nucleotides in length. In further embodiments of the invention, the sgRNA may adopt a +85 nt or longer architecture and the tracr sequence may be 61 or more nucleotides in length, 62 or more nucleotides in length, 63 or more nucleotides in length, 64 or more nucleotides in length and so forth in accordance with the guide sequence length.

In any of the sgRNAs described herein the 5' or 3' terminal end of the tracr sequence opposite the region of antisense sequence comprises a poly uracil (U) tract, preferably wherein the poly U tract comprises 5 or more U nucleotides, optionally wherein the poly U tract consists of 5 U nucleotides, preferably wherein the poly U tract consists of 6 U nucleotides or consists of 7 U nucleotides.

In any of the sgRNAs described herein when complexed with the CRISPR enzyme within the cell the guide sequence is capable of hybridizing to a target nucleic acid associated with a PAM sequence comprising NNGGR or NNGRRT (e.g. 5'-TTGAAT-3' PAM or 5'-TTGGGT-3')

In an aspect, the invention as herein discussed provides DNA polynucleotide molecule(s) encoding:
 a. any chimeric RNA molecule as described herein;
 b. any tracr RNA according as described herein; or
 c. both any chimeric RNA molecule as described herein and any tracr RNA as described herein.

In an aspect, the invention as herein discussed provides a DNA polynucleotide molecule encoding any CRISPR-Cas system chimeric single guide RNA molecule (sgRNA) as described herein.

In an aspect, the invention as herein discussed also provides a DNA expression vector comprising a DNA polynucleotide molecule encoding any chimeric RNA molecule as described herein, or a DNA expression vector comprising a DNA polynucleotide molecule encoding any tracr RNA according as described herein, or a DNA expression vector comprising a DNA polynucleotide molecule encoding any chimeric RNA molecule as described herein and a DNA polynucleotide molecule encoding any tracr RNA according as described herein; wherein each expression vector further comprises one or more regulatory element(s) operably linked to sequences encoding said RNAs and capable of directing expression of the RNAs within the cell.

In an aspect, the invention as herein discussed also provides a DNA expression vector comprising a DNA polynucleotide molecule encoding any sgRNA as described herein, wherein the vector further comprises one or more regulatory element(s) operably linked to sequences encoding the sgRNA and capable of directing expression of the sgRNA within the cell.

In an aspect, the invention as herein discussed also provides a delivery vector carrying:
 a. any chimeric RNA molecule as described herein;
 b. any tracr RNA according as described herein; or
 c. both any chimeric RNA molecule as described herein and any tracr RNA as described herein.

In an aspect, the invention as herein discussed also provides a delivery vector carrying any CRISPR-Cas system chimeric single guide RNA molecule (sgRNA) described herein.

In an aspect, the invention as herein discussed also provides delivery vector carrying:
 a. a DNA expression vector comprising a DNA polynucleotide molecule encoding any chimeric RNA molecule as described herein;
 b. a DNA expression vector comprising a DNA polynucleotide molecule encoding any tracr RNA according as described herein; or
 c. a DNA expression vector comprising a DNA polynucleotide molecule encoding any chimeric RNA molecule as described herein and additionally comprising a DNA polynucleotide molecule encoding any tracr RNA according as described herein.

In an aspect, the invention as herein discussed also provides a delivery vector carrying a DNA expression vector comprising a DNA polynucleotide molecule encoding any sgRNA as described herein, wherein the vector further comprises one or more regulatory element(s) operably linked to sequences encoding the sgRNA and capable of directing expression of the sgRNA within the cell.

Any such delivery vectors described above may further carry the CRISPR enzyme; or may further carry an RNA molecule encoding the CRISPR enzyme and which is capable of expressing the enzyme.

Alternatively, any such delivery vectors may further carry a DNA expression vector which comprises a DNA polynucleotide molecule encoding the CRISPR enzyme, and which further comprises one or more regulatory element(s) operably linked to sequences encoding the enzyme and capable of directing expression of the enzyme within the cell. The enzyme and components of the sgRNA may be carried on the same or different vectors.

Any delivery vector carrying any of the components described herein may comprise liposomes, particles, e.g., nanoparticles, exosomes or microvesicles. Alternatively, any delivery vector carrying any of the components described herein may comprise a viral vector which is a retroviral vector, optionally a lentiviral vector, a baculoviral vector, a herpes simplex virus vector, an adenoviral vector, an adeno-associated viral (AAV) vector such as AAV8 vector, or a poxvirus such as a vaccinia virus. Embodiments of the invention relate to CRIPSR-Cas enzymes being modified or truncated to be smaller in size to allow for efficient packaging into vectors and vector systems.

In an aspect, the invention as herein discussed provides a non-naturally occurring or engineered CRISPR-Cas complex comprising:
 a. a CRISPR-Cas system chimeric single guide RNA molecule (sgRNA) as described herein; and
 b. a CRISPR enzyme comprising a SaCas9 enzyme;
wherein within the cell:
 i. the region of antisense sequence of the tracr sequence hybridizes with the sense sequence of the tracr mate sequence;
 ii. the CRISPR enzyme forms a CRISPR/Cas complex with the sgRNA; and
 iii. the guide sequence is capable of hybridizing to a sequence of the at least one target nucleic acid to direct sequence-specific binding of the CRISPR/Cas complex to a sequence of the target nucleic acid, whereupon the CRISPR enzyme is capable of effecting the manipulation of said sequence.

In the methods or compositions described herein the CRISPR enzyme of the composition may be provided as a polynucleotide sequence which comprises either (a) RNA, which is capable of expressing the enzyme or (b) DNA, wherein the polynucleotide sequence is operably linked to one or more regulatory element(s) capable of directing expression of RNA encoding the CRISPR enzyme.

In such methods or compositions comprising a sgRNA, in the composition the sgRNA is provided via a DNA expression vector comprising a DNA polynucleotide molecule encoding a CRISPR-Cas system chimeric single guide RNA molecule (sgRNA) as described herein, wherein the vector further comprises one or more regulatory element(s) operably linked to sequences encoding the sgRNA and capable of directing expression of the sgRNA within the cell; and wherein in the composition the enzyme is provided via a DNA expression vector further comprising one or more regulatory element(s) operably linked to polynucleotide sequences encoding the enzyme and capable of directing expression thereof; wherein polynucleotides encoding sgRNA and enzyme are provided on the same or different DNA expression vectors, preferably on the same DNA expression vector.

In such methods or compositions:
 a. polynucleotides comprising or encoding sgRNA, or a DNA expression vector encoding and capable of expressing the same; or
 b. polynucleotides comprising or encoding the chimeric RNA molecule of the sgRNA, or a DNA expression vector encoding and capable of expressing the same; and polynucleotides comprising or a DNA expression vector comprising a DNA polynucleotide molecule encoding and capable of expressing the same; and
 i. the CRISPR enzyme, or
 ii. a DNA expression vector comprising polynucleotides encoding the enzyme and further comprising one or more regulatory element(s) operably linked to polynucleotide sequences encoding the enzyme and capable of directing expression thereof may be comprised in one or more delivery vectors.

In such methods or compositions:
 a. the polynucleotides comprising or encoding sgRNA or the DNA expression vectors encoding sgRNA; and b. the CRISPR enzyme or the DNA expression vector comprising polynucleotides encoding the enzyme; are comprised in the same delivery vector or in two or more different delivery vectors.

In such methods or compositions the one or more or two or more delivery vectors is a recombinant virus. The recombinant virus may be a retrovirus, optionally a lentivirus, a baculovirus, a herpes simplex virus, an adenovirus, an adenoassociated virus (AAV) such as AAV8, or a poxvirus such as a vaccinia virus.

In such methods or compositions the one or more or two or more delivery vectors comprise(s) liposomes, particles, e.g., nanoparticles, exosomes or microvesicles.

In any of the sgRNAs, DNA polynucleotide molecules, DNA expression vectors, delivery vectors, methods, systems, compositions or complexes described herein the CRISPR enzyme may further comprise one or more nuclear localization sequences (NLSs) capable of driving the accumulation of the CRISPR enzyme to a detectable amount in the nucleus of the cell of the organism. The CRISPR enzyme may comprise two or more NLSs, three or more NLSs, four or more NLSs, five or more NLSs, six or more NLSs, seven or more NLSs, eight or more NLSs, nine or more NLSs, or ten or more NLSs. The CRISPR enzyme may comprise at least one NLS at or near the amino-terminus of the CRISPR enzyme and/or at least one NLS at or near the carboxy-terminus of the CRISPR enzyme.

In any of the sgRNAs, DNA polynucleotide molecules, DNA expression vectors, delivery vectors, methods, systems, compositions or complexes described herein said manipulation of the at least one target nucleic acid by the CRISPR-Cas complex comprises cleavage of the at least one target nucleic acid. Cleavage may comprise one or more double-strand break(s) introduced into the target nucleic acid, optionally at least two double-strand break(s). Said cleavage may be via one or more single-strand break(s) introduced into the target nucleic acid, optionally at least two single-strand break(s).

In any of the sgRNAs, DNA polynucleotide molecules, DNA expression vectors, delivery vectors, methods, systems, compositions or complexes described herein one or more double-strand break(s) or one or more single-strand break(s) may lead to the formation of one or more insertion and deletion mutations (INDELs) in the target nucleic acid.

In any of the methods, systems or compositions described herein involving cleavage, the composition may comprise components of at least two types of Sa CRISPR/Cas complex, wherein each type of complex comprises a guide sequence capable of hybridizing to different sequences of the target nucleic acid.

In such methods, systems or compositions said cleavage is cleavage of first and second strands of the target nucleic acid via at least two double-strand breaks introduced into the target nucleic acid;
wherein a first double-strand break is introduced at a first position of the target nucleic acid by manipulating a first target sequence and a second double-strand break is introduced at a second position of the target nucleic acid by manipulating a second target sequence;
wherein upon introduction of first and second double-strand breaks sequences between first and second double-strand breaks are excised.

In any of the methods, systems or compositions described herein involving cleavage, the composition may comprise comprises components of at least four types of Sa CRISPR/Cas complex, wherein each type of complex comprises a guide sequence capable of hybridizing to different sequences of the target DNA.

In such methods, systems or compositions said cleavage is via at least two pairs of single-strand breaks introduced into the target DNA;
wherein to introduce a first pair of single-strand breaks a first single-strand break is introduced into a first strand of DNA by manipulating a first target sequence to create a first nick and a second single-strand break is introduced into the opposite strand of DNA by manipulating a second target sequence to create a second nick;
wherein to introduce a second pair of single-strand breaks a third single-strand break is introduced into said first strand of DNA by manipulating a third target sequence to create a third nick and a fourth single-strand break is introduced into said opposite strand of DNA by manipulating a fourth target sequence to create a fourth nick;
wherein upon introduction of first and second pairs of single-strand breaks target sequences between first and second pairs of single-strand breaks are excised.

First and second nicks may be offset relative to each other by at least one base pair so creating a first overhang, and wherein third and fourth nicks are offset relative to each other by at least one base pair so creating a second overhang.

Following excision upon cleavage the ends of the cleaved first strand of DNA may be ligated together and the ends of the cleaved second strand of DNA may be ligated together thus reforming unbroken first and second strands.

In methods, systems or compositions described herein, said modification, alteration or manipulation may comprise insertion of one or more nucleotides into or adjacent target sequences, deletion of one or more nucleotides in or adjacent target sequences, translocation of target sequences, repression of transcription of target gene sequences or and/or repression or inactivation of target sequences.

In any of the sgRNAs, DNA polynucleotide molecules, DNA expression vectors, delivery vectors, methods, systems, compositions or complexes described herein the enzyme comprising a SaCas9 enzyme, may be a fragment or derivative of SaCas9, or may comprise one or more amino acid substitutions compared to the wild-type SaCas9.

In any of the sgRNAs, DNA polynucleotide molecules, DNA expression vectors, delivery vectors, methods, systems, compositions or complexes described herein the SaCas9 may be a modified SaCas9 enzyme. Modifications to the SaCas9 enzyme may be made in accordance with the crystal structure information provided herein or at corresponding positions to its ortholog SpCas9 enzyme.

The SaCas9 enzyme may comprise one or more substitution(s) to the HNH nuclease domain and/or the RuvC nuclease domain of SaCas9. The substitution may be D10A, E477A, H701A and D704A in the RuvC domain and/or D556A, H557 and N580A in the HNH domain In any of the sgRNAs, DNA polynucleotide molecules, DNA expression vectors, delivery vectors, methods, systems, compositions or complexes described herein a catalytically inactive (e.g. a Cas9 enzyme having reduced or no nuclease activity) SaCas9 may be fused to one or more transcriptional repressor domains, optionally wherein the one or more transcriptional repressor domains comprises KRAB, SID and/or SID4X or any one or more transcriptional repressor domains described herein. The or more transcriptional repressor domain may comprise a NuE domain or a NcoR domain.

In any of the sgRNAs, DNA polynucleotide molecules, DNA expression vectors, delivery vectors, methods, systems, compositions or complexes described herein a catalytically inactive (e.g. a Cas9 enzyme having reduced or no nuclease activity) SaCas9 may be fused to one or more transcriptional activation domains such as VP64 or any one or more transcriptional activation domains described herein.

The transcriptional activation domain associated with the CRISPR enzyme may be a transcriptional activation domain which comprises p65, MyoD1, HSF1, RTA and SET7/9.

In any of the sgRNAs, DNA polynucleotide molecules, DNA expression vectors, delivery vectors, methods, systems, compositions or complexes described herein the SaCas9 may be fused to one or more additional nuclease domain(s) capable of cleaving the target nucleic acid, optionally a Fok1 nuclease domain.

In any of the sgRNAs, DNA polynucleotide molecules, DNA expression vectors, delivery vectors, methods, systems, compositions or complexes described herein the SaCas9 may be fused to one or more functional domains having activities comprising methylase activity, demethylase activity, transcription activation activity, transcription repression activity, transcription release factor activity, histone modification activity, RNA cleavage activity, DNA cleavage activity, DNA integration activity or nucleic acid binding activity.

In any of the sgRNAs, DNA polynucleotide molecules, DNA expression vectors, delivery vectors, methods, systems, compositions or complexes described herein various functional domains may be fused to the SaCas9 enzyme.

Any of the functional domains described herein can be attached to the SaCas9 CRISPR enzyme via a linker, e.g., a flexible glycine-serine (GlyGlyGlySer) (SEQ ID NO: 1) or $(GGGS)_3$ (SEQ ID NO: 2) or a rigid alpha-helical linker such as (Ala(GluAlaAlaAlaLys)Ala) (SEQ ID NO: 3). Linkers such as $(GGGGS)_3$ (SEQ ID NO: 4) are preferably used herein to separate protein or peptide domains. $(GGGGS)_3$ (SEQ ID NO: 4) is preferable because it is a relatively long linker (15 amino acids). The glycine residues are the most flexible and the serine residues enhance the chance that the linker is on the outside of the protein. $(GGGGS)_6$ (SEQ ID NO: 5) $(GGGGS)_9$ (SEQ ID NO: 6) or $(GGGGS)_{12}$ (SEQ ID NO: 7) may preferably be used as alternatives. Other preferred alternatives are $(GGGGS)_1$ (SEQ ID NO: 8), $(GGGGS)_2$ (SEQ ID NO: 9), $(GGGGS)_4$ (SEQ ID NO: 10), $(GGGGS)_5$ (SEQ ID NO: 11), $(GGGGS)_7$ (SEQ ID NO: 12), $(GGGGS)_8$ (SEQ ID NO: 13), $(GGGGS)_{10}$ (SEQ ID NO: 14), or $(GGGGS)_{11}$ (SEQ ID NO: 15). Alternative linkers are available, but highly flexible linkers are thought to work best to allow for maximum opportunity for the 2 parts of the Cas9 to come together and thus reconstitute Cas9 activity. One alternative is that the NLS of nucleoplasmin can be used as a linker. For example, a linker can also be used between the Cas9 and any functional domain. Again, a $(GGGGS)_3$ linker (SEQ ID NO: 4) may be used here (or the 6 (SEQ ID NO: 5), 9 (SEQ ID NO: 6), or 12 (SEQ ID NO: 7) repeat versions therefore) or the NLS of nucleoplasmin can be used as a linker between Cas9 and the functional domain.

In general, the invention comprehends the sgRNA comprising a guide sequence fused to a tracr sequence. The tracr sequence may further comprise at least two regions of secondary structure, preferably at least two stem loops. When said sgRNA molecule is present within the cell, the region of antisense sequence may be hybridized to the region of sense sequence thereby forming the stem loop; and wherein when said sgRNA molecule binds within the cell to the CRISPR enzyme so forming a CRISPR-Cas complex, the guide sequence hybridizes to a sequence of the target nucleic acid thereby directing sequence-specific binding of the CRISPR/Cas complex to the target nucleic acid, whereupon said sequence of said target nucleic acid is manipulated by the CRISPR enzyme of the complex.

In one aspect, the invention provides a method for altering or modifying expression of a gene product. The said method may comprise introducing into a cell containing and expressing a DNA molecule encoding the gene product an engineered, non-naturally occurring CRISPR-Cas system comprising a Cas protein and the present guide RNA.

In general, it will be appreciated that the guide comprise a guide sequence that targets the DNA molecule, so that the guide RNA targets the DNA molecule encoding the gene product and the Cas protein cleaves the DNA molecule encoding the gene product, whereby expression of the gene product is altered; and, wherein the Cas protein and the guide RNA do not naturally occur together.

In general, the invention comprehends the guide RNA comprising a guide sequence fused to a tracr sequence. The invention further comprehends the Cas protein being codon optimized for expression in a Eukaryotic cell. In a preferred embodiment the Eukaryotic cell is a mammalian cell and in a more preferred embodiment the mammalian cell is a human cell. In a further embodiment of the invention, the expression of the gene product is decreased.

In one aspect, the invention provides an engineered, non-naturally occurring CRISPR-Cas system comprising a Cas protein and the present guide RNA that targets a DNA molecule encoding a gene product in a cell, whereby the guide RNA targets the DNA molecule encoding the gene product and the Cas protein cleaves the DNA molecule encoding the gene product, whereby expression of the gene product is altered; and, wherein the Cas protein and the guide RNA do not naturally occur together.

In an embodiment of the invention the Cas protein is a type II CRISPR-Cas protein and in a preferred embodiment the Cas protein is a Cas9 protein. The invention further comprehends the Cas protein being codon optimized for expression in a Eukaryotic cell. In a preferred embodiment the Eukaryotic cell is a mammalian cell and in a more preferred embodiment the mammalian cell is a human cell. In a further embodiment of the invention, the expression of the gene product is decreased.

In another aspect, the invention provides an engineered, non-naturally occurring vector system comprising one or more vectors comprising a first regulatory element operably linked to the present guide RNA that targets a DNA molecule encoding a gene product and a second regulatory element operably linked to a Cas protein. Components (a) and (b) may be located on same or different vectors of the system. The present guide RNA targets the DNA molecule encoding the gene product in a cell and the Cas protein cleaves the DNA molecule encoding the gene product, whereby expression of the gene product is altered; and, wherein the Cas protein and the guide RNA do not naturally occur together.

In some embodiments, the guide further comprises a tracr sequence downstream of a tracr mate sequence.

In some embodiments, component (a) of the above vectors further comprises two or more guide sequences operably linked to the first regulatory element, wherein when expressed, each of the two or more guide sequences direct sequence specific binding of a CRISPR complex to a different target sequence in a eukaryotic cell.

In some embodiments, the system comprises the tracr sequence under the control of a third regulatory element, such as a polymerase III promoter. In some embodiments, the tracr sequence exhibits at least 50%, 60%, 70%, 80%, 90%, 95%, or 99% of sequence complementarity along the length of the tracr mate sequence when optimally aligned. Determining optimal alignment is within the purview of one of skill in the art. For example, there are publically and commercially available alignment algorithms and programs such as, but not limited to, ClustalW, Smith-Waterman in matlab, Bowtie, Geneious, Biopython and SeqMan.

In some embodiments, guide forms a CRISPR complex with the CRISPR enzyme. The CRISPR complex or polynucleotides encoding it preferably comprise one or more nuclear localization sequences of sufficient strength to drive accumulation of said CRISPR complex in a detectable amount in the nucleus of a eukaryotic cell.

In some embodiments, the CRISPR enzyme is a Cas9 enzyme. In some embodiments, the Cas9 enzyme is *S. aureus, S. pneumoniae, S. pyogenes,* or *S. thermophilus* Cas9, and may include mutated Cas9 derived from these organisms. The enzyme may be a Cas9 homolog or ortholog. In some embodiments, the CRISPR enzyme is codon-optimized for expression in a eukaryotic cell. In some embodiments, the CRISPR enzyme directs cleavage of one or two strands at the location of the target sequence. In a preferred embodiment, the Cas9 enzyme is *S. aureus* or a similar smaller Cas9 ortholog.

In some embodiments, the first regulatory element in the present vectors is a polymerase III promoter. In some embodiments, the second regulatory element in the present vectors is a polymerase II promoter.

In some embodiments, the guide sequence is at least 15, 16, 17, 18, 19, 20, 25 nucleotides, or between 10-30, or between 15-25, or between 20-24 nucleotides in length.

In any of the sgRNA, DNA polynucleotide molecule, DNA expression vector, delivery vector, method, system, composition or complex described herein said manipulation may be performed in vitro or ex vivo.

In an aspect, the invention also provides any of the sgRNA, DNA polynucleotide molecule, DNA expression vector, delivery vector, system, composition or complex as described herein for use as a medicament, optionally for use in the treatment of a viral infection. In such cases, treatment is treatment of a mammal, optionally a human.

In an aspect, the invention also provides the use of any of the sgRNA, DNA polynucleotide molecule, DNA expression vector, delivery vector, system, composition or complex as described herein in the manufacture of a medicament, optionally for the treatment of a viral infection. In such cases, treatment is treatment of a mammal, optionally a human.

In an aspect, the invention also provides pharmaceutical compositions comprising any of the sgRNAs, DNA polynucleotide molecules, DNA expression vectors, delivery vectors, systems, compositions or complexes described herein. Such pharmaceutical compositions may contain an excipient. Such pharmaceutical compositions may be formulated for administration to a mammal, optionally a human.

It will be appreciated that the invention described herein involves various components which may display variations in their specific characteristics. It will be appreciated that any combination of features described above and herein, as appropriate, are contemplated as a means for implementing the invention.

In general, applying to any of the aspects discussed herein, the sgRNA is a non-naturally occurring or engineered CRISPR-Cas system chimeric single guide RNA molecule. It is preferably capable of effecting the manipulation of a target nucleic acid within a prokaryotic or eukaryotic cell when in complex within the cell with a CRISPR enzyme. Examples of preferred CRISPR enzymes are a *Staphylococcus aureus* Cas9 enzyme (SaCas9) or other similar smaller Cas9 orthologs. The sgRNA may comprise, in some embodiments, the following, in a tandem arrangement:

I. a guide sequence, which is capable of hybridizing to a sequence of the target nucleic acid to be manipulated;
II. a tracr mate sequence, comprising a region of sense sequence;
III. a linker sequence; and
IV. a tracr sequence, comprising a region of antisense sequence which is positioned adjacent the linker sequence and which is capable of hybridizing with the region of sense sequence thereby forming a stem loop.

In some aspects, especially those relating to SaCas9, the guide sequence comprises a length of 21 or more nucleotides.

Specifically, the invention provides a non-naturally occurring or engineered composition comprising a CRISPR-Cas system comprising a chimeric single guide RNA molecule (sgRNA) capable of effecting the manipulation of a target nucleic acid within a prokaryotic or eukaryotic cell when in complex within the cell with a CRISPR enzyme, the sgRNA comprising a guide sequence capable of hybridizing to a target sequence in a genomic locus of interest in a cell wherein architecture of the sgRNA is modified. Preferred modifications to the architecture are discussed herein.

Example of a preferred CRISPR enzymes is an SaCas9 enzyme. The Sa sgRNA may comprise, in some embodiments, the following, in a tandem arrangement:

I. a guide sequence or a truncated guide sequence (TRU guides), which is capable of hybridizing to a sequence of the target nucleic acid to which it binds or can manipulate;
II. a tracr mate sequence, comprising a region of sense sequence;
III. a linker sequence; and
IV. a tracr sequence, comprising a region of antisense sequence which is positioned adjacent the linker sequence and which is capable of hybridizing with the region of sense sequence thereby forming a stem loop.

In some aspects, especially those relating to SaCas9, the guide sequence comprises a length of 21 or more nucleotides.

In general, and throughout this specification, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell).

The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g. 1, 2, 3, 4, 5, or more pol I promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.).

In one aspect, the invention encompasses embodiments wherein an engineered short, bi-directional U6 promoter (a minimal bi-directional promoter) rationally designed from taking the transcription factor binding sites and elements from human U6 promoter is used to drive two transcripts going in opposite directions: In a preferred embodiment, such a bidirectional U6 promoter is incorporated into the SaCas9 AAV vector to deliver 2 Sa sgRNAs. Further aspects of the invention incorporate embodiments as described in PCT/US2014/041800 titled "DELIVERY, ENGINEERING AND OPTIMIZATION OF TANDEM GUIDE SYSTEMS, METHODS AND COMPOSITIONS FOR SEQUENCE MANIPULATION" filed on Jun. 10, 2014 and its priority documents, the contents of which are herein incorporated by reference in their entirety. Further aspects also incorporate features as described in Ran et al. "Double nicking by RNA-guided CRISPR Cas9 for enhanced genome editing specificity." Cell. 2013 Sep. 12; 154(6):1380-9, the contents of which are also incorporated herein by reference in their entirety.

Advantageous vectors include lentiviruses and adeno-associated viruses, and types of such vectors can also be selected for targeting particular types of cells.

In one aspect, the invention provides a eukaryotic host cell. The host cell may comprise (a) a first regulatory element operably linked to a tracr mate sequence and one or more insertion sites for inserting one or more of the present guide sequences upstream of the tracr mate sequence, wherein when expressed, the guide sequence directs sequence-specific binding of a CRISPR complex to a target sequence in a eukaryotic cell, wherein the CRISPR complex comprises a CRISPR enzyme complexed with (1) the guide sequence that is hybridized to the target sequence, and (2) the tracr mate sequence that is hybridized to the tracr sequence; and/or (b) a second regulatory element operably linked to an enzyme-coding sequence encoding said CRISPR enzyme comprising a nuclear localization sequence. In some embodiments, the host cell comprises components (a) and (b). In some embodiments, component (a), component (b), or components (a) and (b) are stably integrated into a genome of the host eukaryotic cell. In some embodiments, component (a) further comprises the tracr sequence downstream of the tracr mate sequence under the control of the first regulatory element. In some embodiments, component (a) further comprises two or more guide sequences operably linked to the first regulatory element, wherein when expressed, each of the two or more guide sequences direct sequence specific binding of a CRISPR complex to a different target sequence in a eukaryotic cell. In some embodiments, the eukaryotic host cell further comprises a third regulatory element, such as a polymerase III promoter, operably linked to said tracr sequence. In some embodiments, the tracr sequence exhibits at least 50%, 60%, 70%, 80%, 90%, 95%, or 99% of sequence complementarity along the length of the tracr mate sequence when optimally aligned. The enzyme may be a Cas9 homolog or ortholog. In some embodiments, the CRISPR enzyme is codon-optimized for expression in a eukaryotic cell. In some embodiments, the CRISPR enzyme directs cleavage of one or two strands at the location of the target sequence. In some embodiments, the CRISPR enzyme lacks DNA strand cleavage activity. In some embodiments, the first regulatory element is a polymerase III promoter. In some embodiments, the second regulatory element is a polymerase II promoter. In some embodiments, the guide sequence is at least 15, 16, 17, 18, 19, 20, 25 nucleotides, or between 10-30, or between 15-25, or between 15-20 nucleotides in length. In an aspect, the invention provides a non-human eukaryotic organism; preferably a multicellular eukaryotic organism, comprising a eukaryotic host cell according to any of the described embodiments. In other aspects, the invention provides a eukaryotic organism; preferably a multicellular eukaryotic organism, comprising a eukaryotic host cell according to any of the described embodiments. The organism in some embodiments of these aspects may be an animal; for example a mammal. Also, the organism may be an arthropod such as an insect. The organism also may be a plant. Further, the organism may be a fungus.

With respect to use of the CRISPR-Cas system generally, mention is made of the documents, including patent applications, patents, and patent publications cited throughout this disclosure as embodiments of the invention can be used as in those documents. CRISPR-Cas system(s) (e.g., single or multiplexed) can be used in conjunction with recent advances in crop genomics. Such CRISPR-Cas system(s) can be used to perform efficient and cost effective plant gene or genome interrogation or editing or manipulation—for instance, for rapid investigation and/or selection and/or interrogations and/or comparison and/or manipulations and/or transformation of plant genes or genomes; e.g., to create, identify, develop, optimize, or confer trait(s) or characteristic(s) to plant(s) or to transform a plant genome. There can accordingly be improved production of plants, new plants with new combinations of traits or characteristics or new plants with enhanced traits. Such CRISPR-Cas system(s) can be used with regard to plants in Site-Directed Integration (SDI) or Gene Editing (GE) or any Near Reverse Breeding (NRB) or Reverse Breeding (RB) techniques. With respect to use of the CRISPR-Cas system in plants, mention is made of the University of Arizona website "CRISPR-PLANT" (worldwideweb.genome.arizona.edu/crispr/) (supported by Penn State and AGI). Embodiments of the invention can be used in genome editing in plants or where RNAi or similar genome editing techniques have been used previously; see, e.g., Nekrasov, "Plant genome editing made easy: targeted mutagenesis in model and crop plants using the CRISPR/Cas system," Plant Methods 2013, 9:39 (doi:10.1186/1746-4811-9-39); Brooks, "Efficient gene editing in tomato in the first generation using the CRISPR/Cas9 system," Plant Physiology September 2014 pp 114.247577; Shan, "Targeted genome modification of crop plants using a CRISPR-Cas system," Nature Biotechnology 31, 686-688 (2013); Feng, "Efficient genome editing in plants using a CRISPR/Cas system," Cell Research (2013) 23:1229-1232. doi:10.1038/cr.2013.114; published online 20 Aug. 2013; Xie, "RNA-guided genome editing in plants using a CRISPR-Cas system," Mol Plant. 2013 Nov.; 6(6):1975-83. doi:10.1093/mp/sst119. Epub 2013 Aug. 17; Xu, "Gene targeting using the *Agrobacterium tumefaciens*-mediated CRISPR-Cas system in rice," Rice 2014, 7:5 (2014), Zhou et al., "Exploiting SNPs for biallelic CRISPR mutations in the outcrossing woody perennial *Populus* reveals 4-coumarate: CoA ligase specificity and Redundancy," New Phytologist (2015) (Forum) 1-4 (available online only at worldwideweb.newphytologist.com); Caliando et al, "Targeted DNA degradation using a CRISPR device stably carried in the host genome, NATURE COMMUNICATIONS 6:6989, DOI: 10.1038/ncomms7989, worldwideweb.nature.com/naturecommunications DOI: 10.1038/ncomms7989; U.S. Pat. No. 6,603,061—*Agrobacterium*-Mediated Plant Transformation Method; U.S. Pat. No. 7,868,149—Plant Genome Sequences and Uses Thereof and US 2009/0100536—Transgenic Plants with Enhanced Agronomic Traits, all the contents and disclosure of each of which are herein incorporated by reference in their entirety. In the practice of the invention, the contents and disclosure of Morrell et al "Crop genomics: advances and applications," Nat Rev Genet. 2011 Dec. 29; 13(2):85-96; each of which is incorporated by reference herein including as to how herein embodiments may be used as to plants. Accordingly, reference herein to animal cells may also apply, mutatis mutandis, to plant cells unless otherwise apparent.

In one aspect, the invention provides a kit comprising one or more of the components described herein. In some embodiments, the kit comprises a vector system and instructions for using the kit. In some embodiments, the vector system comprises (a) a first regulatory element operably linked to a tracr mate sequence and one or more insertion sites for inserting one or more guide sequences upstream of the tracr mate sequence, wherein when expressed, the guide sequence directs sequence-specific binding of a CRISPR complex to a target sequence in a eukaryotic cell, wherein the CRISPR complex comprises a CRISPR enzyme complexed with (1) the guide sequence that is hybridized to the target sequence, and (2) the tracr mate sequence that is hybridized to the tracr sequence; and/or (b) a second regulatory element operably linked to an enzyme-coding sequence encoding said CRISPR enzyme comprising a nuclear localization sequence. In some embodiments, the kit comprises components (a) and (b) located on the same or different vectors of the system. In some embodiments, component (a) further comprises the tracr sequence downstream of the tracr mate sequence under the control of the first regulatory element. In some embodiments, component (a) further comprises two or more guide sequences operably linked to the first regulatory element, wherein when expressed, each of the two or more guide sequences direct sequence specific binding of a CRISPR complex to a different target sequence in a eukaryotic cell. In some embodiments, the system further comprises a third regulatory element, such as a polymerase III promoter, operably linked to said tracr sequence. In some embodiments, the tracr sequence exhibits at least 50%, 60%, 70%, 80%, 90%, 95%, or 99% of sequence complementarity along the length of the tracr mate sequence when optimally aligned. In some embodiments, the CRISPR enzyme comprises one or more nuclear localization sequences of sufficient strength to drive accumulation of said CRISPR enzyme in a detectable amount in the nucleus of a eukaryotic cell. In some embodiments, the CRISPR enzyme is a type II CRISPR system enzyme. In some embodiments, the CRISPR enzyme is a Cas9 enzyme. In some embodiments, the Cas9 enzyme is *S. aureus, S. pneumoniae, S. pyogenes* or *S. thermophilus* Cas9 (St Cas9), and may include mutated Cas9 derived from these organisms. In preferred embodiments, the Cas9 enzymes are selected for smaller size which allows for easier packaging into vectors. The enzyme may be a Cas9 homolog or ortholog. In some embodiments, the CRISPR enzyme is codon-optimized for expression in a eukaryotic cell. In some embodiments, the CRISPR enzyme directs cleavage of one or two strands at the location of the target sequence. In some embodiments, the CRISPR enzyme lacks DNA strand cleavage activity. In some embodiments, the first regulatory element is a polymerase III promoter. In some embodiments, the second regulatory element is a polymerase II promoter. In some embodiments, the guide sequence is at least 15, 16, 17, 18, 19, 20, 25 nucleotides, or between 10-30, or between 15-25, or between 20-24, or between 18-24 nucleotides in length. As described herein, the preferred guide length for SaCas9 is 21, 22, 23 or 24 nucleotides in length (Ran, 2015), although 20 nucleotides in length can be used.

In one aspect, the invention provides a method of modifying a target polynucleotide in a eukaryotic cell. In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized to a target sequence within said target polynucleotide, wherein said guide sequence is linked to a tracr mate sequence which in turn hybridizes to a tracr sequence. In some embodiments, said cleavage comprises cleaving one or two strands at the location of the target sequence by said CRISPR enzyme. In some embodiments, said cleavage results in decreased transcription of a target gene. In some embodiments, the method further comprises repairing said cleaved target polynucleotide by homologous recombination with an exogenous template polynucleotide, wherein said repair results in a mutation comprising an insertion, deletion, or substitution of one or more nucleotides of said target polynucleotide. In some embodiments, said mutation results in one or more amino acid changes in a protein expressed from a gene comprising the target sequence. In some embodiments, the method further comprises delivering one or more vectors to said eukaryotic cell, wherein the one or more vectors drive expression of one or more of: the CRISPR enzyme, the guide sequence linked to the tracr mate sequence, and the tracr sequence. In some embodiments, said vectors are delivered to the eukaryotic cell in a subject. In some embodiments, said modifying takes place in said eukaryotic cell in a cell culture. In some embodiments, the method further comprises isolating said eukaryotic cell from a subject prior to said modifying. In some embodiments, the method further comprises returning said eukaryotic cell and/or cells derived therefrom to said subject.

In one aspect, the invention provides a method of modifying expression of a polynucleotide in a eukaryotic cell. In some embodiments, the method comprises allowing a CRISPR complex to bind to the polynucleotide such that said binding results in increased or decreased expression of said polynucleotide; wherein the CRISPR complex comprises a CRISPR enzyme complexed with a guide sequence hybridized to a target sequence within said polynucleotide, wherein said guide sequence is linked to a tracr mate sequence which in turn hybridizes to a tracr sequence. In some embodiments, the method further comprises delivering one or more vectors to said eukaryotic cells, wherein the one or more vectors drive expression of one or more of: the CRISPR enzyme, the guide sequence linked to the tracr mate sequence, and the tracr sequence.

In one aspect, the invention provides a method of generating a model eukaryotic cell comprising a mutated disease gene. In some embodiments, a disease gene is any gene associated an increase in the risk of having or developing a disease. In some embodiments, the method comprises (a) introducing one or more vectors into a eukaryotic cell, wherein the one or more vectors drive expression of one or more of: a CRISPR enzyme, a guide sequence linked to a tracr mate sequence, and a tracr sequence; and (b) allowing a CRISPR complex to bind to a target polynucleotide to effect cleavage of the target polynucleotide within said disease gene, wherein the CRISPR complex comprises the CRISPR enzyme complexed with (1) the guide sequence that is hybridized to the target sequence within the target polynucleotide, and (2) the tracr mate sequence that is hybridized to the tracr sequence, thereby generating a model eukaryotic cell comprising a mutated disease gene. In some embodiments, said cleavage comprises cleaving one or two strands at the location of the target sequence by said CRISPR enzyme. In some embodiments, said cleavage results in decreased transcription of a target gene. In some embodiments, the method further comprises repairing said cleaved target polynucleotide by homologous recombination with an exogenous template polynucleotide, wherein said repair results in a mutation comprising an insertion, deletion, or substitution of one or more nucleotides of said target polynucleotide. In some embodiments, said mutation results in one or more amino acid changes in a protein expression from a gene comprising the target sequence.

In one aspect, the invention provides a method for developing a biologically active agent that modulates a cell signaling event associated with a disease gene. In some embodiments, a disease gene is any gene associated an increase in the risk of having or developing a disease. In some embodiments, the method comprises (a) contacting a test compound with a model cell of any one of the described embodiments; and (b) detecting a change in a readout that is indicative of a reduction or an augmentation of a cell signaling event associated with said mutation in said disease gene, thereby developing said biologically active agent that modulates said cell signaling event associated with said disease gene.

In one aspect, the invention provides a recombinant polynucleotide comprising a guide sequence upstream of a tracr mate sequence, wherein the guide sequence when expressed directs sequence-specific binding of a CRISPR complex to a corresponding target sequence present in a eukaryotic cell. In some embodiments, the target sequence is a viral sequence present in a eukaryotic cell. In some embodiments, the target sequence is a proto-oncogene or an oncogene.

In one aspect the invention provides for a method of selecting one or more cell(s) by introducing one or more mutations in a gene in the one or more cell (s), the method comprising: introducing one or more vectors into the cell (s), wherein the one or more vectors drive expression of one or more of: a CRISPR enzyme, the present guide (which may comprise of a guide sequence linked to a tracr mate sequence and a tracr sequence), and an editing template; wherein the editing template comprises the one or more mutations that abolish CRISPR enzyme cleavage; allowing homologous recombination of the editing template with the target polynucleotide in the cell(s) to be selected; allowing a CRISPR complex to bind to a target polynucleotide to effect cleavage of the target polynucleotide within said gene, wherein the CRISPR complex comprises the CRISPR enzyme complexed with the present guide in which the guide sequence is hybridized to the target sequence, wherein binding of the CRISPR complex to the target polynucleotide induces cell death, thereby allowing one or more cell(s) in which one or more mutations have been introduced to be selected. In a preferred embodiment, the CRISPR enzyme is Cas9. In another preferred embodiment of the invention the cell to be selected may be a eukaryotic cell. Aspects of the invention allow for selection of specific cells without requiring a selection marker or a two-step process that may include a counter-selection system.

In another aspect the invention comprehends a CRISPR-cas9 (*S. aureus*) system having an X-ray diffraction pattern corresponding to or resulting from any or all of the foregoing and/or a crystal having the structure defined by the crystal co-ordinates in Example 1.

In a further aspect, the invention involves a computer-assisted method for identifying or designing potential compounds to fit within or bind to CRISPR-cas9 system or a functional portion thereof or vice versa (a computer-assisted method for identifying or designing potential CRISPR-cas9 systems or a functional portion thereof for binding to desired compounds) or a computer-assisted method for identifying or designing potential CRISPR-cas9 systems (e.g., with regard to predicting areas of the CRISPR-cas9 system to be able to be manipulated—for instance, based on crystal structure data or based on data of cas9 orthologs, or with respect to where a functional group such as an activator or repressor can be attached to the CRISPR-cas9 system, or as to cas9 truncations or as to designing nickases), said method comprising:

using a computer system, e.g., a programmed computer comprising a processor, a data storage system, an input device, and an output device, the steps of:

(a) inputting into the programmed computer through said input device data comprising the three-dimensional co-ordinates of a subset of the atoms from or pertaining to the CRISPR-cas9 crystal structure, e.g., in the CRISPR-cas9 system binding domain or alternatively or additionally in domains that vary based on variance among cas9 orthologs or as to cas9s or as to nickases or as to functional groups, optionally with structural information from CRISPR-cas9 system complex(es), thereby generating a data set;

(b) comparing, using said processor, said data set to a computer database of structures stored in said computer data storage system, e.g., structures of compounds that bind or putatively bind or that are desired to bind to a CRISPR-cas9 system or as to cas9 orthologs (e.g., as cas9s or as to domains or regions that vary amongst cas9 orthologs) or as to the CRISPR-cas9 crystal structure or as to nickases or as to functional groups;

(c) selecting from said database, using computer methods, structure(s)—e.g., CRISPR-cas9 structures that may bind to desired structures, desired structures that may bind to certain CRISPR-cas9 structures, portions of the CRISPR-cas9 system that may be manipulated, e.g., based on data from other portions of the CRISPR-cas9 crystal structure and/or from cas9 orthologs, truncated cas9s, novel nickases or particular functional groups, or positions for attaching functional groups or functional-group-CRISPR-cas9 systems;

(d) constructing, using computer methods, a model of the selected structure(s); and (e) outputting to said output device the selected structure(s); and optionally synthesizing one or more of the selected structure(s); and further optionally testing said synthesized selected structure(s) as or in a CRISPR-cas9 system;

or, said method comprising: providing the co-ordinates of at least two atoms of the CRISPR-cas9 crystal structure, e.g., at least two atoms of the herein Crystal Structure Table of the CRISPR-cas9 crystal structure or co-ordinates of at least a sub-domain of the CRISPR-cas9 crystal structure ("selected co-ordinates"), providing the structure of a candidate comprising a binding molecule or of portions of the CRISPR-cas9 system that may be manipulated, e.g., based on data from other portions of the CRISPR-cas9 crystal structure and/or from cas9 orthologs, or the structure of functional groups, and fitting the structure of the candidate to the selected co-ordinates, to thereby obtain product data comprising CRISPR-cas9 structures that may bind to desired structures, desired structures that may bind to certain CRISPR-cas9 structures, portions of the CRISPR-cas9 system that may be manipulated, truncated cas9s, novel nickases, or particular functional groups, or positions for attaching functional groups or functional-group-CRISPR-cas9 systems, with output thereof, and optionally synthesizing compound(s) from said product data and further optionally comprising testing said synthesized compound(s) as or in a CRISPR-cas9 system.

In a further aspect, the invention involves a computer-assisted method for identifying or designing i) a potential compound to fit within or bind to a CRISPR-Cas9 system or a portion thereof, which comprises: a) providing the co-ordinates of at least two atoms of the CRISPR-Cas9 system of the Crystal Structure of Table 7, b) providing the structure of a candidate molecule i) for binding to or within the CRISPR-Cas9 system, or ii) for manipulating a portion of the CRISPR-Cas9 system, c) fitting the structure of the candidate molecule to the at least two atoms of the CRISPR-Cas9 system, wherein fitting comprises determining interactions between one or more atoms of the candidate molecule and atoms of the CRISPR-SpCas9 system, and d) selecting the candidate molecule if it is predicted to bind to or within the CRISPR-Cas9 system.

The testing can comprise analyzing the CRISPR-cas9 system resulting from said synthesized selected structure(s), e.g., with respect to binding, or performing a desired function.

The output in the foregoing methods can comprise data transmission, e.g., transmission of information via telecommunication, telephone, video conference, mass communication, e.g., presentation such as a computer presentation (eg POWERPOINT), internet, email, documentary communication such as a computer program (eg WORD) document and the like. Accordingly, the invention also comprehends computer readable media containing: atomic co-ordinate data according to the herein Crystal Structure Coordinates and/or the Figures, said data defining the three dimensional structure of CRISPR-cas9 or at least one sub-domain thereof, or structure factor data for CRISPR-cas9, said structure factor data being derivable from the atomic co-ordinate data of herein Crystal Structure Coordinates and/or the Figures. The computer readable media can also contain any data of the foregoing methods. The invention further comprehends methods a computer system for generating or performing rational design as in the foregoing methods containing either: atomic co-ordinate data according to herein Crystal Structure Coordinates and/or the Figures, said data defining the three dimensional structure of CRISPR-cas9 or at least one sub-domain thereof, or structure factor data for CRISPR-cas9, said structure factor data being derivable from the atomic co-ordinate data of herein Crystal Structure Coordinates and/or the Figures. The invention further comprehends a method of doing business comprising providing to a user the computer system or the media or the three dimensional structure of CRISPR-cas9 or at least one sub-domain thereof, or structure factor data for CRISPR-cas9, said structure set forth in and said structure factor data being derivable from the atomic co-ordinate data of herein Crystal Structure Coordinates and/or the Figures, or the herein computer media or a herein data transmission.

In aspects of the invention, the engineered and optimized guide RNAs and Cas9 enzymes described herein are used in compositions and methods of targeted genome modification.

In some embodiments, phenotypic alteration is preferably the result of genome modification when a genetic disease is targeted, especially in methods of therapy and preferably where a repair template is provided to correct or alter the phenotype.

In some embodiments diseases that may be targeted include those concerned with disease-causing splice defects.

In some embodiments, cellular targets include Hemopoietic Stem/Progenitor Cells (CD34+); Human T cells; and Eye (retinal cells)—for example photoreceptor precursor cells.

In some embodiments Gene targets include: Human Beta Globin—HBB (for treating Sickle Cell Anemia, including by stimulating gene-conversion (using closely related HBD gene as an endogenous template)); CD3 (T-Cells); and CEP920—retina (eye).

In some embodiments disease targets also include: Cancer; HIV, HBV, Thalassemia, Sickle Cell Anemia (based on a point mutation); and ophthalmic disease—for example Leber Congenital Amaurosis (LCA)-causing Splice Defect.

In some embodiments delivery methods include: Cationic Lipid Mediated "direct" delivery of Enzyme-Guide complex (RiboNucleoProtein) and electroporation of plasmid DNA. Aspects of in vivo electroporation are further described in "Plasmid DNA gene therapy by electroporation: principles and recent advances." Murakami T, Sunada Y. Curr Gene Ther. 2011 Dec.; 11(6):447-56 and further Non-Viral approaches are described in "Nonviral approach for targeted nucleic acid delivery." Jafari M, Soltani M, Naahidi S, Karunaratne D N, Chen P. Curr Med Chem. 2012; 19(2): 197-208, herein incorporated by reference in their entirety.

In preferred embodiments, the ortholog is *Staphylococcus aureus* so that the Cas9 is that from or derived from *Staphylococcus aureus* (referred to as SaCas9). In some embodiments, the *Staphylococcus aureus* is *Staphylococcus aureus* subspecies *aureus*.

Although alanine is preferred as the replacement residue in the mutant, other alternatives are available, provided that they retain the function of the modified Cas9. For example, in the case of a residue such as N580, the usual mutant is to Ala to provide N580A. However, alternatives are envisaged that retain the certain function, i.e. are catalytically inactive. Suitable guidance is given below, but preferred alternatives to alanine, may include, in some embodiments, other small and/or non-polar amino acids. These can include glycine, isoleucine, leucine, methionine, phenylalanine, tryptophan, or valine. For example amino acid substitutions in SpCas9 at N863 can include, e.g., N863G, N863V, N863L, N863I, N863F, or N863M; and similarly in SaCas9, N580G, N580V, N580L, N580I, N580F or N580M. The same approach can be applied to any of the other mutants mentioned herein, in particular those mutated to alanine. Further guidance is provided in the table below and accompanying discussion.

It will be appreciated that the terms tracrRNA and tracr sequence can be used interchangeably herein Inventive methods can further comprise delivery of templates, such as repair templates, which may be dsODN or ssODN, see below. Delivery of templates may be via the cotemporaneous or separate from delivery of any or all the CRISPR enzyme, guide, tracr mate or tracrRNA and via the same delivery mechanism or different. In some embodiments, it is preferred that the template is delivered together with the guide, tracr mate and/or tracrRNA and, preferably, also the CRISPR enzyme. An example may be an AAV vector where the CRISPR enzyme is an SaCas9 as described herein.

In some embodiments, the present invention provides modified enzymes that are nickases. Methods directed to use of two or more nickases are also provided, in particular a dual or double nickase approach. In some aspects and embodiments, a single type Cas9 nickase may be delivered, for example a modified SpCas9 or a modified SaCas9 nickase as described herein. This results in the target DNA being bound by either two SpCas9s or 2 SaCas9s. However, it is also envisaged that the different Cas9 orthologs may be used, one Cas9 ortholog on the coding strand of the DNA and another ortholog Cas9 on the non-coding or opposite DNA strand. For instance, a SpCas9 could be used to form a CRISPR complex with a target on one DNA strand and a SaCas9 could be used to form a CRISPR complex with a target on the other DNA strand. Alternatively, a SpCas9 could be used on one strand and an ortholog Cas9 could be used on another strand, or a SaCas9 could be used on one strand and an ortholog Cas9 could be used on another strand. Using dual, but different Cas9 will require delivery or constitutional expression of an additional Cas9, with an ortholog-specific sgRNAs or guide scaffolds for each Cas9 ortholog. However, it may be advantageous to do so as the two different ortholog Cas9s require different PAMs and may also have different guide requirements, thus allowing a greater deal of control for the user, especially if one of the two orthologs was controllable, i.e. inducible.

Guidance is provided below in respect of guide length (the spacer or guide sequence). In some embodiments, for Sp, optimal guide length can vary as low as Keith Joung's 17-nucleotide 'tru-guide.' In some embodiments, for Sa, the optimal guide length may be 20 or 21 or 22 or 23 or 24 nucleotides in length (Ran 2015).

Also provided is a host cell or cell line. This may be an in vivo, ex vivo or in vitro host cell or cell line. The host cell or cell line may, in some embodiments, comprise or have been modified by the composition or enzyme according to the present invention. Also provided are progeny of said host cell or cell line. In some embodiments, the cells of the host cell, cell line or progeny are stem cells or a stem cell line.

Methods, products and uses described herein may be used for non-therapeutic purposes. Furthermore, any of the methods described herein may be applied in vitro and ex vivo.

In relation to the guides in general, but specifically in respect of the sgRNA and the CRISPR complex formed therewith, it is preferable that the guide has one or more of the following features. In some embodiments, the tracr sequence has one or more hairpins and is 30 or more nucleotides in length, more preferably 40 or more nucleotides in length, or more preferably 50 or more nucleotides in length. In some embodiments, the guide sequence is between 10 to 30 nucleotides in length. In some embodiments, the CRISPR/Cas enzyme is a Type II Cas9 enzyme. In some embodiments, the tracr sequence has one or more hairpins and is 30 or more nucleotides in length, more preferably 40 or more nucleotides in length, or more preferably 50 or more nucleotides in length, the guide sequence is between 10 to 30 nucleotides in length and the CRISPR/Cas enzyme is a Type II Cas9 enzyme.

In an aspect, the invention provides use of the modified enzymes and/or guides in double nicking (Cas9 nickase) methods, double dead-Cas9 methods or dual Cas9 nickase+ dead Cas9 methods, i.e. where two Cas9s form CRISPR complexes with (nearby) targets on separate strands of the DNA. These two targets are nearby with an offset creating overhangs as described herein. Optimal overhang lengths are described herein, but range from 1 to 10, 20, 30, 40, 50, 60, 70, 80, 90, or 100, such as 1 to 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 nucleotides on each 3' overhanging end. The offset between the 5' end of each of guide pair is, in some embodiments 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 nucleotides. Ranges of around 15-60, 16-60, 17-60, 18-60, 19-60, 20-60, 21-60, 22-60, 23-60, 24-60, 25-60, 15-55, 16-55, 17-55, 18-55, 19-55, 20-55, 21-55, 22-55, 23-55, 24-, 25-55, 35-60, 15-40, 16-40, 17-40, 18-40, 19-40, 20-40, 21-40, 22-40, 23-40, 24-40, 25-40, 15-45, 16-45, 17-45, 18-45, 19-45, 20-45, 21-45, 22-45, 23-45, 24-45, 25-45, 30-50, 35-55, and especially 35-45 are also preferred in some embodiments.

It is preferred, and this can apply to any of the aspects or embodiments of the invention, that the methods, systems and compositions described herein do not include an NLS. In other words, although generally useful, use of an NLS can be optional. For example, if mitochondrial DNA is to be targeted, then an NLS is not required.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention. It may be advantageous in the practice of the invention to be in compliance with Art. 53(c) EPC and Rule 28(b) and (c) EPC. Nothing herein is to be construed as a promise.

These and other embodiments are disclosed or are obvious from and encompassed by, the following Detailed Description.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2A discloses SEQ ID NOS 109-110. (B) Overview of the sgRNA-target DNA complex. (C and D) Close-up view of the repeat:anti-repeat duplex (C) and stem loop 1 (D). Key interactions are shown as dashed lines. (E) Mutational analysis of sgRNA scaffolds. Effects of mutations on the ability to induce indels in the target EMX locus were examined. Base changes from the sgRNA (+77) scaffold are shown at the respective positions, with dashes indicating unaltered bases (n=3, error bars show mean±S.E.M.). FIG. 2E discloses SEQ ID NOS 111-122 and 111, respectively, in order of appearance. (F) Transcriptional activation of the target ASCL1 (left) and MYOD1 (right) genes by dSaCas9-based activators. See also FIG. 10. (G) Superimposition of the SaCas9 sgRNA and SpCas9 sgRNA (PDB ID 4OO8 (stereoview).

FIG. 4A-4F shows the recognition mechanism of the sgRNA. (A-D) Recognition of the seed region (A), the repeat:anti-repeat duplex (B), stem loop 1 (C), and the basal region of stem loop 1 (D). Hydrogen bonds and salt bridges are shown as dashed lines. In (A), the target DNA strand is omitted for clarity. The inset shows the view positions of panels A-D superimposed on the overall structure of the complex. (E and F) The REC and WED domains of SpCas9 (PDB ID 4UN3) (E) and SaCas9 (F) are depicted. The SpCas9-specific insertions are highlighted in pale blue.

FIGS. 7A-7F show the structural comparison of SpCas9 and SaCas9. (A) Quaternary complex structures of SpCas9 (PDB ID 4UN3) (A) and SaCas9 (B). Stereoviews of REC lobes of SpCas9 (PDB ID 4UN3) (C) and SaCas9 (D). The SpCas9-specific insertions are highlighted in pale blue. WED and PI domains of SpCas9 (PDB ID 4UN3) (E) and SaCas9 (F). The core β-strands in the PI domains are numbered. The PAM sequences are highlighted in purple. Hydrogen bonds are shown as dashed lines. The target DNA strands are omitted for clarity. The SpCas9-specific insertion is highlight in pale blue. PL, phosphate lock loop.

FIG. 8A-8J shows depicts structure-guided engineering of SaCas9 system and its applications. (A) Schematic of the three-component SaCas9 activator system. (B) Design of the dSaCas9-based transcriptional activator and the reporter system. NLS, nuclear localization signal. Lk, peptide linker. 2A, 2A self-cleaving peptide. CMV, cytomegalovirus. (C) Representative fluorescent microscopy images showing the activation of the reporter gene and the low background level of the new reporter design. Scale bar, 100 µm. (D) Optimization of different fusion scaffolds for the dSaCas9-based activator using the reporter system. MS2-SL, stem-loop of the MS2 aptamer. 'IS' denotes the insertion site of the MS2-SL. FIG. 8D discloses SEQ ID NOS 125-131, 126, 132, 129, 126, 133, 131 and 125, respectively, in order of appearance. (E) Transcriptional activation of the endogenous target ASCL1 and MYOD1 genes by dSaCas9-based activators, with previously described dSpCas9-based activators as positive controls. (F) Structural-guided design of split-SaCas9 system. Split sites 1 and 2 were designed at flexible linker regions, whereas split site 3 was designed at the β-strand in the WED domain as a negative control. (G) Cleavage activity of wild-type (WT) SaCas9 and the three different auto-assembled split-SaCas9 designs. (H and I) Schematic of the inducible SaCas9 system. NES, nuclear export signal. ABA, abscisic acid. DA, dimerization domain A. DB, dimerization domain B. (J) Cleavage activity of the wild-type (WT) SaCas9 and three different inducible SaCas9 systems. 'ABA' denotes inducible SaCas9 design based on the abscisic acid sensing system; 'AC' denotes design based on A/C heterodimerizer; 'Rapa' denotes design based on the FRB/FKBP system (see Experimental Procedures section for additional details).

FIG. 10A discloses SEQ ID NOS 134-135, respectively, in order of appearance. (B) Comparison of the genome cleavage activities of the WT and C946A mutant of SaCas9. The activities were evaluated by percentage of indel formation at the DYRK1A locus using next-generation sequencing of targeted amplicon (n=3 for all experiments, error bars indicate MLE) (see Methods for more detail). (n=3, error bars show mean S.E.M.).

FIG. 13A discloses SEQ ID NO: 136 and FIG. 13B discloses SEQ ID NO: 125. (C) Effect of the stem loop 2 truncation on in vitro DNA cleavage activity. An EcoRI-linearized plasmid substrate (150 ng) was cleaved with SaCas9-sgRNA (8, 16, 32 nM) at 37° C. for 1 h, and then resolved on an ethidium bromide-stained 1% agarose gel. (D) Effect of the stem loop 2 truncation on in vivo DNA cleavage activity (n=3, error bars show mean S.E.M.). (E) Superimposition of the SaCas9 sgRNA and SpCas9 sgRNA.

FIG. 15A discloses SEQ ID NOS 134-135, respectively, in order of appearance. (B) Comparison of the genome cleavage activities of the wild-type (WT) and different mutants of SaCas9. The activities were evaluated by percentage of indel formation at the DYRK1A locus using next-generation sequencing of targeted amplicon (n=3 for all experiments, error bars indicate MLE) (see Methods for more detail).

FIG. 22A discloses SEQ ID NO: 139. Panel B shows wild type *S. aureus* Cas9 with the indicated gRNAs targeting five different loci. NHEJ % on the Y axis represents on-target cleavage rates as measured by T7E1 assay.

Figures 1A, 1B, 1C:
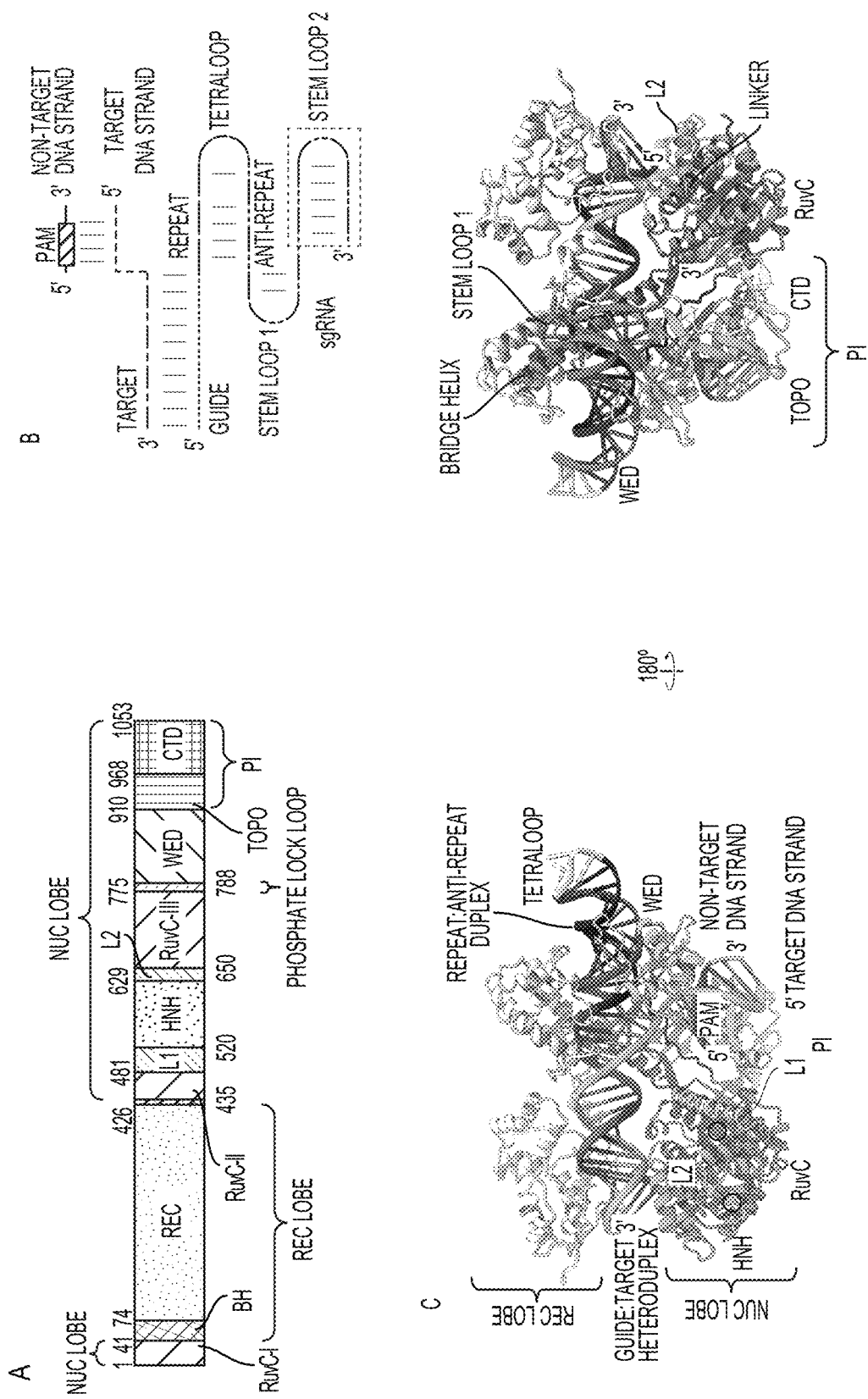
FIG. 1A-1F shows the structure of the SaCas9-sgRNA-target DNA quaternary complex. (A) Domain organization of SaCas9. BH, bridge helix. CTD, C-terminal domain. (B) Schematic of the sgRNA-target DNA complex. The putative stem loop 2 was truncated to facilitate crystallization. (C and D) Ribbon (C) and surface (D) representations of the SaCas9-sgRNA-target DNA complex. The active sites of the RuvC (Asp10) and HNH (Asn580) domains are indicated by red circles. Molecular graphic images were prepared using CueMol (www.cuemol.org). (E and F) Ribbon (E) and surface (F) representations of the SpCas9-sgRNA-target DNA complex (PDB ID 4UN3). The SpCas9-specific insertions in the REC and PI domains are highlighted in pale blue. In (F), the L1 and L2 linker regions and the HNH domain are omitted for clarity.

The figures herein are for illustrative purposes only and are not necessarily drawn to scale.

DETAILED DESCRIPTION OF THE INVENTION

With respect to general information on CRISPR-Cas Systems, components thereof, and delivery of such components, including methods, materials, delivery vehicles, vectors, particles, AAV, and making and using thereof, including as to amounts and formulations, all useful in the practice of the instant invention, reference is made to: U.S. Pat. Nos. 8,999,641, 8,993,233, 8,945,839, 8,932,814, 8,906,616, 8,895,308, 8,889,418, 8,889,356, 8,871,445, 8,865,406, 8,795,965, 8,771,945 and 8,697,359; US Patent Publications US 2014-0310830 (U.S. application Ser. No. 14/105,031), US 2014-0287938 A1 (U.S. application Ser. No. 14/213,991), US 2014-0273234 A1 (U.S. application Ser. No. 14/293,674), US2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429), US 2015-0184139 (U.S. application Ser. No. 14/324,960), Ser. No. 14/054,414; European Patents EP 2 784 162 B1 (EP14170383.5), EP 2 764 103 (EP13824232.6) and EP 2 771 468 B1 (EP13818570.7); and PCT Patent Publications WO 2014/093661 (PCT/US2013/074743), WO 2014/093694 (PCT/US2013/074790), WO 2014/093595 (PCT/US2013/074611), WO 2014/093718 (PCT/US2013/074825), WO 2014/093709 (PCT/US2013/074812), WO 2014/093622 (PCT/US2013/074667), WO 2014/093635 (PCT/US2013/074691), WO 2014/093655 (PCT/US2013/074736), WO 2014/093712 (PCT/US2013/074819), WO 2014/093701 (PCT/US2013/074800), WO2014/018423 (PCT/US2013/051418), WO 2014/204723 (PCT/US2014/041790), WO 2014/204724 (PCT/US2014/041800), WO 2014/204725 (PCT/US2014/041803), WO 2014/204726 (PCT/US2014/041804), WO 2014/204727 (PCT/US2014/041806), WO 2014/204728 (PCT/US2014/041808), WO 2014/204729 (PCT/US2014/041809), WO 2015/089351 (PCT/US2014/069897), WO 2015/089354 (PCT/US2014/069902), WO 2015/089364 (PCT/US2014/069925), WO 2015/089427 (PCT/US2014/070068), WO 2015/089462 (PCT/US2014/070127), WO 2015/089419 (PCT/US2014/070057), WO 2015/089465 (PCT/US2014/070135), WO 2015/089486 (PCT/US2014/070175), PCT/US2015/051691, PCT/US2015/051830. Reference is also made to U.S. provisional patent applications 61/758,468; 61/802,174; 61/806,375; 61/814,263; 61/819,803 and 61/828,130, filed on Jan. 30, 2013; Mar. 15, 2013; Mar. 28, 2013; Apr. 20, 2013; May 6, 2013 and May 28, 2013 respectively. Reference is also made to U.S. provisional patent application 61/836,123, filed on Jun. 17, 2013. Reference is additionally made to U.S. provisional patent applications 61/835,931, 61/835,936, 61/836,127, 61/836,101, 61/836,080 and 61/835,973, each filed Jun. 17, 2013. Further reference is made to U.S. provisional patent applications 61/862,468 and 61/862,355 filed on Aug. 5, 2013; 61/871,301 filed on Aug. 28, 2013; 61/960,777 filed on Sep. 25, 2013 and 61/961,980 filed on Oct. 28, 2013. Reference is yet further made to: PCT Patent applications Nos: PCT/US2014/041803, PCT/US2014/041800, PCT/US2014/041809, PCT/US2014/041804 and PCT/US2014/041806, each filed Jun. 10, 2014; PCT/US2014/041808 filed Jun. 11, 2014; and PCT/US2014/62558 filed Oct. 28, 2014, and U.S. Provisional Patent Application Ser. Nos. 61/915,148, 61/915,150, 61/915,153, 61/915,203, 61/915,251, 61/915,301, 61/915,267,61/915,260, and 61/915,397, each filed Dec. 12, 2013; 61/757,972 and 61/768,959, filed on Jan. 29, 2013 and Feb. 25, 2013; 61/835,936, 61/836,127, 61/836,101, 61/836,080, 61/835,973, and 61/835,931, filed Jun. 17, 2013; 62/010,888 and 62/010,879, both filed Jun. 11, 2014; 62/010,329 and 62/010,441, each filed Jun. 10, 2014; 61/939,228 and 61/939,242, each filed Feb. 12, 2014; 61/980,012, filed Apr. 15, 2014; 62/038,358, filed Aug. 17, 2014; 62/054,490, 62/055,484, 62/055,460 and 62/055,487, each filed Sep. 25, 2014; and 62/069,243, filed Oct. 27, 2014. Reference is made to U.S. provisional patent application 61/930,214 filed on Jan. 22, 2014.

Mention is also made of U.S. application 62/180,709, filed 17 Jun. 2015, PROTECTED GUIDE RNAS (PGRNAS); U.S. application 62/091,455, filed, 12 Dec. 2014, PROTECTED GUIDE RNAS (PGRNAS); U.S. application 62/096,708, 24 Dec. 2014, PROTECTED GUIDE RNAS (PGRNAS); U.S. application 62/091,462, 12 Dec. 2014, DEAD GUIDES FOR CRISPR TRANSCRIPTION FACTORS; U.S. application 62/096,324, 23 Dec. 2014, 62/180,681, 17 Jun. 2015, and 62/237,496, 5 Oct. 2015, DEAD GUIDES FOR CRISPR TRANSCRIPTION FACTORS; U.S. application 62/091,456, 12 Dec. 2014, and 62/180,692, 17 Jun. 2015, ESCORTED AND FUNCTIONALIZED GUIDES FOR CRISPR-CAS SYSTEMS; U.S. application 62/091,461, 12 Dec 2014, DELIVERY, USE AND THERAPEUTIC APPLICATIONS OF THE CRISPR-CAS SYSTEMS AND COMPOSITIONS FOR GENOME EDITING AS TO HEMATOPOETIC STEM CELLS (HSCs); U.S. application 62/094,903, 19 Dec. 2014, UNBIASED IDENTIFICATION OF DOUBLE-STRAND BREAKS AND GENOMIC REARRANGEMENT BY GENOME-WISE INSERT CAPTURE SEQUENCING; U.S. application 62/096,761, 24 Dec. 2014, ENGINEERING OF SYSTEMS, METHODS AND OPTIMIZED ENZYME AND GUIDE SCAFFOLDS FOR SEQUENCE MANIPULATION; U.S. application 62/098,059, 30 Dec. 2014, and 62/181,667, 18 Jun. 2015, RNA-TARGETING SYSTEM; U.S. application 62/096,656, 24 Dec. 2014, and 62/181,151, 17 Jun. 2015, CRISPR HAVING OR ASSOCIATED WITH DESTABILIZATION DOMAINS; U.S. application 62/096,697, 24 Dec. 2014, CRISPR HAVING OR ASSOCIATED WITH AAV; U.S. application 62/098,158, 30 Dec. 2014, ENGINEERED CRISPR COMPLEX INSERTIONAL TARGETING SYSTEMS; U.S. application 62/151,052, 22 Apr. 2015, CELLULAR TARGETING FOR EXTRACELLULAR EXOSOMAL REPORTING; U.S. application 62/054,490, 24 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 61/939,154, 12 Feb. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/055,484, 25 Sep. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, 4 Dec. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, 24 Sep. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, 23 Oct. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/054,675, 24 Sep. 2014, and 62/181,002, 17 Jun. 2015, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, 24 Sep. 2014, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, 25 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, 25 Sep. 2014, MULTIFUNCTIONAL-CRISPR COMPLEXES AND/OR OPTIMIZED ENZYME LINKED FUNCTIONAL-CRISPR COMPLEXES; U.S. application 62/087,475, 4 Dec. 2014, FUNCTIONAL SCREENING WITH OPTIMIZED FUNCTIONAL CRISPR-CAS SYSTEMS; U.S. application 62/055,487, 25 Sep. 2014, FUNCTIONAL SCREENING WITH OPTIMIZED FUNCTIONAL CRISPR-CAS SYSTEMS; U.S. application 62/087,546, 4 Dec. 2014, and 62/181,687, 18 Jun. 2015, MULTIFUNCTIONAL CRISPR COMPLEXES AND/OR OPTIMIZED ENZYME LINKED FUNCTIONAL-CRISPR COMPLEXES; and U.S. application 62/098,285, 30 Dec. 2014, CRISPR MEDIATED IN VIVO MODELING AND GENETIC SCREENING OF TUMOR GROWTH AND METASTASIS.

Mention is made of U.S. applications 62/181,659, 18 Jun. 2015 and 62/207,318, 19 Aug. 2015, ENGINEERING AND OPTIMIZATION OF SYSTEMS, METHODS, ENZYME AND GUIDE SCAFFOLDS OF CAS9 ORTHOLOGS AND VARIANTS FOR SEQUENCE MANIPULATION. Mention is made of U.S. applications 62/181,675, 18 Jun. 2015, and filed 22 Oct. 2015, NOVEL CRISPR ENZYMES AND SYSTEMS, U.S. application 62/232,067, 24 Sep. 2015, U.S. application 62/205,733, 16 Aug. 2015, U.S. application 62/201,542, 5 Aug. 2015, U.S. application 62/193,507, 16 Jul. 2015, and U.S. application 62/181,739, 18 Jun. 2015, each entitled NOVEL CRISPR ENZYMES AND SYSTEMS and of U.S. application 62/245,270, 22 Oct. 2015, NOVEL CRISPR ENZYMES AND SYSTEMS. Mention is also made of U.S. application 61/939,256, 12 Feb. 2014, and WO 2015/089473 (PCT/US2014/070152), 12 Dec. 2014, each entitled ENGINEERING OF SYSTEMS, METHODS AND OPTIMIZED GUIDE COMPOSITIONS WITH NEW ARCHITECTURES FOR SEQUENCE MANIPULATION. Mention is also made of PCT/US2015/045504, 15 Aug. 2015, U.S. application 62/180,699, 17 Jun. 2015, and U.S. application 62/038,358, 17 Aug. 2014, each entitled GENOME EDITING USING CAS9 NICKASES.

Each of these patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

Also with respect to general information on CRISPR-Cas Systems, mention is made of the following (also hereby incorporated herein by reference):

Multiplex genome engineering using CRISPR/Cas systems.
  Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121):819-23 (2013);

RNA-guided editing of bacterial genomes using CRISPR-Cas systems. Jiang W., Bikard D., Cox D., Zhang F, Marraffini L A. Nat Biotechnol March; 31(3):233-9 (2013);

One-Step Generation of Mice Carrying Mutations in Multiple Genes by CRISPR/Cas-Mediated Genome Engineering. Wang H., Yang H., Shivalila C S., Dawlaty M M., Cheng A W., Zhang F., Jaenisch R. Cell May 9; 153(4): 910-8 (2013);

Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. August 22; 500(7463): 472-6. doi: 10.1038/Nature12466. Epub 2013 Aug. 23 (2013);

Double Nicking by RNA-Guided CRISPR Cas9 for Enhanced Genome Editing Specificity. Ran, F A., Hsu, P D., Lin, C Y., Gootenberg, J S., Konermann, S., Trevino, A E., Scott, D A., Inoue, A., Matoba, S., Zhang, Y., & Zhang, F. Cell August 28. pii: S0092-8674(13)01015-5 (2013-A);

DNA targeting specificity of RNA-guided Cas9 nucleases. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. Nat Biotechnol doi:10.1038/nbt.2647 (2013);

Genome engineering using the CRISPR-Cas9 system. Ran, F A., Hsu, P D., Wright, J., Agarwala, V., Scott, D A., Zhang, F. Nature Protocols November; 8(11):2281-308 (2013-B);

Genome-Scale CRISPR-Cas9 Knockout Screening in Human Cells. Shalem, O., Sanjana, N E., Hartenian, E., Shi, X., Scott, D A., Mikkelson, T., Heckl, D., Ebert, B L., Root, D E., Doench, J G., Zhang, F. Science December 12. (2013). [Epub ahead of print];

Crystal structure of cas9 in complex with guide RNA and target DNA. Nishimasu, H., Ran, F A., Hsu, P D., Konermann, S., Shehata, S I., Dohmae, N., Ishitani, R., Zhang, F., Nureki, O. Cell February 27, 156(5):935-49 (2014);

Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. April 20. doi: 10.1038/nbt.2889 (2014);

CRISPR-Cas9 Knockin Mice for Genome Editing and Cancer Modeling. Platt R J, Chen S, Zhou Y, Yim M J, Swiech L, Kempton H R, Dahlman J E, Parnas O, Eisenhaure T M, Jovanovic M, Graham D B, Jhunjhunwala S, Heidenreich M, Xavier R J, Langer R, Anderson D G, Hacohen N, Regev A, Feng G, Sharp P A, Zhang F. Cell 159(2): 440-455 DOI: 10.1016/j.cell.2014.09.014 (2014);

Development and Applications of CRISPR-Cas9 for Genome Engineering, Hsu P D, Lander E S, Zhang F., Cell. June 5; 157(6):1262-78 (2014).

Genetic screens in human cells using the CRISPR/Cas9 system, Wang T, Wei J J, Sabatini D M, Lander E S., Science. January 3; 343(6166): 80-84. doi:10.1126/science.1246981 (2014);

Rational design of highly active sgRNAs for CRISPR-Cas9-mediated gene inactivation, Doench J G, Hartenian E, Graham D B, Tothova Z, Hegde M, Smith I, Sullender M, Ebert B L, Xavier R J, Root D E., (published online 3 Sep. 2014) Nat Biotechnol. December; 32(12):1262-7 (2014);

In vivo interrogation of gene function in the mammalian brain using CRISPR-Cas9, Swiech L, Heidenreich M, Banerjee A, Habib N, Li Y, Trombetta J, Sur M, Zhang F., (published online 19 Oct. 2014) Nat Biotechnol. January; 33(1):102-6 (2015);

Genome-scale transcriptional activation by an engineered CRISPR-Cas9 complex, Konermann S, Brigham M D, Trevino A E, Joung J, Abudayyeh O O, Barcena C, Hsu P D, Habib N, Gootenberg J S, Nishimasu H, Nureki O, Zhang F., Nature. January 29; 517(7536):583-8 (2015).

A split-Cas9 architecture for inducible genome editing and transcription modulation, Zetsche B, Volz S E, Zhang F., (published online 2 Feb. 2015) Nat Biotechnol. February; 33(2):139-42 (2015);

Genome-wide CRISPR Screen in a Mouse Model of Tumor Growth and Metastasis, Chen S, Sanjana N E, Zheng K, Shalem O, Lee K, Shi X, Scott D A, Song J, Pan J Q, Weissleder R, Lee H, Zhang F, Sharp P A. Cell 160, 1246-1260, Mar. 12, 2015 (multiplex screen in mouse), and In vivo genome editing using *Staphylococcus aureus* Cas9, Ran F A, Cong L, Yan W X, Scott D A, Gootenberg J S, Kriz A J, Zetsche B, Shalem O, Wu X, Makarova K S, Koonin E V, Sharp P A, Zhang F., (published online 1 Apr. 2015), Nature. April 9; 520(7546):186-91(2015).

Shalem et al., "High-throughput functional genomics using CRISPR-Cas9," Nature Reviews Genetics 16, 299-311 (May 2015).

Xu et al., "Sequence determinants of improved CRISPR sgRNA design," Genome Research 25, 1147-1157 (August 2015).

Parnas et al., "A Genome-wide CRISPR Screen in Primary Immune Cells to Dissect Regulatory Networks," Cell 162, 675-686 (Jul. 30, 2015).

Ramanan et al., CRISPR/Cas9 cleavage of viral DNA efficiently suppresses hepatitis B virus," Scientific Reports 5:10833. doi: 10.1038/srep10833 (Jun. 2, 2015)

Nishimasu et al., Crystal Structure of *Staphylococcus aureus* Cas9," Cell 162, 1113-1126 (Aug. 27, 2015)

BCL11A enhancer dissection by Cas9-mediated in situ saturating mutagenesis, Canver et al., Nature 527(7577): 192-7 (Nov. 12, 2015) doi: 10.1038/nature15521. Epub 2015 Sep. 16.

*Cpf1 Is a Single RNA-Guided Endonuclease of a Class 2 CRISPR-Cas System*, Zetsche et al., Cell 163, 759-71 (Sep. 25, 2015).

*Discovery and Functional Characterization of Diverse Class 2 CRISPR-Cas Systems*, Shmakov et al., Molecular Cell, 60(3), 385-397 doi: 10.1016/j.molcel.2015.10.008 Epub Oct. 22, 2015.

*Rationally engineered Cas9 nucleases with improved specificity*, Slaymaker et al., Science 2015 Dec. 1. pii: aad5227. [Epub ahead of print].

each of which is incorporated herein by reference, may be considered in the practice of the instant invention, and discussed briefly below:

Cong et al. engineered type II CRISPR-Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of Streptococcus pneumoniae and Escherichia coli. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in S. pneumoniae, nearly 100% of cells that were recovered using the described approach contained the desired mutation, and in E. coli, 65% that were recovered contained the mutation.

Wang et al. (2013) used the CRISPR/Cas system for the one-step generation of mice carrying mutations in multiple genes which were traditionally generated in multiple steps by sequential recombination in embryonic stem cells and/or time-consuming intercrossing of mice with a single mutation. The CRISPR/Cas system will greatly accelerate the in vivo study of functionally redundant genes and of epistatic gene interactions.

Konermann et al. (2013) addressed the need in the art for versatile and robust technologies that enable optical and chemical modulation of DNA-binding domains based CRISPR Cas9 enzyme and also Transcriptional Activator Like Effectors Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors showed that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and sgRNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knockout (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of Streptococcus pyogenes Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from Streptococcus pyogenes loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays.

Shalem et al. (2015) described ways in which catalytically inactive Cas9 (dCas9) fusions are used to synthetically repress (CRISPRi) or activate (CRISPRa) expression, showing. advances using Cas9 for genome-scale screens, including arrayed and pooled screens, knockout approaches that inactivate genomic loci and strategies that modulate transcriptional activity.

Xu et al. (2015) assessed the DNA sequence features that contribute to single guide RNA (sgRNA) efficiency in CRISPR-based screens. The authors explored efficiency of CRISPR/Cas9 knockout and nucleotide preference at the cleavage site. The authors also found that the sequence preference for CRISPRi/a is substantially different from that for CRISPR/Cas9 knockout.

Parnas et al. (2015) introduced genome-wide pooled CRISPR-Cas9 libraries into dendritic cells (DCs) to identify genes that control the induction of tumor necrosis factor (Tnf) by bacterial lipopolysaccharide (LPS). Known regulators of Tlr4 signaling and previously unknown candidates were identified and classified into three functional modules with distinct effects on the canonical responses to LPS. Ramanan et al (2015) demonstrated cleavage of viral episomal DNA (cccDNA) in infected cells. The HBV genome exists in the nuclei of infected hepatocytes as a 3.2 kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Nishimasu et al. (2015) reported the crystal structures of SaCas9 in complex with a single guide RNA (sgRNA) and its double-stranded DNA targets, containing the 5'-TTGAAT-3' PAM and the 5'-TTGGGT-3' PAM. A structural comparison of SaCas9 with SpCas9 highlighted both structural conservation and divergence, explaining their distinct PAM specificities and orthologous sgRNA recognition.

Canver et al. (2015) demonstrated a CRISPR-Cas9-based functional investigation of non-coding genomic elements. The authors we developed pooled CRISPR-Cas9 guide RNA libraries to perform in situ saturating mutagenesis of the human and mouse BCL11A enhancers which revealed critical features of the enhancers.

Zetsche et al. (2015) reported characterization of Cpf1, a class 2 CRISPR nuclease from *Francisella novicida* U112 having features distinct from Cas9. Cpf1 is a single RNA-guided endonuclease lacking tracrRNA, utilizes a T-rich protospacer-adjacent motif, and cleaves DNA via a staggered DNA double-stranded break.

Shmakov et al. (2015) reported three distinct Class 2 CRISPR-Cas systems. Two system CRISPR enzymes (C2c1 and C2c3) contain RuvC-like endonuclease domains distantly related to Cpf1. Unlike Cpf1, C2c1 depends on both crRNA and tracrRNA for DNA cleavage. The third enzyme (C2c2) contains two predicted HEPN RNase domains and is tracrRNA independent.

Slaymaker et al (2015) reported the use of structure-guided protein engineering to improve the specificity of *Streptococcus pyogenes* Cas9 (SpCas9). The authors developed "enhanced specificity" SpCas9 (eSpCas9) variants which maintained robust on-target cleavage with reduced off-target effects.

Also, "Dimeric CRISPR RNA-guided FokI nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), relates to dimeric RNA-guided FokI Nucleases that recognize extended sequences and can edit endogenous genes with high efficiencies in human cells.

In addition, mention is made of PCT application PCT/US14/70057, entitled "DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS (claiming priority from one or more or all of U.S. provisional patent applications: 62/054,490, filed Sep. 24, 2014; 62/010,441, filed Jun. 10, 2014; and 61/915,118, 61/915,215 and 61/915,148, each filed on Dec. 12, 2013) ("the Particle Delivery PCT"), incorporated herein by reference, with respect to a method of preparing an sgRNA-and-Cas9 protein containing particle comprising admixing a mixture comprising an sgRNA and Cas9 protein (and optionally HDR template) with a mixture comprising or consisting essentially of or consisting of surfactant, phospholipid, biodegradable polymer, lipoprotein and alcohol;

and particles from such a process. For example, wherein Cas9 protein and sgRNA were mixed together at a suitable, e.g., 3:1 to 1:3 or 2:1 to 1:2 or 1:1 molar ratio, at a suitable temperature, e.g., 15-30 C, e.g., 20-25 C, e.g., room temperature, for a suitable time, e.g., 15-45, such as 30 minutes, advantageously in sterile, nuclease free buffer, e.g., 1×PBS. Separately, particle components such as or comprising: a surfactant, e.g., cationic lipid, e.g., 1,2-dioleoyl-3-trimethylammonium-propane (DOTAP); phospholipid, e.g., dimyristoylphosphatidylcholine (DMPC); biodegradable polymer, such as an ethylene-glycol polymer or PEG, and a lipoprotein, such as a low-density lipoprotein, e.g., cholesterol were dissolved in an alcohol, advantageously a C1-6 alkyl alcohol, such as methanol, ethanol, isopropanol, e.g., 100% ethanol. The two solutions were mixed together to form particles containing the Cas9-sgRNA complexes. Accordingly, sgRNA may be pre-complexed with the Cas9 protein, before formulating the entire complex in a particle. Formulations may be made with a different molar ratio of different components known to promote delivery of nucleic acids into cells (e.g. 1,2-dioleoyl-3-trimethylammonium-propane (DOTAP), 1,2-ditetradecanoyl-sn-glycero-3-phosphocholine (DMPC), polyethylene glycol (PEG), and cholesterol) For example DOTAP:DMPC:PEG:Cholesterol Molar Ratios may be DOTAP 100, DMPC 0, PEG 0, Cholesterol 0; or DOTAP 90, DMPC 0, PEG 10, Cholesterol 0; or DOTAP 90, DMPC 0, PEG 5, Cholesterol 5. DOTAP 100, DMPC 0, PEG 0, Cholesterol 0. That application accordingly comprehends admixing sgRNA, Cas9 protein and components that form a particle; as well as particles from such admixing. Aspects of the instant invention can involve particles; for example, particles using a process analogous to that of the Particle Delivery PCT, e.g., by admixing a mixture comprising sgRNA and/or Cas9 as in the instant invention and components that form a particle, e.g., as in the Particle Delivery PCT, to form a particle and particles from such admixing (or, of course, other particles involving sgRNA and/or Cas9 as in the instant invention).

Applicants solved the structures of SaCas9 (residues 1-1053; N580A/C946A). The role of the N580A mutation was to prevent full cleavage of the target DNA during crystallization. Other mutations are known, such as D10A. Applicants replaced a non-conserved cysteine residue (Cys946) with alanine for crystallization, since the C946A mutation was tested and did not affect the DNA cleavage activity in vivo. Accordingly, in one aspect, the present invention provides a modified Cas9 comprising a single nickase mutation and a further mutation in a non-conserved residue. This modified SaCas9 is useful in forming a crystal, for example, if further studies are required. The single nickase mutation includes either a mutation at the active (catalytic) site in the HNH domain or a mutation at the active (catalytic) site in the RuvC domain. The non-conserved residue is, in some embodiments, a cysteine residue. Cys946 is preferred in SaCas9 or a corresponding position in an orthologous CRISPR-Cas9 enzyme. Potential nickase compostions may be generated by introducing one or more mutations in one of the catalytic domains, either RuvC or HNH. Embodiments further include modified SaCas9 comprising double, triple, and quadruple mutants which may include mutations at D10 & C946, preferably D10A and C946A; or N580 and C946, preferably N580A and C946A. Other useful embodiments for crystallization include a complex comprising at least one, preferably two, more preferably three and most preferably all four of the following: the modified Cas9 just described; a 73-nucleotide (nt) sgRNA; a 28-nt target DNA strand; and/or a 8-nt non-target DNA strand containing the PAM. In an embodiment of the invention, the PAM is NNGRRN. In some such embodiments, the PAM is, without limitation, 5'-TTGAAT-3', 5'-TTGGGT-3', 5'-TTGAAA-3', 5'-TTGAAG-3', 5'-TTGAAT-3'

The herein provided structural information for SaCas9 relates to a crystal structure of a complex comprising SaCas9, a SaCas9 sgRNA, a target DNA and a non-target DNA strand. The SaCas9 sgRNA has a +73 architecture wherein one of the putative stem loops (stem loop 2) is truncated for improved crystal quality. Given that SaCas9 sgRNA lacking stem loop 2 supports cleavage in vitro but not in vivo, the herein described compositions, methods and systems of the invention encompass any alteration or one or more modifications to arrive at optimized enzymes and guide scaffolds that allow for a CRISPR-Cas system that is functional in a physiologically relevant environment, e.g. in an in vivo environment. Furthermore, any such alteration or one or more modifications, e.g. mutations to the nucleotide sequence of the SaCas9 sg RNA achieves a favorable thermodynamic state for binding and functionality.

A "favorable thermodynamic state" relates to an equilibrium state comprising a form of the product (e.g., molecule, compound, protein, etc.) wherein the Gibbs free energy is lower than that of the energy of the reactant or starting material thus producing an energetically favorable state. The energetically favorable state will proceed through a higher energy state than the reactant overcoming any activation energy (Ea) to arrive at a lower energy conformation. Factors which influence the energy conformation include, but are not limited to, the nature of the solution (e.g., temperature or pH), the primary nucleotide sequence, secondary conformation (e.g, hydrogen bonding, Van der Waals forces, electrostatic interactions, dipole-dipole interaction) the size of the protein, etc.

The CRISPR-SaCas9 complex structure described herein has been elucidated by X-ray crystallography and describes structural features which are key to understanding the biological functionality of the CRISPR-Cas9 system in general and the comparative data between the CRISPR-SaCa9 complex structure and the CRISPR-SpCas9 structure allow for a rational design basis that extends to other orthologous Cas9 enzyme complexes. Applicants determined that the larger SpCas9 enzyme allowed for more modifications and optimizations, whereas the smaller SaCas9 enzyme was less forgiving. Thus, an aspect of the invention encompasses identifying parameters of the system which are important for an Cas enzyme and/or its sgRNA to work within the CRISPR system.

Generally, the basic element of specific site recognition is between a short stretch of base pairs (e.g., three) and a small piece of protein usually part of an alpha-helix or even a beta-sheet in some instances. Despite differences in which the protein inserts into the major groove of a DNA, for example, there are common features among different eukaryotic families.

Figure 23:
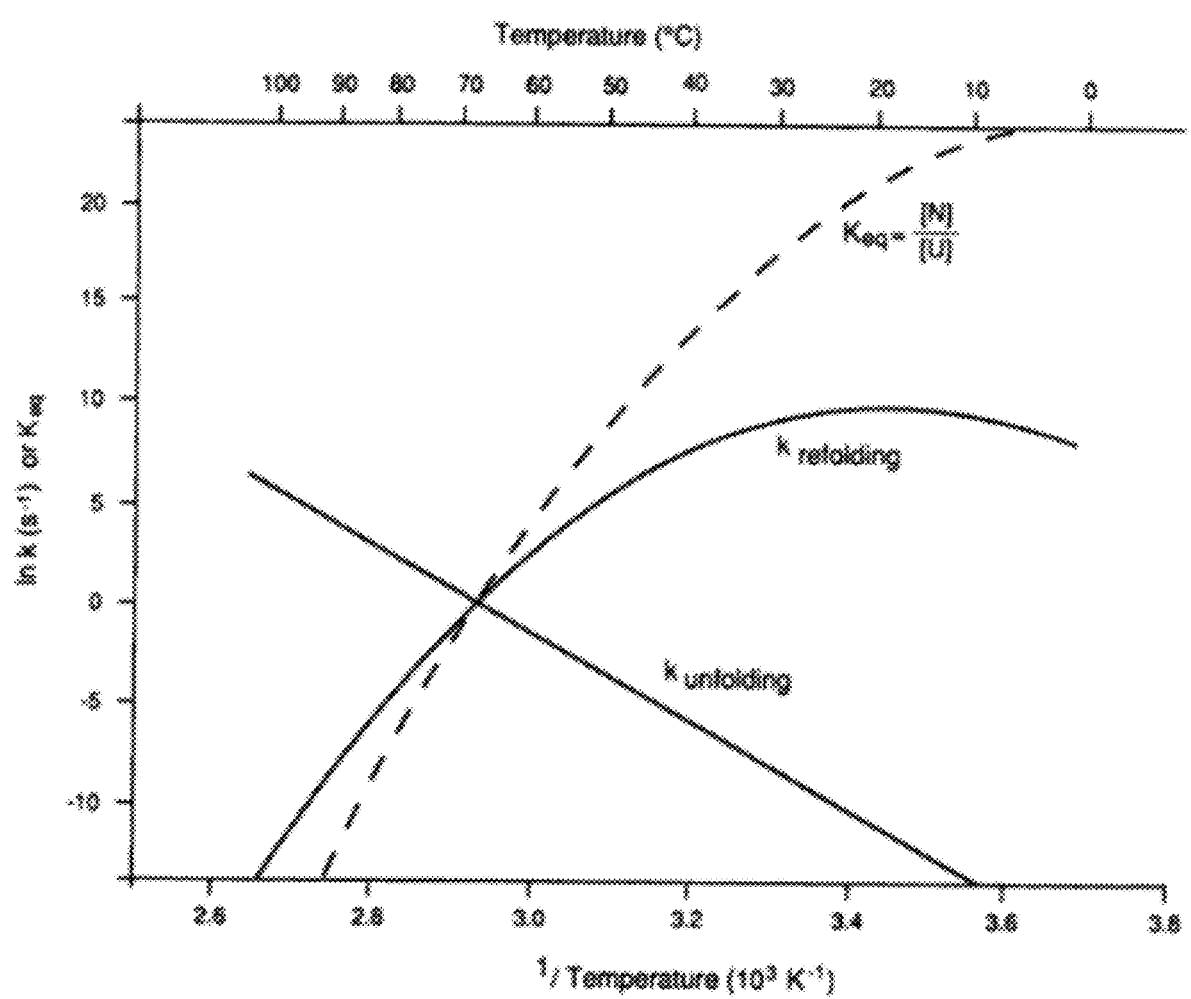
FIG. 23 is a plot showing typical temperature dependence of the rates of equilibria of protein folding transitions.

In the plot in FIG. 23, typical temperature dependence of the rates of equilibria of protein folding transitions do not involve intrinsically slow isomerizations. The natural logarithms of the rate constants for unfolding and refolding are plotted as a function of reciprocal temperature, in an Arrhenius plot. The similar plot of the equilibrium constant Keq between the native (N) and unfolded (U) states is a Van't Hoff plot. The curvature of the Van't Hoff plot is due to the greater apparent heat capacity of U than of N. The linear Arrhenius plot for the rates of unfolding indicates that the transition state has the same heat capacity as N. The greater heat capacity of U is reflected entirely in the curvature of the Arrhenius plot for the rate of refolding, because ln Keq=ln $k_{refolding}$-ln $k_{folding}$. (Data generated by Creighton, T. Biochem. J. 270:1-16(1990), reproduced from Meyers, R. A., ed., "Molecular Biology and Biotechnology: A Comprehensive Desk Reference" 1995, p. 756).

With respect to the refolding of the protein, the protein will often times adopt a non-random conformation and often appears similar to the molten globule state. However, the refolded protein consists of subdomains of native-like secondary structure which interact and are stable with each other. (Meyers, R. A., ed., "Molecular Biology and Biotechnology: A Comprehensive Desk Reference" 1995).

The transition state of a protein ($E^{\ddagger}$) is the high energy conformation which usually appears as the distorted form of the native conformation. It is possible to characterize the transition state by altering the folding conditions and/or the covalent structure of the protein to determine the effects on the rates of unfolding and refolding. (Meyers, R. A., ed., "Molecular Biology and Biotechnology: A Comprehensive Desk Reference" 1995).

Protein structures are also constantly changing in solution, thus when modeling or elucidating a protein structure, the model most often represents the average of the most frequently observed positions of the atoms. It is important, therefore, to take into account the effect of the solution on the protein structure in vivo. (Meyers, R. A., ed., "Molecular Biology and Biotechnology: A Comprehensive Desk Reference" 1995). Solution properties which can influence the protein structure include intermolecular forces between solute (e.g., protein) and solvent particles and energy changes in the solution (e.g., separation of solute particles, separation of solvent particles, and new interactions between solute and solvent).

As such, dynamic models can predict or ascertain catalytically important residues which would otherwise be difficult to determine via a static protein model. A residue which may appear to be inaccessible to the ligand molecule may play a significant role of the molecular trajectory calculated in a dynamic model. (Meyers, R. A., ed., "Molecular Biology and Biotechnology: A Comprehensive Desk Reference" 1995).

Aspects of the invention relate to arriving at new crystal structures (e.g. quaternary complexes of SaCas9 with a sgRNA including stem loop 2 and other CRISPR-Cas complexes of orthologues CRISPR enzymes) as well as making modifications and optimizations to the CRISPR-Cas enzyme and its sgRNA to arrive at a favorable thermodynamic state. The favorable thermodynamic state can be influenced by one or more of the solution properties and/or the secondary structure of the protein. Factors include but are not limited to temperature, pH, pressure, and/or protein folding dynamics and these should be taken into account to ensure that the CRISPR-Cas enzyme complex is functional in a physiologically relevant environment, e.g. in vivo.

The structure revealed that SaCas9 has a bilobed architecture consisting of a REC lobe (residues 41-425) and a NUC lobe (residues 1-40 and 435-1053). The two lobes are connected by an arginine-rich bridge helix (residues 41-73) and a linker loop (residues 426-434) (see FIG. 1). As such, any of these residues in SaCas9, or corresponding positions in ortholog Cas9s, are envisaged to be suitable split sites for a Split Cas9 approach.

In an aspect, the invention provides a non-naturally occurring or engineered inducible CRISPR-Cas system. In an aspect, the inducible CRISPR-Cas system comprises separate NUC and REC lobes from a Cas9 (Wright, A. V. et al. Rational design of a splitCas9 enzyme complex. Proc. Natl. Acad. Sci. USA 112, 2984-2989 (2015)). Upon addition of gRNA, the two Cas9 parts assemble into an intact complex with cleavage activity similar to that of the wildtype protein. However, although a truncated gRNA is no longer able to assemble the split Cas9, it can still bring intact Cas9 to its target sequence, which encompasses an alternative approach of using this system.

In an aspect the invention provides a non-naturally occurring or engineered inducible CRISPR-Cas system wherein peptide dimerization domains, rather than gRNA, bring the Cas9 parts together in response to small molecules or light. In other words, two or more parts of the Cas9 are brought together to reconstitute the Cas9 by peptide-driven dimerization as further described in Zetsche, B. et al. "A splitCas9 architecture for inducible genome editing and transcription modulation". Nat. Biotechnol. 33, 139-142 (2015), herein incorporated by reference in its entirety. A split in the Cas9 sequence was used to separate the C' and N' terminal domains. The N' and C' terminal parts are fused with proteins that dimerize upon the addition of rapamycin. Background cleavage can be eliminated in the absence of rapamycin by shuttling the N' terminal part of Cas9 out of the nucleus with a nuclear export signal and ensuring that only the assembled complex would be transported back into the nucleus by outfitting the C' terminal fragments with two import signals. This can be used for genome editing and inducible transcriptional activation.

In other words, Cas9 can be split into two distinct fragments, which reconstitute a functional full-length Cas9 nuclease when brought back together using chemical induction. The split Cas9 architecture will be useful for a variety of applications. For example, split Cas9 may enable genetic strategies for restricting Cas9 activity to intersectional cell populations by putting each fragment under a different tissue specific promoter. Additionally, different chemically inducible dimerization domains such as APA and gibberellin may also be employed. This split Cas9 system can be used in the present invention in order to control activity of the Cas9 described herein.

Applicants have also now determined new and specific split points for SaCas9 based on the crystal coordinate data. These are described below with reference to SaCas9.

In an aspect, the inducer energy source is preferably chemical induction (or is provided by such).

The split position or location is the point at which the first part of the Cas9 enzyme is separated from the second part. In some embodiments, the first will comprise or encode amino acids 1 to X, whilst the second part will comprise or encode amino acids X+1 to the end. In this example, the numbering is contiguous, but this may not always be necessary as amino acids (or the nucleotides encoding them) could be trimmed from the end of either of the split ends, provided that sufficient DNA binding activity and, if required, DNA nickase or cleavage activity is retained, for example at least 40%, 50%, 60%, 70%, 80%, 90% or 95% activity compared to wildtype Cas9.

The exemplary numbering provided herein may be in reference to the wildtype protein, preferably the wildtype SpCas9 protein. However, it is envisaged that mutants of the wildtype SpCas9 protein can be used. For example, in the crystal data paper itself, a deadCas9 was used and these are preferred in some embodiments, see the discussion elsewhere herein. The numbering may also not follow exactly the SpCas9 numbering as, for instance, some N' or C' terminal truncations or deletions may be used, but this can be addressed suing standard sequence alignment tools. Orthologs are also preferred as a sequence alignment tool.

Thus, the split position may be selected using ordinary skill in the art, for instance based on the crystal data provided in the herein cited materials.

In SpCas9, all of the split points in the following table worked in that Applicants were able to reconstitute Cas9 with the inducible dimerization domains.

| Fusion Side | Structure | Domain |
|---|---|---|
| 202A/203S | Outside loop | Rec 2 |
| 255F/256D | Outside loop | Rec 2 |
| 310E/311I | Outside loop | Rec 1 |
| 534R/535K | Outside loop | Rec 1 |
| 572E/573C | Unstructured | Rec 1 |
| 713S/714G | Unstructured | Rec 1 |
| 1003L/104E | Unstructured | RuvC3 |
| 1054G/1055E | Unstructured | RuvC3 |
| 1114N/1115S | Unstructured | PI |
| 1152K/1153S | Outside loop | PI |
| 1245K/1246G | Unstructured | PI |

Table showing Amino Acid position of split in SpCas9 (1368 a.a. in total)

Identifying potential split sites is most simply done with the help of a crystal structure. For Sp mutants, it should be readily apparent what the corresponding position for, for example, a sequence alignment. For non-Sp enzymes one can use the crystal structure of an ortholog if a relatively high degree of homology exists between the ortholog and the intended Cas9.

Ideally, the split position should be located within a region or loop. Preferably, the split position occurs where an interruption of the amino acid sequence does not result in the partial or full destruction of a structural feature (e.g. alpha-helixes or beta-sheets). Unstructured regions (regions that did not show up in the crystal structure because these regions are not structured enough to be "frozen" in a crystal) are often preferred options. Applicants previously made splits in all unstructured regions that are exposed on the surface of SpCas9. The positions within the unstructured regions or outside loops may not need to be exactly the numbers provided above, but may vary by, for example 1, 2, 3, 4, 5, 6, 7, 8, 9, or even 10 amino acids either side of the position given above, depending on the size of the loop, so long as the split position still falls within an unstructured region of outside loop. In an aspect, amino acids at the split may be deleted or substituted in the modified enzyme. For example, there may be deleted 1, 2, 3, 4, 5, 6, 7, 8, 9, or even 10 amino acids. Further, additions or substitutions may be made at the N-terminal and or C-terminal amino acids that comprise the split, for example to enhance stability of the split protein, or to reduce or prevent degradation of the subunits of the split protein. In an aspect, the split point falls in an unstructured loop. In an aspect, the split point does not fall in an area of secondary structure. In an aspect, the split point does not fall in a region interacting with the sgRNA and/or the DNA.

A split in an outside loop of the Rec 2 domain is preferred in some embodiments. In other embodiments, a split in an outside loop of Rec 1 is preferred. In other embodiments, a split in an outside loop of PI is preferred. In other embodiments, a split in an unstructured region of Rec 1 is preferred. In other embodiments, a split in an unstructured region of RuvC-III is preferred. In other embodiments, a split in an unstructured region of PI is preferred. In an embodiment of the invention, a split is made in SaCas9 between amino acids 739 and 740 in RuvC-III. In an embodiment of the invention, a split is made in a linker of SaCas9 between amino acids 430 and 431.

Applicants have now determined new split sites for SaCas9.

| Fusion Side | Structure | Domain |
|---|---|---|
| 430/431 | Unstructured loop | Between REC and NUC lobes (between 3'/C' terminal end of Rec Domain and 5'/N' terminal end of RuvCII domain). |
| 739/740 | Unstructured region | RuvCIII domain |

Table showing Amino Acid position of split in SaCas9 (1053 a.a. in total)

In some embodiments, with any Cas9, the split is preferably positioned in an unstructured loop or an unstructured region. In some embodiments, with split SaCas9, the split is preferably positioned at or around amino acid position 430 or 431, in particular between 430 and 431. In some embodiments, with split SaCas9, the split is preferably positioned at or around amino acid position 739 or 740, in particular between 739 and 740.

With split SaCas9, a certain amount of variation should be tolerated on each side of each split. For example, for split point 1: −4 to +2 amino acid positions is ideal. In some embodiments, the split is positioned at (ideally C' terminal to) amino acid positions 426, 427, 428, 429 or 430. In some embodiments, the split is positioned at (ideally C' terminal to) amino acid positions 431, 432 or even 433. In some embodiments, the split is positioned at (ideally C' terminal to) amino acid positions 426-433.

Without being bound by theory, it is understood that any further towards the N' terminal than −4 and the split position gets too close to the sgRNA. Further towards the C' terminal than +2 and the split position gets too close to an alpha-helix.

For split point 2: the split point at 739-740 may be moved within −7 to +4 amino acid positions. In some embodiments, the split is positioned at (ideally C' terminal to) amino acid positions 732, 733, 734, 735, 736, 737, 738, or 739. In some embodiments, the split is positioned at (ideally C' terminal to) amino acid positions 740, 471, 742, 743, 744 or even 745. In some embodiments, the split is positioned at (ideally C' terminal to) amino acid positions 732-745. Without being bound by theory, it is understood that split 2 is located in the middle of an unstructured region flanked by alpha-helixes. Corresponding positions in other orthologues are also envisaged.

The promoter used for SaCas9 splits is CBh, and bGHpA is the polyA signal in all constructs cloned so far and are planning to clone. However, we know that CMV, EF1alpha and EFS (minimal EF1a promoter) work well for SpCas9 and will also work for SaCas9. In an aspect, the promoter used for SaCas9 splits is CBh. In other aspects, CMV, EF1alpha and EFS (minimal EF1a promoter) may be used as promoters. In an aspect, a polyA tail such as bGHpA may be used.

An inducer energy source may be considered to be simply an inducer or a dimerizing agent. The term 'inducer energy source' is used herein throughout for consistency. The inducer energy source (or inducer) acts to reconstitute the Cas9. In some embodiments, the inducer energy source brings the two parts of the Cas9 together through the action of the two halves of the inducible dimer. The two halves of the inducible dimer therefore are brought together in the presence of the inducer energy source. The two halves of the dimer will not form into the dimer (dimerize) without the inducer energy source. Thus, the two halves of the inducible dimer cooperate with the inducer energy source to dimerize the dimer. This in turn reconstitutes the Cas9 by bringing the first and second parts of the Cas9 together.

The CRISPR enzyme fusion constructs each comprise one part of the split Cas9. These are fused, preferably via a linker such as a GlySer linker described herein, to one of the two halves of the dimer. The two halves of the dimer may be substantially the same two monomers that together form the homodimer, or they may be different monomers that together form the heterodimer. As such, the two monomers can be thought of as one half of the full dimer.

The Cas9 is split in the sense that the two parts of the Cas9 enzyme substantially comprise a functioning Cas9. That Cas9 may function as a genome editing enzyme (when forming a complex with the target DNA and the guide), such as a nickase or a nuclease (cleaving both strands of the DNA), or it may be a deadCas9 which is essentially a DNA-binding protein with very little or no catalytic activity, due to typically two or more mutations in its catalytic domains (D10 combined with H840 or N863, and especially D10A combined with H840A or N863A are most preferable in Sp Cas9 and corresponding mutants will be appropriate for orthologs). The two parts of the split Cas9 can be thought of as the N' terminal part and the C' terminal part of the split Cas9. The fusion is typically at the split point of the Cas9. In other words, the C' terminal of the N' terminal part of the split Cas9 is fused to one of the dimer halves, whilst the N' terminal of the C' terminal part is fused to the other dimer half.

The Cas9 does not have to be split in the sense that the break is newly created. The split point is typically designed in silico and cloned into the constructs. Together, the two parts of the split Cas9, the N' terminal and C' terminal parts, form a full Cas9, comprising preferably at least 70% or more of the wildtype amino acids (or nucleotides encoding them), preferably at least 80% or more, preferably at least 90% or more, preferably at least 95% or more, and most preferably at least 99% or more of the wildtype amino acids (or nucleotides encoding them). Some trimming may be possible, and mutants are envisaged. Non-functional domains such as the Rec2 domain may be removed entirely. What is important is that the two parts may be brought together and that the desired Cas9 function is restored or reconstituted. The dimer may be a homodimer or a heterodimer.

One or more, preferably two, NLSs may be used in operable linkage to the first CRISPR enzyme construct. One or more, preferably two, NESs may be used in operable linkage to the first CRISPR enzyme construct. The NLSs and/or the NESs preferably flank the split Cas9-dimer (i.e. half dimer) fusion, i.e. one NLS may be positioned at the N' terminal of the first CRISPR enzyme construct and one NLS may be at the N' terminal of the first CRISPR enzyme construct. Similarly, one NES may be positioned at the N' terminal of the second CRISPR enzyme construct and one NES may be at the N' terminal of the second CRISPR enzyme construct. Where reference is made to N' or C' terminals, it will be appreciated that these correspond to 5' and 3' ends in the corresponding nucleotide sequence.

A preferred arrangement is that the first CRISPR enzyme construct is arranged 5'-NLS-(N' terminal Cas9 part)-linker-(first half of the dimer)-NLS-3'. A preferred arrangement is that the second CRISPR enzyme construct is arranged 5'-NES-(second half of the dimer)-linker-(C' terminal Cas9 part)-NES-3'. A suitable promoter is preferably upstream of each of the constructs. The two constructs may be delivered separately or together. In some embodiments, one or all of the NES(s) in operable linkage to the second CRISPR enzyme construct may be swapped out for an NLS. However, this is typically not preferred and, in other embodiments, the localization signal in operable linkage to the second CRISPR enzyme construct is one or more NES(s). It will also be appreciated that the NES may be operably linked to the N' terminal fragment of the split Cas9 and that the NLS may be operably linked to the C' terminal fragment of the split Cas9. However, the arrangement where the NLS is operably linked to the N' terminal fragment of the split Cas9 and that the NES is operably linked to the C' terminal fragment of the split Cas9 is preferred.

The NES functions to localize the second CRISPR enzyme fusion construct outside of the nucleus, at least until the inducer energy source is provided (e.g., at least until an energy source is provided to the inducer to perform its function). The presence of the inducer stimulates dimerization of the two CRISPR enzyme fusions within the cytoplasm and makes it thermodynamically worthwhile for the dimerized, first and second, CRISPR enzyme fusions to localize to the nucleus. Without being bound by theory, Applicants believe that the NES sequesters the second CRISPR enzyme to the cytoplasm (i.e. outside of the nucleus). The NLS on the first CRISPR enzyme localizes it to the nucleus. In both cases, Applicants use the NES or NLS to shift an equilibrium (the equilibrium of nuclear transport) to a desired direction. The dimerization typically occurs outside of the nucleus (a very small fraction might happen in the nucleus) and the NLSs on the dimerized complex shift the equilibrium of nuclear transport to nuclear localization, so the dimerized and hence reconstituted Cas9 enters the nucleus.

Beneficially, Applicants have been able to reconstitute function in the split Cas9, e.g. a split SpCas9. Transient transfection was used to prove the concept and dimerization occurred in the background in the presence of the inducer energy source. No activity was seen with separate fragments of the CRISPR enzyme. Stable expression through lentiviral delivery was then used to develop this and show that a split Cas9 approach can be used.

This present split Cas9 approach is beneficial as it allows the Cas9 activity to be inducible, thus allowing for temporal control. Furthermore, different localization sequences may be used (i.e. the NES and NLS as preferred) to reduce background activity from auto-assembled complexes. Tissue specific promoters, for example one for each of the first and second CRISPR enzyme fusion constructs, may also be used for tissue-specific targeting, thus providing spatial control. Two different tissue specific promoters may be used to exert a finer degree of control if required. The same approach may be used in respect of stage-specific promoters or there may a mixture of stage and tissue specific promoters, where one of the first and second CRISPR enzyme fusion constructs is under the control of (i.e. operably linked to or comprises) a tissue-specific promoter, whilst the other of the first and second CRISPR enzyme fusion constructs is under the control of (i.e. operably linked to or comprises) a stage-specific promoter.

The inducible CRISPR-Cas system comprises one or more nuclear localization sequences (NLSs), as described herein, for example as operably linked to the first CRISPR enzyme fusion construct. These nuclear localization sequences are ideally of sufficient strength to drive accumulation of said first CRISPR enzyme fusion construct in a detectable amount in the nucleus of a eukaryotic cell. Without wishing to be bound by theory, it is believed that a nuclear localization sequence is not necessary for CRISPR complex activity in eukaryotes, but that including such sequences enhances activity of the system, especially as to targeting nucleic acid molecules in the nucleus, and assists with the operation of the present 2-part system.

Equally, the second CRISPR enzyme fusion construct is operably linked to a nuclear export sequence (NES). Indeed, it may be linked to one or more nuclear export sequences. In other words, the number of export sequences used with the second CRISPR enzyme fusion construct is preferably 1 or 2 or 3. Typically 2 is preferred, but 1 is enough and so is preferred in some embodiments. Suitable examples of NLS and NES are known in the art. Preferred examples are those used in the Examples herein. For example, a preferred nuclear export signal (NES) is human protein tyrosin kinase 2; and (NLS). Preferred signals will be species specific.

Where the FRB and FKBP system are used, the FKBP is preferably flanked by nuclear localization sequences (NLSs). Where the FRB and FKBP system are used, the preferred arrangement is N' terminal Cas9-FRB-NES:C' terminal Cas9-FKBP-NLS. Thus, the first CRISPR enzyme fusion construct would comprise the C' terminal Cas9 part and the second CRISPR enzyme fusion construct would comprise the N' terminal Cas9 part.

Another beneficial aspect to the present invention is that it may be turned on quickly, i.e. that is has a rapid response. It is believed, without being bound by theory, that Cas9 activity can be induced through dimerization of existing (already present) fusion constructs (through contact with the inducer energy source) more rapidly than through the expression (especially translation) of new fusion constructs. As such, the first and second CRISPR enzyme fusion constructs may be expressed in the target cell ahead of time, i.e. before Cas9 activity is required. Cas9 activity can then be temporarily controlled and then quickly constituted through addition of the inducer energy source, which ideally acts more quickly (to dimerize the heterodimer and thereby provide Cas9 activity) than through expression (including induction of transcription) of Cas9 delivered by a vector, for example.

Based on the structural information provided herein, Applicants arrive at a SaCas9 that can be split into two components, which reconstitute a functional nuclease when brought back together. Applicants demonstrate that SaCas9 can be rendered chemically inducible by being split into two fragments and that rapamycin-sensitive dimerization domains may be used for controlled reassembly of the Cas9. Applicants show that the re-assembled Cas9 may be used to mediate genome editing (through nuclease/nickase activity) as well as transcription modulation (as a DNA-binding domain, the so-called "dead Cas9"). As such, the use of rapamycin-sensitive dimerization domains is preferred. Reassembly of the SaCas9 is preferred. Reassembly can be determined by restoration of binding activity. Where the SaCas9 is a nickase or induces a double-strand break, suitable comparison percentages compared to a wildtype are described herein.

Rapamycin treatments lasted 12 days. This was dosed at 200 nM. This temporal and/or molar dosage is an example of an appropriate dose for Human embryonic kidney 293FT (HEK293FT) cell lines and this may also be used in other cell lines. This figure can be extrapolated out for therapeutic use in vivo into, for example, mg/kg. However, it is also envisaged that the standard dosage for administering rapamycin to a subject is used here as well. By the "standard dosage", it is meant the dosage under rapamycin's normal therapeutic use or primary indication (i.e. the dose used when rapamycin is administered for use to prevent organ rejection).

Aspects of the invention, as particularly related to SaCas9 systems and other orthologus CRISPR-Cas systems, may be practiced using structural and functional comparisons to an SpCas9 system as used in the methods and systems further described in International Patent Application PCT/US14/70068 titled "CRISPR-CAS SYSTEMS AND METHODS FOR ALTERING EXPRESSION OF GENE PRODUCTS, STRUCTURAL INFORMATION AND INDUCIBLE MODULAR CAS ENZYMES" filed on Dec. 12, 2014, which claims priority to U.S. provisional patent application Serial Nos. 61/915,267, filed Dec. 12, 2013 and U.S. 61/939,228 filed on Feb. 12, 2014, each of which is incorporated herein by reference in its entirety.

Further to using split CRISPR-Cas systems (e.g. SaCas9 split systems) as inducible systems, other inducible systems which may be used in the practice of the inventions are further described in International Patent Application PCT/US13/051418 filed on Jul. 21, 2013 and published on Jun. 19, 2014 (Publication No. WO2014/018423) which claims priority to U.S. provisional patent application Serial Nos. 61/675,778 filed Jul. 25, 2012, 61/721,283 filed Nov. 1, 2012, 61/736,465 filed Dec. 12, 2012, 61/794,458 filed Mar. 15, 2013 and 61/835,973 filed Jun. 17, 2013 titled INDUCIBLE DNA BINDING PROTEINS AND GENOME PERTURBATION TOOLS AND APPLICATIONS THEREOF.

In one aspect the invention provides a non-naturally occurring or engineered CRISPR-Cas system which may comprise at least one switch wherein the activity of said CRISPR-Cas system is controlled by contact with at least one inducer energy source as to the switch. In an embodiment of the invention the control as to the at least one switch or the activity of said CRISPR-Cas system may be activated, enhanced, terminated or repressed. The contact with the at least one inducer energy source may result in a first effect and a second effect. The first effect may be one or more of nuclear import, nuclear export, recruitment of a secondary component (such as an effector molecule), conformational change (of protein, DNA or RNA), cleavage, release of cargo (such as a caged molecule or a co-factor), association or dissociation. The second effect may be one or more of activation, enhancement, termination or repression of the control as to the at least one switch or the activity of said CRISPR-Cas system. In one embodiment the first effect and the second effect may occur in a cascade.

In another aspect of the invention the CRISPR-Cas system may further comprise at least one nuclear localization signal (NLS), nuclear export signal (NES), functional domain, flexible linker, mutation, deletion, alteration or truncation. The one or more of the NLS, the NES or the functional domain may be conditionally activated or inactivated. In another embodiment, the mutation may be one or more of a mutation in a transcription factor homology region, a mutation in a DNA binding domain (such as mutating basic residues of a basic helix loop helix), a mutation in an endogenous NLS or a mutation in an endogenous NES. The invention comprehends that the inducer energy source may be heat, ultrasound, electromagnetic energy or chemical. In a preferred embodiment of the invention, the inducer energy source may be an antibiotic, a small molecule, a hormone, a hormone derivative, a steroid or a steroid derivative. In a more preferred embodiment, the inducer energy source maybe abscisic acid (ABA), doxycycline (DOX), cumate, rapamycin, 4-hydroxytamoxifen (4-HT), estrogen or ecdysone. The invention provides that the at least one switch may be selected from the group consisting of antibiotic based inducible systems, electromagnetic energy based inducible systems, small molecule based inducible systems, nuclear receptor based inducible systems and hormone based inducible systems. In a more preferred embodiment the at least one switch may be selected from the group consisting of tetracycline (Tet)/DOX inducible systems, light inducible systems, ABA inducible systems, cumate repressor/operator systems, 4-HT/estrogen inducible systems, ecdysone-based inducible systems and FKBP12/FRAP (FKBP12-rapamycin complex) inducible systems. Aspects of functional domains are described herein. In one aspect of the invention the inducer energy source is electromagnetic energy. The electromagnetic energy may be a component of visible light having a wavelength in the range of 450 nm-700 nm. In a preferred embodiment the component of visible light may have a wavelength in the range of 450 nm-500 nm and may be blue light. The blue light may have an intensity of at least 0.2 m W/cm <2>, or more preferably at least 4 mW/cm$^2$. In another embodiment, the component of visible light may have a wavelength in the range of 620-700 nm and is red light.

In aspects of the invention, wherein the inducer energy source is light, methods and systems described in "Optical control of mammalian endogenous transcription and epigenetic states." Konermann S, Brigham M D, Trevino A E, Hsu P D, Heidenreich M, Cong L, Platt R J, Scott D A, Church G M, Zhang F. Nature. August 22; 500(7463):472-6, incorporated herein by reference in its entirety, may be used to generate SaCas9 systems which may be optically controlled. Furthermore, photoactivatable SaCas9 systems may be made in accordance with the techniques described in "CRISPR-Cas9-based photoactivatable transcription system". Nihongaki Y, Yamamoto S, Kawano F, Suzuki H, Sato M. Chem Biol. 2015 Feb. 19; 22(2):169-74, incorporated herein by reference in its entirety. Nihongaki et al. relates to an engineered photoactivatable SpCas9 (paSpCas9) that allows for the optogenetic control of CRISPR-SpCas9 in human cells, wherein the paSpCas9 consists of split SpCas9 fragments and photoinducible dimerization domains named Magnets (pMag and nMag). Blue light irradiation induces heterodimerization between pMag and nMag, which enables split Cas9 fragments to reassociate, thereby reconstituting RNA-guided nuclease activity When the paSpCas9 is expressed in human embryonic kidney 293T cells, it induces targeted genome sequence modifications through both non-homologous end joining and homology-directed repair pathways and genome editing activity can be switched off simply by extinguishing the light. The magnets were fused to N713 and C714 positions of SpCas9 and with the structural information of SaCas9 provided herein, Applicants can arrive at an SaCas9 with fusions to photoinducible dimerizations domains at corresponding amino acid locations or at compatible locations which still allow for the SaCas9 enzyme to function in a photoinducible manner, preferably in a physiologically relevant environment.

In certain aspects, the Cas9 enzymes according to the present invention may provide increased specificity of targeting by combination with heterologous, non-Cas9 domains or other functional domains. Such heterologous domains may be prokaryotic or eukaryotic in origin, and in one embodiment may comprise heterologous DNA-cleaving domains. The domains may cleave double stranded or single stranded DNA, on one or two strands.

In this context, "in combination with" may signify a protein fusion, for example where a domain is attached to the N or C terminus of a protein, added internally with a protein structure, or used to replace an existing protein domain. However, alternative means of physical coupling of protein domains are also envisaged, such as attachment by non-covalent interactions including biotin/avidin systems, and the like.

In certain embodiments, the heterologous domain may be a restriction enzyme cleavage domain. Such domains are for example provided in combination with Cas9 in which the DNA cleavage (or catalytic) domain has been inactivated, such that the restriction enzyme domain is responsible for the DNA cleavage activity of the combined enzyme.

For example, restriction enzyme domains may be used which are active when present as dimers, such that two domains are required. In this embodiment, Cas9 enzymes are targeted to two adjacent spacer regions in the genome, which are close enough that the two restriction enzyme domains can cooperate and cleave DNA. In this manner, off-target activity is eliminated, as two target sites are required in close proximity before the enzyme can exert any cleavage activity. Specificity of targeting is thus increased significantly.

For example, restriction endonuclease (RE) domains may be fused to a catalytically inactive Cas9. On such RE is Fok1 which is a homodimeric enzyme, requiring two copies of the Fok1 monomer to form an active enzyme. The Fok1 domain can be fused to the N-terminus or the C-terminus of Cas9. Another RE is PvuI. Fusion to the N-terminus provides superior activity, since the N-terminus protrudes beyond the RuvC domain of Cas9, which interacts with the sgRNA:DNA duplex formed by Cas9; therefore, N-terminal fusion allows greater flexibility for Fok1 activity in the combined protein. Nuclear localization signal(s) (NLS) may also be provided, and are located for example N-terminal to the Fok1 domain. Here, as in general, one or more NLSs may be used. Two NLSs or even three or more NLSs may be used and these may be homogenous (i.e. the same signal with a similar or identical sequence) or heterogeneous (i.e. different signals with different sequences).

Target sites, defined by the presence of a PAM sequence and regions complementary to the selected sgRNA, can be up to 50 nucleotides apart (i.e. offset as described herein), for example also preferably between 5 and 43 nucleotides apart, for instance about 15 or about 25 nucleotides apart, in order for cleavage to occur; however, the exact length of the spacer in between cleavage sites is dependent on the linker length selected to join or associate the Cas9 with the functional domain.

The domains may be linked using any suitable linker, but for example are linked using one or more copies of the sequence Gly-Gly-Ser (GGS). For example, 1, 2, 3, 4, 5, 6, 8 or more copies may be used. Other potential linkers include SGSETPGTSESATPES (SEQ ID NO: 16), MKIIEQLPSA (SEQ ID NO: 17), VRHKLKRVGS (SEQ ID NO: 18), VPFLLEPDNINGKTC (SEQ ID NO: 19), GHGTGSTGSGSS (SEQ ID NO: 20), MSRPDPA (SEQ ID NO: 21), GSAGSAAGSGEF (SEQ ID NO: 22), SGSETPGTSESA (SEQ ID NO: 23), GGSM (SEQ ID NO: 24) and SGSETPGTSESATPEGGSGGS (SEQ ID NO: 25), as well as multiples thereof. The linkers should be sufficiently long and flexible to permit the Fok1 domains to align with the DNA for optimal cleavage, which is believed to be 1.5 to 2.5 helical turns apart. The NLS is in turn linked to the Fok1 domain via a linker, which may be GGS or a multiple thereof. The guide RNAs which target the Cas9/Fok1 fusion to the DNA to be cleaved should be oriented such that the PAM is distal to the cleaved spacer in both instances. This means that the sgRNA molecules will align in opposite orientations along the DNA strand to be cleaved. This provides a further level of specificity, since PAM sequences need to be present in the correct orientation in target DNA. For example, see Guilinger et al., (2014) Nature Biotechnology 32:577.

In some embodiments, domains which may be fused or linked to a catalytically inactive Cas9 (e.g. dCas9) include the functional domains that may be selected from the group consisting of: transposase domain, integrase domain, recombinase domain, resolvase domain, invertase domain, protease domain, DNA methyltransferase domain, DNA hydroxylmethylase domain, DNA demethylase domain, histone acetylase domain, histone deacetylases domain, nuclease domain, repressor domain, activator domain, nuclear-localization signal domains, transcription-regulatory protein (or transcription complex recruiting) domain, cellular uptake activity associated domain, nucleic acid binding domain, antibody presentation domain, histone modifying enzymes, recruiter of histone modifying enzymes; inhibitor of histone modifying enzymes, histone methyltransferase, histone demethylase, histone kinase, histone phosphatase, histone ribosylase, histone deribosylase, histone ubiquitinase, histone deubiquitinase, histone biotinase and histone tail protease.

In another embodiment, the inserted domain may comprise an intein domain which excises to reconstitute the activity of one or more domains of Cas9, and is subject to influence from an external activator or repressor.

Because the specificity of Cas9 is imperfect, with off-target effects being observable in many instances in the absence of suitable precautions being taken, techniques which increase the on target/off target cleavage ratio of Cas9 are advantageous. The use of Fok1-dCas9 fusions, as well as small-molecule regulated split Cas9 approaches (Zetsche, B., Volz, S. E. & Zhang, F. Nat. Biotechnol. 33, 139-142 (2015)) and truncated guide RNAs (Fu, Y., Sander, J. D., Reyon, D., Cascio, V. M. & Joung, J. K. Nat. Biotechnol. 32, 279-284 (2014)), paired Cas9 nickases (Ran, F. A. et al. Cell 154, 1380-1389 (2013); Mali, P. et al. *Nat. Biotechnol.* 31, 833-838 (2013)) can increase the specificity of Cas9 by proportionally reducing the level of off-target enzyme activity, compared to on-target activity. However, the regulation of wild-type Cas9 using exogenous molecules does not appear to be possible.

In embodiments, an intein domain can be used to regulate the activity of a modified Cas9 enzyme. Inteins are protein domains which can be inserted into heterologous proteins such that they undergo splicing to excise themselves from their integration site, splicing together the remaining segments of the heterologous protein. A wide variety of inteins is known in the art; an extensive database of inteins is available (Perler, F. B. (2002). InBase, the Intein Database. Nucleic Acids Res. 30, 383-384).

Inteins that undergo protein splicing only in the presence of 4-hydroxytamoxifen (4-HT) are known (Buskirk, A. R., Ong, Y. C., Gartner, Z. J. & Liu, D. R. *Proc. Natl. Acad. Sci. USA* 101, 10505-10510 (2004)). These inteins were developed by inserting the human estrogen receptor ligand-binding domain into the *M. tuberculosis* RecA intein and evolving the resulting inactive fusion protein into a conditionally active intein that requires the presence of 4-HT. Subsequent evolution at 37° C. yielded a second-generation intein, 37R3-2, with improved splicing properties in mammalian cells (Peck, S. H., Chen, I. & Liu, D. R. *Chem. Biol.* 18, 619-630 (2011)). The 37R3-2 intein has been inserted into Cas9 at a location that disrupts Cas9 activity until protein splicing has taken place, which results in conditionally active Cas9 nucleases that are active only in the presence of 4-HT (Davis et al., "Small molecule-triggered Cas9 protein with improved genome-editing specificity." *Nat Chem Biol.* 2015 May; 11(5):316-8).

The domain may be inserted at any suitable site, including for example at Ala127, Thr146, Ser219, Thr333, Thr519, Cys574, Ser1006 and/or Ser1159 of spCas9. Preferred insertion points include Ser219 and Cys574. Sites of interest for SaCas9 include, without limitation, L70, H80, A91, S142, A258, D309, A711, L842. Intein-modified Cas9 exhibits an on-target cleavage activity similar to wild-type Cas9 in the presence of 4-HT. However, on-target/off-target indel modification ratios for intein-Cas9 fusions are on average sixfold higher and as much as 25-fold higher than those of wild-type Cas9.

In some embodiments, it may be necessary to further engineer the intein domain to prevent activation by endogenous potential activators, such as steroids. For example, 37R3-2 is susceptible to activation by endogenous β-estradiol. In order to minimise activation by unwanted signals, the intein can be further modified and/or evolved to resist activation except by the intended activator. For example, a mutation in the estrogen receptor ligand-binding domain (G521R) renders the domain more specific for 4-HT. This mutation slightly reduces affinity for 4-HT but almost abolishes affinity for β-estradiol.

In a further example, the intein may be photosensitive, with protein splicing induced by light treatment. In one example, a photocaged cysteine amino acid residue can be genetically introduced into a *Nostoc punctiforme* (Npu) DnaE intein. A light-induced photochemical reaction can to reactivate the intein and trigger protein splicing (Wen et al., J. Am. Chem. Soc., (2015), 137 (6), pp 2155-2158). Such an approach permits optical control of gene editing by Cas9.

Inteins may also be used to provide temporal control of Cas9 activity, effectively allowing the user to switch Cas9 activity on or off at will, by administering an activator such as 4-HT. Alternatively, inteins may be used to make Cas9 responsive to endogenous signals which are under the control of other processes in a cell or organism.

Furthermore, any of these residues in SaCas9, or corresponding positions in ortholog Cas9s, are envisaged to be suitable sites for creation of single lobed mutant Cas9s. For example, deletion of one lobe may mean that the amino acid sequence or polynucleotide encoding it starts or stops at one of these bridge helix (residues 41-73) and/or a linker loop (residues 426-434) residues. For example, to create a single-lobed (REC-lobed) modified SaCas9, deletion of the NUC lobe could be achieved by deletion of residues 1-40 with the first amino acid occurring in the bridge helix (at any one of residues 41-73) and then ending in the linker loop (at any one of residues 426-434). To create a single-lobed (NUC-lobed) modified SaCas9, deletion of the REC lobe could be achieved by retention of residues 1-40 in a first part, and deletion of some or all of the bridge helix (any one of residues 41-73) and then re-starting in a second ending in the linker loop (at any one of residues 426-434) followed by retention of residues 435-1053. Accordingly, provided are single-lobed modified SaCas9s. In some embodiments, the single-lobed modified SaCas9 lacks a NUC lobe. In other embodiments, the single-lobed modified SaCas9 lacks a REC lobe.

It is also envisaged that either or both of the bridge helix (residues 41-73) and/or a linker loop (residues 426-434) may be engineered to further reduce the number of amino acids in a modified Cas9, or that these are suitable regions for functionalization, for example by linkage, fusion or tethering to a functional domain. Accordingly, in one aspect, the present invention provides a modified Cas9, preferably a modified SaCa9, wherein all or part of bridge helix (residues 41-73) have been replaced with a linker. In one aspect, the present invention provides a modified SaCa9, wherein all or part of linker loop (residues 426-434) have been replaced with a linker. In one aspect, the present invention provides a modified SaCa9, wherein all or part of bridge helix (residues 41-73) have been replaced with a linker and all or part of linker loop (residues 426-434) have been replaced with a linker. Suitable examples of linkers include Gly-Ser linkers described herein.

In one aspect, the present invention provides a modified SaCa9, wherein the bridge helix (residues 41-73) and/or the linker loop (residues 426-434) has been functionalized or comprises a functionalization, for example by linkage, fusion or tethering to a functional domain.

Figures 2A, 2B, 2C, 2D:
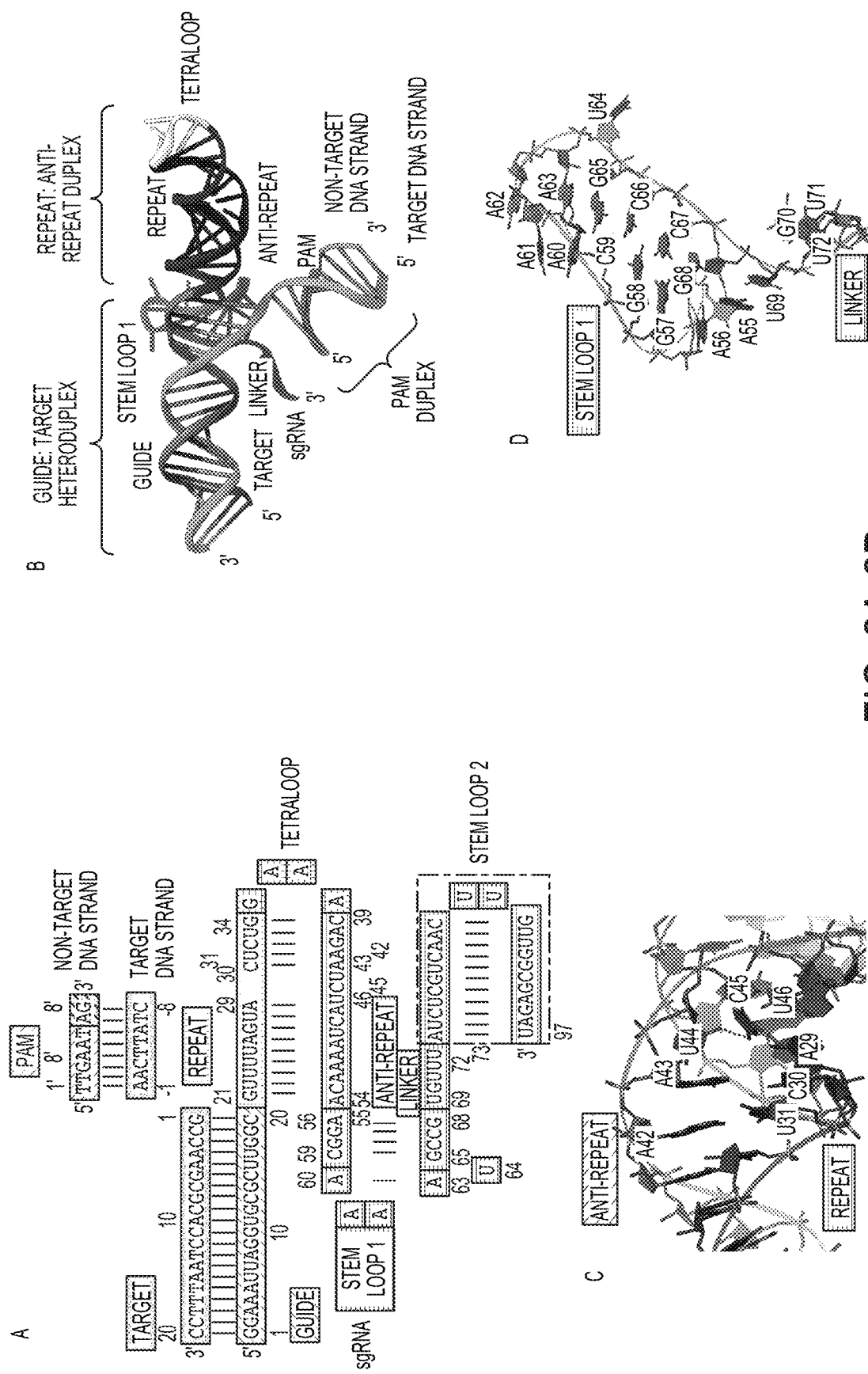
FIG. 2A-2G depicts the sgRNA-target DNA complex. (A) Nucleotide sequence of the sgRNA and target DNA. The putative stem loop 2 (dashed box) was truncated to facilitate crystallization. U73 is disordered in the structure.

The repeat (G21-G34) and anti-repeat (C39-C54) regions form a distorted duplex (referred to as a repeat:anti-repeat duplex) via 13 Watson-Crick base pairs (FIGS. 2A and 2B). What is particularly interesting is that the unpaired nucleotides (C30, A43, U44 and C45) form an internal loop, which is stabilized by a hydrogen bonding-interaction between the O2 of U44 and the N4 of C45 (see FIG. 2C). The repeat:anti-repeat duplex is recognized by the REC and WED domains (described herein). Indeed, a GAU insertion into the repeat region, which would disrupt the internal loop, reduced the Cas9-mediated DNA cleavage (FIG. 2E), confirming the functional importance of the distorted structure of the repeat:anti-repeat duplex. Thus, it is clear that the internal loop comprising unpaired nucleotides, specifically C30, A43, U44 and C45 in the crRNA:tracrRNA repeat: anti-repeat duplex in Sa or corresponding residues in, or corresponding residues in a chimeric or sgRNA, can be maintained to retain or increase cutting activity. However, it is also envisaged that disruption such a loop, for example by insertion of additional residues, preferably GAU, can reduce or destroy cutting activity. Guides that recruit the Cas9 to a genomic locus, but tamper with or hamper DNA cutting or achieve no cutting (i.e. dead guides) are useful, especially with WT Cas9. Their use in combination with WT Cas9 is beneficial since one can simultaneously use them in a knock down (cutting) application along with (i.e. at the same time as) activation from binding, allowing a single Cas9 to be delivered together with different guides with different effects. Alternatively, dCas9 (deadCas9s) can be used in place of the WT Cas9 and disruptive guide arrangement.

Figures 2E, 2F:
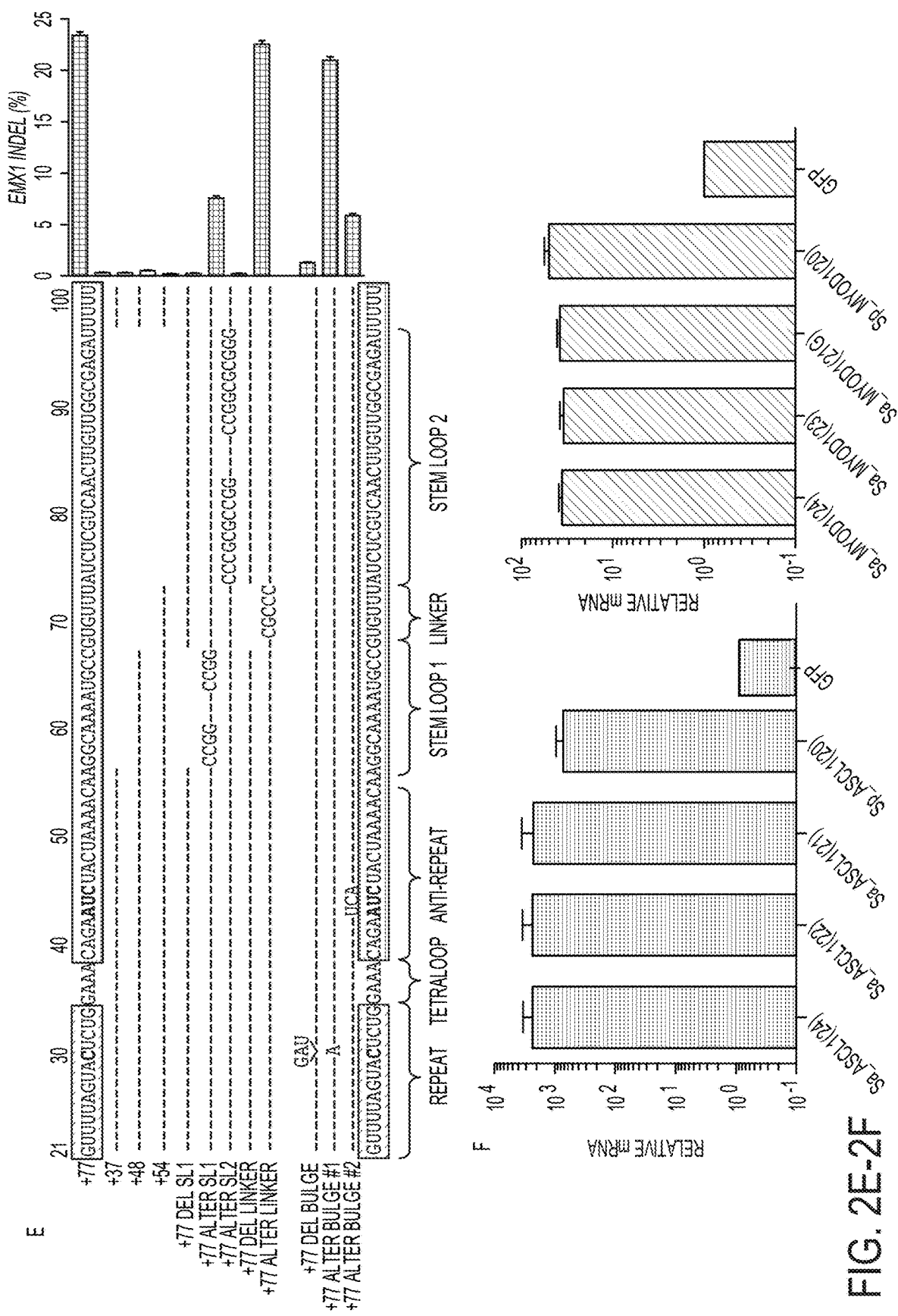
Figure 3:
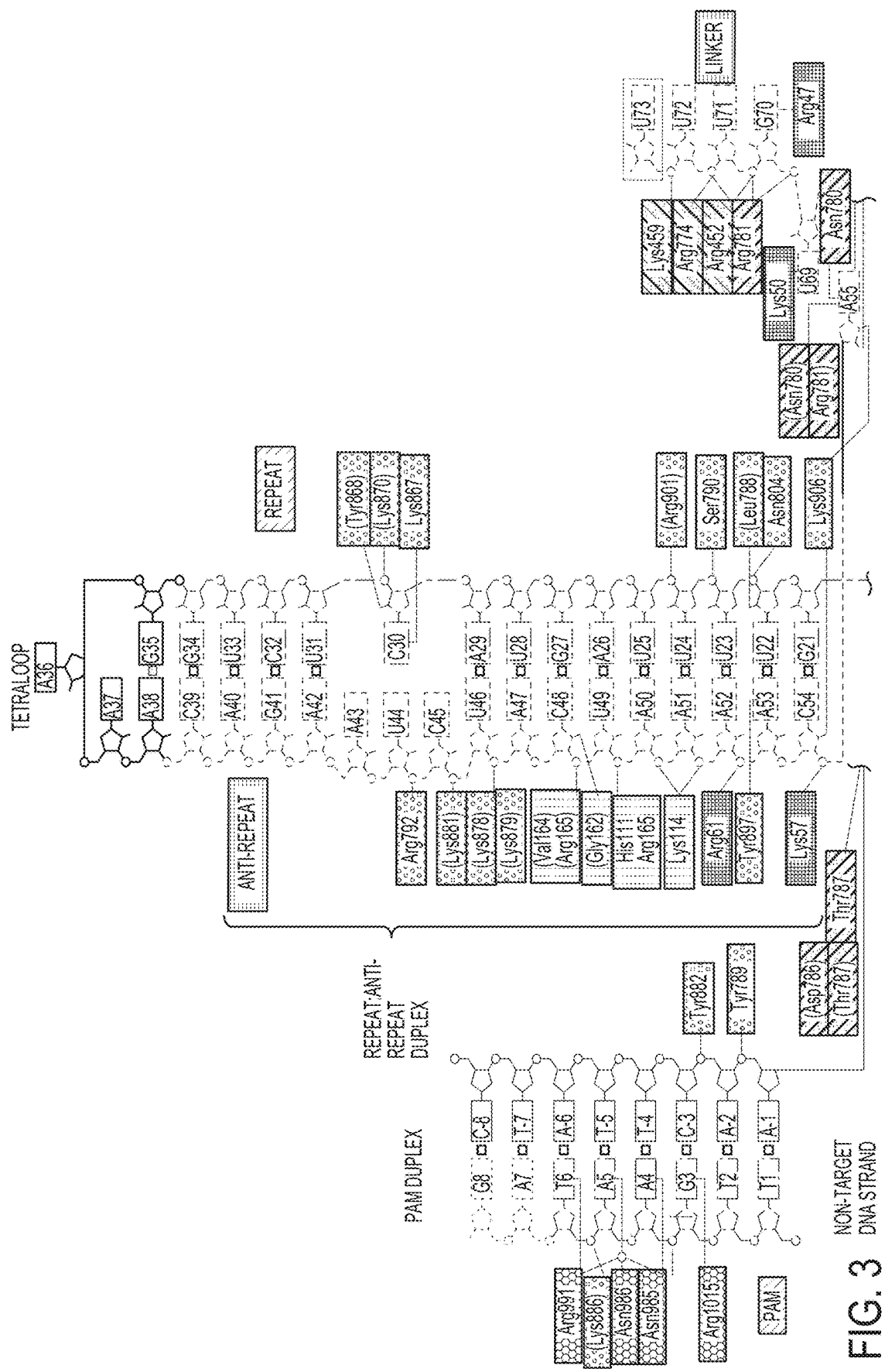
FIG. 3 shows a schematic of the nucleic-acid recognition by SaCas9. SaCas9 residues that interact with sgRNA and target DNA via their main chain are shown in parentheses. Water-mediated hydrogen-bonding interactions are omitted for clarity. U73 is disordered in the structure. Figure discloses SEQ ID NOS 123-124, respectively, in order of appearance.
Figure 3:
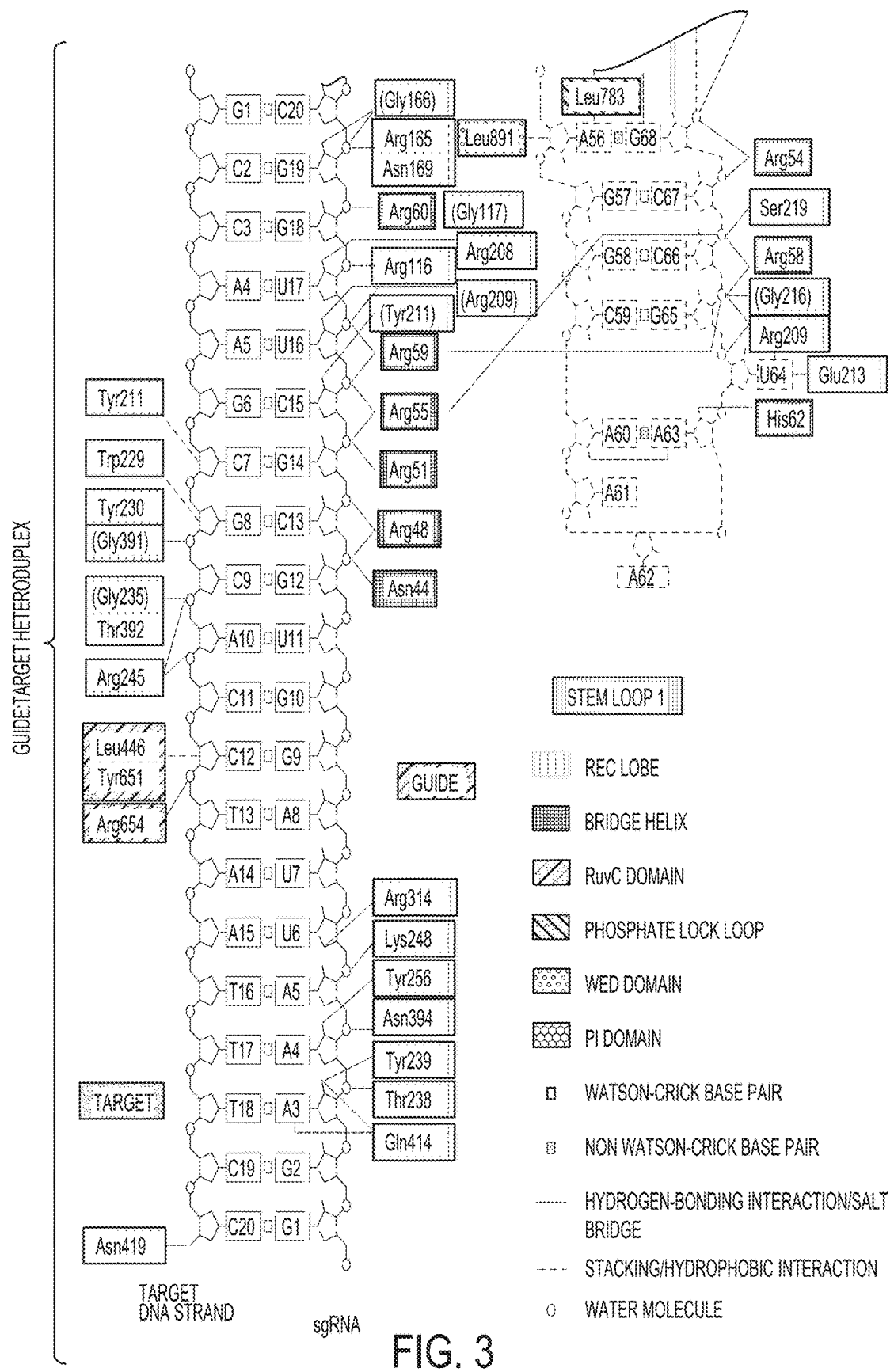

In terms of recognition of the crRNA:tracrRNA scaffolds, the repeat:anti-repeat duplex is recognized by the REC and WED domains, primarily through interactions between the sugar-phosphate backbone and protein (see FIG. 3). Consistent with Applicants' data showing that the sgRNA containing the fully-paired repeat:anti-repeat duplex fails to support Cas9-catalyzed DNA cleavage (FIG. 2E), the internal loop (C30, U44 and C45) is extensively recognized by the WED domain (FIG. 4B). The 2' OH and O2 of C30 hydrogen bond with Tyr868 and Lys867, respectively, and the phosphate groups of U31, C45 and U46 interact with Lys870, Arg792 and Lys881, respectively. These structural observations explain the structure-dependent recognition of the repeat:anti-repeat duplex by SaCas9.

Accordingly, it is envisaged that one or more of Tyr868, Lys867, Lys870, Arg792 and Lys881 of Sa or corresponding residues in orthologs may be mutated to increase or disrupt (reduce) stabilization of the guide's internal loop (comprising unpaired nucleotides, specifically C30, A43, U44 and C45 in the crRNA:tracrRNA repeat:anti-repeat duplex in Sa or corresponding residues in, or corresponding residues in a chimeric or sgRNA), as required.

Corresponding residues, domains, regions etc in Cas9 orthologs can be identified by the methods of Zhang et al., 2012 (Nature; 490(7421): 556-60) and Chen et al., 2015 (PLoS Comput Biol; 11(5): e1004248). These two groups describe a computational protein-protein interaction (PPI) method to predict interactions mediated by domain-motif interfaces. PrePPI (Predicting PPI), a structure based PPI prediction method, combines structural evidence with non-structural evidence using a Bayesian statistical framework. The method involves taking a pair a query proteins and using structural alignment to identify structural representatives that correspond to either their experimentally determined structures or homology models. Structural alignment is further used to identify both close and remote structural neighbours by considering global and local geometric relationships. Whenever two neighbours of the structural representatives form a complex reported in the Protein Data Bank, this defines a template for modelling the interaction between the two query proteins. Models of the complex are created by superimposing the representative structures on their corresponding structural neighbour in the template. This approach is further described in Dey et al., 2013 (Prot Sci; 22: 359-66).

Thus, any of the herein described improved functionalities of a CRISPR enzyme may be made to any CRISPR enzyme, such as a Cas9 enzyme. Cas9 enzymes described herein are derived e.g. from Cas9 enzymes from S. pyogenes and S. aureus. However, it will be appreciated that any of the functionalities described herein may be engineered into Cas9 enzymes from other orthologs, including chimeric enzymes comprising fragments from multiple orthologs. Examples of such orthologs are described elsewhere herein.

As in SpCas9, the sgRNA lacking stem loop 2 supported Cas9-catalyzed DNA cleavage in vitro but not in vivo (see FIGS. 13C and 13D), suggesting that the SaCas9 sgRNA contains stem loop 2, which is important for in vivo function. Accordingly, provided is an sgRNA, suitable for use with SaCas9, comprising secondary structure consisting of or corresponding to stem loop 2.

In Sp, the tetraloop and stem loop 2 of the SpCas9 sgRNA are exposed to the solvent (Anders et al., 2014; Nishimasu et al., 2014) (see FIG. 13A). Thus, these two loops are available for the fusion of RNA aptamers, and the three components system consisting of (1) catalytically inactive SpCas9 (D10A/N863A) fused with a VP64 transcriptional activator domain, (2) a MS2 bacteriophage coat protein fused with p65 and HSF1 transcriptional activator domains, and (3) the engineered sgRNA fused to MS2-interacting RNA aptamers can induce the RNA-guided transcriptional activation of target endogenous loci (Konermann et al., 2015).

Applicants examined whether tetraloop and stem loop 2 of the SaCas9 sgRNA are available for the MS2-interacting aptamer fusion, Applicants co-expressed in HEK293F cells the three components:

(1) dSpCas9 (deadCas9 bearing both D10A/N863A mutations)-VP64 or dSaCas9 (dead Cas9 bearing both D10A/N580A mutations)-VP64, (2) its engineered sgRNA (i.e. the engineered sgRNA fused to MS2-interacting RNA aptamers to induce the RNA-guided transcriptional activation of target endogenous loci, per Konermann et al., 2015), and (3) MS2-p65-HSF1, i.e. a MS2 bacteriophage coat protein fused with p65 and HSF1 transcriptional activator domains.

Transcription activation of the target genes (ASCL1 and MYOD1) was found at levels comparable to those of the dSpCas9-based activator. These results indicate that the SaCas9 sgRNA has solvent-exposed stem loop 2. Furthermore, Applicants have demonstrated that the engineered SaCas9 sgRNA can recruit multiple MS2-fused proteins. Accordingly, in one aspect, the present invention provides for the loops (e.g. tetraloop or stemloop) of the sgRNA being extended, without colliding with the Cas9 protein by the insertion of distinct RNA loop(s) or distinct sequence(s) that may recruit adaptor proteins that can bind to the distinct RNA loop(s) or distinct sequence(s). In a particular embodiment of the invention, stem loop 2 (SL2) of SaCas9 may be modified or engineered to recruit proteins to enable specific functionality. The adaptor proteins may include but are not limited to orthogonal RNA-binding protein/aptamer combinations that exist within the diversity of bacteriophage coat proteins. A list of such coat proteins includes, but is not limited to MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s, PRR1. These adaptor proteins or orthogonal RNA binding proteins can further recruit effector proteins or fusions which comprise one or more functional domains. In some embodiments, the functional domain may be selected from the group consisting of: transposase domain, integrase domain, recombinase domain, resolvase domain, invertase domain, protease domain, DNA methyltransferase domain, DNA hydroxylmethylase domain, DNA demethylase domain, histone acetylase domain, histone deacetylases domain, nuclease domain, repressor domain, activator domain, nuclear-localization signal domains, transcription-regulatory protein (or transcription complex recruiting) domain, cellular uptake activity associated domain, nucleic acid binding domain, antibody presentation domain, histone modifying enzymes, recruiter of histone modifying enzymes; inhibitor of histone modifying enzymes, histone methyltransferase, histone demethylase, histone kinase, histone phosphatase, histone ribosylase, histone deribosylase, histone ubiquitinase, histone deubiquitinase, histone biotinase and histone tail protease.

In some preferred embodiments, the functional domain is a transcriptional activation domain, preferably VP64. In some embodiments, the functional domain is a transcription repression domain, preferably KRAB. In some embodiments, the transcription repression domain is SID, or concatemers of SID (eg SID4X). In some embodiments, the functional domain is an epigenetic modifying domain, such that an epigenetic modifying enzyme is provided. In some embodiments, the functional domain is an activation domain, which may be the P65 activation domain.

The sugar-phosphate backbone of the PAM-distal region (A3-U6) of the sgRNA interacts with the REC lobe (Thr238, Tyr239, Lys248, Tyr256, Arg314, Asn394 and Gln414) (see FIG. 3). Accordingly, it is envisaged that one or more of these residues in Sa or corresponding residues in orthologs may be mutated to increase or disrupt (reduce) stabilization of the guide's PAM-distal region (A3-U6), as required.

The phosphate backbone of the sgRNA seed region (C13-C20) is extensively recognized by the bridge helix (Ans44, Arg48, Arg51, Arg55, Arg59 and Arg60) and the REC lobe (Arg116, Gly117, Arg165, Gly166, Asn169 and Arg209) (see FIGS. 3 and 4A). In addition, the 2' OH groups of C15, U16, U17 and G19 interact with the REC lobe (Gly166, Arg208, Arg209 and Tyr211). Accordingly, it is envisaged that one or more of these residues in Sa or corresponding residues in orthologs may be mutated to increase or disrupt (reduce) stabilization of the guide's seed region (C13-C20), as required.

In addition, the sugar-phosphate backbone of the target DNA strand interacts with the REC lobe (Tyr211, Trp229, Tyr230, Gly235, Arg245, Gly391, Thr392, Ans412, Arg654 and Arg661) and the RuvC domain (Leu446, Tyr651 and Arg654) (FIG. 3). Accordingly, it is envisaged that one or more of these residues in Sa or corresponding residues in orthologs may be mutated to increase or disrupt (reduce) stabilization of the target DNA strand, as required.

The sgRNA's Stem Loop 1 (SL1) (part of the tracrRNA) interacts with the bridge helix and REC lobe, specifically Arg47, Arg54, Arg55, Arg58 and Arg59 (BH) and Arg209, Gly216 and Ser219 (REC) and also including Arg47, Arg54, Arg55, Arg58 Arg59, Arg209, Gly216, Ser219, His64, Glu213, Arg209, Asn780/Arg781, Leu783, Lys906, Lys57, Leu783, Arg452, Lys459, Arg774, and Arg781. Accordingly, it is envisaged that one or more of these residues in Sa or corresponding residues in orthologs may be mutated to increase or disrupt (reduce) stabilization of the guide's stem loop 1, as required.

Arg1015, Asn985, Asn985, Asn986, Arg991, Asn985/Asn986/Arg991, Glu993, Arg1015 and Tyr789, Tyr882, Lys886, Ans888, Ala889, Leu909 are all involved in recognition of the NNGRRT PAM by the SaCas9 system. Accordingly, it is envisaged that one or more of these residues in Sa or corresponding residues in orthologs may be mutated to increase or disrupt (reduce) PAM recognition, as required. In particular, mutation of the Asn985/Asn986/Arg991 cluster or any one of Asn985, Asn986 and/or Arg991 is envisaged to be useful in accepting PAMs that do not have purines at positions 4 and 5 (corresponding to NNGRRT). Together, these structural findings demonstrated that distinct PAM specificities of Cas9 orthologs are primarily defined by their structurally diverse PI domains. This allows for PAM swapping as first shown by Nishimasu (2014), where the PI domain of SpCas9 was swapped with StCas9. It is envisaged that the prevent invention will provide useful variants in which domains or subdomains are exchanged between or among Cas9 variants.

In an aspect, therefore, provided is a modified Cas9 comprising the PI domain of SaCas9. In some embodiments, one or more of Arg1015, Asn985, Asn985, Asn986, Arg991, Asn985/Asn986/Arg991, Glu993, Arg1015 and Tyr789, Tyr882, Lys886, Ans888, Ala889 and/or Leu909 are mutated, optionally to Ala or a similar amino acid, in the SaCas9 PI domain.

Further aspects of the invention encompass mutagenizing SaCas9 to arrive at new variants that can target different PAMs and expand our targeting ability. In embodiments of the invention, a non-screening approach may be used. In one embodiment, the PI domain of SaCas9 may be replaced with other DNA-binding domains from TALEs or ZFNs. In another embodiment, C-terminal truncations/replacements may be performed with SaCas9 to determine which parts are important and to assess any effects on cutting efficiency.

In other embodiments of the invention, screening approaches may be used. In one such screen, residues which interact with the PAM as described herein may be mutagenized. The number of residues to be varied in such a screen can be, for example, 1, 2, 3, 4 or more, or up to 3, or up to 4. In one embodiment, a directed evolution screen may be performed in bacteria to select for efficient cutters (e.g. a semi-randomly generated SaCas9 library). Region(s) of interest in SaCas9 may be PCR mutagenized to generate a diverse library of SaCas9 mutants, and then efficient cutters in bacteria may be selected. In another embodiment, a PAM screen in the drug resistance model used for the GeCKO and SAM papers referenced herein with A375 cells and vemurafenib/PLX may be conducted. A few residues are initially mutated and an oligo library synthesized by Agilent or BTL will allow for the screen of effective mutants. In certain embodiments, target genes are designed or selected so as to have non-canonical PAMs so that wild type SaCas9 would not cut but a mutant Cas9 would potentially cut. This approach will allow for immediately assessing cutting efficiency in a mammalian system, as opposed to having to confirm whether results carry over from bacteria to mammals.

Asp786 and Thr787 are in the phosphate lock loop. The SaCas9 T787A mutant showed reduced DNA cleavage activity (see FIG. 5C), confirming the functional significance of Thr787 in the phosphate lock loop. Accordingly, it is envisaged that one or more of these residues in Sa or corresponding residues in orthologues may be mutated to increase or disrupt (reduce) stabilization of the guide via the phosphate lock, as required. Provided, therefore, in one aspect, is a modified SaCas9 comprising a T787 mutation, preferably T787A. Modified Cas9 orthologues with corresponding mutations are also provided. These are useful where it is beneficial to reduce DNA cleavage activity, for example in reducing off-target effects or when the Cas9 or guide is functionalized with a functional domain, for example a deadCas9, or in this case nearly deadCas9.

The catalytic residues of SaCas9 are Asp10, Glu477, His701 and Asp704. Mutation thereof is therefore envisaged to remove or reduce catalytic activity, as seen with D10A. In one aspect, the present invention provides a modified SaCa9, comprising a mutation at Glu477, preferably E477A. In one aspect, the present invention provides a modified SaCa9, comprising a mutation at His701, preferably H701A. In one aspect, the present invention provides a modified SaCa9, comprising a mutation at Asp704, preferably D704A. Such mutants may be useful nickases or deadCas9s if combined with an HNH domain mutant.

In one aspect, the present invention provides a modified SaCa9, comprising mutations at D10 and Glu477, preferably D10A and Glu477A. In one aspect, the present invention provides a modified SaCa9, comprising mutations at D10 and His701, preferably D10A and His701A. In one aspect, the present invention provides a modified SaCa9, comprising mutations at D10 and Asp704, preferably D10A and Asp704A. In one aspect, the present invention provides a modified SaCa9, comprising mutations at Glu477 and 701, preferably Glu477A and H701A. In one aspect, the present invention provides a modified SaCa9, comprising mutations at Glu477 and Asp704, preferably Glu477A and Asp704A. In one aspect, the present invention provides a modified SaCa9, comprising mutations at D10 and Asp704 and H701, preferably Asp704A and H701A. Such mutants may be useful nickases or deadCas9s if combined with an HNH domain mutant.

The catalytic residues of SaCas9 are Asp556, His557 and Asn580. The D556A, H557A and N580A mutants of SaCas9 showed almost no DNA cleavage activities. These observations indicated that the SaCas9 HNH domain cleaves the target DNA strand through a one-metal ion mechanism as in other aab-metal endonucleases (Biertumpfel et al., 2007).

Mutation thereof is therefore envisaged to remove or reduce catalytic activity, as seen with N580A. In one aspect, the present invention provides a modified SaCa9, comprising a mutation at D556, preferably D556A. In one aspect, the present invention provides a modified SaCa9, comprising a mutation at H557, preferably H557A. Such mutants may be useful nickases or deadCas9s if combined with a RuvC domain mutant.

In one aspect of the invention, nickase mutations can be identified by sequence homology with respect to known Type II CRISPR enzymes and nuclease domains. In certain embodiments, the nuclease domains are of known structure. In another aspect, mutations of the invention are identified from the SaCas9 structure by proximity to the nuclease catalytic sites. In certain embodiments, the mutation position comprise one or more of E477, N580, D10, H701, D704, and H557. In certain embodiments, the mutation are E477A, N580D, N580A, D10A, H701A, D704A, or H557A. In certain embodiments, combinations of the mutations are useful to create a dead Cas9 protein. Examples of such combinations include, without limitation, D10A and N580A.

Taken with SpCas9, the SaCas9 structure provided herein further allows identification of mutations in Cas9 orthologs. Thus, modified Cas9 orthologs may comprise mutations at positions coinciding with, e.g., E477, N580, D10, H701, D704, and H557 including, but not limited to mutations coinciding with E477A, N580D, N580A, D10A, H701A, D704A, or H557A of SaCas9 or similar (i.e., conservative) changes.

In one aspect, the present invention provides a modified SaCa9, comprising mutations at N580 and D556, preferably N580A and D556A. In one aspect, the present invention provides a modified SaCa9, comprising mutations at N580 and H557, preferably N580A and H557A. Such mutants may be useful nickases, or deadCas9s when combined with a RuvC domain mutant.

Figures 6A, 6B, 6C:
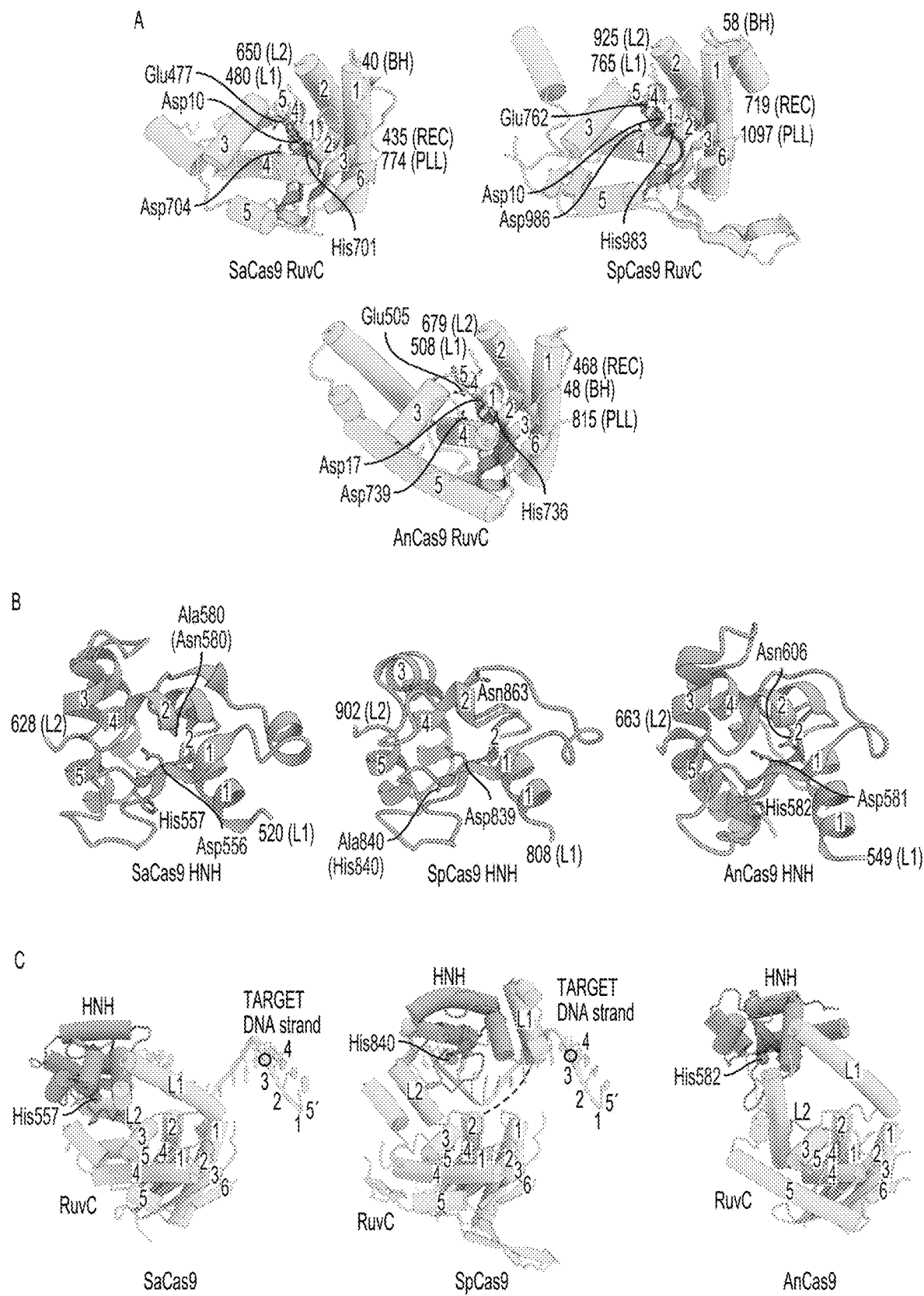
FIG. 6A-6C shows RuvC and HNH nuclease domains. (A and B) Structural comparison of the RuvC (A) and HNH (B) domains of SaCas9, SpCas9 (PDB ID 4UN3) and AnCas9 (PDB ID 4OGE). The conserved a helices and b strands are numbered. The catalytic residues are shown as stick models. BH, bridge helix. PLL, phosphate lock loop. (C) Comparison of the spatial arrangements between the RuvC and HNH domains in SaCas9, SpCas9 (PDB ID 4UN3) and AnCas9 (PDB ID 4OGE). The Ca atoms of the catalytic histidine residues in the HNH domains are shown as spheres. The cleavage sites of the target DNA strands are indicated by magenta circles. In SpCas9, the disordered region in the L1 linker is indicated by dashed lines.

Interestingly, Asn863 is oriented away from the active site in the ternary and quaternary complex structures of SpCas9 (see FIG. 6B). This may explain the provision of 3' overhangs in the target strand seen with N863A mutant nickases. In order for HDR to proceed, the broken DNA ends need to be resected to generate a 3' overhang, which will in turn inhibit NHEJ. HDR in mammalian cells proceeds via the generation of 3' overhangs followed by strand invasion of a homologous locus by the 3' end.

Applicants' structural observations demonstrate that the Cas9 orthologs recognize their cognate crRNA:tracrRNA in an orthogonal manner, using a combination of the structurally diverse REC and WED domains. This suggests that the REC and/or the WED domain can be swapped in and out of different Cas9s, especially between closely related Cas9s. This may allow the user to tailor a Cas9 to different tracrs. For example, it might be useful to swap in spCas9 WED and/or REC domains into saCas9, thereby allowing use of sp-specific tracrs with the modified SaCas9. This may reduce or destroy cutting activity, which can be beneficial In an aspect, therefore, provided is a modified SaCas9 comprising a WED domain from an ortholog Cas9. In an aspect, therefore, provided is a modified SaCas9 comprising a REC domain from an ortholog Cas9, for example SpCas9. In an aspect, therefore, provided is a modified SaCas9 comprising a WED domain and a REC domain from an ortholog Cas9, for example SpCas9.

In an aspect, also provided is a modified Cas9 form a non-Sa ortholog, such as spCas9, comprising a WED domain from SaCas9. In an aspect, also provided is a modified Cas9 form a non-Sa ortholog, such as spCas9, comprising a REC domain from SaCas9. In an aspect, also provided is a modified Cas9 form a non-Sa ortholog, such as spCas9, comprising a WED domain and a REC domain from SaCas9.

In an aspect, the present invention provides a modified Cas9 enzyme as herein described comprising a mutation at N985, optionally N985A, in SaCas9 or a corresponding residue in an ortholog of SaCas9.

In an aspect, the present invention provides a modified Cas9 enzyme as herein described comprising a mutation at N986, optionally N986A, in SaCas9 or a corresponding residue in an ortholog of SaCas9.

In an aspect, the present invention provides a modified Cas9 enzyme as herein described comprising a mutation at R991, optionally R991A, in SaCas9 or a corresponding residue in an ortholog of SaCas9.

In an aspect, the present invention provides a modified Cas9 enzyme as herein described comprising a mutation at E993, optionally E993A, in SaCas9 or a corresponding residue in an ortholog of SaCas9.

In an aspect, the present invention provides a modified Cas9 enzyme as herein described comprising a mutation at R1015, optionally R1015A, in SaCas9 or a corresponding residue in an ortholog of SaCas9.

In an aspect, the present invention provides a modified Cas9 enzyme as herein described comprising a mutation at T787, optionally T787A, in SaCas9 or a corresponding residue in an ortholog of SaCas9.

Any combination of these of these single mutants is possible a double or even triple mutants.

In an aspect, the present invention provides a modified Cas9 enzyme as herein described comprising a mutation at N985, optionally N985A, and a mutation at N986, optionally N986A, in SaCas9 or a corresponding residue in an ortholog of SaCas9.

In an aspect, the present invention provides a modified Cas9 enzyme as herein described comprising a mutation at N985, optionally N985A, and a mutation at R991, optionally R991A, in SaCas9 or a corresponding residue in an ortholog of SaCas9.

In an aspect, the present invention provides a modified Cas9 enzyme as herein described comprising a mutation at N986, optionally N986A, and a mutation R991, optionally R991A, in SaCas9 or a corresponding residue in an ortholog of SaCas9.

In an aspect, the present invention provides a modified Cas9 enzyme as herein described comprising a mutation at N985, optionally N985A, and a mutation at R1015, optionally R1015A, in SaCas9 or a corresponding residue in an ortholog of SaCas9.

In an aspect, the present invention provides a modified Cas9 enzyme as herein described comprising a mutation at N986, optionally N986A, and a mutation at R1015, optionally R1015A, in SaCas9 or a corresponding residue in an ortholog of SaCas9.

In an aspect, the present invention provides a modified Cas9 enzyme as herein described comprising a mutation at R991, optionally R991A, and a mutation at R1015, optionally R1015A, in SaCas9 or a corresponding residue in an ortholog of SaCas9.

In an aspect, the present invention provides a modified Cas9 enzyme as herein described comprising a mutation at E993, optionally E993A, and a mutation at R1015, optionally R1015A, in SaCas9 or a corresponding residue in an ortholog of SaCas9.

The sgRNA or modifications thereto shown in these figures are preferred in some embodiments. Corresponding structures, especially secondary structures, will be apparent, even if the primary sequence differs. Although packing constrains are pertinent, these are less keenly felt with the sgRNA, being a polynucleotide, compared to say the CRISPR enzyme. As such, as far as packaging goes, there is less restriction on the use of longer sgRNAs. A +73 architecture is used as the starting point of the present modification. However, Applicants may use +85 or longer architectures (especially those in which stem loop 2 has not been truncated). In some embodiments, the sgRNA comprises, before or after modification, at least 3 loops. Examples are the tetraloop, the stem loop 1 and stem loop 2. In some embodiments, the sgRNA comprises, before or after modification, at least 4 loops. Examples are the tetraloop, the stem loop 1, stem loop 2, and stem loop 3. The herein-cited materials, based on the crystal structure of sgRNA in complex with the SaCas9 and target DNA provides further detail on these loops and Applicants also exemplify the sequences discussed above, so the skilled person will be able to determine these loops or refer to the literature.

The modifications of the invention are therefore preferably made to an sgRNA as discussed herein. The modifications to the sgRNA are such that the architecture of the sgRNA is altered. By architecture, Applicants mean the primary structure (i.e. the sequence) and also, particularly preferably, the resulting secondary structure of the sgRNA.

In some aspects, the system may further comprise a CRISPR enzyme as defined herein, which is preferably a Cas9. The optimized guides provide herein may be used with a range of CRISPR enzymes including wildtype (wt) nucleases, as well as nickases and deadCas9s as discussed herein. In preferred embodiments the Cas 9 is a SaCas9 enzyme.

In some aspects, the cell is a eukaryotic cell, for instance a mammalian cell and preferably a mouse or human cell, including stem cell lines. As such, also provided is a model organism, preferably an ape, rat or mouse, transformed with above system. The cell line or mode may be prepared, for instance by injecting or otherwise introducing the system into a fertilized zygote to thereby achieve heritable gene modification (see the review by Hsu et al. (Cell 157, Jun. 5, 2014)). The model may constitutively express the CRISPR enzyme when transfected. Progeny of the model are also envisaged.

In some aspects, the invention also provides a method of modifying a genomic locus of interest to alter gene expression in a cell by introducing into the cell the composition comprising an optimized and/or modified Sa sgRNA and a SaCas9 enzyme. This may include a method of treating a subject with a condition correctable by genome editing. Such conditions are numerous, and are further discussed herein, but may include conditions resulting from SNPs or trinucleotide repeat disorders. The system may also be used to transform and thereby modify the genome of, somatic tissue.

These methods may preferably be ex vivo, for example, creating a modified cell line. Another example is Chimeric Antigen Receptor (CAR)T cells which can be modified ex vivo and re-infused into a patient to target cancers. Thus, methods of treating suitable cancers are provided. Such methods may include delivering CRISPR-Cas complex(es) in a manner analogous to delivery of RNA or siRNA to a cancer cell to stop tumor growth herein discussed, or for RNA, e.g., sgRNA of the invention can be used in cancer modeling, e.g., with a Cas9 mouse; see, e.g., herein-cited Platt et al.

An engineered, programmable, non-naturally occurring Type II Cas (CRISPR-Cas) system that alters expression of at least one gene product in a eukaryotic cell containing and expressing a DNA molecule having a target sequence and encoding said gene product, wherein the CRISPR-Cas system comprises a CRISPR enzyme of and the present guide, preferably an optimized and/or modified Sa sgRNA and a SaCas9 enzyme.

Also provided is a polynucleotide comprising a regulatory element operable in a eukaryotic cell operably linked to a nucleotide sequence comprising the present modified guide RNA. Also provided is a vector comprising the present guide. Ideally, this guide is operably linked to a regulatory element operable in a eukaryotic cell. Also provided is a vector comprising a regulatory element operable in a eukaryotic cell operably linked to at least one nucleotide sequence encoding the present modified guide RNA (preferably a Sa sgRNA).

Further provided is a vector comprising:
a) a first regulatory element operable in a eukaryotic cell operably linked to at least one nucleotide sequence encoding the present CRISPR-Cas system guide RNA that hybridizes with the target sequence, and
b) a second regulatory element operable in a eukaryotic cell operably linked to a nucleotide sequence encoding a CRISPR enzyme,
wherein said CRISPR-Cas system further comprises one or more nuclear localization signal(s) (NLS(s)), and components (a) and (b) are located on same or different vectors of the system;
whereby said guide RNA targets the target sequence and said CRISPR enzyme binds to and optionally cleaves the DNA molecule; and
whereby expression of said at least one gene product is altered, wherein the guide RNA is preferably an optimized and/or modified Sa sgRNA and the CRISPR enzyme is a SaCas9 enzyme.

Also provided is a method of altering expression of at least one gene product in a eukaryotic cell containing and expressing a DNA molecule having a target sequence and encoding said gene product comprising introducing into said eukaryotic cell an engineered, non-naturally occurring Clustered Regularly Interspaced Short Palindromic Repeats (CRISPR)-CRISPR associated (Cas) system comprising one or more vectors comprising:
a) a first regulatory element operable in a eukaryotic cell operably linked to at least one nucleotide sequence encoding the present guide RNA that hybridizes with the target sequence, and
b) a second regulatory element operable in a eukaryotic cell operably linked to a nucleotide sequence encoding a CRISPR enzyme,
wherein said CRISPR-Cas system further comprises one or more nuclear localization signal(s) (NLS(s)), and components (a) and (b) are located on same or different vectors of the system; and
whereby said guide RNA targets the target sequence and said CRISPR enzyme binds to and optionally cleaves the DNA molecule. The method may further comprise inserting DNA into a cleaved strand of the DNA molecule. Optionally, expression of said at least one gene product is altered. The CRISPR-Cas system preferably comprises an optimized and/or modified Sa sgRNA and a SaCas9 enzyme.

Provided is a CRISPR-Cas system-mediated genome targeting method in a eukaryotic cell containing a DNA molecule having a target sequence comprising introducing into said eukaryotic cell an engineered, non-naturally occurring CRISPR-Cas system comprising one or more vectors comprising:
a) a first regulatory element operable in a eukaryotic cell operably linked to at least one nucleotide sequence encoding the present CRISPR-Cas system guide RNA that hybridizes with the target sequence, and
b) a second regulatory element operable in a eukaryotic cell operably linked to a nucleotide sequence encoding a CRISPR enzyme,
wherein said CRISPR-Cas system further comprises one or more nuclear localization signal(s) (NLS(s)), and components (a) and (b) are located on same or different vectors of the system;
the method further comprising inserting DNA into a cleaved strand of the DNA molecule;
whereby there is CRISPR-Cas system-mediated genome targeting through said CRISPR-Cas system acting as to the DNA molecule comprising said guide RNA directing sequence-specific binding of the CRISPR-Cas system, whereby there is genome editing. The CRISPR-Cas system preferably comprises an optimized and/or modified Sa sgRNA and a SaCas9 enzyme.

In general, as the guide is modified, it is not envisaged that the CRISPR enzyme and said guide naturally occur together.

The present guides may also be used in accordance with the approach taken in Konermann et al. Nature 10 Dec. 2014 (Genome-scale transcriptional activation with an engineered CRISPR-Cas9 complex). In these instances, it will be appreciated that the present modification will be in addition to and should interfere with the modification to at least one loop of the sgRNA (by the insertion of distinct RNA sequence(s) that bind to one or more adaptor proteins) as used by Konermann. Accordingly, in an aspect the invention provides a non-naturally occurring or engineered composition comprising the present modified guide RNA (sgRNA) comprising a guide sequence capable of hybridizing to a target sequence in a genomic locus of interest in a cell, wherein at least one loop of the sgRNA is further modified by the insertion of distinct RNA sequence(s) that bind to one or more adaptor proteins, and wherein the adaptor protein is associated with one or more functional domains. And when there is more than one functional domain, the functional domains can be same or different, e.g., two of the same or two different activators or repressors. In an aspect the invention provides a non-naturally occurring or engineered CRISPR-Cas complex composition comprising the herein-mentioned sgRNA and a CRISPR enzyme. In an aspect the invention provides a herein-mentioned non-naturally occurring or engineered CRISPR-Cas complex composition wherein: the CRISPR enzyme comprises at least one mutation, such that the CRISPR enzyme has no more than 5% of the nuclease activity of the CRISPR enzyme not having the at least one mutation; and/or at least one or more nuclear localization sequences. In an aspect the invention provides the herein-mentioned sgRNA or the CRISPR-Cas complex wherein one or more adaptor proteins associated with one or more functional domains is present and bound to the distinct RNA sequence(s) inserted into the at least one loop of the sgRNA. The CRISPR-Cas system as described herein preferably comprises an optimized and/or modified Sa sgRNA and a SaCas9 enzyme.

In an aspect the invention provides a non-naturally occurring or engineered composition comprising: one or more of the present modified guide RNA (sgRNA) comprising a guide sequence capable of hybridizing to a target sequence in a genomic locus of interest in a cell, a CRISPR enzyme comprising at least one or more nuclear localization sequences, wherein the CRISPR enzyme comprises at least one mutation, such that the CRISPR enzyme has no more than 5% of the nuclease activity of the CRISPR enzyme not having the at least one mutation, wherein at least one loop of at least one sgRNA is modified by the insertion of distinct RNA sequence(s) that bind to one or more adaptor proteins, and wherein the adaptor protein is associated with one or more functional domains. In an aspect the invention provides any herein-mentioned composition wherein the CRISPR enzyme has a diminished nuclease activity of at least 97%, or 100% as compared with the CRISPR enzyme not having the at least one mutation. The one or more mutations may include but are not limited to D10A, E477A, H701A and D704A mutations in the RuvC domain and/or D556A, H557 and N580A in the HNH domain of an SaCas9. Aspects of the invention also encompass at least one mutation in each of the catalytic domains (e.g. the HNH domain and the RuvC domain) of the Cas9 enzyme such that the resultant Cas9 enzyme is catalytically dead (dCas9).

In an aspect the invention provides any herein-mentioned composition wherein the CRISPR enzyme (e.g. a dCas9) is associated with one or more functional domains. In an aspect the invention provides any herein-mentioned composition wherein the one or more functional domains associated with the adaptor protein is a heterologous functional domain. In an aspect the invention provides any herein-mentioned composition wherein the one or more functional domains associated with the CRISPR enzyme is a heterologous functional domain.

In an aspect the invention provides a composition as herein discussed, wherein the adaptor protein is a fusion protein comprising the functional domain, the fusion protein optionally comprising a linker between the adaptor protein and the functional domain, the linker optionally including a GlySer linker.

In an aspect the invention provides a composition as herein discussed compositions, wherein the at least one loop of the sgRNA is not modified by the insertion of distinct RNA sequence(s) that bind to one or more adaptor proteins and wherein, optionally one of the unmodified sgRNA loops is either one of the tetraloop or the stem loop 2.

In an aspect the invention provides a composition as herein discussed wherein the one or more functional domains associated with the adaptor protein is a transcriptional activation domain.

In an aspect the invention provides a composition as herein discussed wherein the one or more functional domains associated with the CRISPR enzyme is a transcriptional activation domain.

In an aspect the invention provides a composition as herein discussed wherein the one or more functional domains associated with the adaptor protein is a transcriptional activation domain comprising VP64, p65, MyoD1, HSF1, RTA or SET7/9. Other references herein to activation (or activator) domains in respect of those associated with the adaptor protein(s) include any known transcriptional activation domain and specifically VP64, p65, MyoD1, HSF1, RTA or SET7/9. In some embodiments, the one or more functional domains is an NLS (Nuclear Localization Sequence) or an NES (Nuclear Export Signal). In some embodiments, the one or more functional domains is a transcriptional activation domain comprising and a histone acetyltransferase.

In an aspect the invention provides a composition as herein discussed wherein the one or more functional domains associated with the CRISPR enzyme is a transcriptional activation domain comprising VP64, p65, MyoD1, HSF1, RTA or SET7/9. Other references herein to activation (or activator) domains in respect of those associated with the adaptor protein(s) include any known transcriptional activation domain and specifically VP64, p65, MyoD1, HSF1, RTA or SET7/9. In some embodiments, the one or more functional domains is an NLS (Nuclear Localization Sequence) or an NES (Nuclear Export Signal). In some embodiments, the one or more functional domains is a transcriptional activation domain comprising and a histone acetyltransferase.

In an aspect the invention provides a composition as herein discussed wherein the one or more functional domains associated with the adaptor protein is a transcriptional repressor domain. In an aspect the invention provides a composition as herein discussed wherein the one or more functional domains associated with the CRISPR enzyme is a transcriptional repressor domain. In an aspect the invention provides a composition as herein discussed wherein the transcriptional repressor domain is a KRAB domain. In an aspect the invention provides a composition as herein discussed wherein the transcriptional repressor domain is a NuE domain, NcoR domain, SID domain or a SID4X domain.

In an aspect the invention provides a composition as herein discussed wherein the one or more functional domains associated with the adaptor protein have one or more activities comprising methylase activity, demethylase activity, transcription activation activity, transcription repression activity, transcription release factor activity, histone modification activity, RNA cleavage activity, DNA cleavage activity, DNA integration activity or nucleic acid binding activity.

In an aspect the invention provides a composition as herein discussed wherein the one or more functional domains associated with the CRISPR enzyme have one or more activities comprising methylase activity, demethylase activity, transcription activation activity, transcription repression activity, transcription release factor activity, histone modification activity, RNA cleavage activity, DNA cleavage activity, DNA integration activity, nucleic acid binding activity, or molecular switch activity or chemical inducibility or light inducibility.

Histone modifying domains are also preferred in some embodiments. Exemplary histone modifying domains are discussed below. Transposase domains, HR (Homologous Recombination) machinery domains, recombinase domains, and/or integrase domains are also preferred as the present functional domains. In some embodiments, DNA integration activity includes HR machinery domains, integrase domains, recombinase domains and/or transposase domains. Histone acetyltransferases are preferred in some embodiments.

Endogenous transcriptional repression is often mediated by chromatin modifying enzymes such as histone methyltransferases (HMTs) and deacetylases (HDACs). Repressive histone effector domains are known and an exemplary list is provided below. In the exemplary table, preference was given to proteins and functional truncations of small size to facilitate efficient viral packaging (for instance via AAV). In general, however, the domains may include HDACs, histone methyltransferases (HMTs), and histone acetyltransferase (HAT) inhibitors, as well as HDAC and HMT recruiting proteins. The functional domain may be or include, in some embodiments, HDAC Effector Domains, HDAC Recruiter Effector Domains, Histone Methyltransferase (HMT) Effector Domains, Histone Methyltransferase (HMT) Recruiter Effector Domains, or Histone Acetyltransferase Inhibitor Effector Domains.

TABLE 1

HDAC Effector Domains

| Subtype/ Complex | Name | Substrate (if known) | Modification (if known) | Organism | Full size (aa) | Selected truncation (aa) | Final size (aa) | Catalytic domain |
|---|---|---|---|---|---|---|---|---|
| HDAC I | HDAC8 | — | — | X. laevis | 325 | 1-325 | 325 | 1-272: HDAC |
| HDAC I | RPD3 | — | — | S. cerevisiae | 433 | 19-340 | 322 (Vannier) | 19-331: HDAC |
| HDAC IV | MesoLo4 | — | — | M. loti | 300 | 1-300 (Gregoretti) | 300 | — |
| HDAC IV | HDAC11 | — | — | H. sapiens | 347 | 1-347 (Gao) | 347 | 14-326: HDAC |
| HD2 | HDT1 | — | — | A. thaliana | 245 | 1-211 (Wu) | 211 | — |
| SIRT I | SIRT3 | H3K9Ac H4K16Ac H3K56Ac | — | H. sapiens | 399 | 143-399 (Scher) | 257 | 126-382: SIRT |
| SIRT I | HST2 | — | — | C. albicans | 331 | 1-331 (Hnisz) | 331 | — |
| SIRT I | CobB | — | — | E. coli (K12) | 242 | 1-242 (Landry) | 242 | — |
| SIRT I | HST2 | — | — | S. cerevisiae | 357 | 8-298 (Wilson) | 291 | — |
| SIRT III | SIRT5 | H4K8Ac H4K16Ac | — | H. sapiens | 310 | 37-310 (Gertz) | 274 | 41-309: SIRT |
| SIRT III | Sir2A | — | — | P. falciparum | 273 | 1-273 (Zhu) | 273 | 19-273: SIRT |
| SIRT IV | SIRT6 | H3K9Ac H3K56Ac | — | H. sapiens | 355 | 1-289 (Tennen) | 289 | 35-274: SIRT |

Accordingly, the repressor domains of the present invention may be selected from histone methyltransferases (HMNTs), histone deacetylases (HIDACs), histone acetyltransferase (HAT) inhibitors, as well as HIDAC and HMNT recruiting proteins.

The HIDAC domain may be any of those in the table above, namely: HIDAC8, RPD3, MesoLo4, HIDAC11, HIDT1, SIRT3, HST2, CobB, HST2, SIRT5, Sir2A, or SIRT6.

In some embodiments, the functional domain may be a iDAC Recruiter Effector Domain. Preferred examples include those in the Table below, namely MeCP2, MBD2b, Sin3a, NcoR, SALL1, RCOR1. NcoR is exemplified in the present Examples and, although preferred, it is envisaged that others in the class will also be useful.

TABLE 2

HDAC Recruiter Effector Domains

| Subtype/ Complex | Name | Substrate (if known) | Modification (if known) | Organism | Full size (aa) | Selected truncation (aa) | Final size (aa) | Catalytic domain |
|---|---|---|---|---|---|---|---|---|
| Sin3a | MeCP2 | — | — | R. norvegicus | 492 | 207-492 (Nan) | 286 | — |
| Sin3a | MBD2b | — | — | H. sapiens | 262 | 45-262 (Boeke) | 218 | — |
| Sin3a | Sin3a | — | — | H. sapiens | 1273 | 524-851 (Laherty) | 328 | 627-829: HDAC1 interaction |
| NcoR | NcoR | — | — | H. sapiens | 2440 | 420-488 (Zhang) | 69 | — |
| NuRD | SALL1 | — | — | M. musculus | 1322 | 1-93 (Lauberth) | 93 | — |
| COREST | RCOR1 | — | — | H. sapiens | 482 | 81-300 (Gu, Ouyang) | 220 | — |

In some embodiments, the functional domain may be a Methyltransferase (HMT) Effector Domain. Preferred examples include those in the Table below, namely NUE, vSET, EHMT2/G9A, SUV39H1, dim-5, KYP, SUVR4, SET4, SET1, SETD8, and TgSET8. NUE is exemplified in the present Examples and, although preferred, it is envisaged that others in the class will also be useful.

TABLE 3

Histone Methyltransferase (HMT) Effector Domains

| Subtype/Complex | Name | Substrate (if known) | Modification (if known) | Organism | Full size (aa) | Selected truncation (aa) | Final size (aa) | Catalytic domain |
|---|---|---|---|---|---|---|---|---|
| SET | NUE | H2B, H3, H4 | — | C. trachomatis | 219 | 1-219 (Pennini) | 219 | — |
| SET | vSET | — | H3K27me3 | P. bursaria chlorella virus | 119 | 1-119 (Mujtaba) | 119 | 4-112: SET2 |
| SUV39 family | EHMT2/G9A | H1.4K2, H3K9, H3K27 | H3K9me1/2, H1K25me1 | M. musculus | 1263 | 969-1263 (Tachibana) | 295 | 1025-1233: preSET, SET, postSET |
| SUV39 | SUV39H1 | — | H3K9me2/3 | H. sapiens | 412 | 79-412 (Snowden) | 334 | 172-412: preSET, SET, postSET |
| Suvar3-9 | dim-5 | — | H3K9me3 | N. crassa | 331 | 1-331 (Rathert) | 331 | 77-331: preSET, SET postSET |
| Suvar3-9 (SUVH subfamily) | KYP | — | H3K9me1/2 | A. thaliana | 624 | 335-601 | 267 (Jackson) | — |
| Suvar3-9 (SUVR subfamily) | SUVR4 | H3K9me1 | H3K9me2/3 | A. thaliana | 492 | 180-492 | 313 (Thorstensen) | 192-462: preSET, SET, postSET |
| Suvar4-20 | SET4 | — | H4K20me3 | C. elegans | 288 | 1-288 (Vielle) | 288 | — |
| SET8 | SET1 | — | H4K20me1 | C. elegans | 242 | 1-242 (Vielle) | 242 | — |
| SET8 | SETD8 | — | H4K20me1 | H. sapiens | 393 | 185-393 | 209 (Couture) | 256-382: SET |
| SET8 | TgSET8 | — | H4K20me1/2/3 | T. gondii | 1893 | 1590-1893 (Sautel) | 304 | 1749-1884: SET |

In some embodiments, the functional domain may be a Histone Methyltransferase (HMT) Recruiter Effector Domain. Preferred examples include those in the Table below, namely Hp1a, PHF19, and NIPP1.

TABLE 4

Histone Methyltransferase (HMT) Recruiter Effector Domains

| Subtype/Complex | Name | Substrate (if known) | Modification (if known) | Organism | Full size (aa) | Selected truncation (aa) | Final size (aa) | Catalytic domain |
|---|---|---|---|---|---|---|---|---|
| — | Hp1a | — | H3K9me3 | M. musculus | 191 | 73-191 | 119 (Hathaway) | 121-179: chromoshadow |
| — | PHF19 | — | H3K27me3 | H. sapiens | 580 | (1-250) + GGSG linker (SEQ ID NO: 26) + (500-580) | 335 (Ballaré) | 163-250: PHD2 |
| — | NIPP1 | — | H3K27me3 | H. sapiens | 351 | 1-329 (Jin) | 329 | 310-329: EED |

In some embodiment, the functional domain may be Histone Acetyltransferase Inhibitor Effector Domain. Preferred examples include SET/TAF-1β listed in the Table below.

TABLE 5

Histone Acetyltransferase Inhibitor Effector Domains

| Subtype/ Complex | Name | Substrate (if known) | Modification (if known) | Organism | Full size (aa) | Selected truncation (aa) | Final size (aa) | Catalytic domain |
|---|---|---|---|---|---|---|---|---|
| — | SET/TAF-1β | — | — | M. musculus | 289 | 1-289 (Cervoni) | 289 | — |

It is also preferred to target endogenous (regulatory) control elements (such as enhancers and silencers) in addition to a promoter or promoter-proximal elements. Thus, the invention can also be used to target endogenous control elements (including enhancers and silencers) in addition to targeting of the promoter. These control elements can be located upstream and downstream of the transcriptional start site (TSS), starting from 200 bp from the TSS to 100 kb away. Targeting of known control elements can be used to activate or repress the gene of interest. In some cases, a single control element can influence the transcription of multiple target genes. Targeting of a single control element could therefore be used to control the transcription of multiple genes simultaneously.

Targeting of putative control elements on the other hand (e.g. by tiling the region of the putative control element as well as 200 bp up to 100 kB around the element) can be used as a means to verify such elements (by measuring the transcription of the gene of interest) or to detect novel control elements (e.g. by tiling 100 kb upstream and downstream of the TSS of the gene of interest). In addition, targeting of putative control elements can be useful in the context of understanding genetic causes of disease. Many mutations and common SNP variants associated with disease phenotypes are located outside coding regions. Targeting of such regions with either the activation or repression systems described herein can be followed by readout of transcription of either a) a set of putative targets (e.g. a set of genes located in closest proximity to the control element) or b) whole-transcriptome readout by e.g. RNAseq or microarray. This would allow for the identification of likely candidate genes involved in the disease phenotype. Such candidate genes could be useful as novel drug targets.

Histone acetyltransferase (HAT) inhibitors are mentioned herein. However, an alternative in some embodiments is for the one or more functional domains to comprise an acetyltransferase, preferably a histone acetyltransferase. These are useful in the field of epigenomics, for example in methods of interrogating the epigenome. Methods of interrogating the epigenome may include, for example, targeting epigenomic sequences. Targeting epigenomic sequences may include the guide being directed to an epigenomic target sequence. Epigenomic target sequence may include, in some embodiments, include a promoter, silencer or an enhancer sequence.

Use of a functional domain linked to a CRISPR-Cas enzyme as described herein, preferably a dead-Cas, more preferably a dead-Cas9, to target epigenomic sequences can be used to activate or repress promoters, silencer or enhancers.

Examples of acetyltransferases are known but may include, in some embodiments, histone acetyltransferases. In some embodiments, the histone acetyltransferase may comprise the catalytic core of the human acetyltransferase p300 (As further described in "Epigenome editing by a CRISPR/Cas9-based acetyltransferase activates genes from promoters and enhancers". I B Hilton, A M D'Ippolito, C M Vockley, P I Thakore, G E Crawford, T E Reddy, and C A Gersbach. Nature Biotechnology 33(5):510-7 (2015), incorporated herein by reference in its entirety).

In some preferred embodiments, the functional domain is linked to a dead-Cas9 enzyme to target and activate epigenomic sequences such as promoters or enhancers. One or more guides directed to such promoters or enhancers may also be provided to direct the binding of the CRISPR enzyme to such promoters or enhancers.

The term "associated with" is used here in respect of how one molecule 'associates' with respect to another, for example between an adaptor protein and a functional domain, or between the CRISPR enzyme and a functional domain. In the case of such protein-protein interactions, this association may be viewed in terms of recognition in the way an antibody recognises an epitope. Alternatively, one protein may be associated with another protein via a fusion of the two, for instance one subunit being fused to another subunit. Fusion typically occurs by addition of the amino acid sequence of one to that of the other, for instance via splicing together of the nucleotide sequences that encode each protein or subunit. Alternatively, this may essentially be viewed as binding between two molecules or direct linkage, such as a fusion protein. In any event, the fusion protein may include a linker between the two subunits of interest (i.e. between the enzyme and the functional domain or between the adaptor protein and the functional domain). Thus, in some embodiments, the CRISPR enzyme or adaptor protein is associated with a functional domain by binding thereto. In other embodiments, the CRISPR enzyme or adaptor protein is associated with a functional domain because the two are fused together, optionally via an intermediate linker. Aspects of the linkers mentioned herein also encompass linkers between different segments of the sgRNA, e.g. between the repeat and anti-repeat sequences.

Attachment can be via a linker, e.g., a flexible glycine-serine (GlyGlyGlySer) (SEQ ID NO: 1) or (GGGS)$_3$ (SEQ ID NO: 2) or a rigid alpha-helical linker such as (Ala (GluAlaAlaAlaLys)Ala) (SEQ ID NO: 3). Linkers such as (GGGGS)$_3$ (SEQ ID NO: 4) are preferably used herein to separate protein or peptide domains. (GGGGS)3 (SEQ ID NO: 4) is preferable because it is a relatively long linker (15 amino acids). The glycine residues are the most flexible and the serine residues enhance the chance that the linker is on the outside of the protein. (GGGGS)$_6$ (SEQ ID NO: 5) (GGGGS)$_9$ (SEQ ID NO: 6) or (GGGGS)$_{12}$ (SEQ ID NO: 7) may preferably be used as alternatives. Other preferred alternatives are (GGGGS)$_1$ (SEQ ID NO: 8), (GGGGS)$_2$ (SEQ ID NO: 9), (GGGGS)$_4$ (SEQ ID NO: 10), (GGGGS)$_5$ (SEQ ID NO: 11), (GGGGS)$_7$ (SEQ ID NO: 12), (GGGGS)$_8$ (SEQ ID NO: 13), (GGGGS)$_{10}$ (SEQ ID NO: 14), or (GGGGS)$_{11}$ (SEQ ID NO: 15). Alternative linkers are available, but highly flexible linkers are thought to work best to allow for maximum opportunity for the 2 parts of the Cas9 to come together and thus reconstitute Cas9 activity. One alternative is that the NLS of nucleoplasmin can be used as a linker. For example, a linker can also be used between the Cas9 and any functional domain. Again, a (GGGGS)$_3$ (SEQ ID NO: 4) linker may be used here (or the 6 (SEQ ID NO: 5), 9 (SEQ ID NO: 6), or 12 (SEQ ID NO: 7) repeat versions therefore) or the NLS of nucleoplasmin can be used as a linker between Cas9 and the functional domain.

In an aspect the invention provides a composition as herein discussed wherein the DNA cleavage activity is due to a nuclease. In an aspect the invention provides a composition as herein discussed wherein the nuclease comprises a Fok1 nuclease.

Preferably, the tracr sequence has one or more hairpins and is 30 or more nucleotides in length, 40 or more nucleotides in length, or 50 or more nucleotides in length, preferably 49-53 nucleotides in length. Preferably, the guide sequence is between 10 to 30 nucleotides in length, most preferably 20-24 nucleotides in length. The CRISPR/Cas enzyme is most preferably a Type II Cas9 enzyme, a SaCas9 enzyme is highly preferred in this invention. Chimeras, especially those that blend Sp, Sa, St or domains of other orthologs are also preferred.

In general, where a nucleotide or stretch of nucleotides is modified by replacement, then the same number of nucleotides should be inserted as removed. Thus, if one nucleotide is replaced, one is inserted, or if four nucleotides are replaced, four are inserted.

The number of stem loops in the optimized Sa sgRNA is preferably 2 (not including the tetraloop). The number of stem loops can be easily engineered in or out as desired by introducing or removing nucleotides which result in the desired secondary structure.

The tetraloop may be further engineered in view of Konermann et al ("Genome-scale transcriptional activation with an engineered CRISPR-Cas9 complex" Nature published online 10 Dec. 2014). Particularly preferred are guides further modified in accordance with the Konermann Nature 10 Dec. 2014 paper mentioned above. These guides are further modified so that protein-binding RNA portions (such as aptamers) are added to or replace the tetraloop and/or stemloop 2. Corresponding RNA-binding protein domains can be sued to then recognize the RNA and recruit functional domains, such as those described herein, to the guide. This is primarily for use with deadCas9s leading to transcriptional activation or repression or DNA cleavage through nucleases such as Fok1. The use of such guides in combination with deadCas9s is powerful, and it is especially powerful if the Cas9 itself is also associated with its own functional domain, as discussed herein. When a deadCas9 (with or without its own associated functional domain) is induced to reconstitute in accordance with the present invention, i.e. is a split Cas9, then the tool is especially useful.

Konermann provides a guide RNA (sgRNA), also preferred for use in the present invention, comprising a guide sequence capable of hybridizing to a target sequence in a genomic locus of interest in a cell, wherein at least one loop of the sgRNA is further modified by the insertion of distinct RNA sequence(s) that bind to one or more adaptor proteins, and wherein the adaptor protein is associated with one or more functional domains. The CRISPR enzyme is preferably a deadCas9. It may comprise at least one mutation, such that the CRISPR enzyme has no more than 5% of the nuclease activity of the CRISPR enzyme not having the at least one mutation; and/or at least one or more nuclear localization sequences. Also provided is a non-naturally occurring or engineered composition comprising: one or more guide RNA (sgRNA) comprising a guide sequence capable of hybridizing to a target sequence in a genomic locus of interest in a cell, a CRISPR enzyme comprising at least one or more nuclear localization sequences, wherein the CRISPR enzyme comprises at least one mutation, such that the CRISPR enzyme has no more than 5% of the nuclease activity of the CRISPR enzyme not having the at least one mutation, wherein at least one loop of at least one sgRNA is modified by the insertion of distinct RNA sequence(s) that bind to one or more adaptor proteins, and wherein the adaptor protein is associated with one or more functional domains. The CRISPR-Cas system as described herein preferably comprises an optimized and/or modified Sa sgRNA and a SaCas9 enzyme.

The at least one loop of the sgRNA that is preferably modified by the insertion of distinct RNA sequence(s) that bind to one or more adaptor proteins is either one or both of the tetraloop or the stem loop 2. The insertion of distinct RNA sequence(s) that bind to one or more adaptor proteins is preferably an aptamer sequence or two or more aptamer sequences specific to the same or different adaptor protein(s). The adaptor protein preferably comprises MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s, PRR1.

The one or more functional domains may be transcriptional activation domain or a repressor domain. Although they may be different domains it is preferred that all the functional domains are either activator or repressor and that a mixture of the two is not used.

The transcriptional activation domain may comprise VP64, p65, MyoD1, HSF1, RTA or SET7/9.

The one or more functional domains associated with the Cas9 may be a transcriptional repressor domain. The transcriptional repressor domain may be a KRAB domain. The transcriptional repressor domain may be a NuE domain, NcoR domain, SID domain or a SID4X domain.

The one or more functional domains associated with the adaptor protein may have one or more activities comprising methylase activity, demethylase activity, transcription activation activity, transcription repression activity, transcription release factor activity, histone modification activity, RNA cleavage activity, DNA cleavage activity, DNA integration activity or nucleic acid binding activity.

Histone modifying domains are also preferred in some embodiments. Exemplary histone modifying domains are discussed below. Transposase domains, HR (Homologous Recombination) machinery domains, recombinase domains, and/or integrase domains are also preferred as the present functional domains. In some embodiments, DNA integration activity includes HR machinery domains, integrase domains, recombinase domains and/or transposase domains. The DNA cleavage activity may be due to a nuclease, for example a Fok1 nuclease.

The term "associated with" is used here in respect of how one molecule 'associates' with respect to another, for example between an adaptor protein and a functional domain, or between the CRISPR enzyme and a functional domain. In the case of such protein-protein interactions, this association may be viewed in terms of recognition in the way an antibody recognizes an epitope. Alternatively, one protein may be associated with another protein via a fusion of the two, for instance one subunit being fused to another subunit. Fusion typically occurs by addition of the amino acid sequence of one to that of the other, for instance via splicing together of the nucleotide sequences that encode each protein or subunit. Alternatively, this may essentially be viewed as binding between two molecules or direct linkage, such as a fusion protein. In any event, the fusion protein may include a linker between the two subunits of interest (i.e. between the enzyme and the functional domain or between the adaptor protein and the functional domain). Thus, in some embodiments, the CRISPR enzyme or adaptor protein is associated with a functional domain by binding thereto. In other embodiments, the CRISPR enzyme or adaptor protein is associated with a functional domain because the two are fused together, optionally via an intermediate linker.

In an aspect, the invention provides a CRISPR-Cas system comprising the present guide together with a CRISPR-Cas enzyme, in particular Cas9. Thus, also provided is a non-naturally occurring or engineered composition comprising a CRISPR-Cas system, comprising the present guide and a CRISPR-Cas enzyme, in particular Cas9, especially Sa Cas9 or Sp Cas9.

In an aspect, the invention provides a non-naturally occurring or engineered composition comprising a CRISPR-Cas system comprising a guide RNA (sgRNA) comprising a guide sequence capable of hybridizing to a target sequence in a genomic locus of interest in a cell wherein architecture of the sgRNA is modified. The guide preferably also includes a tracr sequence and a tracr mate as described herein. The sgRNA typically includes a PAM-proximal region. It typically also include a repeat;anti-repeat duplex. These are most preferably retained but they can be modified, provided at 50% of binding specificity to the target is retained.

In general, the CRISPR-Cas or CRISPR system is as used in the foregoing documents, such as WO 2014/093622 (PCT/US2013/074667) and refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise any polynucleotide, such as DNA or RNA polynucleotides. In some embodiments, a target sequence is located in the nucleus or cytoplasm of a cell. In some embodiments, direct repeats may be identified in silico by searching for repetitive motifs that fulfill any or all of the following criteria: 1. found in a 2 Kb window of genomic sequence flanking the type II CRISPR locus; 2. span from 20 to 50 bp; and 3. interspaced by 20 to 50 bp. In some embodiments, 2 of these criteria may be used, for instance 1 and 2, 2 and 3, or 1 and 3. In some embodiments, all 3 criteria may be used.

In embodiments of the invention the terms guide sequence and guide RNA are used interchangeably as in foregoing cited documents such as WO 2014/093622 (PCT/US2013/074667). In general, a guide sequence is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies; available at www.novocraft.com), ELAND (Illumina, San Diego, CA), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. Preferably the guide sequence is 10-30 nucleotides long. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art. A guide sequence may be selected to target any target sequence. In some embodiments, the target sequence is a sequence within a genome of a cell. Exemplary target sequences include those that are unique in the target genome. For example, for the S. pyogenes Cas9, a unique target sequence in a genome may include a Cas9 target site of the form MMMMMMMMNNNNNNNNNNNXGG (SEQ ID NO: 27) where NNNNNNNNNNNXGG (SEQ ID NO: 28) (N is A, G, T, or C; and X can be anything) has a single occurrence in the genome. A unique target sequence in a genome may include an S. pyogenes Cas9 target site of the form MMMMMMMMMNNNNNNNNNNNXGG (SEQ ID NO: 29) where NNNNNNNNNNNXGG (SEQ ID NO: 30) (N is A, G, T, or C; and X can be anything) has a single occurrence in the genome. For the S. thermophilus CRISPR1 Cas9, a unique target sequence in a genome may include a Cas9 target site of the form MMMMMMMMNNNNNNNNNNNXXAGAAW (SEQ ID NO: 31) where NNNNNNNNNNNNNXXAGAAW (SEQ ID NO: 32) (N is A, G, T, or C; X can be anything; and W is A or T) has a single occurrence in the genome. A unique target sequence in a genome may include an *S. thermophilus* CRISPR1 Cas9 target site of the form MMMMMMMMMNNNNNNNNNNNXXAGAAW (SEQ ID NO: 33) where NNNNNNNNNNNXXAGAAW (SEQ ID NO: 34) (N is A, G, T, or C; X can be anything; and W is A or T) has a single occurrence in the genome. For the *S. pyogenes* Cas9, a unique target sequence in a genome may include a Cas9 target site of the form MMMMMMMMMNNNNNNNNNNNNXGGXG (SEQ ID NO: 35) where NNNNNNNNNNNNXGGXG (SEQ ID NO: 36) (N is A, G, T, or C; and X can be anything) has a single occurrence in the genome. A unique target sequence in a genome may include an *S. pyogenes* Cas9 target site of the form MMMMMMMMMNNNNNNNNNNNNXGGXG (SEQ ID NO: 37) where NNNNNNNNNNNXGGXG (SEQ ID NO: 38) (N is A, G, T, or C; and X can be anything) has a single occurrence in the genome. In each of these sequences "M" may be A, G, T, or C, and need not be considered in identifying a sequence as unique. In some embodiments, a guide sequence is selected to reduce the degree secondary structure within the guide sequence. In some embodiments, about or less than about 75%, 50%, 40%, 30%, 25%, 20%, 15%, 10%, 5%, 1%, or fewer of the nucleotides of the guide sequence participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g. A. R. Gruber et al., 2008, Cell 106(1): 23-24; and P A Carr and G M Church, 2009, Nature Biotechnology 27(12): 1151-62).

In general, a tracr mate sequence includes any sequence that has sufficient complementarity with a tracr sequence to promote one or more of: (1) excision of a guide sequence flanked by tracr mate sequences in a cell containing the corresponding tracr sequence; and (2) formation of a CRISPR complex at a target sequence, wherein the CRISPR complex comprises the tracr mate sequence hybridized to the tracr sequence. In general, degree of complementarity is with reference to the optimal alignment of the tracr mate sequence and tracr sequence, along the length of the shorter of the two sequences. Optimal alignment may be determined by any suitable alignment algorithm, and may further account for secondary structures, such as self-complementarity within either the tracr sequence or tracr mate sequence. In some embodiments, the degree of complementarity between the tracr sequence and tracr mate sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and tracr mate sequence are contained within a single transcript, such that hybridization between the two produces a transcript having a secondary structure, such as a hairpin. In an embodiment of the invention, the transcript or transcribed polynucleotide sequence has at least two or more hairpins. In preferred embodiments, the transcript has two, three, four or five hairpins. In a further embodiment of the invention, the transcript has at most five hairpins. In a hairpin structure the portion of the sequence 5' of the final "N" and upstream of the loop corresponds to the tracr mate sequence, and the portion of the sequence 3' of the loop corresponds to the tracr sequence Further non-limiting examples of single polynucleotides comprising a guide sequence, a tracr mate sequence, and a tracr sequence are as follows (listed 5' to 3'), where "N" represents a base of a guide sequence, the first block of lower case letters represent the tracr mate sequence, and the second block of lower case letters represent the tracr sequence, and the final poly-T sequence represents the transcription terminator: (1) NNNNNNNNNNNNNNNNNNNNgttttgtactctcaagatt-taGAAAtaaatcttgcagaagctacaaagataa ggcttcatgccgaaat-caacaccctgtcattttatggcagggtgttttcgttatttaaTTTTTT (SEQ ID NO: 39); (2) NNNNNNNNNNNNNNNNNNNNgttttgtactctcaGAAAtgc agaagctacaaagataaggcttcatgccg aaatcaacaccctgtcattt-tatggcagggtgttttcgttatttaaTTTTTT (SEQ ID NO: 40); (3) NNNNNNNNNNNNNNNNNNNNgttttgtactctcaGAAAtg cagaagctacaaagataaggcttcatgccg aaatcaacaccctgtcattt-tatggcagggtgtTTTTTT (SEQ ID NO: 41); (4) NNNNNNNNNNNNNNNNNNNNgttt-tagagctaGAAAtagcaagttaaaataaggctagtccgttatcaactt gaaaaagtggcaccgagtcggtgcTTTTTTT (SEQ ID NO: 42); (5) NNNNNNNNNNNNNNNNNNNNgttt-tagagctaGAAATAGcaagttaaaataaggctagtccgttatcaac ttgaaaaagtgTTTTTTT (SEQ ID NO: 43); and (6) NNNNNNNNNNNNNNNNNNNNgttt-tagagctagAAATAGcaagttaaaataaggctagtccgttatcaTT TTTTTT (SEQ ID NO: 44). In some embodiments, sequences (1) to (3) are used in combination with Cas9 from *S. thermophilus* CRISPR1. In some embodiments, sequences (4) to (6) are used in combination with Cas9 from *S. pyogenes*. In some embodiments, the tracr sequence is a separate transcript from a transcript comprising the tracr mate sequence.

In some embodiments, candidate tracrRNA may be subsequently predicted by sequences that fulfill any or all of the following criteria: 1. sequence homology to direct repeats (motif search in Geneious with up to 18-bp mismatches); 2. presence of a predicted Rho-independent transcriptional terminator in direction of transcription; and 3. stable hairpin secondary structure between tracrRNA and direct repeat. In some embodiments, 2 of these criteria may be used, for instance 1 and 2, 2 and 3, or 1 and 3. In some embodiments, all 3 criteria may be used.

In some embodiments, chimeric synthetic guide RNAs (sgRNAs) designs may incorporate at least 12 bp of duplex structure between the direct repeat and tracrRNA.

For minimization of toxicity and off-target effect, it will be important to control the concentration of CRISPR enzyme mRNA and guide RNA delivered. Optimal concentrations of CRISPR enzyme mRNA and guide RNA can be determined by testing different concentrations in a cellular or non-human eukaryote animal model and using deep sequencing the analyze the extent of modification at potential off-target genomic loci. For example, for the guide sequence targeting 5'-GAGTCCGAGCAGAAGAAGAA-3' (SEQ ID NO: 45) in the EMX1 gene of the human genome, deep sequencing can be used to assess the level of modification at the following two off-target loci, 1: 5'-GAGTCCTAGCAGGAGAAGAA-3' (SEQ ID NO: 46) and 2: 5'-GAGTCTAAGCAGAAGAAGAA-3' (SEQ ID NO: 47). The concentration that gives the highest level of on-target modification while minimizing the level of off-target modification should be chosen for in vivo delivery. Alternatively, to minimize the level of toxicity and off-target effect, CRISPR enzyme nickase mRNA (for example *S. pyogenes* Cas9 with the D10A mutation) can be delivered with a pair of guide RNAs targeting a site of interest. The two guide RNAs need to be spaced as follows. Guide sequences and strategies to minimize toxicity and off-target effects can be as in WO 2014/093622 (PCT/US2013/074667).

The CRISPR system is derived advantageously from a type II CRISPR system. In some embodiments, one or more elements of a CRISPR system is derived from a particular organism comprising an endogenous CRISPR system, such as *Streptococcus pyogenes*. In preferred embodiments of the invention, the CRISPR system is a type II CRISPR system and the Cas enzyme is Cas9, which catalyzes DNA cleavage. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof.

In some embodiments, the unmodified CRISPR enzyme has DNA cleavage activity, such as Cas9. In some embodiments, the CRISPR enzyme directs cleavage of one or both strands at the location of a target sequence, such as within the target sequence and/or within the complement of the target sequence. In some embodiments, the CRISPR enzyme directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, a vector encodes a CRISPR enzyme that is mutated to with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). Other examples of mutations that render Cas9 a nickase include, without limitation, H840A, N854A, and N863A. As a further example, two or more catalytic domains of Cas9 (RuvC I, RuvC II, and RuvC III or the HNH domain) may be mutated to produce a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity. In some embodiments, a CRISPR enzyme is considered to substantially lack all DNA cleavage activity when the DNA cleavage activity of the mutated enzyme is about no more than 25%, 10%, 5%, 1%, 0.1%, 0.01%, or less of the DNA cleavage activity of the non-mutated form of the enzyme; an example can be when the DNA cleavage activity of the mutated form is nil or negligible as compared with the non-mutated form. Where the enzyme is not SpCas9, mutations may be made at any or all residues corresponding to positions 10, 762, 840, 854, 863 and/or 986 of SpCas9 (which may be ascertained for instance by standard sequence comparison tools). In particular, any or all of the following mutations are preferred in SpCas9: D10A, E762A, H840A, N854A, N863A and/or D986A; as well as conservative substitution for any of the replacement amino acids is also envisaged. The same (or conservative substitutions of these mutations) at corresponding positions in other Cas9s are also preferred. Particularly preferred are D10 and H840 in SpCas9. However, in other Cas9s, residues corresponding to SpCas9 D10 and H840 are also preferred.

Orthologs of SpCas9 can be used in the practice of the invention. A Cas enzyme may be identified Cas9 as this can refer to the general class of enzymes that share homology to the biggest nuclease with multiple nuclease domains from the type II CRISPR system. Type II CRISPR-Cas9 enzymes, are large multidomain proteins sufficient for targeting and cleaving DNA. Orthologs of Cas9 also refer to enzymes of Class 2 CRISPR-Cas systems. Class 2 is an evolutionary classification which encompasses single-subunit effector complexes. Most preferably, the Cas9 enzyme is from, or is derived from, spCas9 (*S. pyogenes* Cas9) or saCas9 (*S. aureus* Cas9). StCas9" refers to wild type Cas9 from *S. thermophilus*, the protein sequence of which is given in the SwissProt database under accession number G3ECR1. Similarly, *S pyogenes* Cas9 or spCas9 is included in SwissProt under accession number Q99ZW2. By derived, Applicants mean that the derived enzyme is largely based, in the sense of having a high degree of sequence homology with, a wildtype enzyme, but that it has been mutated (modified) in some way as described herein. It will be appreciated that the terms Cas and CRISPR enzyme are generally used herein interchangeably, unless otherwise apparent. As mentioned above, many of the residue numberings used herein refer to the Cas9 enzyme from the type II CRISPR locus in *Streptococcus pyogenes*. However, it will be appreciated that this invention includes many more Cas9s from other species of microbes, such as SpCas9, SaCa9, St1Cas9 and so forth. Enzymatic action by Cas9 derived from *Streptococcus pyogenes* or any closely related Cas9 generates double stranded breaks at target site sequences which hybridize to 20 nucleotides of the guide sequence and that have a protospacer-adjacent motif (PAM) sequence (examples include NGG/NRG or a PAM that can be determined as described herein) following the 20 nucleotides of the target sequence. CRISPR activity through Cas9 for site-specific DNA recognition and cleavage is defined by the guide sequence, the tracr sequence that hybridizes in part to the guide sequence and the PAM sequence. More aspects of the CRISPR system are described in Karginov and Hannon, The CRISPR system: small RNA-guided defence in bacteria and archaea, Mole Cell 2010, January 15; 37(1): 7. The type II CRISPR locus from *Streptococcus pyogenes* SF370, which contains a cluster of four genes Cas9, Cas1, Cas2, and Csn1, as well as two non-coding RNA elements, tracrRNA and a characteristic array of repetitive sequences (direct repeats) interspaced by short stretches of non-repetitive sequences (spacers, about 30 bp each). In this system, targeted DNA double-strand break (DSB) is generated in four sequential steps. First, two non-coding RNAs, the pre-crRNA array and tracrRNA, are transcribed from the CRISPR locus. Second, tracrRNA hybridizes to the direct repeats of pre-crRNA, which is then processed into mature crRNAs containing individual spacer sequences. Third, the mature crRNA:tracrRNA complex directs Cas9 to the DNA target consisting of the protospacer and the corresponding PAM via heteroduplex formation between the spacer region of the crRNA and the protospacer DNA. Finally, Cas9 mediates cleavage of target DNA upstream of PAM to create a DSB within the protospacer. A pre-crRNA array consisting of a single spacer flanked by two direct repeats (DRs) is also encompassed by the term "tracr-mate sequences"). In certain embodiments, Cas9 may be constitutively present or inducibly present or conditionally present or administered or delivered. Cas9 optimization may be used to enhance function or to develop new functions, one can generate chimeric Cas9 proteins. And Cas9 may be used as a generic DNA binding protein.

In an aspect, the CRISPR enzyme comprises H840A, or D10A and H840A, or D10A and N863A, according to SpCas9 protein or any corresponding ortholog. N580 in Sa corresponds to N863 in Sp Cas9. Accordingly, in an aspect, the CRISPR enzyme comprises: N580A according to SaCas9 protein or any corresponding ortholog; or D10A according to SpCas9 protein, or any corresponding ortholog, and N580A according to SaCas9 protein.

Typically, in the context of an endogenous CRISPR system, formation of a CRISPR complex (comprising a guide sequence hybridized to a target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. Without wishing to be bound by theory, the tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence.

An example of a codon optimized sequence, is in this instance a sequence optimized for expression in a eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a CRISPR enzyme is codon optimized for expression in particular cells, such as eukaryotic cells. The eukaryotic cells may be those of or derived from a particular organism, such as a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.orjp/codon/and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g. 1, 2, 3, 4, 5, 10, 15, 20, 25, 50, or more, or all codons) in a sequence encoding a CRISPR enzyme correspond to the most frequently used codon for a particular amino acid.

In some embodiments, a vector encodes a CRISPR enzyme comprising one or more nuclear localization sequences (NLSs), such as about or more than about 1, 2, 3, 4, 5, 6, 7, 8, 9, 10, or more NLSs. In some embodiments, the CRISPR enzyme comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g. zero or at least one or more NLS at the amino-terminus and zero or at one or more NLS at the carboxy terminus). When more than one NLS is present, each may be selected independently of the others, such that a single NLS may be present in more than one copy and/or in combination with one or more other NLSs present in one or more copies. In a preferred embodiment of the invention, the CRISPR enzyme comprises at most 6 NLSs. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Non-limiting examples of NLSs include an NLS sequence derived from: the NLS of the SV40 virus large T-antigen, having the amino acid sequence PKKKRKV (SEQ ID NO: 48); the NLS from nucleoplasmin (e.g. the nucleoplasmin bipartite NLS with the sequence KRPAATKKAGQAKKKK (SEQ ID NO: 49)); the c-myc NLS having the amino acid sequence PAAKRVKLD (SEQ ID NO: 50) or RQRRNELKRSP (SEQ ID NO: 51); the hRNPA1 M9 NLS having the sequence NQSSNFGPMKGGNFGGRSSGPYGGGGQYFAKPRNQGGY (SEQ ID NO: 52); the sequence RMRIZFKNKGKDTAELRRRRVEVSVELRKAKKDEQILKRRNV (SEQ ID NO: 53) of the IBB domain from importin-alpha; the sequences VSRKRPRP (SEQ ID NO: 54) and PPKKARED (SEQ ID NO: 55) of the myoma T protein; the sequence PQPKKKPL (SEQ ID NO: 56) of human p53; the sequence SALIKKKKKMAP (SEQ ID NO: 57) of mouse c-abl IV; the sequences DRLRR (SEQ ID NO: 58) and PKQKKRK (SEQ ID NO: 59) of the influenza virus NS1; the sequence RKLKKKIKKL (SEQ ID NO: 60) of the Hepatitis virus delta antigen; the sequence REKKKFLKRR (SEQ ID NO: 61) of the mouse Mx1 protein; the sequence KRKGDEVDGVDEVAKKKSKK (SEQ ID NO: 62) of the human poly(ADP-ribose) polymerase; and the sequence RKCLQAGMNLEARKTKK (SEQ ID NO: 63) of the steroid hormone receptors (human) glucocorticoid. In general, the one or more NLSs are of sufficient strength to drive accumulation of the CRISPR enzyme in a detectable amount in the nucleus of a eukaryotic cell. In general, strength of nuclear localization activity may derive from the number of NLSs in the CRISPR enzyme, the particular NLS(s) used, or a combination of these factors. Detection of accumulation in the nucleus may be performed by any suitable technique. For example, a detectable marker may be fused to the CRISPR enzyme, such that location within a cell may be visualized, such as in combination with a means for detecting the location of the nucleus (e.g. a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of CRISPR complex formation (e.g. assay for DNA cleavage or mutation at the target sequence, or assay for altered gene expression activity affected by CRISPR complex formation and/or CRISPR enzyme activity), as compared to a control no exposed to the CRISPR enzyme or complex, or exposed to a CRISPR enzyme lacking the one or more NLSs.

Aspects of the invention relate to the expression of the gene product being decreased or a template polynucleotide being further introduced into the DNA molecule encoding the gene product or an intervening sequence being excised precisely by allowing the two 5' overhangs to reanneal and ligate or the activity or function of the gene product being altered or the expression of the gene product being increased. In an embodiment of the invention, the gene product is a protein. Only sgRNA pairs creating 5' overhangs with less than 8 bp overlap between the guide sequences (offset greater than −8 bp) were able to mediate detectable indel formation. Importantly, each guide used in these assays is able to efficiently induce indels when paired with wildtype Cas9, indicating that the relative positions of the guide pairs are the most important parameters in predicting double nicking activity. Since Cas9n and Cas9H840A nick opposite strands of DNA, substitution of Cas9n with Cas9H840A with a given sgRNA pair should have resulted in the inversion of the overhang type; but no indel formation is observed as with Cas9H840A indicating that Cas9H840A is a CRISPR enzyme substantially lacking all DNA cleavage activity (which is when the DNA cleavage activity of the mutated enzyme is about no more than 25%, 10%, 5%, 1%, 0.1%, 0.01%, or less of the DNA cleavage activity of the non-mutated form of the enzyme; whereby an example can be when the DNA cleavage activity of the mutated form is nil or negligible as compared with the non-mutated form, e.g., when no indel formation is observed as with Cas9H840A in the eukaryotic system in contrast to the biochemical or prokaryotic systems). Nonetheless, a pair of sgRNAs that will generate a 5' overhang with Cas9n should in principle generate the corresponding 3' overhang instead, and double nicking. Therefore, sgRNA pairs that lead to the generation of a 3' overhang with Cas9n can be used with another mutated Cas9 to generate a 5' overhang, and double nicking. Accordingly, in some embodiments, a recombination template is also provided. A recombination template may be a component of another vector as described herein, contained in a separate vector, or provided as a separate polynucleotide. In some embodiments, a recombination template is designed to serve as a template in homologous recombination, such as within or near a target sequence nicked or cleaved by a CRISPR enzyme as a part of a CRISPR complex. A template polynucleotide may be of any suitable length, such as about or more than about 10, 15, 20, 25, 50, 75, 100, 150, 200, 500, 1000, or more nucleotides in length. In some embodiments, the template polynucleotide is complementary to a portion of a polynucleotide comprising the target sequence. When optimally aligned, a template polynucleotide might overlap with one or more nucleotides of a target sequences (e.g. about or more than about 1, 5, 10, 15, 20, or more nucleotides). In some embodiments, when a template sequence and a polynucleotide comprising a target sequence are optimally aligned, the nearest nucleotide of the template polynucleotide is within about 1, 5, 10, 15, 20, 25, 50, 75, 100, 200, 300, 400, 500, 1000, 5000, 10000, or more nucleotides from the target sequence.

In some embodiments, one or more vectors driving expression of one or more elements of a CRISPR system are introduced into a host cell such that expression of the elements of the CRISPR system direct formation of a CRISPR complex at one or more target sites. For example, a Cas enzyme, a guide sequence linked to a tracr-mate sequence, and a tracr sequence could each be operably linked to separate regulatory elements on separate vectors. Or, RNA(s) of the CRISPR System can be delivered to a transgenic Cas9 animal or mammal, e.g., an animal or mammal that constitutively or inducibly or conditionally expresses Cas9; or an animal or mammal that is otherwise expressing Cas9 or has cells containing Cas9, such as by way of prior administration thereto of a vector or vectors that code for and express in vivo Cas9. Alternatively, two or more of the elements expressed from the same or different regulatory elements, may be combined in a single vector, with one or more additional vectors providing any components of the CRISPR system not included in the first vector. CRISPR system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding a CRISPR enzyme and one or more of the guide sequence, tracr mate sequence (optionally operably linked to the guide sequence), and a tracr sequence embedded within one or more intron sequences (e.g. each in a different intron, two or more in at least one intron, or all in a single intron). In some embodiments, the CRISPR enzyme, guide sequence, tracr mate sequence, and tracr sequence are operably linked to and expressed from the same promoter. Delivery vehicles, vectors, particles, nanoparticles, formulations and components thereof for expression of one or more elements of a CRISPR system are as used in the foregoing documents, such as WO 2014/093622 (PCT/US2013/074667). In some embodiments, a vector comprises one or more insertion sites, such as a restriction endonuclease recognition sequence (also referred to as a "cloning site"). In some embodiments, one or more insertion sites (e.g. about or more than about 1, 2, 3, 4, 5, 6, 7, 8, 9, 10, or more insertion sites) are located upstream and/or downstream of one or more sequence elements of one or more vectors. In some embodiments, a vector comprises an insertion site upstream of a tracr mate sequence, and optionally downstream of a regulatory element operably linked to the tracr mate sequence, such that following insertion of a guide sequence into the insertion site and upon expression the guide sequence directs sequence-specific binding of a CRISPR complex to a target sequence in a eukaryotic cell. In some embodiments, a vector comprises two or more insertion sites, each insertion site being located between two tracr mate sequences so as to allow insertion of a guide sequence at each site. In such an arrangement, the two or more guide sequences may comprise two or more copies of a single guide sequence, two or more different guide sequences, or combinations of these. When multiple different guide sequences are used, a single expression construct may be used to target CRISPR activity to multiple different, corresponding target sequences within a cell. For example, a single vector may comprise about or more than about 1, 2, 3, 4, 5, 6, 7, 8, 9, 10, 15, 20, or more guide sequences. In some embodiments, about or more than about 1, 2, 3, 4, 5, 6, 7, 8, 9, 10, or more such guide-sequence-containing vectors may be provided, and optionally delivered to a cell. In some embodiments, a vector comprises a regulatory element operably linked to an enzyme-coding sequence encoding a CRISPR enzyme, such as a Cas protein. CRISPR enzyme or CRISPR enzyme mRNA or CRISPR guide RNA or RNA(s) can be delivered separately; and advantageously at least one of these is delivered via a particle or nanoparticle complex. CRISPR enzyme mRNA can be delivered prior to the guide RNA to give time for CRISPR enzyme to be expressed. CRISPR enzyme mRNA might be administered 1-12 hours (preferably around 2-6 hours) prior to the administration of guide RNA. Alternatively, CRISPR enzyme mRNA and guide RNA can be administered together. Advantageously, a second booster dose of guide RNA can be administered 1-12 hours (preferably around 2-6 hours) after the initial administration of CRISPR enzyme mRNA+guide RNA. Additional administrations of CRISPR enzyme mRNA and/or guide RNA might be useful to achieve the most efficient levels of genome modification.

In one aspect, the invention provides methods for using one or more elements of a CRISPR system. The CRISPR complex of the invention provides an effective means for modifying a target polynucleotide. The CRISPR complex of the invention has a wide variety of utility including modifying (e.g., deleting, inserting, translocating, inactivating, activating) a target polynucleotide in a multiplicity of cell types. As such the CRISPR complex of the invention has a broad spectrum of applications in, e.g., gene therapy, drug screening, disease diagnosis, and prognosis. An exemplary CRISPR complex comprises a CRISPR enzyme complexed with a guide sequence hybridized to a target sequence within the target polynucleotide. The guide sequence is linked to a tracr mate sequence, which in turn hybridizes to a tracr sequence. In one embodiment, this invention provides a method of cleaving a target polynucleotide. The method comprises modifying a target polynucleotide using a CRISPR complex that binds to the target polynucleotide and effect cleavage of said target polynucleotide. Typically, the CRISPR complex of the invention, when introduced into a cell, creates a break (e.g., a single or a double strand break) in the genome sequence. For example, the method can be used to cleave a disease gene in a cell. The break created by the CRISPR complex can be repaired by a repair processes such as the error prone non-homologous end joining (NHEJ) pathway or the high fidelity homology-directed repair (HDR). During these repair process, an exogenous polynucleotide template can be introduced into the genome sequence. In some methods, the HDR process is used modify genome sequence. For example, an exogenous polynucleotide template comprising a sequence to be integrated flanked by an upstream sequence and a downstream sequence is introduced into a cell. The upstream and downstream sequences share sequence similarity with either side of the site of integration in the chromosome. Where desired, a donor polynucleotide can be DNA, e.g., a DNA plasmid, a bacterial artificial chromosome (BAC), a yeast artificial chromosome (YAC), a viral vector, a linear piece of DNA, a PCR fragment, a naked nucleic acid, or a nucleic acid complexed with a delivery vehicle such as a liposome or poloxamer. The exogenous polynucleotide template comprises a sequence to be integrated (e.g., a mutated gene). The sequence for integration may be a sequence endogenous or exogenous to the cell. Examples of a sequence to be integrated include polynucleotides encoding a protein or a non-coding RNA (e.g., a microRNA). Thus, the sequence for integration may be operably linked to an appropriate control sequence or sequences. Alternatively, the sequence to be integrated may provide a regulatory function. The upstream and downstream sequences in the exogenous polynucleotide template are selected to promote recombination between the chromosomal sequence of interest and the donor polynucleotide. The upstream sequence is a nucleic acid sequence that shares sequence similarity with the genome sequence upstream of the targeted site for integration. Similarly, the downstream sequence is a nucleic acid sequence that shares sequence similarity with the chromosomal sequence downstream of the targeted site of integration. The upstream and downstream sequences in the exogenous polynucleotide template can have 75%, 80%, 85%, 90%, 95%, or 100% sequence identity with the targeted genome sequence. Preferably, the upstream and downstream sequences in the exogenous polynucleotide template have about 95%, 96%, 97%, 98%, 99%, or 100% sequence identity with the targeted genome sequence. In some methods, the upstream and downstream sequences in the exogenous polynucleotide template have about 99% or 100% sequence identity with the targeted genome sequence. An upstream or downstream sequence may comprise from about 20 bp to about 2500 bp, for example, about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 bp. In some methods, the exemplary upstream or downstream sequence have about 200 bp to about 2000 bp, about 600 bp to about 1000 bp, or more particularly about 700 bp to about 1000 bp. In some methods, the exogenous polynucleotide template may further comprise a marker. Such a marker may make it easy to screen for targeted integrations. Examples of suitable markers include restriction sites, fluorescent proteins, or selectable markers. The exogenous polynucleotide template of the invention can be constructed using recombinant techniques (see, for example, Sambrook et al., 2001 and Ausubel et al., 1996). In a method for modifying a target polynucleotide by integrating an exogenous polynucleotide template, a double stranded break is introduced into the genome sequence by the CRISPR complex, the break is repaired via homologous recombination an exogenous polynucleotide template such that the template is integrated into the genome. The presence of a double-stranded break facilitates integration of the template. In other embodiments, this invention provides a method of modifying expression of a polynucleotide in a eukaryotic cell. The method comprises increasing or decreasing expression of a target polynucleotide by using a CRISPR complex that binds to the polynucleotide. In some methods, a target polynucleotide can be inactivated to effect the modification of the expression in a cell. For example, upon the binding of a CRISPR complex to a target sequence in a cell, the target polynucleotide is inactivated such that the sequence is not transcribed, the coded protein is not produced, or the sequence does not function as the wild-type sequence does. For example, a protein or microRNA coding sequence may be inactivated such that the protein or microRNA or pre-microRNA transcript is not produced. In some methods, a control sequence can be inactivated such that it no longer functions as a control sequence. As used herein, "control sequence" refers to any nucleic acid sequence that effects the transcription, translation, or accessibility of a nucleic acid sequence. Examples of a control sequence include, a promoter, a transcription terminator, and an enhancer are control sequences. The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA). Examples of target polynucleotides include a sequence associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. In preferred embodiments of the invention the disease associate gene may be a gene associated with Cancer; Thalassemia, Sickle Cell Anemia (based on a point mutation); and ophthalmic disease—for example Leber Congenital Amaurosis (LCA)-causing Splice Defect.

The transcribed or translated products may be known or unknown, and may be at a normal or abnormal level. The target polynucleotide of a CRISPR complex can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA). Without wishing to be bound by theory, it is believed that the target sequence should be associated with a PAM (protospacer adjacent motif); that is, a short sequence recognized by the CRISPR complex. The precise sequence and length requirements for the PAM differ depending on the CRISPR enzyme used, but PAMs are typically 2-5 base pair sequences adjacent the protospacer (that is, the target sequence). Examples of PAM sequences are given in the examples section below, and the skilled person will be able to identify further PAM sequences for use with a given CRISPR enzyme. In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized to a target sequence within said target polynucleotide, wherein said guide sequence is linked to a tracr mate sequence which in turn hybridizes to a tracr sequence. In one aspect, the invention provides a method of modifying expression of a polynucleotide in a eukaryotic cell. In some embodiments, the method comprises allowing a CRISPR complex to bind to the polynucleotide such that said binding results in increased or decreased expression of said polynucleotide; wherein the CRISPR complex comprises a CRISPR enzyme complexed with a guide sequence hybridized to a target sequence within said polynucleotide, wherein said guide sequence is linked to a tracr mate sequence which in turn hybridizes to a tracr sequence. Similar considerations and conditions apply as above for methods of modifying a target polynucleotide. In fact, these sampling, culturing and re-introduction options apply across the aspects of the present invention.

As described herein elsewhere, it will also be apparent that in certain embodiments "modified", "altered", "manipulated" or like terms corresponds to alterations of target loci such as the activation or repression of the transcription of a gene, methylation or demethylation of CpG sites and the like, which may not require point mutations, deletions, substitutions, or insertions of one or more nucleotides at target loci. Furthermore as described herein elsewhere, it will also be apparent that reference to a CRISPR-Cas enzyme as "altering" or "modifying" or "manipulating" one or more target polynucleotide loci encompasses direct alteration or modification, e.g. via the catalytic activity of the enzyme itself but also indirect alteration or modification, e.g. via a catalytic activity associated with the CRISPR-Cas enzyme such as a heterologous functional domain, e.g. a transcriptional activation domain or e.g. via a catalytic activity of one or more heterologous functional domains associated with the guide RNA via a protein-binding aptamer, e.g. a transcriptional activation domain. In addition, as it will be appreciated it is intended that the one or more target polynucleotide loci which are "altered" or "modified" by the action of the CRISPR-Cas enzyme may be comprised in or adjacent the polynucleotide sequence complementary to the guide sequence portion of a guide RNA, e.g. in embodiments wherein the alteration or modification is effected by the catalytic activity of the CRISPR-Cas enzyme itself, e.g. cleavage of DNA by the nuclease activity of the CRISPR-Cas enzyme. However, also encompassed are embodiments wherein one or more target loci to be "altered" or "modified" are at a location distinct from the sequence complementary to the guide sequence portion of the guide RNA, e.g. in embodiments wherein the alteration or modification is effected via a heterologous functional domain associated with the CRISPR-Cas enzyme and/or guide RNA, e.g. activation or repression of the transcription of a gene. As such, "alteration" or "modification" (or analogous terms) of a target locus means via direct or indirect action of the CRISPR-Cas enzyme, and furthermore the "target locus" to be altered or modified and the "target sequence" which is complementary to the guide sequence portion of the guide RNA may or may not be the same.

In one aspect, the invention provides for methods of modifying a target polynucleotide in a eukaryotic cell, which may be in vivo, ex vivo or in vitro. In some embodiments, the method comprises sampling a cell or population of cells from a human or non-human animal, and modifying the cell or cells. Culturing may occur at any stage ex vivo. The cell or cells may even be re-introduced into the non-human animal or plant. For re-introduced cells it is particularly preferred that the cells are stem cells.

Indeed, in any aspect of the invention, the CRISPR complex may comprise a CRISPR enzyme complexed with a guide sequence hybridized to a target sequence, wherein said guide sequence may be linked to a tracr mate sequence which in turn may hybridize to a tracr sequence.

The invention relates to the engineering and optimization of systems, methods and compositions used for the control of gene expression involving sequence targeting, such as genome perturbation or gene-editing, that relate to the CRISPR-Cas system and components thereof. In advantageous embodiments, the Cas enzyme is Cas9. An advantage of the present methods is that the CRISPR system minimizes or avoids off-target binding and its resulting side effects.

This is achieved using systems arranged to have a high degree of sequence specificity for the target DNA.

Delivery Generally

Vector delivery, e.g., plasmid, viral delivery: The CRISPR enzyme, for instance a Cas9, and/or any of the present RNAs, for instance a guide RNA, can be delivered using any suitable vector, e.g., plasmid or viral vectors, such as adeno associated virus (AAV), lentivirus, adenovirus or other viral vector types, or combinations thereof. Cas9 and one or more guide RNAs can be packaged into one or more vectors, e.g., plasmid or viral vectors. In some embodiments, the vector, e.g., plasmid or viral vector is delivered to the tissue of interest by, for example, an intramuscular injection, while other times the delivery is via intravenous, transdermal, intranasal, oral, mucosal, or other delivery methods. Such delivery may be either via a single dose, or multiple doses. One skilled in the art understands that the actual dosage to be delivered herein may vary greatly depending upon a variety of factors, such as the vector choice, the target cell, organism, or tissue, the general condition of the subject to be treated, the degree of transformation/modification sought, the administration route, the administration mode, the type of transformation/modification sought, etc.

Such a dosage may further contain, for example, a carrier (water, saline, ethanol, glycerol, lactose, sucrose, calcium phosphate, gelatin, dextran, agar, pectin, peanut oil, sesame oil, etc.), a diluent, a pharmaceutically-acceptable carrier (e.g., phosphate-buffered saline), a pharmaceutically-acceptable excipient, and/or other compounds known in the art. The dosage may further contain one or more pharmaceutically acceptable salts such as, for example, a mineral acid salt such as a hydrochloride, a hydrobromide, a phosphate, a sulfate, etc.; and the salts of organic acids such as acetates, propionates, malonates, benzoates, etc. Additionally, auxiliary substances, such as wetting or emulsifying agents, pH buffering substances, gels or gelling materials, flavorings, colorants, microspheres, polymers, suspension agents, etc. may also be present herein. In addition, one or more other conventional pharmaceutical ingredients, such as preservatives, humectants, suspending agents, surfactants, antioxidants, anticaking agents, fillers, chelating agents, coating agents, chemical stabilizers, etc. may also be present, especially if the dosage form is a reconstitutable form. Suitable exemplary ingredients include microcrystalline cellulose, carboxymethylcellulose sodium, polysorbate 80, phenylethyl alcohol, chlorobutanol, potassium sorbate, sorbic acid, sulfur dioxide, propyl gallate, the parabens, ethyl vanillin, glycerin, phenol, parachlorophenol, gelatin, albumin and a combination thereof. A thorough discussion of pharmaceutically acceptable excipients is available in REMINGTON'S PHARMACEUTICAL SCIENCES (Mack Pub. Co., N.J. 1991) which is incorporated by reference herein.

In an embodiment herein the delivery is via an adenovirus, which may be at a single booster dose containing at least $1 \times 10^5$ particles (also referred to as particle units, pu) of adenoviral vector. In an embodiment herein, the dose preferably is at least about $1 \times 10^6$ particles (for example, about $1 \times 10^6$-$1 \times 10^{12}$ particles), more preferably at least about $1 \times 10^7$ particles, more preferably at least about $1 \times 10^8$ particles (e.g., about $1 \times 10^8$-$1 \times 10^{11}$ particles or about $1 \times 10^8$-$1 \times 10^{12}$ particles), and most preferably at least about $1 \times 10^0$ particles (e.g., about $1 \times 10^9$-$1 \times 10^{10}$ particles or about $1 \times 10^9$-$1 \times 10^{12}$ particles), or even at least about $1 \times 10^{10}$ particles (e.g., about $1 \times 10^{10}$-$1 \times 10^{12}$ particles) of the adenoviral vector. Alternatively, the dose comprises no more than about $1 \times 10^{14}$ particles, preferably no more than about $1 \times 10^{13}$ particles, even more preferably no more than about $1 \times 10^{12}$ particles, even more preferably no more than about $1 \times 10^{11}$ particles, and most preferably no more than about $1 \times 10^{10}$ particles (e.g., no more than about $1 \times 10^9$ articles). Thus, the dose may contain a single dose of adenoviral vector with, for example, about $1 \times 10^6$ particle units (pu), about $2 \times 10^6$ pu, about $4 \times 10^6$ pu, about $1 \times 10^7$ pu, about $2 \times 10^7$ pu, about $4 \times 10^7$ pu, about $1 \times 10^8$ pu, about $2 \times 10^8$ pu, about $4 \times 10^8$ pu, about $1 \times 10^9$ pu, about $2 \times 10^9$ pu, about $4 \times 10^9$ pu, about $1 \times 10^{10}$ pu, about $2 \times 10^{10}$ pu, about $4 \times 10^{10}$ pu, about $1 \times 10^{11}$ pu, about $2 \times 10^{11}$ pu, about $4 \times 10^{11}$ pu, about $1 \times 10^{12}$ pu, about $2 \times 10^{12}$ pu, or about $4 \times 10^{12}$ pu of adenoviral vector. See, for example, the adenoviral vectors in U.S. Pat. No. 8,454,972 B2 to Nabel, et. al., granted on Jun. 4, 2013; incorporated by reference herein, and the dosages at col 29, lines 36-58 thereof. In an embodiment herein, the adenovirus is delivered via multiple doses.

In an embodiment herein, the delivery is via an AAV. A therapeutically effective dosage for in vivo delivery of the AAV to a human is believed to be in the range of from about 20 to about 50 ml of saline solution containing from about $1 \times 10^{10}$ to about $1 \times 10^{10}$ functional AAV/ml solution. The dosage may be adjusted to balance the therapeutic benefit against any side effects. In an embodiment herein, the AAV dose is generally in the range of concentrations of from about $1 \times 10^5$ to $1 \times 10^{50}$ genomes AAV, from about $1 \times 10^8$ to $1 \times 10^{20}$ genomes AAV, from about $1 \times 10^{10}$ to about $1 \times 10^{16}$ genomes, or about $1 \times 10^{11}$ to about $1 \times 10^{16}$ genomes AAV. A human dosage may be about $1 \times 10^{13}$ genomes AAV. Such concentrations may be delivered in from about 0.001 ml to about 100 ml, about 0.05 to about 50 ml, or about 10 to about 25 ml of a carrier solution. Other effective dosages can be readily established by one of ordinary skill in the art through routine trials establishing dose response curves. See, for example, U.S. Pat. No. 8,404,658 B2 to Hajjar, et al., granted on Mar. 26, 2013, at col. 27, lines 45-60.

In an embodiment herein the delivery is via a plasmid. In such plasmid compositions, the dosage should be a sufficient amount of plasmid to elicit a response. For instance, suitable quantities of plasmid DNA in plasmid compositions can be from about 0.1 to about 2 mg, or from about 1 µg to about 10 µg per 70 kg individual. Plasmids of the invention will generally comprise (i) a promoter; (ii) a sequence encoding a CRISPR enzyme, operably linked to said promoter; (iii) a selectable marker; (iv) an origin of replication; and (v) a transcription terminator downstream of and operably linked to (ii). The plasmid can also encode the RNA components of a CRISPR complex, but one or more of these may instead be encoded on a different vector.

The doses herein are based on an average 70 kg individual. The frequency of administration is within the ambit of the medical or veterinary practitioner (e.g., physician, veterinarian), or scientist skilled in the art. It is also noted that mice used in experiments are typically about 20 g and from mice experiments one can scale up to a 70 kg individual.

In some embodiments the RNA molecules of the invention are delivered in liposome or lipofectin formulations and the like and can be prepared by methods well known to those skilled in the art. Such methods are described, for example, in U.S. Pat. Nos. 5,593,972, 5,589,466, and 5,580,859, which are herein incorporated by reference. Delivery systems aimed specifically at the enhanced and improved delivery of siRNA into mammalian cells have been developed, (see, for example, Shen et al FEBS Let. 2003, 539: 111-114; Xia et al., Nat. Biotech. 2002, 20:1006-1010; Reich et al., Mol. Vision. 2003, 9: 210-216; Sorensen et al., J. Mol. Biol. 2003, 327: 761-766; Lewis et al., Nat. Gen.

2002, 32: 107-108 and Simeoni et al., NAR 2003, 31, 11: 2717-2724) and may be applied to the present invention. siRNA has recently been successfully used for inhibition of gene expression in primates (see for example. Tolentino et al., Retina 24(4):660 which may also be applied to the present invention.

Indeed, RNA delivery is a useful method of in vivo delivery. It is possible to deliver Cas9 and gRNA (and, for instance, HR repair template) into cells using liposomes or particle or nanoparticles. Thus delivery of the CRISPR enzyme, such as a Cas9 and/or delivery of the RNAs of the invention may be in RNA form and via microvesicles, liposomes or particle or nanoparticles. For example, Cas9 mRNA and gRNA can be packaged into liposomal particles for delivery in vivo. Liposomal transfection reagents such as lipofectamine from Life Technologies and other reagents on the market can effectively deliver RNA molecules into the liver.

Means of delivery of RNA also preferred include delivery of RNA via particles or nanoparticles (Cho, S., Goldberg, M., Son, S., Xu, Q., Yang, F., Mei, Y., Bogatyrev, S., Langer, R. and Anderson, D., Lipid-like nanoparticles for small interfering RNA delivery to endothelial cells, Advanced Functional Materials, 19: 3112-3118, 2010) or exosomes (Schroeder, A., Levins, C., Cortez, C., Langer, R., and Anderson, D., Lipid-based nanotherapeutics for siRNA delivery, Journal of Internal Medicine, 267: 9-21, 2010, PMID: 20059641). Indeed, exosomes have been shown to be particularly useful in delivery siRNA, a system with some parallels to the CRISPR system. For instance, El-Andaloussi S, et al. ("Exosome-mediated delivery of siRNA in vitro and in vivo." Nat Protoc. 2012 Dec.; 7(12):2112-26. doi: 10.1038/nprot.2012.131. Epub 2012 Nov. 15.) describe how exosomes are promising tools for drug delivery across different biological barriers and can be harnessed for delivery of siRNA in vitro and in vivo. Their approach is to generate targeted exosomes through transfection of an expression vector, comprising an exosomal protein fused with a peptide ligand. The exosomes are then purify and characterized from transfected cell supernatant, then RNA is loaded into the exosomes. Delivery or administration according to the invention can be performed with exosomes, in particular but not limited to the brain. Vitamin E (α-tocopherol) may be conjugated with CRISPR Cas and delivered to the brain along with high density lipoprotein (HDL), for example in a similar manner as was done by Uno et al. (HUMAN GENE THERAPY 22:711-719 (June 2011)) for delivering short-interfering RNA (siRNA) to the brain. Mice were infused via Osmotic minipumps (model 1007D; Alzet, Cupertino, CA) filled with phosphate-buffered saline (PBS) or free TocsiBACE or Toc-siBACE/HDL and connected with Brain Infusion Kit 3 (Alzet). A brain-infusion cannula was placed about 0.5 mm posterior to the bregma at midline for infusion into the dorsal third ventricle. Uno et al. found that as little as 3 nmol of Toc-siRNA with HDL could induce a target reduction in comparable degree by the same ICV infusion method. A similar dosage of CRISPR Cas conjugated to α-tocopherol and co-administered with HDL targeted to the brain may be contemplated for humans in the present invention, for example, about 3 nmol to about 3 μmol of CRISPR Cas targeted to the brain may be contemplated. Zou et al. ((HUMAN GENE THERAPY 22:465-475 (April 2011)) describes a method of lentiviral-mediated delivery of short-hairpin RNAs targeting PKCγ for in vivo gene silencing in the spinal cord of rats. Zou et al. administered about 10 μl of a recombinant lentivirus having a titer of $1\times10^9$ transducing units (TU)/ml by an intrathecal catheter. A similar dosage of CRISPR Cas expressed in a lentiviral vector targeted to the brain may be contemplated for humans in the present invention, for example, about 10-50 ml of CRISPR Cas targeted to the brain in a lentivirus having a titer of $1\times10^9$ transducing units (TU)/ml may be contemplated.

In terms of local delivery to the brain, this can be achieved in various ways. For instance, material can be delivered intrastriatally e.g. by injection. Injection can be performed stereotactically via a craniotomy.

Enhancing NHEJ or HR efficiency is also helpful for delivery. It is preferred that NHEJ efficiency is enhanced by co-expressing end-processing enzymes such as Trex2 (Dumitrache et al. Genetics. 2011 August; 188(4): 787-797). It is preferred that HR efficiency is increased by transiently inhibiting NHEJ machineries such as Ku70 and Ku86. HR efficiency can also be increased by co-expressing prokaryotic or eukaryotic homologous recombination enzymes such as RecBCD, RecA.

Packaging and Promoters Generally

Ways to package Cas9 coding nucleic acid molecules, e.g., DNA, into vectors, e.g., viral vectors, to mediate genome modification in vivo include:

To achieve NHEJ-mediated gene knockout:
Single virus vector:
Vector containing two or more expression cassettes:
Promoter-Cas9 coding nucleic acid molecule-terminator
Promoter-gRNA1-terminator
Promoter-gRNA2-terminator
Promoter-gRNA(N)-terminator (up to size limit of vector)
Double virus vector:
Vector 1 containing one expression cassette for driving the expression of Cas9
Promoter-Cas9 coding nucleic acid molecule-terminator
Vector 2 containing one more expression cassettes for driving the expression of one or more guideRNAs
Promoter-gRNA1-terminator
Promoter-gRNA(N)-terminator (up to size limit of vector)
To mediate homology-directed repair.
In addition to the single and double virus vector approaches described above, an additional vector may be used to deliver a homology-direct repair template.

The promoter used to drive Cas9 coding nucleic acid molecule expression can include: AAV ITR can serve as a promoter: this is advantageous for eliminating the need for an additional promoter element (which can take up space in the vector). The additional space freed up can be used to drive the expression of additional elements (gRNA, etc.). Also, ITR activity is relatively weaker, so can be used to reduce potential toxicity due to over expression of Cas9. For ubiquitous expression, any of the following promoters may be used: CMV, CAG, CBh, PGK, SV40, Ferritin heavy or light chains, and so forth.

For brain or other CNS expression, can use promoters: SynapsinI for all neurons, CaMKIIalpha for excitatory neurons, GAD67 or GAD65 or VGAT for GABAergic neurons, etc. For liver expression, one can use the Albumin promoter. For lung expression, one can use the use SP-B. For endothelial cells, one can use the use ICAM. For hematopoietic cells one can use the use IFNbeta or CD45. For Osteoblasts can one can use the OG-2.

The promoter used to drive guide RNA can include:
Pol III promoters such as U6 or H1
Use of Pol II promoter and intronic cassettes to express gRNA Adeno Associated Virus (AAV)

Cas9 and one or more guide RNA can be delivered using adeno associated virus (AAV), lentivirus, adenovirus or other plasmid or viral vector types, in particular, using formulations and doses from, for example, U.S. Pat. No. 8,454,972 (formulations, doses for adenovirus), U.S. Pat. No. 8,404,658 (formulations, doses for AAV) and U.S. Pat. No. 5,846,946 (formulations, doses for DNA plasmids) and from clinical trials and publications regarding the clinical trials involving lentivirus, AAV and adenovirus. For examples, for AAV, the route of administration, formulation and dose can be as in U.S. Pat. No. 8,454,972 and as in clinical trials involving AAV. For Adenovirus, the route of administration, formulation and dose can be as in U.S. Pat. No. 8,404,658 and as in clinical trials involving adenovirus. For plasmid delivery, the route of administration, formulation and dose can be as in U.S. Pat. No. 5,846,946 and as in clinical studies involving plasmids. Doses may be based on or extrapolated to an average 70 kg individual (e.g. a male adult human), and can be adjusted for patients, subjects, mammals of different weight and species. Frequency of administration is within the ambit of the medical or veterinary practitioner (e.g., physician, veterinarian), depending on usual factors including the age, sex, general health, other conditions of the patient or subject and the particular condition or symptoms being addressed. The viral vectors can be injected into the tissue of interest. For cell-type specific genome modification, the expression of Cas9 can be driven by a cell-type specific promoter. For example, liver-specific expression might use the Albumin promoter and neuron-specific expression (e.g. for targeting CNS disorders) might use the Synapsin I promoter.

| Species | Cas9 Size |
|---|---|
| Corynebacter diphtheriae | 3252 |
| Eubacterium ventriosum | 3321 |
| Streptococcus pasteurianus | 3390 |
| Lactobacillus farciminis | 3378 |
| Sphaerochaeta globus | 3537 |
| Azospirillum B510 | 3504 |
| Gluconacetobacter diazotrophicus | 3150 |
| Neisseria cinerea | 3246 |
| Roseburia intestinalis | 3420 |
| Parvibaculum lavamentivorans | 3111 |
| Staphylococcus aureus | 3159 |
| Nitratifractor salsuginis DSM 16511 | 3396 |
| Campylobacter lari CF89-12 | 3009 |
| Streptococcus thermophilus LMD-9 | 3396 |

These species are therefore, in general, preferred Cas9 species.

As to AAV, the AAV can be AAV1, AAV2, AAV5 or any combination thereof. One can select the AAV of the AAV with regard to the cells to be targeted; e.g., one can select AAV serotypes 1, 2, 5 or a hybrid capsid AAV1, AAV2, AAV5 or any combination thereof for targeting brain or neuronal cells; and one can select AAV4 for targeting cardiac tissue. AAV8 is useful for delivery to the liver. The herein promoters and vectors are preferred individually. A tabulation of certain AAV serotypes as to these cells (see Grimm, D. et al, J. Virol. 82: 5887-5911 (2008)) is as follows:

TABLE 6

Exemplary AAV Serotypes

| Cell Line | AAV-1 | AAV-2 | AAV-3 | AAV-4 | AAV-5 | AAV-6 | AAV-8 | AAV-9 |
|---|---|---|---|---|---|---|---|---|
| Huh-7 | 13 | 100 | 2.5 | 0.0 | 0.1 | 10 | 0.7 | 0.0 |
| HEK293 | 25 | 100 | 2.5 | 0.1 | 0.1 | 5 | 0.7 | 0.1 |
| HeLa | 3 | 100 | 2.0 | 0.1 | 6.7 | 1 | 0.2 | 0.1 |
| HepG2 | 3 | 100 | 16.7 | 0.3 | 1.7 | 5 | 0.3 | ND |
| Hep1A | 20 | 100 | 0.2 | 1.0 | 0.1 | 1 | 0.2 | 0.0 |
| 911 | 17 | 100 | 11 | 0.2 | 0.1 | 17 | 0.1 | ND |
| CHO | 100 | 100 | 14 | 1.4 | 333 | 50 | 10 | 1.0 |
| COS | 33 | 100 | 33 | 3.3 | 5.0 | 14 | 2.0 | 0.5 |
| MeWo | 10 | 100 | 20 | 0.3 | 6.7 | 10 | 1.0 | 0.2 |
| NIH3T3 | 10 | 100 | 2.9 | 2.9 | 0.3 | 10 | 0.3 | ND |
| A549 | 14 | 100 | 20 | ND | 0.5 | 10 | 0.5 | 0.1 |
| HT1180 | 20 | 100 | 10 | 0.1 | 0.3 | 33 | 0.5 | 0.1 |
| Monocytes | 1111 | 100 | ND | ND | 125 | 1429 | ND | ND |
| Immature DC | 2500 | 100 | ND | ND | 222 | 2857 | ND | ND |
| Mature DC | 2222 | 100 | ND | ND | 333 | 3333 | ND | ND |

In terms of in vivo delivery, AAV is advantageous over other viral vectors for a couple of reasons:
- Low toxicity (this may be due to the purification method not requiring ultra centrifugation of cell particles that can activate the immune response)
- Low probability of causing insertional mutagenesis because it doesn't integrate into the host genome.

AAV has a packaging limit of 4.5 or 4.75 Kb. This means that Cas9 as well as a promoter and transcription terminator have to be all fit into the same viral vector. Constructs larger than 4.5 or 4.75 Kb will lead to significantly reduced virus production. SpCas9 is quite large, the gene itself is over 4.1 Kb, which makes it difficult for packing into AAV. Therefore embodiments of the invention include utilizing homologs of Cas9 that are shorter. For example:

Lentivirus

Lentiviruses are complex retroviruses that have the ability to infect and express their genes in both mitotic and post-mitotic cells. The most commonly known lentivirus is the human immunodeficiency virus (HIV), which uses the envelope glycoproteins of other viruses to target a broad range of cell types.

Lentiviruses may be prepared as follows. After cloning pCasES10 (which contains a lentiviral transfer plasmid backbone), HEK293FT at low passage (p=5) were seeded in a T-75 flask to 50% confluence the day before transfection in DMEM with 10% fetal bovine serum and without antibiotics. After 20 hours, media was changed to OptiMEM (serum-free) media and transfection was done 4 hours later. Cells were transfected with 10 μg of lentiviral transfer plasmid (pCasES10) and the following packaging plasmids: 5 µg of pMD2.G (VSV-g pseudotype), and 7.5 ug of psPAX2 (gag/pol/rev/tat). Transfection was done in 4 mL OptiMEM with a cationic lipid delivery agent (50 uL Lipofectamine 2000 and 100 ul Plus reagent). After 6 hours, the media was changed to antibiotic-free DMEM with 10% fetal bovine serum. These methods use serum during cell culture, but serum-free methods are preferred.

Lentivirus may be purified as follows. Viral supernatants were harvested after 48 hours. Supernatants were first cleared of debris and filtered through a 0.45 um low protein binding (PVDF) filter. They were then spun in a ultracentrifuge for 2 hours at 24,000 rpm. Viral pellets were resuspended in 50 ul of DMEM overnight at 4 C. They were then aliquoted and immediately frozen at −80° C.

In another embodiment, minimal non-primate lentiviral vectors based on the equine infectious anemia virus (EIAV) are also contemplated, especially for ocular gene therapy (see, e.g., Balagaan, J Gene Med 2006; 8: 275-285). In another embodiment, RetinoStat®, an equine infectious anemia virus-based lentiviral gene therapy vector that expresses angiostatic proteins endostatin and angiostatin that is delivered via a subretinal injection for the treatment of the web form of age-related macular degeneration is also contemplated (see, e.g., Binley et al., HUMAN GENE THERAPY 23:980-991 (September 2012)) and this vector may be modified for the CRISPR-Cas system of the present invention.

In another embodiment, self-inactivating lentiviral vectors with an siRNA targeting a common exon shared by HIV tat/rev, a nucleolar-localizing TAR decoy, and an anti-CCR5-specific hammerhead ribozyme (see, e.g., DiGiusto et al. (2010) Sci Transl Med 2:36ra43) may be used/and or adapted to the CRISPR-Cas system of the present invention. A minimum of $2.5 \times 10^6$ CD34+ cells per kilogram patient weight may be collected and prestimulated for 16 to 20 hours in X-VIVO 15 medium (Lonza) containing 2 µmol/L-glutamine, stem cell factor (100 ng/ml), Flt-3 ligand (Flt-3L) (100 ng/ml), and thrombopoietin (10 ng/ml) (CellGenix) at a density of $2 \times 10^6$ cells/ml. Prestimulated cells may be transduced with lentiviral at a multiplicity of infection of 5 for 16 to 24 hours in 75-cm2 tissue culture flasks coated with fibronectin (25 mg/cm2) (RetroNectin, Takara Bio Inc.).

Lentiviral vectors have been disclosed as in the treatment for Parkinson's Disease, see, e.g., US Patent Publication No. 20120295960 and U.S. Pat. Nos. 7,303,910 and 7,351,585. Lentiviral vectors have also been disclosed for the treatment of ocular diseases, see e.g., US Patent Publication Nos. 20060281180, 20090007284, US20110117189; US20090017543; US20070054961, US20100317109. Lentiviral vectors have also been disclosed for delivery to the brain, see, e.g., US Patent Publication Nos. US20110293571; US20110293571, US20040013648, US20070025970, US20090111106 and U.S. Pat. No. 7,259,015.

RNA Delivery

RNA delivery: The CRISPR enzyme, for instance a Cas9, and/or any of the present RNAs, for instance a guide RNA, can also be delivered in the form of RNA. Cas9 mRNA can be generated using in vitro transcription. For example, Cas9 mRNA can be synthesized using a PCR cassette containing the following elements: T7_promoter-kozak sequence (GCCACC)-Cas9-3' UTR from beta globin-polyA tail (a string of 120 or more adenines). The cassette can be used for transcription by T7 polymerase. Guide RNAs can also be transcribed using in vitro transcription from a cassette containing T7_promoter-GG-guide RNA sequence.

To enhance expression and reduce possible toxicity, the CRISPR enzyme-coding sequence and/or the guide RNA can be modified to include one or more modified nucleoside e.g. using pseudo-U or 5-Methyl-C.

mRNA delivery methods are especially promising for liver delivery currently.

Much clinical work on RNA delivery has focused on RNAi or antisense, but these systems can be adapted for delivery of RNA for implementing the present invention. References below to RNAi etc. should be read accordingly.

Nanoparticles

Nanoparticles are a type of particle.

CRISPR enzyme mRNA and guide RNA may be delivered simultaneously using nanoparticles or lipid envelopes.

For example, Su X, Fricke J, Kavanagh D G, Irvine D J ("In vitro and in vivo mRNA delivery using lipid-enveloped pH-responsive polymer nanoparticles" Mol Pharm. 2011 Jun. 6; 8(3):774-87. doi: 10.1021/mp100390w. Epub 2011 Apr. 1) describes biodegradable core-shell structured nanoparticles with a poly(O-amino ester) (PBAE) core enveloped by a phospholipid bilayer shell. These were developed for in vivo mRNA delivery. The pH-responsive PBAE component was chosen to promote endosome disruption, while the lipid surface layer was selected to minimize toxicity of the polycation core. Such are, therefore, preferred for delivering RNA of the present invention.

In one embodiment, nanoparticles based on self assembling bioadhesive polymers are contemplated, which may be applied to oral delivery of peptides, intravenous delivery of peptides and nasal delivery of peptides, all to the brain. Other embodiments, such as oral absorption and ocular delivery of hydrophobic drugs are also contemplated. The molecular envelope technology involves an engineered polymer envelope which is protected and delivered to the site of the disease (see, e.g., Mazza, M. et al. ACSNano, 2013. 7(2): 1016-1026; Siew, A., et al. Mol Pharm, 2012. 9(1):14-28; Lalatsa, A., et al. J Contr Rel, 2012. 161(2):523-36; Lalatsa, A., et al., Mol Pharm, 2012. 9(6):1665-80; Lalatsa, A., et al. Mol Pharm, 2012. 9(6):1764-74; Garrett, N. L., et al. J Biophotonics, 2012. 5(5-6):458-68; Garrett, N. L., et al. J Raman Spect, 2012. 43(5):681-688; Ahmad, S., et al. J Royal Soc Interface 2010. 7:S423-33; Uchegbu, I. F. Expert Opin Drug Deliv, 2006. 3(5):629-40; Qu, X., et al. Biomacromolecules, 2006. 7(12):3452-9 and Uchegbu, I. F., et al. Int J Pharm, 2001. 224:185-199). Doses of about 5 mg/kg are contemplated, with single or multiple doses, depending on the target tissue.

In one embodiment, nanoparticles that can deliver RNA to a cancer cell to stop tumor growth developed by Dan Anderson's lab at MIT may be used/and or adapted to the CRISPR Cas system of the present invention. In particular, the Anderson lab developed fully automated, combinatorial systems for the synthesis, purification, characterization, and formulation of new biomaterials and nanoformulations. See, e.g., Alabi et al., Proc Natl Acad Sci USA. 2013 Aug. 6; 110(32):12881-6; Zhang et al., Adv Mater. 2013 Sep. 6; 25(33):4641-5; Jiang et al., Nano Lett. 2013 Mar. 13; 13(3):1059-64; Karagiannis et al., ACS Nano. 2012 Oct. 23; 6(10):8484-7; Whitehead et al., ACS Nano. 2012 Aug. 28; 6(8):6922-9 and Lee et al., Nat Nanotechnol. 2012 Jun. 3; 7(6):389-93.

US patent application 20110293703 relates to lipidoid compounds are also particularly useful in the administration of polynucleotides, which may be applied to deliver the CRISPR Cas system of the present invention. In one aspect, the aminoalcohol lipidoid compounds are combined with an agent to be delivered to a cell or a subject to form microparticles, nanoparticles, liposomes, or micelles. The agent to be delivered by the particles, liposomes, or micelles may be in the form of a gas, liquid, or solid, and the agent may be a polynucleotide, protein, peptide, or small molecule. The aminoalcohol lipidoid compounds may be combined with other aminoalcohol lipidoid compounds, polymers (synthetic or natural), surfactants, cholesterol, carbohydrates, proteins, lipids, etc. to form the particles. These particles may then optionally be combined with a pharmaceutical excipient to form a pharmaceutical composition.

US Patent Publication No. 20110293703 also provides methods of preparing the aminoalcohol lipidoid compounds. One or more equivalents of an amine are allowed to react with one or more equivalents of an epoxide-terminated compound under suitable conditions to form an aminoalcohol lipidoid compound of the present invention. In certain embodiments, all the amino groups of the amine are fully reacted with the epoxide-terminated compound to form tertiary amines. In other embodiments, all the amino groups of the amine are not fully reacted with the epoxide-terminated compound to form tertiary amines thereby resulting in primary or secondary amines in the aminoalcohol lipidoid compound. These primary or secondary amines are left as is or may be reacted with another electrophile such as a different epoxide-terminated compound. As will be appreciated by one skilled in the art, reacting an amine with less than excess of epoxide-terminated compound will result in a plurality of different aminoalcohol lipidoid compounds with various numbers of tails. Certain amines may be fully functionalized with two epoxide-derived compound tails while other molecules will not be completely functionalized with epoxide-derived compound tails. For example, a diamine or polyamine may include one, two, three, or four epoxide-derived compound tails off the various amino moieties of the molecule resulting in primary, secondary, and tertiary amines. In certain embodiments, all the amino groups are not fully functionalized. In certain embodiments, two of the same types of epoxide-terminated compounds are used. In other embodiments, two or more different epoxide-terminated compounds are used. The synthesis of the aminoalcohol lipidoid compounds is performed with or without solvent, and the synthesis may be performed at higher temperatures ranging from 30-100° C., preferably at approximately 50-90° C. The prepared aminoalcohol lipidoid compounds may be optionally purified. For example, the mixture of aminoalcohol lipidoid compounds may be purified to yield an aminoalcohol lipidoid compound with a particular number of epoxide-derived compound tails. Or the mixture may be purified to yield a particular stereo- or regioisomer. The aminoalcohol lipidoid compounds may also be alkylated using an alkyl halide (e.g., methyl iodide) or other alkylating agent, and/or they may be acylated.

US Patent Publication No. 20110293703 also provides libraries of aminoalcohol lipidoid compounds prepared by the inventive methods. These aminoalcohol lipidoid compounds may be prepared and/or screened using high-throughput techniques involving liquid handlers, robots, microtiter plates, computers, etc. In certain embodiments, the aminoalcohol lipidoid compounds are screened for their ability to transfect polynucleotides or other agents (e.g., proteins, peptides, small molecules) into the cell.

US Patent Publication No. 20130302401 relates to a class of poly(beta-amino alcohols) (PBAAs) has been prepared using combinatorial polymerization. The inventive PBAAs may be used in biotechnology and biomedical applications as coatings (such as coatings of films or multilayer films for medical devices or implants), additives, materials, excipients, non-biofouling agents, micropatterning agents, and cellular encapsulation agents. When used as surface coatings, these PBAAs elicited different levels of inflammation, both in vitro and in vivo, depending on their chemical structures. The large chemical diversity of this class of materials allowed us to identify polymer coatings that inhibit macrophage activation in vitro. Furthermore, these coatings reduce the recruitment of inflammatory cells, and reduce fibrosis, following the subcutaneous implantation of carboxylated polystyrene microparticles. These polymers may be used to form polyelectrolyte complex capsules for cell encapsulation. The invention may also have many other biological applications such as antimicrobial coatings, DNA or siRNA delivery, and stem cell tissue engineering. The teachings of US Patent Publication No. 20130302401 may be applied to the CRISPR Cas system of the present invention.

In another embodiment, lipid nanoparticles (LNPs) are contemplated. An antitransthyretin small interfering RNA has been encapsulated in lipid nanoparticles and delivered to humans (see, e.g., Coelho et al., N Engl J Med 2013; 369:819-29), and such a system may be adapted and applied to the CRISPR Cas system of the present invention. Doses of about 0.01 to about 1 mg per kg of body weight administered intravenously are contemplated. Medications to reduce the risk of infusion-related reactions are contemplated, such as dexamethasone, acetampinophen, diphenhydramine or cetirizine, and ranitidine are contemplated. Multiple doses of about 0.3 mg per kilogram every 4 weeks for five doses are also contemplated.

LNPs have been shown to be highly effective in delivering siRNAs to the liver (see, e.g., Tabernero et al., Cancer Discovery, April 2013, Vol. 3, No. 4, pages 363-470) and are therefore contemplated for delivering RNA encoding CRISPR Cas to the liver. A dosage of about four doses of 6 mg/kg of the LNP every two weeks may be contemplated. Tabernero et al. demonstrated that tumor regression was observed after the first 2 cycles of LNPs dosed at 0.7 mg/kg, and by the end of 6 cycles the patient had achieved a partial response with complete regression of the lymph node metastasis and substantial shrinkage of the liver tumors. A complete response was obtained after 40 doses in this patient, who has remained in remission and completed treatment after receiving doses over 26 months. Two patients with RCC and extrahepatic sites of disease including kidney, lung, and lymph nodes that were progressing following prior therapy with VEGF pathway inhibitors had stable disease at all sites for approximately 8 to 12 months, and a patient with PNET and liver metastases continued on the extension study for 18 months (36 doses) with stable disease.

However, the charge of the LNP must be taken into consideration. As cationic lipids combined with negatively charged lipids to induce nonbilayer structures that facilitate intracellular delivery. Because charged LNPs are rapidly cleared from circulation following intravenous injection, ionizable cationic lipids with pKa values below 7 were developed (see, e.g., Rosin et al, Molecular Therapy, vol. 19, no. 12, pages 1286-2200, December 2011). Negatively charged polymers such as RNA may be loaded into LNPs at low pH values (e.g., pH 4) where the ionizable lipids display a positive charge. However, at physiological pH values, the LNPs exhibit a low surface charge compatible with longer circulation times. Four species of ionizable cationic lipids have been focused upon, namely 1,2-dilineoyl-3-dimethyl-ammonium-propane (DLinDAP), 1,2-dilinoleyloxy-3-N,N- dimethylaminopropane (DLinDMA), 1,2-dilinoleyloxy-keto-N,N-dimethyl-3-aminopropane (DLinKDMA), and 1,2-dilinoleyl-4-(2-dimethylaminoethyl)-[1,3]-dioxolane (DLinKC2-DMA). It has been shown that LNP siRNA systems containing these lipids exhibit remarkably different gene silencing properties in hepatocytes in vivo, with potencies varying according to the series DLinKC2-DMA>DLinKDMA>DLinDMA>>DLinDAP employing a Factor VII gene silencing model (see, e.g., Rosin et al, Molecular Therapy, vol. 19, no. 12, pages 1286-2200, December 2011). A dosage of 1 µg/ml of LNP or CRISPR-Cas RNA in or associated with the LNP may be contemplated, especially for a formulation containing DLinKC2-DMA.

Preparation of LNPs and CRISPR Cas encapsulation may be used/and or adapted from Rosin et al, Molecular Therapy, vol. 19, no. 12, pages 1286-2200, December 2011). The cationic lipids 1,2-dilineoyl-3-dimethylammonium-propane (DLinDAP), 1,2-dilinoleyloxy-3-N,N-dimethylaminopropane (DLinDMA), 1,2-dilinoleyloxyketo-N,N-dimethyl-3-aminopropane (DLinK-DMA), 1,2-dilinoleyl-4-(2-dimethylaminoethyl)-[1,3]-dioxolane (DLinKC2-DMA), (3-o-[2"-(methoxypolyethyleneglycol 2000) succinoyl]-1,2-dimyristoyl-sn-glycol (PEG-S-DMG), and R-3-[(o-methoxy-poly(ethylene glycol)2000) carbamoyl]-1,2-dimyristyloxlpropyl-3-amine (PEG-C-DOMG) may be provided by Tekmira Pharmaceuticals (Vancouver, Canada) or synthesized. Cholesterol may be purchased from Sigma (St Louis, MO). The specific CRISPR Cas RNA may be encapsulated in LNPs containing DLinDAP, DLinDMA, DLinK-DMA, and DLinKC2-DMA (cationic lipid:DSPC: CHOL:PEGS-DMG or PEG-C-DOMG at 40:10:40:10 molar ratios). When required, 0.2% SP-DiOC18 (Invitrogen, Burlington, Canada) may be incorporated to assess cellular uptake, intracellular delivery, and biodistribution. Encapsulation may be performed by dissolving lipid mixtures comprised of cationic lipid:DSPC:cholesterol:PEG-c-DOMG (40:10:40:10 molar ratio) in ethanol to a final lipid concentration of 10 mmol/l. This ethanol solution of lipid may be added drop-wise to 50 mmol/l citrate, pH 4.0 to form multilamellar vesicles to produce a final concentration of 30% ethanol vol/vol. Large unilamellar vesicles may be formed following extrusion of multilamellar vesicles through two stacked 80 nm Nuclepore polycarbonate filters using the Extruder (Northern Lipids, Vancouver, Canada). Encapsulation may be achieved by adding RNA dissolved at 2 mg/ml in 50 mmol/l citrate, pH 4.0 containing 30% ethanol vol/vol drop-wise to extruded preformed large unilamellar vesicles and incubation at 31° C. for 30 minutes with constant mixing to a final RNA/lipid weight ratio of 0.06/1 wt/wt. Removal of ethanol and neutralization of formulation buffer were performed by dialysis against phosphate-buffered saline (PBS), pH 7.4 for 16 hours using Spectra/Por 2 regenerated cellulose dialysis membranes. Nanoparticle size distribution may be determined by dynamic light scattering using a NICOMP 370 particle sizer, the vesicle/intensity modes, and Gaussian fitting (Nicomp Particle Sizing, Santa Barbara, CA). The particle size for all three LNP systems may be ~70 nm in diameter. RNA encapsulation efficiency may be determined by removal of free RNA using VivaPureD MiniH columns (Sartorius Stedim Biotech) from samples collected before and after dialysis. The encapsulated RNA may be extracted from the eluted nanoparticles and quantified at 260 nm. RNA to lipid ratio was determined by measurement of cholesterol content in vesicles using the Cholesterol E enzymatic assay from Wako Chemicals USA (Richmond, VA). In conjunction with the herein discussion of LNPs and PEG lipids, PEGylated liposomes or LNPs are likewise suitable for delivery of a CRISPR-Cas system or components thereof.

Preparation of large LNPs may be used/and or adapted from Rosin et al, Molecular Therapy, vol. 19, no. 12, pages 1286-2200, December 2011. A lipid premix solution (20.4 mg/ml total lipid concentration) may be prepared in ethanol containing DLinKC2-DMA, DSPC, and cholesterol at 50:10:38.5 molar ratios. Sodium acetate may be added to the lipid premix at a molar ratio of 0.75:1 (sodium acetate: DLinKC2-DMA). The lipids may be subsequently hydrated by combining the mixture with 1.85 volumes of citrate buffer (10 mmol/l, pH 3.0) with vigorous stirring, resulting in spontaneous liposome formation in aqueous buffer containing 35% ethanol. The liposome solution may be incubated at 37° C. to allow for time-dependent increase in particle size. Aliquots may be removed at various times during incubation to investigate changes in liposome size by dynamic light scattering (Zetasizer Nano ZS, Malvern Instruments, Worcestershire, UK). Once the desired particle size is achieved, an aqueous PEG lipid solution (stock=10 mg/ml PEG-DMG in 35% (vol/vol) ethanol) may be added to the liposome mixture to yield a final PEG molar concentration of 3.5% of total lipid. Upon addition of PEG-lipids, the liposomes should their size, effectively quenching further growth. RNA may then be added to the empty liposomes at an RNA to total lipid ratio of approximately 1:10 (wt:wt), followed by incubation for 30 minutes at 37° C. to form loaded LNPs. The mixture may be subsequently dialyzed overnight in PBS and filtered with a 0.45-µm syringe filter.

Spherical Nucleic Acid (SNA™) constructs and other nanoparticles (particularly gold nanoparticles) are also contemplated as a means to delivery CRISPR-Cas system to intended targets. Significant data show that AuraSense Therapeutics' Spherical Nucleic Acid (SNA™) constructs, based upon nucleic acid-functionalized gold nanoparticles, are useful.

Literature that may be employed in conjunction with herein teachings include: Cutler et al., J. Am. Chem. Soc. 2011 133:9254-9257, Hao et al., Small. 2011 7:3158-3162, Zhang et al., ACS Nano. 2011 5:6962-6970, Cutler et al., J. Am. Chem. Soc. 2012 134:1376-1391, Young et al., Nano Lett. 2012 12:3867-71, Zheng et al., Proc. Natl. Acad. Sci. USA. 2012 109:11975-80, Mirkin, Nanomedicine 2012 7:635-638 Zhang et al., J. Am. Chem. Soc. 2012 134:16488-1691, Weintraub, Nature 2013 495:S14-S16, Choi et al., Proc. Natl. Acad. Sci. USA. 2013 110(19):7625-7630, Jensen et al., Sci. Transl. Med. 5, 209ra152 (2013) and Mirkin, et al., Small, 10:186-192.

Self-assembling nanoparticles with RNA may be constructed with polyethyleneimine (PEI) that is PEGylated with an Arg-Gly-Asp (RGD) peptide ligand attached at the distal end of the polyethylene glycol (PEG). This system has been used, for example, as a means to target tumor neovasculature expressing integrins and deliver siRNA inhibiting vascular endothelial growth factor receptor-2 (VEGF R2) expression and thereby achieve tumor angiogenesis (see, e.g., Schiffelers et al., Nucleic Acids Research, 2004, Vol. 32, No. 19). Nanoplexes may be prepared by mixing equal volumes of aqueous solutions of cationic polymer and nucleic acid to give a net molar excess of ionizable nitrogen (polymer) to phosphate (nucleic acid) over the range of 2 to 6. The electrostatic interactions between cationic polymers and nucleic acid resulted in the formation of polyplexes with average particle size distribution of about 100 nm, hence referred to here as nanoplexes. A dosage of about 100 to 200 mg of CRISPR Cas is envisioned for delivery in the self-assembling nanoparticles of Schiffelers et al.

The nanoplexes of Bartlett et al. (PNAS, Sep. 25, 2007, vol. 104, no. 39) may also be applied to the present invention. The nanoplexes of Bartlett et al. are prepared by mixing equal volumes of aqueous solutions of cationic polymer and nucleic acid to give a net molar excess of ionizable nitrogen (polymer) to phosphate (nucleic acid) over the range of 2 to 6. The electrostatic interactions between cationic polymers and nucleic acid resulted in the formation of polyplexes with average particle size distribution of about 100 nm, hence referred to here as nanoplexes. The DOTA-siRNA of Bartlett et al. was synthesized as follows: 1,4,7,10-tetraazacyclodo-decane-1,4,7,10-tetraacetic acid mono(N-hydroxysuccinim-ide ester) (DOTA-NHSester) was ordered from Macrocy-clics (Dallas, TX). The amine modified RNA sense strand with a 100-fold molar excess of DOTA-NHS-ester in carbonate buffer (pH 9) was added to a microcentrifuge tube. The contents were reacted by stirring for 4 h at room temperature. The DOTA-RNAsense conjugate was ethanol-precipitated, resuspended in water, and annealed to the unmodified antisense strand to yield DOTA-siRNA. All liquids were pretreated with Chelex-100 (Bio-Rad, Hercules, CA) to remove trace metal contaminants. Tf-targeted and nontargeted siRNA nanoparticles may be formed by using cyclodextrin-containing polycations. Typically, nanoparticles were formed in water at a charge ratio of 3 (+/−) and an siRNA concentration of 0.5 g/liter. One percent of the adamantane-PEG molecules on the surface of the targeted nanoparticles were modified with Tf (adamantane-PEG-Tf). The nanoparticles were suspended in a 5% (wt/vol) glucose carrier solution for injection.

Davis et al. (Nature, Vol 464, 15 Apr. 2010) conducts a RNA clinical trial that uses a targeted nanoparticle-delivery system (clinical trial registration number NCT00689065). Patients with solid cancers refractory to standard-of-care therapies are administered doses of targeted nanoparticles on days 1, 3, 8 and 10 of a 21-day cycle by a 30-min intravenous infusion. The nanoparticles consist of a synthetic delivery system containing: (1) a linear, cyclodextrin-based polymer (CDP), (2) a human transferrin protein (TF) targeting ligand displayed on the exterior of the nanoparticle to engage TF receptors (TFR) on the surface of the cancer cells, (3) a hydrophilic polymer (polyethylene glycol (PEG) used to promote nanoparticle stability in biological fluids), and (4) siRNA designed to reduce the expression of the RRM2 (sequence used in the clinic was previously denoted siR2B+5). The TFR has long been known to be upregulated in malignant cells, and RRM2 is an established anti-cancer target. These nanoparticles (clinical version denoted as CALAA-01) have been shown to be well tolerated in multi-dosing studies in non-human primates. Although a single patient with chronic myeloid leukaemia has been administered siRNA by liposomal delivery, Davis et al.'s clinical trial is the initial human trial to systemically deliver siRNA with a targeted delivery system and to treat patients with solid cancer. To ascertain whether the targeted delivery system can provide effective delivery of functional siRNA to human tumours, Davis et al. investigated biopsies from three patients from three different dosing cohorts; patients A, B and C, all of whom had metastatic melanoma and received CALAA-01 doses of 18, 24 and 30 mg m$^{-2}$ siRNA, respectively. Similar doses may also be contemplated for the CRISPR Cas system of the present invention. The delivery of the invention may be achieved with nanoparticles containing a linear, cyclodextrin-based polymer (CDP), a human transferrin protein (TF) targeting ligand displayed on the exterior of the nanoparticle to engage TF receptors (TFR) on the surface of the cancer cells and/or a hydrophilic polymer (for example, polyethylene glycol (PEG) used to promote nanoparticle stability in biological fluids).

In terms of this invention, it is preferred to have one or more components of CRISPR complex, e.g., CRISPR enzyme or mRNA or guide RNA delivered using nanoparticles or lipid envelopes. Other delivery systems or vectors are may be used in conjunction with the nanoparticle aspects of the invention.

In general, a "nanoparticle" refers to any particle having a diameter of less than 1000 nm. In certain preferred embodiments, nanoparticles of the invention have a greatest dimension (e.g., diameter) of 500 nm or less. In other preferred embodiments, nanoparticles of the invention have a greatest dimension ranging between 25 nm and 200 nm. In other preferred embodiments, nanoparticles of the invention have a greatest dimension of 100 nm or less. In other preferred embodiments, nanoparticles of the invention have a greatest dimension ranging between 35 nm and 60 nm.

Nanoparticles encompassed in the present invention may be provided in different forms, e.g., as solid nanoparticles (e.g., metal such as silver, gold, iron, titanium), non-metal, lipid-based solids, polymers), suspensions of nanoparticles, or combinations thereof. Metal, dielectric, and semiconductor nanoparticles may be prepared, as well as hybrid structures (e.g., core-shell nanoparticles). Nanoparticles made of semiconducting material may also be labeled quantum dots if they are small enough (typically sub 10 nm) that quantization of electronic energy levels occurs. Such nanoscale particles are used in biomedical applications as drug carriers or imaging agents and may be adapted for similar purposes in the present invention.

Semi-solid and soft nanoparticles have been manufactured, and are within the scope of the present invention. A prototype nanoparticle of semi-solid nature is the liposome. Various types of liposome nanoparticles are currently used clinically as delivery systems for anticancer drugs and vaccines. Nanoparticles with one half hydrophilic and the other half hydrophobic are termed Janus particles and are particularly effective for stabilizing emulsions. They can self-assemble at water/oil interfaces and act as solid surfactants.

U.S. Pat. No. 8,709,843, incorporated herein by reference, provides a drug delivery system for targeted delivery of therapeutic agent-containing particles to tissues, cells, and intracellular compartments. The invention provides targeted particles comprising polymer conjugated to a surfactant, hydrophilic polymer or lipid.

U.S. Pat. No. 6,007,845, incorporated herein by reference, provides particles which have a core of a multiblock copolymer formed by covalently linking a multifunctional compound with one or more hydrophobic polymers and one or more hydrophilic polymers, and contain a biologically active material.

U.S. Pat. No. 5,855,913, incorporated herein by reference, provides a particulate composition having aerodynamically light particles having a tap density of less than 0.4 g/cm3 with a mean diameter of between 5 μm and 30 μm, incorporating a surfactant on the surface thereof for drug delivery to the pulmonary system.

U.S. Pat. No. 5,985,309, incorporated herein by reference, provides particles incorporating a surfactant and/or a hydrophilic or hydrophobic complex of a positively or negatively charged therapeutic or diagnostic agent and a charged molecule of opposite charge for delivery to the pulmonary system.

U.S. Pat. No. 5,543,158, incorporated herein by reference, provides biodegradable injectable nanoparticles having a biodegradable solid core containing a biologically active material and poly(alkylene glycol) moieties on the surface.

WO2012135025 (also published as US20120251560), incorporated herein by reference, describes conjugated polyethyleneimine (PEI) polymers and conjugated aza-macrocycles (collectively referred to as "conjugated lipomer" or "lipomers"). In certain embodiments, it can envisioned that such conjugated lipomers can be used in the context of the CRISPR-Cas system to achieve in vitro, ex vivo and in vivo genomic perturbations to modify gene expression, including modulation of protein expression.

In one embodiment, the nanoparticle may be epoxide-modified lipid-polymer, advantageously 7C1 (see, e.g., James E. Dahlman and Carmen Barnes et al. Nature Nanotechnology (2014) published online 11 May 2014, doi: 10.1038/nnano.2014.84). C71 was synthesized by reacting C15 epoxide-terminated lipids with PEI600 at a 14:1 molar ratio, and was formulated with C14PEG2000 to produce nanoparticles (diameter between 35 and 60 nm) that were stable in PBS solution for at least 40 days.

An epoxide-modified lipid-polymer may be utilized to deliver the CRISPR-Cas system of the present invention to pulmonary, cardiovascular or renal cells, however, one of skill in the art may adapt the system to deliver to other target organs. Dosage ranging from about 0.05 to about 0.6 mg/kg are envisioned. Dosages over several days or weeks are also envisioned, with a total dosage of about 2 mg/kg.

Particle Delivery Systems and/or Formulations:

Several types of particle delivery systems and/or formulations are known to be useful in a diverse spectrum of biomedical applications. In general, a particle is defined as a small object that behaves as a whole unit with respect to its transport and properties. Particles are further classified according to diameter Coarse particles cover a range between 2,500 and 10,000 nanometers. Fine particles are sized between 100 and 2,500 nanometers. Ultrafine particles, or nanoparticles, are generally between 1 and 100 nanometers in size. The basis of the 100-nm limit is the fact that novel properties that differentiate particles from the bulk material typically develop at a critical length scale of under 100 nm.

As used herein, a particle delivery system/formulation is defined as any biological delivery system/formulation which includes a particle in accordance with the present invention. A particle in accordance with the present invention is any entity having a greatest dimension (e.g. diameter) of less than 100 microns (μm). In some embodiments, inventive particles have a greatest dimension of less than 10 μm. In some embodiments, inventive particles have a greatest dimension of less than 2000 nanometers (nm). In some embodiments, inventive particles have a greatest dimension of less than 1000 nanometers (nm). In some embodiments, inventive particles have a greatest dimension of less than 900 nm, 800 nm, 700 nm, 600 nm, 500 nm, 400 nm, 300 nm, 200 nm, or 100 nm. Typically, inventive particles have a greatest dimension (e.g., diameter) of 500 nm or less. In some embodiments, inventive particles have a greatest dimension (e.g., diameter) of 250 nm or less. In some embodiments, inventive particles have a greatest dimension (e.g., diameter) of 200 nm or less. In some embodiments, inventive particles have a greatest dimension (e.g., diameter) of 150 nm or less. In some embodiments, inventive particles have a greatest dimension (e.g., diameter) of 100 nm or less. Smaller particles, e.g., having a greatest dimension of 50 nm or less are used in some embodiments of the invention. In some embodiments, inventive particles have a greatest dimension ranging between 25 nm and 200 nm.

Particle characterization (including e.g., characterizing morphology, dimension, etc.) is done using a variety of different techniques. Common techniques are electron microscopy (TEM, SEM), atomic force microscopy (AFM), dynamic light scattering (DLS), X-ray photoelectron spectroscopy (XPS), powder X-ray diffraction (XRD), Fourier transform infrared spectroscopy (FTIR), matrix-assisted laser desorption/ionization time-of-flight mass spectrometry (MALDI-TOF), ultraviolet-visible spectroscopy, dual polarisation interferometry and nuclear magnetic resonance (NMR). Characterization (dimension measurements) may be made as to native particles (i.e., preloading) or after loading of the cargo (herein cargo refers to e.g., one or more components of CRISPR-Cas system e.g., CRISPR enzyme or mRNA or guide RNA, or any combination thereof, and may include additional carriers and/or excipients) to provide particles of an optimal size for delivery for any in vitro, ex vivo and/or in vivo application of the present invention. In certain preferred embodiments, particle dimension (e.g., diameter) characterization is based on measurements using dynamic laser scattering (DLS). Mention is made of U.S. Pat. Nos. 8,709,843; 6,007,845; 5,855,913; 5,985,309; 5,543,158; and the publication by James E. Dahlman and Carmen Barnes et al. Nature Nanotechnology (2014) published online 11 May 2014, doi:10.1038/nnano.2014.84, concerning particles, methods of making and using them and measurements thereof.

Particles delivery systems within the scope of the present invention may be provided in any form, including but not limited to solid, semi-solid, emulsion, or colloidal particles. As such any of the delivery systems described herein, including but not limited to, e.g., lipid-based systems, liposomes, micelles, microvesicles, exosomes, or gene gun may be provided as particle delivery systems within the scope of the present invention.

Exosomes

Exosomes are endogenous nano-vesicles that transport RNAs and proteins, and which can deliver RNA to the brain and other target organs. To reduce immunogenicity, Alvarez-Erviti et al. (2011, Nat Biotechnol 29: 341) used self-derived dendritic cells for exosome production. Targeting to the brain was achieved by engineering the dendritic cells to express Lamp2b, an exosomal membrane protein, fused to the neuron-specific RVG peptide. Purified exosomes were loaded with exogenous RNA by electroporation. Intravenously injected RVG-targeted exosomes delivered GAPDH siRNA specifically to neurons, microglia, oligodendrocytes in the brain, resulting in a specific gene knockdown. Pre-exposure to RVG exosomes did not attenuate knockdown, and non-specific uptake in other tissues was not observed. The therapeutic potential of exosome-mediated siRNA delivery was demonstrated by the strong mRNA (60%) and protein (62%) knockdown of BACE1, a therapeutic target in Alzheimer's disease.

To obtain a pool of immunologically inert exosomes, Alvarez-Erviti et al. harvested bone marrow from inbred C57BL/6 mice with a homogenous major histocompatibility complex (MHC) haplotype. As immature dendritic cells produce large quantities of exosomes devoid of T-cell activators such as MHC-II and CD86, Alvarez-Erviti et al. selected for dendritic cells with granulocyte/macrophage-colony stimulating factor (GM-CSF) for 7 d. Exosomes were purified from the culture supernatant the following day using well-established ultracentrifugation protocols. The exosomes produced were physically homogenous, with a size distribution peaking at 80 nm in diameter as determined by nanoparticle tracking analysis (NTA) and electron microscopy. Alvarez-Erviti et al. obtained 6-12 µg of exosomes (measured based on protein concentration) per $10^6$ cells.

Next, Alvarez-Erviti et al. investigated the possibility of loading modified exosomes with exogenous cargoes using electroporation protocols adapted for nanoscale applications. As electroporation for membrane particles at the nanometer scale is not well-characterized, nonspecific Cy5-labeled RNA was used for the empirical optimization of the electroporation protocol. The amount of encapsulated RNA was assayed after ultracentrifugation and lysis of exosomes. Electroporation at 400 V and 125 µF resulted in the greatest retention of RNA and was used for all subsequent experiments.

Alvarez-Erviti et al. administered 150 µg of each BACE1 siRNA encapsulated in 150 µg of RVG exosomes to normal C57BL/6 mice and compared the knockdown efficiency to four controls: untreated mice, mice injected with RVG exosomes only, mice injected with BACE1 siRNA complexed to an in vivo cationic liposome reagent and mice injected with BACE1 siRNA complexed to RVG-9R, the RVG peptide conjugated to 9 D-arginines that electrostatically binds to the siRNA. Cortical tissue samples were analyzed 3 d after administration and a significant protein knockdown (45%, P<0.05, versus 62%, P<0.01) in both siRNA-RVG-9R-treated and siRNARVG exosome-treated mice was observed, resulting from a significant decrease in BACE1 mRNA levels (66% [+ or −] 15%, P<0.001 and 61% [+ or −] 13% respectively, P<0.01). Moreover, Applicants demonstrated a significant decrease (55%, P<0.05) in the total [beta]-amyloid 1-42 levels, a main component of the amyloid plaques in Alzheimer's pathology, in the RVG-exosome-treated animals. The decrease observed was greater than the β-amyloid 1-40 decrease demonstrated in normal mice after intraventricular injection of BACE1 inhibitors. Alvarez-Erviti et al. carried out 5'-rapid amplification of cDNA ends (RACE) on BACE1 cleavage product, which provided evidence of RNAi-mediated knockdown by the siRNA.

Finally, Alvarez-Erviti et al. investigated whether RNA-RVG exosomes induced immune responses in vivo by assessing IL-6, IP-10, TNFα and IFN-α serum concentrations. Following exosome treatment, nonsignificant changes in all cytokines were registered similar to siRNA-transfection reagent treatment in contrast to siRNA-RVG-9R, which potently stimulated IL-6 secretion, confirming the immunologically inert profile of the exosome treatment. Given that exosomes encapsulate only 20% of siRNA, delivery with RVG-exosome appears to be more efficient than RVG-9R delivery as comparable mRNA knockdown and greater protein knockdown was achieved with fivefold less siRNA without the corresponding level of immune stimulation. This experiment demonstrated the therapeutic potential of RVG-exosome technology, which is potentially suited for long-term silencing of genes related to neurodegenerative diseases. The exosome delivery system of Alvarez-Erviti et al. may be applied to deliver the CRISPR-Cas system of the present invention to therapeutic targets, especially neurodegenerative diseases. A dosage of about 100 to 1000 mg of CRISPR Cas encapsulated in about 100 to 1000 mg of RVG exosomes may be contemplated for the present invention.

El-Andaloussi et al. (Nature Protocols 7, 2112-2126 (2012)) discloses how exosomes derived from cultured cells can be harnessed for delivery of RNA in vitro and in vivo. This protocol first describes the generation of targeted exosomes through transfection of an expression vector, comprising an exosomal protein fused with a peptide ligand. Next, El-Andaloussi et al. explain how to purify and characterize exosomes from transfected cell supernatant. Next, El-Andaloussi et al. detail crucial steps for loading RNA into exosomes. Finally, El-Andaloussi et al. outline how to use exosomes to efficiently deliver RNA in vitro and in vivo in mouse brain. Examples of anticipated results in which exosome-mediated RNA delivery is evaluated by functional assays and imaging are also provided. The entire protocol takes ~3 weeks. Delivery or administration according to the invention may be performed using exosomes produced from self-derived dendritic cells. From the herein teachings, this can be employed in the practice of the invention In another embodiment, the plasma exosomes of Wahlgren et al. (Nucleic Acids Research, 2012, Vol. 40, No. 17 e130) are contemplated. Exosomes are nano-sized vesicles (30-90 nm in size) produced by many cell types, including dendritic cells (DC), B cells, T cells, mast cells, epithelial cells and tumor cells. These vesicles are formed by inward budding of late endosomes and are then released to the extracellular environment upon fusion with the plasma membrane. Because exosomes naturally carry RNA between cells, this property may be useful in gene therapy, and from this disclosure can be employed in the practice of the instant invention.

Exosomes from plasma can be prepared by centrifugation of buffy coat at 900 g for 20 min to isolate the plasma followed by harvesting cell supernatants, centrifuging at 300 g for 10 min to eliminate cells and at 16 500 g for 30 min followed by filtration through a 0.22 mm filter. Exosomes are pelleted by ultracentrifugation at 120 000 g for 70 min. Chemical transfection of siRNA into exosomes is carried out according to the manufacturer's instructions in RNAi Human/Mouse Starter Kit (Quiagen, Hilden, Germany). siRNA is added to 100 ml PBS at a final concentration of 2 mmol/ml. After adding HiPerFect transfection reagent, the mixture is incubated for 10 min at RT. In order to remove the excess of micelles, the exosomes are re-isolated using aldehyde/sulfate latex beads. The chemical transfection of CRISPR Cas into exosomes may be conducted similarly to siRNA. The exosomes may be co-cultured with monocytes and lymphocytes isolated from the peripheral blood of healthy donors. Therefore, it may be contemplated that exosomes containing CRISPR Cas may be introduced to monocytes and lymphocytes of and autologously reintroduced into a human. Accordingly, delivery or administration according to the invention may be performed using plasma exosomes.

Liposomes

Delivery or administration according to the invention can be performed with liposomes. Liposomes are spherical vesicle structures composed of a uni- or multilamellar lipid bilayer surrounding internal aqueous compartments and a relatively impermeable outer lipophilic phospholipid bilayer. Liposomes have gained considerable attention as drug delivery carriers because they are biocompatible, non-toxic, can deliver both hydrophilic and lipophilic drug molecules, protect their cargo from degradation by plasma enzymes, and transport their load across biological membranes and the blood brain barrier (BBB) (see, e.g., Spuch and Navarro, Journal of Drug Delivery, vol. 2011, Article ID 469679, 12 pages, 2011. doi:10.1155/2011/469679 for review).

Liposomes can be made from several different types of lipids; however, phospholipids are most commonly used to generate liposomes as drug carriers. Although liposome formation is spontaneous when a lipid film is mixed with an aqueous solution, it can also be expedited by applying force in the form of shaking by using a homogenizer, sonicator, or an extrusion apparatus (see, e.g., Spuch and Navarro, Journal of Drug Delivery, vol. 2011, Article ID 469679, 12 pages, 2011. doi:10.1155/2011/469679 for review).

Several other additives may be added to liposomes in order to modify their structure and properties. For instance, either cholesterol or sphingomyelin may be added to the liposomal mixture in order to help stabilize the liposomal structure and to prevent the leakage of the liposomal inner cargo. Further, liposomes are prepared from hydrogenated egg phosphatidylcholine or egg phosphatidylcholine, cholesterol, and dicetyl phosphate, and their mean vesicle sizes were adjusted to about 50 and 100 nm. (see, e.g., Spuch and Navarro, Journal of Drug Delivery, vol. 2011, Article ID 469679, 12 pages, 2011. doi:10.1155/2011/469679 for review).

A liposome formulation may be mainly comprised of natural phospholipids and lipids such as 1,2-distearoryl-sn-glycero-3-phosphatidyl choline (DSPC), sphingomyelin, egg phosphatidylcholines and monosialoganglioside. Since this formulation is made up of phospholipids only, liposomal formulations have encountered many challenges, one of the ones being the instability in plasma. Several attempts to overcome these challenges have been made, specifically in the manipulation of the lipid membrane. One of these attempts focused on the manipulation of cholesterol. Addition of cholesterol to conventional formulations reduces rapid release of the encapsulated bioactive compound into the plasma or 1,2-dioleoyl-sn-glycero-3-phosphoethanolamine (DOPE) increases the stability (see, e.g., Spuch and Navarro, Journal of Drug Delivery, vol. 2011, Article ID 469679, 12 pages, 2011. doi:10.1155/2011/469679 for review).

In a particularly advantageous embodiment, Trojan Horse liposomes (also known as Molecular Trojan Horses) are desirable and protocols may be found at cshprotocols.cshlp.org/content/2010/4/pdb.prot5407.long. These particles allow delivery of a transgene to the entire brain after an intravascular injection. Without being bound by limitation, it is believed that neutral lipid particles with specific antibodies conjugated to surface allow crossing of the blood brain barrier via endocytosis. Applicant postulates utilizing Trojan Horse Liposomes to deliver the CRISPR family of nucleases to the brain via an intravascular injection, which would allow whole brain transgenic animals without the need for embryonic manipulation. About 1-5 g of DNA or RNA may be contemplated for in vivo administration in liposomes.

In another embodiment, the CRISPR Cas system may be administered in liposomes, such as a stable nucleic-acid-lipid particle (SNALP) (see, e.g., Morrissey et al., Nature Biotechnology, Vol. 23, No. 8, August 2005). Daily intravenous injections of about 1, 3 or 5 mg/kg/day of a specific CRISPR Cas targeted in a SNALP are contemplated. The daily treatment may be over about three days and then weekly for about five weeks. In another embodiment, a specific CRISPR Cas encapsulated SNALP) administered by intravenous injection to at doses of about 1 or 2.5 mg/kg are also contemplated (see, e.g., Zimmerman et al., Nature Letters, Vol. 441, 4 May 2006). The SNALP formulation may contain the lipids 3-N-[(wmethoxypoly(ethylene glycol) 2000) carbamoyl]-1,2-dimyristyloxy-propylamine (PEG-C-DMA), 1,2-dilinoleyloxy-N,N-dimethyl-3-aminopropane (DLinDMA), 1,2-distearoyl-sn-glycero-3-phospho-choline (DSPC) and cholesterol, in a 2:40:10:48 molar percent ratio (see, e.g., Zimmerman et al., Nature Letters, Vol. 441, 4 May 2006).

In another embodiment, stable nucleic-acid-lipid particles (SNALPs) have proven to be effective delivery molecules to highly vascularized HepG2-derived liver tumors but not in poorly vascularized HCT-116 derived liver tumors (see, e.g., Li, Gene Therapy (2012) 19, 775-780). The SNALP liposomes may be prepared by formulating D-Lin-DMA and PEG-C-DMA with distearoylphosphatidylcholine (DSPC), Cholesterol and siRNA using a 25:1 lipid/siRNA ratio and a 48/40/10/2 molar ratio of Cholesterol/D-Lin-DMA/DSPC/PEG-C-DMA. The resulted SNALP liposomes are about 80-100 nm in size.

In yet another embodiment, a SNALP may comprise synthetic cholesterol (Sigma-Aldrich, St Louis, MO, USA), dipalmitoylphosphatidylcholine (Avanti Polar Lipids, Alabaster, AL, USA), 3-N-[(w-methoxy poly(ethylene glycol) 2000)carbamoyl]-1,2-dimyrestyloxypropylamine, and cationic 1,2-dilinoleyloxy-3-N,Ndimethylaminopropane (see, e.g., Geisbert et al., Lancet 2010; 375: 1896-905). A dosage of about 2 mg/kg total CRISPR Cas per dose administered as, for example, a bolus intravenous infusion may be contemplated.

In yet another embodiment, a SNALP may comprise synthetic cholesterol (Sigma-Aldrich), 1,2-distearoyl-sn-glycero-3-phosphocholine (DSPC; Avanti Polar Lipids Inc.), PEG-cDMA, and 1,2-dilinoleyloxy-3-(N;N-dimethyl)aminopropane (DLinDMA) (see, e.g., Judge, J. Clin. Invest. 119:661-673 (2009)). Formulations used for in vivo studies may comprise a final lipid/RNA mass ratio of about 9:1.

The safety profile of RNAi nanomedicines has been reviewed by Barros and Gollob of Alnylam Pharmaceuticals (see, e.g., Advanced Drug Delivery Reviews 64 (2012) 1730-1737). The stable nucleic acid lipid particle (SNALP) is comprised of four different lipids an ionizable lipid (DLinDMA) that is cationic at low pH, a neutral helper lipid, cholesterol, and a diffusible polyethylene glycol (PEG)-lipid. The particle is approximately 80 nm in diameter and is charge-neutral at physiologic pH. During formulation, the ionizable lipid serves to condense lipid with the anionic RNA during particle formation. When positively charged under increasingly acidic endosomal conditions, the ionizable lipid also mediates the fusion of SNALP with the endosomal membrane enabling release of RNA into the cytoplasm. The PEG-lipid stabilizes the particle and reduces aggregation during formulation, and subsequently provides a neutral hydrophilic exterior that improves pharmacokinetic properties.

To date, two clinical programs have been initiated using SNALP formulations with RNA. Tekmira Pharmaceuticals recently completed a phase I single-dose study of SNALP-ApoB in adult volunteers with elevated LDL cholesterol. ApoB is predominantly expressed in the liver and jejunum and is essential for the assembly and secretion of VLDL and LDL. Seventeen subjects received a single dose of SNALP-ApoB (dose escalation across 7 dose levels). There was no evidence of liver toxicity (anticipated as the potential dose-limiting toxicity based on preclinical studies). One (of two) subjects at the highest dose experienced flu-like symptoms consistent with immune system stimulation, and the decision was made to conclude the trial.

Alnylam Pharmaceuticals has similarly advanced ALN-TTR01, which employs the SNALP technology described above and targets hepatocyte production of both mutant and wild-type TTR to treat TTR amyloidosis (ATTR). Three ATTR syndromes have been described: familial amyloidotic polyneuropathy (FAP) and familial amyloidotic cardiomyopathy (FAC) both caused by autosomal dominant mutations in TTR; and senile systemic amyloidosis (SSA) cause by wildtype TTR. A placebo-controlled, single dose-escalation phase I trial of ALN-TTR01 was recently completed in patients with ATTR. ALN-TTR01 was administered as a 15-minute IV infusion to 31 patients (23 with study drug and 8 with placebo) within a dose range of 0.01 to 1.0 mg/kg (based on siRNA). Treatment was well tolerated with no significant increases in liver function tests. Infusion-related reactions were noted in 3 of 23 patients at ≥0.4 mg/kg; all responded to slowing of the infusion rate and all continued on study. Minimal and transient elevations of serum cytokines IL-6, IP-10 and IL-1ra were noted in two patients at the highest dose of 1 mg/kg (as anticipated from preclinical and NHP studies). Lowering of serum TTR, the expected pharmacodynamics effect of ALN-TTR01, was observed at 1 mg/kg.

In yet another embodiment, a SNALP may be made by solubilizing a cationic lipid, DSPC, cholesterol and PEG-lipid e.g., in ethanol, e.g., at a molar ratio of 40:10:40:10, respectively (see, Semple et al., Nature Niotechnology, Volume 28 Number 2 Feb. 2010, pp. 172-177). The lipid mixture was added to an aqueous buffer (50 mM citrate, pH 4) with mixing to a final ethanol and lipid concentration of 30% (vol/vol) and 6.1 mg/ml, respectively, and allowed to equilibrate at 22° C. for 2 min before extrusion. The hydrated lipids were extruded through two stacked 80 nm pore-sized filters (Nuclepore) at 22° C. using a Lipex Extruder (Northern Lipids) until a vesicle diameter of 70-90 nm, as determined by dynamic light scattering analysis, was obtained. This generally required 1-3 passes. The siRNA (solubilized in a 50 mM citrate, pH 4 aqueous solution containing 30% ethanol) was added to the pre-equilibrated (35° C.) vesicles at a rate of ~5 ml/min with mixing. After a final target siRNA/lipid ratio of 0.06 (wt/wt) was reached, the mixture was incubated for a further 30 min at 35° C. to allow vesicle reorganization and encapsulation of the siRNA. The ethanol was then removed and the external buffer replaced with PBS (155 mM NaCl, 3 mM $Na_2HPO_4$, 1 mM $KH_2PO_4$, pH 7.5) by either dialysis or tangential flow diafiltration. siRNA were encapsulated in SNALP using a controlled step-wise dilution method process. The lipid constituents of KC2-SNALP were DLin-KC2-DMA (cationic lipid), dipalmitoylphosphatidylcholine (DPPC; Avanti Polar Lipids), synthetic cholesterol (Sigma) and PEG-C-DMA used at a molar ratio of 57.1:7.1:34.3:1.4. Upon formation of the loaded particles, SNALP were dialyzed against PBS and filter sterilized through a 0.2 μm filter before use. Mean particle sizes were 75-85 nm and 90-95% of the siRNA was encapsulated within the lipid particles. The final siRNA/lipid ratio in formulations used for in vivo testing was ~0.15 (wt/wt). LNP-siRNA systems containing Factor VII siRNA were diluted to the appropriate concentrations in sterile PBS immediately before use and the formulations were administered intravenously through the lateral tail vein in a total volume of 10 ml/kg. This method and these delivery systems may be extrapolated to the CRISPR Cas system of the present invention.

Other Lipids

Other cationic lipids, such as amino lipid 2,2-dilinoleyl-4-dimethylaminoethyl-[1,3]-dioxolane (DLin-KC2-DMA) may be utilized to encapsulate CRISPR Cas or components thereof or nucleic acid molecule(s) coding therefor e.g., similar to SiRNA (see, e.g., Jayaraman, Angew. Chem. Int. Ed. 2012, 51, 8529-8533), and hence may be employed in the practice of the invention. A preformed vesicle with the following lipid composition may be contemplated: amino lipid, distearoylphosphatidylcholine (DSPC), cholesterol and (R)-2,3-bis(octadecyloxy) propyl-1-(methoxy poly(ethylene glycol)2000)propylcarbamate (PEG-lipid) in the molar ratio 40/10/40/10, respectively, and a FVII siRNA/total lipid ratio of approximately 0.05 (w/w). To ensure a narrow particle size distribution in the range of 70-90 nm and a low polydispersity index of 0.11±0.04 (n=56), the particles may be extruded up to three times through 80 nm membranes prior to adding the CRISPR Cas RNA. Particles containing the highly potent amino lipid 16 may be used, in which the molar ratio of the four lipid components 16, DSPC, cholesterol and PEG-lipid (50/10/38.5/1.5) which may be further optimized to enhance in vivo activity.

Michael S D Kormann et al. ("Expression of therapeutic proteins after delivery of chemically modified mRNA in mice: Nature Biotechnology, Volume:29, Pages: 154-157 (2011)) describes the use of lipid envelopes to deliver RNA. Use of lipid envelopes is also preferred in the present invention.

In another embodiment, lipids may be formulated with the CRISPR Cas system of the present invention to form lipid nanoparticles (LNPs). Lipids include, but are not limited to, DLin-KC2-DMA4, C12-200 and colipids disteroylphosphatidyl choline, cholesterol, and PEG-DMG may be formulated with CRISPR Cas instead of siRNA (see, e.g., Novobrantseva, Molecular Therapy-Nucleic Acids (2012) 1, e4; doi:10.1038/mtna.2011.3) using a spontaneous vesicle formation procedure. The component molar ratio may be about 50/10/38.5/1.5 (DLin-KC2-DMA or C12-200/disteroylphosphatidyl choline/cholesterol/PEG-DMG). The final lipid:siRNA weight ratio may be ~12:1 and 9:1 in the case of DLin-KC2-DMA and C12-200 lipid nanoparticles (LNPs), respectively. The formulations may have mean particle diameters of ~80 nm with >90% entrapment efficiency. A 3 mg/kg dose may be contemplated.

Tekmira has a portfolio of approximately 95 patent families, in the U.S. and abroad, that are directed to various aspects of LNPs and LNP formulations (see, e.g., U.S. Pat. Nos. 7,982,027; 7,799,565; 8,058,069; 8,283,333; 7,901,708; 7,745,651; 7,803,397; 8,101,741; 8,188,263; 7,915,399; 8,236,943 and 7,838,658 and European Pat. Nos 1766035; 1519714; 1781593 and 1664316), all of which may be used and/or adapted to the present invention.

The CRISPR Cas system or components thereof or nucleic acid molecule(s) coding therefor may be delivered encapsulated in PLGA Microspheres such as that further described in US published applications 20130252281 and 20130245107 and 20130244279 (assigned to Moderna Therapeutics) which relate to aspects of formulation of compositions comprising modified nucleic acid molecules which may encode a protein, a protein precursor, or a partially or fully processed form of the protein or a protein precursor. The formulation may have a molar ratio 50:10:38.5:1.5-3.0 (cationic lipid:fusogenic lipid:cholesterol:PEG lipid). The PEG lipid may be selected from, but is not limited to PEG-c-DOMG, PEG-DMG. The fusogenic lipid may be DSPC. See also, Schrum et al., Delivery and Formulation of Engineered Nucleic Acids, US published application 20120251618.

Nanomerics' technology addresses bioavailability challenges for a broad range of therapeutics, including low molecular weight hydrophobic drugs, peptides, and nucleic acid based therapeutics (plasmid, siRNA, miRNA). Specific administration routes for which the technology has demonstrated clear advantages include the oral route, transport across the blood-brain-barrier, delivery to solid tumours, as well as to the eye. See, e.g., Mazza et al., 2013, ACS Nano. 2013 Feb. 26; 7(2):1016-26; Uchegbu and Siew, 2013, J Pharm Sci. 102(2):305-10 and Lalatsa et al., 2012, J Control Release. 2012 Jul. 20; 161(2):523-36.

US Patent Publication No. 20050019923 describes cationic dendrimers for delivering bioactive molecules, such as polynucleotide molecules, peptides and polypeptides and/or pharmaceutical agents, to a mammalian body. The dendrimers are suitable for targeting the delivery of the bioactive molecules to, for example, the liver, spleen, lung, kidney or heart (or even the brain). Dendrimers are synthetic 3-dimensional macromolecules that are prepared in a step-wise fashion from simple branched monomer units, the nature and functionality of which can be easily controlled and varied. Dendrimers are synthesised from the repeated addition of building blocks to a multifunctional core (divergent approach to synthesis), or towards a multifunctional core (convergent approach to synthesis) and each addition of a 3-dimensional shell of building blocks leads to the formation of a higher generation of the dendrimers. Polypropylenimine dendrimers start from a diaminobutane core to which is added twice the number of amino groups by a double Michael addition of acrylonitrile to the primary amines followed by the hydrogenation of the nitriles. This results in a doubling of the amino groups. Polypropylenimine dendrimers contain 100% protonable nitrogens and up to 64 terminal amino groups (generation 5, DAB 64). Protonable groups are usually amine groups which are able to accept protons at neutral pH. The use of dendrimers as gene delivery agents has largely focused on the use of the polyamidoamine. and phosphorous containing compounds with a mixture of amine/amide or N—P($O_2$)S as the conjugating units respectively with no work being reported on the use of the lower generation polypropylenimine dendrimers for gene delivery. Polypropylenimine dendrimers have also been studied as pH sensitive controlled release systems for drug delivery and for their encapsulation of guest molecules when chemically modified by peripheral amino acid groups. The cytotoxicity and interaction of polypropylenimine dendrimers with DNA as well as the transfection efficacy of DAB 64 has also been studied.

US Patent Publication No. 20050019923 is based upon the observation that, contrary to earlier reports, cationic dendrimers, such as polypropylenimine dendrimers, display suitable properties, such as specific targeting and low toxicity, for use in the targeted delivery of bioactive molecules, such as genetic material. In addition, derivatives of the cationic dendrimer also display suitable properties for the targeted delivery of bioactive molecules. See also, Bioactive Polymers, US published application 20080267903, which discloses "Various polymers, including cationic polyamine polymers and dendrimeric polymers, are shown to possess anti-proliferative activity, and may therefore be useful for treatment of disorders characterised by undesirable cellular proliferation such as neoplasms and tumours, inflammatory disorders (including autoimmune disorders), psoriasis and atherosclerosis. The polymers may be used alone as active agents, or as delivery vehicles for other therapeutic agents, such as drug molecules or nucleic acids for gene therapy. In such cases, the polymers' own intrinsic anti-tumour activity may complement the activity of the agent to be delivered." The disclosures of these patent publications may be employed in conjunction with herein teachings for delivery of CRISPR Cas system(s) or component(s) thereof or nucleic acid molecule(s) coding therefor.

Supercharged Proteins

Supercharged proteins are a class of engineered or naturally occurring proteins with unusually high positive or negative net theoretical charge and may be employed in delivery of CRISPR Cas system(s) or component(s) thereof or nucleic acid molecule(s) coding therefor. Both supernegatively and superpositively charged proteins exhibit a remarkable ability to withstand thermally or chemically induced aggregation. Superpositively charged proteins are also able to penetrate mammalian cells. Associating cargo with these proteins, such as plasmid DNA, RNA, or other proteins, can enable the functional delivery of these macromolecules into mammalian cells both in vitro and in vivo. David Liu's lab reported the creation and characterization of supercharged proteins in 2007 (Lawrence et al., 2007, Journal of the American Chemical Society 129, 10110-10112).

The nonviral delivery of RNA and plasmid DNA into mammalian cells are valuable both for research and therapeutic applications (Akinc et al., 2010, Nat. Biotech. 26, 561-569). Purified +36 GFP protein (or other superpositively charged protein) is mixed with RNAs in the appropriate serum-free media and allowed to complex prior addition to cells. Inclusion of serum at this stage inhibits formation of the supercharged protein-RNA complexes and reduces the effectiveness of the treatment. The following protocol has been found to be effective for a variety of cell lines (McNaughton et al., 2009, Proc. Natl. Acad. Sci. USA 106, 6111-6116). However, pilot experiments varying the dose of protein and RNA should be performed to optimize the procedure for specific cell lines.

(1) One day before treatment, plate $1\times10^5$ cells per well in a 48-well plate.
(2) On the day of treatment, dilute purified +36 GFP protein in serum free media to a final concentration 200 nM. Add RNA to a final concentration of 50 nM. Vortex to mix and incubate at room temperature for 10 min.
(3) During incubation, aspirate media from cells and wash once with PBS.
(4) Following incubation of +36 GFP and RNA, add the protein-RNA complexes to cells.
(5) Incubate cells with complexes at 37° C. for 4 h.
(6) Following incubation, aspirate the media and wash three times with 20 U/mL heparin PBS. Incubate cells with serum-containing media for a further 48 h or longer depending upon the assay for activity.
(7) Analyze cells by immunoblot, qPCR, phenotypic assay, or other appropriate method.

David Liu's lab has further found +36 GFP to be an effective plasmid delivery reagent in a range of cells. As plasmid DNA is a larger cargo than siRNA, proportionately more +36 GFP protein is required to effectively complex plasmids. For effective plasmid delivery Applicants have developed a variant of +36 GFP bearing a C-terminal HA2 peptide tag, a known endosome-disrupting peptide derived from the influenza virus hemagglutinin protein. The following protocol has been effective in a variety of cells, but as above it is advised that plasmid DNA and supercharged protein doses be optimized for specific cell lines and delivery applications.

(1) One day before treatment, plate $1\times10^5$ per well in a 48-well plate.
(2) On the day of treatment, dilute purified þ 36 GFP protein in serum free media to a final concentration 2 mM. Add 1 mg of plasmid DNA. Vortex to mix and incubate at room temperature for 10 min.
(3) During incubation, aspirate media from cells and wash once with PBS.

(4) Following incubation of þ 36 GFP and plasmid DNA, gently add the protein-DNA complexes to cells.
(5) Incubate cells with complexes at 37 C for 4 h.
(6) Following incubation, aspirate the media and wash with PBS. Incubate cells in serum-containing media and incubate for a further 24-48 h.
(7) Analyze plasmid delivery (e.g., by plasmid-driven gene expression) as appropriate.

See also, e.g., McNaughton et al., Proc. Natl. Acad. Sci. USA 106, 6111-6116 (2009); Cronican et al., ACS Chemical Biology 5, 747-752 (2010); Cronican et al., Chemistry & Biology 18, 833-838 (2011); Thompson et al., Methods in Enzymology 503, 293-319 (2012); Thompson, D. B., et al., Chemistry & Biology 19 (7), 831-843 (2012). The methods of the super charged proteins may be used and/or adapted for delivery of the CRISPR Cas system of the present invention. These systems of Dr. Lui and documents herein in inconjunction with herein teachings can be employed in the delivery of CRISPR Cas system(s) or component(s) thereof or nucleic acid molecule(s) coding therefor.

Implantable Devices

In another embodiment, implantable devices are also contemplated for delivery of the CRISPR Cas system or component(s) thereof or nucleic acid molecule(s) coding therefor. For example, US Patent Publication 20110195123 discloses an implantable medical device which elutes a drug locally and in prolonged period is provided, including several types of such a device, the treatment modes of implementation and methods of implantation. The device comprising of polymeric substrate, such as a matrix for example, that is used as the device body, and drugs, and in some cases additional scaffolding materials, such as metals or additional polymers, and materials to enhance visibility and imaging. An implantable delivery device can be advantageous in providing release locally and over a prolonged period, where drug is released directly to the extracellular matrix (ECM) of the diseased area such as tumor, inflammation, degeneration or for symptomatic objectives, or to injured smooth muscle cells, or for prevention. One kind of drug is RNA, as disclosed above, and this system may be used/and or adapted to the CRISPR Cas system of the present invention. The modes of implantation in some embodiments are existing implantation procedures that are developed and used today for other treatments, including brachytherapy and needle biopsy. In such cases the dimensions of the new implant described in this invention are similar to the original implant. Typically a few devices are implanted during the same treatment procedure.

As described in US Patent Publication 20110195123, there is provided a drug delivery implantable or insertable system, including systems applicable to a cavity such as the abdominal cavity and/or any other type of administration in which the drug delivery system is not anchored or attached, comprising a biostable and/or degradable and/or bioabsorbable polymeric substrate, which may for example optionally be a matrix. It should be noted that the term "insertion" also includes implantation. The drug delivery system is preferably implemented as a "Loder" as described in US Patent Publication 20110195123.

The polymer or plurality of polymers are biocompatible, incorporating an agent and/or plurality of agents, enabling the release of agent at a controlled rate, wherein the total volume of the polymeric substrate, such as a matrix for example, in some embodiments is optionally and preferably no greater than a maximum volume that permits a therapeutic level of the agent to be reached. As a non-limiting example, such a volume is preferably within the range of 0.1 $m^3$ to 1000 $mm^3$, as required by the volume for the agent load. The Loder may optionally be larger, for example when incorporated with a device whose size is determined by functionality, for example and without limitation, a knee joint, an intra-uterine or cervical ring and the like.

The drug delivery system (for delivering the composition) is designed in some embodiments to preferably employ degradable polymers, wherein the main release mechanism is bulk erosion; or in some embodiments, non degradable, or slowly degraded polymers are used, wherein the main release mechanism is diffusion rather than bulk erosion, so that the outer part functions as membrane, and its internal part functions as a drug reservoir, which practically is not affected by the surroundings for an extended period (for example from about a week to about a few months). Combinations of different polymers with different release mechanisms may also optionally be used. The concentration gradient at the surface is preferably maintained effectively constant during a significant period of the total drug releasing period, and therefore the diffusion rate is effectively constant (termed "zero mode" diffusion). By the term "constant" it is meant a diffusion rate that is preferably maintained above the lower threshold of therapeutic effectiveness, but which may still optionally feature an initial burst and/or may fluctuate, for example increasing and decreasing to a certain degree. The diffusion rate is preferably so maintained for a prolonged period, and it can be considered constant to a certain level to optimize the therapeutically effective period, for example the effective silencing period.

The drug delivery system optionally and preferably is designed to shield the nucleotide based therapeutic agent from degradation, whether chemical in nature or due to attack from enzymes and other factors in the body of the subject.

The drug delivery system as described in US Patent Publication 20110195123 is optionally associated with sensing and/or activation appliances that are operated at and/or after implantation of the device, by non and/or minimally invasive methods of activation and/or acceleration/deceleration, for example optionally including but not limited to thermal heating and cooling, laser beams, and ultrasonic, including focused ultrasound and/or RF (radiofrequency) methods or devices.

According to some embodiments of US Patent Publication 20110195123, the site for local delivery may optionally include target sites characterized by high abnormal proliferation of cells, and suppressed apoptosis, including tumors, active and or chronic inflammation and infection including autoimmune diseases states, degenerating tissue including muscle and nervous tissue, chronic pain, degenerative sites, and location of bone fractures and other wound locations for enhancement of regeneration of tissue, and injured cardiac, smooth and striated muscle.

The site for implantation of the composition, or target site, preferably features a radius, area and/or volume that is sufficiently small for targeted local delivery. For example, the target site optionally has a diameter in a range of from about 0.1 mm to about 5 cm.

The location of the target site is preferably selected for maximum therapeutic efficacy. For example, the composition of the drug delivery system (optionally with a device for implantation as described above) is optionally and preferably implanted within or in the proximity of a tumor environment, or the blood supply associated thereof.

For example the composition (optionally with the device) is optionally implanted within or in the proximity to pancreas, prostate, breast, liver, via the nipple, within the vascular system and so forth.

The target location is optionally selected from the group consisting of (as non-limiting examples only, as optionally any site within the body may be suitable for implanting a Loder): 1. brain at degenerative sites like in Parkinson or Alzheimer disease at the basal ganglia, white and gray matter; 2. spine as in the case of amyotrophic lateral sclerosis (ALS); 3. uterine cervix to prevent HPV infection; 4. active and chronic inflammatory joints; 5. dermis as in the case of psoriasis; 6. sympathetic and sensoric nervous sites for analgesic effect; 7. Intra osseous implantation; 8. acute and chronic infection sites; 9. Intra vaginal; 10. Inner ear—auditory system, labyrinth of the inner ear, vestibular system; 11. Intra tracheal; 12. Intra-cardiac; coronary, epicardiac; 13. urinary bladder; 14. biliary system; 15. parenchymal tissue including and not limited to the kidney, liver, spleen; 16. lymph nodes; 17. salivary glands; 18. dental gums; 19. Intra-articular (into joints); 20. Intra-ocular; 21. Brain tissue; 22. Brain ventricles; 23. Cavities, including abdominal cavity (for example but without limitation, for ovary cancer); 24. Intra esophageal and 25. Intra rectal.

Optionally insertion of the system (for example a device containing the composition) is associated with injection of material to the ECM at the target site and the vicinity of that site to affect local pH and/or temperature and/or other biological factors affecting the diffusion of the drug and/or drug kinetics in the ECM, of the target site and the vicinity of such a site.

Optionally, according to some embodiments, the release of said agent could be associated with sensing and/or activation appliances that are operated prior and/or at and/or after insertion, by non and/or minimally invasive and/or else methods of activation and/or acceleration/deceleration, including laser beam, radiation, thermal heating and cooling, and ultrasonic, including focused ultrasound and/or RF (radiofrequency) methods or devices, and chemical activators.

According to other embodiments of US Patent Publication 20110195123, the drug preferably comprises a RNA, for example for localized cancer cases in breast, pancreas, brain, kidney, bladder, lung, and prostate as described below. Although exemplified with RNAi, many drugs are applicable to be encapsulated in Loder, and can be used in association with this invention, as long as such drugs can be encapsulated with the Loder substrate, such as a matrix for example, and this system may be used and/or adapted to deliver the CRISPR Cas system of the present invention.

As another example of a specific application, neuro and muscular degenerative diseases develop due to abnormal gene expression. Local delivery of RNAs may have therapeutic properties for interfering with such abnormal gene expression. Local delivery of anti apoptotic, anti inflammatory and anti degenerative drugs including small drugs and macromolecules may also optionally be therapeutic. In such cases the Loder is applied for prolonged release at constant rate and/or through a dedicated device that is implanted separately. All of this may be used and/or adapted to the CRISPR Cas system of the present invention.

As yet another example of a specific application, psychiatric and cognitive disorders are treated with gene modifiers. Gene knockdown is a treatment option. Loders locally delivering agents to central nervous system sites are therapeutic options for psychiatric and cognitive disorders including but not limited to psychosis, bi-polar diseases, neurotic disorders and behavioral maladies. The Loders could also deliver locally drugs including small drugs and macromolecules upon implantation at specific brain sites. All of this may be used and/or adapted to the CRISPR Cas system of the present invention.

As another example of a specific application, silencing of innate and/or adaptive immune mediators at local sites enables the prevention of organ transplant rejection. Local delivery of RNAs and immunomodulating reagents with the Loder implanted into the transplanted organ and/or the implanted site renders local immune suppression by repelling immune cells such as CD8 activated against the transplanted organ. All of this may be used/and or adapted to the CRISPR Cas system of the present invention.

As another example of a specific application, vascular growth factors including VEGFs and angiogenin and others are essential for neovascularization. Local delivery of the factors, peptides, peptidomimetics, or suppressing their repressors is an important therapeutic modality; silencing the repressors and local delivery of the factors, peptides, macromolecules and small drugs stimulating angiogenesis with the Loder is therapeutic for peripheral, systemic and cardiac vascular disease.

The method of insertion, such as implantation, may optionally already be used for other types of tissue implantation and/or for insertions and/or for sampling tissues, optionally without modifications, or alternatively optionally only with non-major modifications in such methods. Such methods optionally include but are not limited to brachytherapy methods, biopsy, endoscopy with and/or without ultrasound, such as ERCP, stereotactic methods into the brain tissue, Laparoscopy, including implantation with a laparoscope into joints, abdominal organs, the bladder wall and body cavities.

Patient-Specific Screening Methods

A CRISPR-Cas system that targets nucleotide, e.g., trinucleotide repeats can be used to screen patients or patent samples for the presence of such repeats. The repeats can be the target of the RNA of the CRISPR-Cas system, and if there is binding thereto by the CRISPR-Cas system, that binding can be detected, to thereby indicate that such a repeat is present. Thus, a CRISPR-Cas system can be used to screen patients or patient samples for the presence of the repeat. The patient can then be administered suitable compound(s) to address the condition; or, can be administered a CRISPR-Cas system to bind to and cause insertion, deletion or mutation and alleviate the condition.

Nucleic Acids, Amino Acids and Proteins, Regulatory Sequences, Vectors, Etc

Nucleic acids, amino acids and proteins: The invention uses nucleic acids to bind target DNA sequences. This is advantageous as nucleic acids are much easier and cheaper to produce than proteins, and the specificity can be varied according to the length of the stretch where homology is sought. Complex 3-D positioning of multiple fingers, for example is not required. The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro- RNA (miRNA), ribozymes, cDNA, recombinant polynucleotides, branched polynucleotides, plasmids, vectors, isolated DNA of any sequence, isolated RNA of any sequence, nucleic acid probes, and primers. The term also encompasses nucleic-acid-like structures with synthetic backbones, see, e.g., Eckstein, 1991; Baserga et al., 1992; Milligan, 1993; WO 97/03211; WO 96/39154; Mata, 1997; Strauss-Soukup, 1997; and Samstag, 1996. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. As used herein the term "wild type" is a term of the art understood by skilled persons and means the typical form of an organism, strain, gene or characteristic as it occurs in nature as distinguished from mutant or variant forms. A "wild type" can be a base line. As used herein the term "variant" should be taken to mean the exhibition of qualities that have a pattern that deviates from what occurs in nature. The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature. "Complementarity" refers to the ability of a nucleic acid to form hydrogen bond(s) with another nucleic acid sequence by either traditional Watson-Crick base pairing or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions. As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part I, Second Chapter "Overview of principles of hybridization and the strategy of nucleic acid probe assay", Elsevier, N.Y. Where reference is made to a polynucleotide sequence, then complementary or partially complementary sequences are also envisaged. These are preferably capable of hybridising to the reference sequence under highly stringent conditions. Generally, in order to maximize the hybridization rate, relatively low-stringency hybridization conditions are selected: about 20 to 25° C. lower than the thermal melting point ($T_m$). The $T_m$ is the temperature at which 50% of specific target sequence hybridizes to a perfectly complementary probe in solution at a defined ionic strength and pH. Generally, in order to require at least about 85% nucleotide complementarity of hybridized sequences, highly stringent washing conditions are selected to be about 5 to 15° C. lower than the $T_m$. In order to require at least about 70% nucleotide complementarity of hybridized sequences, moderately-stringent washing conditions are selected to be about 15 to 30° C. lower than the $T_m$. Highly permissive (very low stringency) washing conditions may be as low as 50° C. below the $T_m$, allowing a high level of mis-matching between hybridized sequences. Those skilled in the art will recognize that other physical and chemical parameters in the hybridization and wash stages can also be altered to affect the outcome of a detectable hybridization signal from a specific level of homology between target and probe sequences. Preferred highly stringent conditions comprise incubation in 50% formamide, 5×SSC, and 1% SDS at 42° C., or incubation in 5×SSC and 1% SDS at 65° C., with wash in 0.2×SSC and 0.1% SDS at 65° C. "Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence. As used herein, the term "genomic locus" or "locus" (plural loci) is the specific location of a gene or DNA sequence on a chromosome. A "gene" refers to stretches of DNA or RNA that encode a polypeptide or an RNA chain that has functional role to play in an organism and hence is the molecular unit of heredity in living organisms. For the purpose of this invention it may be considered that genes include regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions. As used herein, "expression of a genomic locus" or "gene expression" is the process by which information from a gene is used in the synthesis of a functional gene product. The products of gene expression are often proteins, but in non-protein coding genes such as rRNA genes or tRNA genes, the product is functional RNA. The process of gene expression is used by all known life—eukaryotes (including multicellular organisms), prokaryotes (bacteria and archaea) and viruses to generate functional products to survive. As used herein "expression" of a gene or nucleic acid encompasses not only cellular gene expression, but also the transcription and translation of nucleic acid(s) in cloning systems and in any other context. As used herein, "expression" also refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell. The terms "polypeptide", "peptide" and "protein" are used interchangeably herein to refer to polymers of amino acids of any length. The polymer may be linear or branched, it may comprise modified amino acids, and it may be interrupted by non amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics. As used herein, the term "domain" or "protein domain" refers to a part of a protein sequence that may exist and function independently of the rest of the protein chain. As described in aspects of the invention, sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences. In some preferred embodiments, the capping region of the dTALEs described herein have sequences that are at least 95% identical or share identity to the capping region amino acid sequences provided herein. Sequence homologies may be generated by any of a number of computer programs known in the art, for example BLAST or FASTA, etc. A suitable computer program for carrying out such an alignment is the GCG Wisconsin Bestfit package (University of Wisconsin, U.S.A; Devereux et al., 1984, Nucleic Acids Research 12:387). Examples of other software than may perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program. Percentage (%) sequence homology may be calculated over contiguous sequences, i.e., one sequence is aligned with the other sequence and each amino acid or nucleotide in one sequence is directly compared with the corresponding amino acid or nucleotide in the other sequence, one residue at a time. This is called an "ungapped" alignment. Typically, such ungapped alignments are performed only over a relatively short number of residues. Although this is a very simple and consistent method, it fails to take into consideration that, for example, in an otherwise identical pair of sequences, one insertion or deletion may cause the following amino acid residues to be put out of alignment, thus potentially resulting in a large reduction in % homology when a global alignment is performed. Consequently, most sequence comparison methods are designed to produce optimal alignments that take into consideration possible insertions and deletions without unduly penalizing the overall homology or identity score. This is achieved by inserting "gaps" in the sequence alignment to try to maximize local homology or identity. However, these more complex methods assign "gap penalties" to each gap that occurs in the alignment so that, for the same number of identical amino acids, a sequence alignment with as few gaps as possible—reflecting higher relatedness between the two compared sequences—may achieve a higher score than one with many gaps. "Affinity gap costs" are typically used that charge a relatively high cost for the existence of a gap and a smaller penalty for each subsequent residue in the gap. This is the most commonly used gap scoring system. High gap penalties may, of course, produce optimized alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension. Calculation of maximum % homology therefore first requires the production of an optimal alignment, taking into consideration gap penalties. A suitable computer program for carrying out such an alignment is the GCG Wisconsin Bestfit package (Devereux et al., 1984 Nuc. Acids Research 12 p 387). Examples of other software than may perform sequence comparisons include, but are not limited to, the BLAST package (see Ausubel et al., 1999 Short Protocols in Molecular Biology, $4^{th}$ Ed.—Chapter 18), FASTA (Altschul et al., 1990 J. Mol. Biol. 403-410) and the GENEWORKS suite of comparison tools. Both BLAST and FASTA are available for offline and online searching (see Ausubel et al., 1999, Short Protocols in Molecular Biology, pages 7-58 to 7-60). However, for some applications, it is preferred to use the GCG Bestfit program. A new tool, called BLAST 2 Sequences is also available for comparing protein and nucleotide sequences (see FEMS Microbiol Lett. 1999 174 (2): 247-50; FEMS Microbiol Lett. 1999 177(1): 187-8 and the website of the National Center for Biotechnology information at the website of the National Institutes for Health). Although the final % homology may be measured in terms of identity, the alignment process itself is typically not based on an all-or-nothing pair comparison. Instead, a scaled similarity score matrix is generally used that assigns scores to each pair-wise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table, if supplied (see user manual for further details). For some applications, it is preferred to use the public default values for the GCG package, or in the case of other software, the default matrix, such as BLOSUM62. Alternatively, percentage homologies may be calculated using the multiple alignment feature in DNASIS™ (Hitachi Software), based on an algorithm, analogous to CLUSTAL (Higgins D G & Sharp P M (1988), Gene 73(1), 237-244). Once the software has produced an optimal alignment, it is possible to calculate % homology, preferably % sequence identity. The software typically does this as part of the sequence comparison and generates a numerical result. The sequences may also have deletions, insertions or substitutions of amino acid residues which produce a silent change and result in a functionally equivalent substance. Deliberate amino acid substitutions may be made on the basis of similarity in amino acid properties (such as polarity, charge, solubility, hydrophobicity, hydrophilicity, and/or the amphipathic nature of the residues) and it is therefore useful to group amino acids together in functional groups. Amino acids may be grouped together based on the properties of their side chains alone. However, it is more useful to include mutation data as well. The sets of amino acids thus derived are likely to be conserved for structural reasons. These sets may be described in the form of a Venn diagram (Livingstone C. D. and Barton G. J.

(1993) "Protein sequence alignments: a strategy for the hierarchical analysis of residue conservation" *Comput. Appl. Biosci.* 9: 745-756) (Taylor W. R. (1986) "The classification of amino acid conservation" *J. Theor. Biol.* 119; 205-218). Conservative substitutions may be made, for example according to the table below which describes a generally accepted Venn diagram grouping of amino acids.

| Set | | Sub-set | |
|---|---|---|---|
| Hydrophobic | F W Y H K M I L V A G C | Aromatic Aliphatic | F W Y H I L V |
| Polar | W Y H K R E D C S T N Q | Charged Positively charged Negatively charged | H K R E D H K R E D |
| Small | V C A G S P T N D | Tiny | A G S |

Embodiments of the invention include sequences (both polynucleotide or polypeptide) which may comprise homologous substitution (substitution and replacement are both used herein to mean the interchange of an existing amino acid residue or nucleotide, with an alternative residue or nucleotide) that may occur i.e., like-for-like substitution in the case of amino acids such as basic for basic, acidic for acidic, polar for polar, etc. Non-homologous substitution may also occur i.e., from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine. Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, which involves the presence of one or more amino acid residues in peptoid form, may be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., *PNAS* (1992) 89(20), 9367-9371 and Horwell D C, *Trends Biotechnol.* (1995) 13(4), 132-134.

For purpose of this invention, amplification means any method employing a primer and a polymerase capable of replicating a target sequence with reasonable fidelity. Amplification may be carried out by natural or recombinant DNA polymerases such as TaqGold™, T7 DNA polymerase, Klenow fragment of *E. coli* DNA polymerase, and reverse transcriptase. A preferred amplification method is PCR.

In certain aspects the invention involves vectors. A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are herein incorporated by reference in their entirety.

Aspects of the invention relate to bicistronic vectors for chimeric RNA and Cas9. Bicistronic expression vectors for chimeric RNA and Cas9 are preferred. In general and particularly in this embodiment Cas9 is preferably driven by the CBh promoter. The chimeric RNA may preferably be driven by a Pol III promoter, such as a U6 promoter. Ideally the two are combined. The chimeric guide RNA typically consists of a 20 bp guide sequence (Ns) and this may be joined to the tracr sequence (running from the first "U" of the lower strand to the end of the transcript). The tracr sequence may be truncated at various positions as indicated. The guide and tracr sequences are separated by the tracr-mate sequence, which may be GUUUUAGAGCUA (SEQ ID NO: 64). This may be followed by the loop sequence GAAA as shown. Both of these are preferred examples. Applicants have demonstrated Cas9-mediated indels at the human EMX1 and PVALB loci by SURVEYOR assays. ChiRNAs are indicated by their "+n" designation, and crRNA refers to a hybrid RNA where guide and tracr sequences are expressed as separate transcripts. Throughout this application, chimeric RNA may also be called single guide, or synthetic guide RNA (sgRNA). The loop is preferably GAAA, but it is not limited to this sequence or indeed to being only 4 bp in length. Indeed, preferred loop forming sequences for use in hairpin structures are four nucleotides in length, and most preferably have the sequence GAAA. However, longer or shorter loop sequences may be used, as may alternative sequences. The sequences preferably include a nucleotide triplet (for example, AAA), and an additional nucleotide (for example C or G). Examples of loop forming sequences include CAAA and AAAG. In practicing any of the methods disclosed herein, a suitable vector can be introduced to a cell or an embryo via one or more methods known in the art, including without limitation, microinjection, electroporation, sonoporation, biolistics, calcium phosphate-mediated transfection, cationic transfection, liposome transfection, dendrimer transfection, heat shock transfection, nucleofection transfection, magnetofection, lipofection, impalefection, optical transfection, proprietary agent-enhanced uptake of nucleic acids, and delivery via liposomes, immunoliposomes, virosomes, or artificial virions. In some methods, the vector is introduced into an embryo by microinjection. The vector or vectors may be microinjected into the nucleus or the cytoplasm of the embryo. In some methods, the vector or vectors may be introduced to a cell by nucleofection.

The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g. 1, 2, 3, 4, 5, or more pol III promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.). With regards to regulatory sequences, mention is made of U.S. patent application Ser. No. 10/491,026, the contents of which are incorporated by reference herein in their entirety. With regards to promoters, mention is made of PCT publication WO 2011/028929 and U.S. application Ser. No. 12/511,940, the contents of which are incorporated by reference herein in their entirety.

Vectors can be designed for expression of CRISPR transcripts (e.g. nucleic acid transcripts, proteins, or enzymes) in prokaryotic or eukaryotic cells. For example, CRISPR transcripts can be expressed in bacterial cells such as *Escherichia coli*, insect cells (using baculovirus expression vectors), yeast cells, or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Vectors may be introduced and propagated in a prokaryote or prokaryotic cell. In some embodiments, a prokaryote is used to amplify copies of a vector to be introduced into a eukaryotic cell or as an intermediate vector in the production of a vector to be introduced into a eukaryotic cell (e.g. amplifying a plasmid as part of a viral vector packaging system). In some embodiments, a prokaryote is used to amplify copies of a vector and express one or more nucleic acids, such as to provide a source of one or more proteins for delivery to a host cell or host organism. Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, such as to the amino terminus of the recombinant protein. Such fusion vectors may serve one or more purposes, such as: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Example fusion expression vectors include pGEX (Pharmacia Biotech Inc; Smith and Johnson, 1988. *Gene* 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein. Examples of suitable inducible non-fusion *E. coli* expression vectors include pTrc (Amrann et al., (1988) Gene 69:301-315) and pET lid (Studier et al., GENE EXPRESSION TECHNOLOGY: METHODS IN ENZYMOLOGY 185, Academic Press, San Diego, Calif. (1990) 60-89). In some embodiments, a vector is a yeast expression vector. Examples of vectors for expression in yeast *Saccharomyces cerevisae* include pYepSec1 (Baldari, et al., 1987. EMBO J. 6: 229-234), pMFa (Kuijan and Herskowitz, 1982. Cell 30: 933-943), pJRY88 (Schultz et al., 1987. Gene 54: 113-123), pYES2 (Invitrogen Corporation, San Diego, Calif.), and picZ (InVitrogen Corp, San Diego, Calif.). In some embodiments, a vector drives protein expression in insect cells using baculovirus expression vectors. Baculovirus vectors available for expression of proteins in cultured insect cells (e.g., SF9 cells) include the pAc series (Smith, et al., 1983. Mol. Cell. Biol. 3: 2156-2165) and the pVL series (Lucklow and Summers, 1989. Virology 170: 31-39).

In some embodiments, a vector is capable of driving expression of one or more sequences in mammalian cells using a mammalian expression vector. Examples of mammalian expression vectors include pCDM8 (Seed, 1987. Nature 329: 840) and pMT2PC (Kaufman, et al., 1987. EMBO J. 6: 187-195). When used in mammalian cells, the expression vector's control functions are typically provided by one or more regulatory elements. For example, commonly used promoters are derived from polyoma, adenovirus 2, cytomegalovirus, simian virus 40, and others disclosed herein and known in the art. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In some embodiments, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. *Genes Dev.* 1: 268-277), lymphoid-specific promoters (Calame and Eaton, 1988. *Adv. Immunol.* 43: 235-275), in particular promoters of T cell receptors (Winoto and Baltimore, 1989. *EMBO J.* 8: 729-733) and immunoglobulins (Baneiji, et al., 1983. *Cell* 33: 729-740; Queen and Baltimore, 1983. *Cell* 33: 741-748), neuron-specific promoters (e.g., the neurofilament promoter; Byrne and Ruddle, 1989. *Proc. Natl. Acad. Sci. USA* 86: 5473-5477), pancreas-specific promoters (Edlund, et al., 1985. *Science* 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. *Science* 249: 374-379) and the α-fetoprotein promoter (Campes and Tilghman, 1989. *Genes Dev.* 3: 537-546). With regards to these prokaryotic and eukaryotic vectors, mention is made of U.S. Pat. No. 6,750,059, the contents of which are incorporated by reference herein in their entirety. Other embodiments of the invention may relate to the use of viral vectors, with regards to which mention is made of U.S. patent application Ser. No. 13/092,085, the contents of which are incorporated by reference herein in their entirety. Tissue-specific regulatory elements are known in the art and in this regard, mention is made of U.S. Pat. No. 7,776,321, the contents of which are incorporated by reference herein in their entirety. In some embodiments, a regulatory element is operably linked to one or more elements of a CRISPR system so as to drive expression of the one or more elements of the CRISPR system. In general, CRISPRs (Clustered Regularly Interspaced Short Palindromic Repeats), also known as SPIDRs (SPacer Interspersed Direct Repeats), constitute a family of DNA loci that are usually specific to a particular bacterial species. The CRISPR locus comprises a distinct class of interspersed short sequence repeats (SSRs) that were recognized in *E. coli* (Ishino et al., J. Bacteriol., 169:5429-5433 [1987]; and Nakata et al., J. Bacteriol., 171:3553-3556 [1989]), and associated genes. Similar interspersed SSRs have been identified in *Haloferax mediterranei, Streptococcus pyogenes, Anabaena*, and *Mycobacterium tuberculosis* (See, Groenen et al., Mol. Microbiol., 10:1057-1065 [1993]; Hoe et al., Emerg. Infect. Dis., 5:254-263 [1999]; Masepohl et al., Biochim. Biophys. Acta 1307: 26-30 [1996]; and Mojica et al., Mol. Microbiol., 17:85-93 [1995]). The CRISPR loci typically differ from other SSRs by the structure of the repeats, which have been termed short regularly spaced repeats (SRSRs) (Janssen et al., OMICS J. Integ. Biol., 6:23-33 [2002]; and Mojica et al., Mol. Microbiol., 36:244-246 [2000]). In general, the repeats are short elements that occur in clusters that are regularly spaced by unique intervening sequences with a substantially constant length (Mojica et al., [2000], supra). Although the repeat sequences are highly conserved between strains, the number of interspersed repeats and the sequences of the spacer regions typically differ from strain to strain (van Embden et al., J. Bacteriol., 182:2393-2401 [2000]). CRISPR loci have been identified in more than 40 prokaryotes (See e.g., Jansen et al., Mol. Microbiol., 43:1565-1575 [2002]; and Mojica et al., [2005]) including, but not limited to Aeropyrum, *Pyrobaculum, Sulfolobus, Archaeoglobus, Halocarcula, Methanobacterium, Methanococcus, Methanosarcina, Methanopyrus, Pyrococcus, Picrophilus, Thermoplasma, Corynebacterium, Mycobacterium, Streptomyces, Aquifex, Porphyromonas, Chlorobium, Thermus, Bacillus, Listeria, Staphylococcus, Clostridium, Thermoanaerobacter, Mycoplasma, Fusobacterium, Azarcus, Chromobacterium, Neisseria, Nitrosomonas, Desulfovibrio, Geobacter, Myxococcus, Campylobacter, Wolinella, Acinetobacter, Erwinia, Escherichia, Legionella, Methylococcus, Pasteurella, Photobacterium, Salmonella, Xanthomonas, Yersinia, Treponema*, and *Thermotoga*.

In some embodiments, the CRISPR enzyme is part of a fusion protein comprising one or more heterologous protein domains (e.g. about or more than about 1, 2, 3, 4, 5, 6, 7, 8, 9, 10, or more domains in addition to the CRISPR enzyme). A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). A CRISPR enzyme may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4 DNA binding domain fusions, and herpes simplex virus (HSV) BP16 protein fusions. Additional domains that may form part of a fusion protein comprising a CRISPR enzyme are described in US20110059502, incorporated herein by reference. In some embodiments, a tagged CRISPR enzyme is used to identify the location of a target sequence.

In some embodiments, a CRISPR enzyme may form a component of an inducible system. The inducible nature of the system would allow for spatiotemporal control of gene editing or gene expression using a form of energy. The form of energy may include but is not limited to electromagnetic radiation, sound energy, chemical energy and thermal energy. Examples of inducible system include tetracycline inducible promoters (Tet-On or Tet-Off), small molecule two-hybrid transcription activations systems (FKBP, ABA, etc), or light inducible systems (Phytochrome, LOV domains, or cryptochrome). In one embodiment, the CRISPR enzyme may be a part of a Light Inducible Transcriptional Effector (LITE) to direct changes in transcriptional activity in a sequence-specific manner. The components of a light may include a CRISPR enzyme, a light-responsive cytochrome heterodimer (e.g. from *Arabidopsis thaliana*), and a transcriptional activation/repression domain. Further examples of inducible DNA binding proteins and methods for their use are provided in U.S. 61/736,465 and U.S. 61/721,283, which is hereby incorporated by reference in its entirety.

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

Modifying a Target

In one aspect, the invention provides for methods of modifying a target polynucleotide in a eukaryotic cell, which may be in vivo, ex vivo or in vitro. In some embodiments, the method comprises sampling a cell or population of cells from a human or non-human animal, and modifying the cell or cells. Culturing may occur at any stage ex vivo. The cell or cells may even be re-introduced into the non-human animal or plant. For re-introduced cells it is particularly preferred that the cells are stem cells.

In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized or hybridizable to a target sequence within said target polynucleotide, wherein said guide sequence is linked to a tracr mate sequence which in turn hybridizes to a tracr sequence.

In one aspect, the invention provides a method of modifying expression of a polynucleotide in a eukaryotic cell. In some embodiments, the method comprises allowing a CRISPR complex to bind to the polynucleotide such that said binding results in increased or decreased expression of said polynucleotide; wherein the CRISPR complex comprises a CRISPR enzyme complexed with a guide sequence hybridized or hybridizable to a target sequence within said polynucleotide, wherein said guide sequence is linked to a tracr mate sequence which in turn hybridizes to a tracr sequence. Similar considerations and conditions apply as above for methods of modifying a target polynucleotide. In fact, these sampling, culturing and re-introduction options apply across the aspects of the present invention.

Indeed, in any aspect of the invention, the CRISPR complex may comprise a CRISPR enzyme complexed with a guide sequence hybridized or hybridizable to a target sequence, wherein said guide sequence may be linked to a tracr mate sequence which in turn may hybridize to a tracr sequence. Similar considerations and conditions apply as above for methods of modifying a target polynucleotide.

Kits

In one aspect, the invention provides kits containing any one or more of the elements disclosed in the above methods and compositions. Elements may be provided individually or in combinations, and may be provided in any suitable container, such as a vial, a bottle, or a tube. In some embodiments, the kit includes instructions in one or more languages, for example in more than one language.

In some embodiments, a kit comprises one or more reagents for use in a process utilizing one or more of the elements described herein. Reagents may be provided in any suitable container. For example, a kit may provide one or more reaction or storage buffers. Reagents may be provided in a form that is usable in a particular assay, or in a form that requires addition of one or more other components before use (e.g. in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10. In some embodiments, the kit comprises one or more oligonucleotides corresponding to a guide sequence for insertion into a vector so as to operably link the guide sequence and a regulatory element. In some embodiments, the kit comprises a homologous recombination template polynucleotide. In some embodiments, the kit comprises one or more of the vectors and/or one or more of the polynucleotides described herein. The kit may advantageously allows to provide all elements of the systems of the invention.

CRISPR Enzyme mRNA and Guide RNA

CRISPR enzyme mRNA and guide RNA might also be delivered separately. CRISPR enzyme mRNA can be delivered prior to the guide RNA to give time for CRISPR enzyme to be expressed. CRISPR enzyme mRNA might be administered 1-12 hours (preferably around 2-6 hours) prior to the administration of guide RNA.

Alternatively, CRISPR enzyme mRNA and guide RNA can be administered together. Advantageously, a second booster dose of guide RNA can be administered 1-12 hours (preferably around 2-6 hours) after the initial administration of CRISPR enzyme mRNA+guide RNA.

Additional administrations of CRISPR enzyme mRNA and/or guide RNA might be useful to achieve the most efficient levels of genome modification.

For minimization of toxicity and off-target effect, it will be important to control the concentration of CRISPR enzyme mRNA and guide RNA delivered. Optimal concentrations of CRISPR enzyme mRNA and guide RNA can be determined by testing different concentrations in a cellular or animal model and using deep sequencing the analyze the extent of modification at potential off-target genomic loci. For example, for the guide sequence targeting 5'-GAGTCCGAGCAGAAGAAGAA-3' (SEQ ID NO: 45) in the EMX1 gene of the human genome, deep sequencing can be used to assess the level of modification at the following two off-target loci, 1: 5'-GAGTCCTAGCAG- GAGAAGAA-3' (SEQ ID NO: 46) and 2: 5'-GAGTCTAAGCAGAAGAAGAA-3' (SEQ ID NO: 47). The concentration that gives the highest level of on-target modification while minimizing the level of off-target modification should be chosen for in vivo delivery.

Uses of the Crystals, Crystal Structure and Atomic Structure Co-Ordinates:

The crystals of SaCas9, and particularly the atomic structure co-ordinates obtained therefrom, have a wide variety of uses. The crystals and structure co-ordinates are particularly useful for identifying compounds (nucleic acid molecules) that bind to CRISPR-Cas9, and CRISPR-Cas9s that can bind to particular compounds (nucleic acid molecules). Thus, the structure co-ordinates described herein can be used as phasing models in determining the crystal structures of additional synthetic or mutated CRISPR-Cas9s, Cas9s, nickases, binding domains and may be used as the basis of the rational design of optimized CRISPR-Cas systems. The provision of the crystal structure of CRISPR-SaCas9 complexed with a nucleic acid molecule as in the herein-cited materials provide the skilled artisan with a detailed insight into the mechanisms of action of CRISPR-SaCas9. This insight provides a means to design modified CRISPR-SaCas9s, such as by attaching thereto a functional group, such as a repressor or activator. In a particular embodiment of the invention, modifications to permit such attachments may be made to the solvent-exposed stem loop 2 of SaCas9. Attachment can be via a linker, e.g., a flexible glycine-serine (GlyGlyGlySer) (SEQ ID NO: 1) or (GGGS)$_3$ (SEQ ID NO: 2) or a rigid alpha-helical linker such as (Ala(GluAlaAlaAlaLys)Ala) (SEQ ID NO: 3). In addition to the flexible loop there is also a nuclease or H3 region, an H2 region and a helical region. By "helix" or "helical", is meant a helix as known in the art, including, but not limited to an alpha-helix. Additionally, the term helix or helical may also be used to indicate a C-terminal helical element with an N-terminal turn.

The provision of the crystal structure of CRISPR-Cas9 complexed with a nucleic acid molecule allows a novel approach for drug or compound discovery, identification, and design for compounds that can bind to CRISPR-SaCas9 and thus the invention provides tools useful in diagnosis, treatment, or prevention of conditions or diseases of multicellular organisms, e.g., algae, plants, invertebrates, fish, amphibians, reptiles, avians, mammals; for example domesticated plants, animals (e.g., production animals such as swine, bovine, chicken; companion animal such as felines, canines, rodents (rabbit, gerbil, hamster); laboratory animals such as mouse, rat), and humans. Accordingly, the invention provides a computer-based method of rational design of one or more orthologous CRISPR-Cas9 complexes. This rational design can comprise: providing the structure of the CRISPR-Cas9 complex as defined by some or all (e.g., at least 2 or more, e.g., at least 5, advantageously at least 10, more advantageously at least 50 and even more advantageously at least 100 atoms of the structure) co-ordinates in the herein-cited materials; providing a structure of a desired nucleic acid molecule as to which a CRISPR-Cas9 complex is desired; and fitting the structure of the CRISPR-Cas9 complex as defined by some or all co-ordinates in the herein-cited materials to the desired nucleic acid molecule, including in said fitting obtaining putative modification(s) of the CRISPR-Cas9 complex as defined by some or all co-ordinates in the herein-cited materials for said desired nucleic acid molecule to bind for CRISPR-Cas9 complex (es) involving the desired nucleic acid molecule. The method or fitting of the method may use the co-ordinates of atoms of interest of the CRISPR-Cas9 complex as defined by some or all co-ordinates in the herein-cited materials which are in the vicinity of the active site or binding region (e.g., at least 2 or more, e.g., at least 5, advantageously at least 10, more advantageously at least 50 and even more advantageously at least 100 atoms of the structure) in order to model the vicinity of the active site or binding region. These co-ordinates may be used to define a space which is then screened "in silico" against a desired or candidate nucleic acid molecule. Thus, the invention provides a computer-based method of rational design of CRISPR-Cas9 complexes. This method may include: providing the co-ordinates of at least two atoms of the herein-cited materials e ("selected co-ordinates"); providing the structure of a candidate or desired nucleic acid molecule; and fitting the structure of the candidate to the selected co-ordinates. In this fashion, the skilled person may also fit a functional group and a candidate or desired nucleic acid molecule. For example, providing the structure of the CRISPR-Cas9 complex as defined by some or all (e.g., at least 2 or more, e.g., at least 5, advantageously at least 10, more advantageously at least 50 and even more advantageously at least 100 atoms of the structure) co-ordinates in the herein-cited materials; providing a structure of a desired nucleic acid molecule as to which a CRISPR-Cas9 complex is desired; fitting the structure of the CRISPR-Cas9 complex as defined by some or all co-ordinates in the herein-cited materials to the desired nucleic acid molecule, including in said fitting obtaining putative modification(s) of the CRISPR-Cas9 complex as defined by some or all co-ordinates in the herein-cited materials for said desired nucleic acid molecule to bind for CRISPR-Cas9 complex(es) involving the desired nucleic acid molecule; selecting putative fit CRISPR-Cas9-desired nucleic acid molecule complex(es), fitting such putative fit CRISPR-Cas9-desired nucleic acid molecule complex(es) to the functional group (e.g., activator, repressor), e.g., as to locations for situating the functional group (e.g., positions within the flexible loop) and/or putative modifications of the putative fit CRISPR-Cas9-desired nucleic acid molecule complex(es) for creating locations for situating the functional group. As alluded to, the invention can be practiced using co-ordinates in the herein-cited materials which are in the vicinity of the active site or binding region; and therefore, the methods of the invention can employ a sub-domain of interest of the CRISPR-SaCas9 complex. Methods of the invention can be practiced using coordinates of a domain or sub-domain. The methods can optionally include synthesizing the candidate or desired nucleic acid molecule and/or the CRISPR-Cas9 systems from the "in silico" output and testing binding and/or activity of "wet" or actual a functional group linked to a "wet" or actual CRISPR-Cas9 system bound to a "wet" or actual candidate or desired nucleic acid molecule. The methods can include synthesizing the CRISPR-Cas9 systems (including a functional group) from the "in silico" output and testing binding and/or activity of "wet" or actual a functional group linked to a "wet" or actual CRISPR-Cas9 system bound to an in vivo "wet" or actual candidate or desired nucleic acid molecule, e.g., contacting "wet" or actual CRISPR-Cas9 system including a functional group from the "in silico" output with a cell containing the desired or candidate nucleic acid molecule. These methods can include observing the cell or an organism containing the cell for a desired reaction, e.g., reduction of symptoms or condition or disease. The step of providing the structure of a candidate nucleic acid molecule may involve selecting the compound by computationally screening a database containing nucleic acid molecule data, e.g., such data as to conditions or diseases. A 3-D descriptor for binding of the candidate nucleic acid molecule may be derived from geometric and functional constraints derived from the architecture and chemical nature of the CRISPR-Cas9 complex or domains or regions thereof from the crystal structure of herein-cited materials. In effect, the descriptor can be a type of virtual modification(s) of the CRISPR-SaCas9 complex crystal structure herein for binding the CRISPR-SaCas9 system to the candidate or desired nucleic acid molecule. The descriptor may then be used to interrogate the nucleic acid molecule database to ascertain those nucleic acid molecules of the database that have putatively good binding to the descriptor. The herein "wet" steps can then be performed using the descriptor and nucleic acid molecules that have putatively good binding.

"Fitting" can mean determining, by automatic or semi-automatic means, interactions between at least one atom of the candidate and at least one atom of the CRISPR-Cas9 complex and calculating the extent to which such an interaction is stable. Interactions can include attraction, repulsion, brought about by charge, steric considerations, and the like. A "sub-domain" can mean at least one, e.g., one, two, three, or four, complete element(s) of secondary structure. Particular regions or domains of the CRISPR-Cas9 include those identified in the herein-cited materials.

In any event, the determination of the three-dimensional structure of CRISPR-Cas 9 (*S. aureus* Cas9) complex provides a basis for the rational design of new and specific, optimized SaCas enzymes and guide scaffolds, as well as the design of CRISPR-SaCas9 systems with new functionality, such as by way of modification of the CRISPR-SaCas9 system to bind to various nucleic acid molecules or other modifying components, by way of modification of the CRISPR-Cas9 system to have linked thereto to any one or more of various functional groups that may interact with each other, with the CRISPR-SaCas9 (e.g., an inducible system that provides for self-activation and/or self-termination of function), with the nucleic acid molecule nucleic acid molecules (e.g., the functional group may be a regulatory or functional domain which may be selected from the group consisting of a transcriptional repressor, a transcriptional activator, a nuclease domain, a DNA methyl transferase, a protein acetyltransferase, a protein deacetylase, a protein methyltransferase, a protein deaminase, a protein kinase, and a protein phosphatase; and, in some aspects, the functional domain is an epigenetic regulator; see, e.g., Zhang et al., U.S. Pat. No. 8,507,272, and it is again mentioned that it and all documents cited herein and all appln cited documents are hereby incorporated herein by reference), by way of modification of Cas9, by way of novel nickases). Indeed, the herewith CRISPR-Cas9 (*S. aureus* Cas9) crystal structure has a multitude of uses. For example, from knowing the three-dimensional structure of CRISPR-Cas9 (*S. aureus* Cas9) crystal structure, computer modelling programs may be used to design or identify different molecules expected to interact with possible or confirmed sites such as binding sites or other structural or functional features of the CRISPR-Cas9 system (e.g., *S. aureus* Cas9). Compound that potentially bind ("binder") can be examined through the use of computer modeling using a docking program. Docking programs are known; for example GRAM, DOCK or AUTODOCK (see Walters et al. Drug Discovery Today, vol. 3, no. 4 (1998), 160-178, and Dunbrack et al. Folding and Design 2 (1997), 27-42). This procedure can include computer fitting of potential binders ascertain how well the shape and the chemical structure of the potential binder will bind to a CRISPR-Cas9 system (e.g., *S. aureus* Cas9).

Computer-assisted, manual examination of the active site or binding site of a CRISPR-Cas9 system (e.g., *S. aureus* Cas9) may be performed. Programs such as GRID (P. Goodford, J. Med. Chem, 1985, 28, 849-57)—a program that determines probable interaction sites between molecules with various functional groups—may also be used to analyze the active site or binding site to predict partial structures of binding compounds. Computer programs can be employed to estimate the attraction, repulsion or steric hindrance of the two binding partners, e.g., CRISPR-Cas9 system (e.g., *S. aureus* Cas9) and a candidate nucleic acid molecule or a nucleic acid molecule and a candidate CRISPR-Cas9 system (e.g., *S. aureus* Cas9); and the CRISPR-Cas9 crystal structure (*S. aureus* Cas9) herewith enables such methods. Generally, the tighter the fit, the fewer the steric hindrances, and the greater the attractive forces, the more potent the potential binder, since these properties are consistent with a tighter binding constant. Furthermore, the more specificity in the design of a candidate CRISPR-Cas9 system (e.g., *S. aureus* Cas9), the more likely it is that it will not interact with off-target molecules as well. Also, "wet" methods are enabled by the instant invention.

The invention further involves, in place of or in addition to "in silico" methods, other "wet" methods, including high throughput screening of a binder (e.g., target nucleic acid molecule) and a candidate CRISPR-Cas9 system (e.g., *S. aureus* Cas9), or a candidate binder (e.g., target nucleic acid molecule) and a CRISPR-Cas9 system (e.g., *S. aureus* Cas9) or a candidate binder (e.g., target nucleic acid molecule) and a candidate CRISPR-Cas9 system (e.g., an orthologous CRISPR-Cas9 or the foregoing CRISPR-SaCas9 system(s) with or without one or more functional group(s)), to select compounds with binding activity. Those pairs of binder and CRISPR-Cas9 system which show binding activity may be selected and further crystallized with the CRISPR-Cas9 crystal having a structure herein, e.g., by co-crystallization or by soaking, for X-ray analysis. The resulting X-ray structure may be compared with that of the herein-cited materials for a variety of purposes, e.g., for areas of overlap. Having designed, identified, or selected possible pairs of binder and CRISPR-Cas9 system by determining those which have favorable fitting properties, e.g., predicted strong attraction based on the pairs of binder and CRISPR-Cas9 crystal structure data herein, these possible pairs can then be screened by "wet" methods for activity.

Consequently, in an aspect the invention can involve: obtaining or synthesizing the possible pairs; and contacting a binder (e.g., target nucleic acid molecule) and a candidate CRISPR-Cas9 system (e.g., *S. aureus* Cas9), or a candidate binder (e.g., target nucleic acid molecule) and a CRISPR-Cas9 system (e.g., *S. aureus* s Cas9), or a candidate binder (e.g., target nucleic acid molecule) and a candidate CRISPR-Cas9 system (e.g., an orthologous CRISPR-Cas9 or the foregoing CRISPR-SaCas9 system(s) with or without one or more functional group(s)) to determine ability to bind. In the latter step, the contacting is advantageously under conditions to determine function. Instead of, or in addition to, performing such an assay, the invention may comprise: obtaining or synthesizing complex(es) from said contacting and analyzing the complex(es), e.g., by X-ray diffraction or NMR or other means, to determine the ability to bind or interact. Detailed structural information can then be obtained about the binding, and in light of this information, adjustments can be made to the structure or functionality of a candidate CRISPR-Cas9 system or components thereof. These steps may be repeated and re-repeated as necessary. Alternatively or additionally, potential CRISPR-Cas9 systems from or in the foregoing methods can be with nucleic acid molecules in vivo, including without limitation by way of administration to an organism (including non-human animal and human) to ascertain or confirm function, including whether a desired outcome (e.g., reduction of symptoms, treatment) results therefrom.

The invention further involves a method of determining three dimensional structures of orthologous or variant CRISPR-cas systems or complex(es) of unknown structure by using the structural co-ordinates of the herein-cited materials. For example, if X-ray crystallographic or NMR spectroscopic data are provided for a CRISPR-cas system or complex of unknown crystal structure, the structure of a CRISPR-SaCas9 complex as defined in the herein-cited materials as well as the structural comparative information obtained against *S. pyogenes* Cas9 crystallographic information may be used to interpret that data to provide a likely structure for the unknown system or complex by such techniques as by phase modeling in the case of X-ray crystallography. Thus, an inventive method can comprise: aligning a representation of the CRISPR-cas system or complex having an unknown crystal structure with an analogous representation of the CRISPR-cas(9) system and complex of the crystal structure herein to match homologous or analogous regions (e.g., homologous or analogous sequences); modeling the structure of the matched homologous or analogous regions (e.g., sequences) of the CRISPR-cas system or complex of unknown crystal structure based on the structure as defined in the herein-cited materials of the corresponding regions (e.g., sequences); and, determining a conformation (e.g. taking into consideration favorable interactions should be formed so that a low energy conformation is formed) for the unknown crystal structure which substantially preserves the structure of said matched homologous regions.

"Homologous regions" describes, for example as to amino acids, amino acid residues in two sequences that are identical or have similar, e.g., aliphatic, aromatic, polar, negatively charged, or positively charged, side-chain chemical groups. Homologous regions as to nucleic acid molecules can include at least 85% or 86% or 87% or 88% or 89% or 90% or 91% or 92% or 93% or 94% or 95% or 96% or 97% or 98% or 99% homology or identity. Identical and similar regions are sometimes described as being respectively "invariant" and "conserved" by those skilled in the art. Advantageously, the first and third steps are performed by computer modeling. Homology modeling is a technique that is well known to those skilled in the art (see, e.g., Greer, Science vol. 228 (1985) 1055, and Blundell et al. Eur J Biochem vol 172 (1988), 513). The computer representation of the conserved regions of the CRISPR-Cas9 crystal structure herein and those of a CRISPR-cas system of unknown crystal structure aid in the prediction and determination of the crystal structure of the CRISPR-cas system of unknown crystal structure. Further still, the aspects of the invention which employ the CRISPR-Cas9 crystal structure in silico may be equally applied to new CRISPR-cas crystal structures divined by using the herein CRISPR-Cas9 crystal structure. In this fashion, a library of CRISPR-cas crystal structures can be obtained. Rational CRISPR-cas system design is thus provided by the instant invention. For instance, having determined a conformation or crystal structure of a CRISPR-cas system or complex, by the methods described herein, such a conformation may be used in a computer-based methods herein for determining the conformation or crystal structure of other CRISPR-cas systems or complexes whose crystal structures are yet unknown. Data from all of these crystal structures can be in a database, and the herein methods can be more robust by having herein comparisons involving the herein crystal structure or portions thereof be with respect to one or more crystal structures in the library. The invention further provides systems, such as computer systems, intended to generate structures and/or perform rational design of a CRISPR-cas system or complex. The system can contain: atomic co-ordinate data according to the herein-cited materials or be derived therefrom e.g., by modeling, said data defining the three-dimensional structure of a CRISPR-cas system or complex or at least one domain or sub-domain thereof, or structure factor data therefor, said structure factor data being derivable from the atomic co-ordinate data of the herein-cited materials.

The invention also involves computer readable media with: atomic co-ordinate data according to the herein-cited materials or derived therefrom e.g., by homology modeling, said data defining the three-dimensional structure of a CRISPR-cas system or complex or at least one domain or sub-domain thereof, or structure factor data therefor, said structure factor data being derivable from the atomic co-ordinate data of the herein-cited materials. "Computer readable media" refers to any media which can be read and accessed directly by a computer, and includes, but is not limited to: magnetic storage media; optical storage media; electrical storage media; cloud storage and hybrids of these categories. By providing such computer readable media, the atomic co-ordinate data can be routinely accessed for modeling or other "in silico" methods. The invention further comprehends methods of doing business by providing access to such computer readable media, for instance on a subscription basis, via the Internet or a global communication/computer network; or, the computer system can be available to a user, on a subscription basis. A "computer system" refers to the hardware means, software means and data storage means used to analyze the atomic co-ordinate data of the present invention. The minimum hardware means of computer-based systems of the invention may comprise a central processing unit (CPU), input means, output means, and data storage means. Desirably, a display or monitor is provided to visualize structure data. The invention further comprehends methods of transmitting information obtained in any method or step thereof described herein or any information described herein, e.g., via telecommunications, telephone, mass communications, mass media, presentations, internet, email, etc. The crystal structures of the invention can be analyzed to generate Fourier electron density map(s) of CRISPR-cas systems or complexes; advantageously, the three-dimensional structure being as defined by the atomic co-ordinate data according to the herein-cited materials. Fourier electron density maps can be calculated based on X-ray diffraction patterns. These maps can then be used to determine aspects of binding or other interactions. Electron density maps can be calculated using known programs such as those from the CCP4 computer package (Collaborative Computing Project, No. 4. The CCP4 Suite: Programs for Protein Crystallography, Acta Crystallographica, D50, 1994, 760-763). For map visualization and model building programs such as "QUANTA" (1994, San Diego, Calif.: Molecular Simulations, Jones et al., Acta Crystallography A47 (1991), 110-119) can be used.

The Crystal Structure Coordinates (see herein-cited materials) gives atomic co-ordinate data for a CRISPR-Cas9 (*S. aureus*), and lists each atom by a unique number; the chemical element and its position for each amino acid residue (as determined by electron density maps and antibody sequence comparisons), the amino acid residue in which the element is located, the chain identifier, the number of the residue, co-ordinates (e.g., X, Y, Z) which define with respect to the crystallographic axes the atomic position (in angstroms) of the respective atom, the occupancy of the atom in the respective position, "B", isotropic displacement parameter (in angstroms$^2$) which accounts for movement of the atom around its atomic center, and atomic number. See also the herein-cited materials.

A further aspect of the invention provides for chimeric Cas9 proteins and methods of generating chimeric Cas9 proteins. Chimeric Cas9 proteins are proteins that comprise fragments that originate from different Cas9 orthologs. For instance, a domain of a first Cas9 ortholog may be replaced with the equivalent domain of a second Cas9 ortholog to generate a resultant Cas9 chimeric protein. These chimeric Cas9 proteins may have a higher specificity or a higher efficiency than the original specificity or efficiency of either of the individual Cas9 enzymes from which the chimeric protein was generated, or may have other advantages, such as reduced size. These chimeric proteins may also comprise one or more mutations or may be linked to one or more functional domains. Therefore, aspects of the invention relate to a chimeric Cas enzyme wherein the enzyme comprises one or more domains or fragments of domains from a first Cas ortholog and one or more domains or fragments of domains from a second Cas ortholog. In a further embodiment the first or second Cas ortholog is selected from a genus belonging to the group consisting of *Corynebacter, Sutterella, Legionella, Treponema, Filifactor, Eubacterium, Streptococcus, Lactobacillus, Mycoplasma, Bacteroides, Flaviivola, Flavobacterium, Sphaerochaeta, Azospirillum, Gluconacetobacter, Neisseria, Roseburia, Parvibaculum, Staphylococcus, Nitratifractor, Mycoplasma* and *Campylobacter.*

Identification of domains suitable for adding, interchanging or modifying in a chimeric, truncated or otherwise modified protein can be achieved by sequence comparison and/or comparison of crystal structure data, for example as provided herein. Interaction between domains should, where possible, be conserved in order to promote protein functionality. Methods for predicting protein domain interaction based on the structural data as provided herein are available to those skilled in the art. Also, the structural information provided guides development of Cas9 chimeras having domains or subdomains from one or more sources. For a review, see Petery and Honig, (2014) Annu Rev Biophys. 43; 193-210.

The development of reliable computational approaches to identify protein-protein interactions is based on criteria such as sequence orthology (Matthews L R, Vaglio P, Reboul J, Ge H, Davis B P, Garrels J, et al. Identification of potential interaction networks using sequence-based searches for conserved protein-protein interactions or "interologs". Genome Res. 2001; 11: 2120-2126. PMID: 11731503), similarity in evolutionary history (de Juan D, Pazos F, Valencia A. Emerging methods in protein co-evolution. Nat Rev Genet. 2013; 14: 249-261. doi: 10.1038/nrg3414 PMID: 23458856), genomic context (Dandekar T, Snel B, Huynen M, Bork P. Conservation of gene order: a fingerprint of proteins that physically interact. Trends Biochem Sci. 1998; 23: 324-328. PMID: 9787636), and literature curation (Reguly T, Breitkreutz A, Boucher L, Breitkreutz B J, Hon G C, Myers C L, et al. Comprehensive curation and analysis of global interaction networks in *Saccharomyces cerevisiae*. J Biol. 2006; 5: 11. PMID: 16762047). Predictions based on detailed structural modeling of PPIs have also been developed (Mosca R, Ceol A, Aloy P. Interactome3D: adding structural details to protein networks. Nat Methods. 2013; 10: 47-53. doi: 10.1038/nmeth.2289 PMID: 23399932) and recent approaches that combine low resolution structural modeling with non-structural information have begun to expand the applicability of structure to a genome-wide scale. Interactions determined by HT experiments and computationally have been deposited in databases such as STRING (Franceschini A, Szklarczyk D, Frankild S, Kuhn M, Simonovic M, Roth A, et al. STRING v9.1: protein-protein interaction networks, with increased coverage and integration. Nucleic Acids Res. 2013; 41: D808-D815. doi: 10.1093/nar/gks1094 PMID: 23203871) and PrePPI (Zhang et al., (2012) Nature 490:556-60).

A Bayesian network can be used to classify objects into binary categories (e.g., two proteins do or do not share a GO annotation, they do or do not physically interact, etc.). Membership in a category is quantified using a "likelihood ratio" (LR), which reflects the increase/decrease in the probability that an object belongs to a category after learning that it has a particular characteristic, or "clue"

A distinct advantage of Bayesian approaches is that even if a particular clue is not a strong indicator of membership in a category on its own (e.g., remote structural similarity), different clues can be combined to yield a reliable classifier (in some implementations this can be accomplished in practice by simply multiplying the LRs generated by different clues).

For example, interactions can be predicted according to the method of Zhang et al., supra, in which a combination of structural and non-structural clues are integrated using a Bayesian approach and used to create an algorithm (PrePPI) and thus construct a database which can be used to predict interactions between proteins.

A development of this technique employs databases such as the eukaryotic linear motif resource (ELM; Dinkel H, Van Roey K, Michael S, Davey N E, Weatheritt R J, Born D, et al. The eukaryotic linear motif resource ELM: 10 years and counting. Nucleic Acids Res. 2014; 42: D259-D266. doi: 10.1093/nar/gkt1047 PMID: 24214962), which provide consensus sequence patterns for peptide motifs binding to many different PRD families. Methods such as iELM have been developed to make new predictions based on such information (Weatheritt R J, Luck K, Petsalaki E, Davey N E, Gibson T J. The identification of short linear motif-mediated interfaces within the human interactome. Bioinformatics. 2012; 28: 976-982. doi: 10.1093/bioinformatics/bts072 PMID: 22328783).

Chen et al., PLOS Computational Biology (2015) DOI: 10.1371, provide a computational framework to predict interactions mediated by domain-motif interfaces. The method uses a Bayesian approach to integrate knowledge from the ELM database, domain-peptide structures from the PDB, and non-structural information.

The method is incorporated into PrePPI and can be employed to predict protein-protein interactions very broadly at the domain/motif level.

Unlike certain protein families, Cas9 orthologs may share relatively little sequence homology, yet maintain similarity of structure. Structural similarity can be studied and exploited, for example using the methods described above, to provide information on domain-domain and domain-motif interactions involving saCas9 and saCas9 orthologs.

Structural similarity can also be used as an indicator of function, which can be assessed using a "structural BLAST" approach as described by Dey et al., (2013) Protein Science 22:359-366, based on the PrePPI algorithm. Protein domains from Cas9 orthologs can be compared using the BLAST approach to identify structural neighbors in any given homolog. These can then be visualized and filtered using a number of different properties (e.g., interaction with guide RNA or PAM sequence), to identify domains of similar function. Properties of one Cas9 homolog that determine function (catalytic residues, biophysical properties, conservation) can be displayed and compared to the same properties in other homologs to determine if they are consistent with the known function of the selected domain.

Knowledge of the structure/function relationships of Cas9 orthologs and Cas9 ortholog domains permits synthetic Cas9 enzymes to be constructed, in which one or more domains is added, removed or mutated.

Removal of domains is advantageous because the overall size of the Cas9 enzyme can thus be reduced. Size is a limitation in packaging and delivery of CRISPR/Cas9 systems using a variety of vectors, including viral vectors as described above.

Figures 7A, 7B, 7C, 7D, 7E:
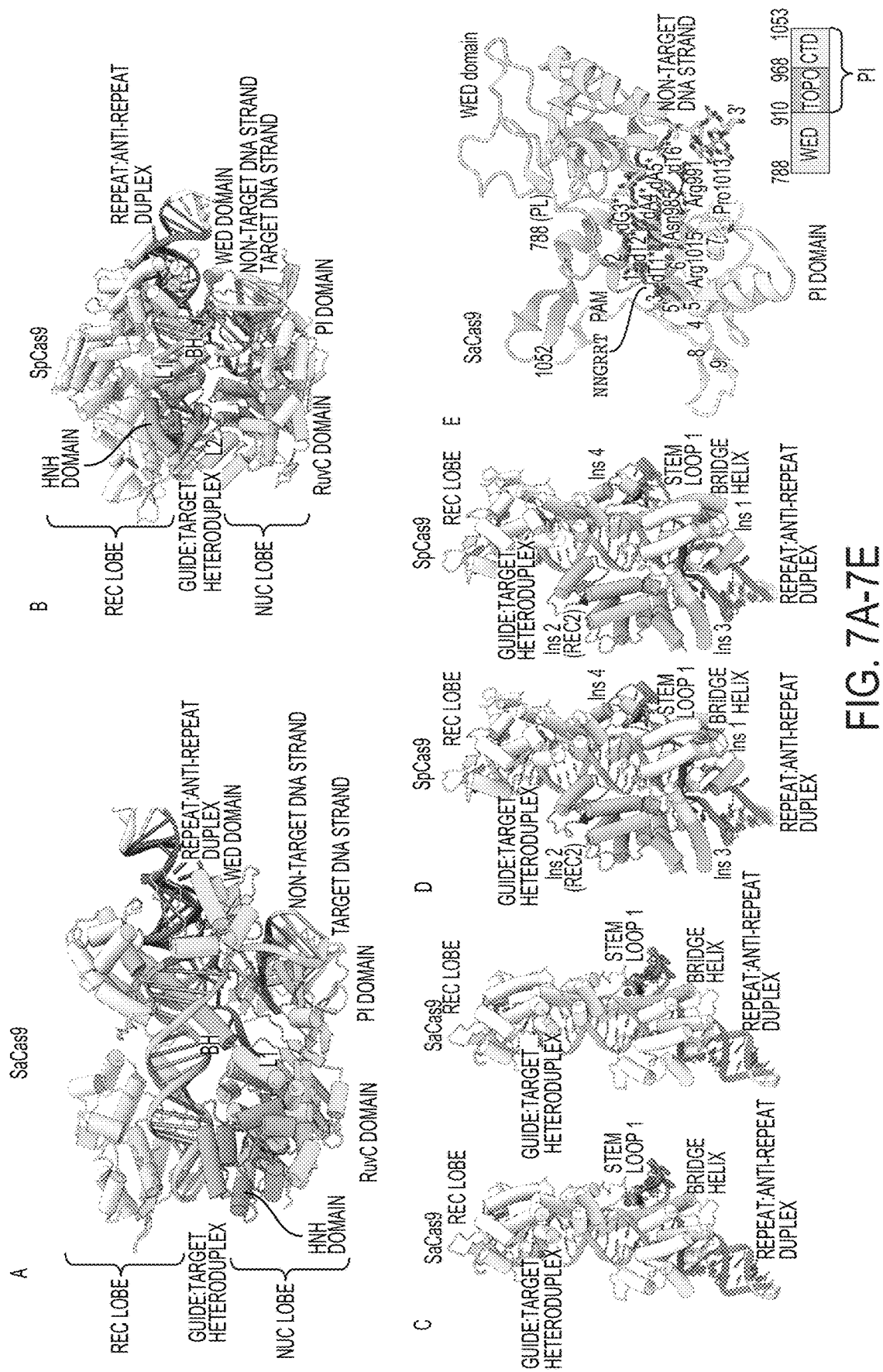

Therefore, in some embodiments, the invention provides a Cas9 enzyme in which one or more domains are truncated or deleted. The crystal structure of saCas9 reveals that the REC2 domain of SpCas9 is lacking (FIG. 7B). It is known that spCas9 is functional without the REC2 domain, and the SaCas9 data confirms the possibility for rational design of engineered Cas9 enzymes to be produced which are reduced in size compared to wild-type enzymes, by removal of domains, or parts thereof, which are identified as functionally redundant.

Similarly, it is apparent from the data presented herein that the PAM specificity of Cas9 enzymes is dictated by the structurally diverse PI domains. Mutation, truncation or replacement of the PI domain in a Cas9 enzyme can be employed to alter the PAM specificity thereof, either to a known PAM specificity from another Cas9 enzyme, or to a novel specificity which can be provided by rational design and selection of mutated Cas9 PI domains. For example, PI domains can be selected for any desired PAM by selecting a library of dCas9 proteins comprising targeted variation in the PI domain which have been fused to a transcriptional activator by their ability to promote or repress transcription from a promoter or other regulatory element which is operationally coupled to an enhancer which comprises or is adjacent to the desired PAM sequence. This PAM screening could also occur in a bacterial system on the basis of antibiotic resistance. In a recent report, PAM specificity of SaCas9 was investigated by mutagenizing the PAM interacting domain of wild type SaCas9 and selecting for activity against a PAM target site on a plasmid encoding an inducible toxic gene (Kleinstiver et al., 2015, Nature 2015, doi: 10.1038/nature14592 [Epub ahead of print]). For example, the authors identified SaCas9 variants with amino acid substitutions at D1135, R1335 and T1337 with activity against an NGA PAM, that could discriminate against an NGG PAM, and also defined global PAM specificity profiles of the variants. The authors also identified an SaCas9 variant with reduced activity against off-target sites with non-canonical NAG or NGA PAMs.

In particular embodiments of the invention, the conformational variations in the crystal structures of the CRISPR-SaCas9 system or of components of the CRISPR-SaCas9 provide important and critical information about the flexibility or movement of protein structure regions relative to nucleotide (RNA or DNA) structure regions that may be important for CRISPR-SaCas system function. The SaCas9 crystal coordinates and information disclosed provide an understanding of mechanisms governing CRISPR-SaCas9 function and guide alteration of CRISPR-SaCas9 structural components. Further, the SaCas9 structural information provides guidance for altering SaCas9 orthologs, as well as for incorporating aspects of such orthologs into modified SaCas9 proteins. In some embodiments, guidance is based on the structure of CRISPR-SaCas9 as disclosed herein. In some embodiments, guidance is obtained by comparing aspects of the structures of SaCas9 with those of SpCas9. In some embodiments, guidance is obtained by comparing aspects of the structure of SaCas9 with those of an ortholog, such as, without limitation, AnCas9. In some embodiments, guidance is obtained by examining sequence alignments between or among Cas9 orthologs in view of structural information provided herein. Exemplary aligned sequences can be found, e.g., in Chylinski et al., 2014, Nucleic Acids Research 42:6091, supplemental FIG. 1. Thus, the structural information provided for Cas9 (e.g. *S. aureus* Cas9) as the CRISPR enzyme in the present application may be used to further engineer and optimize the CRISPR-Cas system and this may be extrapolated to interrogate structure-function relationships in other orthologous or variant CRISPR enzyme systems as well.

An aspect of the invention is the realization that among Cas9 orthologs there is a high degree of conservation of domain structure as well as flexibility of domain positioning. For example, sequence alignment provides evidence of conservation of amino acids on the basis of binding interactions or enzymatic function. Even where there is a question of structural similarity, perhaps due to dissimilar environments of such conserved amino acids in view of little or no homology elsewhere, it is understood from the structural information provided for SaCas9 herein that there is extensive preservation of, e.g., alpha helical domain structure between SaCas9 and SpCas9, and among Cas9 proteins in general. Further, there is flexibility in the positioning of such domains, evidenced, for example, by domain location in the crystal (compare SaCas9 and SpCas9 in FIG. 7), conformational changes triggered by non-target DNA binding to RuvC, and conserved guide-RNA-induced conformational rearrangement.

Thus, modifications made to one Cas9 enzyme can be expected to apply to other Cas9 enzymes as well. Furthermore, complementary portions of different Cas9 orthologs may can be mixed and matched. For example, recognition domain may be substituted one for another, catalytic domains may be substituted one for another, and the like.

SaCas9 domain structures disclosed herein, and further by comparison to SpCas9 inform mixing of domains among orthologs, for example, but not limited to Cas9 from *Corynebacter, Sutterella, Legionella, Treponema, Filifactor, Eubacterium, Lactobacillus, Mycoplasma, Bacteroides, Flaviivola, Flavobacterium, Sphaerochaeta, Azospirillum, Gluconacetobacter, Neisseria, Roseburia, Parvibaculum, Nitratifactor*, and *Campylobacter*. Non-limiting examples further include *Actinomyces coleocanis, Coriobacterium glomerans, Streptococcus mutans Streptococcus thermophiles, Oenococcus kitaharae, Fructobacillus fructosus, Staphylococcus pseudintermedius, Planococcus antarcticus*.

An aspect of the invention relates to both crystal structures of *S. aureus* Cas9 in complex with sgRNA and its target DNA at 2.6 and 2.8 Å resolution when the target DNA contains the 5'-TTGAAT-3' PAM or 5'-TTGGGT-3' PAM sequences. The structure revealed a bilobed architecture composed of target recognition (REC) and nuclease (NUC) lobes, accommodating a sgRNA:DNA duplex in a central channel between the REC and NUC lobes. The recognition lobe is essential for sgRNA and DNA binding and the nuclease lobe contains the HNH and RuvC nuclease domains, which are properly positioned for the cleavage of complementary and non-complementary strands of the target DNA, respectively as well as the Wedge (WED) domain and the PAM interacting (PI) domain. This high-resolution structure and the functional analyses provided herein elucidate the molecular mechanism of RNA-guided DNA targeting by the CRISPR-SaCas9 system, and provides an abundance of information for generating optimized CRISPR-Cas systems and components thereof.

In particular embodiments of the invention, the crystal structure provides a critical step towards understanding the molecular mechanism of RNA-guided DNA targeting by SaCas9. The structural and functional analyses herein provide a useful scaffold for rational engineering of Cas9-based genome modulating technologies and may provide guidance as to Cas9-mediated recognition of PAM sequences on the target DNA or mismatch tolerance between the sgRNA: DNA duplex. Aspects of the invention also relate to truncation mutants, e.g. an *S. aureus* Cas9 truncation mutant may facilitate packaging of Cas9 into size-constrained viral vectors for in vivo and therapeutic applications Similarly, future engineering of the PAM Interacting (PI) domain may allow programing of PAM specificity, improve target site recognition fidelity, and increase the versatility of the Cas9 genome engineering platform.

The invention comprehends optimized functional CRISPR-Cas enzyme systems. In particular the CRISPR enzyme (e.g. SaCas9) comprises one or more mutations that converts it to a DNA binding protein to which functional domains exhibiting a function of interest may be recruited or appended or inserted or attached. In certain embodiments, the CRISPR enzyme (e.g. SaCas9) comprises one or more mutations that reduce or eliminate a nuclease activity. In SaCas9, such mutations include, without limitation, amino acid substitutions or deletions at D10, E477, H701, and D704 of the RuvC domain and D556, H557, and N580 of the HNH domain. In general, envisioned substitutions replace acidic, basic, or polar amino acids at those positions with amino acids having different or no charge, preferably amino acids that retain DNA binding capacity of the Cas9. Examples of such substitutions include, but are not limited to D10A, E477A, H701A and D704A mutations in the RuvC domain and/or D556A, H557A and N580A in the HNH domain and/or the one or more other mutations is in a RuvC or HNH domain of the CRISPR enzyme (e.g. SaCas9) or is a mutation as otherwise as discussed herein. Mutations can also be made at neighboring residues, e.g., at amino acids near those indicated above that participate in the nuclease activity. In some embodiments, only HNH is inactivated, and in other embodiments, only RuvC is inactivated (producing Cas9 nickases which cleave only one DNA strand). In some embodiments, two Cas9 variants (each a different nickase) are used to increase specificity, two nickase variants are used to cleave DNA at a target (where both nickases cleave a DNA strand, while immunizing or eliminating off-target modifications where only one DNA strand is cleaved and subsequently repaired. It is expected that the same or similarly located amino acids can be mutated in Type II CRISPR orthologs with similar effect. In some embodiments, the CRISPR enzyme has one or more mutations in a catalytic domain, wherein when transcribed, the tracr mate sequence hybridizes to the tracr sequence and the guide sequence directs sequence-specific binding of a CRISPR complex to the target sequence, and wherein the enzyme further comprises a functional domain.

The invention contemplates a strategy for the modification of SaCas9 and orthologs intended to generate modified variant Cas9 enzymes which show improved target specificity. The same rationale can be applied to any Cas9 ortholog. This improved specificity may be achieved in variants which show reduced activity towards non-target (off-target) loci whilst at the same time maintaining appropriate activity towards the intended target locus. Activity in the assays described below relates to nuclease activity manifest by cleavage of DNA as measured by the formation of INDELS. Such activity is expected to relate to the ability of the CRISPR complex (that is to say the complex between the Cas9 enzyme and guide RNA) to bind to the relevant site on DNA. Thus, a reduction in activity toward a non-target site may be expected to arise from reduced binding of the CRISPR complex at that site. Modified Cas9 enzymes which show reduced activity towards non-target loci compared to unmodified (e.g. wild-type) enzymes may therefore be expected to bind less well to non-target sites. Nishimasu et al. (Cell, 2014, 156(5), pp 935-49) reports the crystal structure at 2.5 Å resolution of an SpCas9 variant enzyme in complex with a single-guide RNA (sgRNA) of 98 nucleotides in length and a stretch of target DNA comprising 23 nucleotides in length. Based on these structural data, the inventors identified a positively-charged region situated between the RuvC-III and HNH domains. The inventors inferred that the groove may accommodate the non-target strand following disruption of normal Watson-Crick base-paring upon binding of the Cas9 enzyme to a relevant region of DNA. Positively charges residues of this region of Cas9 may act to stabilize the interaction between enzyme and DNA by interacting with the negatively-charged phosphodiester backbone of the non-target strand of DNA. The inventors hypothesize that by substitution of positively charged residues of Cas9, interactions with the non-target strand may be disrupted. Sufficient disruption of this interaction may maintain appropriate activity towards target sites but reduce the activity of the enzyme towards non-target sites (which will ordinarily be expected to have weaker interactions with the guide sequence on account of one or more mismatches compared the target sequence). The inventors surprisingly discovered that modification of Cas9 can indeed reduce off-target activity. The same or similar mutations and modifications are useful to increase specificity of Cas9 orthologs as well.

The invention contemplates domain truncation, domain swapping, and/or domain removal. According to the invention, modified CRISPR enzymes bearing functional domains are contemplated. Accordingly, enzyme fragments that bind to sgRNA:target heteroduplexes and lacking endonuclease activity, for example deleted for the portion that interacts with the 5' end of sgRNA are contemplated. Non-limiting examples further include *Actinomyces coleocanis, Coriobacterium glomerans, Streptococcus mutans Streptococcus thermophiles, Oenococcus kitaharae, Fructobacillus fructosus, Staphylococcus pseudintermedius, Planococcus antarcticus.*

The structural information provided herein allows for interrogation of sgRNA (or chimeric RNA) interaction with the target DNA and the CRISPR enzyme (e.g. Cas9) permitting engineering or alteration of sgRNA structure to optimize functionality of the entire CRISPR-Cas system. For example, loops of the sgRNA may be extended, without colliding with the Cas9 protein by the insertion of distinct RNA loop(s) or distinct sequence(s) that may recruit adaptor proteins that can bind to the distinct RNA loop(s) or distinct sequence(s). In a particular embodiment of the invention, stem loop 2 of SaCas9 may be modified or engineered to recruit proteins to enable specific functionality. The adaptor proteins may include but are not limited to orthogonal RNA-binding protein/aptamer combinations that exist within the diversity of bacteriophage coat proteins. A list of such coat proteins includes, but is not limited to MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s, PRR1. These adaptor proteins or orthogonal RNA binding proteins can further recruit effector proteins or fusions which comprise one or more functional domains. In some embodiments, the functional domain may be selected from the group consisting of: transposase domain, integrase domain, recombinase domain, resolvase domain, invertase domain, protease domain, DNA methyltransferase domain, DNA hydroxylmethylase domain, DNA demethylase domain, histone acetylase domain, histone deacetylases domain, nuclease domain, repressor domain, activator domain, nuclear-localization signal domains, transcription-regulatory protein (or transcription complex recruiting) domain, cellular uptake activity associated domain, nucleic acid binding domain, antibody presentation domain, histone modifying enzymes, recruiter of histone modifying enzymes; inhibitor of histone modifying enzymes, histone methyltransferase, histone demethylase, histone kinase, histone phosphatase, histone ribosylase, histone deribosylase, histone ubiquitinase, histone deubiquitinase, histone biotinase and histone tail protease.

In some preferred embodiments, the functional domain is a transcriptional activation domain, preferably VP64. In some embodiments, the functional domain is a transcription repression domain, preferably KRAB. In some embodiments, the transcription repression domain is SID, or concatemers of SID (eg SID4X). In some embodiments, the functional domain is an epigenetic modifying domain, such that an epigenetic modifying enzyme is provided. In some embodiments, the functional domain is an activation domain, which may be the P65 activation domain.

The invention provides assays and systems for modulating multiple targets in gene regulation circuits/pathways. In an embodiment of the invention, the expression of two or more genes is modulated, for example modulating one element of a circuit/pathway with a CRISPR-Cas9 system based on a first Cas9 enzyme and a modulating a second element of a circuit/pathway with a CRISPR-Cas9 system based on a second Cas9 enzyme. In certain embodiments, the first Cas9 is SpCas9 and the second Cas9 is SaCas. In certain embodiments, one CRISPR-Cas9 system comprises an activator of a circuit/pathway element. In certain embodiments, one CRISPR-Cas9 system comprises a repressor of a circuit/pathway element. In certain embodiments two CRISPR-Cas9 systems are employed, each comprising an activator of circuit/pathway element. In certain embodiments two CRISPR-Cas9 systems are employed, each comprising a repressor of circuit/pathway element. In certain embodiments two CRISPR-Cas9 systems are employed, one comprising an activator of circuit/pathway element and the second comprising a repressor of a circuit/pathway element.

The invention provides compositions and methods for treating viral infections, including curing or suppressing infections comprising latent viral reservoirs. In certain embodiments, CRISPR/Cas9 systems of the invention are useful to cleave viral DNA, for example targeting regions of the HBV genome, the HIV genome, or other virus of interest. In certain embodiments, a CRISPR/Cas system of the invention is used to cleave and inactivate a chromosomally integrated retroviral genome. In certain embodiments, a CRISPR/Cas9 system of the invention is used to cleave covalently closed circular DNA (cccDNA) which arises during propagation and is required for transcription of certain viruses.

The invention will now be further described by way of the following non-limiting examples.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1: Crystal Structure of *Staphylococcus aureus* Cas9

The RNA-guided Cas9 endonucleases from type II CRISPR (clustered regularly interspaced short palindromic repeat)-Cas systems have been harnessed for a variety of genome engineering applications (Cong et al., 2013; Esvelt et al., 2013; Hsu et al., 2013; Jinek et al., 2013; Mali et al., 2013). Cas9 binds dual guide RNAs, CRISPR RNA (crRNA) and trans-activating crRNA (tracrRNA), and cleaves the target double-stranded DNA complementary to the crRNA guide sequence (Gasiunas et al., 2012; Jinek et al., 2012). In the reconstituted systems, an artificial fusion of the crRNA and tracrRNA, known as a single guide RNA (sgRNA), can also mediate Cas9-catalyzed DNA cleavage (Cong et al., 2013; Jinek et al., 2012). Cas9 contains two endonuclease domains, HNH and RuvC, which cleave the DNA strands complementary (target DNA strand) and non-complementary (non-target DNA strand) to the crRNA, respectively. (Gasiunas et al., 2012; Jinek et al., 2012) Cas9-catalyzed DNA cleavage further requires the presence of a unique, short sequence, known as a protospacer-adjacent motif (PAM), immediately downstream of the target DNA sequence. PAM sequences are variable among orthologous CRISPR-Cas9 systems, and the widely used Cas9 from *Streptococcus pyogenes* (SpCas9) recognizes a 5'-NGG-3' PAM (N represents any nucleotide) on the non-target DNA strand.

The crystal structures of SpCas9 alone and in complex with its sgRNA and single-stranded, target DNA revealed that Cas9 adopts a bilobed architecture consisting of recognition (REC) and nuclease (NUC) lobes, and provided insights into the RNA-guided DNA cleavage mechanism (Jinek et al., 2014; Nishimasu et al., 2014). In addition, the crystal structure of SpCas9 in complex with its sgRNA and target DNA containing the 5'-NGG-3' PAM revealed the PAM-dependent DNA targeting mechanism (Anders et al., 2014). The structural information has already facilitated rational design of Cas9 variants and sgRNA scaffolds with expanded capabilities (Konermann et al., 2015; Wright et al., 2015; Zalatan et al., 2015; Zetsche et al., 2015).

Recently, Ran et al. (2015) reported that a small Cas9 from *Staphylococcus aureus* (SaCas9) can be harnessed for eukaryotic genome editing. Although several Cas9 orthologs can cleave DNA targets in vitro, only SaCas9 and SpCas9 exhibit robust activities in different mammalian cell types. SaCas9 shares only 17% sequence identity with SpCas9, highlighting the structural and functional variations among orthologous CRISPR-Cas9 systems. SaCas9 (1053 amino acid residues) is significantly smaller than SpCas9 (1368 amino acid residues). Thus, SaCas9 can be packaged into adeno-associated virus vectors more readily than SpCas9, thereby enabling efficient genome editing in somatic tissue. In addition, SaCas9 recognizes a 5'-NNGRRT-3' PAM (R represents a purine, A or G), which are different from the 5'-NGG-3' PAM for SpCas9. However, the mechanism of action of SaCas9 remains elusive.

Applicants now provide the crystal structures of SaCas9 in complex with sgRNA and its target DNA containing the 5'-TTGAAT-3' PAM or 5'-TTGGGT-3' PAM at 2.6 and 2.8 Å resolution, respectively. Applicants' structural and functional data provided insights into the PAM-dependent, RNA-guided DNA cleavage mechanism of SaCas9. A structural comparison between SaCas9 and SpCas9 revealed notable differences in their REC lobe-sgRNA scaffold and PAM-interacting (PI) domain-PAM sequence interactions, highlighting conservation and divergence among orthologous CRISPR-Cas9 systems. A structural comparison of Cas9 orthologs also revealed the flexible nature of the RuvC and HNH nuclease domains, and allowed the identification of a previously uncharacterized and evolutionarily divergent wedge (WED) domain. From a genome engineering perspective, Applicants' comparative study further facilitates the structure-guided engineering of this compact endonuclease, and paves the way for the rational design of Cas9 variants with expanded target space and improved target specificities.

The *S. aureus* Cas9 N580A/C946A mutant (residues 1-1053) was expressed in *Escherichia coli* Rosetta 2 (DE3) (Novagen) and purified by chromatography on Ni-NTA Superflow (QIAGEN), Mono S (GE Healthcare) and HiLoad Superdex 200 16/60 (GE Healthcare) columns. The SeMet-labeled protein was expressed in *E. coli* B834 (DE3), and was purified using a similar protocol as for the native protein. The 73-nt sgRNA was in vitro transcribed with T7 RNA polymerase and purified by 8% denaturing (7 M urea) polyacrylamide gel electrophoresis. The target DNAs were purchased from Sigma-Aldrich. The purified SaCas9 protein was mixed with the sgRNA, target DNA strand and non-target DNA strand (molar ratio, 1:1.5:2.3:3.4), and the SaCas9-sgRNA-target DNA complex was purified by gel filtration chromatography on a Superdex 200 Increase column (GE Healthcare).

The purified SaCas9-sgRNA-target DNA complex containing either the 5'-TTGAAT-3' PAM or the 5'-TTGGGT-3' PAM was crystallized at 20° C. by the hanging-drop vapor diffusion method. Crystals were obtained by mixing 1 µl of the complex solution (A260 nm, 15) and 1 µl of the reservoir solution (10-12% PEG 4,000, 0.75 M NaCl, 0.15 M $Na_2HPO_4$ and 0.15 M $NaN_3$). The SeMet-labeled complex (containing the 5'-TTGAA-3' PAM) was crystallized under similar conditions. X-ray diffraction data were collected at 100 K on the beamlines BL32XU and BL41XU at SPring-8 (Hyogo, Japan). The structure was determined by the Se-SAD method, using the 3 Å resolution data set from the SeMet-labeled crystal. The final models of the 5'-TTGAAT-3' PAM complex (2.6 Å resolution) and the 5'-TTGGGT-3' PAM complex (2.8 Å resolution) were refined using the native data sets.

About 24 h prior to transfection, the human embryonic kidney 293FT (Life Technologies) were seeded into 24-well plates (Corning) at a density of 250,000 cells/well, and transfected at 70-80% confluency using Lipofectamine 2000 (Life Technologies), according to the manufacturer's recommended protocol. A total of 600 ng DNA was used for each well on a 24-well plate. About 72 h after transfection, genomic DNA was extracted, and then genomic modifications were examined using the SURVEYOR assay and targeted deep sequencing, as previously described (Cong et al., 2013b).

Crystal Structure of the SaCas9-sgRNA-Target DNA Quaternary Complex

Figure 9:
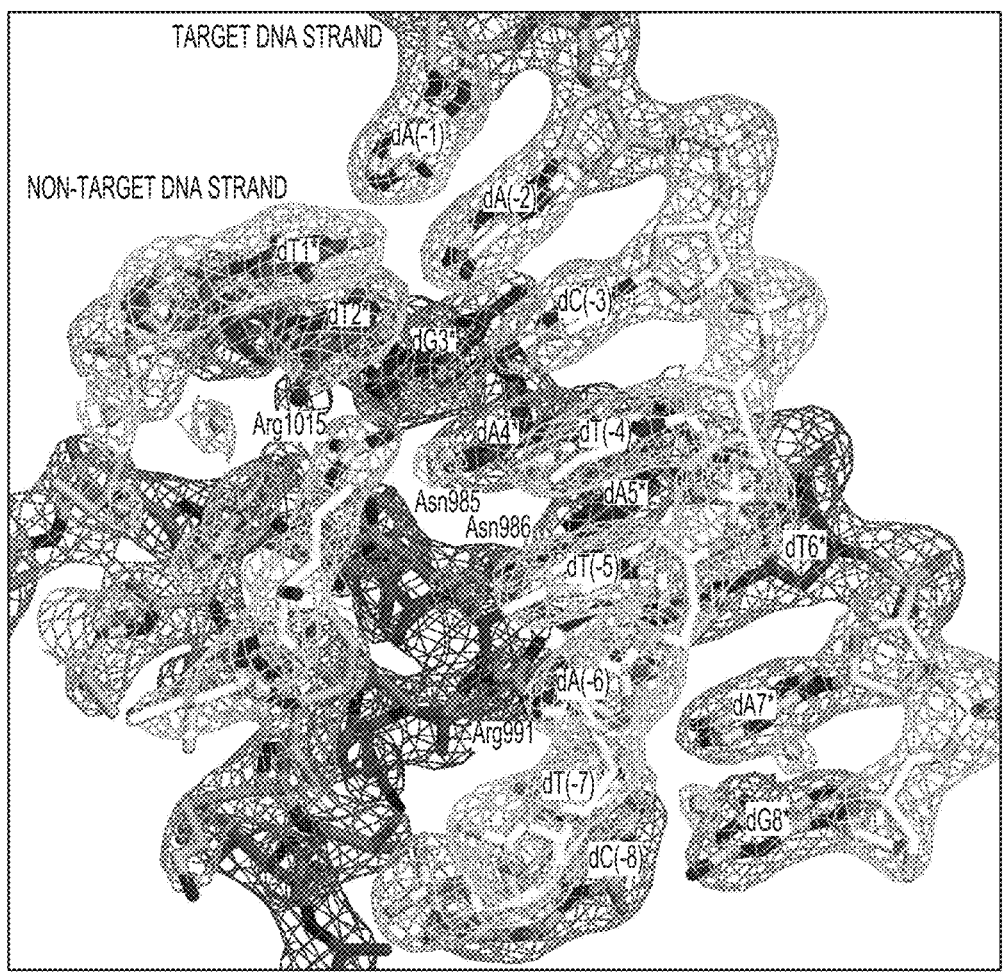
FIG. 9 shows an Electron density map. The 2mFo-DFc electron density map around the PAM is shown as a gray mesh, contoured at 1σ and 2σ for water molecules and the Cas9-sgRNA-DNA complex, respectively. The PAM is highlighted in purple. Water molecules are shown as red spheres.
Figure 10A:
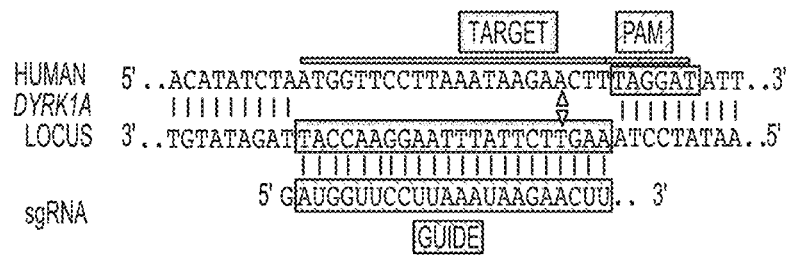
FIG. 10A-10B shows the activity of wild-type and C946A mutant of SaCas9. The abilities of the wild-type and C946A mutant of SaCas9 to induce indels in the target DYRK1A locus were examined. (A) Target sequence in the human DYRK1A locus used to test endogenous genome cleavage by the wild-type (WT) and mutants of SaCas9. The cleavage sites by the RuvC and HNH domains are indicated by cyan and pink triangles, respectively.
Figure 10B:
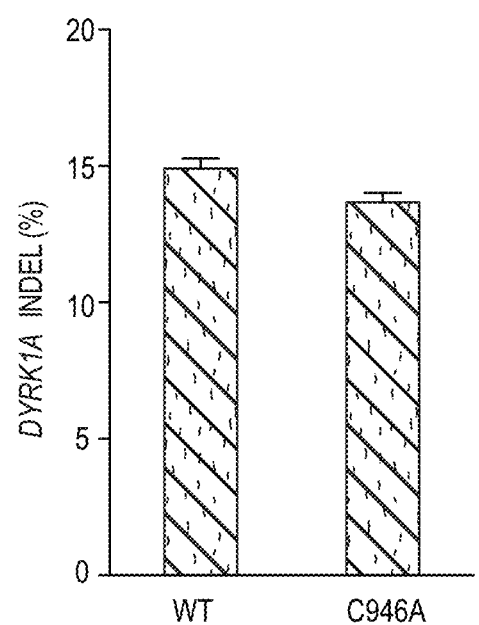
Figure 11:
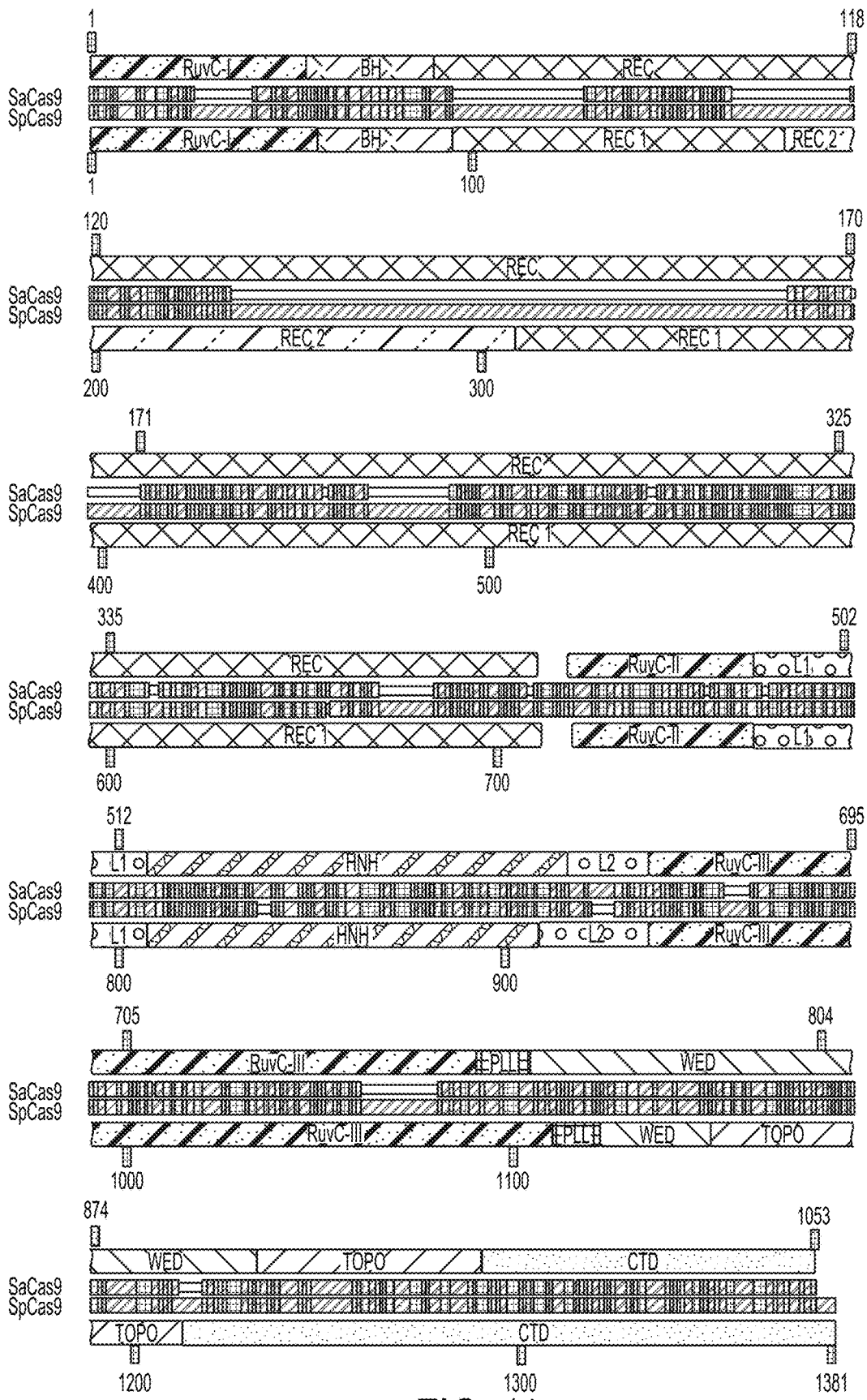
FIG. 11 shows a sequence alignment of SaCas9 and SpCas9 with domain annotation. Sequence alignment was performed using Geneious package. All domain name annotations and coloring are the same as in FIG. 1. Residues numbers for SaCas9 and SpCas9 are labeled on top and bottom, respectively.

Applicants solved the crystal structures of SaCas9 (residues 1-1053; N580A/C946A) in complex with 73-nucleotide (nt) sgRNA, 28-nt complementary target DNA strand and 8-nt non-target DNA strand containing the 5'-TTGAAT-3' PAM and 5'-TTGGGT-3' PAM at 2.6 and 2.8 Å resolution, respectively (FIG. 9 and Table 6). Applicants replaced a non-conserved cysteine residue (Cys946) with alanine for crystallization, since the C946A mutation did not affect the DNA cleavage activity in vivo (FIG. 10). To prevent potential cleavage of the target DNA during crystallization, Applicants replaced the catalytic residue (Asn580) in the HNH domain with alanine. The two structures are virtually identical (root-mean-square deviation [rmsd] of 0.3 Å for the all Cα atoms). In this application, Applicants describe the quaternary complex structure containing the 5'-TTGAAT-3' PAM, unless otherwise stated.

TABLE 6

Data collection and refinement statistics.

| | TTGAAT PAM (Native) | TTGGGT PAM (Native) | TTGAAT PAM (SeMet) |
|---|---|---|---|
| Data collection | | | |
| Beamline | SPring-8 BL41XU | SPring-8 BL32XU | SPring-8 BL41XU |
| Wavelength (Å) | 1.0000 | 1.0000 | 0.9791 |
| Space group | $P2_12_12$ | $P2_12_12$ | $P2_12_12$ |
| Cell dimensions | | | |
| a, b, c (Å) | 67.6, 345.6, 98.1 | 67.4, 345.3, 97.8 | 67.9, 346.0, 98.3 |
| α, β, γ (°) | 90, 90, 90 | 90, 90, 90 | 90, 90, 90 |
| Resolution (Å)* | 49.4-2.6 (2.66-2.60) | 48.9-2.8 (2.88-2.80) | 49.4-3.0 (3.11-3.00) |
| $R_{merge}$ | 0.066 (0.806) | 0.166 (1.09) | 0.169 (2.00) |
| $R_{pim}$ | 0.028 (0.371) | 0.068 (0.462) | 0.046 (0.564) |
| I/σI | 14.6 (1.9) | 7.8 (1.7) | 17.8 (2.2) |
| Completeness (%) | 99.4 (92.8) | 100 (100) | 99.9 (99.8) |
| Multiplicity | 6.7 (5.6) | 6.9 (6.6) | 14.1 (13.4) |
| CC(1/2) | 0.998 (0.833) | 0.990 (0.659) | 0.999 (0.786) |

TABLE 6-continued

Data collection and refinement statistics.

|  | TTGAAT PAM (Native) | TTGGGT PAM (Native) | TTGAAT PAM (SeMet) |
|---|---|---|---|
| Refinement |  |  |  |
| Resolution (Å) | 50-2.6 | 50-2.8 |  |
| No. reflections | 130, 396 | 130, 396 |  |
| $R_{work}/R_{free}$ | 0.20/0.24 | 0.20/0.23 |  |
| No. atoms |  |  |  |
| Protein | 18,997 | 18,997 |  |
| Nucleic acid | 5,012 | 5,012 |  |
| Solvent | 144 | 144 |  |
| B-factors (Å$^2$) |  |  |  |
| Protein | 80.2 | 80.2 |  |
| Nucleic acid | 82.4 | 82.4 |  |
| Ion | 51.4 | 51.4 |  |
| Solvent | 51.4 | 51.4 |  |
| R.m.s. deviations |  |  |  |
| Bond lengths (Å) | 0.002 | 0.002 |  |
| Bond angles (°) | 0.526 | 0.526 |  |
| Ramachandran plot (%) |  |  |  |
| Favored region | 97.0 | 97.0 |  |
| Allowed region | 3.0 | 3.0 |  |
| Outlier region | 0.0 | 0.0 |  |

*Values in parentheses are for the highest resolution shell.

Figure 1D:
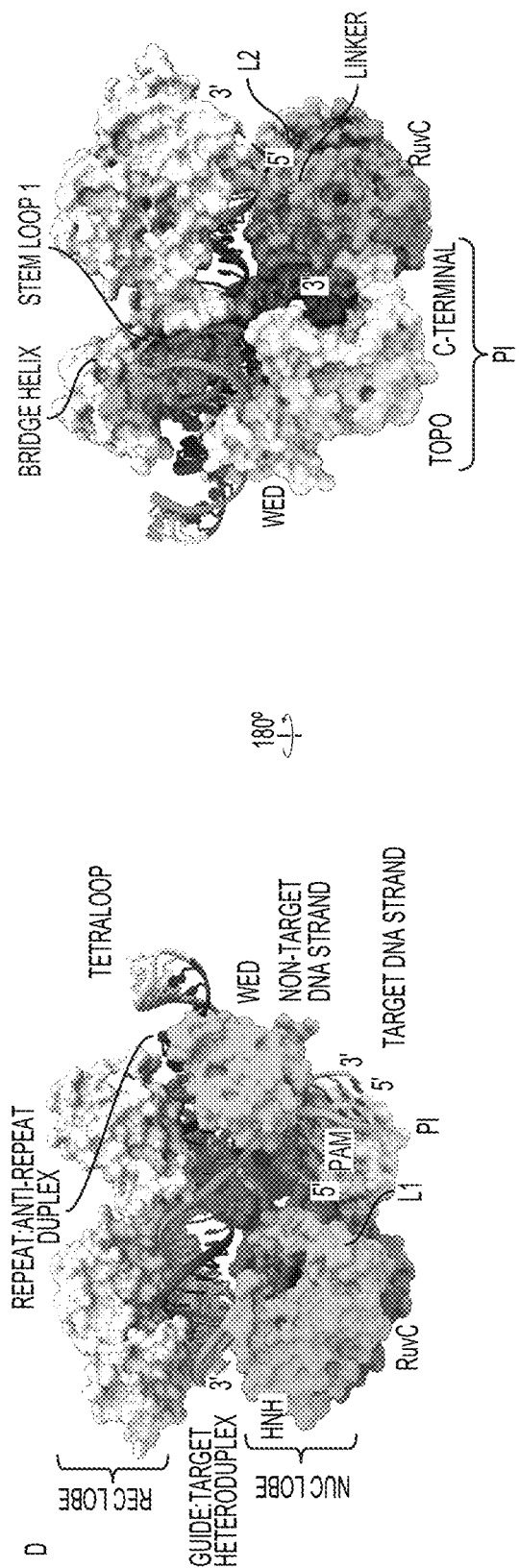
Figure 1E:
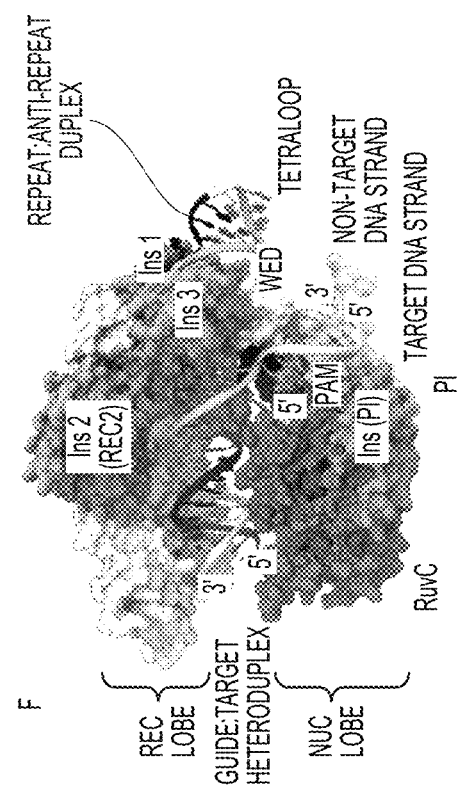
Figure 1F:
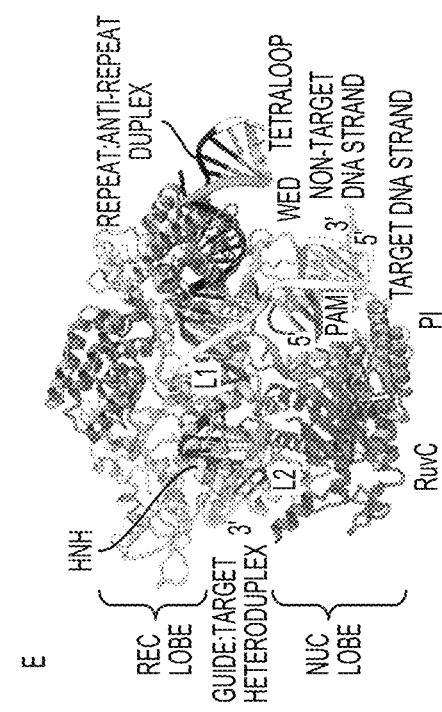
Figure 12:
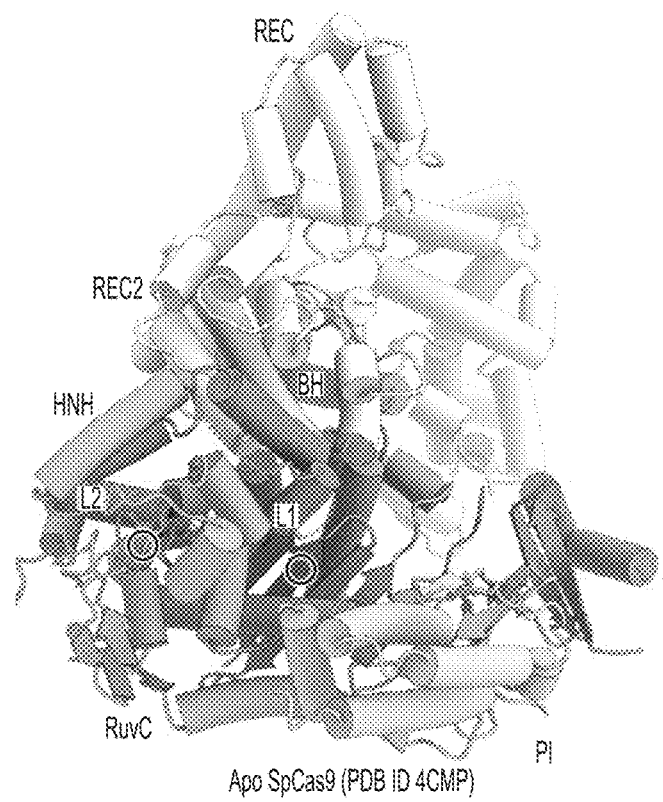
FIG. 12 depicts crystal structures of SpCas9 (PDB ID 4CMP) and AnCas9 (PDB ID 4OGE) in the apo form. The active sites of the HNH and RuvC nuclease domains are indicated by red circles. In AnCas9, residues 99-136 and 171-224 in the REC lobe are disordered, probably due to their flexibility.
Figure 12:
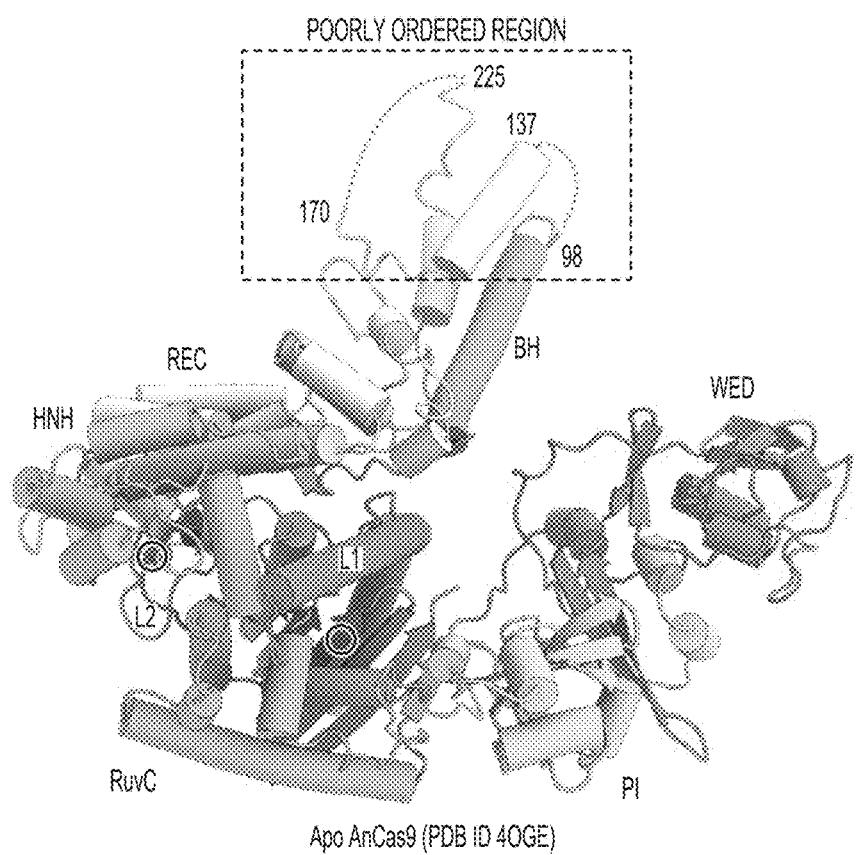

The structure revealed that SaCas9 has a bilobed architecture consisting of a REC lobe (residues 41-425) and a NUC lobe (residues 1-40 and 435-1053). The two lobes are connected by an arginine-rich bridge helix (residues 41-73) and a linker loop (residues 426-434) (FIG. 1). The NUC lobe consists of the RuvC (residues 1-40, 435-480 and 650-774), HNH (residues 520-628), WED (residues 788-909) and PI (residues 910-1053) domains (FIG. 1). The RuvC and WED domains are connected by a phosphate lock loop (residues 775-787). The PI domain can be divided into a Topo-homology (TOPO) domain and a C-terminal domain as in SpCas9 (Jinek et al., 2014). The RuvC domain consists of three separate motifs (RuvC-I-III) and interacts with the HNH and PI domains. The HNH domain is connected to the RuvC-II and RuvC-III by L1 (residues 481-519) and L2 (residues 629-649) linker regions, respectively. The active site of the HNH domain is located away from the cleavage site in the target DNA strand (the phosphodiester linkage between dC3 and dA4), indicating that the herein described structure represents an inactive state, as in the case of the SpCas9-sgRNA-target DNA complex structures (Anders et al., 2014; Nishimasu et al., 2014). SpCas9 undergoes conformational rearrangements upon guide RNA binding, to form the central channel between the REC and NUC lobes (Anders et al., 2014; Jiang et al., 2015; Jinek et al., 2014; Nishimasu et al., 2014). In the absence of the guide RNA, SpCas9 and AnCas9 adopt a closed conformation, where the active site of the HNH domain is covered by the RuvC domain (FIG. 12). In contrast, the ternary and quaternary complex structures of SpCas9 adopt an open conformation and has the central channel, which accommodates the guide RNA-target DNA heteroduplex (referred to as a guide:target heteroduplex) (FIGS. 1E and 1F). The present quaternary complex structure of SaCas9 adopts a similar open conformation to form the central channel, which accommodates the guide:target heteroduplex (FIGS. 1C and 1D). Thus, these structural observations suggested that the guide RNA-induced conformational activation is conserved between SaCas9 and SpCas9.

Structure of the sgRNA-Target DNA Complex

The sgRNA consists of the guide region (G1-C20), repeat region (G21-G34), tetraloop (G35-A38), anti-repeat region (C39-C54), stem loop 1 (A56-G68) and single-stranded linker (U69-U73), with A55 connecting the anti-repeat region and stem loop 1 (FIGS. 2A-2D). No electron density was observed for U73 at the 3' end, suggesting that U73 is disordered in the structure. The guide region (G1-C20) and the target DNA strand (dG1-dC20) form an RNA-DNA heteroduplex (referred to as a guide:target heteroduplex), whereas the target DNA strand (dC(−8)-dA(−1)) and the non-target DNA strand (dT1*-dG8*) form a PAM-containing duplex (referred to as a PAM duplex) (FIGS. 2A and 2B). The repeat (G21-G34) and anti-repeat (C39-C54) regions form a distorted duplex (referred to as a repeat:anti-repeat duplex) via 13 Watson-Crick base pairs (FIGS. 2A and 2B). The unpaired nucleotides (C30, A43, U44 and C45) form an internal loop, which is stabilized by a hydrogen bonding-interaction between the O2 of U44 and the N4 of C45 (FIG. 2C). The repeat:anti-repeat duplex is recognized by the REC and WED domains (described below). Indeed, a GAU insertion into the repeat region, which would disrupt the internal loop, reduced the Cas9-mediated DNA cleavage (FIG. 2E), confirming the functional importance of the distorted structure of the repeat:anti-repeat duplex.

Stem loop 1 is formed via three Watson-Crick base pairs (G57:C67-C59:G65) and two non-canonical base pairs (A56:G68 and A60:A63) (FIGS. 2A and 2D). U64 does not base pair with A60, and is flipped out of the stem loop (FIG. 2D). The N1 and N6 of A63 hydrogen bond with the 2' OH and N3 of A60, respectively. G68 stacks with G57:C67, with the G68 N2 interacting with the backbone phosphate group between A55 and A56. A55 adopts the syn conformation, and its adenine base stacks with U69 (FIG. 2D). In addition, the N1 of A55 hydrogen bonds with the 2' OH of G68, stabilizing the basal region of stem loop 1. An adenosine nucleotide immediately after the repeat:anti-repeat duplex is highly conserved among CRISPR-Cas9 systems, and equivalent adenosine A51 in the SpCas9 crRNA:tracrRNA also adopts the syn conformation (Anders et al., 2014; Nishimasu et al., 2014) (FIG. 13A), suggesting conserved key roles of an adenosine connecting the repeat:anti-repeat duplex and stem loop 1.

Figure 2G:
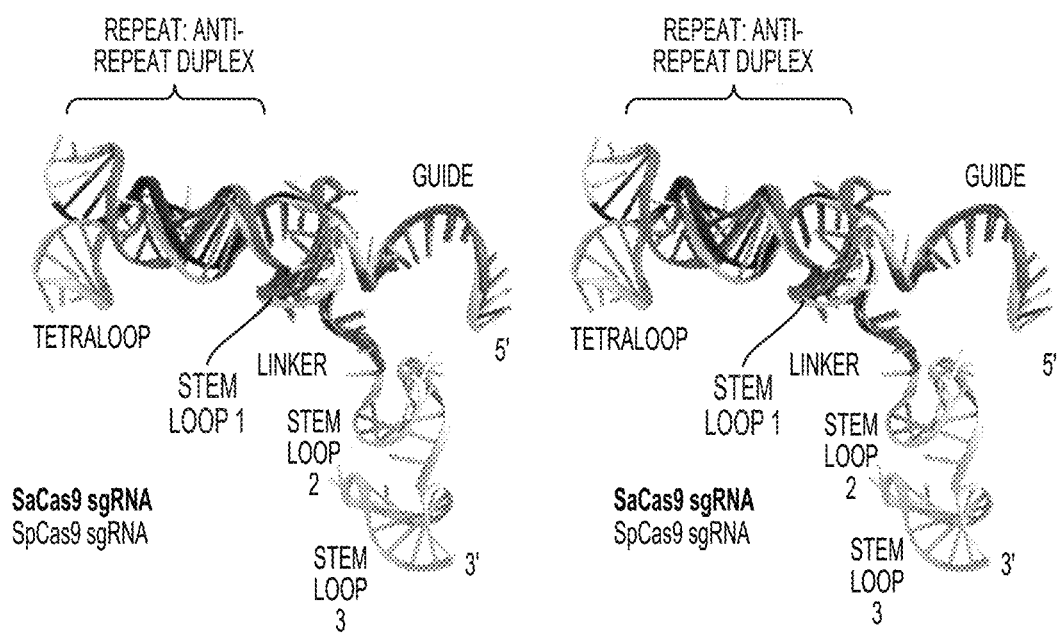
Figures 13A, 13B:
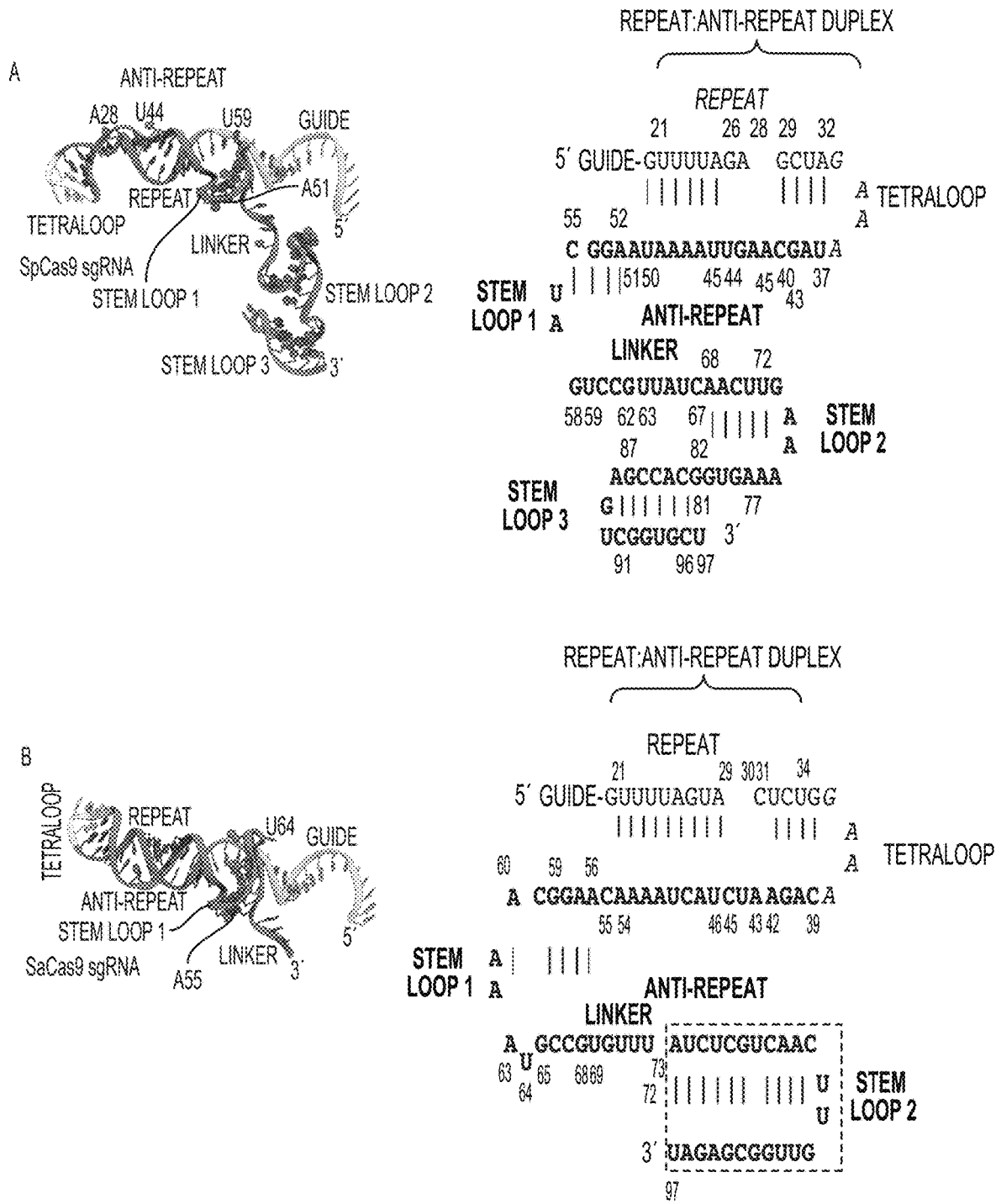
FIG. 13A-13E shows a comparison of SaCas9 sgRNA and SpCas9 sgRNA. (A and B) Crystal structures (left) and nucleotide sequences (right) of the SpCas9 sgRNA (PDB ID 4OO8) (A) and SaCas9 sgRNA (B).
Figure 13C:
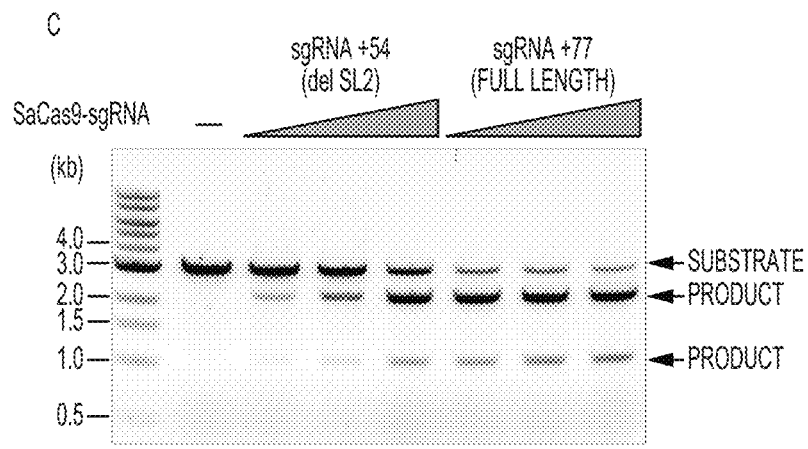
Figure 13D:
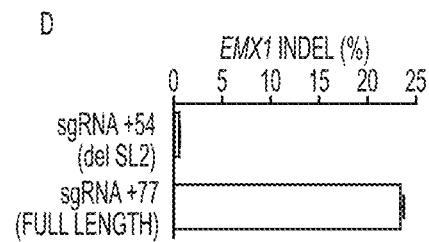
Figure 13E:
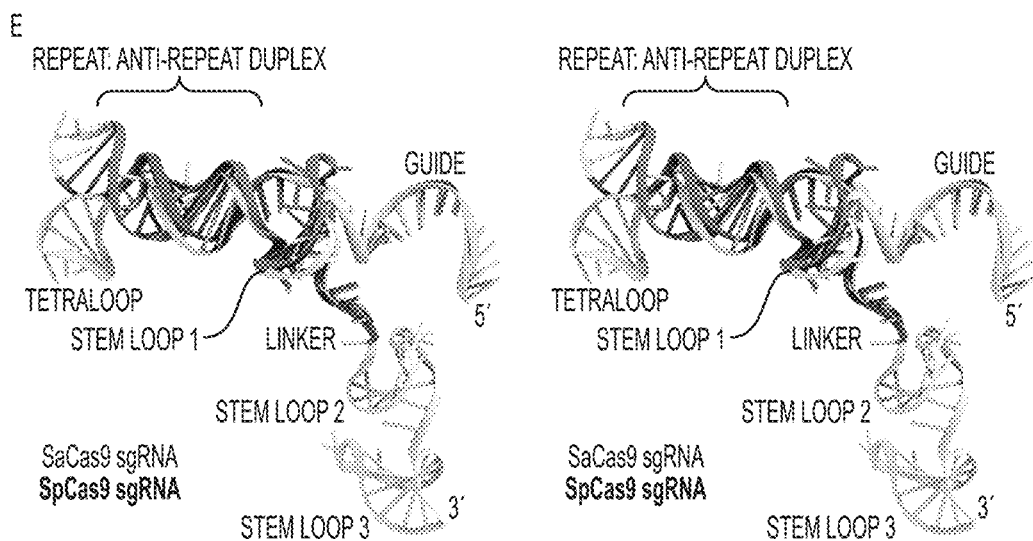

The SpCas9 sgRNA contains three stem loops (stem loops 1-3), which interact with Cas9 and contribute to the complex formation (Nishimasu et al., 2014) (FIGS. 2G and 13A). The sgRNA lacking stem loops 2 and 3 supports the Cas9-catalyzed DNA cleavage in vitro but not in vivo, indicating the importance of stem loops 2 and 3 for the cleavage activity in vivo (Hsu et al., 2013; Jinek et al., 2012; Nishimasu et al., 2014). The nucleotide sequence of the SaCas9 sgRNA indicated that it contains two stem loops (stem loops 1 and 2) based on its nucleotide sequence (FIG. 13B). Truncation of putative stem loop 2 remarkably improved the quality of the crystals. As in SpCas9, the sgRNA lacking stem loop 2 supported Cas9-catalyzed DNA cleavage in vitro but not in vivo (FIGS. 13C and 13D), suggesting that secondary structures on the 3' tail of the SaCas9 sgRNA are important for in vivo function.

Tetraloop and stem loop 2 of the SpCas9 sgRNA are exposed to the solvent (Anders et al., 2014; Nishimasu et al., 2014) (FIG. 13A). Thus, these two loops are available for the fusion of RNA aptamers, and the three components system consisting of (1) catalytically inactive SpCas9 (D10A/N863A) fused with a VP64 transcriptional activator domain, (2) a MS2 bacteriophage coat protein fused with p65 and HSF1 transcriptional activator domains, and (3) the engineered sgRNA fused to MS2-interacting RNA aptamers can induce the RNA-guided transcriptional activation of target endogenous loci (Konermann et al., 2015). To examine whether tetraloop and stem loop 2 of the SaCas9 sgRNA are available for the MS2-interacting aptamer fusion, Applicants co-expressed in HEK293F cells the three components, (1) dSpCas9 (D10A/N863A)-VP64 or dSaCas9 (D10A/N580A)-VP64, (2) its engineered sgRNA, and (3) MS2-p65-HSF1, and then monitored the transcriptional activation of two different endogenous genes (ASCL1 and MYOD1) (FIG. 2F). The results showed that the dSaCas9-based activator induces the transcription activation of the ASCL1 and MYOD1 genes at levels comparable to those of the dSpCas9-based activator. These results indicate that the SaCas9 sgRNA has solvent-exposed stem loop 2, and demonstrate that the engineered SaCas9 sgRNA can recruit multiple MS2-fused proteins.

The sgRNAs used in FIG. 2F were designed with the MS2 stem loop sequence inserted into the Tetraloop. The following table provides full sgRNA sequences and identifies each target guide sequence. The table discloses SEQ ID NOS 65-76, respectively, in order of appearance.

| sgRNA Name | Target Guide Sequence | Full sgRNA sequence |
|---|---|---|
| a_ASCL1_24 | GCGGGGCCAGGGCTGCGCGTGGGG | GCGGGGCCAGGGCTGCGCGTGGGGGTTTTAGTACTCTGGGCCAACATGAGGATCACCCATGTCTGCAGGGCCCAGAATCTACTAAAACAAGGCAAAATGCCGTGTTTATCTCGTCAACTTGTTGGCGAGATTTTT |
| a_ASCL1_22 | GGGGCCAGGGCTGCGCGTGGGG | GGGGCCAGGGCTGCGCGTGGGGGTTTTAGTACTCTGGGCCAACATGAGGATCACCCATGTCTGCAGGGCCCAGAATCTACTAAAACAAGGCAAAATGCCGTGTTTATCTCGTCAACTTGTTGGCGAGATTTTT |
| a_ASCL1_21 | GGGCCAGGGCTGCGCGTGGGG | GGGCCAGGGCTGCGCGTGGGGGTTTTAGTACTCTGGGCCAACATGAGGATCACCCATGTCTGCAGGGCCCAGAATCTACTAAAACAAGGCAAAATGCCGTGTTTATCTCGTCAACTTGTTGGCGAGATTTTT |
| a_MYOD1_24 | GCCCAGGCGGGCAGCTGGGGGAGG | GCCCAGGCGGGCAGCTGGGGGAGGGTTTTAGTACTCTGGGCCAACATGAGGATCACCCATGTCTGCAGGGCCCAGAATCTACTAAAACAAGGCAAAATGCCGTGTTTATCTCGTCAACTTGTTGGCGAGATTTTTT |
| a_MYOD1_22 | CCAGGCGGGCAGCTGGGGGAGG | CCAGGCGGGCAGCTGGGGGAGGGTTTTAGTACTCTGGGCCAACATGAGGATCACCCATGTCTGCAGGGCCCAGAATCTACTAAAACAAGGCAAAATGCCGTGTTTATCTCGTCAACTTGTTGGCGAGATTTTT |
| a_MYOD1_21G | GCAGGCGGGCAGCTGGGGGAGG | GCAGGCGGGCAGCTGGGGGAGGGTTTTAGTACTCTGGGCCAACATGAGGATCACCCATGTCTGCAGGGCCCAGAATCTACTAAAACAAGGCAAAATGCCGTGTTTATCTCGTCAACTTGTTGGCGAGATTTTT |

Recognition Mechanism of the Guide:Target Heteroduplex

The guide:target heteroduplex is accommodated in the central channel between the REC and NUC lobes (FIGS. 1D and 3). The sugar-phosphate backbone of the PAM-distal region (A3-U6) of the sgRNA interacts with the REC lobe (Thr238, Tyr239, Lys248, Tyr256, Arg314, Asn394 and Gln414) (FIG. 3). In SpCas9 and SaCas9, the RNA-DNA base pairing in the 8 bp PAM-proximal "seed" region in the guide:target heteroduplex is critical for Cas9-catalyzed DNA cleavage (Hsu et al., 2013; Jinek et al., 2012; Ran et al., 2015). Consistent with this, the phosphate backbone of the sgRNA seed region (C13-C20) is extensively recognized by the bridge helix (Asn44, Arg48, Arg51, Arg55, Arg59 and Arg60) and the REC lobe (Arg116, Gly117, Arg165, Gly166, Asn169 and Arg209), as in the case of SpCas9 (FIGS. 3 and 4A). In addition, the 2' OH groups of C15, U16, U17 and G19 interact with the REC lobe (Gly166, Arg208, Arg209 and Tyr211). These structural findings suggest that the sgRNA binds to SaCas9, with its seed region pre-ordered in an A-form conformation for base-paring with the target DNA strand, as proposed for SpCas9 (Jiang et al., 2015). In addition, the sugar-phosphate backbone of the target DNA strand interacts with the REC lobe (Tyr211, Trp229, Tyr230, Gly235, Arg245, Gly391, Thr392, and Asn419) and the RuvC domain (Leu446, Tyr651 and Arg654) (FIG. 3). Together, there structural findings explain the RNA-guided DNA targeting mechanism of SaCas9. Notably, the REC lobe of SaCas9 shares structural similarity with those of SpCas9 (PDB code 4UN3, 26% identity, rmsd of 1.9 Å for 177 equivalent Ca atoms) and AnCas9 (PDB ID 4OGE, 16% identity, rmsd of 3.2 Å for 167 equivalent Ca atoms) (FIGS. S6A and S6B), indicating that the Cas9 orthologs recognize the guide:target heteroduplex in a similar manner.

Recognition Mechanism of the crRNA:tracrRNA Scaffolds

The repeat:anti-repeat duplex is recognized by the REC and WED domains, primarily through interactions between the sugar-phosphate backbone and protein (FIG. 3). Consistent with our data showing that the sgRNA containing the fully-paired repeat:anti-repeat duplex fails to support Cas9-catalyzed DNA cleavage (FIG. 2E), the internal loop (C30, U44 and C45) is extensively recognized by the WED domain (FIG. 4B). The 2' OH and O2 of C30 hydrogen bond with Tyr868 and Lys867, respectively, and the phosphate groups of U31, C45 and U46 interact with Lys870, Arg792 and Lys881, respectively. These structural observations explain the structure-dependent recognition of the repeat:anti-repeat duplex by SaCas9.

Stem loop 1 is recognized by the bridge helix and REC lobe (FIG. 3). The phosphate backbone of stem loop 1 interact with the bridge helix (Arg47, Arg54, Arg55, Arg58 and Arg59) and the REC lobe (Arg209, Gly216 and Ser219) (FIG. 4C). The 2' OH of A63 hydrogen bonds with His64. The flipped-out U64 is recognized by Glu213 and Arg209 via hydrogen-bonding and stacking interactions, respectively. A55 is extensively recognized by the phosphate lock loop (FIG. 4D). The N6, N7 and 2' OH of A55 hydrogen bond with Asn780/Arg781, Leu783 and Lys906, respectively. Lys57 interacts with the phosphate group between C54 and A55, and the side chain of Leu783 form hydrophobic contacts with the adenine bases of A55 and A56. The phosphate backbone of the linker region electrostatically interacts with the RuvC domain (Arg452, Lys459 and Arg774) and the phosphate lock loop (Arg781), and the guanine base of G80 stacks with the side chain of Arg47 on the bridge helix (FIG. 4D).

Recognition Mechanism of the 5'-NNGRRT-3'PAM

Figures 5A, 5B:
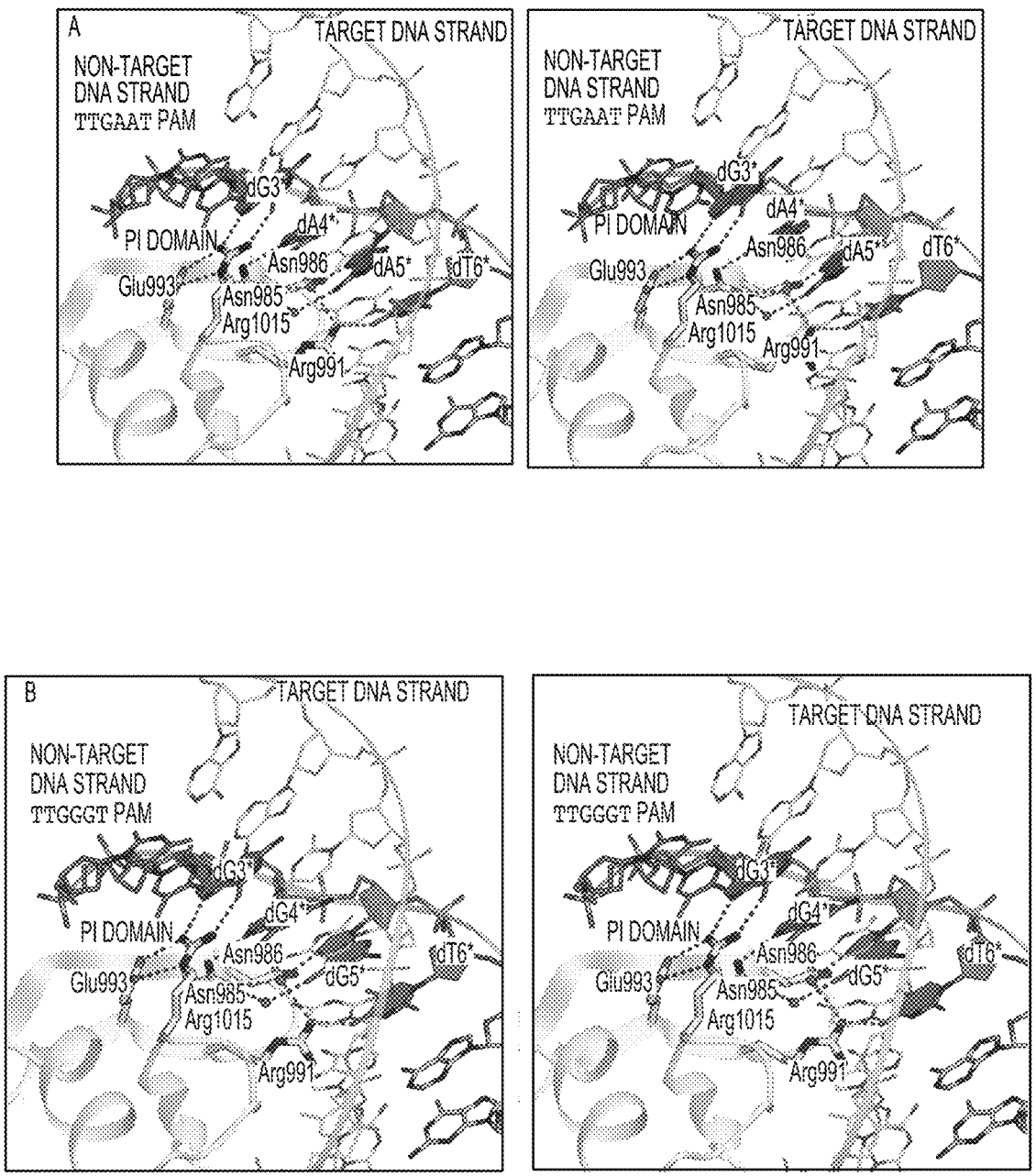
FIG. 5A-5H shows details of PAM recognition. (A and B) Recognition of the 5'-TTGAAT-3' PAM (A) and 5'-TTGGGT-3' PAM (B) (stereoview). The PAM sequences are highlighted in purple. Water molecules are shown as red spheres. Hydrogen bonds are shown as dashed lines. (C) Mutational analysis of the PAM-interacting residues and the phosphate lock loop (PLL) measured by indel rate at two EMX1 targets (n=3, error bars show mean±S.E.M.). (D and E) PAM recognition by the PI domains of SpCas9 (PDB ID 4UN3) (D) and SaCas9 (E). The PAM sequences are highlighted in purple. Hydrogen bonds are shown as dashed lines. The target DNA strands are omitted for clarity. In (D), the SpCas9-specific insertion is highlighted in pale blue. (F and G) +1 phosphate recognition by the phosphate lock loop of SpCas9 (PDB ID 4UN3) (F) and SaCas9 (G). (H) Recognition of the minor groove of the PAM duplex.

SaCas9 recognizes the 5'-NNGRRN-3' PAM with a preference for a thymine base at the 6th position (Ran et al., 2015), which is distinct from the 5'-NGG-3' PAM of SpCas9. In the present structures containing either the 5'-TTGAAT-3' PAM or the 5'-TTGGGT-3' PAM, the PAM duplex is sandwiched between the WED and PI domains, and the PAM in the non-target DNA strand is read out from the major groove side by the PI domain (FIGS. 5A and 5B). dT1* and dT2* form no direct contact with the protein (FIGS. 5A and 5B). Consistent with the observed requirement for the 3rd G in the 5'-NNGRRT-3' PAM, the O6 and N7 of dG3* forms bidentate hydrogen bonds with the side chain of Arg1015, which is anchored via salt bridges with Glu993 in both complexes (FIGS. 5A and 5B). In the 5'-TTGAAT-3' PAM complex, the N7 atoms of dA4* and dA5* form direct and water-mediated hydrogen bonds with Asn985 and Asn985/Asn986/Arg991, respectively (FIG. 5A). In addition, the N6 of dA5* forms a water-mediated hydrogen bond with Asn985. Similarly, in the 5'-TTGGGT-3' PAM complex, the N7 atoms of dG4* and dG5* form direct and water-mediated hydrogen bonds with Asn985 and Asn985/Asn986/Arg991, respectively (FIG. 5B). The O6 of dG5* forms a water-mediated hydrogen bond with Asn985. These structural findings explain the ability of SaCas9 to recognize the purine nucleotides at positions 4 and 5 in the 5'-NNGRRT-3' PAM. The O4 of dT6* hydrogen bonds with Arg991 (FIGS. 5A and 5B), explaining the preference of SaCas9 to the 6th T in the 5'-NNGRRT-3' PAM. Single alanine mutants of these PAM-interacting residues reduced cleavage activities in vivo, and double mutations abolished the activity (FIG. 5C), confirming the importance of Asn985, Asn986, Arg991, Glu993 and Arg1015 for PAM recognition. In addition, the phosphate backbone of the PAM duplex is recognized from the minor groove side by the WED domain (Tyr789, Tyr882, Lys886, Ans888, Ala889 and Leu909) in a manner distinct from SpCas9 (FIG. 3). Together, our structural and functional data reveal the mechanism of relaxed recognition of the 5'-NNGRRT-3' PAM by SaCas9.

Mechanism of Target DNA Unwinding

Figures 5C, 5D, 5E:
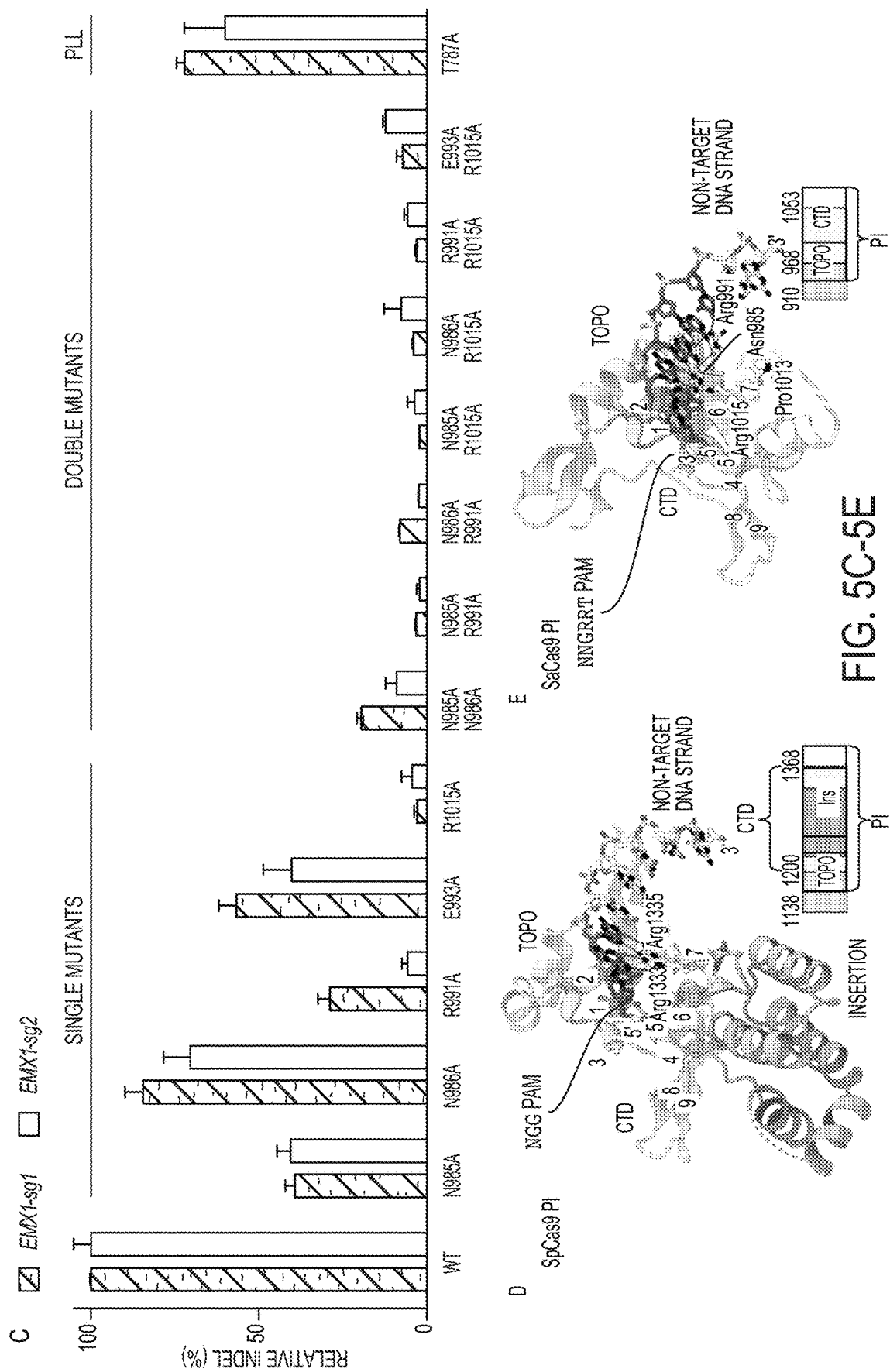
Figures 5F, 5G, 5H:
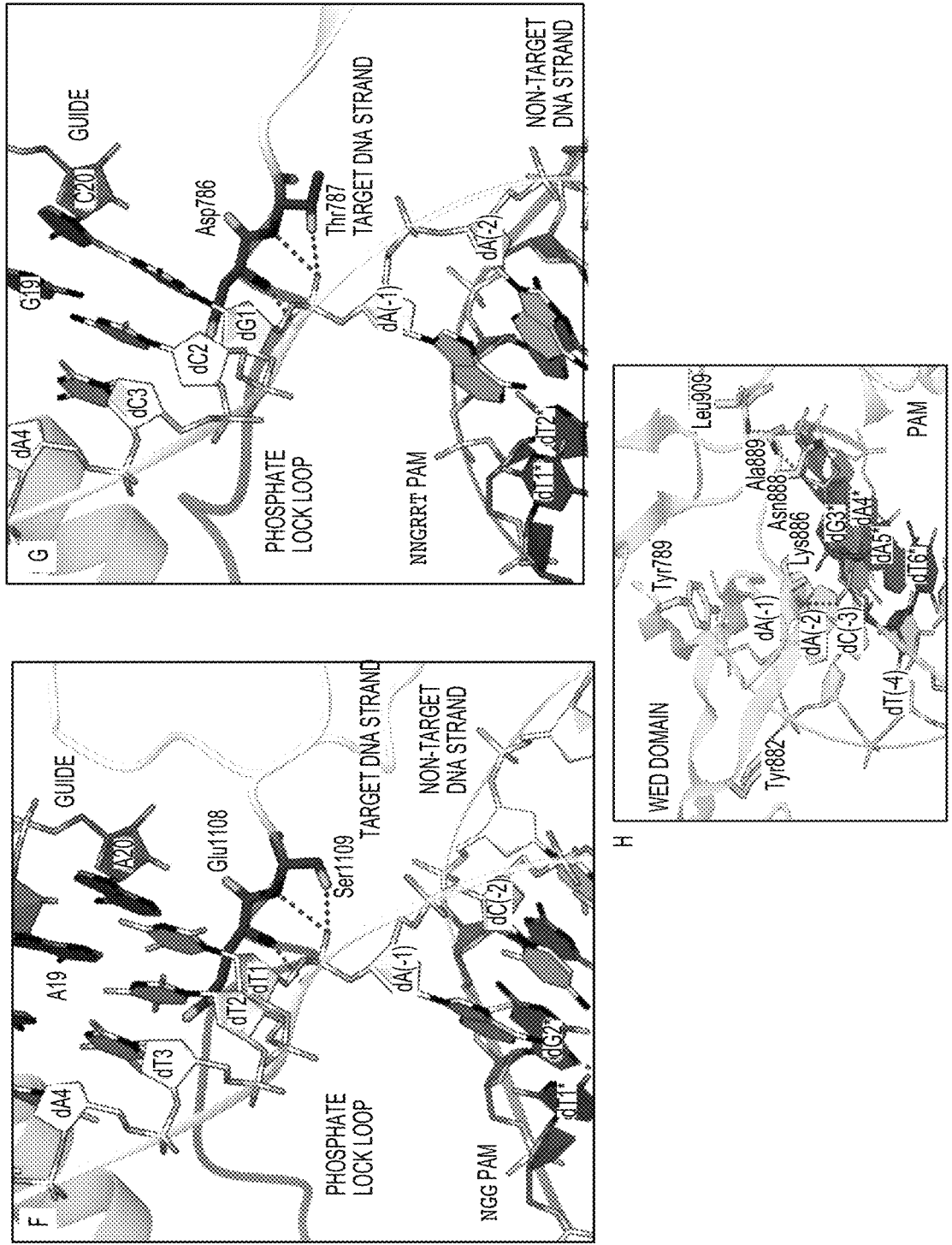
Figure 17:
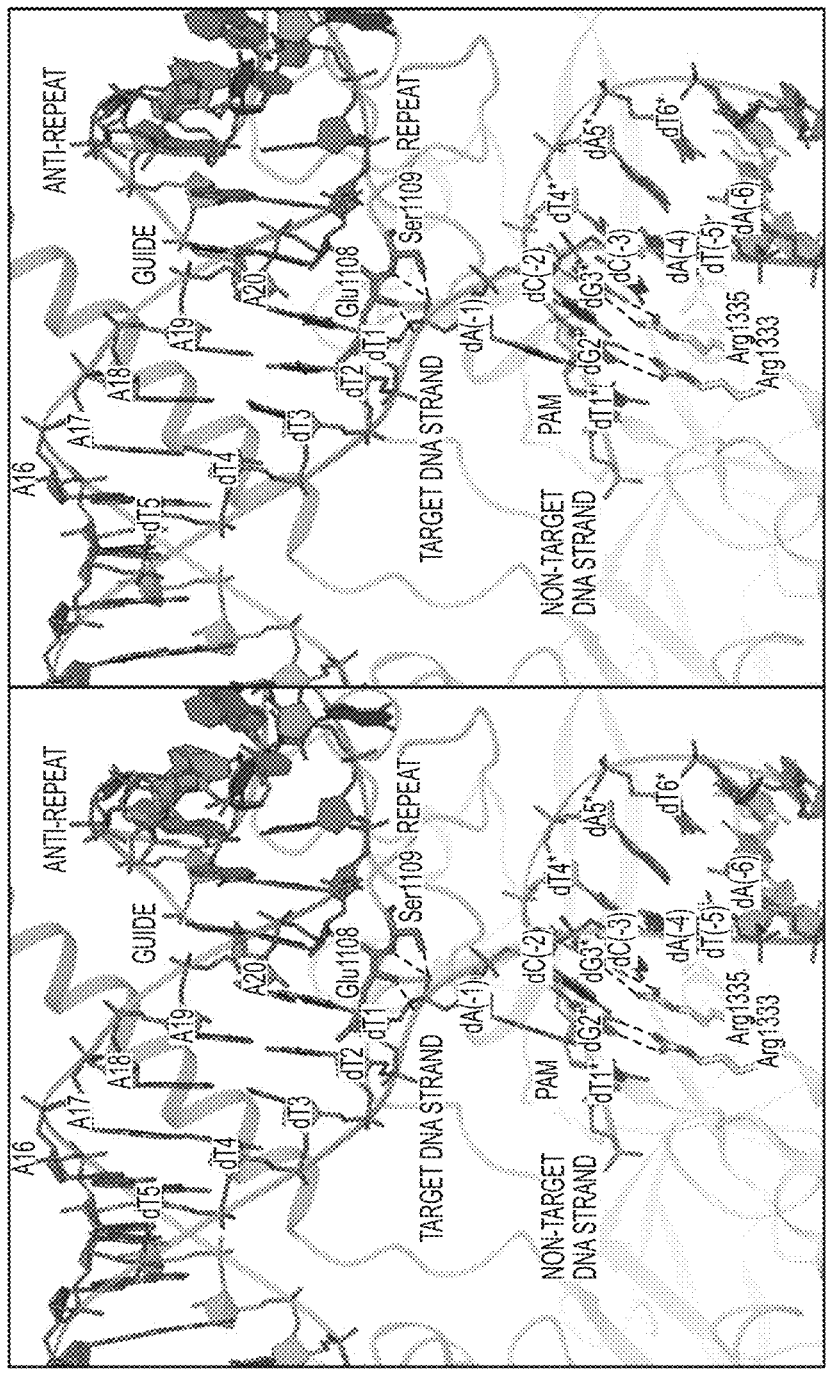
FIG. 17 shows the recognition mechanism of the target DNA in SpCas9 (PDB ID 4UN3). Hydrogen bonds are shown as dashed lines. Related to FIG. 5.

In the quaternary complex structure of SpCas9, Glu1108 and Ser1109 in the phosphate lock loop hydrogen bond with the phosphate group between dA(−1) and dT1 in the target DNA strand (referred to as +1 phosphate), and contribute to unwinding of the target DNA (Anders et al., 2014) (FIGS. 5F and 17). The present structure revealed that SaCas9 also has the phosphate lock loop, although the phosphate lock loops of SaCas9 and SpCas9 share limited sequence similarity (FIG. 5E). In the present structure of SaCas9, the +1 phosphate between dA(−1) and dG1 in the target DNA strand hydrogen bonds with the main-chain amide groups of Asp786 and Thr787 and the side-chain Og atom of Thr787 in the phosphate lock loop. These interactions result in the rotation of the +1 phosphate, thereby facilitating base-pairing between dG1 in the target DNA strand and C20 in the sgRNA. Indeed, the SaCas9 T787A mutant showed reduced DNA cleavage activity (FIG. 5C), confirming the functional significance of Thr787 in the phosphate lock loop. Together, these data indicated that the molecular mechanism of the target DNA unwinding is conserved among SaCas9 and SpCas9.

RuvC and HNH Nuclease Domains

The RuvC domain of SaCas9 has an RNase H fold, and shares structural similarity with those of SpCas9 (PDB code 4UN3, 25% identity, rmsd of 2.5 Å for 191 equivalent Ca atoms) and Actinomyces naeslundii Cas9 (AnCas9) (PDB code 4OGE, 17% identity, rmsd of 3.0 Å for 170 equivalent Ca atoms) (FIG. 6A). The catalytic residues of SaCas9 (Asp10, Glu477, His701 and Asp704) are located at positions similar to those of SpCas9 (Asp10, Glu762, His983 and Asp986) and AnCas9 (Asp17, Glu505, His736 and Asp739) (FIG. 6A). The D10A, E477A, H701A and D704A mutants of SaCas9 showed almost no DNA cleavage activities. These observations indicated that the SaCas9 RuvC domain cleaves the non-target DNA strand through a two-metal ion mechanism as in other endonucleases of the RNase H superfamily (Gorecka et al., 2013).

The HNH domain of SaCas9 has an aab-metal fold, and shares structural similarity with those of SpCas9 (PDB code 4UN3, 27% identity, rmsd of 1.8 Å for 93 equivalent Ca atoms) and AnCas9 (PDB code 4OGE, 18% identity, rmsd of 2.6 Å for 98 equivalent Ca atoms) (FIG. 6B). The catalytic residues of SaCas9 (Asp556, His557 and Asn580) are located at positions similar to those of SpCas9 (Asp839, His840 and Asn863) and AnCas9 (Asp581, His582 and Asn606), although Asn863 is oriented away from the active site in the ternary and quaternary complex structures of SpCas9 (FIG. 6B). The D556A, H557A and N580A mutants of SaCas9 showed almost no DNA cleavage activities). These observations indicated that the SaCas9 HNH domain cleaves the target DNA strand through a one-metal ion mechanism as in other aab-metal endonucleases (Biertumpfel et al., 2007).

Figure 16:
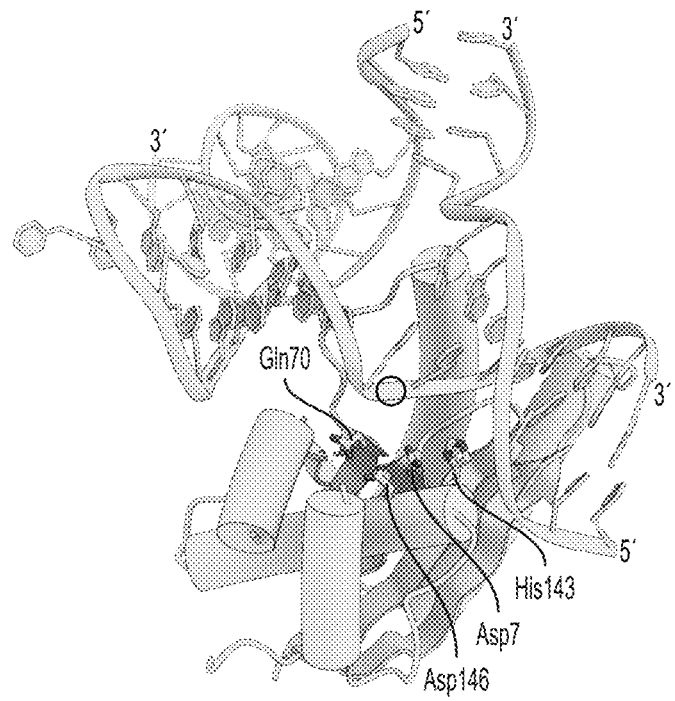
FIG. 16 shows the structural comparison of the SaCas9 RuvC domain with T. thermophilus RuvC in complex with a Holliday junction substrate (PDB ID 4LD0). The non-target DNA strand was modelled into the SaCas9 RuvC domain, based on the superimposition of T. thermophilus RuvC on SaCas9. The catalytic residues are shown as stick models. The cleavage sites of the DNA strands are indicated by magenta circles.
Figure 16:
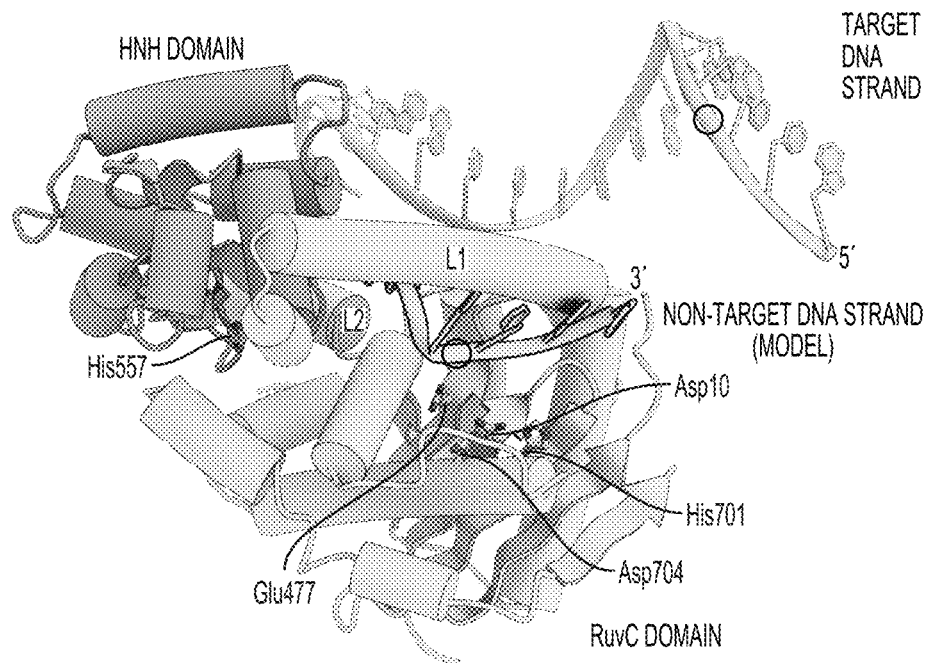

A structural comparison of SaCas9 with SpCas9 and AnCas9 revealed that the RuvC and HNH domains are connected by a-helical linker, L1 and L2, and that there are notable differences in the relative arrangements between the two nuclease domains (FIG. 6C). A biochemical study suggested that the binding of the PAM duplex to SpCas9 facilitates the cleavage of the target DNA strand by the HNH domain (Sternberg et al., 2014). However, in the quaternary complex structures of SaCas9 and SpCas9, the HNH domains are located away from the cleavage site of the target DNA strand (FIG. 6C). A structural comparison of SaCas9 with *Thermus thermophilus* RuvC in complex with a Holliday junction substrate (Gorecka et al., 2013) indicated steric clashes between the L1 linker and the modeled non-target DNA strand bound to the active site of the SaCas9 RuvC domain (FIG. 16). These observations suggested that the binding of the non-target DNA strand to the RuvC domain may contribute to triggering a conformational change in the L1, thereby bringing the HNH domain to the scissile phosphate group in the target DNA strand.

Conserved Mechanism of RNA-Guided DNA Targeting

Figure 18:
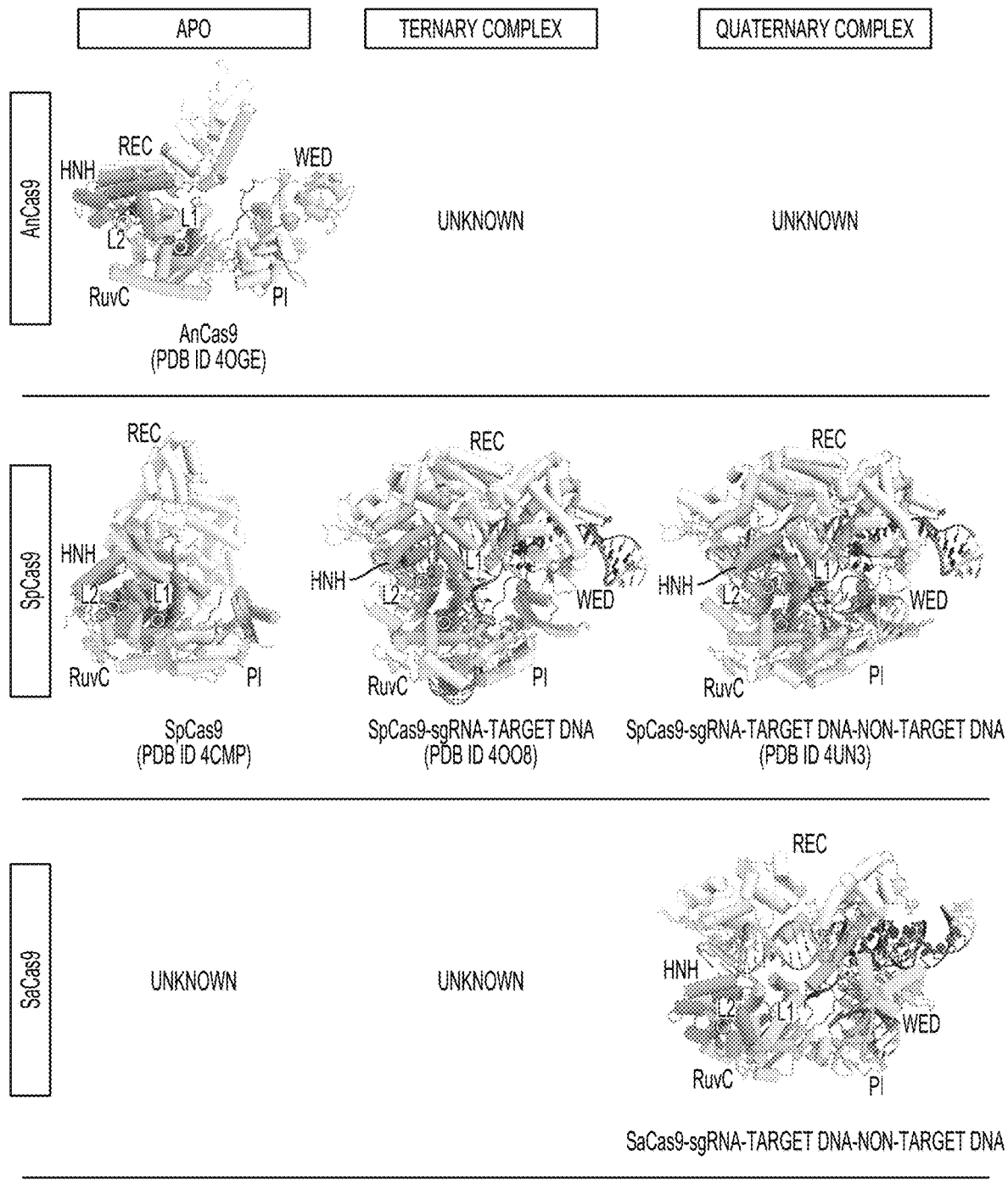
FIG. 18 shows solved crystal structures of Cas9 orthologs. The active sites of the RuvC and HNH domains, and the cleavage sites of the target DNA strands are indicated by red and magenta circles, respectively.
Figures 19A, 19B:
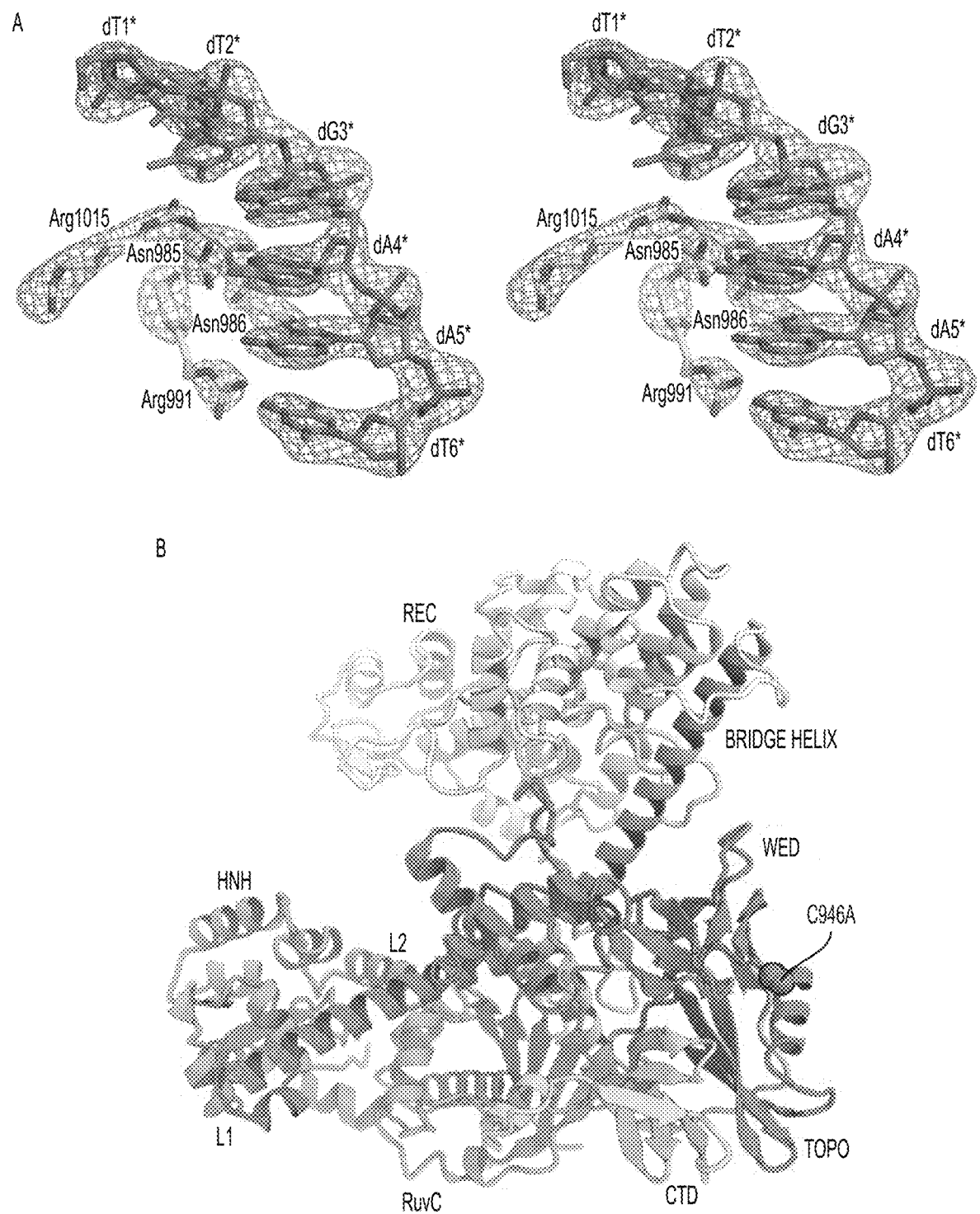
FIG. 19A-19B shows aspects of structure determination. Panel (A) shows simulated annealing omit mFo-DFc electron density map for the PAM and the PAM-interacting residues (shown as a blue mesh, contoured at 4.5σ) (stereoview). Panel (B) shows the location of the C946A mutation used in crystallization. The C946A mutation is located on a surface-exposed α helix in the TOPO domain, and does not contact the bound nucleic acids.
Figure 20:
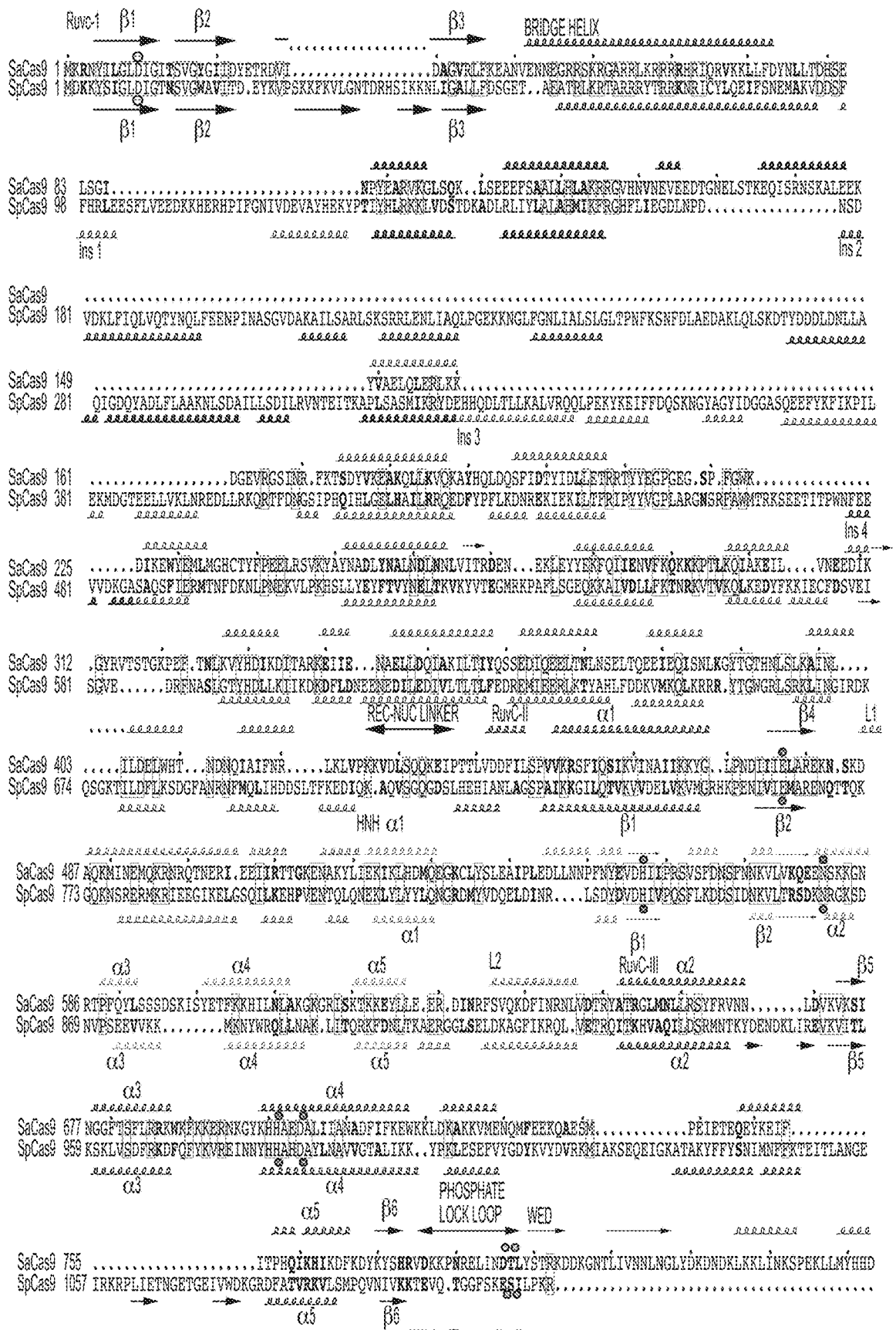
FIG. 20 shows a structure-guided sequence alignment of SaCas9 and SpCas9. The structures of SaCas9 and SpCas9 (PDB ID 4UN3) were superimposed by the secondary-structure matching (SSM) algorithm, using CueMol (worldwideweb.cuemol.org), and then the sequence alignment was manually refined. The figure was prepared using ESPript3 (espript.ibcp.fr/ESPript/ESPript/). The secondary structures of SaCas9 and SpCas9 are shown above and below the sequences, respectively. Figure discloses SEQ ID NOS 137-138, respectively, in order of appearance.
Figure 20:
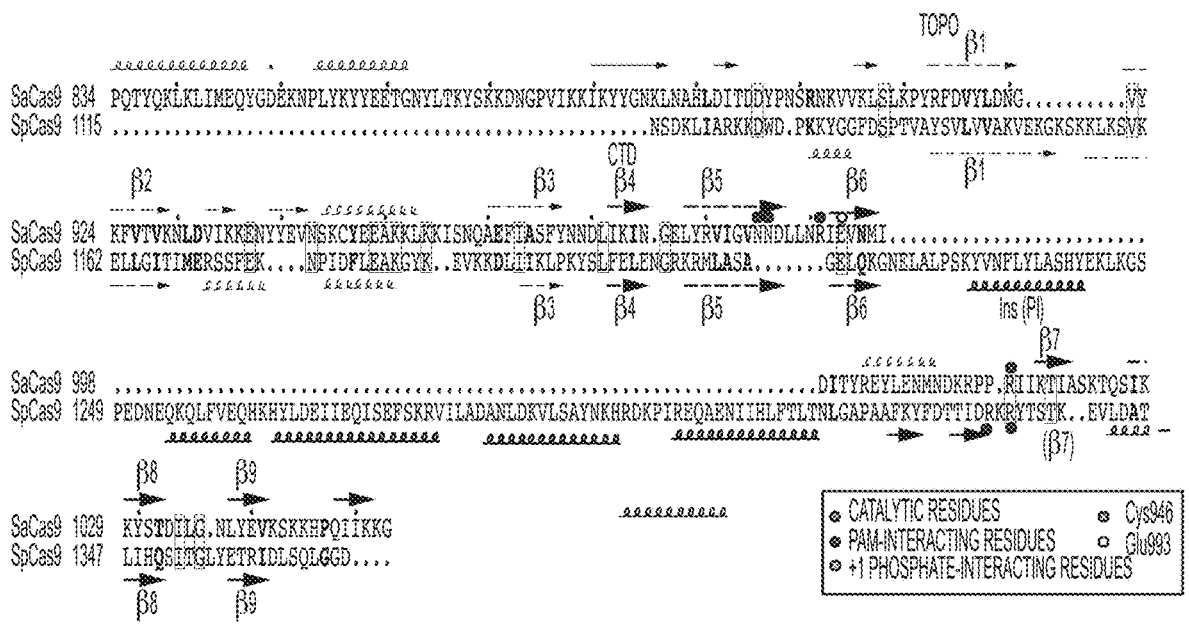
Figure 21A:
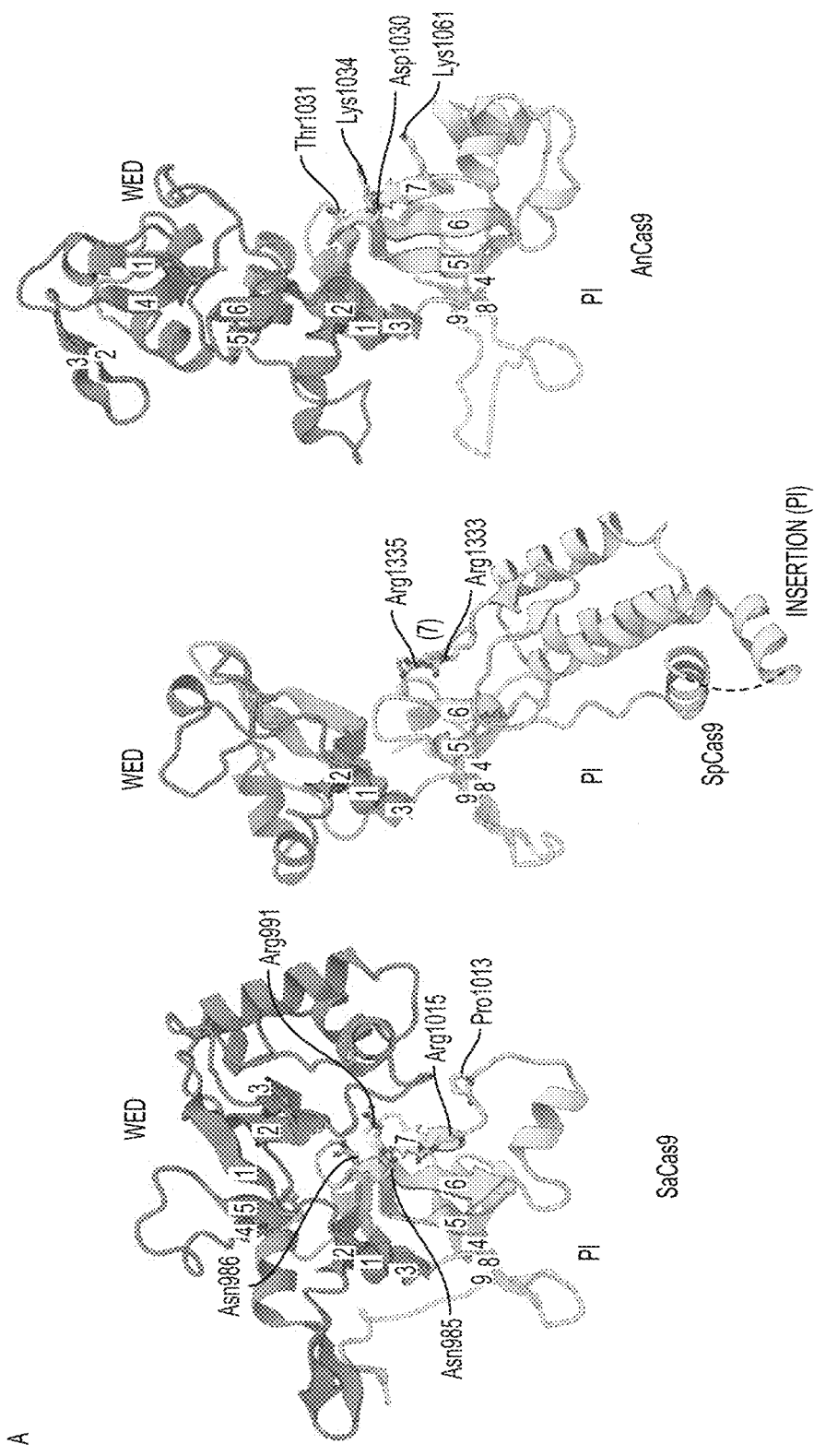
FIG. 21A-21C shows a structural comparison of the REC, WED and PI domains. Panel A depicts a structural comparison of the WED and PI domains of SaCas9, SpCas9 and AnCas9. The core β-strands in the WED and PI domains are numbered. The SpCas9-specific insertion is highlight in pale blue. The PAM-interacting residues in SaCas9 and SpCas9, and the corresponding residues in AnCas9 are shown as stick models. Panels B and C depict recognition of the sgRNA scaffolds in SaCas9 (B) and SpCas9 (PDB ID 4UN3) (C)
Figures 21B, 21C:
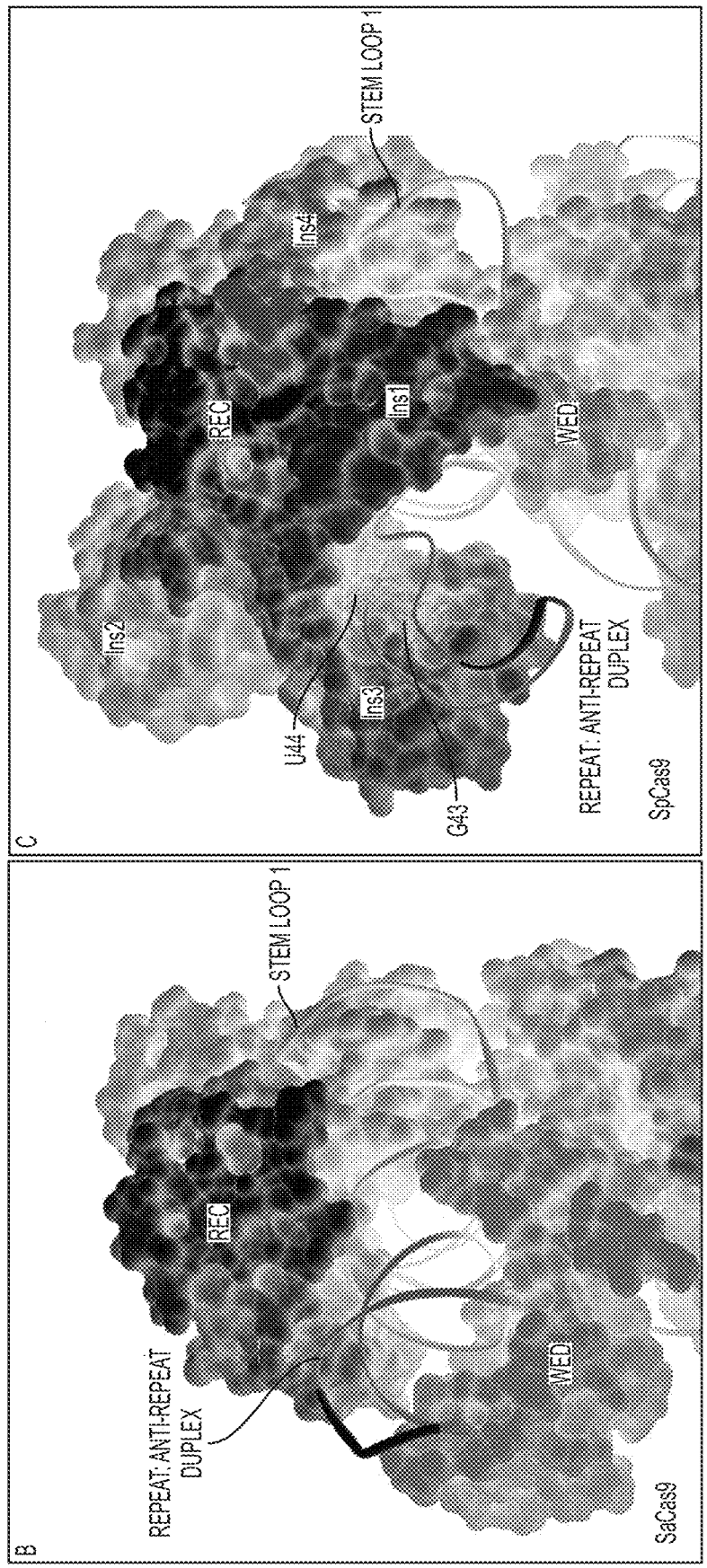

Previous structural studies revealed that SpCas9 undergoes conformational rearrangements upon guide RNA binding, to form the central channel between the REC and NUC lobes (Anders et al., 2014; Jinek et al., 2014; Nishimasu et al., 2014). In the absence of the guide RNA, SpCas9 adopts a closed conformation, where the active site of the HNH domain is covered by the RuvC domain (FIG. 18). In contrast, the ternary and quaternary complex structures of SpCas9 adopt an open conformation and have the central channel, which accommodates the guide:target heteroduplex (FIGS. 7A and 18). The quaternary complex structure of SaCas9 adopts an open conformation and has the central channel, which accommodates the guide:target heteroduplex (FIGS. 7A and 18). Thus, the guide RNA-induced conformational rearrangement is conserved among SaCas9 and SpCas9.

Figures 14A, 14B:
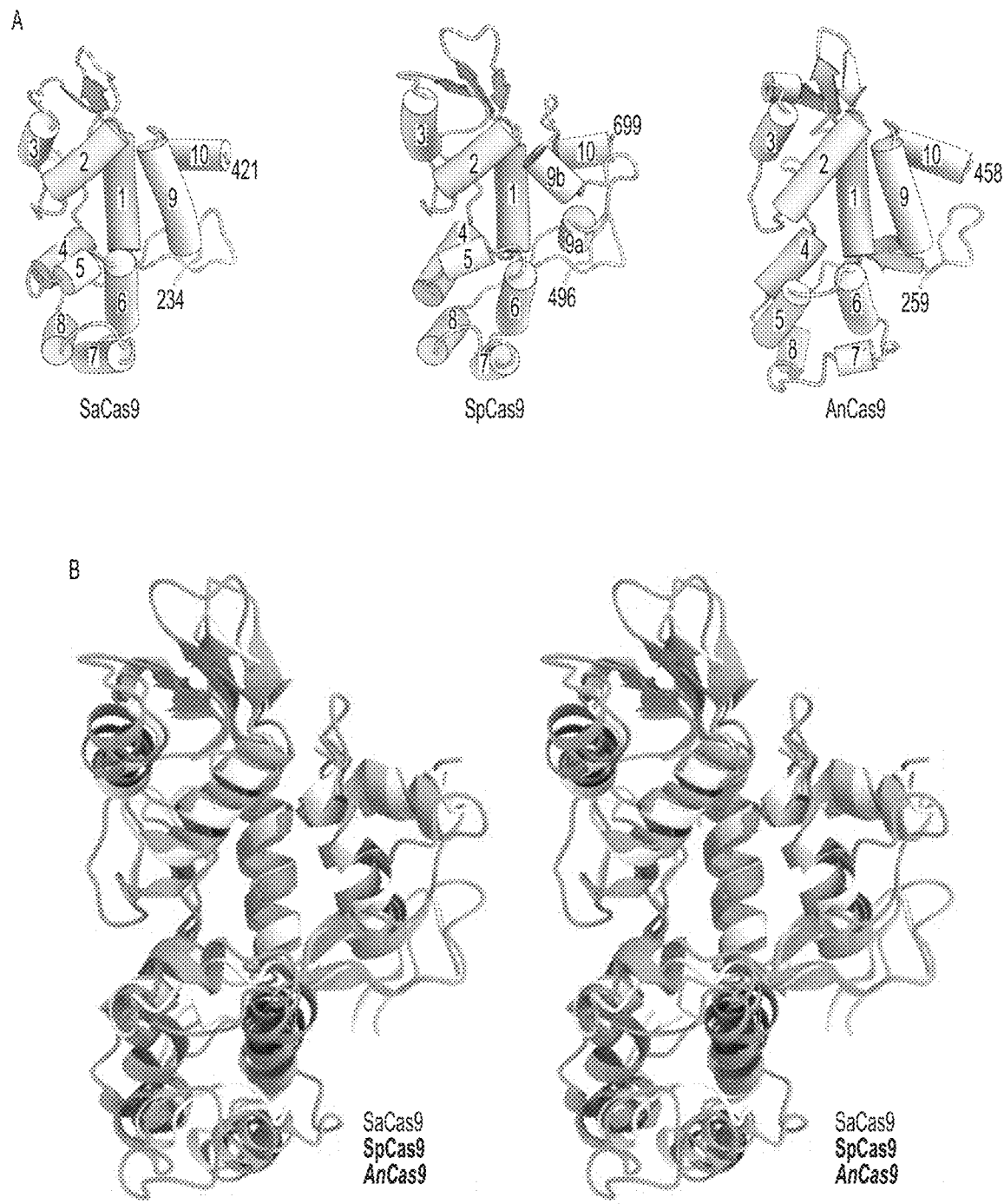
FIGS. 14A-14B shows the structural comparison between SaCas9, SpCas9 (PDB ID 4UN3) and AnCas9 (PDB ID 4OGE). (A) REC lobes (the C-terminal halves) of SaCas9, SpCas9 and AnCas9. The conserved a helices are numbered. (B) Superimposition of the REC lobes (the C-terminal halves) of SaCas9, SpCas9 and AnCas9 (stereoview).
Figures 15A, 15B:
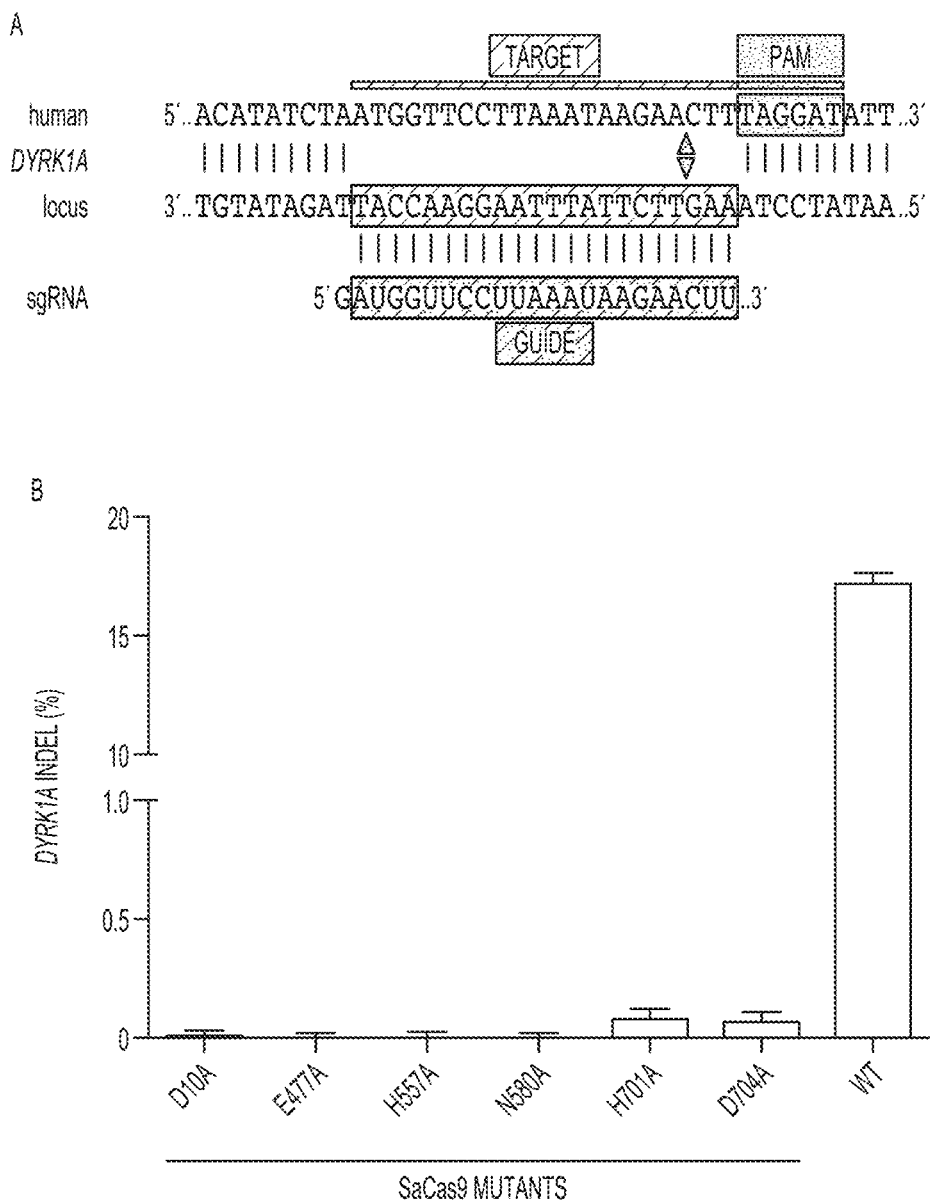
FIG. 15A-15B shows genome cleavage activity of the SaCas9 mutants bearing an alanine substitution in the catalytic residues in the RuvC and HNH nuclease domains. (A) Target sequence in the human DYRK1A locus used to test endogenous genome cleavage by the wild-type (WT) and mutants of SaCas9. The cleavage sites by the RuvC and HNH domains are indicated by cyan and pink triangles, respectively.

The REC lobes of SaCas9 and SpCas9 (PDB code 4UN3) share structural similarity (25% identity, rmsd of 2.9 Å for 353 equivalent Ca atoms), and recognize the guide:target heteroduplex in a similar manner (FIG. 7B). In particular, the seed region of the sgRNA is commonly recognized by the arginine cluster on the bridge helix in SaCas9 and SpCas9 (FIG. 7B). AnCas9 (PDB ID 4OGE) also has a REC lobe similar to those of SaCas9 and SpCas9 (FIGS. 14A and 14B). These observations suggested that the recognition mechanism of the guide:target heteroduplex is conserved among Cas9 orthologs.

Structural Basis for the Orthogonal Recognition of sgRNA Scaffolds

Figures 4E, 4F:
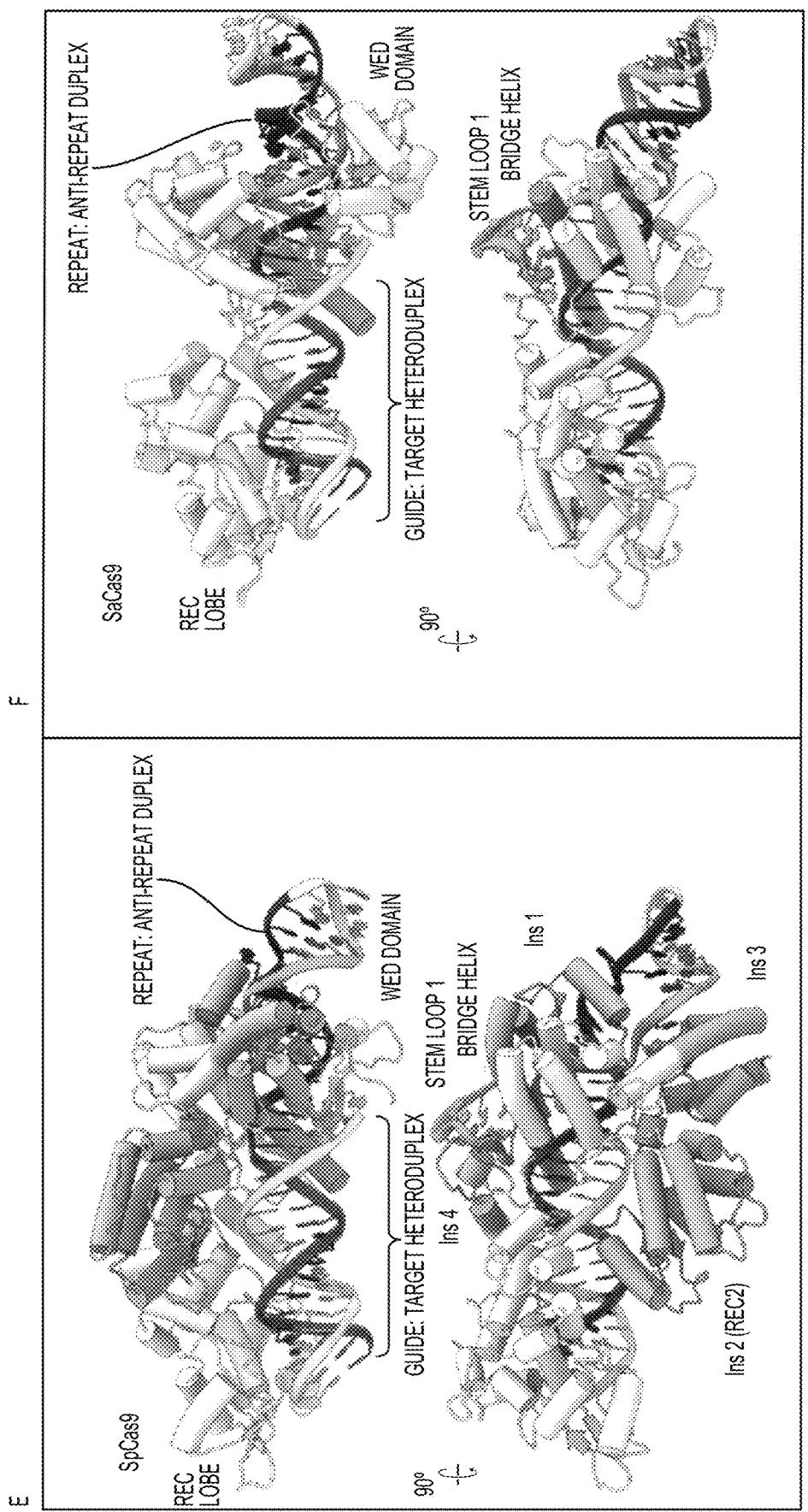

A comparison of the quaternary complex structures of SaCas9 and SpCas9 reveals that the structurally diverse REC and WED domains recognize the distinct structural features of the repeat:anti-repeat duplex, allowing cognate sgRNAs to be distinguished in an orthogonal manner (FIGS. 4E and 4F and 7A to 7D). The SpCas9 WED domain adopts a compact loop conformation (Nishimasu et al., 2014; Anders et al., 2014) (FIG. 4F and FIG. 14C). In contrast, the SaCas9 WED domain has a new fold comprising a twisted five-stranded β-sheet flanked by four α-helices (FIG. 4F and FIG. 14C). The AnCas9 WED domain has yet a different fold containing three antiparallel β-hairpins (Jinek et al., 2014) (FIG. 14C). These structural differences in the WED domains are consistent with variations in sgRNA scaffolds among CRISPR-Cas9 systems (Fonfara et al., 2014; Briner et al., 2014; Ran et al., 2015).

The REC lobe also contributes to the orthogonal recognition of sgRNA scaffolds. Although the REC lobes of SaCas9 and SpCas9 share structural similarity, the SpCas9 REC lobe has four characteristic insertions (Ins 1-4), which are absent in the SaCas9 REC lobe (FIGS. 4E and 4F). Ins 2 (also known as the REC2 domain) forms no contact with the nucleic acids in the SpCas9 structures and is dispensable for DNA cleavage activity (FIG. 4E) (Nishimasu et al., 2014), consistent with the absence of Ins2 in SaCas9 (FIG. 4F). Ins 1 and 3 recognize the SpCas9-specific internal loop in the repeat:anti-repeat duplex (FIG. 4E), while in SaCas9 the WED domain recognizes the internal loop in the repeat:anti-repeat duplex (FIG. 4F), as described above. In addition, Ins 4 interacts with stem loop 1 of the SpCas9 sgRNA, which is shorter than that of the SaCas9 sgRNA (FIG. 4E). Together, these structural observations demonstrate that the Cas9 orthologs recognize their cognate sgRNA in an orthogonal manner, using a combination of the structurally diverse REC and WED domains.

Structural Basis for the Distinct PAM Specificities

A structural comparison of SaCas9, SpCas9 and AnCas9 revealed that, despite lacking sequence homology, their PI domains share a similar protein fold (FIGS. 5D and 5E, and FIG. 14C). The PI domains consist of the Topo-homology domain, which comprises three-stranded anti-parallel β-sheet (β1-β3) flanked by several a helices, and the C-terminal domain, which comprises twisted six-stranded anti-parallel β-sheet (β4-β9) (the β7 in SpCas9 adopts a loop conformation) (FIGS. 5D and 5E, and FIG. 14C). In both SaCas9 and SpCas9, the major groove of the PAM duplex is read out by the β5-β7 region in their PI domains (FIGS. 5D and 5E). The 3rd G in the 5'-NNGRRT-3' PAM is recognized by Arg1015 in SaCas9 (FIG. 5E), and the 3rd G in the 5'-NGG-3' PAM is recognized by Arg1335 in SpCas9 and in a similar manner (FIG. 7C). However, there are also notable differences in the PI domains of SaCas9 and SpCas9, consistent with their distinct PAM specificities. Arg1333 of SpCas9, which recognizes the 2nd G in the NGG PAM, is replaced with Pro1013 in SaCas9 (FIGS. 5D and 5E). In addition, SpCas9 lacks amino acid residues equivalent to Asn985/Asn986 (β5) and Arg991 (β6) of SaCas9, because the β5-β6 region of SpCas9 is shorter than that of SaCas9 (FIGS. 5D and 5E). Moreover, Asn985, Asn986, Arg991 and Arg1015 in SaCas9 are replaced with Asp1030, Thr1031, Lys1034 and Lys1061 in AnCas9, respectively (FIG. 14C), suggesting that the PAM for AnCas9 is different from those for SaCas9 and SpCas9. Together, these structural findings demonstrated that distinct PAM specificities of Cas9 orthologs are primarily defined by their structurally diverse PI domains.

Figures 8C, 8D:
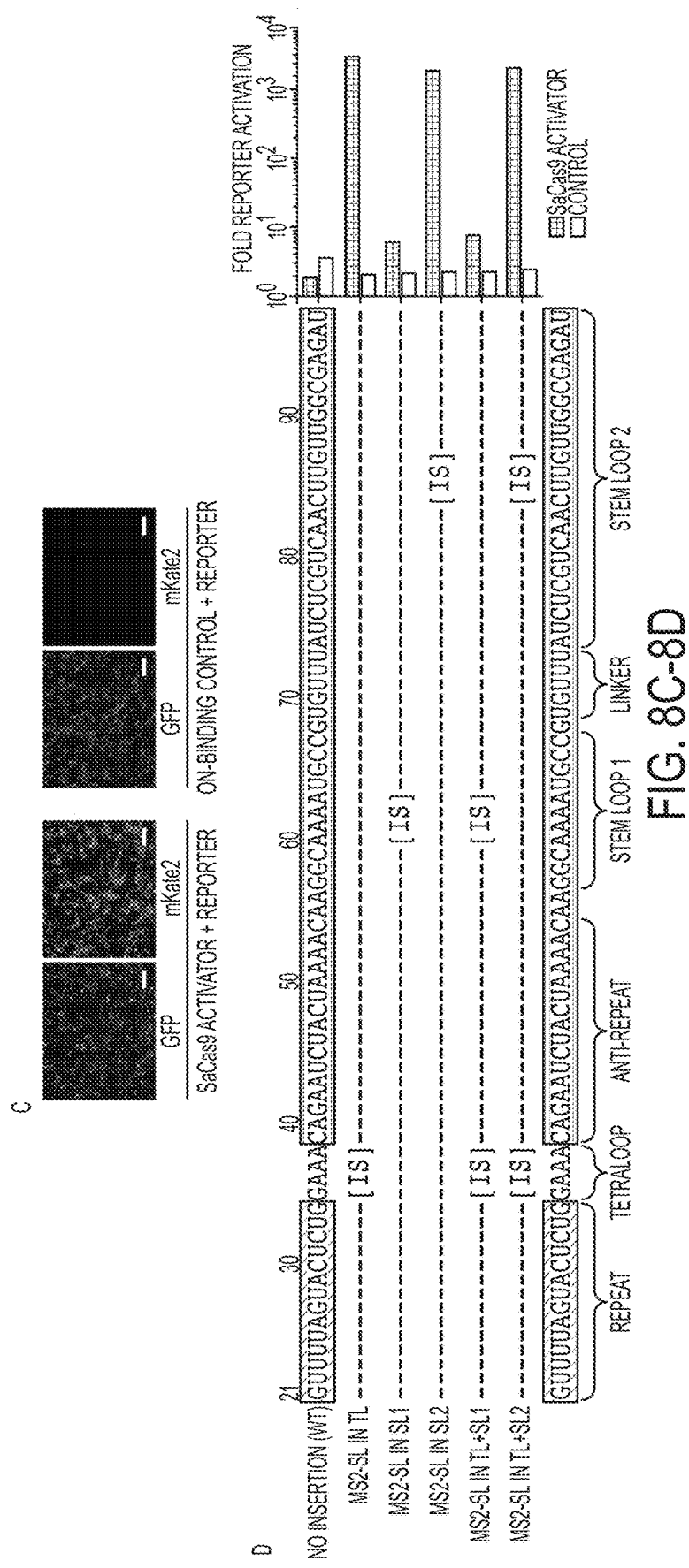
Figures 8E, 8F, 8G, 8H, 8I, 8J:
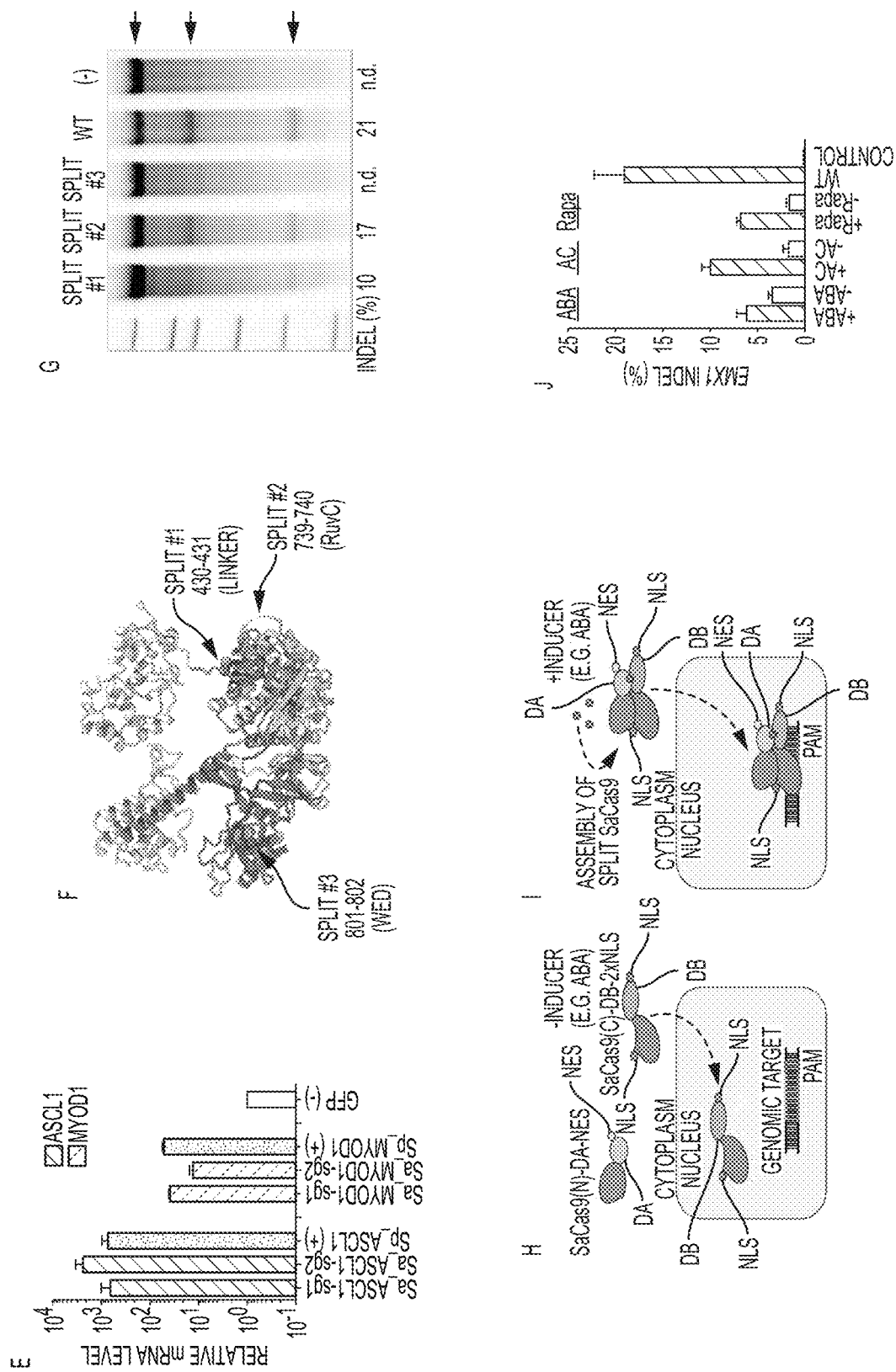

Structure-Guided Engineering of SaCas9 Transcription Activators and Inducible Nucleases Using the crystal structure of SaCas9, we conducted structure-guided engineering to further expand the CRISPR-Cas9 toolbox. Given the similarities in the overall domain organization of SaCas9 and SpCas9, we initially explored the feasibility of engineering the SaCas9 sgRNA to develop robust transcription activators. In the SpCas9 structure, the tetraloop and stem loop 2 of the sgRNA are exposed to solvent (Anders et al., 2014; Nishimasu et al., 2014) (FIG. 2F) and permitted insertion of RNA aptamers into the sgRNA to create robust RNA-guided transcription activators (Konermann et al., 2015). To generate the SaCas9-based activator system, we created a catalytically inactive version of SaCas9 (dSaCas9) by introducing D10A and N580A mutations to inactivate the RuvC and HNH domains, respectively, and attached VP64 to the C-terminus of dSaCas9 (FIG. 8A). The sgRNA scaffold was modified with the insertion of MS2 aptamer stem loop (MS2-SL) to allow recruitment of MS2-p65-HSF1 transcriptional activation modules (FIG. 8A). To evaluate the dSaCas9-based activator design, we constructed a transcriptional activation reporter system consisting of tandem sgRNA target sites upstream of a minimal CMV promoter driving the expression of the fluorescent reporter gene mKate2 (Zhang et al., 2011) (FIG. 8B). We included an additional transcriptional termination signal upstream of the reporter cassette to reduce the background previously observed in a similar reporter design (Cong et al., 2012) (FIG. 8B). We observed robust activation of mKate2 transcription when we expressed the engineered sgRNA complementary to the target sites, whereas the non-binding sgRNA had no detectable effect (FIG. 8C). Based on a screening of different sgRNA designs with this reporter assay, we found that insertions of MS2-SL into the tetraloop and putative stem loop 2 are able to induce strong activation in our reporter system, whereas insertion of MS2-SL into stem loop 1 yielded modest activation, consistent with the structural data (FIG. 8D). The single insertion of MS2-SL into the tetraloop was the simplest design that yielded strong transcriptional activation. Using this optimal sgRNA design, we further tested activation of endogenous targets in the human genome. We selected two guides each for the human ASCL1 and MYOD1 genomic loci, and demonstrated that the dSaCas9-based activator system was able to activate both genes to levels comparable to those of the dSpCas9-based activator (Konermann et al., 2013) (FIG. 8E). Given that the sgRNAs for SaCas9 and SpCas9 are not interchangeable, the SaCas9-based transcription activator platform complement the SpCas9-based activator systems by allowing for independent activation of different sets of genes.

The SpCas9 structure also facilitated the rational design of split-Cas9s (Zetsche et al., 2015; Wright et al., 2015), which can be further engineered into an inducible system (Zetsche et al., 2015). Our SaCas9 structure reveals several flexible regions in SaCas9 that could likewise serve as potential split sites (FIG. 8F). We created three versions of a split-SaCas9, two of which showed robust cleavage activity at the endogenous EMX1 target locus (FIG. 8G). Using the best split design, we then tested inducible schemes based on the abscisic acid (ABA) sensing system (Liang et al., 2011) as well as two versions of the rapamycin-inducible FKBP/FRB system (Banaszynski et al., 2005) (FIGS. 8H and 8I). All three systems were able to support inducible SaCas9 cleavage activity, demonstrating the possibility of an inducible, split-SaCas9 design; however, further optimization will increase its efficiency and reduce its background activity (FIG. 8J).

CONCLUSION

The present structures of SaCas9 in complex with the sgRNA and the PAM-containing target DNA have provided mechanistic insights into the RNA-guided DNA targeting by SaCas9. A structural comparison of SaCas9 with SpCas9 (Anders et al., 2014; Jinek et al., 2014; Nishimasu et al., 2014) and AnCas9 (Jinek et al., 2014) illuminated conserved structural features among the orthologous CRISPR-Cas9 systems. SaCas9 and SpCas9 both have the bilobed architecture consisting of the REC and NUC lobes, which is connected by the bridge helix. The guide:target heteroduplex is accommodated in the central channel between the two lobes. In addition, SaCas9 and SpCas9 have the phosphate lock loop, which participates in the local strand separation of the target DNA. A structural comparison of the Cas9 orthologs also revealed that the HNH and RuvC domains are connected the L1 and L2 linkers. It is likely that these linker regions play a role in the inactive-to-active conformational transition of the HNH domain during catalysis, although further structural and functional studies will be required to elucidate the activation mechanism of Cas9 endonucleases.

A structural comparison of the Cas9 orthologs also highlighted the structural diversity among the CRISPR-Cas9 systems. The REC lobe of SaCas9 lacks a region corresponding to the SpCas9 REC2 domain, providing a molecular framework for the rational design of smaller Cas9 proteins. The PI domains of SaCas9, SpCas9 and AnCas9 share a similar core structure, but contain diverse PAM-interacting residues, consistent with their distinct PAM specificities. Moreover, Applicants found that the structurally diverse WED domains participate in the recognition of the repeat:anti-repeat duplex, which is diverse in structure and sequence among the CRISPR-Cas9 systems, thereby explaining the orthogonal recognition of cognate crRNA:tracrRNA by Cas9 orthologs.

Applicants developed dSaCas9-based transcription activators, and demonstrated that the engineered SaCas9 sgRNA can serve as a platform for recruiting multiple MS2-fused proteins. These results have opened the possibility that the combinatorial use of dSaCas9- and dSpCas9-based transcription regulation systems enables simultaneous activation and repression of multiple target endogenous loci. Overall, the present structural information described herein will serve as a blueprint for further Cas9 engineering, such as the design of smaller Cas9 variants with expanded PAM specificities, which will enable more versatile genome engineering.

REFERENCES

Adams, P. D., Afonine, P. V., Bunkoczi, G., Chen, V. B., Davis, I. W., Echols, N., Headd, J. J., Hung, L. W., Kapral, G. J., Grosse-Kunstleve, R. W., et al. (2010). PHENIX: a comprehensive Python-based system for macromolecular structure solution. Acta Crystallogr D Biol Crystallogr 66, 213-221.

Banaszynski, L. A., Liu, C. W., and Wandless, T. J. (2005). Characterization of the FKBP.rapamycin.FRB ternary complex. Journal of the American Chemical Society 127, 4715-4721.

Barrangou, R., Fremaux, C., Deveau, H., Richards, M., Boyaval, P., Moineau, S., Romero, D. A., and Horvath, P. (2007). CRISPR provides acquired resistance against viruses in prokaryotes. Science 315, 1709-1712.

Anders, C., Niewoehner, O., Duerst, A., and Jinek, M. (2014). Structural basis of PAM-dependent target DNA recognition by the Cas9 endonuclease. Nature 513, 569-573.

Biertumpfel, C., Yang, W., and Suck, D. (2007). Crystal structure of T4 endonuclease VII resolving a Holliday junction. Nature 449, 616-620.

Bolotin, A., Quinquis, B., Sorokin, A., and Ehrlich, S. D. (2005). Clustered regularly interspaced short palindrome repeats (CRISPRs) have spacers of extrachromosomal origin. Microbiology 151, 2551-2561.

Briner, A. E., Donohoue, P. D., Gomaa, A. A., Selle, K., Slorach, E. M., Nye, C. H., Haurwitz, R. E., Beisel, C. L., May, A. P., and Barrangou, R. (2014). Guide RNA functional modules direct Cas9 activity and orthogonality. Molecular cell 56, 333-339.

Brouns, S. J., Jore, M. M., Lundgren, M., Westra, E. R., Slijkhuis, R. J., Snijders, A. P., Dickman, M. J., Makarova, K. S., Koonin, E. V., and van der Oost, J. (2008). Small CRISPR RNAs guide antiviral defense in prokaryotes. Science 321, 960-964.

Cho, S. W., Kim, S., Kim, J. M., and Kim, J. S. (2013). Targeted genome engineering in human cells with the Cas9 RNA-guided endonuclease. Nature biotechnology 31, 230-232.

Chylinski, K., Le Rhun, A., and Charpentier, E. (2013). The tracrRNA and Cas9 families of type II CRISPR-Cas immunity systems. RNA Biol 10, 726-737.

Chylinski, K., Makarova, K. S., Charpentier, E., and Koonin, E. V. (2014). Classification and evolution of type II CRISPR-Cas systems. Nucleic acids research.

Cong, L., Ran, F. A., Cox, D., Lin, S., Barretto, R., Habib, N., Hsu, P. D., Wu, X., Jiang, W., Marraffini, L. A., et al. (2013). Multiplex genome engineering using CRISPR/Cas systems. Science 339, 819-823.

Cong, L., Zhou, R., Kuo, Y. C., Cunniff, M., and Zhang, F. (2012). Comprehensive interrogation of natural TALE DNA-binding modules and transcriptional repressor domains. Nature communications 3, 968.

Cowtan, K. (2006). The Buccaneer software for automated model building. 1. Tracing protein chains. Acta Crystallogr D Biol Crystallogr 62, 1002-1011.

Deltcheva, E., Chylinski, K., Sharma, C. M., Gonzales, K., Chao, Y., Pirzada, Z. A., Eckert, M. R., Vogel, J., and Charpentier, E. (2011). CRISPR RNA maturation by trans-encoded small RNA and host factor RNase III. Nature 471, 602-607.

Deveau, H., Barrangou, R., Garneau, J. E., Labonte, J., Fremaux, C., Boyaval, P., Romero, D. A., Horvath, P., and Moineau, S. (2008). Phage response to CRISPR-encoded resistance in Streptococcus thermophilus. J Bacteriol 190, 1390-1400.

Emsley, P., and Cowtan, K. (2004). Coot: model-building tools for molecular graphics. Acta Crystallogr D Biol Crystallogr 60, 2126-2132.

Esvelt, K. M., Mali, P., Braff, J. L., Moosburner, M., Yaung, S. J., and Church, G. M. (2013). Orthogonal Cas9 proteins for RNA-guided gene regulation and editing. Nat Methods 10, 1116-1121.

Evans, P. R., and Murshudov, G. N. (2013). How good are my data and what is the resolution? Acta Crystallogr D Biol Crystallogr 69, 1204-1214.

Fonfara, I., Le Rhun, A., Chylinski, K., Makarova, K. S., Lecrivain, A. L., Bzdrenga, J., Koonin, E. V., and Charpentier, E. (2014). Phylogeny of Cas9 determines functional exchangeability of dual-RNA and Cas9 among orthologous type II CRISPR-Cas systems. Nucleic Acids Res 42, 2577-2590.

Garneau, J. E., Dupuis, M. E., Villion, M., Romero, D. A., Barrangou, R., Boyaval, P., Fremaux, C., Horvath, P., Magadan, A. H., and Moineau, S. (2010). The CRISPR/Cas bacterial immune system cleaves bacteriophage and plasmid DNA. Nature 468, 67-71.

Gasiunas, G., Barrangou, R., Horvath, P., and Siksnys, V. (2012). Cas9-crRNA ribonucleoprotein complex mediates specific DNA cleavage for adaptive immunity in bacteria. Proc Natl Acad Sci USA 109, E2579-2586.

Gorecka, K. M., Komorowska, W., and Nowotny, M. (2013). Crystal structure of RuvC resolvase in complex with Holliday junction substrate. Nucleic Acids Res 41, 9945-9955.

Hsu, P. D., Scott, D. A., Weinstein, J. A., Ran, F. A., Konermann, S., Agarwala, V., Li, Y., Fine, E. J., Wu, X., Shalem, O., et al. (2013). DNA targeting specificity of RNA-guided Cas9 nucleases. Nat Biotechnol 31, 827-832.

Hwang, W. Y., Fu, Y., Reyon, D., Maeder, M. L., Tsai, S. Q., Sander, J. D., Peterson, R. T., Yeh, J. R., and Joung, J. K. (2013). Efficient genome editing in zebrafish using a CRISPR-Cas system. Nature biotechnology 31, 227-229.

Jiang, F., Zhou, K., Ma, L., Gressel, S., and Doudna, J. A. (2015). A Cas9-guide RNA complex preorganized for target DNA recognition. Science 348, 1477-1481.

Jiang, W., Bikard, D., Cox, D., Zhang, F., and Marraffini, L. A. (2013). RNA-guided editing of bacterial genomes using CRISPR-Cas systems. Nature biotechnology 31, 233-239.

Jinek, M., Chylinski, K., Fonfara, I., Hauer, M., Doudna, J. A., and Charpentier, E. (2012). A programmable dual-RNA-guided DNA endonuclease in adaptive bacterial immunity. Science 337, 816-821.

Jinek, M., East, A., Cheng, A., Lin, S., Ma, E., and Doudna, J. (2013). RNA-programmed genome editing in human cells. Elife 2, e00471.

Jinek, M., Jiang, F., Taylor, D. W., Sternberg, S. H., Kaya, E., Ma, E., Anders, C., Hauer, M., Zhou, K., Lin, S., et al. (2014). Structures of Cas9 endonucleases reveal RNA-mediated conformational activation. Science 343, 1247997.

Kabsch, W. (2010). Xds. Acta Crystallogr D Biol Crystallogr 66, 125-132.

Konermann, S., Brigham, M. D., Trevino, A. E., Hsu, P. D., Heidenreich, M., Cong, L., Platt, R. J., Scott, D. A., Church, G. M., and Zhang, F. (2013). Optical control of mammalian endogenous transcription and epigenetic states. Nature 500, 472-476.

Konermann, S., Brigham, M. D., Trevino, A. E., Joung, J., Abudayyeh, O. O, Barcena, C., Hsu, P. D., Habib, N., Gootenberg, J. S., Nishimasu, H., et al. (2015). Genome-scale transcriptional activation by an engineered CRISPR-Cas9 complex. Nature 517, 583-588.

Liang, F. S., Ho, W. Q., and Crabtree, G. R. (2011). Engineering the ABA plant stress pathway for regulation of induced proximity. Science signaling 4, rs2.

Makarova, K. S., Grishin, N. V., Shabalina, S. A., Wolf, Y. I., and Koonin, E. V. (2006). A putative RNA-interference-based immune system in prokaryotes: computational analysis of the predicted enzymatic machinery, functional analogies with eukaryotic RNAi, and hypothetical mechanisms of action. Biol Direct 1, 7.

Mali, P., Yang, L., Esvelt, K. M., Aach, J., Guell, M., DiCarlo, J. E., Norville, J. E., and Church, G. M. (2013). RNA-guided human genome engineering via Cas9. Science 339, 823-826.

Marraffini, L. A., and Sontheimer, E. J. (2008). CRISPR interference limits horizontal gene transfer in staphylococci by targeting DNA. Science 322, 1843-1845.

Mojica, F. J., Diez-Villasenor, C., Garcia-Martinez, J., and Almendros, C. (2009). Short motif sequences determine the targets of the prokaryotic CRISPR defence system. Microbiology 155, 733-740.

Mojica, F. J., Diez-Villasenor, C., Garcia-Martinez, J., and Soria, E. (2005). Intervening sequences of regularly spaced prokaryotic repeats derive from foreign genetic elements. J Mol Evol 60, 174-182.

Nishimasu, H., Ran, F. A., Hsu, P. D., Konermann, S., Shehata, S. I., Dohmae, N., Ishitani, R., Zhang, F., and Nureki, O. (2014). Crystal structure of Cas9 in complex with guide RNA and target DNA. Cell 156, 935-949.

Pourcel, C., Salvignol, G., and Vergnaud, G. (2005). CRISPR elements in Yersinia pestis acquire new repeats by preferential uptake of bacteriophage DNA, and provide additional tools for evolutionary studies. Microbiology 151, 653-663.

Ran, F. A., Cong, L., Yan, W. X., Scott, D. A., Gootenberg, J. S., Kriz, A. J., Zetsche, B., Shalem, O., Wu, X., Makarova, K. S., et al. (2015). In vivo genome editing using Staphylococcus aureus Cas9. Nature 520, 186-191.

Sapranauskas, R., Gasiunas, G., Fremaux, C., Barrangou, R., Horvath, P., and Siksnys, V. (2011). The Streptococcus thermophilus CRISPR/Cas system provides immunity in Escherichia coli. Nucleic acids research 39, 9275-9282.

Sternberg, S. H., Redding, S., Jinek, M., Greene, E. C., and Doudna, J. A. (2014). DNA interrogation by the CRISPR RNA-guided endonuclease Cas9. Nature 507, 62-67.

Vagin, A., and Teplyakov, A. (2010). Molecular replacement with MOLREP. Acta Crystallogr D Biol Crystallogr 66, 22-25.

Wright, A. V., Sternberg, S. H., Taylor, D. W., Staahl, B. T., Bardales, J. A., Kornfeld, J. E., and Doudna, J. A. (2015). Rational design of a split-Cas9 enzyme complex. Proc Natl Acad Sci USA. 112, 2984-2989.

Zalatan, J. G., Lee, M. E., Almeida, R., Gilbert, L. A., Whitehead, E. H., La Russa, M., Tsai, J. C., Weissman, J. S., Dueber, J. E., Qi, L. S., et al. (2015). Engineering complex synthetic transcriptional programs with CRISPR RNA scaffolds. Cell 160, 339-350.

Zetsche, B., Volz, S. E., and Zhang, F. (2015). A split-Cas9 architecture for inducible genome editing and transcription modulation. Nat Biotechnol 33, 139-142.

Zhang, F., Cong, L., Lodato, S., Kosuri, S., Church, G. M., and Arlotta, P. (2011). Efficient construction of sequence-specific TAL effectors for modulating mammalian transcription. Nature biotechnology 29, 149-153.

Example 2: SaCas9 Crystal

Sample Preparation. The gene encoding full-length S. aureus Cas9 (SaCas9; residues 1-1053) was cloned between the NdeI and XhoI sites of the modified pE-SUMO vector (LifeSensors), and the N580A/C946A mutations were introduced by a PCR-based method. The SaCas9 N580A/C946A mutant protein was expressed at 20° C. in Escherichia coli Rosetta 2 (DE3) (Novagen), and was purified by chromatography on Ni-NTA Superflow resin (QIAGEN). The eluted protein was incubated overnight at 4° C. with TEV protease to remove the His6-SUMO-tag ("His6" disclosed as SEQ ID NO: 77), and was further purified by chromatography on Ni-NTA, Mono S (GE Healthcare) and HiLoad Superdex 200 16/60 (GE Healthcare) columns. The SeMet-labeled SaCas9 N580A/C946A mutant protein was expressed in E. coli B834 (DE3), and was purified using a similar protocol to that for the native protein. The 73-nt sgRNA was transcribed in vitro with T7 RNA polymerase, using a double-stranded DNA template, which was generated by PCR using pairs of oligonucleotides. The transcribed RNA was purified by 8% denaturing (7 M urea) polyacrylamide gel electrophoresis. The 28-nt target and 8-nt non-target DNA strands were purchased from Sigma-Aldrich. The purified SaCas9 protein was mixed with sgRNA, target DNA strand and non-target DNA strand (containing either the 5'-TTGAAT-3' PAM or the 5'-TTGGGT-3' PAM) (molar ratio, 1:1.5:2.3:3.4), and then the SaCas9-sgRNA-target DNA complex was purified by gel filtration chromatography on a Superdex 200 Increase column (GE Healthcare), in a buffer consisting of 10 mM Tris-HCl, pH 8.0, 150 mM NaCl and 1 mM DTT. For in vitro cleavage assays, the wild-type SaCas9 protein was prepared using a similar protocol to that for the N580A/C946A mutant, except that the size-exclusion chromatography step was omitted.

Crystallography. The purified SaCas9-sgRNA-target DNA complex (containing either the 5'-TTGAAT-3' PAM or the 5'-TTGGGT-3' PAM) was crystallized at 20° C. by the hanging-drop vapor diffusion method. Crystals were obtained by mixing 1 μl of complex solution ($A_{260\ nm}$=15) and 1 μl of reservoir solution (10-12% PEG 4,000, 0.75 M NaCl, 0.15 M $Na_2HPO_4$ and 0.15 M $NaN_3$). The SeMet-labeled complex (containing the 5'-TTGAAT-3' PAM) was also crystallized under similar conditions. X-ray diffraction data were collected at 100 K on beamlines BL32XU and BL41XU at SPring-8 (Hyogo, Japan). The crystals were cryoprotected in reservoir solution supplemented with 25% ethylene glycol. X-ray diffraction data were processed using XDS (Kabsch, 2010) and AIMLESS (Evans and Murshudov, 2013). The structure was determined by the Se-SAD method, using PHENIX AutoSol (Adams et al., 2010). The model was automatically built using Buccaneer (Cowtan, 2006), followed by manual model building using COOT (Emsley and Cowtan, 2004) and structural refinement using PHENIX (Adams et al., 2010). The resulting model was refined, using the 2.6 Å resolution native data set (the 5'-TTGAAT-3' PAM complex). The structure of the 5'-TTGGGT-3' PAM complex was solved by molecular replacement with MOLREP (Vagin and Teplyakov, 2010).

Lengthy table referenced here

US12168789-20241217-T00001

Please refer to the end of the specification for access instructions.

Example 3: Experimental Protocols

SURVEYOR Nuclease Assay for Genome Modification and Western Blots.

HEK 293FT cells were transfected with DNA, as described above. Cells were incubated at 37° C. for 72 h post-transfection, prior to genomic DNA extraction. Genomic DNA was extracted using QuickExtract DNA Extraction Solution (Epicentre), according to the manufacturer's protocol. Briefly, pelleted cells were resuspended in QuickExtract solution and incubated at 65° C. for 15 min, 68° C. for 15 min, and 98° C. for 10 min. The genomic region flanking the CRISPR target site for each gene was PCR-amplified, and the products were purified using a QiaQuick Spin Column (Qiagen), according to the manufacturer's protocol. The purified PCR products (400 ng) were mixed with 2 ml of 10× Taq DNA Polymerase PCR buffer (Enzymatics) and ultrapure water to a final volume of 20 ml, and subjected to a re-annealing process to enable heteroduplex formation: 95° C. for 10 min, 95° C. to 85° C. ramping at −2° C./s, 85° C. to 25° C. at −0.25° C./s, and 25° C. hold for 1 min. After re-annealing, the products were treated with SURVEYOR nuclease and SURVEYOR enhancer S (Transgenomics), following the manufacturer's recommended protocol, and analyzed on 4-20% Novex TBE polyacrylamide gels (Life Technologies). The gels were stained with SYBR Gold DNA stain (Life Technologies) for 30 min and imaged with a Gel Doc gel imaging system (Bio-Rad). Quantification was based on relative band intensities. Indel percentage was determined by the following formula: $100 \times (1-(1-(b+c)/(a+b+c))^{1/2})$, where a is the integrated intensity of the undigested PCR product, and b and c are the integrated intensities of each cleavage product.

HEK 293FT cells were transfected and lysed in 1× RIPA buffer (Sigma-Aldrich) supplemented with Protease Inhibitor (Roche). The lysates were loaded onto Bolt 4-12% Bis-Tris Plus Gels (Invitrogen) and transferred to nitrocellulose membranes. The membranes were blocked in Tris-buffered saline containing 0.1% Tween-20 and 5% blocking agent (G-Biosciences). The membranes were probed with rabbit anti-FLAG (1:5,000, Abcam), HRP-conjugated anti-GAPDH (1:5,000 Cell Signaling Technology), and H1RP-conjugated anti-rabbit (1:1,000) antibodies and visualized with a Gel Doc XR+ System (Bio-Rad).

In Vitro Cleavage Assay

In vitro plasmid DNA cleavage experiments were performed essentially as described (Anders et al., 2014). The EcoRI-linearized pUC119 plasmid (150 ng) containing the 20-nt target sequence and the 5'-TTGAAT-3' PAM was incubated at 37° C. for 1 h with the SaCas9-sgRNA complex (8, 16, 32 nM), in 20 mM HEPES pH 7.5, 100 mM KCl, 5% glycerol, 1 mM DTT and 2 mM $MgCl_2$ (10 µl total volume). Reaction products were resolved on an ethidium bromide-stained 1% agarose gel, and then visualized using a Typhoon FLA 9500 scanner (GE Healthcare).

Cell Culture and Transfection

Human embryonic kidney 293FT (Life Technologies) cells were maintained in Dulbecco's modified Eagle's Medium (DMEM) supplemented with 10% FBS and 2 mM GlutaMAX in incubators at 37° C. with 5% CO2 supply.

Around 24 h prior to transfection, cells were seeded into 24-well plates (Corning) at a density of 250,000 cells per well, and transfected at 70-80% confluency using Lipofectamine 2000 (Life Technologies), according to the manufacturer's recommended protocol. A total of 600 ng DNA was used for each well on a 24-well plate.

Detection and Quantification of Genomic Modification

About 72 h after transfection, genomic DNA was extracted using QuickExtract DNA Extraction Solution (Epicentre). Briefly, pelleted cells were resuspended in QuickExtract solution and incubated at 65° C. for 15 min, 68° C. for 15 min, and 98° C. for 10 min (Cong et al., 2013).

Indel analyses by the SURVEYOR assay and targeted deep sequencing were carried out, as previously described (Cong et al., 2013). Briefly, targeted genomic region was amplified using primers for the SURVRYOR assay or next-generation sequencing. For the SURVEYOR assay, the purified PCR product was re-annealed, subjected to SURVEYOR nuclease digestion, then analyzed and quantified using polyacrylamide gel electrophoresis (4-20% TBE PAGE gel, Life Technologies). For deep sequencing, the purified PCR products were amplified again to attach Illumina sequencing adapter and barcodes, and then subjected to sequencing analysis using the Miseq sequencing system (Illumina).

Transcriptional Activation Assay

HEK 293FT cells were seeded into 24- or 96-well plates (Bio-coat, Corning) one day prior to transfection at densities of $2.5 \times 10^5$ cells/well or $2.5 \times 10^4$ cells/well, respectively. Cells were transfected using Lipofectamine 2000 (Life Technology), according to the manufacturer's recommended protocol. For 24-well plates we used 600 ng total plasmids DNA containing 50 ng of reporter plasmid per well. For 96-well plates we used 250 ng total plasmids containing 10 ng of reporter plasmid per well. For reporter assay, the transcriptional activation reporter was co-transfected into 293FT cells with plasmids carrying SaCas9 activator system in 24-well plates, and the MS2-p65-HSF1 plasmids are the same as previously reported (Konermann et al., 2015). For endogenous gene transcriptional activation, a total of 600 ng of plasmids containing the SaCas9 activation system were transfected in 96-well format.

Flow Cytometry Analysis of Reporter Activation

Levels of reporter activation were measured by flow cytometry using an LSRFortessa cell analyzer (BD Biosciences). Cells were trypsinized from their culturing plates approximately 48 h after transfection and re-suspended in 200 µl of PBS for flow cytometry analysis. The flow cytometry data were analyzed using FlowJo (FlowJo LLC). At least 10,000 events were analyzed for each transfection sample. The fold induction of reporter gene expression was determined by flow cytometry analysis of mKate2 expression mean intensity over that from the control group where sgRNA bearing non-binding guide is expressed. The results were further normalized by the fluorescent intensity measured with a control plasmid that expresses GFP (spiked into the DNA mix for all experiments) to control for transfection differences between each experiment.

Endogenous Gene Activation Assay

HEK 293FT cells were seeded in 96-well plates and transfected as in previous section. Transfected cells were incubated for at least 48 h, and then harvested for RNA extraction, cDNA synthesis, and quantitative real-time PCR (qRT-PCR) analysis to measure human ASCL1 and MYOD1 gene expression levels using TaqMan Gene Expression Assays (Life Technology), as described previously (Konermann et al., 2015).

Construction of Split and Inducible SaCas9

Split-SaCas9 fragments where constructed by Gibson Assembly (NEB). SaCas9 fragments and fragments for inducible dimers FRB/FKBP and ABI/PYL where amplified from previously described (Konermann et al., 2015; Zetsche et al., 2015). DmC was amplified from iDimerize plasmid system (Takara Clontech).

Genome Cleavage Test of Split and Inducible SaCas9

HEK293FT cells were plated in 24-well plates as in previous sections. Cells were transfected with 200 ng plasmid DNA for each SaCas9 fragment and 100 ng PCR amplified U6::sgRNA targeting EMX1. Dimerization was induced at time of transfection with 100 nM rapamycin (Sigma) for SaCas9(N)FRB/SaCas9(C)FKBP, 100 nM A/C heterodimerizer (Takara Clontech) for SaCas9(N)DmC/SaCas9(C)FKBP and 200 µM abscisic acid (Sigma) for SaCas9 (N)ABI/SaCas9(C)PYL. DNA was harvested three days after transfection and analyzed with the SURVEYOR nuclease assay, as described previously (Cong et al., 2013).

Sequence Information

```
1. NLS-dSaCas9 (D10A/NS80A)-linker-NLS-VP64
Underlined: NLS sequences
Italic: linker
Underlined and Italic: VP64 activator domain
MAPKKKRKVGIHGVPAAKRNYILGLAIGITSVGYGIIDYETRDVIDAGVRLFKEANVENNEGRRSKRGARRLKRRRHRIQRVKKL
LFDYNLLTDHSELSGINPYEARVKGLSQKLSEEEFSAALLHLAKRRGVHNVNEVEEDTGNELSTKEQISRNSKALEEKYVAELQLE
RLKKDGEVRGSINRFKTSDYVKEAKQLLKVQKAYHQLDQSFIDTYIDLLETRRTYYEGPGEGSPFGWKDIKEWYEMLMGHCTYFPE
ELRSVKYAYNADLYNALNDLNNLVITRDENEKLEYYEKFQIIENVFKQKKKPTLKQIAKEILVNEEDIKGYRVTSTGKPEFTNLKV
YHDIKDITARKEIIENAELLDQIAKILTIYQSSEDIQEELTNLNSELTQEEIEQISNLKGYTGTHNLSLKAINLILDELWHTNDNQ
IAIFNRLKLVPKKVDLSQQKEIPTTLVDDFILSPVVKRSFIQSIKVINAIIKKYGLPNDIIIELAREKNSKDAQKMINEMQKRNRQ
TNERIEEIIRTTGKENAKYLIEKIKLHDMQEGKCLYSLEAIPLEDLLNNPFNYEVDHIIPRSVSFDNSFNNKVLVKQEEASKKGNR
TPFQYLSSSDSKISYETFKKHILNLAKGKGRISKTKKEYLLEERDINRFSVQKDFINRNLVDTRYATRGLMNLLRSYFRVNNLDVK
VKSINGGFTSFLRRKWKFKKERNKGYKHHAEDALIIANADFIFKEWKKLDKAKKVMENQMFEEKQAESMPEIETEQEYKEIFITPH
QIKHIKDFKDYKYSHRVDKKPNRELINDTLYSTRKDDKGNTLIVNNLNGLYDKDNDKLKKLINKSPEKLLMYHHDPQTYQKLKLIM
EQYGDEKNPLYKYYEETGNYLTKYSKKDNGPVIKKIKYYGNKLNAHLDITDDYPNSRNKVVKLSLKPYRFDVYLDNGVYKFVTVKN
LDVIKKENYYEVNSKCYEEAKKLKKISNQAEFIASFYNNDLIKINGELYRVIGVNNDLLNRIEVNMIDITYREYLENMNDKRPPRI
IKTIASKTQSIKKYSTDILGNLYEVKSKKHPQIIKKGSAGGGGSGGGGSGGGGSGPKKKRKVAAAGSGRADALDDFDLDMLGSDAL
DDFDLDMLGSDALDDFDLDMLGSDALDDFDLDMLINAS* (SEQ ID NO: 81)

2. MS2-linker-NLS-p65-linker-HSF1
Underlined: NLS sequences
Italic: linker
MASNFTQFVLVDNGGTGDVTVAPSNFANGVAEWISSNSRSQAYKVTCSVRQSSAQKRKYTIKVEVPKVATQTVGGVELPVAAWRSY
LNMELTIPIFATNSDCELIVKAMQGLLKDGNPIPSAIAANSGIYSAGGGGSGGGGSGGGGSGPKKKRKVAAAGSPSGQISNQALAL
APSSAPVLAQTMVPSSAMVPLAQPPAPAPVLTPGPPQSLSAPVPKSTQAGEGTLSEALLHLQFDADEDLGALLGNSTDPGVFTDLA
SVDNSEFQQLLNOGVSMSHSTAEPMLMEYPEAITRLVTGSQRPPDPAPTPLGTSGLPNGLSGDEDFSSIADMDFSALLSQISSSGQ
GGGGSGFSVDTSALLDLFSPSVTVPDMSLPDLDSSLASIQELLSPQEPPRPPEAENSSPDSGKQLVHYTAQPLFLLDPGSVDTGSN
DLPVLFELGEGSYFSEGDGFAEDPTISLLTGSEPPKAKDPTVS (SEQ ID NO: 82)

3. SaCas9-sgRNA MS2-fusion (TL) scaffold sequence (RNA)
GUUUUAGUACUCUGGGCCAACAUGAGGAUCACCCAUGUCUGCAGGGCCCAGAAUCUACUAAAACAAGGCAAAAUGCCGU
GUUUAUCUCGUCAACUUGUUGGCGAGAU (SEQ ID NO: 83)

4. SaCas9-sgRNA MS2-fusion (SL1) scaffold sequence (RNA)
GUUUUAGUACUCUGGAAACAGAAUCUACUAAAACAAGGCAGGCCAACAUGAGGAUCACCCAUGUCUGCAGGGCCUGCCG
UGUUUAUCUCGUCAACUUGUUGGCGAGAU (SEQ ID NO: 84)

5. SaCas9-sgRNA MS2-fusion (SL2) scaffold sequence (RNA)
GUUUUAGUACUCUGGAAACAGAAUCUACUAAAACAAGGCAAAAUGCCGUGUUUAUCUCGUCAAGGCCAACAUGAGGAUC
ACCCAUGUCUGCAGGGCCUUGGCGAGAU (SEQ ID NO: 85)

6. SaCas9-sgRNA MS2-fusion (TL + SL1) scaffold sequence (RNA)
GUUUUAGUACUCUGGGCCAACAUGAGGAUCACCCAUGUCUGCAGGGCCCAGAAUCUACUAAAACAAGGCAGGCCAACAU
GAGGAUCACCCAUGUCUGCAGGGCCUGCCGUGUUUAUCUCGUCAACUUGUUGGCGAGAU (SEQ ID NO: 86)

7. SaCas9-sgRNA MS2-fusion (TL + SL2) scaffold sequence (RNA)
GUUUUAGUACUCUGGGCCAACAUGAGGAUCACCCAUGUCUGCAGGGCCCAGAAUCUACUAAAACAAGGCAAAAUGCCGU
GUUUAUCUCGUCAAGGCCAACAUGAGGAUCACCCAUGUCUGCAGGGCCUUGGCGAGAU (SEQ ID NO: 87)
```

Mammalian sgRNA guide sequences

| Gene | Guide target | PAM sequence |
| --- | --- | --- |
| DYRK1A | ATGGTTCCTTAAATAAGAACTT (SEQ ID NO: 88) | TAGGAT |
| EMX1-sg1 | TGGCCAGGCTTTGGGGAGGCC (SEQ ID NO: 89) | TGGAGT |
| EMX1-sg2 | GGCCTCCCCAAAGCCTGGCCA (SEQ ID NO: 90) | GGGAGT |

SURVEYOR assay primers

| Gene | Surveyor primer F | Surveyor primer R |
| --- | --- | --- |
| DYRK1A | GGAGCTGGTCTGTTGGAGAA (SEQ ID NO: 91) | TCCCAATCCATAATCCCACGTT (SEQ ID NO: 93) |
| EMX1 | CCATCCCCTTCTGTGAATGT (SEQ ID NO: 92) | GGAGATTGGAGACACGGAGA (SEQ ID NO: 94) |

Targeted sequencing primers

| Gene | NGS primer F (only priming sequence, without adapter) | NGS primer R (only priming sequence, without adapter) |
| --- | --- | --- |
| DYRK1A | CTGTTGTGTTGAGTAACATATACCTG (SEQ ID NO: 95) | TTGCATGCTGAAGTCTCTCC (SEQ ID NO: 97) |

| | | | |
|---|---|---|---|
| EMX1 | AAGAAGGGCTCCCATCACAT (SEQ ID NO: 96) | | AGTGGCCAGAGTCCAGCTT (SEQ ID NO: 98) |

| SaCas9 self-assembly primer | | | |
|---|---|---|---|
| Constructs | Forward (N-term) Ggtaggcgtgtacggtgggagg (SEQ ID NO: 99) | | Reverse (N-term) cacagtcgaggctgatcagcgagctcta ggaattcttaggacaggtccaccttctt gggc (SEQ ID NO: 100) |
| SaCas9 Split 1 | Forward (C-term) agcagagctctctggctaactaccggtgcc accATGCAGCAGAAAGAGATCCCCACCACC (SEQ ID NO: 101) Forward (N-term) ggtaggcgtgtacggtgggagg (SEQ ID NO: 99) | | Reverse (C-term) cagtcgaggctgatcagcgagc (SEQ ID NO: 102) Reverse (N-term) gcacagtcgaggctgatcagcgagctct aggaattcttactcggcctgcttttcct cgaa (SEQ ID NO: 103) |
| SaCas9 Split 2 | Forward (C-term) ataagcagagctctctggctaactaccggt gccaccATGAGCATGCCCGAGATCGAAACC (SEQ ID NO: 104) Forward (N-term) ggtaggcgtgtacggtgggagg (SEQ ID NO: 99) | | Reverse (C-term) cagtcgaggctgatcagcgagc (SEQ ID NO: 102) Reverse (N-term) cacagtcgaggctgatcagcgagctcta ggaattcttagatcagggtgttgcccttt gtcg (SEQ ID NO: 105) |
| SaCas9 Split 3 | Forward (C-term) gcagagctctctggctaactaccggtgcca CcATGGTGAACAATCTGAACGGCCTGTACG (SEQ ID NO: 106) | | Reverse (C-term) cagtcgaggctgatcagcgagc (SEQ ID NO: 102) |

| SaCas9 dimer fusion primer | | | |
|---|---|---|---|
| Constructs | Forward (N-term) taagcagagctctctggctaactaccggtg ccaccATGAAGCGGAACTACATCCTGGGCC (SEQ ID NO: 107) | | Reverse (N-term) gcacagtcgaggctgatcagcgagctct aggaattcttactcggcctgcttttcct cgaa (SEQ ID NO: 103) |
| SaCas9 Dimer Fusion | Forward (C-term) ataagcagagctctctggctaactaccggt gccaccATGAGCATGCCCGAGATCGAAACC (SEQ ID NO: 104) | | Reverse (C-term) cagtcgaggctgatcagcgagctctagg aattcttagcccttttttgatgatctgag ggtg (SEQ ID NO: 108) |

Example 4: SaCas9 Nickases D10A and N580A

Figures 22A, 22B:
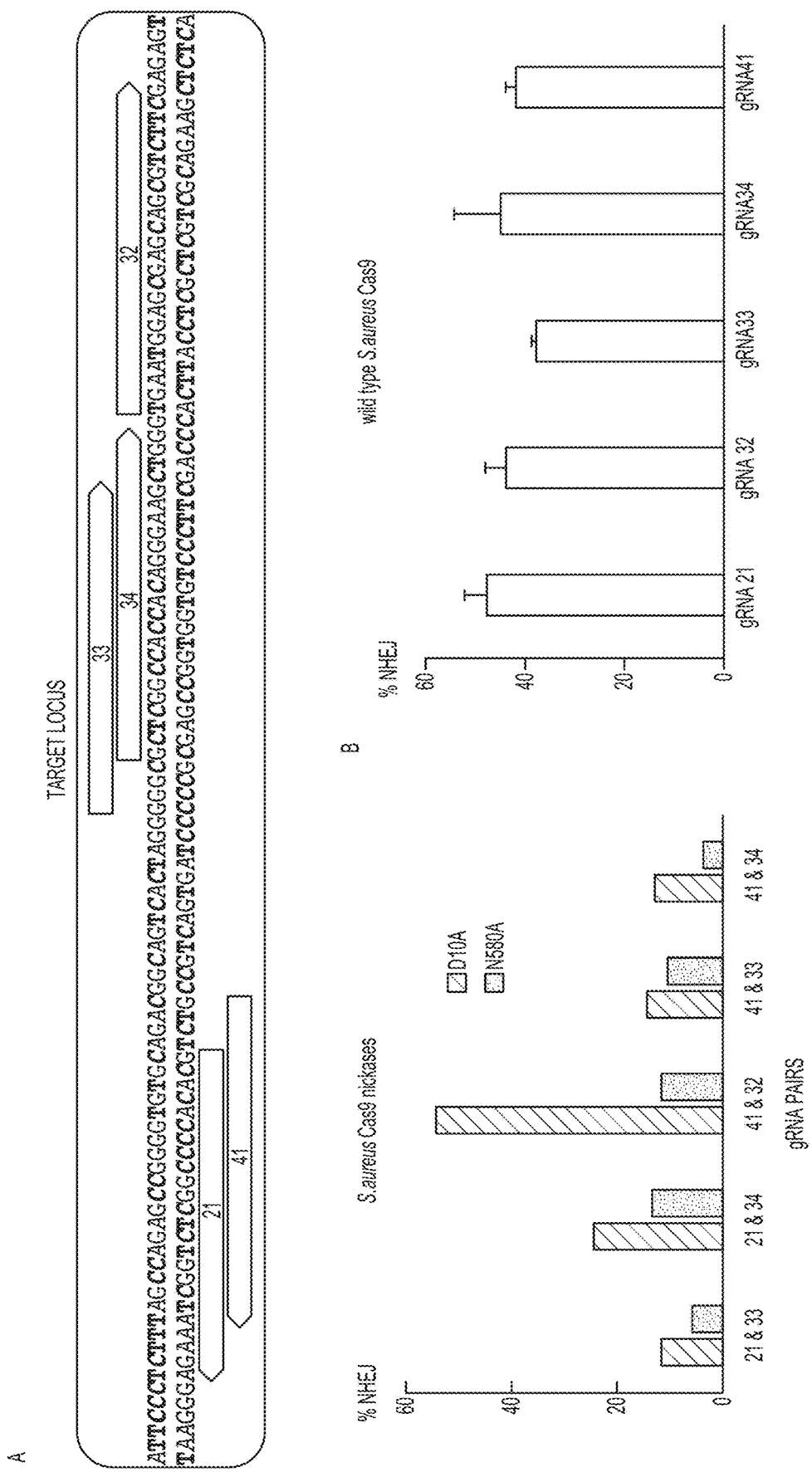
FIG. 22A-22B illustrates the result of an experiment showing nickase activity of D10A and N580A mutants of SaCas9. Panel A illustrates the sequence of the target locus for 5 gRNAs annotated in gray and shows activity of the mutant enzymes with the indicated guides. NHEJ % on the Y axis represents on-target cleavage rates as measured by TOPO sequencing.

Editas Medicine reported data demonstrating nickase activity of D10A and N580A mutants of SaCas9. (FIG. 22).

The invention is further described by the following numbered paragraphs:

1. An engineered SaCas9 protein, wherein:
   the protein complexes with a nucleic acid molecule comprising RNA to form a CRISPR complex,
   wherein when in the CRISPR complex, the nucleic acid molecule targets one or more target polynucleotide loci,
   the protein comprises at least one modification compared to the unmodified protein,
   wherein the CRISPR complex comprising the modified protein has altered activity as compared to the complex comprising the unmodified protein.

2. The engineered SaCas9 protein of numbered paragraph 1, wherein the altered activity comprises an altered binding property as to the nucleic acid molecule comprising RNA or to the target polynucleotide loci, altered binding kinetics as to the nucleic acid molecule comprising RNA or to the target polynucleotide loci, or altered binding specificity as to the nucleic acid molecule comprising RNA or to the target polynucleotide loci compared to off-target polynucleotide loci.

3. The engineered SaCas9 protein of numbered paragraph 1 or 2, wherein the altered activity comprises increased targeting efficiency or decreased off-target binding.

4. The engineered SaCas9 protein of any one of numbered paragraphs 1 to 3, wherein the altered activity comprises modified cleavage activity.

5. The engineered SaCas9 protein of numbered paragraph 4, wherein the modified cleavage activity comprises increased cleavage activity as to the target polynucleotide loci.

6. The engineered SaCas9 protein of numbered paragraph 4, wherein the modified cleavage activity comprises decreased cleavage activity as to the target polynucleotide loci.

7. The engineered SaCas9 protein of any one of numbered paragraphs 4 to 6, wherein the modified cleavage activity comprises decreased cleavage activity as to off-target polynucleotide loci.

8. The engineered SaCas9 protein of any one of numbered paragraphs 4 to 6 wherein the modified cleavage activity comprises increased cleavage activity as to off-target polynucleotide loci.

9. The engineered SaCas9 protein of any one of numbered paragraphs 1 to 8 wherein the altered activity comprises altered helicase kinetics.

10. The engineered SaCas9 protein of any one of numbered paragraphs 1 to 9 wherein the SaCas9 protein comprises a modification that alters association of the protein with the nucleic acid molecule comprising RNA, with the target polynucleotide loci, or with the off-target polynucleotide loci.

11. The engineered SaCas9 protein of any one of numbered paragraphs 1 to 10 wherein the SaCas9 protein comprises a modification that alters formation of the CRISPR complex.

12. The engineered SaCas9 protein of any one of numbered paragraphs 1 to 11 wherein the SaCas9 protein comprises a modification that alters targeting of the nucleic acid molecule to the target polynucleotide loci.

13. The engineered SaCas9 protein of any one of numbered paragraphs 10 to 12, wherein the modification comprises a mutation in a region of the protein that associates with the nucleic acid molecule.

14. The engineered SaCas9 protein of any one of numbered paragraphs 10 to 12, wherein the modification comprises a mutation in a region of the protein that associates with the target polynucleotide loci.

15. The engineered SaCas9 protein of any one of numbered paragraphs 10 to 12, wherein the modification comprises a mutation in a region of the protein that associates with the off-target polynucleotide loci.

16. The engineered SaCas9 protein of any one of numbered paragraphs 10 to 15, wherein the modification or mutation comprises decreased positive charge in a region of the protein that associates with the nucleic acid molecule comprising RNA, with the target polynucleotide loci, or with the off-target polynucleotide loci.

17. The engineered SaCas9 protein of any one of numbered paragraphs 10 to 15, wherein the modification or mutation comprises decreased negative charge in a region of the protein that associates with the nucleic acid molecule comprising RNA, with the target polynucleotide loci, or with the off-target polynucleotide loci.

18. The engineered SaCas9 protein of any one of numbered paragraphs 10 to 15, wherein the modification or mutation comprises increased positive charge in a region of the protein that associates with the nucleic acid molecule comprising RNA, with the target polynucleotide loci, or with the off-target polynucleotide loci.

19. The engineered SaCas9 protein of any one of numbered paragraphs 10 to 15, wherein the modification or mutation comprises increased negative charge in a region of the protein that associates with the nucleic acid molecule comprising RNA, with the target polynucleotide loci, or with the off-target polynucleotide loci.

20. The engineered SaCas9 protein of any one of numbered paragraphs 10 to 19, wherein the modification or mutation increases steric hindrance between the protein and the nucleic acid molecule comprising RNA, the target polynucleotide loci, or the off-target polynucleotide loci.

21. The engineered SaCas9 protein of any one of numbered paragraphs 10 to 19, wherein the modification or mutation comprises a modification or a mutation of one or more nuclease domains.

22. The engineered SaCas9 protein of numbered paragraph 21, wherein the modification or mutation comprises a modification or a mutation of a RuvC domain or an HNH domain.

23. The engineered SaCas9 protein of numbered paragraph 21, wherein the modification or mutation comprises a substitution of a nuclease domain of a SaCas9 ortholog.

24. The engineered SaCas9 protein of any one of numbered paragraphs 10 to 19, wherein the modification or mutation comprises a substitution of Asp, Asn, Glu, or His with a different amino acid.

25. The engineered SaCas9 protein of any one of numbered paragraphs 10 to 19, wherein the modification or mutation comprises a substitution of one or more amino acids with Ala or Asp.

26. The engineered SaCas9 protein of any one of numbered paragraphs 10 to 19, wherein the modification or mutation comprises a substitution selected from the group consisting of E477A, N580D, N580A, D10A, H701A, D704A, H577A and a combination thereof.

27. The engineered SaCas9 protein of any one of numbered paragraphs 10 to 19, wherein the modification or mutation comprises an amino acid substitution in a binding groove.

28. The engineered SaCas9 protein of numbered paragraph 27, wherein the binding groove comprises one or more RuvC domains, RuvC-III domains, HNH domains, or a combination thereof.

29. The engineered SaCas9 protein of any one of numbered paragraphs 10 to 19, wherein the binding groove is between the RuvC and the HNH domains.

30. The engineered SaCas9 protein of any one of numbered paragraphs 10 to 19, wherein the modification or mutation comprises a modification or a mutation of one or more PAM-interacting residues or PAM-interacting domains.

31. The engineered SaCas9 protein of numbered paragraph 30, wherein the modification or mutation comprises a PAM recognition region comprising one or more PAM-interacting residues of an Cas9 ortholog.

32. The engineered SaCas9 protein of numbered paragraph 30, wherein the modification comprises a substitution of a PAM recognition region of an Cas9 ortholog.

33. The engineered SaCas9 protein of numbered paragraph 30, wherein the modification comprises a substitution of one or more WED or PI domains with an analogous domain of a Cas9 ortholog.

34. The engineered SaCas9 protein of numbered paragraph 30, wherein the modification comprises a substitution at one or more of the following amino acids: Y789, Y882, K886, N888, A889, L909, N985, N986, R991, E993, and R1015.

35. The engineered SaCas9 protein of any one of numbered paragraphs 10 to 19, wherein the modification or mutation comprises an addition of one or more heterologous functional domains.

36. The engineered SaCas9 protein of numbered paragraph 35, wherein the heterologous function domain comprises a transcription activation domain, a transcription repressor domain, or a nuclease domain.

37. The engineered SaCas9 protein of numbered paragraph 35, wherein the heterologous functional domain is inserted into a linker loop between amino acids 430 and 431.

38. The engineered SaCas9 protein of numbered paragraph 35, wherein the heterologous functional domain is inserted in a RuvC-III domain between amino acids 739 and 740.

39. The engineered SaCas9 protein of any one of numbered paragraphs 35 to 38, wherein the heterologous functional domain comprises VP64, a KRAB domain, a SID domain, or FokI.

40. The engineered SaCas9 protein of any one of numbered paragraphs 35 to 38, wherein the one or more heterologous functional domains comprise one or more of the following activities: methylase activity, demethylase activity, transcription activation activity, transcription repression activity, transcription release factor activity, histone modification activity, nuclease activity, single-strand RNA cleavage activity, double-strand RNA cleavage activity, single-strand DNA cleavage activity, double-strand DNA cleavage activity and nucleic acid binding activity.

41. The engineered SaCas9 protein of any one of numbered paragraphs 10 to 19, wherein the modification or mutation comprises a split SaCas9 dimer.

42. The engineered SaCas9 protein of numbered paragraph 41, wherein the modification or mutation comprises a split in a RuvC domain.

43. The engineered SaCas9 protein of numbered paragraph 41, wherein the modification or mutation comprises a split between amino acid 739 and amino acid 740.

44. The engineered SaCas9 protein of numbered paragraph 41, wherein the modification or mutation comprises a split in a linker between a RuvC-II domain and an HNH domain.

45. The engineered SaCas9 protein of numbered paragraph 41, wherein the modification or mutation comprises a split between amino acid 430 and amino acid 431.

46. The engineered SaCas9 protein of any one of numbered paragraphs 1 to 45, wherein the SaCas9 protein comprises one or more nuclear localization signal (NLS) domains.

47. The engineered SaCas9 protein of any one of numbered paragraphs 1 to 46, wherein the SaCas9 protein comprises at least two or more NLSs.

48. The engineered SaCas9 protein of any one of numbered paragraphs 1 to 47, wherein the SaCas9 protein comprises one or more heterologous functional domains.

49. An engineered SaCas9 protein according to any one of numbered paragraphs 1 to 48, wherein the SaCas9 protein is encoded by a nucleotide sequence which is codon optimized for expression in a eukaryote.

50. A composition comprising the engineered SaCas9 protein of any one of numbered paragraphs 1 to 49.

51. A system comprising the engineered SaCas9 protein of any one of numbered paragraphs 1 to 51 and a nucleic acid molecule comprising RNA that targets one or more target polynucleotide loci.

52. A vector system comprising one or more vectors, wherein the one or more vectors comprises:
   a) a first regulatory element operably linked to a nucleotide sequence encoding the engineered SaCas9 protein of any one of the preceding numbered paragraphs; and
   b) a second regulatory element operably linked to one or more nucleotide sequences encoding one or more nucleic acid molecules comprising a guide RNA comprising a guide sequence, a tracr sequence, and a tracr mate sequence, wherein components (a) and (b) are located on same or different vectors.

53. The vector system of numbered paragraph 52, wherein the guide RNA is chimeric, truncated, dead, escorted, protected or modified.

54. A method of modifying a locus of interest in a cell comprising contacting the cell with the engineered SaCas9 protein or composition or system or vector system of any one of the preceding numbered paragraphs.

55. A method of modulating gene expression, wherein the method comprises introducing the engineered SaCas9 protein of any one of the preceding numbered paragraphs into a cell.

56. The method of numbered paragraph 55, wherein the cell is a eukaryotic or a prokaryotic cell.

57. The method of numbered paragraph 55, wherein the method is ex vivo or in vitro.

58. A method of treating a disease, disorder or infection in an individual in need thereof comprising administering an effective amount of the engineered SaCas9 protein or composition or system or vector system of any one of the preceding numbered paragraphs.

59. A non-naturally occurring or engineered CRISPR-Cas system or a non-naturally occurring or engineered composition comprising a CRISPR-Cas system comprising a single guide RNA (sgRNA), wherein when the sgRNA is in complex with a CRISPR enzyme within a prokaryotic or eukaryotic cell forming a CRISPR-SaCas9 quarternary complex having a conformation, the CRISPR enzyme is capable of effecting the manipulation of a target nucleic acid within the cell,
   wherein the sgRNA comprises a guide sequence capable of hybridizing to the complement of a target DNA sequence in a genomic locus of interest in a prokaryotic or eukaryotic cell,
   wherein the sgRNA is modified, and
   wherein the sgRNA is a *Staphylococcus aureus* (Sa) sgRNA and the CRISPR enzyme is a SaCas9.

60. The CRISPR-Cas system or composition of numbered paragraph 59, wherein the modification of the architecture of the sgRNA comprises addition of one or more nucleotides to a tetraloop, stem loop 1 and/or stem loop 2 as indicated in FIG. 2A.

61. The CRISPR-Cas system or composition of numbered paragraph 60, wherein the modification of the architecture of the sgRNA affects the binding of the complement of the target DNA to a RuvC domain.

62. The CRISPR-Cas system or composition of numbered paragraph 59, wherein the modification of the sgRNA alters the conformation of the CRISPR-SaCas9 quaternary complex.

63. The CRISPR-Cas system or composition of numbered paragraph 59, wherein the modification of the sgRNA alters the association of the sgRNA with a REC lobe of the SaCas9.

64. The CRISPR-Cas system or composition of any one of numbered paragraphs 59 to 63, wherein the Sa sgRNA further comprises one or more RNA sequence(s) that binds to one or more adaptor protein(s), wherein the adaptor protein(s) is associated with one or more functional domain(s).

65. The CRISPR-Cas system or composition of numbered paragraph 64, wherein at least one of the one or more RNA sequences is an aptamer sequence that binds to the adaptor protein.

66. The CRISPR-Cas system or composition of numbered paragraph 64 comprising at least two aptamer sequences that bind to the same or different adaptor protein(s).

67. The CRISPR-Cas system or composition of numbered paragraph 64, wherein the adaptor protein comprises MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s, and PRR1.

68. The CRISPR-Cas system or composition of any of numbered paragraphs 64 to 67, wherein the functional domain comprises a transcriptional activation domain, a transcriptional repressor domain or a nuclease domain.

69. A non-naturally occurring or engineered composition comprising the Sa sgRNA of any one of numbered paragraphs 1 to 68 and a type II CRISPR enzyme.

70. The composition of numbered paragraph 69, wherein the type II CRISPR enzyme is a Cas9 enzyme.

71. The composition of numbered paragraph 70, wherein the type II CRISPR enzyme is *Staphylococcus aureus* Cas9 (SaCas9).

72. The composition of numbered paragraph 69, wherein the type II CRISPR enzyme is SaCas9 comprising a REC lobe and/or a NUC lobe, which comprises all or a portion of a REC lobe and/or NUC lobe of a SaCas9 ortholog.

73. The composition of numbered paragraph 72, wherein the SaCas9 ortholog is SpCas9 or AnCas9.

74. The composition of numbered paragraph 69, wherein the type II CRISPR enzyme is SaCas9 and wherein the PAM recognition region comprises one or more PAM-interacting residue(s) of an Cas9 ortholog.

75. The composition of numbered paragraph 74, wherein the PAM recognition region comprises one or more PAM-interacting residues of SpCas9.

76. The composition of numbered paragraph 69, wherein the type II CRISPR enzyme is SaCas9, wherein one or more nuclease domains comprises all or a portion of a corresponding nuclease domain of a Cas9 ortholog.

77. The composition of numbered paragraph 76, wherein the one or more nuclease domains comprises all or a portion of a corresponding nuclease domain of SpCas9.

78. The composition of numbered paragraph 77, wherein the nuclease domain is a RuvC domain.

79. The composition of numbered paragraph 77, wherein the nuclease domain is a HNH domain.

80. The composition of numbered paragraph 69, wherein the type II CRISPR enzyme is SaCas9, wherein the REC lobe and/or the NUC lobe comprises all or a portion of a REC lobe and/or NUC lobe of a SaCas9 ortholog.

81. The composition of numbered paragraph 80, wherein the REC lobe and/or the NUC lobe comprises all or a portion of a REC lobe and/or NUC lobe of SpCas9 and/or AnCas9.

82. The composition of numbered paragraph 69, wherein the type II CRISPR enzyme comprises one or more heterologous functional domains.

83. The composition of numbered paragraph 82, wherein the heterologous functional domain comprises a transcriptional activation domain, a transcriptional repressor domain or a nuclease domain.

84. The composition of numbered paragraph 82, wherein the type II CRISPR enzyme is SaCas9 and the heterologous functional domain is inserted in the linker loop between amino acids 430 and 431.

85. The composition of numbered paragraph 69, wherein the CRISPR enzyme comprises a split-Cas9 dimer.

86. The composition of numbered paragraph 69, wherein the type II CRISPR enzyme comprises a split in the RuvC domain.

87. The composition of numbered paragraph 85, wherein the type II CRISPR enzyme is SaCas9.

88. The composition of numbered paragraph 85, wherein the type II CRISPR enzyme is SaCas9 and comprises a split between amino acid 739 and amino acid 740.

89. The composition of numbered paragraph 69, wherein the type II CRISPR enzyme comprises a split in the linker between the RuvCII domain and the HNH domain.

90. The composition of numbered paragraph 89, wherein the type II CRISPR enzyme is SaCas9.

91. The composition of numbered paragraph 89, wherein the type II CRISPR enzyme is SaCas9 and comprises a split between amino acid 430 and amino acid 431.

92. The composition of any one of numbered paragraphs 85 to 91, wherein one or more components of the split-Cas9 is operably linked to one or more nuclear localization signals (NLS(s)).

93. The composition of any one of numbered paragraphs 85 to 91, wherein the split-Cas9 is inducible.

94. The composition of numbered paragraph 70, wherein the type II CRISPR enzyme comprises a modification of one or more residues located in a nucleic acid binding groove.

95. The composition of numbered paragraph 94, wherein the nucleic acid binding groove comprises one or more of a RuvC domain, a RuvC-III domain, and an HNH domain.

96. The composition of numbered paragraph 94, wherein the modification comprises a modification of one or more residues wherein the one or more residues comprises arginine, histidine or lysine.

97. The composition of numbered paragraph 70, wherein the modification comprises a modification of one or more PAM-interacting residues.

98. The CRISPR-Cas system or composition of any of numbered paragraphs 59 to 97, wherein the cell is a eukaryotic cell.

99. The CRISPR-Cas system or composition of numbered paragraph 98, wherein the eukaryotic cell is a mammalian cell.

100. The CRISPR-Cas system or composition of numbered paragraph 99, wherein the mammalian cell is a human cell or a rodent cell, optionally a mouse cell.

101. A polynucleotide encoding the Sa sgRNA of any one of numbered paragraphs 59 to 100.

102. A vector comprising the polynucleotide of numbered paragraph 101 operably linked to a suitable promoter.

103. The vector of numbered paragraph 102, which comprises a polynucleotide encoding a Type II CRISPR enzyme.

104. The vector of numbered paragraph 103, wherein the Type II CRISPR enzyme is the Type II CRISPR enzyme of any one of numbered paragraphs 71 to 96.

105. A vector system, comprising one vector according to numbered paragraph 101 and a second vector according to numbered paragraph 104.

106. A organism or model transformed with a vector or vector system of any one of numbered paragraphs 102 to 105 to thereby express the Sa sgRNA.

107. The organism or model of numbered paragraph 106, which expresses the type II CRISPR enzyme of any one of numbered paragraphs 71 to 96.

108. An in vivo, ex vivo or in vitro host cell or cell line comprising or modified by the composition or enzyme according to any one of numbered paragraphs 59 to 105, or a progeny thereof.

109. The in vivo, ex vivo or in vitro host cell, cell line or progeny thereof of numbered paragraph 108, which is a stem cell or a stem cell line.

110. A method of modifying a genomic locus of interest to alter gene expression in a cell, which comprises introducing into the cell the Sa sgRNA or composition, polynucleotide, vector, or vector system of any of numbered paragraphs 59 to 105.

111. The composition of any of numbered paragraphs 59 to 105, wherein the sgRNA comprises a tracrRNA sequence that is 30 or more nucleotides in length.

112. The composition of any of numbered paragraphs 59 to 105, wherein the sgRNA comprises a tracrRNA sequence that is 50 or more nucleotides in length.

113. The composition of any of numbered paragraphs 59 to 105, wherein the Type II CRISPR enzyme further comprises one or more nuclear localization sequences (NLSs).

114. The composition or enzyme of any of numbered paragraphs 59 to 105, for use in medicine or for use in therapy.

115. Use of the composition or enzyme according to any one of numbered paragraphs 59 to 105
in the preparation of a medicament;
in the preparation of a medicament for ex vivo gene or genome editing; or
in ex vivo gene or genome editing.

116. A composition for use, method or the use according to any of numbered paragraphs 59 to 105 to correct ocular defects that arise from genetic mutations.

117. A computer-assisted method for identifying or designing i) a potential compound to fit within or bind to a CRISPR-Cas9 system or a portion thereof, which comprises:
  a) providing the co-ordinates of at least two atoms of the CRISPR-Cas9 system of the Crystal Structure of Table 7,
  b) providing the structure of a candidate molecule i) for binding to or within the CRISPR-Cas9 system, or ii) for manipulating a portion of the CRISPR-Cas9 system,
  c) fitting the structure of the candidate molecule to the at least two atoms of the CRISPR-Cas9 system, wherein fitting comprises determining interactions between one or more atoms of the candidate molecule and atoms of the CRISPR-SpCas9 system, and
  d) selecting the candidate molecule if it is predicted to bind to or within the CRISPR-Cas9 system.

118. The method of numbered paragraph 117, wherein the candidate molecule comprises atoms of the CRISPR-Cas9 system of the Crystal Structure Table.

119. The method of numbered paragraph 117, wherein the candidate molecule comprises atoms of the sgRNA:DNA duplex, which comprises comparing atoms of the sgRNA:DNA duplex to atoms of the SaCas9.

120. The method of numbered paragraph 119, wherein the atoms of the SaCas9 comprise atoms of the REC lobe and/or the NUC lobe.

121. The method of numbered paragraph 117, wherein the candidate molecule comprises atoms of the sgRNA repeat: anti-repeat duplex, which comprises comparing atoms of the sgRNA repeat:anti-repeat duplex to atoms of the SpCas9.

122. The method of numbered paragraph 121, wherein the atoms of the SpCas9 comprise atoms of the REC lobe and/or atoms of the NUC lobe.

123. The method of numbered paragraph 117, wherein the candidate molecule comprises atoms of the non-complementary strand of the target DNA, which comprises comparing atoms of the non-complementary strand of the target DNA to atoms of the SpCas9.

124. The method of numbered paragraph 123, wherein the atoms of the SpCas9 comprise atoms of the PAM-interacting (PI) domain.

125. The method of numbered paragraph 123, wherein the atoms of the SpCas9 comprise atoms of the RuvC domain.

126. The method of numbered paragraph 117, wherein the candidate molecule comprises atoms of the complementary strand of the target DNA, which comprises comparing atoms of the complementary strand of the target DNA to atoms of the SpCas9.

127. The method of numbered paragraph 126, wherein the atoms of the SpCas9 comprise atoms of the HNH domain.

128. The method of numbered paragraph 117, wherein the candidate molecule comprises atoms of the guide RNA: DNA duplex, which comprises comparing atoms of the guide RNA:DNA duplex to atoms of the SpCas9.

129. The method of numbered paragraph 117, wherein the candidate molecule comprises atoms of the sgRNA, which comprises comparing atoms of the sgRNA to atoms of the SpCas9.

130. The method of numbered paragraph 129, wherein the candidate molecule comprises atoms of the sgRNA.

131. The method of numbered paragraph 117, which further comprises synthesizing and testing the binding or activity of the compound.

132. The method of numbered paragraph 117, which further comprises testing a CRISPR-Cas9 system comprising the compound to alter expression of a DNA molecule in a cell.

133. The method of numbered paragraph 117, which comprises fitting the structure of the candidate molecule comprises to atomic coordinates comprising at least 2 atoms, or at least 5 atoms, or at least 10 atoms, or at least 50 atoms, or at least 100 atoms of the CRISPR-Cas9 complex.

134. The method of any one of numbered paragraphs 117 to 133, wherein the candidate molecule comprises atoms of the SpCas9 and a transcriptional repressor, a transcriptional activator, a nuclease domain, a DNA methyl transferase, a protein acetyltransferase, a protein deacetylase, a protein methyltransferase, a protein deaminase, a protein kinase, a protein phosphatase, or an epigenetic regulator.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

LENGTHY TABLES

The patent contains a lengthy table section. A copy of the table is available in electronic form from the USPTO web site (https://seqdata.uspto.gov/?pageRequest=docDetail&DocID=US12168789B2). An electronic copy of the table will also be available from the USPTO upon request and payment of the fee set forth in 37 CFR 1.19(b)(3).

What is claimed is:

1. A non-naturally occurring and engineered SaCas9 protein comprising at least one modification or mutation compared to a wild-type SaCas9 protein, wherein the modification or mutation comprises mutation of at least one amino acid of the SaCas9 protein that interacts with sugar-phosphate backbone of an sgRNA or sugar-phosphate backbone of a target DNA strand, wherein the at least one amino acid comprises Thr238, Tyr239, Lys248, Tyr256, Arg314, Asn394, Gln414, Tyr211, Trp229, Tyr230, Gly235, Arg245, Gly391, Thr392, Asn419, Leu446, Tyr651, or Arg654.

2. The non-naturally occurring and engineered SaCas9 protein of claim 1, wherein the SaCas9 protein is fused to one or more nuclear localization signals (NLSs).

3. The non-naturally occurring and engineered SaCas9 protein of claim 1, wherein the SaCas9 protein is fused to two or more NLSs.

4. The non-naturally occurring and engineered SaCas9 protein of claim 1, further comprising a modification or a mutation of one or more catalytic domains.

5. The non-naturally occurring and engineered SaCas9 protein of claim 4, wherein the modification or mutation comprises a modification or a mutation of a RuvC domain or an HNH domain.

6. The non-naturally occurring and engineered SaCas9 protein of claim 5, wherein the modification or mutation comprises an amino acid substitution of E477A, N580D, N580A, D10A, H701A, D704A, H577A, or a combination thereof.

7. The non-naturally occurring and engineered SaCas9 protein of claim 1, wherein the SaCas9 protein is fused to one or more heterologous functional domains.

8. The non-naturally occurring and engineered SaCas9 protein of claim 7, wherein the one or more heterologous functional domains comprise one or more of the following activities: methylase activity, demethylase activity, transcription activation activity, transcription repression activity, transcription release factor activity, histone modification activity, nuclease activity, single-strand RNA cleavage activity, double-strand RNA cleavage activity, single-strand DNA cleavage activity, double-strand DNA cleavage activity, and nucleic acid binding activity.

9. The non-naturally occurring and engineered SaCas9 protein of claim 7, wherein the heterologous functional domain comprises a VP64 domain, a KRAB domain, a SID domain, or a FokI domain.

10. The non-naturally occurring and engineered SaCas9 protein of claim 7, wherein the heterologous functional domain is inserted into a linker loop between amino acids 430 and 431.

11. The non-naturally occurring and engineered SaCas9 protein of claim 7, wherein the heterologous functional domain is inserted in a RuvC-III domain between amino acids 739 and 740.

12. The non-naturally occurring and engineered SaCas9 protein of claim 1, wherein the SaCas9 protein comprises a split SaCas9 dimer structure.

13. The non-naturally occurring and engineered SaCas9 protein of claim 12, wherein the SaCas9 protein comprises a split in a RuvC domain.

14. The non-naturally occurring and engineered SaCas9 protein of claim 12, wherein the SaCas9 protein comprises a split between amino acids 739 and 740.

15. The non-naturally occurring and engineered SaCas9 protein of claim 12, wherein the SaCas9 protein comprises a split in a linker between a RuvC-II domain and an HNH domain.

16. The non-naturally occurring and engineered SaCas9 protein of claim 12, wherein the SaCas9 protein comprises a split between amino acids 430 and 431.

17. The non-naturally occurring and engineered SaCas9 protein of claim 1, wherein the at least one amino acid comprises Tyr239.

18. The non-naturally occurring and engineered SaCas9 protein of claim 1, wherein the at least one amino acid comprises Gln414.

19. The non-naturally occurring and engineered SaCas9 protein of claim 1, wherein the at least one amino acid comprises Arg245.

20. The non-naturally occurring and engineered SaCas9 protein of claim 1, wherein the at least one amino acid comprises Tyr651.

21. The non-naturally occurring and engineered SaCas9 protein of claim 1, wherein the at least one amino acid comprises Arg654.

22. A composition comprising the non-naturally occurring and engineered SaCas9 protein of claim 1, and a CRISPR-Cas system RNA capable of forming a CRISPR-Cas complex with the SaCas9 protein.

23. A composition comprising an mRNA encoding the non-naturally occurring and engineered SaCas9 protein of claim 1, and a CRISPR-Cas system RNA capable of forming a CRISPR-Cas complex with the SaCas9 protein.

24. A vector system comprising one or more vectors, wherein the one or more vectors comprise:
 (a) a first regulatory element operably linked to a nucleotide sequence encoding the non-naturally occurring and engineered SaCas9 protein of claim 1; and
 (b) a second regulatory element operably linked to one or more nucleotide sequences encoding a CRISPR-Cas system RNA capable of forming a CRISPR-Cas complex with the engineered SaCas9 protein, wherein components (a) and (b) are located on same or different vectors.

25. The vector system of claim 24, wherein the nucleotide sequence encoding the engineered SaCas9 protein is codon optimized for expression in a eukaryotic cell.

* * * * *

```
                         SEQUENCE LISTING

Sequence total quantity: 139
SEQ ID NO: 1            moltype = AA  length = 4
FEATURE                 Location/Qualifiers
REGION                  1..4
                        note = Description of Artificial Sequence: Synthetic peptide
source                  1..4
                        mol_type = protein
                        organism = synthetic construct
SEQUENCE: 1
GGGS                                                                    4

SEQ ID NO: 2            moltype = AA  length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 2
GGGSGGGSGG GS                                                           12

SEQ ID NO: 3            moltype = AA  length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 3
AEAAAKA                                                                 7

SEQ ID NO: 4            moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 4
GGGGSGGGGS GGGGS                                                        15

SEQ ID NO: 5            moltype = AA  length = 30
FEATURE                 Location/Qualifiers
REGION                  1..30
                        note = Description of Artificial Sequence: Synthetic
                         polypeptide
source                  1..30
                        mol_type = protein
                        organism = synthetic construct
SEQUENCE: 5
GGGGSGGGGS GGGGSGGGGS GGGGSGGGGS                                        30

SEQ ID NO: 6            moltype = AA  length = 45
FEATURE                 Location/Qualifiers
REGION                  1..45
                        note = Description of Artificial Sequence: Synthetic
                         polypeptide
source                  1..45
                        mol_type = protein
                        organism = synthetic construct
SEQUENCE: 6
GGGGSGGGGS GGGGSGGGGS GGGGSGGGGS GGGGSGGGGS GGGGS                       45

SEQ ID NO: 7            moltype = AA  length = 60
```

```
FEATURE                 Location/Qualifiers
REGION                  1..60
                        note = Description of Artificial Sequence: Synthetic
                         polypeptide
source                  1..60
                        mol_type = protein
                        organism = synthetic construct
SEQUENCE: 7
GGGGSGGGGS GGGGSGGGGS GGGGSGGGGS GGGGSGGGGS GGGGSGGGGS GGGGSGGGGS       60

SEQ ID NO: 8            moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 8
GGGGS                                                                    5

SEQ ID NO: 9            moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 9
GGGGSGGGGS                                                              10

SEQ ID NO: 10           moltype = AA  length = 20
FEATURE                 Location/Qualifiers
REGION                  1..20
                        note = Description of Artificial Sequence: Synthetic peptide
source                  1..20
                        mol_type = protein
                        organism = synthetic construct
SEQUENCE: 10
GGGGSGGGGS GGGGSGGGGS                                                   20

SEQ ID NO: 11           moltype = AA  length = 25
FEATURE                 Location/Qualifiers
REGION                  1..25
                        note = Description of Artificial Sequence: Synthetic peptide
source                  1..25
                        mol_type = protein
                        organism = synthetic construct
SEQUENCE: 11
GGGGSGGGGS GGGGSGGGGS GGGGS                                             25

SEQ ID NO: 12           moltype = AA  length = 35
FEATURE                 Location/Qualifiers
REGION                  1..35
                        note = Description of Artificial Sequence: Synthetic
                         polypeptide
source                  1..35
                        mol_type = protein
                        organism = synthetic construct
SEQUENCE: 12
GGGGSGGGGS GGGGSGGGGS GGGGSGGGGS GGGGS                                  35

SEQ ID NO: 13           moltype = AA  length = 40
FEATURE                 Location/Qualifiers
REGION                  1..40
                        note = Description of Artificial Sequence: Synthetic
                         polypeptide
source                  1..40
                        mol_type = protein
                        organism = synthetic construct
SEQUENCE: 13
GGGGSGGGGS GGGGSGGGGS GGGGSGGGGS GGGGSGGGGS                             40

SEQ ID NO: 14           moltype = AA  length = 50
FEATURE                 Location/Qualifiers
REGION                  1..50
                        note = Description of Artificial Sequence: Synthetic
                         polypeptide
source                  1..50
                        mol_type = protein
```

```
                        organism = synthetic construct
SEQUENCE: 14
GGGGSGGGGS GGGGSGGGGS GGGGSGGGGS GGGGSGGGGS GGGGSGGGGS             50

SEQ ID NO: 15           moltype = AA   length = 55
FEATURE                 Location/Qualifiers
REGION                  1..55
                        note = Description of Artificial Sequence: Synthetic
                        polypeptide
source                  1..55
                        mol_type = protein
                        organism = synthetic construct
SEQUENCE: 15
GGGGSGGGGS GGGGSGGGGS GGGGSGGGGS GGGGSGGGGS GGGGSGGGGS GGGGS       55

SEQ ID NO: 16           moltype = AA   length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 16
SGSETPGTSE SATPES                                                  16

SEQ ID NO: 17           moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 17
MKIIEQLPSA                                                         10

SEQ ID NO: 18           moltype = AA   length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 18
VRHKLKRVGS                                                         10

SEQ ID NO: 19           moltype = AA   length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 19
VPFLLEPDNI NGKTC                                                   15

SEQ ID NO: 20           moltype = AA   length = 12
FEATURE                 Location/Qualifiers
REGION                  1..12
                        note = Description of Artificial Sequence: Synthetic peptide
source                  1..12
                        mol_type = protein
                        organism = synthetic construct
SEQUENCE: 20
GHGTGSTGSG SS                                                      12

SEQ ID NO: 21           moltype = AA   length = 7
FEATURE                 Location/Qualifiers
REGION                  1..7
                        note = Description of Artificial Sequence: Synthetic peptide
source                  1..7
                        mol_type = protein
                        organism = synthetic construct
SEQUENCE: 21
MSRPDPA                                                            7

SEQ ID NO: 22           moltype = AA   length = 12
FEATURE                 Location/Qualifiers
REGION                  1..12
                        note = Description of Artificial Sequence: Synthetic peptide
```

```
source                   1..12
                         mol_type = protein
                         organism = synthetic construct
SEQUENCE: 22
GSAGSAAGSG EF                                                                12

SEQ ID NO: 23            moltype = AA  length = 12
FEATURE                  Location/Qualifiers
REGION                   1..12
                         note = Description of Artificial Sequence: Synthetic peptide
source                   1..12
                         mol_type = protein
                         organism = synthetic construct
SEQUENCE: 23
SGSETPGTSE SA                                                                12

SEQ ID NO: 24            moltype = AA  length = 4
FEATURE                  Location/Qualifiers
REGION                   1..4
                         note = Description of Artificial Sequence: Synthetic peptide
source                   1..4
                         mol_type = protein
                         organism = synthetic construct
SEQUENCE: 24
GGSM                                                                          4

SEQ ID NO: 25            moltype = AA  length = 21
FEATURE                  Location/Qualifiers
REGION                   1..21
                         note = Description of Artificial Sequence: Synthetic peptide
source                   1..21
                         mol_type = protein
                         organism = synthetic construct
SEQUENCE: 25
SGSETPGTSE SATPEGGSGG S                                                      21

SEQ ID NO: 26            moltype = AA  length = 4
FEATURE                  Location/Qualifiers
REGION                   1..4
                         note = Description of Artificial Sequence: Synthetic peptide
source                   1..4
                         mol_type = protein
                         organism = synthetic construct
SEQUENCE: 26
GGSG                                                                          4

SEQ ID NO: 27            moltype =     length =
SEQUENCE: 27
000

SEQ ID NO: 28            moltype =     length =
SEQUENCE: 28
000

SEQ ID NO: 29            moltype =     length =
SEQUENCE: 29
000

SEQ ID NO: 30            moltype =     length =
SEQUENCE: 30
000

SEQ ID NO: 31            moltype =     length =
SEQUENCE: 31
000

SEQ ID NO: 32            moltype =     length =
SEQUENCE: 32
000

SEQ ID NO: 33            moltype =     length =
SEQUENCE: 33
000

SEQ ID NO: 34            moltype =     length =
SEQUENCE: 34
000

SEQ ID NO: 35            moltype =     length =
```

```
SEQUENCE: 35
000

SEQ ID NO: 36          moltype =    length =
SEQUENCE: 36
000

SEQ ID NO: 37          moltype =    length =
SEQUENCE: 37
000

SEQ ID NO: 38          moltype =    length =
SEQUENCE: 38
000

SEQ ID NO: 39          moltype = DNA   length = 137
FEATURE                Location/Qualifiers
misc_difference        1..20
                       note = modified_base - a, c, t, g, unknown or other
misc_feature           1..137
                       note = Description of Artificial Sequence: Synthetic
                        polynucleotide
source                 1..137
                       mol_type = other DNA
                       organism = synthetic construct
SEQUENCE: 39
nnnnnnnnnn nnnnnnnnnn gtttttgtac tctcaagatt tagaaataaa tcttgcagaa   60
gctacaaaga taaggcttca tgccgaaatc aacaccctgt cattttatgg cagggtgttt  120
tcgttattta atttttt                                                 137

SEQ ID NO: 40          moltype = DNA   length = 123
FEATURE                Location/Qualifiers
misc_difference        1..20
                       note = modified_base - a, c, t, g, unknown or other
misc_feature           1..123
                       note = Description of Artificial Sequence: Synthetic
                        polynucleotide
source                 1..123
                       mol_type = other DNA
                       organism = synthetic construct
SEQUENCE: 40
nnnnnnnnnn nnnnnnnnnn gtttttgtac tctcagaaat gcagaagcta caaagataag   60
gcttcatgcc gaaatcaaca ccctgtcatt ttatggcagg gtgttttcgt tatttaattt  120
ttt                                                                123

SEQ ID NO: 41          moltype = DNA   length = 110
FEATURE                Location/Qualifiers
misc_difference        1..20
                       note = modified_base - a, c, t, g, unknown or other
misc_feature           1..110
                       note = Description of Artificial Sequence: Synthetic
                        polynucleotide
source                 1..110
                       mol_type = other DNA
                       organism = synthetic construct
SEQUENCE: 41
nnnnnnnnnn nnnnnnnnnn gtttttgtac tctcagaaat gcagaagcta caaagataag   60
gcttcatgcc gaaatcaaca ccctgtcatt ttatggcagg gtgttttttt             110

SEQ ID NO: 42          moltype = DNA   length = 102
FEATURE                Location/Qualifiers
misc_difference        1..20
                       note = modified_base - a, c, t, g, unknown or other
misc_feature           1..102
                       note = Description of Artificial Sequence: Synthetic
                        polynucleotide
source                 1..102
                       mol_type = other DNA
                       organism = synthetic construct
SEQUENCE: 42
nnnnnnnnnn nnnnnnnnnn gttttagagc tagaaatagc aagttaaaat aaggctagtc   60
cgttatcaac ttgaaaaagt ggcaccgagt cggtgctttt tt                     102

SEQ ID NO: 43          moltype = DNA   length = 88
FEATURE                Location/Qualifiers
misc_difference        1..20
                       note = modified_base - a, c, t, g, unknown or other
misc_feature           1..88
                       note = Description of Artificial Sequence: Synthetic
```

```
                            oligonucleotide
source                  1..88
                        mol_type = other DNA
                        organism = synthetic construct
SEQUENCE: 43
nnnnnnnnnn nnnnnnnnnn gttttagagc tagaaatagc aagttaaaat aaggctagtc   60
cgttatcaac ttgaaaaagt gttttttt                                     88

SEQ ID NO: 44           moltype = DNA  length = 76
FEATURE                 Location/Qualifiers
misc_difference         1..20
                        note = modified_base - a, c, t, g, unknown or other
misc_feature            1..76
                        note = Description of Artificial Sequence: Synthetic
                            oligonucleotide
source                  1..76
                        mol_type = other DNA
                        organism = synthetic construct
SEQUENCE: 44
nnnnnnnnnn nnnnnnnnnn gttttagagc tagaaatagc aagttaaaat aaggctagtc   60
cgttatcatt tttttt                                                  76

SEQ ID NO: 45           moltype = DNA  length = 20
FEATURE                 Location/Qualifiers
source                  1..20
                        mol_type = unassigned DNA
                        organism = Homo sapiens
SEQUENCE: 45
gagtccgagc agaagaagaa                                              20

SEQ ID NO: 46           moltype = DNA  length = 20
FEATURE                 Location/Qualifiers
source                  1..20
                        mol_type = unassigned DNA
                        organism = Homo sapiens
SEQUENCE: 46
gagtcctagc aggagaagaa                                              20

SEQ ID NO: 47           moltype = DNA  length = 20
FEATURE                 Location/Qualifiers
source                  1..20
                        mol_type = unassigned DNA
                        organism = Homo sapiens
SEQUENCE: 47
gagtctaagc agaagaagaa                                              20

SEQ ID NO: 48           moltype = AA  length = 7
FEATURE                 Location/Qualifiers
source                  1..7
                        mol_type = protein
                        organism = unidentified
                        note = Simian virus
SEQUENCE: 48
PKKKRKV                                                            7

SEQ ID NO: 49           moltype = AA  length = 16
FEATURE                 Location/Qualifiers
REGION                  1..16
                        note = Description of Unknown: Nucleoplasmin bipartite NLS
                            sequence
source                  1..16
                        mol_type = protein
                        organism = unidentified
SEQUENCE: 49
KRPAATKKAG QAKKKK                                                  16

SEQ ID NO: 50           moltype = AA  length = 9
FEATURE                 Location/Qualifiers
REGION                  1..9
                        note = Description of Unknown: C-myc NLS sequence
source                  1..9
                        mol_type = protein
                        organism = unidentified
SEQUENCE: 50
PAAKRVKLD                                                          9

SEQ ID NO: 51           moltype = AA  length = 11
FEATURE                 Location/Qualifiers
REGION                  1..11
```

```
                           note = Description of Unknown: C-myc NLS sequence
source                     1..11
                           mol_type = protein
                           organism = unidentified
SEQUENCE: 51
RQRRNELKRS P                                                              11

SEQ ID NO: 52              moltype = AA  length = 38
FEATURE                    Location/Qualifiers
source                     1..38
                           mol_type = protein
                           organism = Homo sapiens
SEQUENCE: 52
NQSSNFGPMK GGNFGGRSSG PYGGGGQYFA KPRNQGGY                                  38

SEQ ID NO: 53              moltype = AA  length = 42
FEATURE                    Location/Qualifiers
REGION                     1..42
                           note = Description of Unknown: IBB domain from
                            importin-alpha sequence
source                     1..42
                           mol_type = protein
                           organism = unidentified
SEQUENCE: 53
RMRIZFKNKG KDTAELRRRR VEVSVELRKA KKDEQILKRR NV                             42

SEQ ID NO: 54              moltype = AA  length = 8
FEATURE                    Location/Qualifiers
REGION                     1..8
                           note = Description of Unknown: Myoma T Protein sequence
source                     1..8
                           mol_type = protein
                           organism = unidentified
SEQUENCE: 54
VSRKRPRP                                                                   8

SEQ ID NO: 55              moltype = AA  length = 8
FEATURE                    Location/Qualifiers
REGION                     1..8
                           note = Description of Unknown: Myoma T Protein sequence
source                     1..8
                           mol_type = protein
                           organism = unidentified
SEQUENCE: 55
PPKKARED                                                                   8

SEQ ID NO: 56              moltype = AA  length = 8
FEATURE                    Location/Qualifiers
source                     1..8
                           mol_type = protein
                           organism = Homo sapiens
SEQUENCE: 56
PQPKKKPL                                                                   8

SEQ ID NO: 57              moltype = AA  length = 12
FEATURE                    Location/Qualifiers
source                     1..12
                           mol_type = protein
                           organism = Mus musculus
SEQUENCE: 57
SALIKKKKM AP                                                              12

SEQ ID NO: 58              moltype = AA  length = 5
FEATURE                    Location/Qualifiers
source                     1..5
                           mol_type = protein
                           organism = unidentified
                           note = Influenza virus
SEQUENCE: 58
DRLRR                                                                      5

SEQ ID NO: 59              moltype = AA  length = 7
FEATURE                    Location/Qualifiers
source                     1..7
                           mol_type = protein
                           organism = unidentified
                           note = Influenza virus
SEQUENCE: 59
PKQKKRK                                                                    7
```

```
SEQ ID NO: 60            moltype = AA   length = 10
FEATURE                  Location/Qualifiers
source                   1..10
                         mol_type = protein
                         organism = unidentified
                         note = Hepatitis delta virus
SEQUENCE: 60
RKLKKKIKKL                                                                10

SEQ ID NO: 61            moltype = AA   length = 10
FEATURE                  Location/Qualifiers
source                   1..10
                         mol_type = protein
                         organism = Mus musculus
SEQUENCE: 61
REKKKFLKRR                                                                10

SEQ ID NO: 62            moltype = AA   length = 20
FEATURE                  Location/Qualifiers
source                   1..20
                         mol_type = protein
                         organism = Homo sapiens
SEQUENCE: 62
KRKGDEVDGV DEVAKKKSKK                                                     20

SEQ ID NO: 63            moltype = AA   length = 17
FEATURE                  Location/Qualifiers
source                   1..17
                         mol_type = protein
                         organism = Homo sapiens
SEQUENCE: 63
RKCLQAGMNL EARKTKK                                                        17

SEQ ID NO: 64            moltype = RNA  length = 12
FEATURE                  Location/Qualifiers
misc_feature             1..12
                         note = Description of Artificial Sequence: Synthetic
                          oligonucleotide
source                   1..12
                         mol_type = other RNA
                         organism = synthetic construct
SEQUENCE: 64
gttttagagc ta                                                             12

SEQ ID NO: 65            moltype = DNA  length = 24
FEATURE                  Location/Qualifiers
misc_feature             1..24
                         note = Description of Artificial Sequence: Synthetic
                          oligonucleotide
source                   1..24
                         mol_type = other DNA
                         organism = synthetic construct
SEQUENCE: 65
gcggggccag ggctgcgcgt gggg                                                24

SEQ ID NO: 66            moltype = DNA  length = 136
FEATURE                  Location/Qualifiers
misc_feature             1..136
                         note = Description of Artificial Sequence: Synthetic
                          polynucleotide
source                   1..136
                         mol_type = other DNA
                         organism = synthetic construct
SEQUENCE: 66
gcggggccag ggctgcgcgt ggggttttta gtactctggg ccaacatgag gatcacccat         60
gtctgcaggg cccagaatct actaaaacaa ggcaaaatgc cgtgtttatc tcgtcaactt        120
gttggcgaga tttttt                                                       136

SEQ ID NO: 67            moltype = DNA  length = 22
FEATURE                  Location/Qualifiers
misc_feature             1..22
                         note = Description of Artificial Sequence: Synthetic
                          oligonucleotide
source                   1..22
                         mol_type = other DNA
                         organism = synthetic construct
SEQUENCE: 67
ggggccaggg ctgcgcgtgg gg                                                  22
```

```
SEQ ID NO: 68            moltype = DNA  length = 134
FEATURE                  Location/Qualifiers
misc_feature             1..134
                         note = Description of Artificial Sequence: Synthetic
                          polynucleotide
source                   1..134
                         mol_type = other DNA
                         organism = synthetic construct
SEQUENCE: 68
ggggccaggg ctgcgcgtgg gggttttagt actctgggcc aacatgagga tcacccatgt    60
ctgcagggcc cagaatctac taaaacaagg caaaatgccg tgtttatctc gtcaacttgt   120
tggcgagatt tttt                                                     134

SEQ ID NO: 69            moltype = DNA  length = 21
FEATURE                  Location/Qualifiers
misc_feature             1..21
                         note = Description of Artificial Sequence: Synthetic
                          oligonucleotide
source                   1..21
                         mol_type = other DNA
                         organism = synthetic construct
SEQUENCE: 69
gggccagggc tgcgcgtggg g                                              21

SEQ ID NO: 70            moltype = DNA  length = 133
FEATURE                  Location/Qualifiers
misc_feature             1..133
                         note = Description of Artificial Sequence: Synthetic
                          polynucleotide
source                   1..133
                         mol_type = other DNA
                         organism = synthetic construct
SEQUENCE: 70
gggccagggc tgcgcgtggg ggttttagta ctctgggcca acatgaggat cacccatgtc    60
tgcagggccc agaatctact aaaacaaggc aaaatgccgt gtttatctcg tcaacttgtt   120
ggcgagattt ttt                                                      133

SEQ ID NO: 71            moltype = DNA  length = 24
FEATURE                  Location/Qualifiers
misc_feature             1..24
                         note = Description of Artificial Sequence: Synthetic
                          oligonucleotide
source                   1..24
                         mol_type = other DNA
                         organism = synthetic construct
SEQUENCE: 71
gcccaggcgg gcagctgggg gagg                                           24

SEQ ID NO: 72            moltype = DNA  length = 136
FEATURE                  Location/Qualifiers
misc_feature             1..136
                         note = Description of Artificial Sequence: Synthetic
                          polynucleotide
source                   1..136
                         mol_type = other DNA
                         organism = synthetic construct
SEQUENCE: 72
gcccaggcgg gcagctgggg gagggttttta gtactctggg ccaacatgag gatcacccat    60
gtctgcaggg cccagaatct actaaaacaa ggcaaaatgc cgtgtttatc tcgtcaactt   120
gttggcgaga tttttt                                                   136

SEQ ID NO: 73            moltype = DNA  length = 22
FEATURE                  Location/Qualifiers
misc_feature             1..22
                         note = Description of Artificial Sequence: Synthetic
                          oligonucleotide
source                   1..22
                         mol_type = other DNA
                         organism = synthetic construct
SEQUENCE: 73
ccaggcgggc agctggggga gg                                             22

SEQ ID NO: 74            moltype = DNA  length = 134
FEATURE                  Location/Qualifiers
misc_feature             1..134
                         note = Description of Artificial Sequence: Synthetic
                          polynucleotide
source                   1..134
```

```
                            mol_type = other DNA
                            organism = synthetic construct
SEQUENCE: 74
ccaggcgggc agctggggga gggttttagt actctgggcc aacatgagga tcacccatgt    60
ctgcagggcc cagaatctac taaaacaagg caaaatgccg tgtttatctc gtcaacttgt   120
tggcgagatt tttt                                                     134

SEQ ID NO: 75              moltype = DNA  length = 22
FEATURE                    Location/Qualifiers
misc_feature               1..22
                           note = Description of Artificial Sequence: Synthetic
                            oligonucleotide
source                     1..22
                           mol_type = other DNA
                           organism = synthetic construct
SEQUENCE: 75
gcaggcgggc agctggggga gg                                             22

SEQ ID NO: 76              moltype = DNA  length = 134
FEATURE                    Location/Qualifiers
misc_feature               1..134
                           note = Description of Artificial Sequence: Synthetic
                            polynucleotide
source                     1..134
                           mol_type = other DNA
                           organism = synthetic construct
SEQUENCE: 76
gcaggcgggc agctggggga gggttttagt actctgggcc aacatgagga tcacccatgt    60
ctgcagggcc cagaatctac taaaacaagg caaaatgccg tgtttatctc gtcaacttgt   120
tggcgagatt tttt                                                     134

SEQ ID NO: 77              moltype = AA  length = 6
FEATURE                    Location/Qualifiers
REGION                     1..6
                           note = Description of Artificial Sequence: Synthetic 6xHis
                            tag
source                     1..6
                           mol_type = protein
                           organism = synthetic construct
SEQUENCE: 77
HHHHHH                                                                6

SEQ ID NO: 78              moltype = AA  length = 121
FEATURE                    Location/Qualifiers
REGION                     1..121
                           note = Description of Artificial Sequence: Synthetic
                            polypeptide
source                     1..121
                           mol_type = protein
                           organism = synthetic construct
SEQUENCE: 78
KRNYILGLDI GITSVGYGII DYETRDVIDA GVRLFKEANV ENNEGRRSKR GARRLKRRRR    60
HRIQRVKKLL FDYNLLTDHS ELSGINPYEA RVKGLSQKLS EEEFSAALLH LAKRRGVHNV   120
N                                                                   121

SEQ ID NO: 79              moltype = AA  length = 603
FEATURE                    Location/Qualifiers
REGION                     1..603
                           note = Description of Artificial Sequence: Synthetic
                            polypeptide
source                     1..603
                           mol_type = protein
                           organism = synthetic construct
SEQUENCE: 79
ELSTKEQISR NSKALEEKYV AELQLERLKK DGEVRGSINR FKTSDYVKEA KQLLKVQKAY    60
HQLDQSFIDT YIDLLETRRT YYEGPGEGSP FGWKDIKEWY EMLMGHCTYF PEELRSVKYA   120
YNADLYNALN DLNNLVITRD ENEKLEYYEK FQIIENVFKQ KKKPTLKQIA KEILVNEEDI   180
KGYRVTSTGK PEFTNLKVYH DIKDITARKE IIENAELLDQ IAKILTIYQS SEDIQEELTN   240
LNSELTQEEI EQISNLKGYT GTHNLSLKAI NLILDELWHT NDNQIAIFNR LKLVPKKVDL   300
SQQKEIPTTL VDDFILSPVV KRSFIQSIKV INAIIKKYGL PNDIIIELAR EKNSKDAQKM   360
INEMQKRNRQ TNERIEEIIR TTGKENAKYL IEKIKLHDMQ EGKCLYSLEA IPLEDLLNNP   420
FNYEVDHIIP RSVSFDNSFN NKVLVKQEEN SKKGNRTPFQ YLSSSDSKIS YETFKKHILN   480
LAKGKGRISK TKKEYLLEER DINRFSVQKD FINRNLVDTR YATRGLMNLL RSYFRVNNLD   540
VKVKSINGGF TSFLRRKWKF KKERNKGYKH HAEDALIIAN ADFIFKEWKK LDKAKKVMEN   600
QMF                                                                 603

SEQ ID NO: 80              moltype = AA  length = 312
FEATURE                    Location/Qualifiers
REGION                     1..312
```

```
                        note = Description of Artificial Sequence: Synthetic
                            polypeptide
source                  1..312
                        mol_type = protein
                        organism = synthetic construct
SEQUENCE: 80
PEIETEQEYK EIFITPHQIK HIKDFKDYKY SHRVDKKPNR ELINDTLYST RKDDKGNTLI    60
VNNLNGLYDK DNDKLKKLIN KSPEKLLMYH HDPQTYQKLK LIMEQYGDEK NPLYKYYEET   120
GNYLTKYSKK DNGPVIKKIK YYGNKLNAHL DITDDYPNSR NKVVKLSLKP YRFDVYLDNG   180
VYKFVTVKNL DVIKKENYYE VNSKAYEEAK KLKKISNQAE FIASFYNNDL IKINGELYRV   240
IGVNNDLLNR IEVNMIDITY REYLENMNDK RPPRIIKTIA SKTQSIKKYS TDILGNLYEV   300
KSKKHPQIIK KG                                                      312

SEQ ID NO: 81           moltype = AA   length = 1156
FEATURE                 Location/Qualifiers
REGION                  1..1156
                        note = Description of Artificial Sequence: Synthetic
                            polypeptide
source                  1..1156
                        mol_type = protein
                        organism = synthetic construct
SEQUENCE: 81
MAPKKKRKVG IHGVPAAKRN YILGLAIGIT SVGYGIIDYE TRDVIDAGVR LFKEANVENN    60
EGRRSKRGAR RLKRRRRHRI QRVKKLLFDY NLLTDHSELS GINPYEARVK GLSQKLSEEE   120
FSAALLHLAK RRGVHNVNEV EEDTGNELST KEQISRNSKA LEEKYVAELQ LERLKKDGEV   180
RGSINRFKTS DYVKEAKQLL KVQKAYHQLD QSFIDTYIDL LETRRTYYEG PGEGSPFGWK   240
DIKEWYEMLM GHCTYFPEEL RSVKYAYNAD LYNALNDLNN LVITRDENEK LEYYEKFQII   300
ENVFKQKKKP TLKQIAKEIL VNEEDIKGYR VTSTGKPEFT NLKVYHDIKD ITARKEIIEN   360
AELLDQIAKI LTIYQSSEDI QEELTNLNSE LTQEEIEQIS NLKGYTGTHN LSLKAINLIL   420
DELWHTNDNQ IAIFNRLKLV PKKVDLSQQK EIPTTLVDDF ILSPVVKRSF IQSIKVINAI   480
IKKYGLPNDI IIELAREKNS KDAQKMINEM QKRNRQTNER IEEIIRTTGK ENAKYLIEKI   540
KLHDMQEGKC LYSLEAIPLE DLLNNPFNYE VDHIIPRSVS FDNSFNNKVL VKQEEASKKG   600
NRTPFQYLSS SDSKISYETF KKHILNLAKG KGRISKTKKE YLLEERDINR FSVQKDFINR   660
NLVDTRYATR GLMNLLRSYF RVNNLDVKVK SINGGFTSPL RKWKFKKER NKGYKHHAED    720
ALIIANADFI FKEWKKLDKA KKVMENQMFE EKQAESMPEI ETEQEYKEIF ITPHQIKHIK   780
DFKDYKYSHR VDKKPNRELI NDTLYSTRKD DKGNTLIVNN LNGLYDKDND KLKKLINKSP   840
EKLLMYHHDP QTYQKLKLIM EQYGDEKNPL YKYYEETGNY LTKYSKKDNG PVIKKIKYYG   900
NKLNAHLDIT DDYPNSRNKV VKLSLKPYRF DVYLDNGVYK FVTVKNLDVI KKENYYEVNS   960
KCYEEAKKLK KISNQAEFIA SFYNNDLIKI NGELYRVIGV NNDLLNRIEV NMIDITYREY  1020
LENMNDKRPP RIIKTIASKT QSIKKYSTDI LGNLYEVKSK KHPQIIKKGS AGGGGSGGGG  1080
SGGGGSGPKK KRKVAAAGSG RADALDDFDL DMLGSDALDD FDLDMLGSDA LDDFDLDMLG  1140
SDALDDFDLD MLINAS                                                 1156

SEQ ID NO: 82           moltype = AA   length = 473
FEATURE                 Location/Qualifiers
REGION                  1..473
                        note = Description of Artificial Sequence: Synthetic
                            polypeptide
source                  1..473
                        mol_type = protein
                        organism = synthetic construct
SEQUENCE: 82
MASNFTQFVL VDNGGTGDVT VAPSNFANGV AEWISSNSRS QAYKVTCSVR QSSAQKRKYT    60
IKVEVPKVAT QTVGGVELPV AAWRSYLNME LTIPIFATNS DCELIVKAMQ GLLKDGNPIP   120
SAIAANSGIY SAGGGGSGGG GSGGGGSGPK KKRKVAAAGS PSGQISNQAL ALAPSSAPVL   180
AQTMVPSSAM VPLAQPPAPA PVLTPGPPQS LSAPVPKSTQ AGEGTLSEAL LHLQFDADED   240
LGALLGNSTD PGVFTDLASV DNSEFQQLLN QGVSMSHSTA EPMLMEYPEA ITRLVTGSQR   300
PPDPAPTPLG TSGLPNGLSG DEDFSSIADM DFSALLSQIS SSGQGGGGSG FSVDTSALLD   360
LFSPSVTVPD MSLPDDSSL ASIQELLSPQ EPPRPPEAEN SSPDSGKQLV HYTAQPLFLL    420
DPGSVDTGSN DLPVLFELGE GSYFSEGDGF AEDPTISLLT GSEPPKAKDP TVS         473

SEQ ID NO: 83           moltype = RNA   length = 107
FEATURE                 Location/Qualifiers
misc_feature            1..107
                        note = Description of Artificial Sequence: Synthetic
                            polynucleotide
source                  1..107
                        mol_type = other RNA
                        organism = synthetic construct
SEQUENCE: 83
gttttagtac tctgggccaa catgaggatc acccatgtct gcagggccca gaatctacta    60
aaacaaggca aaatgccgtg tttatctcgt caacttgttg gcgagat                107

SEQ ID NO: 84           moltype = RNA   length = 108
FEATURE                 Location/Qualifiers
misc_feature            1..108
                        note = Description of Artificial Sequence: Synthetic
                            polynucleotide
source                  1..108
```

```
                        mol_type = other RNA
                        organism = synthetic construct
SEQUENCE: 84
gttttagtac tctggaaaca gaatctacta aaacaaggca ggccaacatg aggatcaccc    60
atgtctgcag ggcctgccgt gtttatctcg tcaacttgtt ggcgagat                108

SEQ ID NO: 85           moltype = RNA   length = 107
FEATURE                 Location/Qualifiers
misc_feature            1..107
                        note = Description of Artificial Sequence: Synthetic
                         polynucleotide
source                  1..107
                        mol_type = other RNA
                        organism = synthetic construct
SEQUENCE: 85
gttttagtac tctggaaaca gaatctacta aaacaaggca aaatgccgtg tttatctcgt    60
caaggccaac atgaggatca cccatgtctg cagggccttg gcgagat                 107

SEQ ID NO: 86           moltype = RNA   length = 138
FEATURE                 Location/Qualifiers
misc_feature            1..138
                        note = Description of Artificial Sequence: Synthetic
                         polynucleotide
source                  1..138
                        mol_type = other RNA
                        organism = synthetic construct
SEQUENCE: 86
gttttagtac tctgggccaa catgaggatc acccatgtct gcagggccca gaatctacta    60
aaacaaggca ggccaacatg aggatcaccc atgtctgcag ggcctgccgt gtttatctcg   120
tcaacttgtt ggcgagat                                                 138

SEQ ID NO: 87           moltype = RNA   length = 137
FEATURE                 Location/Qualifiers
misc_feature            1..137
                        note = Description of Artificial Sequence: Synthetic
                         polynucleotide
source                  1..137
                        mol_type = other RNA
                        organism = synthetic construct
SEQUENCE: 87
gttttagtac tctgggccaa catgaggatc acccatgtct gcagggccca gaatctacta    60
aaacaaggca aaatgccgtg tttatctcgt caaggccaac atgaggatca cccatgtctg   120
cagggccttg gcgagat                                                  137

SEQ ID NO: 88           moltype = DNA   length = 22
FEATURE                 Location/Qualifiers
misc_feature            1..22
                        note = Description of Artificial Sequence: Synthetic
                         oligonucleotide
source                  1..22
                        mol_type = other DNA
                        organism = synthetic construct
SEQUENCE: 88
atggttcctt aaataagaac tt                                             22

SEQ ID NO: 89           moltype = DNA   length = 21
FEATURE                 Location/Qualifiers
misc_feature            1..21
                        note = Description of Artificial Sequence: Synthetic
                         oligonucleotide
source                  1..21
                        mol_type = other DNA
                        organism = synthetic construct
SEQUENCE: 89
tggccaggct ttggggaggc c                                              21

SEQ ID NO: 90           moltype = DNA   length = 21
FEATURE                 Location/Qualifiers
misc_feature            1..21
                        note = Description of Artificial Sequence: Synthetic
                         oligonucleotide
source                  1..21
                        mol_type = other DNA
                        organism = synthetic construct
SEQUENCE: 90
ggcctcccca aagcctggcc a                                              21

SEQ ID NO: 91           moltype = DNA   length = 20
FEATURE                 Location/Qualifiers
```

```
misc_feature               1..20
                           note = Description of Artificial Sequence: Synthetic primer
source                     1..20
                           mol_type = other DNA
                           organism = synthetic construct
SEQUENCE: 91
ggagctggtc tgttggagaa                                                         20

SEQ ID NO: 92              moltype = DNA   length = 20
FEATURE                    Location/Qualifiers
misc_feature               1..20
                           note = Description of Artificial Sequence: Synthetic primer
source                     1..20
                           mol_type = other DNA
                           organism = synthetic construct
SEQUENCE: 92
ccatcccctt ctgtgaatgt                                                         20

SEQ ID NO: 93              moltype = DNA   length = 22
FEATURE                    Location/Qualifiers
misc_feature               1..22
                           note = Description of Artificial Sequence: Synthetic primer
source                     1..22
                           mol_type = other DNA
                           organism = synthetic construct
SEQUENCE: 93
tcccaatcca taatcccacg tt                                                      22

SEQ ID NO: 94              moltype = DNA   length = 20
FEATURE                    Location/Qualifiers
misc_feature               1..20
                           note = Description of Artificial Sequence: Synthetic primer
source                     1..20
                           mol_type = other DNA
                           organism = synthetic construct
SEQUENCE: 94
ggagattgga gacacggaga                                                         20

SEQ ID NO: 95              moltype = DNA   length = 26
FEATURE                    Location/Qualifiers
misc_feature               1..26
                           note = Description of Artificial Sequence: Synthetic primer
source                     1..26
                           mol_type = other DNA
                           organism = synthetic construct
SEQUENCE: 95
ctgttgtgtt gagtaacata tacctg                                                  26

SEQ ID NO: 96              moltype = DNA   length = 20
FEATURE                    Location/Qualifiers
misc_feature               1..20
                           note = Description of Artificial Sequence: Synthetic primer
source                     1..20
                           mol_type = other DNA
                           organism = synthetic construct
SEQUENCE: 96
aagaagggct cccatcacat                                                         20

SEQ ID NO: 97              moltype = DNA   length = 20
FEATURE                    Location/Qualifiers
misc_feature               1..20
                           note = Description of Artificial Sequence: Synthetic primer
source                     1..20
                           mol_type = other DNA
                           organism = synthetic construct
SEQUENCE: 97
ttgcatgctg aagtctctcc                                                         20

SEQ ID NO: 98              moltype = DNA   length = 19
FEATURE                    Location/Qualifiers
misc_feature               1..19
                           note = Description of Artificial Sequence: Synthetic primer
source                     1..19
                           mol_type = other DNA
                           organism = synthetic construct
SEQUENCE: 98
agtggccaga gtccagctt                                                          19

SEQ ID NO: 99              moltype = DNA   length = 22
```

-continued

```
FEATURE                 Location/Qualifiers
misc_feature            1..22
                        note = Description of Artificial Sequence: Synthetic primer
source                  1..22
                        mol_type = other DNA
                        organism = synthetic construct
SEQUENCE: 99
ggtaggcgtg tacggtggga gg                                              22

SEQ ID NO: 100          moltype = DNA  length = 60
FEATURE                 Location/Qualifiers
misc_feature            1..60
                        note = Description of Artificial Sequence: Synthetic primer
source                  1..60
                        mol_type = other DNA
                        organism = synthetic construct
SEQUENCE: 100
cacagtcgag gctgatcagc gagctctagg aattcttagg acaggtccac cttcttgggc     60

SEQ ID NO: 101          moltype = DNA  length = 60
FEATURE                 Location/Qualifiers
misc_feature            1..60
                        note = Description of Artificial Sequence: Synthetic primer
source                  1..60
                        mol_type = other DNA
                        organism = synthetic construct
SEQUENCE: 101
agcagagctc tctggctaac taccggtgcc accatgcagc agaaagagat ccccaccacc     60

SEQ ID NO: 102          moltype = DNA  length = 22
FEATURE                 Location/Qualifiers
misc_feature            1..22
                        note = Description of Artificial Sequence: Synthetic primer
source                  1..22
                        mol_type = other DNA
                        organism = synthetic construct
SEQUENCE: 102
cagtcgaggc tgatcagcga gc                                              22

SEQ ID NO: 103          moltype = DNA  length = 60
FEATURE                 Location/Qualifiers
misc_feature            1..60
                        note = Description of Artificial Sequence: Synthetic primer
source                  1..60
                        mol_type = other DNA
                        organism = synthetic construct
SEQUENCE: 103
gcacagtcga ggctgatcag cgagctctag gaattcttac tcggcctgct tttcctcgaa     60

SEQ ID NO: 104          moltype = DNA  length = 60
FEATURE                 Location/Qualifiers
misc_feature            1..60
                        note = Description of Artificial Sequence: Synthetic primer
source                  1..60
                        mol_type = other DNA
                        organism = synthetic construct
SEQUENCE: 104
ataagcagag ctctctggct aactaccggt gccaccatga gcatgcccga gatcgaaacc     60

SEQ ID NO: 105          moltype = DNA  length = 60
FEATURE                 Location/Qualifiers
misc_feature            1..60
                        note = Description of Artificial Sequence: Synthetic primer
source                  1..60
                        mol_type = other DNA
                        organism = synthetic construct
SEQUENCE: 105
cacagtcgag gctgatcagc gagctctagg aattcttaga tcagggtgtt gcccttgtcg     60

SEQ ID NO: 106          moltype = DNA  length = 60
FEATURE                 Location/Qualifiers
misc_feature            1..60
                        note = Description of Artificial Sequence: Synthetic primer
source                  1..60
                        mol_type = other DNA
                        organism = synthetic construct
SEQUENCE: 106
gcagagctct ctggctaact accggtgcca ccatggtgaa caatctgaac ggcctgtacg     60
```

```
SEQ ID NO: 107          moltype = DNA   length = 60
FEATURE                 Location/Qualifiers
misc_feature            1..60
                        note = Description of Artificial Sequence: Synthetic primer
source                  1..60
                        mol_type = other DNA
                        organism = synthetic construct
SEQUENCE: 107
taagcagagc tctctggcta actaccggtg ccaccatgaa gcggaactac atcctgggcc    60

SEQ ID NO: 108          moltype = DNA   length = 60
FEATURE                 Location/Qualifiers
misc_feature            1..60
                        note = Description of Artificial Sequence: Synthetic primer
source                  1..60
                        mol_type = other DNA
                        organism = synthetic construct
SEQUENCE: 108
cagtcgaggc tgatcagcga gctctaggaa ttcttagccc tttttgatga tctgagggtg    60

SEQ ID NO: 109          moltype = DNA   length = 28
FEATURE                 Location/Qualifiers
misc_feature            1..28
                        note = Description of Artificial Sequence: Synthetic
                        oligonucleotide
source                  1..28
                        mol_type = other DNA
                        organism = synthetic construct
SEQUENCE: 109
ctattcaagc caagcgcacc taatttcc                                       28

SEQ ID NO: 110          moltype = RNA   length = 97
FEATURE                 Location/Qualifiers
misc_feature            1..97
                        note = Description of Artificial Sequence: Synthetic
                        oligonucleotide
source                  1..97
                        mol_type = other RNA
                        organism = synthetic construct
SEQUENCE: 110
ggaaattagg tgcgcttggc gttttagtac tctggaaaca gaatctacta aaacaaggca    60
aaatgccgtg tttatctcgt caacttgttg gcgagat                             97

SEQ ID NO: 111          moltype = RNA   length = 81
FEATURE                 Location/Qualifiers
misc_feature            1..81
                        note = Description of Artificial Sequence: Synthetic
                        oligonucleotide
source                  1..81
                        mol_type = other RNA
                        organism = synthetic construct
SEQUENCE: 111
gttttagtac tctggaaaca gaatctacta aaacaaggca aaatgccgtg tttatctcgt    60
caacttgttg gcgagattttt t                                             81

SEQ ID NO: 112          moltype = RNA   length = 40
FEATURE                 Location/Qualifiers
misc_feature            1..40
                        note = Description of Artificial Sequence: Synthetic
                        oligonucleotide
source                  1..40
                        mol_type = other RNA
                        organism = synthetic construct
SEQUENCE: 112
gttttagtac tctggaaaca gaatctacta aaacaattttt                         40

SEQ ID NO: 113          moltype = RNA   length = 51
FEATURE                 Location/Qualifiers
misc_feature            1..51
                        note = Description of Artificial Sequence: Synthetic
                        oligonucleotide
source                  1..51
                        mol_type = other RNA
                        organism = synthetic construct
SEQUENCE: 113
gttttagtac tctggaaaca gaatctacta aaacaaggca aaatgccttt t             51

SEQ ID NO: 114          moltype = RNA   length = 57
FEATURE                 Location/Qualifiers
```

```
misc_feature           1..57
                       note = Description of Artificial Sequence: Synthetic
                         oligonucleotide
source                 1..57
                       mol_type = other RNA
                       organism = synthetic construct
SEQUENCE: 114
gttttagtac tctggaaaca gaatctacta aaacaaggca aaatgccgtg tttttt       57

SEQ ID NO: 115         moltype = RNA  length = 70
FEATURE                Location/Qualifiers
misc_feature           1..70
                       note = Description of Artificial Sequence: Synthetic
                         oligonucleotide
source                 1..70
                       mol_type = other RNA
                       organism = synthetic construct
SEQUENCE: 115
gttttagtac tctggaaaca gaatctacta aaacaagtgt ttatctcgtc aacttgttgg   60
cgagattttt                                                         70

SEQ ID NO: 116         moltype = RNA  length = 81
FEATURE                Location/Qualifiers
misc_feature           1..81
                       note = Description of Artificial Sequence: Synthetic
                         oligonucleotide
source                 1..81
                       mol_type = other RNA
                       organism = synthetic construct
SEQUENCE: 116
gttttagtac tctggaaaca gaatctacta aaacaaccgg aaaccgggtg tttatctcgt   60
caacttgttg gcgagatttt t                                            81

SEQ ID NO: 117         moltype = RNA  length = 81
FEATURE                Location/Qualifiers
misc_feature           1..81
                       note = Description of Artificial Sequence: Synthetic
                         oligonucleotide
source                 1..81
                       mol_type = other RNA
                       organism = synthetic construct
SEQUENCE: 117
gttttagtac tctggaaaca gaatctacta aaacaaggca aaatgccgtg tttcccgcgc   60
cggcttgccg gcgcgggttt t                                            81

SEQ ID NO: 118         moltype = RNA  length = 75
FEATURE                Location/Qualifiers
misc_feature           1..75
                       note = Description of Artificial Sequence: Synthetic
                         oligonucleotide
source                 1..75
                       mol_type = other RNA
                       organism = synthetic construct
SEQUENCE: 118
gttttagtac tctggaaaca gaatctacta aaacaaggca aaatgccatc tcgtcaactt   60
gttggcgaga ttttt                                                   75

SEQ ID NO: 119         moltype = RNA  length = 81
FEATURE                Location/Qualifiers
misc_feature           1..81
                       note = Description of Artificial Sequence: Synthetic
                         oligonucleotide
source                 1..81
                       mol_type = other RNA
                       organism = synthetic construct
SEQUENCE: 119
gttttagtac tctggaaaca gaatctacta aaacaaggca aaatgccgcg cccatctcgt   60
caacttgttg gcgagatttt t                                            81

SEQ ID NO: 120         moltype = RNA  length = 83
FEATURE                Location/Qualifiers
misc_feature           1..83
                       note = Description of Artificial Sequence: Synthetic
                         oligonucleotide
source                 1..83
                       mol_type = other RNA
                       organism = synthetic construct
SEQUENCE: 120
gttttagtag attctggaaa cagaatctac taaaacaagg caaaatgccg tgtttatctc   60
```

```
gtcaacttgt tggcgagatt ttt                                             83

SEQ ID NO: 121         moltype = RNA   length = 81
FEATURE                Location/Qualifiers
misc_feature           1..81
                       note = Description of Artificial Sequence: Synthetic
                       oligonucleotide
source                 1..81
                       mol_type = other RNA
                       organism = synthetic construct
SEQUENCE: 121
gttttagtaa tctggaaaca gaatctacta aaacaaggca aaatgccgtg tttatctcgt   60
caacttgttg gcgagatttt t                                             81

SEQ ID NO: 122         moltype = RNA   length = 81
FEATURE                Location/Qualifiers
misc_feature           1..81
                       note = Description of Artificial Sequence: Synthetic
                       oligonucleotide
source                 1..81
                       mol_type = other RNA
                       organism = synthetic construct
SEQUENCE: 122
gttttagtac tctggaaaca gatcatacta aaacaaggca aaatgccgtg tttatctcgt   60
caacttgttg gcgagatttt t                                             81

SEQ ID NO: 123         moltype = DNA   length = 20
FEATURE                Location/Qualifiers
misc_feature           1..20
                       note = Description of Artificial Sequence: Synthetic
                       oligonucleotide
source                 1..20
                       mol_type = other DNA
                       organism = synthetic construct
SEQUENCE: 123
gccaagcgca cctaatttcc                                                20

SEQ ID NO: 124         moltype = RNA   length = 73
FEATURE                Location/Qualifiers
misc_feature           1..73
                       note = Description of Artificial Sequence: Synthetic
                       oligonucleotide
source                 1..73
                       mol_type = other RNA
                       organism = synthetic construct
SEQUENCE: 124
ggaaattagg tgcgcttggc gttttagtac tctggaaaca gaatctacta aaacaaggca   60
aaatgccgtg ttt                                                      73

SEQ ID NO: 125         moltype = RNA   length = 77
FEATURE                Location/Qualifiers
source                 1..77
                       mol_type = unassigned RNA
                       organism = Homo sapiens
SEQUENCE: 125
gttttagtac tctggaaaca gaatctacta aaacaaggca aaatgccgtg tttatctcgt   60
caacttgttg gcgagat                                                  77

SEQ ID NO: 126         moltype = RNA   length = 14
FEATURE                Location/Qualifiers
misc_feature           1..14
                       note = Description of Artificial Sequence: Synthetic
                       oligonucleotide
source                 1..14
                       mol_type = other RNA
                       organism = synthetic construct
SEQUENCE: 126
gttttagtac tctg                                                     14

SEQ ID NO: 127         moltype = RNA   length = 59
FEATURE                Location/Qualifiers
misc_feature           1..59
                       note = Description of Artificial Sequence: Synthetic
                       oligonucleotide
source                 1..59
                       mol_type = other RNA
                       organism = synthetic construct
SEQUENCE: 127
cagaatctac taaaacaagg caaaatgccg tgtttatctc gtcaacttgt tggcgagat    59
```

```
SEQ ID NO: 128          moltype = RNA   length = 39
FEATURE                 Location/Qualifiers
misc_feature            1..39
                        note = Description of Artificial Sequence: Synthetic
                          oligonucleotide
source                  1..39
                        mol_type = other RNA
                        organism = synthetic construct
SEQUENCE: 128
gttttagtac tctggaaaca gaatctacta aaacaaggc                              39

SEQ ID NO: 129          moltype = RNA   length = 34
FEATURE                 Location/Qualifiers
misc_feature            1..34
                        note = Description of Artificial Sequence: Synthetic
                          oligonucleotide
source                  1..34
                        mol_type = other RNA
                        organism = synthetic construct
SEQUENCE: 129
tgccgtgttt atctcgtcaa cttgttggcg agat                                   34

SEQ ID NO: 130          moltype = RNA   length = 63
FEATURE                 Location/Qualifiers
misc_feature            1..63
                        note = Description of Artificial Sequence: Synthetic
                          oligonucleotide
source                  1..63
                        mol_type = other RNA
                        organism = synthetic construct
SEQUENCE: 130
gttttagtac tctggaaaca gaatctacta aaacaaggca aaatgccgtg tttatctcgt       60
caa                                                                     63

SEQ ID NO: 131          moltype = RNA   length = 10
FEATURE                 Location/Qualifiers
misc_feature            1..10
                        note = Description of Artificial Sequence: Synthetic
                          oligonucleotide
source                  1..10
                        mol_type = other RNA
                        organism = synthetic construct
SEQUENCE: 131
ttggcgagat                                                              10

SEQ ID NO: 132          moltype = RNA   length = 21
FEATURE                 Location/Qualifiers
misc_feature            1..21
                        note = Description of Artificial Sequence: Synthetic
                          oligonucleotide
source                  1..21
                        mol_type = other RNA
                        organism = synthetic construct
SEQUENCE: 132
cagaatctac taaaacaagg c                                                 21

SEQ ID NO: 133          moltype = RNA   length = 45
FEATURE                 Location/Qualifiers
misc_feature            1..45
                        note = Description of Artificial Sequence: Synthetic
                          oligonucleotide
source                  1..45
                        mol_type = other RNA
                        organism = synthetic construct
SEQUENCE: 133
cagaatctac taaaacaagg caaaatgccg tgtttatctc gtcaa                       45

SEQ ID NO: 134          moltype = DNA   length = 40
FEATURE                 Location/Qualifiers
source                  1..40
                        mol_type = unassigned DNA
                        organism = Homo sapiens
SEQUENCE: 134
acatatctaa tggttcctta aataagaact ttaggatatt                             40

SEQ ID NO: 135          moltype = RNA   length = 23
FEATURE                 Location/Qualifiers
misc_feature            1..23
```

```
                                note = Description of Artificial Sequence: Synthetic
                                 oligonucleotide
source                          1..23
                                mol_type = other RNA
                                organism = synthetic construct
SEQUENCE: 135
gatggttcct taaataagaa ctt                                                   23

SEQ ID NO: 136              moltype = RNA   length = 77
FEATURE                     Location/Qualifiers
misc_feature                1..77
                                note = Description of Artificial Sequence: Synthetic
                                 oligonucleotide
source                          1..77
                                mol_type = other RNA
                                organism = synthetic construct
SEQUENCE: 136
gttttagagc tagaaatagc aagttaaaat aaggctagtc cgttatcaac ttgaaaaagt            60
ggcaccgagt cggtgct                                                          77

SEQ ID NO: 137              moltype = AA   length = 1053
FEATURE                     Location/Qualifiers
REGION                      1..1053
                                note = Description of Artificial Sequence: Synthetic
                                 polypeptide
source                          1..1053
                                mol_type = protein
                                organism = synthetic construct
SEQUENCE: 137
MKRNYILGLD IGITSVGYGI IDYETRDVID AGVRLFKEAN VENNEGRRSK RGARRLKRRR            60
RHRIQRVKKL LFDYNLLTDH SELSGINPYE ARVKGLSQKL SEEEFSAALL HLAKRRGVHN           120
VNEVEEDTGN ELSTKEQISR NSKALEEKYV AELQLERLKK DGEVRGSINR FKTSDYVKEA           180
KQLLKVQKAY HQLDQSFIDT YIDLLETRRT YYEGPGEGSP FGWKDIKEWY EMLMGHCTYF           240
PEELRSVKYA YNADLYNALN DLNNLVITRD ENEKLEYYEK FQIIENVFKQ KKKPTLKQIA           300
KEILVNEEDI KGYRVTSTGK PEFTNLKVYH DIKDITARKE IIENAELLDQ IAKILTIYQS           360
SEDIQEELTN LNSELTQEEI EQISNLKGYT GTHNLSLKAI NLILDELWHT NDNQIAIFNR           420
LKLVPKKVDL SQQKEIPTTL VDDFILSPVV KRSFIQSIKV INAIIKKYGL PNDIIIELAR           480
EKNSKDAQKM INEMQKRNRQ TNERIEEIIR TTGKENAKYL IEKIKLHDMQ EGKCLYSLEA           540
IPLEDLLNNP FNYEVDHIIP RSVSFDNSFN NKVLVKQEEN SKKGNRTPFQ YLSSSDSKIS           600
YETFKKHILN LAKGKGRISK TKKEYLLEER DINRFSVQKD FINRNLVDTR YATRGLMNLL           660
RSYFRVNNLD VKVKSINGGF TSFLRRKWKF KKERNKGYKH HAEDALIIAN ADFIFKEWKK           720
LDKAKKVMEN QMFEEKQAES MPEIETEQEY KEIFITPHQI KHIKDFKDYK YSHRVDKKPN           780
RELINDTLYS TRKDDKGNTL IVNNLNGLYD KDNDKLKKLI NKSPEKLLMY HHDPQTYQKL           840
KLIMEQYGDE KNPLYKYYEE TGNYLTKYSK KDNGPVIKKI KYYGNKLNAH LDITDDYPNS           900
RNKVVKLSLK PYRFDVYLDN GVYKFVTVKN LDVIKKENYY EVNSKCYEEA KKLKKISNQA           960
EFIASFYNND LIKINGELYR VIGVNNDLLN RIEVNMIDIT YREYLENMND KRPPRIIKTI          1020
ASKTQSIKKY STDILGNLYE VKSKKHPQII KKG                                      1053

SEQ ID NO: 138              moltype = AA   length = 1368
FEATURE                     Location/Qualifiers
REGION                      1..1368
                                note = Description of Artificial Sequence: Synthetic
                                 polypeptide
source                          1..1368
                                mol_type = protein
                                organism = synthetic construct
SEQUENCE: 138
MDKKYSIGLD IGTNSVGWAV ITDEYKVPSK KFKVLGNTDR HSIKKNLIGA LLFDSGETAE            60
ATRLKRTARR RYTRRKNRIC YLQEIFSNEM AKVDDSFFHR LEESFLVEED KKHERHPIFG           120
NIVDEVAYHE KYPTIYHLRK KLVDSTDKAD LRLIYLALAH MIKFRGHFLI EGDLNPDNSD           180
VDKLFIQLVQ TYNQLFEENP INASGVDAKA ILSARLSKSR RLENLIAQLP GEKKNGLFGN           240
LIALSLGLTP NFKSNFDLAE DAKLQLSKDT YDDDLDNLLA QIGDQYADLF LAAKNLSDAI           300
LLSDILRVNT EITKAPLSAS MIKRYDEHHQ DLTLLKALVR QQLPEKYKEI FFDQSKNGYA           360
GYIDGGASQE EFYKFIKPIL EKMDGTEELL VKLNREDLLR KQRTFDNGSI PHQIHLGELH           420
AILRRQEDFY PFLKDNREKI EKILTFRIPY YVGPLARGNS RFAWMTRKSE ETITPWNFEE           480
VVDKGASAQS FIERMTNFDK NLPNEKVLPK HSLLYEYFTV YNELTKVKYV TEGMRKPAFL           540
SGEQKKAIVD LLFKTNRKVT VKQLKEDYFK KIECFDSVEI SGVEDRFNAS LGTYHDLLKI           600
IKDKDFLDNE ENEDILEDIV LTLTLFEDRE MIEERLKTYA HLFDDKVMKQ LKRRRYTGWG           660
RLSRKLINGI RDKQSGKTIL DFLKSDGFAN RNFMQLIHDD SLTFKEDIQK AQVSGQGDSL           720
HEHIANLAGS PAIKKGILQT VKVVDELVKV MGRHKPENIV IEMARENQTT QKGQKNSRER           780
MKRIEEGIKE LGSQILKEHP VENTQLQNEK LYLYYLQNGR DMYVDQELDI NRLSDYDVDH           840
IVPQSFLKDD SIDNKVLTRS DKNRGKSDNV PSEEVVKKMK NYWRQLLNAK LITQRKFDNL           900
TKAERGGLSE LDKAGFIKRQ LVETRQITKH VAQILDSRMN TKYDENDKLI REVKVITLKS           960
KLVSDFRKDF QFYKVREINN YHHAHDAYLN AVVGTALIKK YPKLESEFVY GDYKVYDVRK          1020
MIAKSEQEIG KATAKYFFYS NIMNFFKTEI TLANGEIRKR PLIETNGETG EIVWDKGRDF          1080
ATVRKVLSMP QVNIVKKTEV QTGGFSKESI LPKRNSDKLI ARKKDWDPKK YGGFDSPTVA          1140
YSVLVVAKVE KGKSKKLKSV KELLGITIME RSSFEKNPID FLEAKGYKEV KKDLIIKLPK          1200
```

```
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGD              1368

SEQ ID NO: 139          moltype = DNA  length = 105
FEATURE                 Location/Qualifiers
misc_feature            1..105
                        note = Description of Artificial Sequence: Synthetic
                         polynucleotide
source                  1..105
                        mol_type = other DNA
                        organism = synthetic construct
SEQUENCE: 139
attccctctt tagccagagc cggggtgtgc agacggcagt cactaggggg cgctcggcca  60
ccacagggaa gctgggtgaa tggagcgagc agcgtcttcg agagt                 105
```